US011851491B2

(12) United States Patent
Baeuerle et al.

(10) Patent No.: US 11,851,491 B2
(45) Date of Patent: Dec. 26, 2023

(54) COMPOSITIONS AND METHODS FOR TCR REPROGRAMMING USING FUSION PROTEINS

(71) Applicant: TCR2 Therapeutics Inc., Cambridge, MA (US)

(72) Inventors: Patrick Baeuerle, Gauting (DE); Robert Hofmeister, Scituate, MA (US)

(73) Assignee: TCR2 THERAPEUTICS INC., Cambridge, MA (US)

( * ) Notice: Subject to any disclaimer, the term of this patent is extended or adjusted under 35 U.S.C. 154(b) by 479 days.

(21) Appl. No.: 16/462,492

(22) PCT Filed: Nov. 22, 2017

(86) PCT No.: PCT/US2017/063137
§ 371 (c)(1),
(2) Date: May 20, 2019

(87) PCT Pub. No.: WO2018/098365
PCT Pub. Date: May 31, 2018

(65) Prior Publication Data
US 2019/0276540 A1 Sep. 12, 2019

Related U.S. Application Data

(60) Provisional application No. 62/425,697, filed on Nov. 23, 2016, provisional application No. 62/425,884, filed on Nov. 23, 2016, provisional application No. 62/425,407, filed on Nov. 22, 2016, provisional application No. 62/425,535, filed on Nov. 22, 2016.

(51) Int. Cl.
*C07K 16/28* (2006.01)
*A61P 35/00* (2006.01)
*A61K 35/17* (2015.01)
*C07K 14/725* (2006.01)
*C07K 14/735* (2006.01)
*C12N 5/0783* (2010.01)
*C12N 15/86* (2006.01)

(52) U.S. Cl.
CPC ............ *C07K 16/283* (2013.01); *A61K 35/17* (2013.01); *A61P 35/00* (2018.01); *C07K 14/7051* (2013.01); *C07K 14/70535* (2013.01); *C07K 16/2809* (2013.01); *C07K 16/2836* (2013.01); *C12N 5/0636* (2013.01); *C12N 15/86* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 5,199,942 A | 4/1993 | Gillis |
| 5,225,539 A | 7/1993 | Winter |
| 5,350,674 A | 9/1994 | Boenisch et al. |
| 5,399,346 A | 3/1995 | Anderson et al. |
| 5,530,101 A | 6/1996 | Queen et al. |
| 5,565,332 A | 10/1996 | Hoogenboom et al. |
| 5,580,859 A | 12/1996 | Felgner et al. |
| 5,585,089 A | 12/1996 | Queen et al. |
| 5,585,362 A | 12/1996 | Wilson et al. |
| 5,589,466 A | 12/1996 | Felgner et al. |
| 5,766,886 A | 6/1998 | Studnicka et al. |
| 5,858,358 A | 1/1999 | June et al. |
| 5,883,223 A | 3/1999 | Gray |
| 5,912,172 A | 6/1999 | Eshhar et al. |
| 6,120,766 A | 9/2000 | Hale et al. |
| 6,326,193 B1 | 12/2001 | Liu et al. |
| 6,331,415 B1 | 12/2001 | Cabilly et al. |
| 6,352,694 B1 | 3/2002 | June et al. |
| 6,407,213 B1 | 6/2002 | Carter et al. |
| 6,534,055 B1 | 3/2003 | June et al. |
| 6,548,640 B1 | 4/2003 | Winter |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,081,518 B1 | 7/2006 | Pastan et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 7,371,849 B2 | 5/2008 | Honda et al. |
| 7,572,631 B2 | 8/2009 | Berenson et al. |
| 7,695,936 B2 | 4/2010 | Carter et al. |
| 7,741,465 B1 | 6/2010 | Eshhar et al. |
| 8,206,710 B2 | 6/2012 | Ebel et al. |
| 8,389,282 B2 | 3/2013 | Sadelain et al. |
| 8,679,492 B2 | 3/2014 | Blein et al. |
| 8,697,359 B1 | 4/2014 | Zhang |
| 8,911,732 B2 | 12/2014 | Dennis et al. |

(Continued)

FOREIGN PATENT DOCUMENTS

| | | |
|---|---|---|
| CN | 102209728 A | 10/2011 |
| CN | 104136458 A | 11/2014 |
| EP | 0239400 A2 | 9/1987 |
| EP | 0519596 A1 | 12/1992 |
| EP | 0592106 A1 | 4/1994 |

(Continued)

OTHER PUBLICATIONS

T-cell receptor From Wikipedia, the free encyclopedia; ; p. 1-6; downloaded Dec. 2, 2021.*

(Continued)

*Primary Examiner* — Maria G Leavitt
(74) *Attorney, Agent, or Firm* — WILSON SONSINI GOODRICH & ROSATI

(57) ABSTRACT

Provided herein are T-cell receptor (TCR) fusion proteins (TFPs) having specificity for one or more tumor cell associated antigens, T cells engineered to express one or more TFP, and methods of use thereof for the treatment of diseases, including cancer.

15 Claims, 32 Drawing Sheets

Specification includes a Sequence Listing.

(56) References Cited

U.S. PATENT DOCUMENTS

| | | | |
|---|---|---|---|
| 9,023,351 B2 | 5/2015 | Kahnert et al. | |
| 9,062,127 B2 | 6/2015 | Voss et al. | |
| 9,102,736 B2 | 8/2015 | Hofmeister et al. | |
| 9,115,197 B2 | 8/2015 | Ebel et al. | |
| 9,181,527 B2 | 11/2015 | Sentman | |
| 9,217,040 B2 | 12/2015 | Kipps et al. | |
| 9,220,728 B2 | 12/2015 | Sadelain et al. | |
| 9,272,002 B2 | 3/2016 | Powell, Jr. et al. | |
| 9,316,646 B2 | 4/2016 | Rader et al. | |
| 9,365,641 B2 | 6/2016 | June et al. | |
| 9,393,257 B2 | 7/2016 | Osborn et al. | |
| 9,416,190 B2 | 8/2016 | Ho et al. | |
| 9,422,351 B2 | 8/2016 | Scholler et al. | |
| 9,447,194 B2 | 9/2016 | Jensen et al. | |
| 9,464,140 B2 | 10/2016 | June et al. | |
| 9,688,740 B2 | 6/2017 | Choi et al. | |
| 9,758,586 B2 | 9/2017 | Rader et al. | |
| 10,093,900 B2 | 10/2018 | Jantz et al. | |
| 10,208,285 B2 | 2/2019 | Baeuerle et al. | |
| 10,273,280 B2 * | 4/2019 | Ma | A61P 19/08 |
| 10,358,473 B2 | 7/2019 | Baeuerle et al. | |
| 10,358,474 B2 | 7/2019 | Baeuerle et al. | |
| 11,173,179 B2 * | 11/2021 | Ma | A61K 38/177 |
| 2002/0110855 A1 | 8/2002 | Sheppard et al. | |
| 2004/0266390 A1 | 12/2004 | Faucher et al. | |
| 2005/0042664 A1 | 2/2005 | Wu et al. | |
| 2005/0048617 A1 | 3/2005 | Wu et al. | |
| 2005/0100543 A1 | 5/2005 | Hansen et al. | |
| 2005/0175606 A1 | 8/2005 | Huang et al. | |
| 2006/0062780 A1 | 3/2006 | Zocher et al. | |
| 2006/0121005 A1 | 6/2006 | Berenson et al. | |
| 2007/0014794 A1 | 1/2007 | Carter et al. | |
| 2008/0294058 A1 | 11/2008 | Shklarski | |
| 2009/0047211 A1 | 2/2009 | Pastan et al. | |
| 2009/0322513 A1 | 12/2009 | Hwang et al. | |
| 2010/0003249 A1 | 1/2010 | Silence et al. | |
| 2011/0189141 A1 * | 8/2011 | Kieback | A61P 37/06 424/93.21 |
| 2013/0066283 A1 | 3/2013 | Alster et al. | |
| 2013/0251642 A1 | 9/2013 | Rader et al. | |
| 2013/0266551 A1 | 10/2013 | Campana et al. | |
| 2013/0273073 A1 | 10/2013 | Kipps et al. | |
| 2013/0280220 A1 | 10/2013 | Ahmed et al. | |
| 2013/0295011 A1 | 11/2013 | Guise et al. | |
| 2013/0315884 A1 | 11/2013 | Galetto et al. | |
| 2013/0323214 A1 | 12/2013 | Gottschalk et al. | |
| 2013/0323247 A1 | 12/2013 | Zugmaier et al. | |
| 2014/0004132 A1 | 1/2014 | Brenner et al. | |
| 2014/0050708 A1 | 2/2014 | Powell et al. | |
| 2014/0099340 A1 | 4/2014 | June et al. | |
| 2014/0227237 A1 | 8/2014 | June et al. | |
| 2014/0271635 A1 | 9/2014 | Brogdon et al. | |
| 2014/0286973 A1 | 9/2014 | Powell, Jr. et al. | |
| 2014/0301993 A1 | 10/2014 | Powell, Jr. et al. | |
| 2014/0308250 A1 | 10/2014 | Handgretinger et al. | |
| 2014/0308259 A1 | 10/2014 | Scholler et al. | |
| 2014/0322212 A1 | 10/2014 | Brogdon et al. | |
| 2014/0322216 A1 | 10/2014 | Kaplan | |
| 2014/0370045 A1 | 12/2014 | June et al. | |
| 2015/0031624 A1 | 1/2015 | Feldman et al. | |
| 2015/0051266 A1 | 2/2015 | Kochenderfer | |
| 2015/0093822 A1 | 4/2015 | June et al. | |
| 2015/0190428 A1 | 7/2015 | June et al. | |
| 2015/0203817 A1 | 7/2015 | Galetto et al. | |
| 2015/0238631 A1 | 8/2015 | Kim et al. | |
| 2015/0252110 A1 | 9/2015 | Hansen et al. | |
| 2015/0284475 A1 | 10/2015 | Zhou et al. | |
| 2015/0297640 A1 | 10/2015 | Cooper et al. | |
| 2015/0306141 A1 | 10/2015 | Jensen et al. | |
| 2015/0307564 A1 | 10/2015 | Young et al. | |
| 2015/0322169 A1 | 11/2015 | June et al. | |
| 2015/0329640 A1 | 11/2015 | Finer | |
| 2015/0342993 A1 | 12/2015 | Kloss et al. | |
| 2015/0344573 A1 | 12/2015 | Chang et al. | |
| 2015/0344844 A1 | 12/2015 | Better et al. | |
| 2015/0368360 A1 | 12/2015 | Liang et al. | |
| 2015/0376287 A1 | 12/2015 | Vu et al. | |
| 2015/0376296 A1 | 12/2015 | Fedorov et al. | |
| 2016/0008398 A1 | 1/2016 | Sadelain et al. | |
| 2016/0009813 A1 | 1/2016 | Themeli et al. | |
| 2016/0015749 A1 | 1/2016 | Gottschalk et al. | |
| 2016/0017048 A1 * | 1/2016 | Dotti | C12N 15/85 424/93.71 |
| 2016/0030479 A1 | 2/2016 | Abbot et al. | |
| 2016/0039903 A1 | 2/2016 | Ring et al. | |
| 2016/0040127 A1 | 2/2016 | Leventhal et al. | |
| 2016/0045551 A1 | 2/2016 | Brentjens et al. | |
| 2016/0046678 A1 | 2/2016 | Roschke et al. | |
| 2016/0046724 A1 | 2/2016 | Brogdon et al. | |
| 2016/0052990 A1 | 2/2016 | Ring et al. | |
| 2016/0120906 A1 | 5/2016 | Galetto et al. | |
| 2016/0120907 A1 | 5/2016 | Sentman | |
| 2016/0122782 A1 | 5/2016 | Crisman et al. | |
| 2016/0144026 A1 | 5/2016 | Lutteropp et al. | |
| 2016/0145354 A1 | 5/2016 | Bacac et al. | |
| 2016/0158359 A1 | 6/2016 | Gilbert | |
| 2016/0168262 A1 | 6/2016 | Spriggs et al. | |
| 2016/0176973 A1 | 6/2016 | Kufer et al. | |
| 2016/0184362 A1 | 6/2016 | Duchateau et al. | |
| 2016/0185861 A1 | 6/2016 | Bedoya et al. | |
| 2016/0185862 A1 | 6/2016 | Wu et al. | |
| 2016/0186165 A1 | 6/2016 | Dose et al. | |
| 2016/0194375 A1 | 7/2016 | Kitchen et al. | |
| 2016/0206656 A1 | 7/2016 | Gilbert | |
| 2016/0207989 A1 | 7/2016 | Short | |
| 2016/0208018 A1 | 7/2016 | Chen et al. | |
| 2016/0215051 A1 | 7/2016 | Sharma et al. | |
| 2016/0228547 A1 | 8/2016 | Wagner et al. | |
| 2016/0235787 A1 | 8/2016 | June et al. | |
| 2016/0237139 A1 | 8/2016 | Puléet al. | |
| 2016/0237407 A1 | 8/2016 | Wagner et al. | |
| 2016/0256488 A1 | 9/2016 | Wu | |
| 2016/0257762 A1 | 9/2016 | Kwon et al. | |
| 2016/0264665 A1 | 9/2016 | Lim et al. | |
| 2016/0272999 A1 | 9/2016 | Duchateau et al. | |
| 2016/0289343 A1 | 10/2016 | Wu | |
| 2016/0296633 A1 | 10/2016 | Goldenberg et al. | |
| 2016/0340406 A1 | 11/2016 | Zhao et al. | |
| 2017/0166622 A1 | 6/2017 | Baeuerle et al. | |
| 2017/0355766 A1 | 12/2017 | Zack et al. | |
| 2018/0127502 A1 | 5/2018 | Brentjens et al. | |
| 2018/0170992 A1 | 6/2018 | Balyasnikova et al. | |
| 2018/0185434 A1 | 7/2018 | Borrello et al. | |
| 2018/0187149 A1 * | 7/2018 | Ma | C07K 14/7051 |
| 2018/0273601 A1 | 9/2018 | Adusumilli et al. | |
| 2018/0318349 A1 | 11/2018 | Thompson | |
| 2018/0327470 A1 | 11/2018 | Li et al. | |
| 2018/0360884 A1 | 12/2018 | Adusumilli | |
| 2019/0010207 A1 | 1/2019 | Kobold et al. | |
| 2019/0106478 A1 | 4/2019 | Noessner et al. | |
| 2019/0125797 A1 | 5/2019 | Powell, Jr. et al. | |
| 2019/0177694 A1 | 6/2019 | Baeuerle et al. | |
| 2019/0256571 A1 | 8/2019 | Baeuerle et al. | |
| 2019/0330306 A1 | 10/2019 | Noonan et al. | |
| 2019/0345219 A1 | 11/2019 | June et al. | |
| 2019/0359726 A1 | 11/2019 | Wang et al. | |
| 2020/0207828 A1 | 7/2020 | Baeuerle et al. | |
| 2020/0362011 A1 | 11/2020 | Baeuerle et al. | |

FOREIGN PATENT DOCUMENTS

| | | |
|---|---|---|
| EP | 0638119 A1 | 2/1995 |
| EP | 1075517 B1 | 7/2006 |
| EP | 2255719 A1 | 12/2010 |
| EP | 2258720 A1 | 12/2010 |
| EP | 2894164 A1 | 7/2015 |
| EP | 2342227 B1 | 10/2015 |
| EP | 2632954 B1 | 11/2015 |
| EP | 2953974 A1 | 12/2015 |
| EP | 2970472 A1 | 1/2016 |
| EP | 2982692 A1 | 2/2016 |
| EP | 2982696 A2 | 2/2016 |
| EP | 2361936 B1 | 4/2016 |
| EP | 3006459 A1 | 4/2016 |

(56) References Cited

FOREIGN PATENT DOCUMENTS

| | | |
|---|---|---|
| EP | 3018145 A1 | 5/2016 |
| EP | 3019622 A2 | 5/2016 |
| EP | 3023437 A1 | 5/2016 |
| EP | 2686417 B1 | 6/2016 |
| EP | 2982694 B1 | 6/2016 |
| EP | 3025719 A1 | 6/2016 |
| EP | 3029067 A1 | 6/2016 |
| EP | 3029068 A1 | 6/2016 |
| EP | 3057991 A1 | 8/2016 |
| EP | 3057994 A1 | 8/2016 |
| EP | 2370467 B1 | 9/2016 |
| EP | 3087101 A1 | 11/2016 |
| FR | 901228 A | 7/1945 |
| JP | H07505282 A | 6/1995 |
| JP | 2004529636 A | 9/2004 |
| JP | 2007536905 A | 12/2007 |
| JP | 2012508164 A | 4/2012 |
| JP | 2014532642 A | 12/2014 |
| JP | 2014534242 A | 12/2014 |
| KR | 20090092900 A | 9/2009 |
| WO | WO-9109967 A1 | 7/1991 |
| WO | WO-9317105 A1 | 9/1993 |
| WO | WO-9319163 A1 | 9/1993 |
| WO | WO-0077029 A1 | 12/2000 |
| WO | WO-0129058 A1 | 4/2001 |
| WO | WO-0196584 A2 | 12/2001 |
| WO | WO-02077029 A2 | 10/2002 |
| WO | WO-2005052006 A2 | 6/2005 |
| WO | WO-2005102383 A1 | 11/2005 |
| WO | WO-2006020258 A2 | 2/2006 |
| WO | WO-2007024715 A2 | 3/2007 |
| WO | WO-2009059804 A2 | 5/2009 |
| WO | WO-2009059804 A3 | 9/2009 |
| WO | WO-2010029434 A1 | 3/2010 |
| WO | WO-2010052014 A1 | 5/2010 |
| WO | WO-2010104949 A2 | 9/2010 |
| WO | WO-2012076066 A1 | 6/2012 |
| WO | WO-2012079000 A1 | 6/2012 |
| WO | WO-2012138475 A1 | 10/2012 |
| WO | WO-2013040557 A2 | 3/2013 |
| WO | WO-2013063419 A2 | 5/2013 |
| WO | WO-2013072406 A1 | 5/2013 |
| WO | WO-2013072415 A1 | 5/2013 |
| WO | WO-2013126712 A1 | 8/2013 |
| WO | WO-2013126729 A1 | 8/2013 |
| WO | WO-2013154760 A1 | 10/2013 |
| WO | WO-2013176916 A1 | 11/2013 |
| WO | WO-2014031687 A1 | 2/2014 |
| WO | WO-2014055657 A1 | 4/2014 |
| WO | WO-2014122143 A1 | 8/2014 |
| WO | WO-2014122144 A1 | 8/2014 |
| WO | WO-2014140248 A1 | 9/2014 |
| WO | WO-2014153270 A1 | 9/2014 |
| WO | WO-2014184143 A1 | 11/2014 |
| WO | WO-2014190273 A1 | 11/2014 |
| WO | WO-2015006749 A2 | 1/2015 |
| WO | WO-2015057834 A1 | 4/2015 |
| WO | WO-2015057852 A1 | 4/2015 |
| WO | WO-2015090229 A1 | 6/2015 |
| WO | WO-2015092024 A2 | 6/2015 |
| WO | WO-2015095895 A1 | 6/2015 |
| WO | WO-2015107075 A1 | 7/2015 |
| WO | WO-2015112800 A1 | 7/2015 |
| WO | WO-2015112830 A1 | 7/2015 |
| WO | WO-2015121454 A1 | 8/2015 |
| WO | WO-2015123642 A1 | 8/2015 |
| WO | WO-2015124715 A1 | 8/2015 |
| WO | WO-2015142661 A1 | 9/2015 |
| WO | WO-2015142675 A2 | 9/2015 |
| WO | WO-2015158671 A1 | 10/2015 |
| WO | WO-2015164745 A1 | 10/2015 |
| WO | WO-2015168613 A2 | 11/2015 |
| WO | WO-2015177349 A1 | 11/2015 |
| WO | WO-2015179801 A1 | 11/2015 |
| WO | WO-2015188141 A2 | 12/2015 |
| WO | WO-2016011210 A2 | 1/2016 |
| WO | WO-2016014565 A2 | 1/2016 |
| WO | WO-2016014789 A2 | 1/2016 |
| WO | WO-2016016344 A1 | 2/2016 |
| WO | WO-2016019969 A1 | 2/2016 |
| WO | WO-2016025454 A2 | 2/2016 |
| WO | WO-2016030691 A2 | 3/2016 |
| WO | WO-2016036678 A1 | 3/2016 |
| WO | WO-2016040441 A1 | 3/2016 |
| WO | WO-2016044853 A1 | 3/2016 |
| WO | WO-2016054520 A2 | 4/2016 |
| WO | WO-2016055551 A1 | 4/2016 |
| WO | WO-2016070061 A1 | 5/2016 |
| WO | WO-2016073381 A1 | 5/2016 |
| WO | WO-2016079081 A1 | 5/2016 |
| WO | WO-2016081518 A2 | 5/2016 |
| WO | WO-2016087245 A1 | 6/2016 |
| WO | WO-2016090034 A2 | 6/2016 |
| WO | WO-2016090312 A1 | 6/2016 |
| WO | WO-2016090320 A1 | 6/2016 |
| WO | WO-2016090327 A2 | 6/2016 |
| WO | WO-2016097231 A2 | 6/2016 |
| WO | WO-2016115274 A1 | 7/2016 |
| WO | WO-2016115482 A1 | 7/2016 |
| WO | WO-2016116601 A1 | 7/2016 |
| WO | WO-2016123675 A1 | 8/2016 |
| WO | WO-2016126608 A1 | 8/2016 |
| WO | WO-2016127043 A1 | 8/2016 |
| WO | WO-2016127257 A1 | 8/2016 |
| WO | WO-2016130598 A1 | 8/2016 |
| WO | WO-2016132366 A1 | 8/2016 |
| WO | WO-2016141357 A1 | 9/2016 |
| WO | WO-2016151315 A1 | 9/2016 |
| WO | WO-2016161415 A2 | 10/2016 |
| WO | WO-2016187349 A1 | 11/2016 |
| WO | WO-2016203048 A1 | 12/2016 |
| WO | WO 2017/027392 * | 2/2017 |
| WO | WO-2017027392 A1 | 2/2017 |
| WO | WO-2017112741 A1 | 6/2017 |
| WO | WO-2017173256 A1 | 10/2017 |
| WO | WO-2018026953 A1 | 2/2018 |
| WO | WO-2018044866 A1 | 3/2018 |
| WO | WO-2018067993 A1 | 4/2018 |
| WO | WO-2018098365 A2 | 5/2018 |
| WO | WO-2018119298 A1 | 6/2018 |
| WO | WO-2018200583 A1 | 11/2018 |
| WO | WO-2018232020 A1 | 12/2018 |
| WO | WO-2019010383 A1 | 1/2019 |
| WO | WO-2019060174 A1 | 3/2019 |
| WO | WO-2019165116 A1 | 8/2019 |
| WO | WO-2019173693 A1 | 9/2019 |
| WO | WO-2019222275 A2 | 11/2019 |
| WO | WO-2020023888 A2 | 1/2020 |
| WO | WO-2020047501 A1 | 3/2020 |

OTHER PUBLICATIONS

Jackon et al., Mar. 22, 2016; Nature Reviews; pp. 370-383.*
Chen et al. Mesothelin Binding to CA125/MUC16 Promotes Pancreatic Cancer Cell Motility and Invasion via MMP-7 Activation. Scientific Reports 3(1):4-8 (2013).
Dangaj et al. In vivo blocking of CA125/mesothelin-dependent cell adhesion prevents ovarian cancer peritoneal metastasis. Gynecologic Oncology 116(3):S2-S169 (2010).
Han et al. Masked Chimeric Antigen Receptor for Tumor-Specific Activation. Molecular Therapy 25(1):274-284 (2017).
Nicolaides et al. CA125 suppresses amatuximab immune-effector function and elevated serum levels are associated with reduced clinical response in first line mesothelioma patients. Cancer Biology & Therapy 19(7):622-630 (2018).
PCT/US2019/032298 International Search Report and Written Opinion dated Nov. 21, 2019.
PCT/US2019/043690 Invitation to Pay Additional Fees dated Nov. 4, 2019.
Rodriguez-Garcia et al. T-cell target antigens across major gynecologic cancers. Gynecologic Oncology 145(3):426-435 (2017).

(56) References Cited

OTHER PUBLICATIONS

Yao et al. CyTOF supports efficient detection of immune cell subsets from small samples. J Immunol Methods 415:1-5 (2014).
Abate-Daga et al. CAR models: next-generation CAR modifications for enhanced T-cell function. Mol Ther Oncolytics 3:16014 (2016).
Abate-Daga et al. Expression profiling of TCR-engineered T cells demonstrates overexpression of multiple inhibitory receptors in persisting lymphocytes. Blood 122(8):1399-410 (2013).
Acuto et al. Tailoring T-cell receptor signals by proximal negative feedback mechanisms. Nat Rev Immunol 8(9):699-712 (2008).
Adusumilli et al. 342: A Phase 1 Clinical Trial of Malignant Pleural Disease Treated with Regionally Delivered Autologous Mesothelin-Targeted CAR T Cells: Safety and Efficacy—A Preliminary Report. Mol Therapy 26(5S1):158-159 (2018).
Adusumilli et al. Regional delivery of mesothelin-targeted CAR T cell therapy generates potent and long-lasting CD4-dependent tumor immunity. Sci Transl Med 6(261):261ra151 (2014) (w/Supplementary Data).
Agata et al. Expression of the PD-1 antigen on the surface of stimulated mouse T and B lymphocytes. Int Immunol 8:765-775 (1996).
Ager et al. Homing to solid cancers: a vascular checkpoint in adoptive cell therapy using CAR T-cells. Biochemical Society transactions. 44(2):377-385 (2016).
Almasbak et al. CAR T Cell Therapy: A Game Changer in Cancer Treatment. Journal of Immunology Research. 2016:1-10 (2016).
Al-Rawi et al. Interleukin-7 (IL-7) and IL-7 receptor (IL-7R) signalling complex in human solid tumours. Hist Histopathol 18:911-923 (2003).
Altschul et al. Basic local alignment search tool. J Mol Biol 215(3):403-410 (1990).
Altschul et al. Gapped BLAST and PSI-BLAST: a new generation of protein database search programs. Nucleic Acids Res 25:3389-3402 (1977).
Angelo et al. Antitumor Activity Associated with Prolonged Persistence of Adoptively Transferred NY-ESO-1c259 T cells in Synovial Sarcoma. Cancer Disov 8(8):944-957 (2018).
Ankri et al. Human T cells engineered to express a programmed death 1/28 costimulatory retargeting molecule display enhanced antitumor activity. J Immunol 191:4121-4129 (2013).
Baca et al. Antibody humanization using monovalent phage display. J Biol Chem 272(16):10678-10684 (1997).
Badoual et al. PD-1-expressing tumor-infiltrating T cells are a favorable prognostic biomarker in HPV-associated head and neck cancer. Cancer Res. 73(1):128-138 (2013).
Baeuerle. Abstract No. A058. TRuC-T Cells Targeting CD19 or Mesothelin Demonstrate Superior Antitumor Activity in Preclinical Models Compared to CAR-T Cells (Poster session). Third CRI-CIMT-EATI-AACR International Cancer Immunotherapy Conference. URL:https://static1.squarespace.com/static/56dee71e555986fb3ae583e2/t/59ad08b1b8a79b086c865d6c/1504512189107/CIMT_Abstracts_170904.pdf(1 pg.) (2017) [retrieved on Jan. 9, 2018].
Baeuerle et al. A Novel T Cell Therapy Engaging the Complete T Cell Receptor. (45 pgs) (2016).
Bahram et al. A second lineage of mammalian major histocompatibility complex class I genes. PNAS USA 91:6259-6263 (1994).
Barretina et al. The Cancer Cell Line Encyclopedia enables predictive modelling of anticancer drug sensitivity. Nature 483:603-607 (2012).
Barrett et al. Eradication of established CD19-positive leukemia using a single injection of chimeric immunoreceptor modified lentiviral-transduced T cells in a xenograft NOG mouse model. Journal of Immunotherapy 32(9):941 (2009).
Barrett et al. Treatment of advanced leukemia in mice with mRNA engineered T cells. Hum Gene Ther 22:1575-1586 (2011).
Batlevi et al. Novel immunotherapies in lymphoid malignancies. Nat Rev Clin Oncol 13(1):25-40 (2016).
Batzer et al. Enhanced evolutionary PCR using oligonucleotides with inosine at the 3'-terminus. Nucleic Acid Res 19:5081 (1991).

Bauer et al. Activation of NK cells and T cells by NKG2D, a receptor for stress-inducible MICA. Science 285(5428):727-9 (1999).
Beatty et al. Activity of Mesothelin-specific Chimeric Antigen Receptor T cells Against Pancreatic Carcinoma Metastases in a Phase 1 Trial. Gastroenterology 5085(18)30323-30328 (accepted manuscript).
Beatty et al. Mesothelin-Specific Chimeric Antigen Receptor mRNA-Engineered T Cells Induce Antitumor Activity in Solid Malignancies. Cancer Immunol 3(2):217 (2015).
Beatty et al. Mesothelin-specific Chimeric Antigen Receptor mRNA-Engineered T cells Induce Anti-Tumor Activity in Solid Malignancies. Cancer Immunol Res 2(2):112-120 (2014).
Bezverbnaya et al. Tumor-targeting domains for chimeric antigen receptor T cells. Immunotherapy 9(1):33-46 (2017).
Billadeau et al. ITAMs versus ITIMs: striking a balance during cell regulation. J Clin Invest 109:161-168 (2002).
Bird et al. Single-chain antigen-binding proteins. Science 242(4877):423-426 (1988).
Blank et al. Interaction of PD-L1 on tumor cells with PD-1 on tumor-specific T cells as a mechanism of immune evasion: implications for tumor immunotherapy. Cancer Immunol Immunother 54:307-314 (2005).
Bonifant et al. Toxicity and management in CAR T-cell Therapy. Mol Ther Oncolytics 3:16011 (2016).
Borcherding et al. ROR1, an embryonic protein with an emerging role in cancer biology. Protein Cell 5(7):496-502 (2014).
Borroto et al. Crammed signaling motifs in the T-cell receptor. Immunol Lett 161:113-117 (2014).
Brahmer et al. Safety and activity of anti-PD-L1 antibody in patients with advanced cancer. N Engl J Med 366(26):2455-2465 (2012).
Brentjens et al. Genetically targeted T cells eradicate systemic acute lymphoblastic leukemia xenograft. Clin Cancer Res13:5426-5435 (2007).
Brentjens. Novel cellular therapies for leukemia: CAR-modified T cells targeted to the CD19 antigen. Hematology Am Soc Hematol Educ Program 2012:143-151 (2012).
Bridgeman et al. Building better chimeric antigen receptors for adoptive T cell therapy. Current Gene Therapy. 10:77-90 (2010).
Bridgeman et al. Structural and biophysical determinants of αβ T-cell antigen recognition. Immunology 135(1):9-18 (2012).
Brocker et al. Redirecting the complete T cell receptor/CD3 signaling machinery towards native antigen via modified T cell receptor. Eur J. Immunol 26:1770-1774 (1996).
Brocker et al. Signals through T cell receptor-zeta chain alone are insufficient to prime resting T lymphocytes. J Med Chem 181:1653-1659 (1995).
Brocker. Chimeric Fv-zeta or Fv-epsilon receptors are not sufficient to induce activation or cytokine production in peripheral T cells. Blood 96(5):1999-2001 (2000).
Brudno et al. Allogeneic T cells that express an anti-CD19 chimeric antigen receptor induce remissions of B-cell malignancies that progress after allogeneic hematopoietic stem-cell transplantation without causing graft-versus-host disease. J Clin Oncol 34(10):1112-1121 (2016).
Bruhns et al. Specificity and Affinity of Human Fc Receptors and Their Polymorphic Variants for Human IgG Subclasses. Blood 113(16):3716-3725 (2009).
Buck et al. Mitochondrial Dynamics Controls T Cell Fate through Metabolic Programming. Cell 166:63-76 (2016).
Budde et al. Combining a CD20 chimeric antigen receptor and an inducible caspase 9 suicide switch to improve the efficacy and safety of T cell adoptive immunotherapy for lymphoma. PLoS One 8(12):e82742 (2013).
Caldas et al. Design and synthesis of germline-based hemi-humanized single-chain Fv against the CD18 surface antigen. Protein Eng 13(5):353-360 (2000).
Call et al. The organizing principle in the formation of the T cell receptor-CD3 complex. Cell 111(7):967-979 (2002).
Carpenito et al. Control of large, established tumor xenografts with genetically retargeted human T cells containing CD28 and CD137 domains. PNAS USA 106(9):3360-3365 (2009).

(56) References Cited

OTHER PUBLICATIONS

Carpenter et al. B-cell maturation antigen is a promising target for adoptive T-cell therapy of multiple myeloma. Clin Cancer Res 19(8):2048-2060 (2013).
Cartellieri et al. Switching CAR T cells on and off: a novel modular platform for retargeting of T cells to AML blasts. Blood Cancer J 6(8):e458 (2016).
Carter et al. Humanization of an anti-p185HER2 antibody for human cancer therapy. PNAS USA 89(10):4285-4289 (1992).
Carter et al. PD-1: PD-L inhibitory pathway affects both CD4(+) and CD8(+) T cells and is overcome by IL-2. Eur J Immunol 32:634-643 (2002).
Chan et al. Chimeric antigen receptor-redirected CD45RA-negative T cells have potent antileukemia and pathogen memory response without graft-versus-host activity. Leukemia 29:387-395 (2015).
Chen et al. In situ expression and significance of B7 costimulatory molecules within tissues of human gastric carcinoma. World J Gastroenterol. 9(6):1370-1373 (2003).
Chen et al. Novel anti-CD3 chimeric antigen receptor targeting of aggressive T cell malignancies. Oncotarget 7(35):56219-56232 (2016).
Chen et al. Oncology Meets Immunology: The Cancer-Immunity Cycle. Immunity 39(1):1-10 (2013).
Chhabra et al. TCR-Engineered, Customized, Antitumor T Cells for Cancer Immunotherapy: Advantages and Limitations. Scientific World Journal 11:121-129 (2011).
Chmielewski et al. Of CARs and TRUCKS: Chimeric antigen receptor (CAR) T cells engineered with an inducible cytokine to modulate the tumor stroma, Immunological Reviews 257(1):83-90 (2014).
Choi et al. Pre-clinical Specificity and Safety of UC-961, a First-In-Class Monoclonal Antibody Targeting ROR1 Clinical Lymphoma, Myeloma & Leukemia 15(Supp):SI67-S169 (2015).
Chothia et al. Canonical structures for the hypervariable regions of immunoglobulins. J Mol Biol. 196(4):901-917 (1987).
Chu et al. Targeting+ CD20 Aggressive B-cell Non-Hodgkin Lymphoma by Anti-CD20 CAR mRNA-Modified Expanded Natural Killer Cells In Vitro and in NSG Mice. Cancer Immunol Res 3(4):333-344 (2015).
Cieri et al. Adoptive immunotherapy with genetically modified lymphocytes in allogeneic stem cell transplantation. Immun Rev 257(1):165-180 (2014).
Cieri et al. IL-7 and IL-15 instruct the generation of human memory stem T cells from naive precursors. Blood 121(4):573-584 (2013).
Cooper. Adoptive transfer of T cells genetically modified using the Sleeping Beauty system. Adoptive Transfer Session. 24th iSBTc Annual Meeting (30 pgs) (Oct. 31, 2009).
Cougot et al. 'Cap-tabolism'. Trends in Biochem Sci 29:436-444 (2001).
Couto et al. Anti-BA46 monoclonal antibody Mc3: humanization using a novel positional consensus and in vivo and in vitro characterization. Cancer Res 55(8):1717-1722 (1995).
Couto et al. Designing human consensus antibodies with minimal positional templates. Cancer Res 55(23 Supp):5973s-5977s (1995).
Cristaudo et al. Clinical significance of serum mesothelin in patients with mesothelioma and lung cancer. Clin. Cancer Res. 13:5076-5081 (2007).
Cui et al. Targeting ROR1 inhibits epithelial-mesenchymal transition and metastasis. Cancer Research 73(12):3649-3660 (2015).
D'Aloia et al. T Lymphocytes Engineered to Express a CD16-Chimeric Antigen Receptor Redirect T-cell Immune Responses Against Immunoglobulin G-Opsonized Target Cells. Cytotherapy 18(2):278-290 (2016).
Darce et al. Regulated expression of BAFF-binding receptors during human B cell differentiation. J Immunol 179(11):7276-7286 (2007).
D'Argouges. Combination of rituximab with blinatumomab (MT103/MEDI-538), a T cell-engaging CD19-/CD3-bispecific antibody, for highly efficient lysis of human B lymphoma cells. Leukemia Res 33:465-473 (2009).
Davila. Efficacy and toxicity management of 19-28z CAR T cell therapy in B cell acute lymphoblastic leukemia. Sci Transl Med 6(224):224ra25 (2014).
Davila et al. How do CARs work? Early insights from recent clinical studies targeting CD19. Oncoimmunology 1(9):1577-1583 (2012).
Deniger et al. Sleeping Beauty Transposition of Chimeric Antigen Receptors Targeting Receptor Tyrosine Kinase-Like Orphan Receptor-1 (ROR1) into Diverse Memory T-Cell Populations. PLoS ONE 10(6):e0128151 (2015).
Desmyter et al. Crystal structure of a camel single-domain VH antibody fragment in complex with lysozyme. Nat Struct Biol 3(9):803-811 (1996).
Ding et al. CBP loss cooperates with PTEN haploinsufficiency to drive prostate cancer: implications for epigenetic therapy. Cancer Res 74(7):2050-2061 (2014).
Dong et al. B7-H1 pathway and its role in the evasion of tumor immunity. J Mol Med 81:281-287 (2003).
Dong et al. Tumor-associated B7-H1 promotes T-cell apoptosis: a potential mechanism of immune evasion. Nat Med 8:793-800 (2002).
Dopfer et al. The CD3 conformational change in the Gamma Delta T cell receptor is not triggered by antigens but can be enforced to enhance tumor killing. Cell Reports 7(5):1704-1715 (2014).
Dotti et al. Design and Development of Therapies using Chimeric Antigen Receptor-Expressing T cells. Immunol Rev. 257(1):35 pgs (2014).
Dudley et al. Adoptive cell therapy for patients with metastatic melanoma: evaluation of intensive myeloablative chemoradiation preparative regimens. J Clin Oncol 26(32):5233-5239 (2008).
Eagle et al. Cellular expression, trafficking, and function of two isoforms of human ULBP5/RAET1G. PLoS One 4:e4503 (2009).
Eagle et al. ULBP6/RAET1L is an additional human NKG2D ligand. Eur J Immunol 39:3207-3216 (2009).
Elango et al. Optimized transfection of mRNA transcribed from a d(A/T)100 tail-containing vector. Biochim Biophys Res Commun 330:958-966 (2005).
Ellyard et al. Antigen-selected, immunoglobulin-secreting cells persist in human spleen and bone marrow. Blood 103(10):3805-3812 (2004).
Eshhar et al. Chimeric T cell receptor which incorporates the anti-tumour specificity of a monoclonal antibody with the cytolytic activity of T cells: a model system for immunotherapeutical approach. Br J Cancer 62:27-29 (1990).
Eshhar et al., Design of cytotoxic T lymphocytes with antibody-type specificity against tumor cells using chimeric PCR. Journal of Cellular Biochemistry, A.R. Liss, Suppl. 14B: 70 (1990).
Fang et al. Immunotherapy for advanced melanoma. J Invest Derm 128(11):2596-2605 (2008).
Feng et al. A novel human monoclonal antibody that binds with high affinity to mesothelin-expressing cells and kills them by antibody-dependent cell-mediated cytotoxicity. Mol Cancer Ther 8(5):1113-1118.
Finney et al. Activation of resting human primary T cells with chimeric receptors: costimulation from CD28, inducible costimulator, CD134, and CD137 in series with signals from the TCR zeta chain. J Immunol 172:104-113 (2004).
Finney et al. Chimeric Receptors Providing Both Primary and Costimulatory Signaling in T Cells from a Single Gene Product. J Immunol 161:2791-2797 (1998).
Fraietta et al. Ibrutinib enhances chimeric antigen receptor T-cell engraftment and efficacy in leukemia. Blood 127(9):1117-1127 (2016).
Freeman et al. Engagement of the PD-1 immunoinhibitory receptor by a novel B7 family member leads to negative regulation of lymphocyte activation. J Exp Med 192:1027-1034 (2000).
Frigault et al. Chimeric antigen receptor-modified T cells strike back. Int Immunol 28(7):355-363 (2016).
Gabrilovich et al. Myeloid-derived-suppressor cells as regulators of the immune system Nat Rev Immunol 9(3):162-174 (2009).
Gao et al. Overexpression of PD-L1 significantly associates with tumor aggressiveness and postoperative recurrence in human hepatocellular carcinoma. Clin Cancer Res. 15(3):971-979 (2009).

(56) References Cited

OTHER PUBLICATIONS

Garfall. Chimeric Antigen Receptor T Cells against CD19 for Multiple Myeloma. N Engl J Med 373(11):1040-1047 (2015).
Gargett et al. Different cytokine and stimulation conditions influence the expansion and immune phenotype of third-generation chimeric antigen receptor T cells specific for tumor antigen GD2. Cytotherapy 17(4):487-495 (2015).
Garland et al. The use of Teflon cell culture bags to expand functionally active CD8+ cytotoxic T lymphocytes. J Immunol Meth 227(1-2):53-63 (1999).
Garrido et al. The urgent need to recover MHC class I in cancers for effective immunotherapy. Current Opinion in Immunology 39:44-51 (2016).
Gattinoni et al. Paths to stemness: building the ultimate antitumour T cell. Nature Reviews Cancer 12(10):671-684 (2012).
Gattinoni et al. Adoptive immunotherapy for cancer: building on success. Nature Reviews Immunology 6(5):383-393 (2006).
Geng et al. B7-H1 up-regulated expression in human pancreatic carcinoma tissue associates with tumor progression. J Cancer Res Clin Oncol. 134(9):1021-1027 (2008).
Ghebeh et al. The B7-H1 (PD-L1) T Lymphocyte-Inhibitory Molecule Is Expressed in Breast Cancer Patients with Infiltrating Ductal Carcinoma: Correlation with Important High-Risk Prognostic Factors. Neoplasia 8(3):190-198 (2006).
Ghosh et al. Donor CD19 CAR T cells exert potent graft-versus-lymphoma activity with diminished graft-versus-host activity. Nature Medicine 23:242-249 (2017).
Goding et al. Restoring immune function of tumor-specific CD4+ T cells during recurrence of melanoma. J Immunol 190(9):4899-4909 (2013).
Gorochov et al. Functional assembly of chimeric T-cell receptor chains. Int J Cancer Supp 7:53-57 (1992).
Govers et al. TCRs Genetically Linked to CD28 and CD3ζ Do Not Mispair with Endogenous TCR Chains and Mediate Enhanced T Cell Persistence and Anti-Melanoma Activity. J Immunol 193:5315-5326 (2014).
Griffin et al. Antibody fragments as tools in crystallography. Clin Exp Immunol 165(3):285-291 (2011).
Gros et al. PD-1 identifies the patient-specific CD8+ tumor-reactive repertoire infiltrating human tumors. The Journal of clinical investigation, 124(5):2246-2259 (2014).
Gross et al. Generation of effector T cells expressing chimeric T cell receptor with antibody type-specificity. Transplant Proc. 21(1 Pt 1):127-130 (1989).
Grupp et al. Chimeric antigen receptor-modified T cells for acute lymphoid leukemia. NEJM 368:1509-1518 (2013).
Guedan et al. ICOS-based chimeric antigen receptors program bipolar TH17/TH1 cells. Blood 124(7):1070-1080 (2014).
Guest et al. The role of extracellular spacer regions in the optimal design of chimeric immune receptors: evaluation of four different scFvs and antigens. J Immunother 28(3):203-211 (2005).
Guy et al. Distinct T cell receptor signaling pathways drive proliferation and cytokine production in T cells. Nat Immunol 14(3):262-270 (2013).
Guy et al. Distinct T cell receptor signaling pathways drive proliferation and cytokine production in T cells. Nat Immunol 14(3):262-270 and Supp pp. 1-9 (2013).
Haanen et al. Selective expansion of cross-reactive CD8(+) memory T cells by viral variants. J Exp Med 190(9):1319-1328 (1999).
Hassan et al. Major Cancer Regressions in Mesothelioma After Treatment with an Anti-Mesothelin Immunotoxin and Immune Suppression. Sci Transl Med 5:208ra147 (2013).
Hassan et al. Mesothelin: a new target for immunotherapy. Clin Cancer Res 10:3937-3942 (2004).
Hatzoglou et al. TNF receptor family member Bcma (B cell maturation) associates with TNF receptor-associated factor (TRAF) 1, TRAF2, and TRAF3 and activates NF-kappa B, elk-1, c-Jun N-terminal kinase, and p38 mitogen-activated protein kinase. Immunology 165(3):1322-1330 (2000).
Hicklin et al. HLA class I antigen downregulation in human cancers: T-cell immunotherapy revives and old story. Mol Med Today 5(4):178-186 (1999).
Ho et al. Mesothelin expression in human lung cancer. Clin Cancer Res 13:1571-1575 (2007).
Hollinger et al. "Diabodies": Small bivalent and bispeific antibody fragments. PNAS USA 90:6444 6448 (1993).
Holst et al. Scalable signaling mediated by T cell antigen receptor-CD3 ITAMs ensures effective negative selection and prevents autoimmunity. Nat Immunol 9(6):658-666 and Supp pp. 1-21 (2008).
Holzinger et al. The growing world of CAR T cell trials: a systematic review, Cancer Immunology. Immunotherapy 65(12):1433-1450 (2016).
Hombach et al. T cell activation by antibody-like immunoreceptors: the position of the binding epitope within the target molecule determines the efficiency of activation of redirected T cells. J Immunol 178:4650-4657 (2007).
Huang et al. Driving an improved CAR for cancer immunotherapy. J Clin Invest 126(8):2795-2798 (2016).
Hudecek et al. Receptor affinity and extracellular domain modifications affect tumor recognition by ROR1-specific chimeric antigen receptor T cells. Clin Cancer Res 19(12):3153-3164 (2013).
Hudecek et al. The B-cell tumor-associated antigen ROR1 can be targeted with T cells modified to express a ROR1-specific chimeric antigen receptor. Blood 116(22):4532-4541 (2010).
Hudecek et al. The Nonsignaling Extracellular Spacer Domain of Chimeric Antigen Receptors Is Decisive for In Vivo Antitumor Activity. Cancer Immunol Res 3(2):125-135 (2015).
Huston et al. Protein engineering of antibody binding sites: recovery of specific activity in an anti-digoxin single-chain Fv analogue produced in *Escherichia coli*. PNAS USA 85(16):5879-5883 (1988).
Hwan et al. Universal Chimeric Antigen Receptors for Multiplexed and Logical Control of T Cell Responses. Cell 173(6):1426-1438. e11 (2018).
Hwu et al., The genetic modification of T cells for cancer therapy: an overview of laboratory and clinical trials. Cancer Detect Prev. 18(1):43-50 (1994).
Illei et al. Mesothelin Expression in Advanced Gastroesophageal Cancer Represents a Novel Target for Immunotherapy. Appl Immunohistochem Mol Morphol 24(4):246-252 (2016).
Institute for Clinical and Economic review (ICER). Chimeric Antigen Receptor T-Cell Therapy for B-Cell Cancers: Effectiveness and Value. Final Evidence Report dated Mar. 23, 2018 (185 pgs).
Iwahori et al. Engager T cells: a new class of antigen-specific T cells that redirect bystander T cells. Mol Ther 23(1):171-178 (2015).
Izumoto et al. Phase II clinical trial of Wilms tumor 1 peptide vaccination for patients with recurrent glioblastoma multiforme. J Neurosurg 108:963-971 (2008).
Jackson et al. Driving CAR T-cells forward. Nat Rev Clin Oncol 13(6):370-383 (2016).
Jacoby. CD19 CAR immune pressure induces B-precursor acute lymphoblastic leukaemia lineage switch exposing inherent leukaemic plasticity. Nat Commun 7:12320 (2016).
Jacoby et al. Murine models of acute leukemia: important tools in current pediatric leukemia research. Front Oncol 4:95 (2014).
James et al. Antibody-mediated B-cell depletion before adoptive immunotherapy with T cells expressing CD20-specific chimeric T-cell receptors facilitates eradication of leukemia in immunocompetent mice. Blood 114(27):5454-5463 (2009).
James et al. Antigen sensitivity of CD22-specific chimeric TCR is modulated by target epitope distance from the cell membrane. J Immunol 180:7028-7038 (2008).
Jamnani et al. T cells expressing VHH-directed oligoclonal chimeric HER2 antigen receptors: towards tumor-directed oligoclonal T cell therapy. Biochim Biophys Acta 1840(1):378-386 (2014).
Jena et al. Chimeric antigen receptor (CAR)-specific monoclonal antibody to detect CD19-specific T cells in clinical trials. PLoS One. 8(3):e57838 (2013).
Jin et al. Safe engineering of CAR T cells for adoptive cell therapy of cancer using long- term episomal gene transfer. EMBO Mol Med 8(7):702-711 (2016).

(56) References Cited

OTHER PUBLICATIONS

John et al. Anti-PD-1 antibody therapy potently enhances the eradication of established tumors by gene-modified T cells. Clin Cancer Res 19(20):5636-5646 (2013).

Johnson et al. Rational development and characterization of humanized anti-EGFR variant III chimeric antigen receptor T cells for glioblastoma. Immunotherapy 7(275):275ra22 (2015).

Jones et al. Replacing the complementarity-determining regions in a human antibody with those from a mouse. Nature 321:522-525 (1986).

Jonnalagadda et al. Chimeric Antigen Receptors With Mutated IgG4 Fc Spacer Avoid Fc Receptor Binding and Improve T Cell Persistence and Antitumor Efficacy. Mol Ther 23(4):757-768 (2015).

June et al. Chimeric Antigen Receptor Therapy. N Engl J Med 379:64-73 (2018).

June et al. Engineering lymphocyte subsets: tools, trials and tribulations. Nat Rev Immunol 9.10:704-716 (2009).

June et al. Is autoimmunity the Achilles' heel of cancer immunotherapy? Nat Med 23(5):540-547 (2017).

Junghans. The challenges of solid tumor for designer CAR-T therapies: a 25-year perspective. Cancer Gene Ther 24(3):89-99 (2017).

Kabat et al. Sequences of Proteins of Immunological Interest. NIH Pub. No. 91-3242. Public Health Service, National Institutes of Health. 1:647-669 (1991).

Kachala et al. Mesothelin Overexpression Is a Marker of Tumor Aggressiveness and Is Associated with Reduced Recurrence-Free and Overall Survival in Early-Stage Lung Adenocarcinoma. Clin Cancer Res 20(4):1020-1028 (2013).

Kaiser. Towards a commercial process for the manufacture of genetically modified T cells for therapy. Cancer Gene Thera 22(2):72-78 (2015).

Kalos et al. T cells with chimeric antigen receptors have potent antitumor effects and can establish memory in patients with advanced leukemia. Sci Transl Med 3(95):95ra73 (2011).

Karim et al. Tumor-expressed B7-H1 and B7-DC in relation to PD-1+ T-cell infiltration and survival of patients with cervical carcinoma. Clin Cancer Res. 15(20):6341-6347 (2009).

Karlsson et al. Evaluation of Intracellular Signaling Downstream Chimeric Antigen Receptors. PLoS One 10(12):e0144787 (2015).

Karyampudi et al. Accumulation of Memory Precursor CD8 T Cells in Regressing Tumors following Combination Therapy with Vaccine and Anti-PD-1 Antibody. Cancer Res 74(11):2974-85 (2014.

Kawalekar et al. Distinct Signaling of Coreceptors Regulates Specific Metabolism Pathways and Impacts Memory Development in Car T Cells. Immunity 44(2):380-390 (2016).

Kawalekar et al. Supplemental Information. Distinct Signaling of Coreceptors Regulates Specific Metabolism Pathways and Impacts Memory Development in CAR T Cells. Immunity 44(2):380-390 (2016).

Kebriaei et al. Phase I trials using Sleeping Beauty to generate CD19-specific CAR T cells. J Clin Invest 126(9):3363-3376 (2016).

Kershaw et al. Gene-engineered T cells for cancer therapy. Nat Rev Cancer 13(8):525-541 (2013).

Klebanoff et al. Memory T cell-driven differentiation of naive cells impairs adoptive immunotherapy. J Clin Invest 126(1):318-334 (2016).

Klebanoff et al. Prospects for gene-engineered T cell immunotherapy for solid cancers. Nat Med 22(1):26-36 (2016).

Knies et al. An optimized single chain TCR scaffold relying on the assembly with the native CD3-complex prevents residual mispairing with endogenous TCRs in human T-cells. Oncotarget 7(16):21199-211221 (2016).

Kochenderfer et al. B-cell depletion and remissions of malignancy along with cytokine-associated toxicity in a clinical trial of anti-CD19 chimeric-antigen-receptor-transduced T cells. Blood 119(12):2709-2720 (2012).

Kochenderfer et al. Construction and Pre-clinical Evaluation of an Anti-CD19 Chimeric Antigen Receptor. Immunotherapy 32(7):689-702 (2010).

Kojima et al. Molecular cloning and expression of megakaryocyte potentiating factor cDNA. J Biol Chem 270:21984-21990 (1995).

Konishi et al. B7-H1 expression on non-small cell lung cancer cells and its relationship with tumor-infiltrating lymphocytes and their PD-1 expression. Clin Cancer Res 10:5094-5100 (2004).

Kowolik et al. CD28 costimulation provided through a CD19-specific chimeric antigen receptor enhances in vivo persistence and antitumor efficacy of adoptively transferred T cells. Cancer Res 66(22):10995-11004 (2006).

Kozako et al. PD-1/PD-L1 expression in human T-cell leukemia virus type 1 carriers and adult T-cell leukemia/lymphoma patients. Leukemia 23(2):375-382 (2009).

Krenciute et al. Characterization and Functional Analysis of scFv-based Chimeric Antigen Receptors to Redirect T Cells to IL13Rα2-positive Glioma. Mol Ther 24(2):354-363 (2016).

Kudo et al. T lymphocytes expressing a CD16 signaling receptor exert antibody-dependent cancer cell killing. Cancer Res 74(1):93-103 (2013).

Kuhns et al. TCR Signaling Emerges from the Sum of Many Parts. Front. Immunol. 3:159 (2012).

Kunert et al. TCR-engineered T cells meet new challenges to treat solid tumors: Choice of antigen, T cell fitness, and sensitization of tumor milieu. Front Immun 4:363 (2013).

Kunkele et al. Functional Tuning of CARs Reveals Signaling Threshold above Which CD8+ CTL Antitumor Potency Is Attenuated due to Cell Fas-FasL-Dependent AICD. Cancer Immunol Res 3(4):368-379 (2015).

Laabi et al. A new gene, BCM, on chromosome 16 is fused to the interleukin 2 gene by a t(4;16)(q26;p13) translocation in a malignant T cell lymphoma. EMBO 11(11):3897-3904 (1992).

Laabi et al. The BCMA gene, preferentially expressed during B lymphoid maturation, is bidirectionally transcribed. Nucleic Acids Res 22(7):1147-1154 (1994).

Langer. Comparative Evaluation of Peripheral Blood T Cells and Resultant Engineered Anti-CD19 Car T-Cell Products From Patients With Relapsed / Refractory Non-Hodgkin Lymphoma (NHL). Abstract 2305 AACR Apr. 16-20, 2016 (1 pg.).

Lanier. NKG2D Receptor and Its Ligands in Host Defense. Cancer Immunol Res. 3(6):575-582 (2015).

Lanitis et al. Chimeric antigen receptor T Cells with dissociated signaling domains exhibit focused antitumor activity with reduced potential for toxicity in vivo. Cancer Immunol Res 1(1):45-53 (2013).

Lanitis et al. Redirected Antitumor Activity of Primary Human Lymphocytes Transduced With a Fully Human Anti-mesothelin Chimeric Receptor. Mol Ther 20(3):633-643 (2012).

Lanzavecchia et al. The use of hybrid hybridomas to target human cytotoxic T lymphocytes. Eur J Immunol. 17(1):105-111 (1987).

Latchman et al. PD-L2 is a second ligand for PD-1 and inhibits T cell activation. Nat Immunol 2:261-268 (2001).

Lee et al. Current concepts in the diagnosis and management of cytokine release syndrome. Blood 124(2):188-196 (2014).

Lee et al. T cells expressing CD19 chimeric antigen receptors for acute lymphoblastic leukaemia in children and young adults: A phase 1 dose-escalation trial. The Lancet 385(9967):517-528 (2014).

Lee. Solid-state target CAR-T, 'TRUC platform' (KR). Biol.co.kr Retrieved from the Internet: URL:http://www.biospectator.com/view/news_print.php?varAtcId=4037 (7 pgs.) (2017) [retrieved on Jan. 9, 2018] (Machine translation).

Leen et al. Improving T cell therapy for cancer. Annu Rev Immunol 25:243-265 (2007).

Leone et al. MHC Class I Antigen Processing and Presenting Machinery: Organization, Function, and Defects in Tumor Cells. J Natl Cancer Inst 105:1172-1187 (2013).

Li et al. Adoptive immunotherapy using T lymphocytes redirected to glypican-3 for the treatment of lung squamous cell carcinoma. Oncotarget 7(3):2496-2507 (2015).

Li et al. Enhanced Cancer Immunotherapy by Chimeric Antigen Receptor-Modified T Cells Engineered to Secrete Checkpoint Inhibitors. Clin Cancer Res 23(22):6982-6992 (2017).

Lipowska-Bhalla et al. Targeted immunotherapy of cancer with CAR T cells: Achievements and challenges. Cancer Immunol Immuno 61(7):953-962 (2012).

(56) References Cited

OTHER PUBLICATIONS

Liu et al. A Chimeric Switch-Receptor Targeting PD1 Augments the Efficacy of Second-Generation CAR T Cells in Advanced Solid Tumors. Cancer Res 76(6):1578-1590 (2016).
Liu et al. Affinity-Tuned ErbB2 or EGFR Chimeric Antigen Receptor T Cells Exhibit an Increased Therapeutic Index against Tumors in Mice. Cancer Res 75(17):3596-3607 (2015).
Liu et al. Improved anti-leukemia activities of adoptively transferred T cells expressing bispecific T-cell engager in mice. Blood Cancer J 6:e430 (2016).
Liu et al. Plasma cells from multiple myeloma patients express B7-H1 (PD-L1) and increase expression after stimulation with IFN-{gamma} and TLR ligands via a MyD88-, TRAF6-, and MEK-dependent pathway. Blood 110(1):296-304 (2007).
Liu et al. Supplemental Information. A Chimeric Switch-Receptor Targeting PD1 Augments the Efficacy of Second-Generation CAR T Cells in Advanced Solid Tumors. Cancer Res 76(6):1578-1590 (2016).
Long et al. 4-1BB Costimulation Ameliorates T Cell Exhaustion Induced by Tonic Signaling of Chimeric Antigen Receptors. Nat Med 21(6):581-590 (2015).
Love et al. ITAM-mediated signaling by the T-cell antigen receptor. Cold Spring Harb Perspect Biol. 2(6):a002485 (2010).
Lu et al. Treatment of Patients With Metastatic Cancer Using a Major Histocompatibility Complex Class II-Restricted T-Cell Receptor Targeting the Cancer Germline Antigen MAGE-A3. J Clin Oncol 35(29):3322-3329.
Ma et al. Recognition of mesothelin by the therapeutic antibody MORAb-009: structural and mechanistic insights. J Biol Chem 287:33123-33131(2012).
Ma et al. Versatile strategy for controlling the specificity and activity of engineered T cells. PNAS 113(4):E450-E458 (2016).
Maher et al. Human T-lymphocyte cytotoxicity and proliferation directed by a single chimeric TCRzeta /CD28 receptor. Nat Biotech 20(1):70-75 (2002).
Mahmoud et al. Enforced CD19 expression leads to growth inhibition and reduced tumorigenicity. Blood 94(10):3551-3558 (1999).
Malaspina et al. Enhanced programmed death 1 (PD-1) and PD-1 ligand (PD-L1) expression in patients with actinic cheilitis and oral squamous cell carcinoma. Cancer Immunol Immunother. 60(7):965-974 (2011).
Mansfield et al. B7-H1 expression in malignant pleural mesothelioma is associated with sarcomatoid histology and poor prognosis. J Thorac Oncol. 9(7):1036-1040 (2014).
Mato et al. A drive through cellular therapy for CLL in 2015: allogeneic cell transplantation and CARs. Blood 126(4):478-485 (2015).
Maude et al. CD19-targeted chimeric antigen receptor T-cell therapy for acute lymphoblastic leukemia. Blood 125(26):4017-4024 (2015).
Maus et al. Adoptive immunotherapy for cancer of viruses. Annual Review of Immunology 32:189-225 (2014).
Maus et al. Ex vivo expansion of polyclonal and antigen-specific cytotoxic T lymphocytes by artificial APCs expressing ligands for the T-cell receptor, CD28 and 4-1BB. Nature Biotech 20(2):143-148 (2002).
Maus et al. Making Better Chimeric Antigen Receptors for Adoptive T-cell Therapy. Clin Cancer Res 22(8):1875-1884 (2016).
Maus et al. T Cells Expressing Chimeric Antigen Receptors Can Cause Anaphylaxis in Humans. Cancer Immunol Res. 1:26-31 (2013).
Maus et al. Zoom zoom: Racing CARs for multiple myeloma. Clin Cancer Res 19(8):1917-1919 (2013).
Menk et al. 4-1BB costimulation induces T cell mitochondrial function and biogenesis enabling cancer immunotherapeutic responses. J Exp Med 215(4):1091-1100 (2018).
Merry et al. O-glycan sialylation and the structure of the stalk-like region of the T cell co-receptor CD8. J Biol Chem 278(29):27119-27128 (2003).
Miller et al. CD19-Targeted CAR T Cells: A New Tool in the Fight against B Cell Malignancies. Oncol Res Treat 38(12):683-690 (2015).
Milone et al. Chimeric receptors containing CD137 signal transduction domains mediate enhanced survival of T cells and increased antileukemic efficacy in vivo. Mol Ther 17(8):1453-1464 (2009).
Minguet et al. A permissive geometry model for TCR-CD3 activation. Trends in Biochemical Sciences 33(2):51-57 (2008).
Minguet et al. Full Activation of the T Cell Receptor Requires Both Clustering and Conformational Changes at CD3. Immunity 26(1):43-54 (2007).
Moon et al. Expression of a functional CCR2 receptor enhances tumor localization and tumor eradication by retargeted human T cells expressing a mesothelin-specific chimeric antibody receptor. Clin Cancer Res 17(14):4719-4730 (2011).
Morea et al. Antibody modeling: implications for engineering and design. Methods 20(3):267-279 (2000).
Morello et al. Mesothelin-Targeted CARS: Driving T Cells to Solid Tumors. Cancer Discov 6(2):133-146 (2016).
Morton et al. Establishment of human tumor xenografts in immunodeficient mice. Nat Procol 2:247 (2007).
Mosquera et al. In vitro and in vivo characterization of a novel antibody-like single-chain TCR human IgG1 fusion protein. J Immunol 174(7):4381-4388 (2005).
Moynihan et al. Eradication of large established tumors in mice by combination immunotherapy that engages innate and adaptive immune responses. Nat Med 12(22):1402-1410 (2016).
Mumtaz et al. Design of liposomes for circumventing the reticuloendothelial cells. Glycobiology 5:505-10 (1991).
Nacheva et al. Preventing nondesired RNA-primed RNA extension catalyzed by T7 RNA polymerase. Eur J Biochem 270:1458-1465 (2003).
Nakanishi et al. Overexpression of B7-H1 (PD-L1) significantly associates with tumor grade and postoperative prognosis in human urothelial cancers. Cancer Immunol Immunother. 56(8):1173-1182 (2007).
Needleman et al. A general method applicable to the search for similarities in the amino acid sequence of two proteins. J. Mol. Biol. 48:443-453 (1970).
Newick et al. Chimeric antigen receptor T-cell therapy for solid tumors. Molecular Therapy—Oncolytics 3:16006 (2016).
Nicholson et al. Construction and characterisation of a functional CD19 specific single chain Fv fragment for immunotherapy of B lineage leukaemia and lymphoma. Mol Immun 34(16-17):1157-1165 (1997).
Nimmerjahn et al. FcγRIV: a Novel FcR with Distinct IgG Subclass Specificity. Immunity 23(1):41-51 (2005).
Nishikawa et al. Nonviral vectors in the new millennium: delivery barriers in gene transfer. Human Gene Therapy. 12:861-870 (2001).
Nolan et al. Bypassing immunization: optimized design of "designer" T cells" against carcinoembryonic antigen (CEA)-expressing tumors, and lack of suppression by soluble CEA. Clin Cancer Res 5:3928-3941 (1999).
Novak et al. Expression of BLyS and its receptors in B-cell non-Hodgkin lymphoma: correlation with disease activity and patient outcome. Blood 104(8):2247-53 (2004).
Novak et al. Expression of BCMA, TACI, and BAFF-R in multiple myeloma: a mechanism for growth and survival. Blood 103(2):689-94 (2004).
NP 000064, human T-cell surface glycoprotein CD3 gamma chain precursor, NCBI, pp. 1-4, May 4, 2019.
NP 000724, human T-cell surface glycoprotein CD3 epsilon chain precursor, NCBI, pp. 1-4, May 4, 2019.
O'Connor et al. BCMA Is Essential for the Survival of Long-lived Bone Marrow Plasma Cells. J Exp Med 199(1):91-8 (2004).
Oden et al. Potent anti-tumor response by targeting B cell maturation antigen (BCMA) in a mouse model of multiple myeloma. Mole Oncol 9(7):1348-1358 (2015).
O'Hare et al. Mesothelin as a target for chimeric antigen receptor-modified T cells as anticancer therapy. Immunotherapy 8(4):449-460 (2016).

(56) References Cited

OTHER PUBLICATIONS

Ohigashi et al. Clinical significance of programmed death-1 ligand-1 and programmed death-1 ligand-2 expression in human esophageal cancer. Clin Cancer Res 11(8):2947-2953 (2005).
Ohtsuka et al. An alternative approach to deoxyoligonucleotides as hybridization probes by insertion of Deoxyinosine at Ambiguous Codon Positions. J Biol Chem 260(5):2605-2608 (Mar. 10, 1985).
Onda et al. Megakaryocyte potentiation factor cleaved from mesothelin precursor is a useful tumor marker in the serum of patients with mesothelioma. Clin Cancer Res. 12:4225-4231 (2006).
Onda et al. New Monoclonal Antibodies to Mesothelin Useful for Immunohistochemistry, Fluorescence-Activated Cell Sorting, Western Blotting, and ELISA. Clin Cancer Res 11(16):5840-5846 (2005).
Padlan. A possible procedure for reducing the immunogenicity of antibody variable domains while preserving their ligand-binding properties. Mol Immunol 28(4-5):489-498 (1991).
Park et al. Adoptive Immunotherapy for B-cell Malignancies with Autologous Chimeric Antigen Receptor Modified Tumor Targeted T Cells. Disc Med 9(47)277-288 (2010).
Pastan et al. Discovery of Mesothelin and Exploiting It as a Target for Immunotherapy. Cancer Res 74(11):2907-2912 (2014).
Patel et al. Engineering an APRIL-specific B Cell Maturation Antigen. J Bio Chem 279(16):16727-16735 (2004).
Patel et al. PDL-1 Expression as a Predictive Biomarker in cancer Immunotherapy. Mol Cancer Ther 14(4):847-856 (2015).
PCT/US2016/033146 International Preliminary Report on Patentability dated Nov. 30, 2017.
PCT/US2016/033146 International Search Report and Written Opinion dated Oct. 20, 2016.
PCT/US2017/045159 International Search Report and Written Opinion dated Nov. 3, 2017.
PCT/US2017/055628 International Search Report and Written Opinion dated Jan. 24, 2018.
PCT/US2017/063137 International Search Report and Written Opinion dated Jun. 14, 2018.
PCT/US2017/068002 International Search Report and Written Opinion dated Apr. 12, 2018.
PCT/US2018/037387 International Search Report and Written Opinion dated Sep. 17, 2018.
PCT/US2019/021315 International Search Report and Written Opinion dated Jun. 13, 2019.
Pearson, et al. Improved Tools for Biological Sequence Comparison. Proc. Nat'l Acad. Sci. USA. 85 (1988): 2444-48.
Pedersen et al. Comparison of surface accessible residues in human and murine immunoglobulin Fv domains. Implication for humanization of murine antibodies. J Mol Biol 235(3):959-973 (1994).
Philip et al. A highly compact epitope-based marker suicide gene for safer and easier adoptive T-cell gene therapy. Blood 124:1277-1287 (2014).
Poirot et al. Multiplex Genome-Edited T-cell Manufacturing Platform for Off-the-Shelf Adoptive T-cell Immunotherapies. Cancer Research 75(18):3853-3864 (2015).
Porter et al. Chimeric antigen receptor T cells persist and induce sustained remissions in relapsed refractory chronic lymphocytic leukemia. Sci Trans Med 7(303):303ra319 (2015).
Porter et al. Chimeric antigen receptor-modified T cells in chronic lymphoid leukemia. NEJM 365:725-733 (2011).
Porter et al. Pilot study of redirected autologous t cells engineered to contain anti-CD19 attached to TCRZ and 4-1BB signaling domains in patients with chemotherapy resistant or refractory CD19+ leukemia and lymphoma. NCT02374333. Available at https://www.clinicaltrials.gov/ct2/show/NCT02374333?term=13BT022 (3 pgs.) (2016).
Posey et al. Engineered CAR T Cells Targeting the Cancer-Associated Tn-Glycoform of the MembraneMucinMUC1 Control Adenocarcinoma. Immunity 44:1444-1454 (2016).
Presta. Antibody Engineering. Curr Op Struct Biol 2:593-596 (1992).
Presta et al. Humanization of an antibody directed against IgE. J Immunol 151:2623-2632 (1993).
Pule et al. A chimeric T cell antigen receptor that augments cytokine release and supports clonal expansion of primary human T cells. Mol Ther 12(5):933-941 (2005).
Punt et al. Stoichiometry of the T cell antigen receptor (TCR) complex: each TCR/CD3 complex contains one TCR alpha, one TCR beta, and two CD3 epsilon chains. J Exp Med 180(2):587-593 (1994).
Riechmann et al. Reshaping human antibodies for therapy. Nature, 332.6162 (1988): 323-7.
Rivadeneira et al. Antitumor T cell reconditioning: improving metabolic fitness for optimal cancer immunotherapy. Clin Cancer Res 24(11):2473-2481 (2018).
Rodgers et al. Switch-mediated activation and retargeting of CAR-T cells for B-cell malignancies. PNAS USA 113(4):E459-E468 (2016).
Roguska et al. A comparison of two murine monoclonal antibodies humanized by CDR-grafting and variable domain resurfacing. Protein Eng 9(10):895-904 (1996).
Roguska et al. Humanization of murine monoclonal antibodies through variable domain resurfacing. PNAS 91:969-973 (1994).
Rosenberg. Cell transfer immunotherapy for metastatic solid cancer—what clinicians need to know. Nat Rev Clin Oncol 8(10):577-585 (2011).
Rosenberg et al. Adoptive cell transfer as personalized immunotherapy for human cancer. Science 348(6230):62-68 (2015).
Rosenberg et al. Durable complete responses in heavily pretreated patients with metastatic melanoma using T-cell transfer immunotherapy. Clin Cancer Res 17(13):4550-4557 (2011).
Rosenberg et al. Use of tumor-infiltrating lymphocytes and interleukin-2 in the immunotherapy of patients with metastatic melanoma. A preliminary report. NEJM 319:1676 (1988).
Rossolini et al. Use of deoxyinosine-containing primers vs degenerate primers for polymerase chain reaction based on ambiguous sequence information. Mol Cell Probes 8(2):91-98 (1994).
Roybal et al. Precision Tumor Recognition by T Cells With Combinatorial Antigen-Sensing Circuits. Cell 164:1-10 (2016).
Ruella et al. Smart CARS: optimized development of a chimeric antigen receptor (CAR) T cell targeting epidermal growth factor receptor variant III (EGFRvIII) for glioblastoma. Ann Transl Med 4(1):13 (2016).
Rump et al. Binding of ovarian cancer antigen CA125/MUC16 to mesothelin mediates cell adhesion. J Biol Chem 279:9190-9198 (2004).
Rushworth et al. Universal Artificial Antigen Presenting Cells to Selectively Propagate T Cells Expressing Chimeric Antigen Receptor Independent of Specificity. J Immunother 37(4):204-213 (2014).
Sadelain. CAR therapy: The CD19 paradigm. J Clin Invest 135(9):3392-3400 (2015).
Sadelain et al. Tales of Antigen Evasion from CAR Therapy. Cancer Immunol Res 4(6):473 (2016).
Sadelain et al. The Basic Principles of Chimeric Antigen Receptor Design. Cancer Discov 3(4):388-398 (2013).
Sadelain et al. Therapeutic T cell engineering. Nature 545:423-431 (2017).
Sakemura et al. A Tet-On Inducible System for Controlling CD19-Chimeric Antigen Receptor Expression upon Drug Administration. Cancer Immunol Res 4(8):658-668 (2016).
Sander et al. CRISPR-Cas systems for editing, regulating and targeting genomes. Nat. Biotechnol 32:347-355 (2014).
Sandhu. A rapid procedure for the humanization of monoclonal antibodies. Gene 150(2):409-410 (1994).
Sapede et al. Aberrant splicing and protease involvement in mesothelin release from epithelioid mesothelioma cells. Cancer Sci 99(3):590-594 (2008).
Schenborn et al. A novel transcription property of SP6 and T7 RNA polymerases: dependence on template structure. Nuc Acids Res 13:6223-6236 (1985).
Servais et al. An In Vivo Platform for Tumor Biomarker Assessment. PloS One 6(10):e26772.
Sharpe et al. Genetically modified T cells in cancer therapy: opportunities and challenges. Dis Model Mech 8(4):337-350 (2015).
Shimabukuro-Vornhagen et al. Cytokine release syndrome. J Immunother Cancer 6:56 (2018).

(56) References Cited

OTHER PUBLICATIONS

Shin et al. Positive conversion of negative signaling of CTLA4 potentiates antitumor efficacy of adoptive T-cell therapy in murine tumor models. Blood 119(24):5678-5687 (2012).
Simon et al. PD-1 expression conditions T cell avidity within an antigen-specific repertoire. Oncoimmunology 5(1):e1104448 (2015).
Sims et al. A humanized CD18 antibody can block function without cell destruction. J Immunol., 151 (1993): 2296-2308.
Smith, et al. Comparison of Biosequences. Advances in Applied Mathematics. 1981;2: 482-489.
Sommermeyer et al. Designer T cells by T cell receptor replacement. Eur J Immunol 36(11):3052-3059 (2006).
Sommers et al. Function of CD3ε-mediated Signals in T Cell Development. J Exper Med 192(6):913-920 (2000).
Song et al. CD27 costimulation augments the survival and antitumor activity of redirected human T cells in vivo. Blood 119(3):696-706 (2012).
Song et al. In Vivo Persistence, Tumor Localization, and Antitumor Activity of CAR-Engineered T Cells Is Enhanced by Costimulatory Signaling through CD137 (4-1BB). Cancer Res 71(13):4617-4627 (2011).
Spear et al. Collaboration of chimeric antigen receptor (CAR)-expressing T cells and host T cells for optimal elimination of established ovarian tumors. Oncoimmunology 2(4):e23564 (2013).
Spear et al. NKG2D ligands as therapeutic targets. Cancer Immunity 13:8 (2013).
Srivastava et al. Engineering CAR-T cells: Design concepts. Trends Immunol 36(8):494-502 (2015).
Stepinski et al. Synthesis and properties of mRNAs containing the novel 'anti-reverse' cap analogs 7-methyl(3'0-methyl)GpppG and 7-methyl(e'-deoxy)GpppG. RNA 7:1486-1495 (2001).
Stone et al. A novel T cell receptor single-chain signaling complex mediates antigen-specific T cell activity and tumor control. Cancer Immunol Immunother 63(11):1163-1176 (2014).
Stromnes et al. T Cells Engineered against a Native Antigen Can Surmount Immunologic and Physical Barriers to Treat Pancreatic Ductal Adenocarcinoma. Cancer Cell 28:638-652 (2015).
Studnicka et al. Human-engineered monoclonal antibodies retain full specific binding activity by preserving non-CDR complementarity-modulating residues. Pro Eng 7(6):805-814 (1994).
Sun et al. The quest for spatio-temporal control of CAR T cells. Cell Res 25(12):1281-1282 (2015).
Tan et al. "Superhumanized" antibodies: reduction of immunogenic potential by complementarity-determining region grafting with human germline sequences: application to an anti-CD28. J Immunol 169:1119-1125 (2002).
Tang et al. A human single-domain antibody elicits potent antitumor activity by targeting an epitope in mesothelin close to the cancer cell surface. Mol. Cancer Thera 12(4):416-426 (2013).
Tanyi et al. Possible Compartmental Cytokine Release Syndrome in a Patient With Recurrent Ovarian Cancer After Treatment With Mesothelin-targeted CAR-T Cells. J Immunother 40(3):104-107 (2017).
Tchou et al. Safety and efficacy of intratumoral injections of chimeric antigen receptor (CAR) T cells in metastatic breast cancer. Cancer Immunol Res 5(12):1152-1161 (2017).
TCR2 Therapeutics Presents Positive Solid Tumor Data for its Novel TRUC ™ Engineered T Cell Therapies at the World Preclinical Congress. PRNewswire. Available at http://www.prnewswire.com/news-releases/tcr2-therapeutics-presents-positive-solid-tumor-data-for-its-novel-truc-engineered-t-cell-therapies-at-the-world-preclinical-congress-300472629.html (Jun. 13, 2017) (2 pgs.).
Teachey. Identification of Predictive Biomarkers for Cytokine Release Syndrome after Chimeric Antigen Receptor T cell Therapy for Acute Lymphoblastic Leukemia. Cancer Disc 6(6):664-679 (2016).
Ten Berg et al. Selective expansion of a peripheral blood CD8+ memory T cell subset expressing both granzyme B and L-selectin during primary viral infection in renal allograft recipients. Transplant Proc 30(8):3975-3977 (1998).
Themeli et al. Generation of tumor-targeted human T lymphocytes from induced pluripotent stem cells for cancer therapy. Nat Biotech 31:928-933 (2013).
Themeli et al. New cell sources for T cell engineering and adoptive immunotherapy. Cell Stem Cell 16(4):357-366 (2015).
Thokala et al. Redirecting Specificity of T cells Using the Sleeping Beauty System to Express Chimeric Antigen Receptors by Mix-and-Matching of VL and VH Domains Targeting CD123+ Tumors. PLoS One 11(8):e0159477 (2016).
Thompson et al. Costimulatory molecule B7-H1 in primary and metastatic clear cell renal cell carcinoma. Cancer 104(10):2084-2091 (2005).
Topalian et al. Safety, Activity, and Immune Correlates of Anti-PD-1 Antibody in Cancer. N Engl J Med 366:2443-2454 (2012).
Torikai et al. A foundation for universal T-cell based immunotherapy: T cells engineered to express a CD19-specific chimeric-antigen-receptor and eliminate expression of endogenous TCR. Blood 119(24):5697-5705 (2012).
Torikai et al. Translational Implications for Off-the-shelf Immune Cells Expressing Chimeric Antigen Receptors. Mol Ther 24(7):1178-1186 (2016).
Tran et al. Cancer Immunotherapy Based on Mutation-Specific CD4+ T Cells in a Patient with Epithelial Cancer. Science 9:641-645 (2014).
Tsai et al. Producer T cells: Using genetically engineered T cells as vehicles to generate and deliver therapeutics to tumors. Oncoimmunol 5(5):e1122158 (2016).
Tumaini et al. Simplified process for the production of anti-CD19-CAR engineered T cells. Cytotherapy 15(11):1406-1415 (2014).
Turtle et al. CD19 CAR-T cells of defined CD4+:CD8+ composition in adult B cell ALL patients. J Clin Invest 126(6):2123-2138 (2016).
Ui-Tei et al. Sensitive assay of RNA interference in Drosophila and Chinese hamster cultured cells using firefly luciferase gene as target. FEBS Letters 479: 79-82 (2000).
Urnov et al. Genome editing with engineered zinc finger nucleases. Nature Reviews Genetics 11:636-646 (2010).
U.S. Appl. No. 15/419,398 1st Action Interview dated Jul. 3, 2017.
U.S. Appl. No. 15/419,398 Office Action dated Jul. 17, 2019.
U.S. Appl. No. 15/419,398 Office Action dated Mar. 7, 2018.
U.S. Appl. No. 15/419,398 Office Action dated May 24, 2019.
U.S. Appl. No. 15/419,398 Office Action dated Nov. 9, 2017.
U.S. Appl. No. 15/965,738 Preinterview First Action dated Nov. 15, 2018.
U.S. Appl. No. 15/965,739 Preinterview First Action dated Nov. 15, 2018.
Usui et al. Expression of costimulatory molecules on human retinoblastoma cells Y-79: functional expression of CD40 and B7H1. Invest Ophthalmol Vis Sci. 47(10):4607-4613 (2006).
Valton et al. A Multidrug-resistant Engineered CAR T Cell for Allogeneic Combination Immunotherapy. Mol Ther 23(9):1507-1518 (2015).
Van Der Stegen et al. The pharmacology of second-generation chimeric antigen receptors. Nat Rev Drug Discov 14(7):499-509 (2015).
Vanseggelen et al. T Cells Engineered With Chimeric Antigen Receptors Targeting NKG2D Ligands Display Lethal Toxicity in Mice. Molecular Therapy 23(10):1600-1610 (2015).
Velasquez. T cells expressing CD19-specific Engager Molecules for the Immunotherapy of CD19-positive Malignancies. Sci Rep 6:27130 (2016).
Verhoeyen et al. Reshaping human antibodies: grafting an antilysozyme activity. Science 239:1534-1536 (1988).
Vermeire et al. Signal peptide-binding drug as a selective inhibitor of co-translational protein translocation. PLoS Biol 12(12):e1002011 (2014).
Wang et al. Generation of Potent T-cell Immunotherapy for Cancer Using DAP12-Based, Multichain, Chimeric Immunoreceptors. Cancer Immunol Res 3(7):815-826 (2015).
Wang et al. Manufacture of tumor- and virus-specific T lymphocytes for adoptive cell therapies. Cancer Gene Therapy 22(2):85-94 (2015).

(56) References Cited

OTHER PUBLICATIONS

Wang et al. VISTA, a novel mouse Ig superfamily ligand that negatively regulates T cell responses. J Exp Med 208(3):577-592 (2011).
Watanabe et al. Fine-tuning the CAR spacer improves T-cell potency. Oncoimmunology. 5(2):e1253656 (2016).
Weekes et al. Phase I Study of DMOT4039A, an Antibody-Drug Conjugate Targeting Mesothelin, in Patients with Unresectable Pancreatic or Platinum-Resistant Ovarian Cancer. Mol Cancer Ther 15(3):439-447 (2016).
Wegener et al. The T cell receptor/CD3 complex is composed of at least two autonomous transduction modules. Cell 68:83-95 (1992).
Whittington et al. Accounting for All Costs in the Total Cost of Chimeric Antigen Receptor T-Cell Immunotherapy. JAMA Oncol. Published online Oct. 11, 2018 (1 pg.).
Wilkie et al. Selective Expansion of Chimeric Antigen Receptor-targeted T-cells with Potent Effector Function using Interleukin-4. J Biol Chem 285(33):25538-25544 (2010).
Wintterle et al. Expression of the B7-related molecule B7-H1 by glioma cells: a potential mechanism of immune paralysis. Cancer Res. 63(21):7462-7467 (2003).
Wu et al. Protein design of IgG/TCR chimeras for the co-expression of Fab-like moieties within bispecific antibodies. MABS 7(2):364-376 (2015).
Wucherpfennig et al. Structural Biology of the T-cell Receptor: Insights into Receptor Assembly, Ligand Recognition, and Initiation of Signaling. Cold Spring Harb Perspect Biol 2(4):a005140 (2010).
Xerri et al. Programmed death 1 is a marker of angioimmunoblastic T-cell lymphoma and B-cell small lymphocytic lymphoma/chronic lymphocytic leukemia. Hum Pathol. 39(7):1050-1058 (2008).
Xu et al. The basics of CAR T design and challenges in immunotherapy of solid tumors—Ovarian cancer as a model. Hum Vaccin Immunother 13(7):1548-1555 (2017).
Yamamoto et al. PD-1-PD-1 ligand interaction contributes to immunosuppressive microenvironment of Hodgkin lymphoma. Blood 111(6):3220-3224 (2008).
Ye et al. Interaction of B7-H1 on intrahepatic cholangiocarcinoma cells with PD-1 on tumor-infiltrating T cells as a mechanism of immune evasion. J Surg Oncol. 100(6):500-504 (2009).
Yokosuka et al. Programmed cell death 1 forms negative costimulatory microclusters that directly inhibit T cell receptor signaling by recruiting phosphatase SHP2. J Exp Med 209(6):1201-1217 (2012).
Yu et al. Wnt5a induces ROR1/ROR2 heterooligomerization to enhance leukemia chemotaxis and proliferation. J Clin Invest 126(2):585-98 (2016).
Yun et al. Targeting of T Lymphocytes to Melanoma Cells Through Chimeric Anti-GD3 Immunoglobulin T-Cell Receptors. Neoplasia 2(5):449-459 (2000).
Zah et al. T cells expressing CD19/CD20 bi-specific chimeric antigen receptors prevent antigen escape by malignant B cells. Cancer Immunol Res 4(6)498-509 (2016).
Zhang et al. 4-1BB is superior to CD28 costimulation for generating CD8+ cytotoxic lymphocytes for adoptive immunotherapy. J Immunol 179:4910-4918 (2007).
Zhang et al. New High Affinity Monoclonal Antibodies Recognize Non-Overlapping Epitopes on Mesothelin for Monitoring and Treating Mesothelioma. Sci Rep 5:9928 (2015).
Zhang et al. Phase I Escalating-Dose Trial of CAR-T Therapy Targeting CEA+ Metastatic Colorectal Cancers. Mol Ther 25:1248-1258 (2017).
Zhang et al. The onco-embryonic antigen ROR1 is expressed by a variety of human cancers. Am J Path 181(6):1903-1910 (2012).
Zhao et al. A herceptin-based chimeric antigen receptor with modified signaling domains leads to enhanced survival of transduced T lymphocytes and antitumor activity. J Immunol 183:5563-5574 (2009).
Zhao et al. Multiple injections of electroporated autologous T cells expressing a chimeric antigen receptor mediate regression of human disseminated tumor. Cancer Res 70(22):9053-9061 w/Supplemental Information (2010).
Zhao et al. Structural Design of Engineered Costimulation Determines Tumor Rejection Kinetics and Persistence of CAR T cells. Cancer Cell 28(4):415-428 (2015).
Zhou et al. Exclusive Transduction of Human CD4+ T Cells upon Systemic Delivery of CD4-Targeted Lentiviral Vectors. J Immunol 195:2493-2501 (2015).
Pipeline. A Broad Pipeline of T Cell Therapies for Solid and Hematologi Cancers. TCR2 Therapeutics. Available at https://www.tcr2.com/pipeline (Accessed Apr. 15, 2020) (5 pgs).
Rafiq et al. Targeted delivery of a PD-1-blocking scFv by CAR-T cells enhances anti-tumor efficacy in vivo. Nat Biotechnol 36(9):847-856 (2018).
Adams et al., Big Opportunities for small molecules in immuno-oncology. Nature Reviews 14:614-622 (2015).
Adomako, et al., Identification of markers that functionally define a quiescent multiple myeloma cell sub-population surviving bortezomib treatment. BMC Cancer 15:44 (2015).
Altenschmidt et al., Cytolysis of Tumor Cells Expressing the Neu/erbB-2, erbB-3, and erbB-4 Receptors by Genetically Targeted Naïve T Lymphocytes. Clinical Cancer Research 2:1001-1008 (1996).
An, et al., Construction of a new anti-CD19 chimeric antigen receptor and the anti-leukemia function study of the transduced T cells. Oncotarget 7(9):10638-10649 (2016).
Andersen, et al., Lag-3, Tim-3, and TIGIT: Co-inhibitory Receptors with Specialized Functions in Immune Regulations. Immunity 44:989-1004 (2016).
Arasanz et al. PD1 signal transduction pathways in T cells. Oncotarget 8:51936-51945 (2017).
Ausubel, et al., Production of CGMP-Grade Lentiviral Vectors BioProcess International 10(2):32-48 (2012).
Azuma et al. B70 antigen is a second ligand for CTLA-4 and CD28. Nature 366:76-79 (1993).
Baeuerle et al. Synthetic TRUC receptors engaging the complete T cell Receptor for potent anti-tumor response. Nat Commun 10:2087 (2019).
Baitsch, et al., Exhaustion of tumor-specific CD8+ T cells in metastases from melanoma patients. J Clin Invest 121(6):2350-2360 (2011).
Batlevi, et al., Novel immunotherapies in lymphoid malignancies. Nat Rev Clin Onocl 13:25-40 (2015).
Beatty, et al., Chimeric antigen receptor-modified T cells for the treatment of solid tumors: Defining the challenges and next steps. Pharmacology & Therapeutics 166:30-39 (2016).
Better, et al., Manufacturing and Characterization of KTE-C19 in a Multicenter trial of Subjects with Refractory Aggressive Non-Hodgkin Lymphoma (NHL) (ZUMA-1) AACR Poster (Abstract 2308) (2016).
Bettini, et al., Cutting Edge: CD3 ITAM Diversity Is Required for Optimal TCR Signaling and Thymocyte Development. J Immunol 199:1555-1560 (2017).
Budhu, et al., The importance of animal models in tumor immunity and immunotherapy. Curr Opin Genet Dev. 24:46-51 (2014).
Cavalieri, et al., Human T lymphocytes transduced by lentiviral vectors in the absence of TCR activation maintain an intact immune competence. Blood 102(2):497-505 (2003).
Chen et al. Fusion protein linkers: Property, design and functionality. Advanced Drug Delivery Reviews 65:1357-1369 (2013).
Chylek, et al., Phosphorylation Site Dynamics of Early T-cell Receptor Signaling. PLOS One 9(8):e104240 (2014).
Dennehy et al. Cutting Edge: Monovalency of CD28 Maintains the Antigen Dependence of T Cell Costimulatory Responses. J Immunol 176(10):5725-5759 (2006).
Ding et al. Abstract 2307: Preclinical evaluation of TC-210, a mesothelin-specific T cell receptor (TCR) fusion construct (TRUC ™) T cells for the treatment of solid tumors. Cancer Res 79(Supp 13) (2019).
Ding et al. Abstract 3589: Preclinical evaluation of mesothelin-specific T cell receptor (TCR) fusion constructs (TRUC ™s) utilizing the signaling power of the complete TCR complex: A new opportunity for solid tumor therapy. Cancer Res 78(Supp 13):3589 (2018).

(56) References Cited

OTHER PUBLICATIONS

Draper, et al., Targeting of HPV-16+ Epithelial Cancer Cells by TCR Gene Engineered T Cells Directed against E6. Clin Cancer Res 21:4431-4440 (2015).
Dull et al. A third-generation lentivirus vector with a conditional packaging system. J Virol 72:8463-8471 (1998).
Esensten et al. CD28 Costimulation: From Mechanism to Therapy. Immunity 44:973-988 (2016).
Eshhar, et al., Specific activation and targeting of cytotoxic lymphocytes through chimeric single chains consisting of antibody-binding domains and the y or s subunits of the immunoglobulin and T-cell receptors. PNAS USA 90:720-724 (1993).
Fielding, et al., Outcome of 609 adults after relapse of acute lymphoblastic leukemia (ALL); an MRC UKALL12/ECOG 2993 study. Blood 109(3):944-951 (2007).
Fife et al. Control of peripheral T-cell tolerance and autoimmunity via the CTLA-4 and PD-1 pathways. Immunol Rev 224:166-182 (2008).
Finer, et al., A High-Efficiency Retroviral Transduction System for Primary Human T Lymphocytes. Blood 83(1):43-50 (1994).
Fraietta et al., Disruption of TET2 promotes the therapeutic efficacy of CD19-targeted T cells. Nature 558: 307-312 (2018).
Frigault, et al., Identification of Chimeric Antigen Receptors That Mediate Consitutive or Inducible Proliferation of T cells. Cancer Immunol Res 3(4):356-67 (2015).
Fu, et al., A Simple and Sensitive Method for Measuring Tumor-Specific T Cell Cytotoxicity. PLoS One 5(7):e11867 (2010).
Gattinoni, et al. A Human memory T cell subset with stem cell-like properties. Nat Med 17(10):1290-1298 (2011).
Gattinoni, et al., Moving T memory stem cells to the clinic. Blood 121(4):567-569 (2013).
Gattinoni, et al., T memory stem cells in health and disease. Nat Med 23(1):18-27 (2017).
Gaud, et al., Regulatory mechanisms in T cell receptor signalling. Nat Rev Immunol 18:485-497 (2018).
Gentles et al., The prognostic landscape of genes and infiltrating immune cells across human cancers, Nature Medicine, 21(8): 938-945 (2015).
Geraerts, et al., Comparison of lentiviral vector titration methods. BMC Biotechnology 6:34 (2006).
Guo, et al., Chimeric Antigen Receptor-Modified T Cells for Solid Tumors: Challenges and Prospects. J Immunol Res 2016:3850839 (2016).
Haas, et al., Phase I study of lentiviral-transduced chimeric antigen receptor modified T cells recognizing mesothelin in advanced solid cancers. Mol Ther 27(11):1919-1929 (2019).
Haks, et al., A Redundant Role of the CD3γ- Immunoreceptor Tyrosine-Based Activation Motif in Mature T Cell Function. J Immunol 166(4):2576-2588 (2001).
Hammill, et al., Viral Engineering of Chimeric Antigen Receptor Expression on Murine and Human T Lymphocytes. Method Mol Biol 1458:137-157 (2016).
Hardy, et al., Implications of T cell receptor biology on the development of new T cell therapies for cancer. Immunotherapy 12(1):89-103 (2020).
Hay, et al., Kinetics and Biomarkers of Severe Cytokine Release Syndrome after CD19 Chimeric Antigen Receptor-Modified T Cell Therapy. Blood 130(21):2295-2306 (2017).
Hayes, et al., Distinct Structure and Signaling Potential of the TCR Complex. Immunity 16:827-838 (2002).
Helsen, et al., Tri-functional t cell Receptor antigen coupler (TriTAC): a novel method to direct T cells against tumors. Journal for ImmunoTherapy of Cancer 2(Suppl 3):1-1 (2014).
Holehonnur, et al., The production of viral vectors designed to express large and difficult to express transgenes within neurons. Mol Brain 8:12 (2015).
Huehls, et al., Bispecific T-cell engagers for cancer immunotherapy. Immunol Cell Biol 93:290-296 (2015).
Hui et al. T cell costimulatory receptor CD28 is a primary target for PD-1-mediated inhibition. Science 355:1428-1433 (2017).
Humpries. Adoptive cell therapy: Honing that killer instinct. Nature 504(7480):S13-5 (2013).
Hunter et al. Combinatorial proteomic analysis of intercellular signaling applied to the CD28 T-cell costimulatory receptor. PNAS USA 112:E1594-1603 (2015).
Hwang, et al., TCR ITAM multiplicity is required for the generation of follicular helper T-cells. Nature 6:6982 (2015).
Inoue, et al., High-Fidelity Correction of Mutations at Multiple Chromosomal Positions by Adeno-Associated Virus Vectors. J Virol 73(9):7376-7380 (1999).
Juillerat, et al., Design and analysis of stably integrated reporters for inducible transgene expression in human T cells and CAR NK-cell lines. Nature 12(Suppl 2):44 (2015).
June. Remote Controlled CARS: Towards a Safer Therapy for Leukemia. Cancer Immunol Res 4(8):643 (2016).
Kaufman, et al., Oncolytic viruses: a new class of immunotherapy drugs. Nature 14:642-663 (2015).
Khan, et al., Engineering of Human Pluripotent Stem Cells by AAV-mediated Gene Targeting. Mol Ther 18(6):1192-1199 (2010).
Kim, et al., High Cleavage Efficiency of a 2A Peptide Derived from Porcine Teschovirus-1 in Human Cell Lines, Zebrafish and Mice. PLoS One 6(4):e18556 (2011).
Labri, et al., From Truly Naïve to Exhausted Senescent T Cells: When Markers Predict Functionality. Cytometry Part A 85(1):25-35 (2014).
Lamer, et al., Treatment of metastatic renal cell carcinoma (mRCC) with CAIX CAR-engineered T-cells-a completed study overview. Biochem Soc Trans 44(3):951-959 (2016).
Lantis, et al., Redirected Antitumor Activity of Primary Human Lymphocytes Transduced With a Fully Human Anti-mesothelin Chimeric Receptor. Mol Ther 20(3):633-643 (2012).
Leddon et al. The CD28 Transmembrane Domain Contains an Essential Dimerization Motif. Front Immunol 2020; 11:1519 (2020).
Legat, et al., Inhibitory receptor expression depends more dominantly on differentiation and activation than exhaustion of human CD8 T cells. Front Immunol 4:455 (2013).
Lesch et al. PD-1-CD28 fusion protein strengthens mesothelin-specific TRuC T cells in preclinical solid tumor models. Cell Oncol (Dordr) PMID: 36409438 (2022).
Lu, et al., Treatment of Patients with Metastatic Cancer Using a Major Histocompatibility Complex Class II-Restricted T-Cell Receptor Targeting the Cancer Germline Antigen MAGE-A3. J Clin Oncel 35(29):3322-3329 (2017).
Mahmoudjafari, et al., American Society for Blood and Marrow Transplantation Pharmacy Special Interest Group Survey on CAR T Cell Therapy Administrative, Logistical and Toxicity Management Practices in the United States. Biology of Blood and Marrow Transplantation. Cell Ther 25(1):P26-33 (2018).
Majzner, et al., Clinical lessons learned from the first leg of the CAR T cell journey. Nat Med 25:1341-1355 (2019).
Malissen, et al., Early T Cell Activation: Integrating Biochemical, Structural, and Biophysical Cues Annu. Rev. Immunol. 33:539-561 (2015).
Mardiros, et al., Acute myeloid leukemia therapeutics CARs in the driver's seat. Oncolmmunology 2(12):e27214 (2013).
Maude, et al., Chimeric Antigen Receptor T Cells for Sustained Remissions in Leukemia. N. Engl J. Med (2014) 371(16) 1507-1517. With correction published N. Engl J. Med 374(10):998 (2016).
Maude, et al., Managing Cytokine Release Syndrome Associated with Novel T Cell-Engaging Therapies. Cancer J. 20(2):119-122 (2014).
Motz, et al., Deciphering and Reversing Tumor Immune Suppression. Immunity 39:61-73 (2013).
Mueller, et al., Cellular kinetics of CTL019 in relapsed/refractory B-cell acute lymphoblastic leukemia and chronic lymphocytic leukemia. Blood 130(21):2317-2325 (2017).
Okkenhaug et al. Grb2 forms an inducible protein complex with CD28 through a Src homology 3 domain-proline interaction. J Biol Chem 273:21194-21202 (1998).
Ordonez. Application of mesothelin immunostaining in tumor diagnosis. Am J Surg Pathol 27:1418-1428 (2003).

(56) References Cited

OTHER PUBLICATIONS

Park, et al., Adoptive Transfer of Chimeric Antigen Receptor Re-directed Cytolytic T Lymphocyte Clones in Patients with Neuroblastoma. Mol Ther 15(4):825-833 (2007).
Pitts, et al., Resistance Mechanisms to Immune-Checkpoint Blockade in Cancer: Tumor-Intrinsic and -Extrinsic Factors. Immunity 44:1255-1269 (2016).
Pranter, et al., Anti-Mesothelin Nanobodies for Both Conventional and Nanoparticle-Based Biomedical Applications. J Bio Nanotechnol 11:1201-1212 (2015).
Prosser et al. Mechanistic Studies of PD-1 Signaling in the Conversion of Effector T Cells to Functional Exhaustion. Abstract 565. Mol Ther 17(Supp 1):S216 (2009).
Prosser et al. Tumor PD-L1 co-stimulates primary human CD8(+) cytotoxic T cells modified to express a PD1:CD28 chimeric receptor. Mol Immunol 51(3-4):263-272 (2012).
Prosser, Megan E. Development of Genetic Engineering Platforms to Protect T Cells Against Functional Exhaustion. Dissertation. Irell and Maella Graduate School of Biological Sciences of City of Hope Duarte, CA (2011).
Pule, et al., Artificial T-cell receptors. Cytotherapy 5(3):211-26 (2003).
Qasim, et al., Progress and prospects for engineered T cell therapies. Br J Haematol 166:818-829 (2014).
Radcliff, et al., Multiple gene products from a single vector: 'self-cleaving' 2A peptides. Gene Ther 11:1673-1674 (2004).
Rafiq, et al., Engineering strategies to overcome the current roadblocks in CAR T cell therapy. Nat Rev Clin Oncol 17(3):147-167 (2019).
Riches, et al., T cells from CLL patients exhibit features of T-cell exhaustion but retain capacity for cytokine production. Blood 121(9):1612-1622 (2013).
Riolobos, et al., HLA Engineering of Human Pluripotent Stem Cells. Mol Ther 21(6):1232-1241 (2013).
Rohrs et al. ERK Activation in CAR T Cells Is Amplified by CD28-Mediated Increase in CD3zeta Phosphorylation. iScience 23:101023 (2020).
Rossy, et al., The integration of signaling and the spatial organization of the T cell synapse. Front Immunol 3:352 (2012).
Sabbagh, et al., ERK-Dependent Bim Modulation Downstream of the 4-1BB-TRAF1 Signaling Axis Is a Critical Mediator of CD8 T Cell Survival In Vivo. J Immunol 180:8093-8101 (2008).
Savoldo, et al., CD28 costimulation improves expansion and persistence of chimeric antigen receptor-modified T cells in lymphoma patients. J Clin Invest 121:1822-1826 (2011).
Schambach, et al., Biosafety Features of Lentiviral Vectors. Human Gene Therapy 24:132-142 (2013).
Schamel, et al., Coexistence of multivalent and monovalent TCRs explains high sensitivity and wide range of response. JEM 202(4):493-503 (2005).
Scheper, et al., Low and variable tumor reactivity of the intratumoral TCR repertoire in human cancers. Nature Medicine 25:89-94 (2019).
Schumacher, et al., T-Cell-Receptor Gene Therapy. Nature 2:512-519 (2002).
Shultz, et al., Humanized mice in translational biomedical research. Nature 7:118-130 (2007).
Soltes, et al. A new helper phage and phagemid vector system improves viral display of antibody Fab fragments and avoids propagation of insert-less voropms. J Immunol Meth 274:233-244 (2003).
Sommermeyer, et al., Chimeric antigen receptor-modified T cells derived from defined CD8+ and CD4+ subsets confer superior antitumor reactivity in vivo. Leukemia 30(2):492-500 (2016).
Stone, et al., A sensitivity scale for targeting T cells with chimeric antigen receptors (CARs) and bispecific T-cell engagers (BITEs). OncoImmunology 1(6):863-873 (2012).
Swamy, et al., A Cholesterol-Based Allostery Model of T Cell Receptor Phosphorylation. Immunity 44:1091-1101 (2016).
Szymczak, et al., Correction of multi-gene deficiency in vivo using a single 'self-cleaving' 2A peptide-based retroviral vector. Nat Biotechnol 22(5):589-594 (2004).
U.S. Appl. No. 16/436,110 Office Action dated Jul. 15, 2022.
U.S. Appl. No. 16/472,751 Office Action dated Aug. 11, 2022.
Verma et al., TCR Mimic Monoclonal Antibody Targets a Specific Peptide/HLA Class I Complex and Significantly Impedes Tumor Growth In Vivo Using Breast Cancer Model. J Immunol 184:2156-2165 (2010).
Wang, et al., 2A self-cleaving peptide-based multi-gene expression system in the silkworm Bombyx mori. Nature 5:16273 (2015).
Wittman, et al., Antibody Targeting to a Class I MHC-Peptide Epitope Promotes Tumor Cell Death. J Immunol 177:4187-4195 (2006).
Yang, et al., TCR engagement negatively affects CD8 but CD4 CAR T cell expansion and leukemic clearance. Sci Transl Med 9(417):eaag1209 (2017).
Yao, et al., Advances in targeting cell surface signalling molecules for immune modulation. Nat Rev Drug Discov. 12(2):130-146 (2013).
Yu et al. CD28 ligation induces transplantation tolerance by IFN-gamma-dependent depletion of T cells that recognize alloantigens. J Clin Invest 113:1624-1630 (2004).
Yu et al. CD28 signal enhances apoptosis of CD8 T cells after strong TCR ligation. J Immunol 170:3002-3006 (2003).
Zenz. Exhausting T cells in CLL. Blood 121(9):1485-1487 (2013).
Zhang, et al An NKp30-Based Chimeric Antigen Receptor Promotes T cell Effector Functions and Antitumor Efficacy In Vivo. J. Immunol 189(5):2290-2299 (2012).
Zhang, et al., Chimeric NK-receptor-bearing T cells mediate antitumor immunotherapy. Blood 106(5):1544-1552 (2005).
Zhang, et al., Efficiency of CD19 chimeric antigen receptor-modified T cells for treatment of B cell malignancies in phase I clinical trials: a meta-analysis. Oncotarget 6(32):33961 (2015).
Zhang, et al., New High Affinity Monoclonal Antibodies Recognize Non-Overlapping Epitopes on Mesothelin for Montioring and Treating Mesothelioma. Sci Rep 5:9928 (2015).
Zhang, et al., New Strategies for the Treatment of Solid Tumors with CAR-T Cells. Int J Biol Sci 12:718-729 (2016).
Zheng, et al., All Human EFI a Promoters Are Not Equal: Markedly Affect Gene Expression in Constructs from Different Sources. Int J Med Sci 11(5):404-408 (2014).
Co-pending U.S. Appl. No. 18/069,749, inventors Baeuerle; Patrick et al., filed on Dec. 21, 2022.
Goverman et al. Chimeric immunoglobulin-T cell receptor proteins form functional receptors: implications for T cell receptor complex formation and activation. Cell 60(6):929-939 (1990).
Gross et al. Endowing T cells with antibody specificity using chimeric T cell receptors. FASEB J. 6(15):3370-3378 (1992).
U.S. Appl. No. 16/472,751 Office Action dated Apr. 25, 2023.
Koneru et al. IL-12 secreting tumor-targeted chimeric antigen receptor T cells eradicate ovarian tumors in vivo. OncoImmunology 4(3):e994446 (2015).
PCT/US2019/043690 International Search Report and Written Opinion dated Jan. 17, 2020.
Tully et al. The reconstruction of 2,631 draft metagenome-assembled genomes from the global oceans. Sci Data 5:170203 w/Supp. Information (2018).

\* cited by examiner

SEQUENCE LISTING

<160> NUMBER OF SEQ ID NOS: 129

<210> SEQ ID NO 1
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 1

Gly Gly Gly Gly Ser Gly Gly Gly Ser Gly Gly Gly Gly Ser Leu
1               5                   10                  15

Glu

<210> SEQ ID NO 2
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 2

Ala Ala Ala Gly Gly Gly Gly Ser Gly Gly Gly Gly Ser Gly Gly
1               5                   10                  15

Gly Ser Leu Glu
            20

<210> SEQ ID NO 3
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 3

Ala Ala Ala Ile Glu Val Met Tyr Pro Pro Pro Tyr Leu Gly Gly Gly
1               5                   10                  15

Gly Ser Gly Gly Gly Gly Ser Gly Gly Gly Gly Ser Leu Glu
            20                  25                  30

<210> SEQ ID NO 4
<211> LENGTH: 207
<212> TYPE: PRT
<213> ORGANISM: Homo sapiens -continued

```
<400> SEQUENCE: 4

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 5
<211> LENGTH: 182
<212> TYPE: PRT
<213> ORGANISM: Homo sapiens

<400> SEQUENCE: 5

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
130                 135                 140

Ser Arg Ala Ser Asp Lys Gln Thr Leu Leu Pro Asn Asp Gln Leu Tyr
145                 150                 155                 160
```

Gln Pro Leu Lys Asp Arg Glu Asp Gln Tyr Ser His Leu Gln Gly
                165                 170                 175

Asn Gln Leu Arg Arg Asn
            180

<210> SEQ ID NO 6
<211> LENGTH: 172
<212> TYPE: PRT
<213> ORGANISM: Homo sapiens

<400> SEQUENCE: 6

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys Ser
                165                 170

<210> SEQ ID NO 7
<211> LENGTH: 164
<212> TYPE: PRT
<213> ORGANISM: Homo sapiens

<400> SEQUENCE: 7

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 8
<211> LENGTH: 281
<212> TYPE: PRT
<213> ORGANISM: Homo sapiens

<400> SEQUENCE: 8

Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Cys Leu
            35                  40                  45

Val Leu Asp Val Ala Pro Pro Gly Leu Asp Ser Pro Ile Trp Phe Ser
50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
            85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
            115                 120                 125

Ala Ser Thr Ala Arg Thr Cys Pro Gln Glu Pro Leu Arg Gly Thr Pro
130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
            165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
            195                 200                 205

Ser Ser Pro Arg Pro Gln Pro Arg Asp Arg Trp Gly Asp Thr Pro
210                 215                 220

Pro Gly Arg Lys Pro Gly Ser Pro Val Trp Gly Glu Ser Tyr Leu
225                 230                 235                 240

Ser Ser Tyr Pro Thr Cys Pro Ala Gln Ala Trp Cys Ser Arg Ser Ala
            245                 250                 255

Leu Arg Ala Pro Ser Ser Leu Gly Ala Phe Phe Ala Gly Asp Leu
            260                 265                 270

Pro Pro Pro Leu Gln Ala Gly Ala Ala
            275                 280

<210> SEQ ID NO 9
<211> LENGTH: 142
<212> TYPE: PRT
<213> ORGANISM: Homo sapiens

<400> SEQUENCE: 9

Pro Asn Ile Gln Asn Pro Asp Pro Ala Val Tyr Gln Leu Arg Asp Ser

-continued

```
                1               5                      10                      15
            Lys Ser Ser Asp Lys Ser Val Cys Leu Phe Thr Asp Phe Asp Ser Gln
                            20                      25                      30

Thr Asn Val Ser Gln Ser Lys Asp Ser Asp Val Tyr Ile Thr Asp Lys
                            35                      40                      45

Thr Val Leu Asp Met Arg Ser Met Asp Phe Lys Ser Asn Ser Ala Val
                50                          55                      60

Ala Trp Ser Asn Lys Ser Asp Phe Ala Cys Asn Ala Phe Asn Asn
             65                     70                      75                      80

Ser Ile Ile Pro Glu Asp Thr Phe Phe Pro Ser Pro Glu Ser Ser Cys
                                85                      90                      95

Asp Val Lys Leu Val Glu Lys Ser Phe Glu Thr Asp Thr Asn Leu Asn
                            100                     105                     110

Phe Gln Asn Leu Ser Val Ile Gly Phe Arg Ile Leu Leu Leu Lys Val
                            115                     120                     125

Ala Gly Phe Asn Leu Leu Met Thr Leu Arg Leu Trp Ser Ser
                130                     135                     140
```

<210> SEQ ID NO 10
<211> LENGTH: 139
<212> TYPE: PRT
<213> ORGANISM: Homo sapiens

<400> SEQUENCE: 10

```
            Met Ala Met Leu Leu Gly Ala Ser Val Leu Ile Leu Trp Leu Gln Pro
             1               5                      10                      15

Asp Trp Val Asn Ser Gln Gln Lys Asn Asp Asp Gln Gln Val Lys Gln
                            20                      25                      30

Asn Ser Pro Ser Leu Ser Val Gln Glu Gly Arg Ile Ser Ile Leu Asn
                            35                      40                      45

Cys Asp Tyr Thr Asn Ser Met Phe Asp Tyr Phe Leu Trp Tyr Lys Lys
                50                          55                      60

Tyr Pro Ala Glu Gly Pro Thr Phe Leu Ile Ser Ile Ser Ser Ile Lys
             65                     70                      75                      80

Asp Lys Asn Glu Asp Gly Arg Phe Thr Val Phe Leu Asn Lys Ser Ala
                            85                      90                      95

Lys His Leu Ser Leu His Ile Val Pro Ser Gln Pro Gly Asp Ser Ala
                            100                     105                     110

Val Tyr Phe Cys Ala Ala Lys Gly Ala Gly Thr Ala Ser Lys Leu Thr
                            115                     120                     125

Phe Gly Thr Gly Thr Arg Leu Gln Val Thr Leu
                130                     135
```

<210> SEQ ID NO 11
<211> LENGTH: 177
<212> TYPE: PRT
<213> ORGANISM: Homo sapiens

<400> SEQUENCE: 11

```
            Glu Asp Leu Asn Lys Val Phe Pro Pro Glu Val Ala Val Phe Glu Pro
             1               5                      10                      15

Ser Glu Ala Glu Ile Ser His Thr Gln Lys Ala Thr Leu Val Cys Leu
                            20                      25                      30

Ala Thr Gly Phe Phe Pro Asp His Val Glu Leu Ser Trp Trp Val Asn
                            35                      40                      45

Gly Lys Glu Val His Ser Gly Val Ser Thr Asp Pro Gln Pro Leu Lys
```

-continued

```
            50                  55                  60
Glu Gln Pro Ala Leu Asn Asp Ser Arg Tyr Cys Leu Ser Ser Arg Leu
 65                  70                  75                  80

Arg Val Ser Ala Thr Phe Trp Gln Asn Pro Arg Asn His Phe Arg Cys
                 85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
            115                 120                 125

Ala Asp Cys Gly Phe Thr Ser Val Ser Tyr Gln Gln Gly Val Leu Ser
130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 12
<211> LENGTH: 133
<212> TYPE: PRT
<213> ORGANISM: Homo sapiens

<400> SEQUENCE: 12

Met Gly Thr Ser Leu Leu Cys Trp Met Ala Leu Cys Leu Leu Gly Ala
  1               5                  10                  15

Asp His Ala Asp Thr Gly Val Ser Gln Asn Pro Arg His Asn Ile Thr
                 20                  25                  30

Lys Arg Gly Gln Asn Val Thr Phe Arg Cys Asp Pro Ile Ser Glu His
             35                  40                  45

Asn Arg Leu Tyr Trp Tyr Arg Gln Thr Leu Gly Gln Gly Pro Glu Phe
         50                  55                  60

Leu Thr Tyr Phe Gln Asn Glu Ala Gln Leu Glu Lys Ser Arg Leu Leu
 65                  70                  75                  80

Ser Asp Arg Phe Ser Ala Glu Arg Pro Lys Gly Ser Phe Ser Thr Leu
                 85                  90                  95

Glu Ile Gln Arg Thr Glu Gln Gly Asp Ser Ala Met Tyr Leu Cys Ala
                100                 105                 110

Ser Ser Leu Ala Gly Leu Asn Gln Pro Gln His Phe Gly Asp Gly Thr
            115                 120                 125

Arg Leu Ser Ile Leu
        130

<210> SEQ ID NO 13
<211> LENGTH: 135
<212> TYPE: PRT
<213> ORGANISM: Homo sapiens

<400> SEQUENCE: 13

Met Asp Ser Trp Thr Phe Cys Cys Val Ser Leu Cys Ile Leu Val Ala
  1               5                  10                  15

Lys His Thr Asp Ala Gly Val Ile Gln Ser Pro Arg His Glu Val Thr
                 20                  25                  30

Glu Met Gly Gln Glu Val Thr Leu Arg Cys Lys Pro Ile Ser Gly His
             35                  40                  45

Asn Ser Leu Phe Trp Tyr Arg Gln Thr Met Met Arg Gly Leu Glu Leu
         50                  55                  60
```

```
Leu Ile Tyr Phe Asn Asn Val Pro Ile Asp Asp Ser Gly Met Pro
 65                  70                  75                  80

Glu Asp Arg Phe Ser Ala Lys Met Pro Asn Ala Ser Phe Ser Thr Leu
                 85                  90                  95

Lys Ile Gln Pro Ser Glu Pro Arg Asp Ser Ala Val Tyr Phe Cys Ala
            100                 105                 110

Ser Ser Phe Ser Thr Cys Ser Ala Asn Tyr Gly Tyr Thr Phe Gly Ser
            115                 120                 125

Gly Thr Arg Leu Thr Val Val
            130                 135

<210> SEQ ID NO 14
<211> LENGTH: 216
<212> TYPE: PRT
<213> ORGANISM: Homo sapiens

<400> SEQUENCE: 14

Met Gly Trp Ile Arg Gly Arg Arg Ser Arg His Ser Trp Glu Met Ser
  1               5                  10                  15

Glu Phe His Asn Tyr Asn Leu Asp Leu Lys Lys Ser Asp Phe Ser Thr
                 20                  25                  30

Arg Trp Gln Lys Gln Arg Cys Pro Val Val Lys Ser Lys Cys Arg Glu
             35                  40                  45

Asn Ala Ser Pro Phe Phe Cys Cys Phe Ile Ala Val Ala Met Gly
 50                  55                  60

Ile Arg Phe Ile Ile Met Val Ala Ile Trp Ser Ala Val Phe Leu Asn
 65                  70                  75                  80

Ser Leu Phe Asn Gln Glu Val Gln Ile Pro Leu Thr Glu Ser Tyr Cys
                 85                  90                  95

Gly Pro Cys Pro Lys Asn Trp Ile Cys Tyr Lys Asn Asn Cys Tyr Gln
            100                 105                 110

Phe Phe Asp Glu Ser Lys Asn Trp Tyr Glu Ser Gln Ala Ser Cys Met
            115                 120                 125

Ser Gln Asn Ala Ser Leu Leu Lys Val Tyr Ser Lys Glu Asp Gln Asp
            130                 135                 140

Leu Leu Lys Leu Val Lys Ser Tyr His Trp Met Gly Leu Val His Ile
145                 150                 155                 160

Pro Thr Asn Gly Ser Trp Gln Trp Glu Asp Gly Ser Ile Leu Ser Pro
                165                 170                 175

Asn Leu Leu Thr Ile Ile Glu Met Gln Lys Gly Asp Cys Ala Leu Tyr
            180                 185                 190

Ala Ser Ser Phe Lys Gly Tyr Ile Glu Asn Cys Ser Thr Pro Asn Thr
            195                 200                 205

Tyr Ile Cys Met Gln Arg Thr Val
            210                 215

<210> SEQ ID NO 15
<211> LENGTH: 418
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Asn Ser Leu Phe Asn Gln Glu Val Gln Ile Pro Leu Thr Glu Ser Tyr
```

```
1               5                   10                  15
Cys Gly Pro Cys Pro Lys Asn Trp Ile Cys Tyr Lys Asn Asn Cys Tyr
                20                  25                  30
Gln Phe Phe Asp Glu Ser Lys Asn Trp Tyr Glu Ser Gln Ala Ser Cys
                35                  40                  45
Met Ser Gln Asn Ala Ser Leu Leu Lys Val Tyr Ser Lys Glu Asp Gln
                50                  55                  60
Asp Leu Leu Lys Leu Val Lys Ser Tyr His Trp Met Gly Leu Val His
65                  70                  75                  80
Ile Pro Thr Asn Gly Ser Trp Gln Trp Glu Asp Gly Ser Ile Leu Ser
                85                  90                  95
Pro Asn Leu Leu Thr Ile Ile Glu Met Gln Lys Gly Asp Cys Ala Leu
                100                 105                 110
Tyr Ala Ser Ser Phe Lys Gly Tyr Ile Glu Asn Cys Ser Thr Pro Asn
                115                 120                 125
Thr Tyr Ile Cys Met Gln Arg Thr Val Gly Gly Gly Ser Gly Gly
                130                 135                 140
Gly Gly Ser Gly Gly Gly Ser Leu Glu Asn Ser Leu Phe Asn Gln
145                 150                 155                 160
Glu Val Gln Ile Pro Leu Thr Glu Ser Tyr Cys Gly Pro Cys Pro Lys
                165                 170                 175
Asn Trp Ile Cys Tyr Lys Asn Asn Cys Tyr Gln Phe Phe Asp Glu Ser
                180                 185                 190
Lys Asn Trp Tyr Glu Ser Gln Ala Ser Cys Met Ser Gln Asn Ala Ser
                195                 200                 205
Leu Leu Lys Val Tyr Ser Lys Glu Asp Gln Asp Leu Leu Lys Leu Val
                210                 215                 220
Lys Ser Tyr His Trp Met Gly Leu Val His Ile Pro Thr Asn Gly Ser
225                 230                 235                 240
Trp Gln Trp Glu Asp Gly Ser Ile Leu Ser Pro Asn Leu Leu Thr Ile
                245                 250                 255
Ile Glu Met Gln Lys Gly Asp Cys Ala Leu Tyr Ala Ser Ser Phe Lys
                260                 265                 270
Gly Tyr Ile Glu Asn Cys Ser Thr Pro Asn Thr Tyr Ile Cys Met Gln
                275                 280                 285
Arg Thr Val Ala Ala Gly Gly Gly Ser Gly Gly Gly Gly Ser
                290                 295                 300
Gly Gly Gly Ser Leu Glu Asp Gly Asn Glu Glu Met Gly Gly Ile
305                 310                 315                 320
Thr Gln Thr Pro Tyr Lys Val Ser Ile Ser Gly Thr Thr Val Ile Leu
                325                 330                 335
Thr Cys Pro Gln Tyr Pro Gly Ser Glu Ile Leu Trp Gln His Asn Asp
                340                 345                 350
Lys Asn Ile Gly Gly Asp Glu Asp Lys Asn Ile Gly Ser Asp Glu
                355                 360                 365
Asp His Leu Ser Leu Lys Glu Phe Ser Glu Leu Glu Gln Ser Gly Tyr
                370                 375                 380
Tyr Val Cys Tyr Pro Arg Gly Ser Lys Pro Glu Asp Ala Asn Phe Tyr
385                 390                 395                 400
Leu Tyr Leu Arg Ala Arg Val Cys Glu Asn Cys Met Glu Met Asp Val
                405                 410                 415

Met Ser
```

```
<210> SEQ ID NO 16
<211> LENGTH: 496
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Asn Ser Leu Phe Asn Gln Glu Val Gln Ile Pro Leu Thr Glu Ser Tyr
1               5                   10                  15

Cys Gly Pro Cys Pro Lys Asn Trp Ile Cys Tyr Lys Asn Asn Cys Tyr
                20                  25                  30

Gln Phe Phe Asp Glu Ser Lys Asn Trp Tyr Glu Ser Gln Ala Ser Cys
            35                  40                  45

Met Ser Gln Asn Ala Ser Leu Leu Lys Val Tyr Ser Lys Glu Asp Gln
        50                  55                  60

Asp Leu Leu Lys Leu Val Lys Ser Tyr His Trp Met Gly Leu Val His
65                  70                  75                  80

Ile Pro Thr Asn Gly Ser Trp Gln Trp Glu Asp Gly Ser Ile Leu Ser
                85                  90                  95

Pro Asn Leu Leu Thr Ile Ile Glu Met Gln Lys Gly Asp Cys Ala Leu
                100                 105                 110

Tyr Ala Ser Ser Phe Lys Gly Tyr Ile Glu Asn Cys Ser Thr Pro Asn
            115                 120                 125

Thr Tyr Ile Cys Met Gln Arg Thr Val Gly Gly Gly Ser Gly Gly
        130                 135                 140

Gly Gly Ser Gly Gly Gly Ser Leu Glu Asn Ser Leu Phe Asn Gln
145                 150                 155                 160

Glu Val Gln Ile Pro Leu Thr Glu Ser Tyr Cys Gly Pro Cys Pro Lys
                165                 170                 175

Asn Trp Ile Cys Tyr Lys Asn Asn Cys Tyr Gln Phe Phe Asp Glu Ser
            180                 185                 190

Lys Asn Trp Tyr Glu Ser Gln Ala Ser Cys Met Ser Gln Asn Ala Ser
        195                 200                 205

Leu Leu Lys Val Tyr Ser Lys Glu Asp Gln Asp Leu Leu Lys Leu Val
    210                 215                 220

Lys Ser Tyr His Trp Met Gly Leu Val His Ile Pro Thr Asn Gly Ser
225                 230                 235                 240

Trp Gln Trp Glu Asp Gly Ser Ile Leu Ser Pro Asn Leu Leu Thr Ile
                245                 250                 255

Ile Glu Met Gln Lys Gly Asp Cys Ala Leu Tyr Ala Ser Ser Phe Lys
            260                 265                 270

Gly Tyr Ile Glu Asn Cys Ser Thr Pro Asn Thr Tyr Ile Cys Met Gln
        275                 280                 285

Arg Thr Val Ala Ala Gly Gly Gly Ser Gly Gly Gly Ser
    290                 295                 300

Gly Gly Gly Ser Leu Glu Asp Gly Asn Glu Glu Met Gly Gly Ile
305                 310                 315                 320

Thr Gln Thr Pro Tyr Lys Val Ser Ile Ser Gly Thr Thr Val Ile Leu
                325                 330                 335

Thr Cys Pro Gln Tyr Pro Gly Ser Glu Ile Leu Trp Gln His Asn Asp
            340                 345                 350

Lys Asn Ile Gly Gly Asp Glu Asp Asp Lys Asn Ile Gly Ser Asp Glu
```

```
        355                 360                 365
Asp His Leu Ser Leu Lys Glu Phe Ser Glu Leu Glu Gln Ser Gly Tyr
            370                 375                 380

Tyr Val Cys Tyr Pro Arg Gly Ser Lys Pro Glu Asp Ala Asn Phe Tyr
385                 390                 395                 400

Leu Tyr Leu Arg Ala Arg Val Cys Glu Asn Cys Met Glu Met Asp Val
                405                 410                 415

Met Ser Val Ala Thr Ile Val Ile Val Asp Ile Cys Ile Thr Gly Gly
            420                 425                 430

Leu Leu Leu Leu Val Tyr Tyr Trp Ser Lys Asn Arg Lys Ala Lys Ala
            435                 440                 445

Lys Pro Val Thr Arg Gly Ala Gly Ala Gly Gly Arg Gln Arg Gly Gln
        450                 455                 460

Asn Lys Glu Arg Pro Pro Pro Val Pro Asn Pro Asp Tyr Glu Pro Ile
465                 470                 475                 480

Arg Lys Gly Gln Arg Asp Leu Tyr Ser Gly Leu Asn Gln Arg Arg Ile
                485                 490                 495
```

<210> SEQ ID NO 17
<211> LENGTH: 7546
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17

```
acgcgtgtag tcttatgcaa tactctgtag tcttgcaaca tggtaacgat gagttagcaa      60
catgccttac aaggagagaa aaagcaccgt gcatgccgat tggtggaagt aaggtggtac     120
gatcgtgcct tattaggaag gcaacagacg ggtctgacat ggattggacg aaccactgaa     180
ttgccgcatt gcagagatat tgtatttaag tgcctagctc gatacataaa cgggtctctc     240
tggttagacc agatctgagc ctgggagctc tctggctaac tagggaaccc actgcttaag     300
cctcaataaa gcttgccttg agtgcttcaa gtagtgtgtg cccgtctgtt gtgtgactct     360
ggtaactaga tcccctcag acccttttag tcagtgtgga aaatctctag cagtggcgcc     420
cgaacaggga cttgaaagcg aaagggaaac cagaggagct ctctcgacgc aggactcggc     480
ttgctgaagc gcgcacggca agaggcgagg ggcggcgact ggtgagtacg ccaaaaattt     540
tgactagcgg aggctagaag gagagagatg ggtgcgagag cgtcagtatt aagcggggga     600
gaattagatc gcgatgggaa aaaattcggt taaggccagg gggaaagaaa aaatataaat     660
taaaacatat agtatgggca agcagggagc tagaacgatt cgcagttaat cctggcctgt     720
tagaaacatc agaaggctgt agacaaatac tgggacagct acaaccatcc cttcagacag     780
gatcagaaga acttagatca ttatataata cagtagcaac cctctattgt gtgcatcaaa     840
ggatagagat aaaagacacc aaggaagctt tagacaagat agaggaagag caaaacaaaa     900
gtaagaccac cgcacagcaa gcggccactg atcttcagac ctggaggagg agatatgagg     960
gacaattgga gaagtgaatt atataaatat aaagtagtaa aaattgaacc attaggagta    1020
gcacccacca aggcaaagag aagagtggtg cagagagaaa aaagagcagt gggaatagga    1080
gctttgttcc ttgggttctt gggagcagca ggaagcacta tgggcgcagc gtcaatgacg    1140
ctgacggtac aggccagaca attattgtct ggtatagtgc agcagcagaa caatttgctg    1200
agggctattg aggcgcaaca gcatctgttg caactcacag tctgggggcat caagcagctc    1260
```

```
caggcaagaa tcctggctgt ggaaagatac ctaaaggatc aacagctcct ggggatttgg    1320
ggttgctctg gaaaactcat ttgcaccact gctgtgcctt ggaatgctag ttggagtaat    1380
aaatctctgg aacagatttg gaatcacacg acctggatgg agtgggacag agaaattaac    1440
aattacacaa gcttaataca ctccttaatt gaagaatcgc aaaaccagca agaaaagaat    1500
gaacaagaat tattggaatt agataaatgg gcaagtttgt ggaattggtt aacataaca    1560 aattggctgt ggtatataaa attattcata atgatagtag gaggcttggt aggtttaaga    1620 atagttttg ctgtactttc tatagtgaat agagttaggc agggatattc accattatcg     1680
tttcagaccc acctcccaac cccgagggga cccgacaggc ccgaaggaat agaagaagaa    1740
ggtggagaga gagacagaga cagatccatt cgattagtga acggatctcg acggtatcgg    1800 ttaacttta aaagaaaagg ggggattggg ggtacagtg caggggaaag aatagtagac      1860
ataatagcaa cagacataca aactaaagaa ttacaaaaac aaattacaaa attcaaaatt    1920
ttatcgatac tagtggatct gcgatcgctc cggtgcccgt cagtgggcag agcgcacatc    1980
gcccacagtc cccgagaagt tggggggagg ggtcggcaat tgaacgggtg cctagagaag    2040
gtggcgcggg gtaaactggg aaagtgatgt cgtgtactgg ctccgccttt ttcccgaggg    2100
tgggggagaa ccgtatataa gtgcagtagt cgccgtgaac gttctttttc gcaacgggtt    2160
tgccgccaga acacagctga agcttcgagg ggctcgcatc tctccttcac gcgcccgccg    2220
ccctacctga ggccgccatc cacgccggtt gagtcgcgtt ctgccgcctc ccgcctgtgg    2280
tgcctcctga actgcgtccg ccgtctaggt aagtttaaag ctcaggtcga gaccgggcct    2340
ttgtccggcg ctcccttgga gcctacctag actcagccgg ctctccacgc tttgcctgac    2400
cctgcttgct caactctacg tctttgtttc gttttctgtt ctgcgccgtt acagatccaa    2460
gctgtgaccg gcgcctactc tagagccgcc accatgcttc tcctggtgac aagccttctg    2520
ctctgtgagt taccacaccc agcattcctc ctgatcccaa actccctctt caaccaggag    2580
gtgcagatcc ccctcacaga gagctactgc gggccctgtc caaagaattg gatatgttac    2640
aagaacaatt gctaccagtt cttcgatgag tcaaaaaatt ggtatgagag ccaagcttcc    2700
tgcatgtctc agaatgccag ccttctgaag gtgtactcaa aagaagacca ggacttgctg    2760
aaactggtca gtctttacca ctggatgggg ctcgtgcaca ttccaacgaa cggtagctgg    2820
cagtgggaag atggctccat attgtctcct aaccttctca ccataataga gatgcagaag    2880
ggtgattgcg ctctgtacgc tagtagcttc aagggctata ttgagaattg tagtacaccc    2940
aacacataca tttgtatgca gagaaccgtg ggaggtggtg gcagcggtgg cggtggaagt    3000
ggtggcggcg gttctctcga ggatggtaat gaagaaatgg gtggtattac acagacacca    3060 tataagtct ccatctctgg aaccacagta atattgacat gccctcagta tcctggatct     3120
gaaatactat ggcaacacaa tgataaaaac ataggcggtg atgaggatga taaaaacata    3180
ggcagtgatg aggatcacct gtcactgaag gaatttcag aattggagca agtggttat      3240 tatgtctgct accccagagg aagcaaacca gaagatgcga acttttatct ctacctgagg    3300
gcaagagtgt gtgagaactg catggagatg gatgtgatgt cggtggccac aattgtcata    3360
gtggacatct gcatcactgg gggcttgctg ctgctggttt actactggag caagaataga    3420
aaggccaagg ccaagcctgt gacacgagga gcgggtgctg gcggcaggca aggggacaa     3480 aacaaggaga ggccaccacc tgttcccaac ccagactatg agcccatccg gaaaggccag    3540
cgggacctgt attctggcct gaatcagaga cgcatctgat aagaattcga atttaaatcg    3600
```

-continued

```
gatccgcggc cgcgtcgaca atcaacctct ggattacaaa atttgtgaaa gattgactgg      3660
tattcttaac tatgttgctc cttttacgct atgtggatac gctgctttaa tgcctttgta      3720
tcatgctatt gcttcccgta tggctttcat tttctcctcc ttgtataaat cctggttgct      3780
gtctctttat gaggagttgt ggcccgttgt caggcaacgt ggcgtggtgt gcactgtgtt      3840
tgctgacgca accccactg gttggggcat tgccaccacc tgtcagctcc tttccgggac      3900
tttcgctttc cccctcccta ttgccacggc ggaactcatc gccgcctgcc ttgcccgctg      3960
ctggacaggg gctcggctgt tgggcactga caattccgtg gtgttgtcgg ggaaatcatc      4020
gtcctttcct tggctgctcg cctgtgttgc cacctggatt ctgcgcggga cgtccttctg      4080
ctacgtccct tcggccctca atccagcgga ccttccttcc cgcggcctgc tgccggctct      4140
gcggcctctt ccgcgtcttc gccttcgccc tcagacgagt cggatctccc tttgggccgc      4200
ctccccgcct ggtacccttta agaccaatga cttacaaggc agctgtagat cttagccact      4260 tttaaaaga aaggggga ctggaagggc taattcactc ccaacgaaga taagatctgc      4320
tttttgcttg tactgggtct ctctggttag accagatctg agcctgggag ctctctggct      4380
aactagggaa cccactgctt aagcctcaat aaagcttgcc ttgagtgctt caagtagtgt      4440
gtgcccgtct gttgtgtgac tctggtaact agagatccct cagacccttt tagtcagtgt      4500
ggaaaatctc tagcagtagt agttcatgtc atcttattat tcagtattta aacttgcaa      4560 agaaatgaat atcagagagt gagaggaact tgtttattgc agcttataat ggttacaaat      4620
aaagcaatag catcacaaat ttcacaaata aagcatttt ttcactgcat tctagttgtg      4680
gtttgtccaa actcatcaat gtatcttatc atgtctggct ctagctatcc cgcccctaac      4740
tccgcccatc ccgcccctaa ctccgcccag ttccgcccat tctccgcccc atggctgact      4800 aattttttttt atttatgcag aggccgaggc cgcctcggcc tctgagctat tccagaagta      4860
gtgaggaggc ttttttggag gcctagactt ttgcagagac ggcccaaatt cgtaatcatg      4920
gtcatagctg tttcctgtgt gaaattgtta tccgctcaca attccacaca acatacgagc      4980
cggaagcata agtgtaaag cctggggtgc ctaatgagtg agctaactca cattaattgc      5040
gttgcgctca ctgcccgctt tccagtcggg aaacctgtcg tgccagctgc attaatgaat      5100
cggccaacgc gcgggagag gcggtttgcg tattgggcgc tcttccgctt cctcgctcac      5160
tgactcgctg cgctcggtcg ttcggctgcg gcgagcggta tcagctcact caaaggcggt      5220
aatacggtta tccacagaat caggggataa cgcaggaaag aacatgtgag caaaaggcca      5280
gcaaaaggcc aggaaccgta aaaaggccgc gttgctggcg tttttccata ggctccgccc      5340
ccctgacgag catcacaaaa atcgacgctc aagtcagagg tggcgaaacc cgacaggact      5400
ataaagatac caggcgtttc ccctggaag ctccctcgtg cgctctcctg ttccgaccct      5460
gccgcttacc ggatacctgt ccgcctttct cccttcggga agcgtggcgc tttctcatag      5520
ctcacgctgt aggtatctca gttcggtgta ggtcgttcgc tccaagctgg gctgtgtgca      5580 cgaaccccc gttcagcccg accgctgcgc cttatccggt aactatcgtc ttgagtccaa      5640
cccggtaaga cacgacttat cgccactggc agcagccact ggtaacagga ttagcagagc      5700
gaggtatgta ggcggtgcta cagagttctt gaagtggtgg cctaactacg gctacactag      5760
aaggacagta tttggtatct gcgctctgct gaagccagtt accttcggaa aaagagttgg      5820
tagctcttga tccggcaaac aaaccaccgc tggtagcggt ggttttttg tttgcaagca      5880 gcagattacg cgcagaaaaa aaggatctca agaagatcct ttgatctttt ctacggggtc      5940
tgacgctcag tggaacgaaa actcacgtta agggatttg gtcatgagat tatcaaaaag      6000
```

| | |
|---|---|
| gatcttcacc tagatccttt taaattaaaa atgaagtttt aaatcaatct aaagtatata | 6060 |
| tgagtaaact tggtctgaca gttaccaatg cttaatcagt gaggcaccta tctcagcgat | 6120 |
| ctgtctattt cgttcatcca tagttgcctg actcccgtc gtgtagataa ctacgatacg | 6180 |
| ggagggctta ccatctggcc ccagtgctgc aatgataccg cgagacccac gctcaccggc | 6240 |
| tccagattta tcagcaataa accagccagc cggaagggcc gagcgcagaa gtggtcctgc | 6300 |
| aactttatcc gcctccatcc agtctattaa ttgttgccgg gaagctagag taagtagttc | 6360 |
| gccagttaat agtttgcgca acgttgttgc cattgctaca ggcatcgtgg tgtcacgctc | 6420 |
| gtcgtttggt atggcttcat tcagctccgg ttcccaacga tcaaggcgag ttacatgatc | 6480 |
| ccccatgttg tgcaaaaaag cggttagctc cttcggtcct ccgatcgttg tcagaagtaa | 6540 |
| gttggccgca gtgttatcac tcatggttat ggcagcactg cataattctc ttactgtcat | 6600 |
| gccatccgta agatgctttt ctgtgactgg tgagtactca accaagtcat tctgagaata | 6660 |
| gtgtatgcgg cgaccgagtt gctcttgccc ggcgtcaata cgggataata ccgcgccaca | 6720 |
| tagcagaact ttaaaagtgc tcatcattgg aaaacgttct cggggcgaa aactctcaag | 6780 |
| gatcttaccg ctgttgagat ccagttcgat gtaaccact cgtgcaccca actgatcttc | 6840 |
| agcatctttt actttcacca gcgtttctgg gtgagcaaaa acaggaaggc aaaatgccgc | 6900 |
| aaaaaaggga ataagggcga cacggaaatg ttgaatactc atactcttcc ttttcaata | 6960 |
| ttattgaagc atttatcagg gttattgtct catgagcgga tacatatttg aatgtattta | 7020 |
| gaaaaataaa caataggggg ttccgcgcac atttccccga aaagtgccac ctgacgtcta | 7080 |
| agaaaccatt attatcatga cattaaccta taaaaatagg cgtatcacga ggccctttcg | 7140 |
| tctcgcgcgt ttcggtgatg acggtgaaaa cctctgacac atgcagctcc cggagacggt | 7200 |
| cacagcttgt ctgtaagcgg atgccgggag cagacaagcc cgtcagggcg cgtcagcggg | 7260 |
| tgttggcggg tgtcggggct ggcttaacta tgcggcatca gagcagattg tactgagagt | 7320 |
| gcaccatatg cggtgtgaaa taccgcacag atgcgtaagg agaaaatacc gcatcaggcg | 7380 |
| ccattcgcca ttcaggctgc gcaactgttg ggaagggcga tcggtgcggg cctcttcgct | 7440 |
| attacgccag ctggcgaaag ggggatgtgc tgcaaggcga ttaagttggg taacgccagg | 7500 |
| gttttcccag tcacgacgtt gtaaaacgac ggccagtgcc aagctg | 7546 |

<210> SEQ ID NO 18
<211> LENGTH: 8017
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 18

| | |
|---|---|
| acgcgtgtag tcttatgcaa tactctgtag tcttgcaaca tggtaacgat gagttagcaa | 60 |
| catgccttac aaggagagaa aaagcaccgt gcatgccgat tggtggaagt aaggtggtac | 120 |
| gatcgtgcct tattaggaag gcaacagacg ggtctgacat ggattggacg aaccactgaa | 180 |
| ttgccgcatt gcagagatat tgtatttaag tgcctagctc gatacataaa cgggtctctc | 240 |
| tggttagacc agatctgagc ctgggagctc tctggctaac tagggaaccc actgcttaag | 300 |
| cctcaataaa gcttgccttg agtgcttcaa gtagtgtgtg cccgtctgtt gtgtgactct | 360 |
| ggtaactaga gatccctcag acccttttag tcagtgtgga aaatctctag cagtggcgcc | 420 |

```
cgaacaggga cttgaaagcg aaagggaaac cagaggagct ctctcgacgc aggactcggc    480
ttgctgaagc gcgcacggca agaggcgagg ggcggcgact ggtgagtacg ccaaaaattt    540
tgactagcgg aggctagaag gagagagatg ggtgcgagag cgtcagtatt aagcggggga    600
gaattagatc gcgatgggaa aaaattcggt taaggccagg gggaagaaaa aaatataaat    660
taaaacatat agtatgggca agcagggagc tagaacgatt cgcagttaat cctggcctgt    720
tagaaacatc agaaggctgt agacaaatac tgggacagct acaaccatcc cttcagacag    780
gatcagaaga acttagatca ttatataata cagtagcaac cctctattgt gtgcatcaaa    840
ggatagagat aaaagacacc aaggaagctt tagacaagat agaggaagag caaaacaaaa    900
gtaagaccac cgcacagcaa gcggccactg atcttcagac ctggaggagg agatatgagg    960
gacaattgga gaagtgaatt atataaatat aaagtagtaa aaattgaacc attaggagta   1020
gcacccacca aggcaaagag aagagtggtg cagagagaaa aaagagcagt gggaatagga   1080
gctttgttcc ttgggttctt gggagcagca ggaagcacta tgggcgcagc gtcaatgacg   1140
ctgacggtac aggccagaca attattgtct ggtatagtgc agcagcagaa caatttgctg   1200
agggctattg aggcgcaaca gcatctgttg caactcacag tctggggcat caagcagctc   1260
caggcaagaa tcctggctgt ggaaagatac ctaaaggatc aacagctcct ggggatttgg   1320
ggttgctctg gaaaactcat ttgcaccact gctgtgcctt ggaatgctag ttggagtaat   1380
aaatctctgg aacagatttg gaatcacacg acctggatgg agtgggacag agaaattaac   1440
aattacacaa gcttaataca ctccttaatt gaagaatcgc aaaaccagca agaaaagaat   1500
gaacaagaat tattggaatt agataaatgg gcaagtttgt ggaattggtt taacataaca   1560
aattggctgt ggtatataaa attattcata atgatagtag gaggcttggt aggtttaaga   1620
atagtttttg ctgtactttc tatagtgaat agagttaggc agggatattc accattatcg   1680
tttcagaccc acctcccaac cccgagggga cccgacaggc ccgaaggaat agaagaagaa   1740
ggtggagaga gagacagaga cagatccatt cgattagtga acggatctcg acggtatcgg   1800
ttaactttta aaagaaaagg ggggattggg gggtacagtg caggggaaag aatagtagac   1860
ataatagcaa cagacataca aactaaagaa ttacaaaaac aaattacaaa attcaaaatt   1920
ttatcgatac tagtggatct gcgatcgctc cggtgcccgt cagtgggcag agcgcacatc   1980
gcccacagtc cccgagaagt tggggggagg ggtcggcaat tgaacgggtg cctagagaag   2040
gtggcgcggg gtaaactggg aaagtgatgt cgtgtactgg ctccgccttt ttcccgaggg   2100
tgggggagaa ccgtatataa gtgcagtagt cgccgtgaac gttcttttc gcaacgggtt   2160 tgccgccaga acacagctga agcttcgagg ggctcgcatc tctccttcac gcgcccgccg   2220
ccctacctga gccgccatc cacgccggtt gagtcgcgtt ctgccgcctc ccgcctgtgg   2280
tgcctcctga actgcgtccg ccgtctaggt aagtttaaag ctcaggtcga gaccgggcct   2340
ttgtccggcg ctcccttgga gcctacctag actcagccgg ctctccacgc tttgcctgac   2400
cctgcttgct caactctacg tctttgtttc gttttctgtt ctgcgccgtt acagatccaa   2460
gctgtgaccg gcgcctactc tagagccgcc accatgcttc tcctggtgac aagccttctg   2520
ctctgtgagt taccacaccc agcattcctc ctgatcccaa actccctctt caaccaggag   2580
gtgcagatcc ccctcacaga gagctactgc gggccctgtc caaagaattg gatatgttac   2640
aagaacaatt gctaccagtt cttcgatgag tcaaaaaatt ggtatgagag ccaagcttcc   2700
tgcatgtctc agaatgccag ccttctgaag gtgtactcaa agaagaccca ggacttgctg   2760
aaactggtca agtcttacca ctggatgggg ctcgtgcaca ttccaacgaa cggtagctgg   2820
```

```
cagtgggaag atggctccat attgtctcct aaccttctca ccataataga gatgcagaag    2880
ggtgattgcg ctctgtacgc tagtagcttc aagggctata ttgagaattg tagtacaccc    2940
aacacataca tttgtatgca gagaaccgtg ggaggtggtg gcagcggtgg cggtggaagt    3000
ggtggcggtg gcagtctcga gaactcatta ttcaaccaag aagttcaaat tcccttgacc    3060
gaaagttact gtggcccatg tcctaaaaac tggatatgtt acaaaaataa ctgctaccaa    3120
ttttttgatg agagtaaaaa ctggtatgag agccaggctt cttgtatgtc tcaaaatgcc    3180
agccttctga agtatacag caaagaggac caggatttac ttaaactggt gaagtcatat    3240
cattggatgg gactagtaca cattccaaca aatggatctt ggcagtggga agatggctcc    3300
attctctcac ccaacctact aacaataatt gaaatgcaga agggagactg tgcactctat    3360
gcctctagct ttaaaggcta tatagaaaac tgttcaactc caaatacata catctgcatg    3420
caaaggactg tggcggccgc aggtggcggc ggttctggtg gcggcggttc tggtggcggc    3480
ggttctctcg aggatggtaa tgaagaaatg ggtggtatta cacagacacc atataaagtc    3540
tccatctctg gaaccacagt aatattgaca tgccctcagt atcctggatc tgaaatacta    3600
tggcaacaca atgataaaaa cataggcggt gatgaggatg ataaaaacat aggcagtgat    3660
gaggatcacc tgtcactgaa ggaattttca gaattggagc aaagtggtta ttatgtctgc    3720 tacccccagag gaagcaaacc agaagatgcg aactttatc tctacctgag ggcaagagtg    3780
tgtgagaact gcatggagat ggatgtgatg tcggtggcca caattgtcat agtggacatc    3840
tgcatcactg ggggcttgct gctgctggtt tactactgga gcaagaatag aaaggccaag    3900
gccaagcctg tgacacgagg agcgggtgct ggcggcaggc aaaggggaca aaacaaggag    3960
aggccaccac ctgttcccaa cccagactat gagcccatcc ggaaaggcca gcgggacctg    4020
tattctggcc tgaatcagag acgcatctga taagaattcg aatttaaatc ggatccgcgg    4080
ccgcgtcgac aatcaacctc tggattacaa aatttgtgaa agattgactg gtattcttaa    4140
ctatgttgct ccttttacgc tatgtggata cgctgcttta atgcctttgt atcatgctat    4200
tgcttcccgt atggctttca ttttctcctc cttgtataaa tcctggttgc tgtctcttta    4260
tgaggagttg tggcccgttg tcaggcaacg tggcgtggtg tgcactgtgt ttgctgacgc    4320
aacccccact ggttgggca ttgccaccac ctgtcagctc ctttccggga ctttcgcttt    4380 ccccctcct attgccacgg cggaactcat cgccgcctgc cttgcccgct gctgacagg    4440 ggctcggctg ttgggcactg acaattccgt ggtgttgtcg gggaaatcat cgtccttttcc    4500 ttggctgctc gcctgtgttg ccacctggat tctgcgcggg acgtccttct gctacgtccc    4560
ttcggccctc aatccagcgg accttccttc ccgcggcctg ctgccggctc tgcggcctct    4620
tccgcgtctt cgccttcgcc ctcagacgag tcggatctcc ctttgggccg cctccccgcc    4680
tggtaccttt aagaccaatg acttacaagg cagctgtaga tcttagccac ttttttaaag    4740
aaaagggggg actggaaggg ctaattcact cccaacgaag ataagatctg cttttttgctt    4800 gtactgggtc tctctggtta gaccagatct gagcctggga gctctctggc taactaggga    4860
acccactgct taagcctcaa taaagcttgc cttgagtgct tcaagtagtg tgtgcccgtc    4920
tgttgtgtga ctctggtaac tagagatccc tcagaccctt ttagtcagtg tggaaaatct    4980
ctagcagtag tagttcatgt catcttatta tcagtatttt ataacttgca aagaaatgaa    5040
tatcagagag tgagaggaac ttgtttattg cagcttataa tggttacaaa taaagcaata    5100
gcatcacaaa tttcacaaat aaagcatttt tttcactgca ttctagttgt ggtttgtcca    5160
```

```
aactcatcaa tgtatcttat catgtctggc tctagctatc ccgcccctaa ctccgcccat    5220 cccgcccta actccgccca gttccgccca ttctccgccc catggctgac taattttttt    5280
tatttatgca gaggccgagg ccgcctcggc ctctgagcta ttccagaagt agtgaggagg    5340
cttttttgga ggcctagact tttgcagaga cggcccaaat tcgtaatcat ggtcatagct    5400
gtttcctgtg tgaaattgtt atccgctcac aattccacac aacatacgag ccggaagcat    5460
aaagtgtaaa gcctgggtgc ctaatgagt gagctaactc acattaattg cgttgcgctc    5520
actgcccgct ttccagtcgg gaaacctgtc gtgccagctg cattaatgaa tcggccaacg    5580
cgcggggaga ggcggtttgc gtattgggcg ctcttccgct tcctcgctca ctgactcgct    5640
gcgctcggtc gttcggctgc ggcgagcggt atcagctcac tcaaaggcgg taatacggtt    5700
atccacagaa tcaggggata acgcaggaaa gaacatgtga gcaaaaggcc agcaaaaggc    5760
caggaaccgt aaaaaggccg cgttgctggc gtttttccat aggctccgcc ccctgacga    5820 gcatcacaaa aatcgacgct caagtcagag gtggcgaaac ccgacaggac tataaagata    5880
ccaggcgttt ccccctggaa gctccctcgt gcgctctcct gttccgaccc tgccgcttac    5940
cggatacctg tccgcctttc tcccttcggg aagcgtggcg ctttctcata gctcacgctg    6000
taggtatctc agttcggtgt aggtcgttcg ctccaagctg ggctgtgtgc acgaaccccc    6060
cgttcagccc gaccgctgcg ccttatccgg taactatcgt cttgagtcca acccggtaag    6120
acacgactta tcgccactgg cagcagccac tggtaacagg attagcagag cgaggtatgt    6180
aggcggtgct acagagttct tgaagtggtg gcctaactac ggctacacta aggacagt    6240 atttggtatc tgcgctctgc tgaagccagt taccttcgga aaaagagttg gtagctcttg    6300
atccggcaaa caaaccaccg ctggtagcgg tggtttttt gtttgcaagc agcagattac    6360
gcgcagaaaa aaggatctca agaagatcc tttgatcttt tctacggggt ctgacgctca    6420
gtggaacgaa aactcacgtt aagggatttt ggtcatgaga ttatcaaaaa ggatcttcac    6480
ctagatcctt ttaaattaaa aatgaagttt taaatcaatc taaagtatat atgagtaaac    6540
ttggtctgac agttaccaat gcttaatcag tgaggcacct atctcagcga tctgtctatt    6600
tcgttcatcc atagttgcct gactccccgt cgtgtagata actacgatac gggagggctt    6660
accatctggc cccagtgctg caatgatacc gcgagaccca cgctcaccgg ctccagattt    6720
atcagcaata aaccagccag ccggaagggc cgagcgcaga agtggtcctg caactttatc    6780
cgcctccatc cagtctatta attgttgccg ggaagctaga gtaagtagtt cgccagttaa    6840 tagtttcgc aacgttgttg ccattgctac aggcatcgtg gtgtcacgct cgtcgtttgg    6900
tatggcttca ttcagctccg gttcccaacg atcaaggcga gttacatgat cccccatgtt    6960
gtgcaaaaaa gcggttagct ccttcggtcc tccgatcgtt gtcagaagta agttggccgc    7020
agtgttatca ctcatggtta tggcagcact gcataattct cttactgtca tgccatccgt    7080
aagatgcttt tctgtgactg gtgagtactc aaccaagtca ttctgagaat agtgtatgcg    7140
gcgaccgagt tgctcttgcc cggcgtcaat acgggataat accgcgccac atagcagaac    7200
tttaaaagtg ctcatcattg gaaaacgttc ttcggggcga aaactctcaa ggatcttacc    7260
gctgttgaga tccagttcga tgtaacccac tcgtgcaccc aactgatctt cagcatcttt    7320
tactttcacc agcgtttctg ggtgagcaaa aacaggaagg caaaatgccg caaaaaggg    7380 aataagggcg acacggaaat gttgaatact catactcttc ctttttcaat attattgaag    7440
catttatcag ggttattgtc tcatgagcgg atacatattt gaatgtattt agaaaaataa    7500
acaaataggg gttccgcgca catttccccg aaaagtgcca cctgacgtct aagaaaccat    7560
```

-continued

```
tattatcatg acattaacct ataaaaatag gcgtatcacg aggcccttc gtctcgcgcg    7620 tttcggtgat gacggtgaaa acctctgaca catgcagctc ccggagacgg tcacagcttg    7680
tctgtaagcg gatgccggga gcagacaagc ccgtcagggc gcgtcagcgg gtgttggcgg    7740
gtgtcggggc tggcttaact atgcggcatc agagcagatt gtactgagag tgcaccatat    7800
gcggtgtgaa ataccgcaca gatgcgtaag gagaaaatac cgcatcaggc gccattcgcc    7860
attcaggctg cgcaactgtt gggaagggcg atcggtgcgg gcctcttcgc tattacgcca    7920
gctggcgaaa gggggatgtg ctgcaaggcg attaagttgg gtaacgccag ggttttccca    7980
gtcacgacgt tgtaaaacga cggccagtgc caagctg                             8017
```

<210> SEQ ID NO 19

<400> SEQUENCE: 19

000

<210> SEQ ID NO 20
<211> LENGTH: 937
<212> TYPE: PRT
<213> ORGANISM: Homo sapiens

<400> SEQUENCE: 20

```
Met His Arg Pro Arg Arg Gly Thr Arg Pro Leu Leu Ala Leu
1               5                   10                  15

Leu Ala Ala Leu Leu Ala Ala Arg Gly Ala Ala Ala Gln Glu Thr
                20                  25                  30

Glu Leu Ser Val Ser Ala Glu Leu Val Pro Thr Ser Ser Trp Asn Ile
            35                  40                  45

Ser Ser Glu Leu Asn Lys Asp Ser Tyr Leu Thr Leu Asp Glu Pro Met
        50                  55                  60

Asn Asn Ile Thr Thr Ser Leu Gly Gln Thr Ala Glu Leu His Cys Lys
65                  70                  75                  80

Val Ser Gly Asn Pro Pro Pro Thr Ile Arg Trp Phe Lys Asn Asp Ala
                85                  90                  95

Pro Val Val Gln Glu Pro Arg Arg Leu Ser Phe Arg Ser Thr Ile Tyr
                100                 105                 110

Gly Ser Arg Leu Arg Ile Arg Asn Leu Asp Thr Thr Asp Thr Gly Tyr
            115                 120                 125

Phe Gln Cys Val Ala Thr Asn Gly Lys Glu Val Val Ser Ser Thr Gly
        130                 135                 140

Val Leu Phe Val Lys Phe Gly Pro Pro Thr Ala Ser Pro Gly Tyr
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
                180                 185                 190

His Met Gln Gly Glu Ile Glu Asn Gln Ile Thr Ala Ala Phe Thr Met
            195                 200                 205

Ile Gly Thr Ser Ser His Leu Ser Asp Lys Cys Ser Gln Phe Ala Ile
        210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255
```

```
Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
            275                 280             285

Glu Ser Pro Glu Ala Ala Asn Cys Ile Arg Ile Gly Ile Pro Met Ala
290                     295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
            340                 345                 350

Pro Glu Leu Asn Gly Gly His Ser Tyr Cys Arg Asn Pro Gly Asn Gln
            355                 360                 365

Lys Glu Ala Pro Trp Cys Phe Thr Leu Asp Glu Asn Phe Lys Ser Asp
            370                 375                 380

Leu Cys Asp Ile Pro Ala Cys Asp Ser Lys Asp Ser Lys Glu Lys Asn
385                 390                 395                 400

Lys Met Glu Ile Leu Tyr Ile Leu Val Pro Ser Val Ala Ile Pro Leu
                405                 410                 415

Ala Ile Ala Leu Leu Phe Phe Phe Ile Cys Val Cys Arg Asn Asn Gln
            420                 425                 430

Lys Ser Ser Ser Ala Pro Val Gln Arg Gln Pro Lys His Val Arg Gly
            435                 440                 445

Gln Asn Val Glu Met Ser Met Leu Asn Ala Tyr Lys Pro Lys Ser Lys
            450                 455                 460

Ala Lys Glu Leu Pro Leu Ser Ala Val Arg Phe Met Glu Glu Leu Gly
465                 470                 475                 480

Glu Cys Ala Phe Gly Lys Ile Tyr Lys Gly His Leu Tyr Leu Pro Gly
                485                 490                 495

Met Asp His Ala Gln Leu Val Ala Ile Lys Thr Leu Lys Asp Tyr Asn
            500                 505                 510

Asn Pro Gln Gln Trp Thr Glu Phe Gln Gln Glu Ala Ser Leu Met Ala
            515                 520                 525

Glu Leu His His Pro Asn Ile Val Cys Leu Leu Gly Ala Val Thr Gln
            530                 535                 540

Glu Gln Pro Val Cys Met Leu Phe Glu Tyr Ile Asn Gln Gly Asp Leu
545                 550                 555                 560

His Glu Phe Leu Ile Met Arg Ser Pro His Ser Asp Val Gly Cys Ser
                565                 570                 575

Ser Asp Glu Asp Gly Thr Val Lys Ser Ser Leu Asp His Gly Asp Phe
            580                 585                 590

Leu His Ile Ala Ile Gln Ile Ala Ala Gly Met Glu Tyr Leu Ser Ser
            595                 600                 605

His Phe Phe Val His Lys Asp Leu Ala Ala Arg Asn Ile Leu Ile Gly
            610                 615                 620

Glu Gln Leu His Val Lys Ile Ser Asp Leu Gly Leu Ser Arg Glu Ile
625                 630                 635                 640

Tyr Ser Ala Asp Tyr Tyr Arg Val Gln Ser Lys Ser Leu Leu Pro Ile
                645                 650                 655

Arg Trp Met Pro Pro Glu Ala Ile Met Tyr Gly Lys Phe Ser Ser Asp
            660                 665                 670
```

Ser Asp Ile Trp Ser Phe Gly Val Leu Trp Glu Ile Phe Ser Phe
            675                 680                 685

Gly Leu Gln Pro Tyr Tyr Gly Phe Ser Asn Gln Glu Val Ile Glu Met
690                 695                 700

Val Arg Lys Arg Gln Leu Leu Pro Cys Ser Glu Asp Cys Pro Pro Arg
705                 710                 715                 720

Met Tyr Ser Leu Met Thr Glu Cys Trp Asn Glu Ile Pro Ser Arg Arg
                725                 730                 735

Pro Arg Phe Lys Asp Ile His Val Arg Leu Arg Ser Trp Glu Gly Leu
            740                 745                 750

Ser Ser His Thr Ser Ser Thr Thr Pro Ser Gly Gly Asn Ala Thr Thr
            755                 760                 765

Gln Thr Thr Ser Leu Ser Ala Ser Pro Val Ser Asn Leu Ser Asn Pro
            770                 775                 780

Arg Tyr Pro Asn Tyr Met Phe Pro Ser Gln Gly Ile Thr Pro Gln Gly
785                 790                 795                 800

Gln Ile Ala Gly Phe Ile Gly Pro Pro Ile Pro Gln Asn Gln Arg Phe
                805                 810                 815

Ile Pro Ile Asn Gly Tyr Pro Ile Pro Pro Gly Tyr Ala Ala Phe Pro
            820                 825                 830

Ala Ala His Tyr Gln Pro Thr Gly Pro Pro Arg Val Ile Gln His Cys
            835                 840                 845

Pro Pro Pro Lys Ser Arg Ser Pro Ser Ser Ala Ser Gly Ser Thr Ser
            850                 855                 860

Thr Gly His Val Thr Ser Leu Pro Ser Ser Gly Ser Asn Gln Glu Ala
865                 870                 875                 880

Asn Ile Pro Leu Leu Pro His Met Ser Ile Pro Asn His Pro Gly Gly
                885                 890                 895

Met Gly Ile Thr Val Phe Gly Asn Lys Ser Gln Lys Pro Tyr Lys Ile
                900                 905                 910

Asp Ser Lys Gln Ala Ser Leu Leu Gly Asp Ala Asn Ile His Gly His
            915                 920                 925

Thr Glu Ser Met Ile Ser Ala Glu Leu
            930                 935

<210> SEQ ID NO 21
<211> LENGTH: 393
<212> TYPE: PRT
<213> ORGANISM: Homo sapiens

<400> SEQUENCE: 21

Met His Arg Pro Arg Arg Arg Gly Thr Arg Pro Pro Leu Leu Ala Leu
1               5                   10                  15

Leu Ala Ala Leu Leu Ala Ala Arg Gly Ala Ala Ala Gln Glu Thr
            20                  25                  30

Glu Leu Ser Val Ser Ala Glu Leu Val Pro Thr Ser Ser Trp Asn Ile
            35                  40                  45

Ser Ser Glu Leu Asn Lys Asp Ser Tyr Leu Thr Leu Asp Glu Pro Met
            50                  55                  60

Asn Asn Ile Thr Thr Ser Leu Gly Gln Thr Ala Glu Leu His Cys Lys
65                  70                  75                  80

Val Ser Gly Asn Pro Pro Pro Thr Ile Arg Trp Phe Lys Asn Asp Ala
                85                  90                  95

Pro Val Val Gln Glu Pro Arg Arg Leu Ser Phe Arg Ser Thr Ile Tyr
            100                 105                 110

Gly Ser Arg Leu Arg Ile Arg Asn Leu Asp Thr Thr Asp Thr Gly Tyr
        115                 120                 125

Phe Gln Cys Val Ala Thr Asn Gly Lys Glu Val Val Ser Ser Thr Gly
        130                 135                 140

Val Leu Phe Val Lys Phe Gly Pro Pro Thr Ala Ser Pro Gly Tyr
145                 150                 155                 160

Ser Asp Glu Tyr Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
                180                 185                 190

His Met Gln Gly Glu Ile Glu Asn Gln Ile Thr Ala Ala Phe Thr Met
        195                 200                 205

Ile Gly Thr Ser Ser His Leu Ser Asp Lys Cys Ser Gln Phe Ala Ile
        210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
                260                 265                 270

Ile Leu Met Arg Leu Lys Leu Pro Asn Cys Glu Asp Leu Pro Gln Pro
        275                 280                 285

Glu Ser Pro Glu Ala Ala Asn Cys Ile Arg Ile Gly Ile Pro Met Ala
        290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
                340                 345                 350

Pro Glu Leu Asn Gly Gly His Ser Tyr Cys Arg Asn Pro Gly Asn Gln
        355                 360                 365

Lys Glu Ala Pro Trp Cys Phe Thr Leu Asp Glu Asn Phe Lys Ser Asp
        370                 375                 380

Leu Cys Asp Ile Pro Ala Cys Gly Lys
385                 390

<210> SEQ ID NO 22
<211> LENGTH: 874
<212> TYPE: PRT
<213> ORGANISM: Homo sapiens

<400> SEQUENCE: 22

Met Asn Asn Ile Thr Thr Ser Leu Gly Gln Thr Ala Glu Leu His Cys
1               5                   10                  15

Lys Val Ser Gly Asn Pro Pro Thr Ile Arg Trp Phe Lys Asn Asp
                20                  25                  30

Ala Pro Val Val Gln Glu Pro Arg Arg Leu Ser Phe Arg Ser Thr Ile
            35                  40                  45

Tyr Gly Ser Arg Leu Arg Ile Arg Asn Leu Asp Thr Thr Asp Thr Gly
        50                  55                  60

Tyr Phe Gln Cys Val Ala Thr Asn Gly Lys Glu Val Val Ser Ser Thr
65                  70                  75                  80

Gly Val Leu Phe Val Lys Phe Gly Pro Pro Thr Ala Ser Pro Gly

-continued

```
                    85                  90                  95
Tyr Ser Asp Glu Tyr Glu Glu Asp Gly Phe Cys Gln Pro Tyr Arg Gly
                100                 105                 110
Ile Ala Cys Ala Arg Phe Ile Gly Asn Arg Thr Val Tyr Met Glu Ser
                115                 120                 125
Leu His Met Gln Gly Glu Ile Glu Asn Gln Ile Thr Ala Ala Phe Thr
            130                 135                 140
Met Ile Gly Thr Ser Ser His Leu Ser Asp Lys Cys Ser Gln Phe Ala
145                 150                 155                 160
Ile Pro Ser Leu Cys His Tyr Ala Phe Pro Tyr Cys Asp Glu Thr Ser
                165                 170                 175
Ser Val Pro Lys Pro Arg Asp Leu Cys Arg Asp Cys Glu Ile Leu
                180                 185                 190
Glu Asn Val Leu Cys Gln Thr Glu Tyr Ile Phe Ala Arg Ser Asn Pro
                195                 200                 205
Met Ile Leu Met Arg Leu Lys Leu Pro Asn Cys Glu Asp Leu Pro Gln
            210                 215                 220
Pro Glu Ser Pro Glu Ala Ala Asn Cys Ile Arg Ile Gly Ile Pro Met
225                 230                 235                 240
Ala Asp Pro Ile Asn Lys Asn His Lys Cys Tyr Asn Ser Thr Gly Val
                    245                 250                 255
Asp Tyr Arg Gly Thr Val Ser Val Thr Lys Ser Gly Arg Gln Cys Gln
                260                 265                 270
Pro Trp Asn Ser Gln Tyr Pro His Thr His Thr Phe Thr Ala Leu Arg
                275                 280                 285
Phe Pro Glu Leu Asn Gly Gly His Ser Tyr Cys Arg Asn Pro Gly Asn
            290                 295                 300
Gln Lys Glu Ala Pro Trp Cys Phe Thr Leu Asp Glu Asn Phe Lys Ser
305                 310                 315                 320
Asp Leu Cys Asp Ile Pro Ala Cys Asp Ser Lys Asp Ser Lys Glu Lys
                    325                 330                 335
Asn Lys Met Glu Ile Leu Tyr Ile Leu Val Pro Ser Val Ala Ile Pro
                340                 345                 350
Leu Ala Ile Ala Leu Leu Phe Phe Phe Ile Cys Val Cys Arg Asn Asn
                355                 360                 365
Gln Lys Ser Ser Ser Ala Pro Val Gln Arg Gln Pro Lys His Val Arg
            370                 375                 380
Gly Gln Asn Val Glu Met Ser Met Leu Asn Ala Tyr Lys Pro Lys Ser
385                 390                 395                 400
Lys Ala Lys Glu Leu Pro Leu Ser Ala Val Arg Phe Met Glu Glu Leu
                    405                 410                 415
Gly Glu Cys Ala Phe Gly Lys Ile Tyr Lys Gly His Leu Tyr Leu Pro
                420                 425                 430
Gly Met Asp His Ala Gln Leu Val Ala Ile Lys Thr Leu Lys Asp Tyr
                435                 440                 445
Asn Asn Pro Gln Gln Trp Thr Glu Phe Gln Gln Glu Ala Ser Leu Met
            450                 455                 460
Ala Glu Leu His His Pro Asn Ile Val Cys Leu Leu Gly Ala Val Thr
465                 470                 475                 480
Gln Glu Gln Pro Val Cys Met Leu Phe Glu Tyr Ile Asn Gln Gly Asp
                    485                 490                 495
Leu His Glu Phe Leu Ile Met Arg Ser Pro His Ser Asp Val Gly Cys
                500                 505                 510
```

Ser Ser Asp Glu Asp Gly Thr Val Lys Ser Ser Leu Asp His Gly Asp
    515                 520                 525

Phe Leu His Ile Ala Ile Gln Ile Ala Ala Gly Met Glu Tyr Leu Ser
530                 535                 540

Ser His Phe Phe Val His Lys Asp Leu Ala Ala Arg Asn Ile Leu Ile
545                 550                 555                 560

Gly Glu Gln Leu His Val Lys Ile Ser Asp Leu Gly Leu Ser Arg Glu
                565                 570                 575

Ile Tyr Ser Ala Asp Tyr Tyr Arg Val Gln Ser Lys Ser Leu Leu Pro
            580                 585                 590

Ile Arg Trp Met Pro Pro Glu Ala Ile Met Tyr Gly Lys Phe Ser Ser
        595                 600                 605

Asp Ser Asp Ile Trp Ser Phe Gly Val Val Leu Trp Glu Ile Phe Ser
    610                 615                 620

Phe Gly Leu Gln Pro Tyr Tyr Gly Phe Ser Asn Gln Glu Val Ile Glu
625                 630                 635                 640

Met Val Arg Lys Arg Gln Leu Leu Pro Cys Ser Glu Asp Cys Pro Pro
                645                 650                 655

Arg Met Tyr Ser Leu Met Thr Glu Cys Trp Asn Glu Ile Pro Ser Arg
            660                 665                 670

Arg Pro Arg Phe Lys Asp Ile His Val Arg Leu Arg Ser Trp Glu Gly
        675                 680                 685

Leu Ser Ser His Thr Ser Ser Thr Thr Pro Ser Gly Gly Asn Ala Thr
    690                 695                 700

Thr Gln Thr Thr Ser Leu Ser Ala Ser Pro Val Ser Asn Leu Ser Asn
705                 710                 715                 720

Pro Arg Tyr Pro Asn Tyr Met Phe Pro Ser Gln Gly Ile Thr Pro Gln
                725                 730                 735

Gly Gln Ile Ala Gly Phe Ile Gly Pro Pro Ile Pro Gln Asn Gln Arg
            740                 745                 750

Phe Ile Pro Ile Asn Gly Tyr Pro Ile Pro Gly Tyr Ala Ala Phe
        755                 760                 765

Pro Ala Ala His Tyr Gln Pro Thr Gly Pro Pro Arg Val Ile Gln His
    770                 775                 780

Cys Pro Pro Pro Lys Ser Arg Ser Pro Ser Ala Ser Gly Ser Thr
785                 790                 795                 800

Ser Thr Gly His Val Thr Ser Leu Pro Ser Ser Gly Ser Asn Gln Glu
                805                 810                 815

Ala Asn Ile Pro Leu Leu Pro His Met Ser Ile Pro Asn His Pro Gly
            820                 825                 830

Gly Met Gly Ile Thr Val Phe Gly Asn Lys Ser Gln Lys Pro Tyr Lys
        835                 840                 845

Ile Asp Ser Lys Gln Ala Ser Leu Leu Gly Asp Ala Asn Ile His Gly
    850                 855                 860

His Thr Glu Ser Met Ile Ser Ala Glu Leu
865                 870

<210> SEQ ID NO 23
<211> LENGTH: 254
<212> TYPE: PRT
<213> ORGANISM: Homo sapiens

<400> SEQUENCE: 23

Met Trp Gln Leu Leu Leu Pro Thr Ala Leu Leu Leu Leu Val Ser Ala

```
            1               5                  10                 15
        Gly Met Arg Thr Glu Asp Leu Pro Lys Ala Val Val Phe Leu Glu Pro
                        20                  25                  30

Gln Trp Tyr Arg Val Leu Glu Lys Asp Ser Val Thr Leu Lys Cys Gln
                    35                  40                  45

Gly Ala Tyr Ser Pro Glu Asp Asn Ser Thr Gln Trp Phe His Asn Glu
                50                  55                  60

Ser Leu Ile Ser Ser Gln Ala Ser Ser Tyr Phe Ile Asp Ala Ala Thr
        65                  70                  75                  80

Val Asp Asp Ser Gly Glu Tyr Arg Cys Gln Thr Asn Leu Ser Thr Leu
                        85                  90                  95

Ser Asp Pro Val Gln Leu Glu Val His Ile Gly Trp Leu Leu Leu Gln
                    100                 105                 110

Ala Pro Arg Trp Val Phe Lys Glu Glu Asp Pro Ile His Leu Arg Cys
                115                 120                 125

His Ser Trp Lys Asn Thr Ala Leu His Lys Val Thr Tyr Leu Gln Asn
            130                 135                 140

Gly Lys Gly Arg Lys Tyr Phe His His Asn Ser Asp Phe Tyr Ile Pro
        145                 150                 155                 160

Lys Ala Thr Leu Lys Asp Ser Gly Ser Tyr Phe Cys Arg Gly Leu Phe
                        165                 170                 175

Gly Ser Lys Asn Val Ser Ser Glu Thr Val Asn Ile Thr Ile Thr Gln
                    180                 185                 190

Gly Leu Ala Val Ser Thr Ile Ser Ser Phe Phe Pro Pro Gly Tyr Gln
                195                 200                 205

Val Ser Phe Cys Leu Val Met Val Leu Leu Phe Ala Val Asp Thr Gly
            210                 215                 220

Leu Tyr Phe Ser Val Lys Thr Asn Ile Arg Ser Ser Thr Arg Asp Trp
        225                 230                 235                 240

Lys Asp His Lys Phe Lys Trp Arg Lys Asp Pro Gln Asp Lys
                        245                 250

<210> SEQ ID NO 24
<211> LENGTH: 254
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Met Trp Gln Leu Leu Leu Pro Thr Ala Leu Leu Leu Leu Val Ser Ala
1               5                  10                 15

Gly Met Arg Thr Glu Asp Leu Pro Lys Ala Val Val Phe Leu Glu Pro
                    20                  25                  30

Gln Trp Tyr Arg Val Leu Glu Lys Asp Ser Val Thr Leu Lys Cys Gln
                35                  40                  45

Gly Ala Tyr Ser Pro Glu Asp Asn Ser Thr Gln Trp Phe His Asn Glu
            50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                    85                  90                  95

Ser Asp Pro Val Gln Leu Glu Val His Ile Gly Trp Leu Leu Leu Gln
                100                 105                 110
```

Ala Pro Arg Trp Val Phe Lys Glu Glu Asp Pro Ile His Leu Arg Cys
         115                 120                 125

His Ser Trp Lys Asn Thr Ala Leu His Lys Val Thr Tyr Leu Gln Asn
     130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
             180                 185                 190

Gly Leu Ala Val Ser Thr Ile Ser Ser Phe Phe Pro Pro Gly Tyr Gln
             195                 200                 205

Val Ser Phe Cys Leu Val Met Val Leu Leu Phe Ala Val Asp Thr Gly
         210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 25
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
agggcaagtc aggacattag taaa                                          24

<210> SEQ ID NO 26
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Arg Ala Ser Gln Asp Ile Ser Lys
1               5

<210> SEQ ID NO 27
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
atctaccata catcaagatt a                                             21

<210> SEQ ID NO 28
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 28

Ile Tyr His Thr Ser Arg Leu
1               5

<210> SEQ ID NO 29
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
caacagggta atacgcttcc gtacacg                                        27

<210> SEQ ID NO 30
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Gln Gln Gly Asn Thr Leu Pro Tyr Thr
1               5

<210> SEQ ID NO 31
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
ggggtctcat tacccgacta tggtgtaagc                                     30

<210> SEQ ID NO 32
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gly Val Ser Leu Pro Asp Tyr Gly Val Ser
1               5                   10

<210> SEQ ID NO 33
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
gtaatatggg gtagtgaaac cacatactat aattcagctc tc                       42

<210> SEQ ID NO 34
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Val Ile Trp Gly Ser Glu Thr Thr Tyr Tyr Asn Ser Ala Leu
1               5                   10

<210> SEQ ID NO 35
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
cattattact acggtggtag ctatgctatg gactac                              36

<210> SEQ ID NO 36
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

His Tyr Tyr Tyr Gly Gly Ser Tyr Ala Met Asp Tyr
1               5                   10

<210> SEQ ID NO 37
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37
gacatccaga tgacacagac tacatcctcc ctgtctgcct ctctgggaga cagagtcacc      60
atcagttgca gggcaagtca ggacattagt aaatatttaa attggtatca gcagaaacca     120
gatggaactg ttaaactcct gatctaccat acatcaagat tacactcagg agtcccatca     180
aggttcagtg gcagtgggtc tggaacagat tattctctca ccattagcaa cctggagcaa     240
gaagatattg ccacttactt tgccaacag ggtaatacgc ttccgtacac gttcggaggg      300
gggactaagt tggaaataac a                                               321

<210> SEQ ID NO 38
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

```
Asp Ile Gln Met Thr Gln Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
            35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65              70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105
```

```
<210> SEQ ID NO 39
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 39
gaggtgaaac tgcaggagtc aggacctggc ctggtggcgc cctcacagag cctgtccgtc      60
acatgcactg tctcaggggt ctcattaccc gactatggtg taagctggat tcgccagcct    120
ccacgaaagg gtctggagtg gctgggagta atatgggta gtgaaaccac atactataat     180
tcagctctca aatccagact gaccatcatc aaggacaact ccaagagcca agttttctta    240
aaaatgaaca gtctgcaaac tgatgacaca gccatttact actgtgccaa acattattac    300
tacggtggta gctatgctat ggactactgg ggtcaaggaa cctcagtcac cgtctcctca    360
```

```
<210> SEQ ID NO 40
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
            35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65              70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110
```

Gly Thr Ser Val Thr Val Ser Ser
        115                 120

<210> SEQ ID NO 41
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
aaaagcagcc agagcctggt gcatagcaac ggcaacacct atctgcat                    48

<210> SEQ ID NO 42
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Lys Ser Ser Gln Ser Leu Val His Ser Asn Gly Asn Thr Tyr Leu His
1               5                   10                  15

<210> SEQ ID NO 43
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
aaagtgagca accgctttag c                                                 21

<210> SEQ ID NO 44
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Lys Val Ser Asn Arg Phe Ser
1               5

<210> SEQ ID NO 45
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
gcggaaacca gccatgtgcc gtggacc                                           27

<210> SEQ ID NO 46
<211> LENGTH: 9
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Ala Glu Thr Ser His Val Pro Trp Thr
1               5

<210> SEQ ID NO 47
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
aaagcgagcg gctatagctt tccggattat tatattaac                          39

<210> SEQ ID NO 48
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Lys Ala Ser Gly Tyr Ser Phe Pro Asp Tyr Tyr Ile Asn
1               5                   10

<210> SEQ ID NO 49
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
tggatttatt ttgcgagcgg caacagcgaa tataaccaga aatttaccgg c            51

<210> SEQ ID NO 50
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Trp Ile Tyr Phe Ala Ser Gly Asn Ser Glu Tyr Asn Gln Lys Phe Thr
1               5                   10                  15

Gly

<210> SEQ ID NO 51
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 51
ctgtatgatt atgattggta ttttgatgtg                                    30

<210> SEQ ID NO 52
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Leu Tyr Asp Tyr Asp Trp Tyr Phe Asp Val
1               5                   10

<210> SEQ ID NO 53
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 53
caggtgcagc tggtgcagag cggcgcggaa gtgaaaaaac cgggcgcgag cgtgaaagtg       60
agctgcaaag cgagcggcta tagctttccg gattattata ttaactgggt gcgccaggcg      120
ccgggccagg gcctggaatg gatgggctgg atttattttg cgagcggcaa cagcgaatat      180
aaccagaaat ttaccggccg cgtgaccatg acccgcgata ccagcagcag caccgcgtat      240
atggaactga gcagcctgcg cagcgaagat accgcggtgt atttttgcgc gagcctgtat      300
gattatgatt ggtatttga tgtgtggggc cagggcacca tggtgaccgt gagcagc         357

<210> SEQ ID NO 54
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Pro Asp Tyr
            20                  25                  30

Tyr Ile Asn Trp Val Arg Gln Ala Pro Gly Gln Gly Leu Glu Trp Met
        35                  40                  45

Gly Trp Ile Tyr Phe Ala Ser Gly Asn Ser Glu Tyr Asn Gln Lys Phe
    50                  55                  60

Thr Gly Arg Val Thr Met Thr Arg Asp Thr Ser Ser Ser Thr Ala Tyr
65                  70                  75                  80

Met Glu Leu Ser Ser Leu Arg Ser Glu Asp Thr Ala Val Tyr Phe Cys
                85                  90                  95

Ala Ser Leu Tyr Asp Tyr Asp Trp Tyr Phe Asp Val Trp Gly Gln Gly
            100                 105                 110

Thr Met Val Thr Val Ser Ser

<210> SEQ ID NO 55
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 55

```
gatattgtga tgacccagac cccgctgagc ctgagcgtga ccccgggcga accggcgagc    60
attagctgca aaagcagcca gagcctggtg catagcaacg gcaacaccta tctgcattgg   120
tatctgcaga aaccgggcca gagcccgcag ctgctgattt ataaagtgag caaccgcttt   180
agcggcgtgc cggatcgctt tagcggcagc ggcagcggcg cggattttac cctgaaaatt   240
agccgcgtgg aagcggaaga tgtgggcgtg tattattgcg cggaaaccag ccatgtgccg   300
tggacctttg gccagggcac caaactggaa attaaaagc                          339
```

<210> SEQ ID NO 56
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 56

Asp Ile Val Met Thr Gln Thr Pro Leu Ser Leu Ser Val Thr Pro Gly
1               5                   10                  15

Glu Pro Ala Ser Ile Ser Cys Lys Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Ala Asp Phe Thr Leu Lys Ile
65                  70                  75                  80

Ser Arg Val Glu Ala Glu Asp Val Gly Val Tyr Tyr Cys Ala Glu Thr
                85                  90                  95

Ser His Val Pro Trp Thr Phe Gly Gln Gly Thr Lys Leu Glu Ile Lys
            100                 105                 110

Ser

<210> SEQ ID NO 57
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 57

Gln Asp Ile His Gly Tyr
1               5

<210> SEQ ID NO 58
<211> LENGTH: 3

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Tyr Thr Ser
1

<210> SEQ ID NO 59
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Gln Gln Gly Asn Thr Leu Pro Trp Thr
1               5

<210> SEQ ID NO 60
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Gly Phe Ala Phe Ser Ile Tyr Asp
1               5

<210> SEQ ID NO 61
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Ile Ser Ser Gly Gly Gly Thr Thr
1               5

<210> SEQ ID NO 62
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Ala Arg His Ser Gly Tyr Gly Thr His Trp Gly Val Leu Phe Ala Tyr
1               5                   10                  15

<210> SEQ ID NO 63
<211> LENGTH: 229
<212> TYPE: PRT
<213> ORGANISM: Artificial Sequence
<220> FEATURE:
<221> NAME/KEY: source
```

<223> OTHER INFORMATION: /note="Description of Artificial Sequence:
    Synthetic polypeptide"

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Trp Ser Tyr
            20                  25                  30

Leu Asn Trp Tyr Gln Gln Arg Pro Gly Lys Ala Pro Asn Leu Leu Ile
        35                  40                  45

Tyr Ala Ala Ser Ser Leu Gln Ser Gly Val Pro Ser Arg Phe Ser Gly
50                  55                  60

Arg Gly Ser Gly Thr Asp Phe Thr Leu Thr Ile Ser Ser Leu Gln Ala
65                  70                  75                  80

Glu Asp Phe Ala Thr Tyr Tyr Cys Gln Gln Ser Tyr Ser Ile Pro Gln
                85                  90                  95

Thr Phe Gly Gln Gly Thr Lys Leu Glu Ile Lys Glu Val Gln Leu Val
            100                 105                 110

Glu Ser Gly Gly Gly Leu Val Lys Pro Gly Gly Ser Leu Lys Leu Ser
        115                 120                 125

Cys Ala Ala Ser Gly Phe Ala Phe Ser Ile Tyr Asp Met Ser Trp Val
130                 135                 140

Arg Gln Thr Pro Glu Lys Arg Leu Glu Trp Val Ala Tyr Ile Ser Ser
145                 150                 155                 160

Gly Gly Gly Thr Thr Tyr Tyr Pro Asp Thr Val Lys Gly Arg Phe Thr
                165                 170                 175

Ile Ser Arg Asp Asn Ala Lys Asn Thr Leu Tyr Leu Gln Met Ser Ser
            180                 185                 190

Leu Lys Ser Glu Asp Thr Ala Met Tyr Tyr Cys Ala Arg His Ser Gly
        195                 200                 205

Tyr Gly Thr His Trp Gly Val Leu Phe Ala Tyr Trp Gln Gly Thr Leu
210                 215                 220

Val Thr Val Ser Ala
225

<210> SEQ ID NO 64
<211> LENGTH: 469
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 64

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Val Thr Gly Asp Leu Glu Asp Ala Phe Asp
            100                 105                 110

Ile Trp Gly Gln Gly Thr Met Val Thr Val Ser Ser Gly Gly Ser Leu
        115                 120                 125

Ala Ala Leu Thr Ala His Gln Ala Cys His Leu Pro Leu Glu Thr Phe
    130                 135                 140

Thr Arg His Arg Gln Pro Arg Gly Trp Glu Gln Leu Glu Gln Cys Gly
145                 150                 155                 160

Tyr Pro Val Gln Arg Leu Val Ala Leu Tyr Leu Ala Ala Arg Leu Ser
                165                 170                 175

Trp Asn Gln Val Asp Gln Val Ile Arg Asn Ala Leu Ala Ser Pro Gly
            180                 185                 190

Ser Gly Gly Asp Leu Gly Glu Ala Ile Arg Glu Gln Pro Glu Gln Ala
        195                 200                 205

Arg Leu Ala Leu Thr Leu Ala Ala Ala Glu Ser Glu Arg Phe Val Arg
    210                 215                 220

Gln Gly Thr Gly Asn Asp Glu Ala Gly Ala Ala Asn Gly Pro Ala Asp
225                 230                 235                 240

Ser Gly Asp Ala Leu Leu Glu Arg Asn Tyr Pro Thr Gly Ala Glu Phe
                245                 250                 255

Leu Gly Asp Gly Gly Asp Val Ser Phe Ser Thr Arg Gly Thr Gln Asn
            260                 265                 270

Trp Thr Val Glu Arg Leu Leu Gln Ala His Arg Gln Leu Glu Glu Arg
        275                 280                 285

Gly Tyr Val Phe Val Gly Tyr His Gly Thr Phe Leu Glu Ala Ala Gln
    290                 295                 300

Ser Ile Val Phe Gly Gly Val Arg Ala Arg Ser Gln Asp Leu Asp Ala
305                 310                 315                 320

Ile Trp Arg Gly Phe Tyr Ile Ala Gly Asp Pro Ala Leu Ala Tyr Gly
                325                 330                 335

Tyr Ala Gln Asp Gln Glu Pro Asp Ala Ala Gly Arg Ile Arg Asn Gly
            340                 345                 350

Ala Leu Leu Arg Val Tyr Val Pro Arg Ser Ser Leu Pro Gly Phe Tyr
        355                 360                 365

Arg Thr Ser Leu Thr Leu Ala Ala Pro Glu Ala Ala Gly Glu Val Glu
    370                 375                 380

Arg Leu Ile Gly His Pro Leu Pro Leu Arg Leu Asp Ala Ile Thr Gly
385                 390                 395                 400

Pro Glu Glu Glu Gly Gly Arg Leu Glu Thr Ile Leu Gly Trp Pro Leu
                405                 410                 415

Ala Glu Arg Thr Val Val Ile Pro Ser Ala Ile Pro Thr Asp Pro Arg
            420                 425                 430

Asn Val Gly Gly Asp Leu Asp Pro Ser Ser Ile Pro Asp Lys Glu Gln
        435                 440                 445

Ala Ile Ser Ala Leu Pro Asp Tyr Ala Ser Gln Pro Gly Lys Pro Pro
    450                 455                 460

Arg Glu Asp Leu Lys
465

<210> SEQ ID NO 65
<211> LENGTH: 729
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 65

```
gaagtgcagc tgctggaaag cggcggtggt ctggttcagc cgggtggcag cctgcgtctg      60
agctgtgcgg cgagcggctt tacctttagc agctatgcca tgagctgggt gcgtcaggca     120
ccgggtaaag gcctggaatg ggtgagcgcg attagcggca gcggcggcag cacctattat     180
gcggatagcg tgaaaggccg ttttaccatt agccgtgata acagcaaaaa caccctgtat     240
ctgcagatga acagcctgcg tgcggaagat accgcggtgt attattgcgc gaaagataag     300
ggttggttta actggcaatt cgattattgg ggccagggca ccctggttac cgttagcagc     360
ggtggaggcg gttctggtgg aggcggttcg gatggcggag gttcagaaat tgtgctgacc     420
cagagcccgg gcacgctgtc tctgagcccg ggtgaacgtg cgaccctgag ctgtcgtgcg     480
agccaaagcg tgagcagcag ctatctggcc tggtatcagc agaaaccggg ccaggcaccg     540
cgtctgctga tttatggcgc gagcagccgt gcgaccggca ttccggatcg ttttagcggc     600
agcggtagcg gcaccgattt taccctgacc attagccgtc tggaaccgga agattttgcg     660
gtgtattatt gccagcagta tggcagcagc ccgtggacct ttggccaggg caccaaagtg     720
gaaattaaa                                                             729
```

<210> SEQ ID NO 66
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66

```
ggtggaggcg gttctggtgg aggcggttcg gatggcggag gttca                      45
```

<210> SEQ ID NO 67
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 67

```
gaagtgcaac ttctcgagag cggtggggga ctcgtccagc cgggaggttc cctgcgactc      60
agctgtgcag cctcaggctt tacctttcc agttacgcaa tgagttgggt ccggcaggcg     120
cctggtaaag gactcgagtg ggtgagtgca atcagcggaa gtggcgggtc tacatactat     180
gcggactctg ttaaaggcag gttcactatt tcaaggaca attccaagaa cacgctctac     240
ctgcagatga atagccttag agctgaagac acggccgtgt actattgtgc caaagacaag     300
ggatggttca actggcagtt cgactactgg gggcagggaa ctctcgtcac cgtgagctcc     360
```

<210> SEQ ID NO 68
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 68

```
gaaattgttc tcacacagtc acccggaacc ctttcattgt cccccggcga gcgcgccacc    60
ctcagctgtc gggccagtca gagcgtgtct agctcttacc tggcctggta ccagcagaaa   120
cctgggcaag ctcccagact cctgatatat ggggccagca gccgggccac tggcattccg   180
gacaggttta gtggatcagg ctctggcact gatttacac tgacgatttc aaggttggaa   240
cccgaagact cgcagtgta ctattgtcag cagtatgggc tagcccgtg gactttcggg   300
caaggcacca aggtggaaat caag                                          324
```

<210> SEQ ID NO 69
<211> LENGTH: 717
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 69

```
gaagtgcagc tgctggaaag cggcggtggt ctggttcagc cgggtggcag cctgcgtctg    60
agctgtgcgg cgagcggctt tacctttagc agctatgcca tgagctgggt gcgtcaggca   120
ccgggtaaag gcctggaatg ggtgagcgcg attagcggca gcggcggcag cacctattat   180
gcggatagcg tgaaaggccg ttttaccatt agccgtgata acagcaaaaa caccctgtat   240
ctgcagatga acagcctgcg tgcggaagat accgcggtgt attattgcgc gaaaaaacaa   300
tatcacttcg attattgggg ccaggcaccc ctggttaccg ttagcagcgg tggaggcggt   360
tctggtggag gcggttcggg tggcggaggt tcagaaattg tgctgaccca gagcccgggc   420
acgctgtctc tgagcccggg tgaacgtgcg accctgagct gtcgtgcgag ccagagcgtg   480
agcagcagct atctggcctg gtatcagcag aaaccgggcc aggcaccgcg tctgctgatt   540
tatggcgcga gcagccgtgc gaccggcatt ccggatcgtt ttagcggcag cggtagcggc   600
accgattta ccctgaccat tagccgtctg gaaccggaag attttgcggt gtattattgc   660
cagcagtatg gcagcagccc gtggaccttt ggccagggca ccaaagtgga aattaaa     717
```

<210> SEQ ID NO 70
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 70

```
gaagtgcaac ttctcgagag cggtgggga ctcgtccagc cgggaggttc cctgcgactc    60
agctgtgcag cctcaggctt tacctttcc agttacgcaa tgagttgggt ccggcaggcg   120
cctggtaaag gactcgagtg ggtgagtgca atcagcggaa gtggcgggtc tacatactat   180
gcggactctg ttaaaggcag gttcactatt tcaaggaca attccaagaa cacgctctac   240
ctgcagatga atagccttag agctgaagac acggccgtgt actattgtgc caaaaagcag   300
taccatttcg actactgggg gcagggaact ctcgtcaccg tgagctcc               348
```

<210> SEQ ID NO 71
<211> LENGTH: 324
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 71

```
gaaattgttc tcacacagtc acccggaacc ctttcattgt cccccggcga gcgcgccacc    60
ctcagctgtc gggccagtca gagcgtgtct agctcttacc tggcctgta ccagcagaaa    120
cctgggcaag ctcccagact cctgatatat ggggccagca gccgggccac tggcattccg    180
gacaggttta gtggatcagg ctctggcact gattttacac tgacgatttc aaggttggaa    240
cccgaagact tcgcagtgta ctattgtcag cagtatgggt ctagcccgtg gactttcggg    300
caaggcacca aggtggaaat caag                                          324
```

<210> SEQ ID NO 72
<211> LENGTH: 738
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 72

```
cagtctgccc tgactcagcc tgcctccgtg tctgggtctc ctggacagtc gatcaccatc    60
tcctgcactg gaaccagcag tgacgttggt ggttataact atgtctcctg gtaccaacag    120
cacccaggca aagcccccaa agtcatgatt tatgatgtca gtaatcggcc ctcagggggtt    180
tctgatcgct tctctggctc caagtctggc aacacggcct ccctgaccat ctctgggctc    240
caggttgagg acgaggctga ttattactgc agctcatatt caaccagcat caccccagtt    300
ttcggcgggg ggaccaagct caccgtccta ggagagggta atcttccgg atctggttcc    360
gaaagcaagg ctagccaggt ccagctggtg cagtctggag cagaggtgaa aaagcccggg    420
gagtctctga gatctcctg tgaggcttct ggatacagct ttaccagcta ctggatcggc    480
tgggtgcgcc agatgcccgg gaaaggcctg gagtggatgg ggatcatcta tcctggtgac    540
tctgatacca gatacagccc gtccttccaa ggccaggtca ccatctcagc cgacaagtcc    600
atcagcaccg cctacctgca gtggagcagc ctgaaggcct cggacaccgc catgtattac    660
tgtgcgagac tggaactcgg ttactactac tacggtatgg acgtctgggg ccaaggaacc    720
acggtcaccg tctcctca                                                 738
```

<210> SEQ ID NO 73
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 73

```
ggagagggta atcttccgg atctggttcc gaaagcaagg ctagc                     45
```

<210> SEQ ID NO 74
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 74
cagtcagctc tgacccaacc tgcctccgtc tctgggagtc caggccagag tatcacaatt     60
tcttgtacag gcacctcatc tgatgtcggc ggttacaatt acgttagttg gtatcagcaa    120
catccaggta aggctccaaa ggtgatgatc tatgacgtct caaatagacc ctctggcgtc    180
agcgacaggt ttagtggtag caaatccggg aacacagctt cacttacaat tagcggcctc    240
caagtagaag acgaagctga ctattactgc tctagttatt caacgtcaat tacccctgtg    300
tttggtggcg gtacaaaact cacagtgctt                                     330

<210> SEQ ID NO 75
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 75
caagtgcaac ttgtgcaatc aggagctgaa gtcaaaaagc cgggagaatc cctgaaaata     60
agctgcgaag caagtggtta ctcttttact tcttactgga ttggatgggt cggcagatg    120 cccggaaagg gactcgagtg gatgggaatt atttaccctg agacagcga cacaagatac    180 agcccttcat tccaggggca ggtgaccatt tctgctgaca aatcaatcag tacagcctat    240
ctgcaatgga gttccctcaa agccagtgac actgctatgt attactgcgc gcgactggaa    300
ctgggatact actactacgg aatggacgta tggggacagg gaaccaccgt tactgttagt    360
agc                                                                  363

<210> SEQ ID NO 76
<211> LENGTH: 10124
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 76
ccaattaacc aattctgatt agaaaaactc atcgagcatc aaatgaaact gcaatttatt     60
cacatcagga ttatcaatac catattttg aaaaagccgt ttctgtaatg aaggagaaaa    120
ctcaccgagg cagttccata ggatggcaag atcctggtat cggtctgcga ttccgactcg    180
tccaacatca atacaaccta ttaatttccc ctcgtcaaaa ataaggttat caagtgagaa    240
atcaccatga gtgacgactg aatccggtga gaatggcaaa agtttatgca tttctttcca    300
gacttgttca acaggccagc cattacgctc gtcatcaaaa tcactcgcat caaccaaacc    360
gttattcatt cgtgattgcg cctgagcaag acgaaatacg cgatcgctgt taaaaggaca    420
attacaaaca ggaatcgaat gcaaccggcg caggaacact gccagcgcat caacaatatt    480
ttcacctgaa tcaggatatt cttctaatac ctggaatgct gttttccgg ggatcgcagt    540 ggtgagtaac catgcatcat caggagtacg gataaaatgc ttgatggtcg gaagaggcat    600
aaattccgtc agccagttta gtctgaccat ctcatctgta acatcattgg caacgctacc    660
tttgccatgt ttcagaaaca actctggcgc atcgggcttc ccatacaagc gatagattgt    720

```
cgcacctgat tgcccgacat tatcgcgagc ccatttatac ccatataaat cagcatccat    780
gttggaattt aatcgcggcc tcgacgtttc ccgttgaata tggctcataa cacccccttgt   840 attactgttt atgtaagcag acagttttat tgttcatgat gatatatttt tatcttgtgc    900
aatgtaacat cagagatttt gagacacaac gtggctttcc cccccccccc catgacatta    960
acctataaaa ataggcgtat cacgaggcca gcttgggaaa ccataagacc gagatagagt   1020
tgagtgttgt tccagtttgg aacaagagtc cactattaaa gaacgtggac tccaacgtca   1080
aagggcgaaa aaccgtctat cagggcgatg gcccactacg tgaaccatca cccaaatcaa   1140
gttttttggg gtcgaggtgc cgtaaagcac taaatcggaa ccctaaaggg agcccccgat   1200
ttagagcttg acggggaaag ccggcgaacg tggcgagaaa ggaagggaag aaagcgaaag   1260
gagcgggcgc taaggcgctg gcaagtgtag cggtcacgct gcgcgtaacc accacacccg   1320
ccgcgcttaa tgcgccgcta cagggcgcgt actatggttg ctttgacgta tgcggtgtga   1380 ataccgcac agatgcgtaa ggagaaaata ccgcatcagg cgccattcgc cattcaggct    1440
gcgcaactgt tgggaagggc gatcggtgcg ggcctcttcg ctattacgcc agctggcgaa   1500
agggggatgt gctgcaaggc gattaagttg ggtaacgcca gggttttccc agtcacgacg   1560
ttgtaaaacg acgccagtg aattgatcga gatcgtgatc cggatcaaga tccagatcga   1620
attggaggct acagtcagtg gagaggactt tcactgactg actgactgcg tctcaacctc   1680
ctaggggaca ttgattattg actagttatt aatagtaatc aattacgggg tcattagttc   1740
atagcccata tatggagttc cgcgttacat aacttacggt aaatggcccg cctggctgac   1800
cgcccaacga ccccccgccca ttgacgtcaa taatgacgta tgttcccata gtaacgccaa   1860
tagggacttt ccattgacgt caatgggtgg agtatttacg gtaaactgcc cacttggcag   1920
tacatcaagt gtatcatatg ccaagtacgc ccctattga cgtcaatgac ggtaaatggc   1980
ccgcctggca ttatgcccag tacatgacct tatgggactt tcctacttgg cagtacatct   2040
acgtattagt catcgctatt accatggtga tgcggttttg gcagtacatc aatgggcgtg   2100
gatagcggtt tgactcacgg ggatttccaa gtctccaccc cattgacgtc aatgggagtt   2160
tgttttggca ccaaaatcaa cgggactttc caaaatgtcg taacaactcc gccccattga   2220
cgcaaatggg cggtaggcgt gtacggtggg aggtctatat aagcagagct cgtttagtga   2280
accgggtctc tctggttaga ccagatctga gcctgggagc tctctggcta actagggaac   2340
ccactgctta agcctcaata aagcttgcct tgagtgctca agtagtgtg tgcccgtctg    2400 ttgtgtgact ctggtaacta gagatccctc agacccttttt agtcagtgtg gaaaatctct   2460
agcagtggcg cccgaacagg gacttgaaag cgaaagtaaa gccagaggag atctctcgac   2520
gcaggactcg gcttgctgaa gcgcgcacgg caagaggcga ggggcggcga ctggtgagta   2580
cgccaaaaat tttgactagc ggaggctaga aggagagagt agggtgcgag agcgtcggta   2640
ttaagcgggg gagaattaga taatgggaa aaaattcggt taaggccagg gggaaagaaa    2700
caatataaac taaaacatat agttagggca agcagggagc tagaacgatt cgcagttaat   2760
cctggccttt tagagacatc agaaggctgt agacaaatac tgggacagct acaaccatcc   2820
cttcagacag gatcagaaga acttagatca ttatataata caatagcagt cctctattgt   2880
gtgcatcaaa ggatagatgt aaaagacacc aaggaagcct tagataagat agaggaagag   2940
caaaacaaaa gtaagaaaaa ggcacagcaa gcgatcttca gacctggagg aggcaggagg   3000
cgatatgagg gacaattgga gaagtgaatt atataaatat aaagtagtaa aaattgaacc   3060
attaggagta gcacccacca aggcaaagag aagagtggtg cagagagaaa aaagagcagt   3120
```

```
gggaatagga gctttgttcc ttgggttctt gggagcagca ggaagcacta tgggcgcagc  3180
gtcaatgacg ctgacggtac aggccagaca attattgtct gatatagtgc agcagcagaa  3240
caatttgctg agggctattg aggcgcaaca gcatctgttg caactcacag tctggggcat  3300
caaacagctc caggcaagaa tcctggctgt ggaaagatac ctaaaggatc aacagctcct  3360
ggggatttgg ggttgctctg gaaaactcat ttgcaccact gctgtgcctt ggaatgctag  3420
ttggagtaat aaatctctgg aacagatttg gaataacatg acctggatgg agtgggacag  3480
agaaattaac aattacacaa gcttaataca ctccttaatt gaagaatcgc aaaaccagca  3540
agaaaagaat gaacaagaat tattggaatt agataaatgg gcaagtttgt ggaattggtt  3600
taacataaca aattggctgt ggtatataaa attattcata atgatagtag gaggcttggt  3660
aggtttaaga atagtttttg ctgtactttc tatagtgaat agagttaggc agggatattc  3720
accattatcg tttcagaccc acctcccaat cccgagggga ccacgcgtac aaatggcagt  3780
attcatccac aattttaaaa gaaaaggggg gattgggggg tacagtgcag gggaaagaat  3840
agtagacata atagcaacag acatacaaac taaagaatta caaaaacaaa ttacaaaaat  3900
tcaaaatttt cgggtttatt acagggacag cagaaatcca ctttggaaag ctgagcatcc  3960
ggctccggtg cccgtcagtg gcagagcgc acatcgccca cagtccccga aagttgggg  4020 ggaggggtcg gcaattgaac cggtgcctag agaaggtggc gcggggtaaa ctgggaaagt  4080
gatgtcgtgt actggctccg cctttttccc gagggtgggg gagaaccgta tataagtgca  4140
gtagtcgccg tgaacgttct ttttcgcaac gggtttgccg ccagaacaca ggtaagtgcc  4200
gtgtgtggtt cccgcgggcc tggcctcttt acgggttatg gcccttgcgt gccttgaatt  4260
acttccacgc ccctgctgc agtacgtgat tcttgatccc gagcttcggg ttggaagtgg  4320
gtgggagagt tcgaggcctt gcgcttaagg agccccttcg cctcgtgctt gagttgaggc  4380
ctggcctggg cgctgggcc gccgcgtgcg aatctggtgg caccttcgcg cctgtctcgc  4440
tgctttcgat aagtctctag ccatttaaaa tttttgatga cctgctgcga cgcttttttt  4500
ctggcaagat agtcttgtaa atgcgggcca agatctgcac actggtattt cggttttgg  4560 ggccgcgggc ggcgacgggg cccgtgcgtc ccagcgcaca tgttcggcga ggcggggcct  4620
gcgagcgcgg ccaccgagaa tcggacgggg gtagtctcaa gctggccggc ctgctctgt  4680 gcctggcctc gcgccgccgt gtatcgcccc gccctgggcg gcaaggctgg cccggtcggc  4740
accagttgcg tgagcggaaa gatggccgct tcccggccct gctgcaggga gctcaaaatg  4800
gaggacgcgc cgctcgggag agcgggcggg tgagtcaccc acacaaagga aaagggcctt  4860
tccgtcctca gccgtcgctt catgtgactc cacggagtac cgggcgccgt ccaggcacct  4920
cgattagttc tcgagctttt ggagtacgtc gtctttaggt tgggggagg ggttttatgc  4980 gatggagttt ccccacactg agtgggtgga gactgaagtt aggccagctt ggcacttgat  5040
gtaattctcc ttgaatttg ccttttttga gtttggatct tggttcattc tcaagcctca  5100
gacagtggtt caaagttttt ttcttccatt tcaggtgtcg tgaaaactac ccctctagag  5160
ccgccaccat gctcctcctc gtgactagcc ttctcctgtg cgagctccca caccctgcat  5220
tcctcctgat cccagaagtg caacttctcg agagcggtgg gggactcgtc cagccgggag  5280
gttccctgcg actcagctgt gcagcctcag ctttaccttt tccagttac gcaatgagtt  5340 gggtccggca ggcgcctggt aaaggactcg agtgggtgag tgcaatcagc ggaagtggcg  5400
ggtctacata ctatgcggac tctgttaaag gcaggttcac tatttcaagg gacaattcca  5460
```

```
agaacacgct ctacctgcag atgaatagcc ttagagctga agacacggcc gtgtactatt    5520
gtgccaaaga caagggatgg ttcaactggc agttcgacta ctgggggcag ggaactctcg    5580
tcaccgtgag ctccggcgga ggtggaagcg ggggaggggg ctccggtggt gggggatcag    5640
aaattgttct cacacagtca cccggaaccc tttcattgtc ccccggcgag cgcgccaccc    5700
tcagctgtcg ggccagtcag agcgtgtcta gctcttacct ggcctggtac cagcagaaac    5760
ctgggcaagc tcccagactc ctgatatatg gggccagcag ccgggccact ggcattccgg    5820
acaggtttag tggatcaggc tctggcactg attttacact gacgatttca aggttggaac    5880
ccgaagactt cgcagtgtac tattgtcagc agtatgggtc tagcccgtgg actttcgggc    5940
aaggcaccaa ggtggaaatc aaggcagctg ctggaggtgg gggaagtggc ggtggtggct    6000
caggcggcgg ggggagcctc gaggacggta atgaagagat gggggggcatt acacaaaccc    6060
cgtacaaggt ctctatcagt gggacgactg tgattctgac atgcccacag tatccaggtt    6120
cagaaatcct gtggcagcat aatgacaaga acatcggtgg ggatgaggat gataagaata    6180
tcggaagcga cgaagaccac ctgtctctca aagagtttag cgagctggag cagagtgggt    6240
attatgtctg ctatcctaga ggtagcaagc cagaggacgc aaacttttac ctttacctca    6300
gagccagggt ctgcgagaac tgcatggaaa tggacgtgat gagtgttgca actatagtga    6360
tagttgacat ttgcatcacc gggggtctgc tcctgctggt ttactattgg agcaagaacc    6420
gcaaggctaa agccaagcca gtaacacggg gcgcaggcgc gggaggcagg cagcgagggc    6480
agaataagga gcgcccccca cccgtcccga atccggatta cgaacccatt cggaaaggcc    6540
agagggactt gtactcaggg ctcaaccaaa gacggatcga ggggcgagga tccttgctga    6600
catgtggtga cgtggaggag aatcctggtc cttctcgcgc cgccaccatg tgtctaaag    6660
gcgaagagct gttcaccggt gtggtgccga ttccttgtaga gctggatgga gatgttaatg    6720
gtcacaagtt ttcagtgtct ggggagggcg aaggcgacgc gacctatggt aaactcacgc    6780
ttaagtttat ctgcaccaca gggaagctcc ctgttccatg gccaacccett gtgacaacac    6840
ttacttacgg cgtgcagtgt ttcagcaggt atcctgacca tatgaagcag cacgatttct    6900
tcaagtctgc aatgcccgag gggtacgtac aagagcggac aatttttcttc aaggacgacg    6960
gaaattacaa aactagggca gaggttaagt tcgaagggga tacacttgtt aataggatcg    7020
aactgaaagg cattgatttc aaggaggatg gaaacatact cgggcacaaa ctggaatata    7080
actacaattc acataatgtg tatatcatgg ctgataagca gaaaaacggt atcaaagtga    7140
actttaagat ccggcataac attgaagacg gtagcgtgca gctcgctgac cactaccagc    7200
agaacactcc aatcggggac gggccggtcc tcctgcccga caaccactac ctcagcaccc    7260
agagcgcact tagcaaagac ccaaacgaga agagagacca tatggtgctg ctggagttcg    7320
ttaccgcagc cggaatcacc ttgggcatgg acgagctcta taaatgagaa ttcgaacgga    7380
tatcgagcat cttaccgcca tttataccca tatttgttct gttttttcttg atttgggtat    7440
acatttaaat gttaataaaa caaaatggtg ggcaatcat ttacatttt agggatatgt    7500
aattactagt tcaggtgtat tgccacaaga caaacatgtt aagaaacttt cccgttattt    7560
acgctctgtt cctgttaatc aacctctgga ttacaaaatt tgtgaaagat tgactgatat    7620
tcttaactat gttgctcctt ttacgctgtg tggatatgct gctttatagc ctctgtatct    7680
agctattgct tcccgtacgg ctttcgtttt ctcctccttg tataaatcct ggttgctgtc    7740
tcttttagag gagttgtggc ccgttgtccg tcaacgtggc gtggtgtgct ctgtgtttgc    7800
tgacgcaacc cccactggct ggggcattgc caccacctgt caactccttt ctgggacttt    7860
```

```
cgctttcccc ctcccgatcg ccacggcaga actcatcgcc gcctgccttg cccgctgctg    7920 gacagggct aggttgctgg gcactgataa ttccgtggtg ttgtcagtac tggtacctttt     7980 aagaccaatg acttacaagg cagctgtaga tcttagccac ttttttaaaag aaaagggggg    8040 actggaaggg ctaattcact cccaaagaag acaagatctg cttttttgcct gtactgggtc    8100 tctctggtta gaccagatct gagcctggga gctctctggc taactaggga acccactgct    8160
taagcctcaa taaagcttgc cttgagtgct tcaatgatca taatcaagcc atatcacatc    8220
tgtagaggtt tacttgcttt aaaaaacctc cacacctccc cctgaacctg aaacataaaa    8280
tgaatgcaat tgttgttgtt aacttgttta ttgcagctta taatggttac aaataaagca    8340
atagcatcac aaatttcaca aataaagcat ttttttcact gcattctagt tgtggtttgt    8400
ccaaactcat caatgtatct tatcatgtct ggatctgcgt cgacacgaag agacgactga    8460
ctgactgact ggaagagga agggctggaa gaggaaggag cttgatccag atcccgatct    8520
cgatccagat ccggatcgca gcttggcgta atcatggtca tagctgtttc ctgtgtgaaa    8580
ttgttatccg ctcacaattc cacacaacat acgagccgga agcataaagt gtaaagcctg    8640
gggtgcctaa tgagtgagct aactcacatt aattgcgttg cgctcactgc ccgctttcca    8700
gtcgggaaac ctgtcgtgcc agctgcatta atgaatcggc caacgcgcgg ggagaggcgg    8760
tttgcgtatt gggcgctctt ccgcttcctc gctcactgac tcgctgcgct cggtcgttcg    8820
gctgcggcga gcggtatcag ctcactcaaa ggcggtaata cggttatcca cagaatcagg    8880
ggataacgca ggaaagaaca tgtgagcaaa aggccagcaa aaggccagga accgtaaaaa    8940
ggccgcgttg ctggcgtttt tccataggct ccgcccccct gacgagcatc acaaaaatcg    9000
acgctcaagt cagaggtggc gaaacccgac aggactataa agataccagg cgtttccccc    9060
tggaagctcc ctcgtgcgct ctcctgttcc gaccctgccg cttaccggat acctgtccgc    9120
ctttctccct tcgggaagcg tggcgctttc tcatagctca cgctgtaggt atctcagttc    9180
ggtgtaggtc gttcgctcca agctgggctg tgtgcacgaa ccccccgttc agcccgaccg    9240
ctgcgcctta tccggtaact atcgtcttga gtccaacccg gtaagacacg acttatcgcc    9300
actggcagca gccactggta acaggattag cagagcgagg tatgtaggcg gtgctacaga    9360
gttcttgaag tggtggccta actacggcta cactagaaga acagtatttg gtatctgcgc    9420
tctgctgaag ccagttacct tcggaaaaag agttggtagc tcttgatccg gcaaacaaac    9480
caccgctggt agcggtggtt tttttgtttg caagcagcag attacgcgca gaaaaaaggg    9540
atctcaagaa gatcctttga tcttttctac ggggtctgac gctcagtgga acgaaaactc    9600
acgttaaggg attttggtca tgagattatc aaaaggatc ttcacctaga tccttttaaa    9660
ttaaaaatga agttttaaat caatctaaag tatatatgag taaacttggt ctgacagtta    9720
ccaatgctta atcagtgagg cacctatctc agcgatctgt ctatttcgtt catccatagt    9780
tgcctgactc cccgtcgtgt agataactac gatacgggag gcttaccat ctggccccag    9840 tgctgcaatg ataccgcagc ttgggaaacc ataagagctg aagccagtta ccttcggaaa    9900
aagagttggt agctcttgat ccggcaaaca accaccgct ggtagcggtg gtttttttgt    9960
ttgcaagcag cagattacgc gcagaaaaaa aggatctcaa gaagatcctt tgatcttttc    10020
tacggggtct gacgctcagt ggaacgaaaa ctcacgttaa gggattttgg tcatgagctt    10080
gcgccgtccc gtcaagtcag cgtaatgctc tgccagtgtt acaa                    10124
```

<210> SEQ ID NO 77

<211> LENGTH: 720
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 77

```
atggtgtcta aaggcgaaga gctgttcacc ggtgtggtgc cgattcttgt agagctggat      60
ggagatgtta atggtcacaa gttttcagtg tctggggagg gcgaaggcga cgcgacctat     120
ggtaaactca cgcttaagtt tatctgcacc acagggaagc tccctgttcc atggccaacc     180
cttgtgacaa cacttactta cggcgtgcag tgtttcagca ggtatcctga ccatatgaag     240
cagcacgatt tcttcaagtc tgcaatgccc gaggggtacg tacaagagcg acaattttc      300
ttcaaggacg acggaaatta caaaactagg gcagaggtta agttcgaagg ggatacactt     360
gttaatagga tcgaactgaa aggcattgat ttcaaggagg atggaaacat actcgggcac     420
aaactggaat ataactacaa ttcacataat gtgtatatca tggctgataa gcagaaaaac     480
ggtatcaaag tgaactttaa gatccggcat aacattgaag acggtagcgt gcagctcgct     540
gaccactacc agcagaacac tccaatcggg gacgggccgg tcctcctgcc cgacaaccac     600
tacctcagca cccagagcgc acttagcaaa gacccaaacg agaagagaga ccatatggtg     660
ctgctggagt tcgttaccgc agccggaatc accttgggca tggacgagct ctataaatga     720
```

<210> SEQ ID NO 78
<211> LENGTH: 10112
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 78

```
ccaattaacc aattctgatt agaaaaactc atcgagcatc aaatgaaact gcaatttatt      60
cacatcagga ttatcaatac catattttg aaaaagccgt ttctgtaatg aaggagaaaa     120
ctcaccgagg cagttccata ggatggcaag atcctggtat cggtctgcga ttccgactcg     180
tccaacatca atacaaccta ttaatttccc ctcgtcaaaa ataaggttat caagtgagaa     240
atcaccatga gtgacgactg aatccggtga gaatggcaaa agtttatgca tttcttttcca    300
gacttgttca acaggccagc cattacgctc gtcatcaaaa tcactcgcat caaccaaacc     360
gttattcatt cgtgattgcg cctgagcaag acgaaatacg cgatcgctgt taaaaggaca     420
attacaaaca ggaatcgaat gcaaccggcg caggaacact gccagcgcat caacaatatt     480
ttcacctgaa tcaggatatt cttctaatac ctggaatgct gttttccgg ggatcgcagt      540
ggtgagtaac catgcatcat caggagtacg ataaaatgc ttgatggtcg aagaggcat      600
aaattccgtc agccagttta gtctgaccat ctcatctgta acatcattgg caacgctacc     660
tttgccatgt ttcagaaaca actctggcgc atcgggcttc ccatacaagc gatagattgt     720
cgcacctgat tgcccgacat tatcgcgagc ccatttatac ccatataaat cagcatccat     780
gttggaattt aatcgcggcc tcgacgtttc ccgttgaata tggctcataa cacccccttgt    840
attactgttt atgtaagcag acagttttat tgttcatgat gatatatttt tatcttgtgc     900
aatgtaacat cagagatttt gagacacaac gtggctttcc cccccccccc catgacatta     960
acctataaaa ataggcgtat cacgaggcca gcttgggaaa ccataagacc gagatagagt    1020
```

```
tgagtgttgt tccagtttgg aacaagagtc cactattaaa gaacgtggac tccaacgtca   1080
aagggcgaaa aaccgtctat cagggcgatg gcccactacg tgaaccatca cccaaatcaa   1140
gttttttggg gtcgaggtgc cgtaaagcac taaatcggaa ccctaaaggg agccccgat    1200 ttagagcttg acggggaaag ccggcgaacg tggcagaaa  ggaagggaag aaagcgaaag   1260
gagcgggcgc taaggcgctg gcaagtgtag cggtcacgct gcgcgtaacc accacacccg   1320
ccgcgcttaa tgcgccgcta cagggcgcgt actatggttg ctttgacgta tgcggtgtga   1380
aataccgcac agatgcgtaa ggagaaaata ccgcatcagg cgccattcgc cattcaggct   1440
gcgcaactgt tgggaagggc gatcggtgcg ggcctcttcg ctattacgcc agctggcgaa   1500
agggggatgt gctgcaaggc gattaagttg ggtaacgcca gggttttccc agtcacgacg   1560
ttgtaaaacg acggccagtg aattgatcga gatcgtgatc cggatcaaga tccagatcga   1620
attggaggct acagtcagtg gagaggactt tcactgactg actgactgcg tctcaacctc   1680 ctagggggaca ttgattattg actagttatt aatagtaatc aattacgggg tcattagttc   1740
atagcccata tatggagttc cgcgttacat aacttacggt aaatggcccg cctggctgac   1800
cgcccaacga ccccgcccca ttgacgtcaa taatgacgta tgttcccata gtaacgccaa   1860
tagggacttt ccattgacgt caatgggtgg agtatttacg gtaaactgcc cacttggcag   1920
tacatcaagt gtatcatatg ccaagtacgc ccccctattga cgtcaatgac ggtaaatggc   1980
ccgcctggca ttatgcccag tacatgacct tatgggactt tcctacttgg cagtacatct   2040
acgtattagt catcgctatt accatggtga tgcggttttg gcagtacatc aatgggcgtg   2100
gatagcggtt tgactcacgg ggatttccaa gtctccaccc cattgacgtc aatgggagtt   2160
tgttttggca ccaaaatcaa cgggactttc caaaatgtcg taacaactcc gccccattga   2220
cgcaaatggg cggtaggcgt gtacggtggg aggtctatat aagcagagct cgtttagtga   2280
accgggtctc tctggttaga ccagatctga gcctgggagc tctctggcta actagggaac   2340
ccactgctta agcctcaata aagcttgcct tgagtgctca aagtagtgtg tgcccgtctg   2400
ttgtgtgact ctggtaacta gagatccctc agacccttt  agtcagtgtg gaaaatctct   2460
agcagtggcg cccgaacagg gacttgaaag cgaaagtaaa gccagaggag atctctcgac   2520
gcaggactcg gcttgctgaa gcgcgcacgg caagaggcga ggggcggcga ctggtgagta   2580
cgccaaaaat tttgactagc ggaggctaga aggagagagt agggtgcgag agcgtcggta   2640
ttaagcgggg gagaattaga taaatgggaa aaaattcggt taaggccagg gggaaagaaa   2700
caatataaac taaaacatat agttagggca agcagggagc tagaacgatt cgcagttaat   2760
cctggccttt tagagacatc agaaggctgt agacaaatac tgggacagct acaaccatcc   2820
cttcagacag gatcagaaga acttagatca ttatataata caatagcagt cctctattgt   2880
gtgcatcaaa ggatagatgt aaaagacacc aaggaagcct tagataagat agaggaagag   2940
caaaacaaaa gtaagaaaaa ggcacagcaa gcgatcttca gacctggagg aggcaggagg   3000
cgatatgagg gacaattgga gaagtgaatt atataaatat aaagtagtaa aaattgaacc   3060
attaggagta gcacccacca aggcaaagag aagagtggtg cagagagaaa aaagagcagt   3120
gggaatagga gctttgttcc ttgggttctt gggagcagca ggaagcacta tgggcgcagc   3180
gtcaatgacg ctgacggtac aggccagaca attattgtct gatatagtgc agcagcagaa   3240
caatttgctg agggctattg aggcgcaaca gcatctgttg caactcacag tctgggggcat   3300 caaacagctc caggcaagaa tcctggctgt ggaaagatac ctaaaggatc aacagctcct   3360
```

```
gggatttgg ggttgctctg gaaaactcat ttgcaccact gctgtgcctt ggaatgctag    3420
ttggagtaat aaatctctgg aacagatttg gaataacatg acctggatgg agtgggacag    3480
agaaattaac aattacacaa gcttaataca ctccttaatt gaagaatcgc aaaaccagca    3540
agaaaagaat gaacaagaat tattggaatt agataaatgg gcaagtttgt ggaattggtt    3600
taacataaca aattggctgt ggtatataaa attattcata atgatagtag gaggcttggt    3660
aggtttaaga atagttttg ctgtactttc tatagtgaat agagttaggc agggatattc    3720
accattatcg tttcagaccc acctcccaat cccgagggga ccacgcgtac aaatggcagt    3780
attcatccac aatttttaaaa gaaaggggg gattggggg tacagtgcag gggaaagaat    3840
agtagacata atagcaacag acatacaaac taaagaatta caaaaacaaa ttacaaaaat    3900
tcaaaatttt cgggtttatt acagggacag cagaaatcca ctttggaaag ctgagcatcc    3960
ggctccggtg cccgtcagtg ggcagagcgc acatcgccca cagtccccga aagttgggg    4020 ggaggggtcg gcaattgaac cggtgcctag agaaggtggc gcggggtaaa ctgggaaagt    4080
gatgtcgtgt actggctccg cctttttccc gagggtgggg gagaaccgta tataagtgca    4140
gtagtcgccg tgaacgttct ttttcgcaac gggtttgccg ccagaacaca gtaagtgcc    4200 gtgtgtggtt cccgcgggcc tggcctcttt acgggttatg gcccttgcgt gccttgaatt    4260
acttccacgc ccctggctgc agtacgtgat tcttgatccc gagcttcggg ttggaagtgg    4320
gtgggagagt tcgaggcctt gcgcttaagg agccccttcg cctcgtgctt gagttgaggc    4380
ctggcctggg cgctggggcc gccgcgtgcg aatctggtgg caccttcgcg cctgtctcgc    4440
tgctttcgat aagtctctag ccatttaaaa tttttgatga cctgctgcga cgcttttttt    4500
ctggcaagat agtcttgtaa atgcgggcca agatctgcac actggtattt cggttttgg    4560 ggccgcgggg ggcgacgggg cccgtgcgtc ccagcgcaca tgttcggcga ggcggggcct    4620
gcgagcgcgg ccaccgagaa tcggacgggg gtagtctcaa gctggccggc ctgctctggt    4680
gcctggcctc gcgccgccgt gtatcgcccc gccctgggcg gcaaggctgg cccgtcggc    4740 accagttgcg tgagcggaaa gatggccgct tcccggccct gctgcaggga gctcaaaatg    4800
gaggacgcgg cgctcgggag agcgggcggg tgagtcaccc acacaaagga aaagggcctt    4860
tccgtcctca gccgtcgctt catgtgactc cacggagtac cgggcgccgt ccaggcacct    4920
cgattagttc tcgagctttt ggagtacgtc gtctttaggt tggggggagg ggttttatgc    4980
gatggagttt ccccacactg agtgggtgga gactgaagtt aggccagctt ggcacttgat    5040
gtaattctcc ttggaatttg cccttttttga gtttggatct tggttcattc tcaagcctca    5100
gacagtggtt caaagttttt ttcttccatt tcaggtgtcg tgaaaactac ccctctagag    5160
ccgccaccat gctcctcctc gtgactagcc ttctcctgtg cgagctccca cacctgcat    5220 tcctcctgat cccagaagtg caacttctcg agagcggtgg gggactcgtc cagccgggag    5280
gttccctgcg actcagctgt gcagcctcag gctttacctt ttccagttac gcaatgagtt    5340
gggtccggca ggcgcctggt aaaggactcg agtgggtgag tgcaatcagc ggaagtggcg    5400
ggtctacata ctatgcggac tctgttaaag gcaggttcac tatttcaagg gacaattcca    5460
agaacacgct ctacctgcag atgaatagcc ttagagctga agacacggcc gtgtactatt    5520
gtgccaaaaa gcagtaccat ttcgactact gggggcaggg aactctcgtc accgtgagct    5580 ccggcgagg tggaagcggg ggagggggct ccggtggtgg gggatcagaa attgttctca    5640
cacagtcacc cggaaccctt tcattgtccc ccggcgagcg cgccaccctc agctgtcggg    5700
ccagtcagag cgtgtctagc tcttacctgg cctggtacca gcagaaacct gggcaagctc    5760
```

```
ccagactcct gatatatggg gccagcagcc gggccactgg cattccggac aggtttagtg    5820
gatcaggctc tggcactgat tttacactga cgatttcaag gttggaaccc gaagacttcg    5880
cagtgtacta ttgtcagcag tatgggtcta gcccgtggac tttcgggcaa ggcaccaagg    5940
tggaaatcaa ggcagctgct ggaggtgggg aagtggcgg tggtggctca ggcggcgggg     6000
ggagcctcga ggacggtaat gaagagatgg ggggcattac acaaaccccg tacaaggtct    6060
ctatcagtgg gacgactgtg attctgacat gcccacagta tccaggttca gaaatcctgt    6120
ggcagcataa tgacaagaac atcggtgggg atgaggatga taagaatatc ggaagcgacg    6180
aagaccacct gtctctcaaa gagtttagcg agctggagca gagtgggtat tatgtctgct    6240
atcctagagg tagcaagcca gaggacgcaa acttttacct ttacctcaga gccagggtct    6300
gcgagaactg catggaaatg gacgtgatga gtgttgcaac tatagtgata gttgacattt    6360
gcatcaccgg gggtctgctc ctgctggttt actattggag caagaaccgc aaggctaaag    6420
ccaagccagt aacacggggc gcaggcgcgg gaggcaggca gcgagggcag aataaggagc    6480
gcccccacc cgtcccgaat ccggattacg aacccattcg gaaaggccag agggacttgt     6540
actcaggget caaccaaaga cggatcgagg gcgaggatc cttgctgaca tgtggtgacg     6600
tggaggagaa tcctggtcct tctcgcgccg ccaccatggt gtctaaaggc gaagagctgt    6660
tcaccggtgt ggtgccgatt cttgtagagc tggatggaga tgttaatggt cacaagtttt    6720
cagtgtctgg ggagggcgaa ggcgacgcga cctatggtaa actcacgctt aagtttatct    6780
gcaccacagg gaagctccct gttccatggc caacccttgt gacaacactt acttacggcg    6840
tgcagtgttt cagcaggtat cctgaccata tgaagcagca cgatttcttc aagtctgcaa    6900
tgcccgaggg gtacgtacaa gagcggacaa ttttcttcaa ggacgacgga attacaaaa    6960
ctagggcaga ggttaagttc gaaggggata cacttgttaa taggatcgaa ctgaaaggca    7020
ttgatttcaa ggaggatgga aacatactcg gcacaaact ggaatataac tacaattcac     7080
ataatgtgta tatcatggct gataagcaga aaaacggtat caaagtgaac tttaagatcc    7140
ggcataacat tgaagacggt agcgtgcagc tcgctgacca ctaccagcag aacactccaa    7200
tcggggacgg gccggtcctc ctgcccgaca accactacct cagcacccag agcgcactta    7260
gcaaagaccc aaacgagaag agagaccata tggtgctgct ggagttcgtt accgcagccg    7320
gaatcacctt gggcatggac gagctctata atgagaatt cgaacggata tcgagcatct     7380
taccgccatt tatcccata tttgttctgt ttttcttgat ttgggtatac atttaaatgt     7440
taataaaaca aaatggtggg gcaatcattt acatttttag ggatatgtaa ttactagttc    7500
aggtgtattg ccacaagaca aacatgttaa gaaactttcc cgttatttac gctctgttcc    7560
tgttaatcaa cctctggatt acaaaatttg tgaaagattg actgatattc ttaactatgt    7620
tgctcctttt acgctgtgtg gatatgctgc tttatagcct ctgtatctag ctattgcttc    7680
ccgtacggct ttcgttttct cctccttgta taaatcctgg ttgctgtctc ttttagagga    7740
gttgtggccc gttgtccgtc aacgtggcgt ggtgtgctct gtgtttgctg acgcaacccc    7800
cactggctgg ggcattgcca ccacctgtca actcctttct gggactttcg ctttccccct    7860
cccgatcgcc acgcagaac tcatcgccgc ctgccttgcc cgctgctgga caggggctag    7920
gttgctgggc actgataatt ccgtggtgtt gtcagtactg gtacctttaa gaccaatgac    7980
ttacaaggca gctgtagatc ttagccactt ttttaaagaa aaggggggac tggaagggct    8040
aattcactcc caaagaagac aagatctgct ttttgcctgt actgggtctc tctggttaga    8100
```

```
ccagatctga gcctgggagc tctctggcta actagggaac ccactgctta agcctcaata    8160
aagcttgcct tgagtgcttc aatgatcata atcaagccat atcacatctg tagaggttta    8220
cttgctttaa aaaacctcca cacctccccc tgaacctgaa acataaaatg aatgcaattg    8280
ttgttgttaa cttgtttatt gcagcttata atggttacaa ataaagcaat agcatcacaa    8340
atttcacaaa taaagcattt ttttcactgc attctagttg tggtttgtcc aaactcatca    8400
atgtatctta tcatgtctgg atctgcgtcg acacgaagag acgactgact gactgactgg    8460
aaagaggaag ggctggaaga ggaaggagct tgatccagat cccgatctcg atccagatcc    8520
ggatcgcagc ttggcgtaat catggtcata gctgtttcct gtgtgaaatt gttatccgct    8580
cacaattcca cacaacatac gagccggaag cataaagtgt aaagcctggg gtgcctaatg    8640
agtgagctaa ctcacattaa ttgcgttgcg ctcactgccc gctttccagt cgggaaacct    8700
gtcgtgccag ctgcattaat gaatcggcca acgcgcgggg agaggcggtt tgcgtattgg    8760
gcgctcttcc gcttcctcgc tcactgactc gctgcgctcg tcgttcggc tgcggcgagc    8820 ggtatcagct cactcaaagg cggtaatacg gttatccaca gaatcagggg ataacgcagg    8880
aaagaacatg tgagcaaaag gccagcaaaa ggccaggaac cgtaaaaagg ccgcgttgct    8940
ggcgtttttc cataggctcc gccccctga cgagcatcac aaaaatcgac gctcaagtca    9000
gaggtggcga aacccgacag gactataaag ataccaggcg tttccccctg gaagctccct    9060
cgtgcgctct cctgttccga ccctgccgct taccggatac ctgtccgcct ttctcccttc    9120
gggaagcgtg gcgctttctc atagctcacg ctgtaggtat ctcagttcgg tgtaggtcgt    9180
tcgctccaag ctgggctgtg tgcacgaacc ccccgttcag cccgaccgct gcgccttatc    9240
cggtaactat cgtcttgagt ccaacccggt aagacacgac ttatcgccac tggcagcagc    9300
cactggtaac aggattagca gagcgaggta tgtaggcggt gctacagagt tcttgaagtg    9360
gtggcctaac tacggctaca ctagaagaac agtatttggt atctgcgctc tgctgaagcc    9420
agttaccttc ggaaaaagag ttggtagctc ttgatccggc aaacaaacca ccgctggtag    9480
cggtggtttt tttgtttgca agcagcagat tacgcgcaga aaaaaggat ctcaagaaga    9540 tcctttgatc ttttctacgg ggtctgacgc tcagtggaac gaaaactcac gttaagggat    9600
tttggtcatg agattatcaa aaaggatctt cacctagatc cttttaaatt aaaaatgaag    9660
ttttaaatca atctaaagta tatatgagta aacttggtct gacagttacc aatgcttaat    9720
cagtgaggca cctatctcag cgatctgtct atttcgttca tccatagttg cctgactccc    9780
cgtcgtgtag ataactacga tacgggaggg cttaccatct ggccccagtg ctgcaatgat    9840
accgcagctt gggaaaccat aagagctgaa gccagttacc ttcggaaaaa gagttggtag    9900
ctcttgatcc ggcaaacaaa ccaccgctgg tagcggtggt tttttgttt gcaagcagca    9960 gattacgcgc agaaaaaaag gatctcaaga agatcctttg atcttttcta cggggtctga   10020
cgctcagtgg aacgaaaact cacgttaagg gattttggtc atgagcttgc gccgtcccgt   10080
caagtcagcg taatgctctg ccagtgttac aa                                  10112
```

<210> SEQ ID NO 79
<211> LENGTH: 10133
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 79

| | |
|---|---:|
| ccaattaacc aattctgatt agaaaaactc atcgagcatc aaatgaaact gcaatttatt | 60 |
| cacatcagga ttatcaatac catattttg aaaaagccgt ttctgtaatg aaggagaaaa | 120 |
| ctcaccgagg cagttccata ggatggcaag atcctggtat cggtctgcga ttccgactcg | 180 |
| tccaacatca atacaaccta ttaatttccc ctcgtcaaaa ataaggttat caagtgagaa | 240 |
| atcaccatga gtgacgactg aatccggtga gaatggcaaa agtttatgca tttctttcca | 300 |
| gacttgttca acaggccagc cattacgctc gtcatcaaaa tcactcgcat caaccaaacc | 360 |
| gttattcatt cgtgattgcg cctgagcaag acgaaatacg cgatcgctgt taaaaggaca | 420 |
| attacaaaca ggaatcgaat gcaaccggcg caggaacact gccagcgcat caacaatatt | 480 |
| ttcacctgaa tcaggatatt cttctaatac ctggaatgct gttttccgg ggatcgcagt | 540 |
| ggtgagtaac catgcatcat caggagtacg gataaaatgc ttgatggtcg aagaggcat | 600 |
| aaattccgtc agccagtta gtctgaccat ctcatctgta acatcattgg caacgctacc | 660 |
| tttgccatgt ttcagaaaca actctggcgc atcgggcttc ccatacaagc gatagattgt | 720 |
| cgcacctgat tgcccgacat tatcgcgagc ccatttatac ccatataaat cagcatccat | 780 |
| gttgaatttt aatcgcggcc tcgacgtttc ccgttgaata tggctcataa cacccttgt | 840 |
| attactgttt atgtaagcag acagttttat tgttcatgat gatatatttt tatcttgtgc | 900 |
| aatgtaacat cagagatttt gagacacaac gtggctttcc cccccccccc catgacatta | 960 |
| acctataaaa ataggcgtat cacgaggcca gcttgggaaa ccataagacc gagatagagt | 1020 |
| tgagtgttgt tccagtttgg aacaagagtc cactattaaa gaacgtggac tccaacgtca | 1080 |
| aagggcgaaa aaccgtctat cagggcgatg gcccactacg tgaaccatca cccaaatcaa | 1140 |
| gttttttggg gtcgaggtgc cgtaaagcac taaatcggaa ccctaaaggg agcccccgat | 1200 |
| ttagagcttg acggggaaag ccggcgaacg tggcgagaaa ggaagggaag aaagcgaaag | 1260 |
| gagcgggcgc taaggcgctg gcaagtgtag cggtcacgct gcgcgtaacc accacacccg | 1320 |
| ccgcgcttaa tgcgccgcta cagggcgcgt actatggttg ctttgacgta tgcggtgtga | 1380 |
| aataccgcac agatgcgtaa ggagaaaata ccgcatcagg cgccattcgc cattcaggct | 1440 |
| gcgcaactgt tgggaagggc gatcggtgcg ggcctcttcg ctattacgcc agctggcgaa | 1500 |
| agggggatgt gctgcaaggc gattaagttg ggtaacgcca gggttttccc agtcacgacg | 1560 |
| ttgtaaaacg acggccagtg aattgatcga gatcgtgatc cggatcaaga tccagatcga | 1620 |
| attggaggct acagtcagtg gagaggactt tcactgactg actgactgcg tctcaacctc | 1680 |
| ctaggggaca ttgattattg actagttatt aatagtaatc aattacgggg tcattagttc | 1740 |
| atagcccata tatggagttc cgcgttacat aacttacggt aaatggcccg cctggctgac | 1800 |
| cgcccaacga ccccgccca ttgacgtcaa taatgacgta tgttcccata gtaacgccaa | 1860 |
| tagggacttt ccattgacgt caatgggtgg agtatttacg gtaaactgcc cacttggcag | 1920 |
| tacatcaagt gtatcatatg ccaagtacgc ccctattga cgtcaatgac ggtaaatggc | 1980 |
| ccgcctggca ttatgcccag tacatgacct tatgggactt tcctacttgg cagtacatct | 2040 |
| acgtattagt catcgctatt accatggtga tgcggttttg gcagtacatc aatgggcgtg | 2100 |
| gatagcggtt tgactcacgg ggatttccaa gtctccaccc cattgacgtc aatgggagtt | 2160 |
| tgttttggca ccaaaatcaa cgggactttc caaaatgtcg taacaactcc gccccattga | 2220 |
| cgcaaatggg cggtaggcgt gtacggtggg aggtctatat aagcagagct cgtttagtga | 2280 |
| accgggtctc tctggttaga ccagatctga gcctgggagc tctctggcta actagggaac | 2340 |

```
ccactgctta agcctcaata aagcttgcct tgagtgctca aagtagtgtg tgcccgtctg    2400
ttgtgtgact ctggtaacta gagatccctc agacccttt  agtcagtgtg gaaaatctct    2460
agcagtggcg cccgaacagg gacttgaaag cgaaagtaaa gccagaggag atctctcgac    2520
gcaggactcg gcttgctgaa gcgcgcacgg caagaggcga ggggcggcga ctggtgagta    2580
cgccaaaaat tttgactagc ggaggctaga aggagagagt agggtgcgag agcgtcggta    2640
ttaagcgggg gagaattaga taatgggaa  aaaattcggt taaggccagg ggaaagaaa     2700 caatataaac taaaacatat agttagggca agcagggagc tagaacgatt cgcagttaat    2760
cctggccttt tagagacatc agaaggctgt agacaaatac tgggacagct acaaccatcc    2820
cttcagacag gatcagaaga acttagatca ttatataata caatagcagt cctctattgt    2880
gtgcatcaaa ggatagatgt aaaagacacc aaggaagcct tagataagat agaggaagag    2940
caaaacaaaa gtaagaaaaa ggcacagcaa gcgatcttca gacctggagg aggcaggagg    3000
cgatatgagg gacaattgga gaagtgaatt atataaatat aaagtagtaa aaattgaacc    3060
attaggagta gcacccacca aggcaaagag aagagtggtg cagagagaaa aaagagcagt    3120
gggaatagga gctttgttcc ttgggttctt gggagcagca ggaagcacta tgggcgcagc    3180
gtcaatgacg ctgacggtac aggccagaca attattgtct gatatagtgc agcagcagaa    3240
caatttgctg agggctattg aggcgcaaca gcatctgttg caactcacag tctgggcat     3300 caaacagctc caggcaagaa tcctggctgt ggaaagatac ctaaaggatc aacagctcct    3360
ggggatttgg ggttgctctg gaaaactcat ttgcaccact gctgtgcctt ggaatgctag    3420
ttggagtaat aaatctctgg aacagatttg gaataacatg acctggatgg agtgggacag    3480
agaaattaac aattacacaa gcttaataca ctccttaatt gaagaatcgc aaaaccagca    3540
agaaaagaat gaacaagaat tattggaatt agataaatgg gcaagtttgt ggaattggtt    3600
taacataaca aattggctgt ggtatataaa attattcata atgatagtag gaggcttggt    3660
aggtttaaga atagttttg  ctgtactttc tatagtgaat agagttaggc agggatattc    3720
accattatcg tttcagaccc acctcccaat cccgagggga ccacgcgtac aaatggcagt    3780
attcatccac aattttaaaa gaaaaggggg gattgggggg tacagtgcag gggaaagaat    3840
agtagacata atagcaacag acatacaaac taaagaatta caaaaacaaa ttacaaaaat    3900
tcaaaatttt cgggtttatt acagggacag cagaaatcca cttggaaag  ctgagcatcc    3960 ggctccggtg cccgtcagtg gcagagcgc  acatcgccca cagtccccga aagttggggg    4020
ggaggggtcg gcaattgaac cggtgcctag agaaggtggc gcgggtaaa  ctgggaaagt    4080 gatgtcgtgt actggctccg cctttttccc gagggtgggg gagaaccgta tataagtgca    4140
gtagtcgccg tgaacgttct ttttcgcaac gggtttgccg ccagaacaca ggtaagtgcc    4200
gtgtgtggtt cccgcgggcc tggcctcttt acgggttatg gcccttgcgt gccttgaatt    4260
acttccacgc cctgctgc  agtacgtgat tcttgatccc gagcttcggg ttggaagtgg    4320
gtgggagagt tcgaggcctt gcgcttaagg agccccttcg cctcgtgctt gagttgaggc    4380
ctggcctggg cgctggggcc gccgcgtgcg aatctggtgg caccttcgcg cctgtctcgc    4440
tgctttcgat aagtctctag ccatttaaaa ttttgatga  cctgctgcga cgcttttttt    4500
ctggcaagat agtcttgtaa atgcgggcca agatctgcac actggtattt cggttttgg    4560 ggccgcgggc ggcgacgggg cccgtgcgtc ccagcgcaca tgttcggcga ggcggggcct    4620
gcgagcgcgc ccaccgagaa tcggacgggg gtagtctcaa gctggccggc ctgctctggt    4680
gcctggcctc gcgccgccgt gtatcgcccc gccctgggcg gcaaggctgg cccggtcggc    4740
```

```
accagttgcg tgagcggaaa gatggccgct tcccggccct gctgcaggga gctcaaaatg    4800
gaggacgcgg cgctcgggag agcgggcggg tgagtcaccc acacaaagga aaagggcctt    4860
tccgtcctca gccgtcgctt catgtgactc cacggagtac cgggcgccgt ccaggcacct    4920
cgattagttc tcgagctttt ggagtacgtc gtctttaggt tggggggagg ggttttatgc    4980
gatggagttt ccccacactg agtgggtgga gactgaagtt aggccagctt ggcacttgat    5040
gtaattctcc ttggaatttg ccctttttga gtttggatct tggttcattc tcaagcctca    5100
gacagtggtt caaagttttt ttcttccatt tcaggtgtcg tgaaaactac ccctctagag    5160
ccgccaccat gcttctcctt gttacatcac tgttgctttg tgaactgccc caccccgcgt    5220
ttcttttgat ccctcagtca gctctgaccc aacctgcctc cgtctctggg agtccaggcc    5280
agagtatcac aatttcttgt acaggcacct catctgatgt cggcggttac aattacgtta    5340
gttggtatca gcaacatcca ggtaaggctc caaaggtgat gatctatgac gtctcaaata    5400
gaccctctgg cgtcagcgac aggtttagtg gtagcaaatc cgggaacaca gcttcactta    5460
caattagcgg cctccaagta gaagacgaag ctgactatta ctgctctagt tattcaacgt    5520
caattacccc tgtgtttggt ggcggtacaa aactcacagt gcttggcgga ggcgggtctg    5580
gaggtggagg ttctggaggc ggaggttccc aagtgcaact tgtgcaatca ggagctgaag    5640
tcaaaaagcc gggagaatcc ctgaaaataa gctgcgaagc aagtggttac tcttttactt    5700
cttactggat tggatgggtt cggcagatgc ccggaaaggg actcgagtgg atgggaatta    5760
tttaccctgg agacagcgac acaagataca gcccttcatt ccaggggcag gtgaccattt    5820
ctgctgacaa atcaatcagt acagcctatc tgcaatggag ttccctcaaa gccagtgaca    5880
ctgctatgta ttactgcgcg cgactggaac tgggatacta ctactacgga atggacgtat    5940
ggggacaggg aaccaccgtt actgttagta gcgccgccgc tggaggggga ggatccggag    6000
gaggggggag cggaggagga ggatcattgg aggatggaaa tgaagagatg ggcggcatca    6060
ctcagacacc gtacaaagtg agtatttctg gaaccaccgt cattttgact tgtcctcagt    6120
acccaggaag cgagattctg tggcagcata acgacaagaa catcggggc gacgaggacg    6180 ataaaaatat agggtctgac gaggaccacc ttagccttaa ggagtttagc gagctggaac    6240
agtccggata ctatgtatgc tatccacgcg gcagcaaacc cgaggatgct aactttttact    6300 tgtacttgag ggcgcgcgtt tgtgagaact gcatggagat ggatgttatg tccgtagcta    6360
ccattgttat cgtcgacatt tgtattaccg gtggattgct gctgttggtc tactattggt    6420
ccaaaaatcg gaaagccaag gccaaacccg taacgagagg tgccggcgct ggaggaagac    6480
agaggggcca gaataaagag aggccgccgc cagttcccaa tcctgattat gaacccattc    6540
gaaaagggca gagggacctc tattccgggc tcaaccagag gaggatcgaa ggaagggggat    6600 ccttgcttac ctgtggcgac gtagaagaga tccaggcccc tcaagggcc gccaccatgg    6660 tgtcaaaggg cgaagagttg tttactggag tcgtacccat cctggtggaa ttggacgggg    6720
acgtgaacgg ccacaagttc tctgtgtctg gagaaggcga gggcgacgct acttatggaa    6780
aactgactct gaaatttatt tgcactacag gaaaactgcc tgtcccatgg cccacgctgg    6840
ttacaaccct cacatatggt gttcaatgtt tctctcgcta ccccgaccac atgaagcagc    6900 atgactttt caagtccgcg atgcccgaag ggtacgttca agaacgcact atattttca    6960 aggatgatgg caactacaag acaagagctg aggtgaaatt cgaaggtgat acacttgtaa    7020
acagaatcga actcaaggga atcgacttca aggaagacgg aaatatcctc gggcacaaac    7080
```

-continued

```
tggaatataa ctacaatagc cacaacgtat atatcatggc cgacaaacag aagaatggga    7140
tcaaggtaaa ttttaagata agacacaata tagaagacgg atctgtgcaa ttggccgacc    7200
attatcagca gaatacccc attggagatg gcccagtgct ccttccagac aatcactacc     7260
tttcaacaca gtccgcgttg tctaaagacc ccaatgagaa gagggaccac atggtgttgc    7320
tcgaatttgt tactgccgct gggatcactc tgggcatgga tgagttgtat aaatgagaat    7380
tcgaacggat atcgagcatc ttaccgccat ttatacccat atttgttctg tttttcttga    7440
tttgggtata catttaaatg ttaataaaac aaaatggtgg ggcaatcatt tacatttta     7500 gggatatgta attactagtt caggtgtatt gccacaagac aaacatgtta agaaactttc    7560
ccgttattta cgctctgttc ctgttaatca acctctggat tacaaaattt gtgaaagatt    7620
gactgatatt cttaactatg ttgctccttt tacgctgtgt ggatatgctg ctttatagcc    7680
tctgtatcta gctattgctt cccgtacggc tttcgttttc tcctccttgt ataaatcctg    7740
gttgctgtct cttttagagg agttgtggcc cgttgtccgt caacgtggcg tggtgtgctc    7800
tgtgtttgct gacgcaaccc ccactggctg gggcattgcc accacctgtc aactcctttc    7860
tgggactttc gctttccccc tcccgatcgc cacggcagaa ctcatcgccg cctgccttgc    7920
ccgctgctgg acaggggcta ggttgctggg cactgataat tccgtggtgt tgtcagtact    7980 ggtacctta agaccaatga cttcaaggc agctgtagat cttagccact tttaaaaga     8040 aaagggggga ctggaagggc taattcactc ccaaagaaga caagatctgc ttttgcctg    8100 tactgggtct ctctggttag accagatctg agcctgggag ctctctggct aactagggaa    8160
cccactgctt aagcctcaat aaagcttgcc ttgagtgctt caatgatcat aatcaagcca    8220
tatcacatct gtagaggttt acttgcttta aaaacctcc acctccccc ctgaacctga     8280 aacataaaat gaatgcaatt gttgttgtta acttgtttat tgcagcttat aatggttaca    8340
aataaagcaa tagcatcaca aatttcacaa ataaagcatt ttttcactg cattctagtt    8400 gtggtttgtc caaactcatc aatgtatctt atcatgtctg gatctgcgtc gacacgaaga    8460
gacgactgac tgactgactg aaagaggaa gggctggaag aggaaggagc ttgatccaga    8520
tcccgatctc gatccagatc cggatcgcag cttggcgtaa tcatggtcat agctgtttcc    8580
tgtgtgaaat tgttatccgc tcacaattcc acacaacata cgagccggaa gcataaagtg    8640
taaagcctgg ggtgcctaat gagtgagcta actcacatta attgcgttgc gctcactgcc    8700
cgctttccag tcgggaaacc tgtcgtgcca gctgcattaa tgaatcggcc aacgcgcggg    8760
gagaggcggt ttgcgtattg ggcgctcttc cgcttcctcg ctcactgact cgctgcgctc    8820
ggtcgttcgg ctgcggcgag cggtatcagc tcactcaaag gcggtaatac ggttatccac    8880
agaatcaggg gataacgcag gaaagaacat gtgagcaaaa ggccagcaaa aggccaggaa    8940
ccgtaaaaag gccgcgttgc tggcgttttt ccataggctc cgcccccctg acgagcatca    9000
caaaaatcga cgctcaagtc agaggtggcg aaacccgaca ggactataaa gataccaggc    9060
gtttccccct ggaagctccc tcgtgcgctc tcctgttccg accctgccgc ttaccggata    9120
cctgtccgcc tttctccctt cgggaagcgt ggcgctttct catagctcac gctgtaggta    9180
tctcagttcg gtgtaggtcg ttcgctccaa gctgggctgt gtgcacgaac cccccgttca    9240
gcccgaccgc tgcgccttat ccggtaacta tcgtcttgag tccaacccgg taagacacga    9300
cttatcgcca ctggcagcag ccactggtaa caggattagc agagcgaggt atgtaggcgg    9360
tgctacagag ttcttgaagt ggtggcctaa ctacggctac actagaagaa cagtatttgg    9420
tatctgcgct ctgctgaagc cagttacctt cggaaaaaga gttggtagct cttgatccgg    9480
```

```
caaacaaacc accgctggta gcggtggttt ttttgtttgc aagcagcaga ttacgcgcag    9540
aaaaaaagga tctcaagaag atcctttgat cttttctacg gggtctgacg ctcagtggaa    9600
cgaaaactca cgttaaggga ttttggtcat gagattatca aaaggatct tcacctagat     9660 cctttaaat taaaaatgaa gttttaaatc aatctaaagt atatatgagt aaacttggtc     9720
tgacagttac caatgcttaa tcagtgaggc acctatctca gcgatctgtc tatttcgttc    9780
atccatagtt gcctgactcc ccgtcgtgta gataactacg atacgggagg cttaccatc    9840 tggcccagt gctgcaatga taccgcagct gggaaaccga taagagctga agccagttac    9900
cttcggaaaa agagttggta gctcttgatc cggcaaacaa accaccgctg gtagcggtgg   9960 ttttttttgtt tgcaagcagc agattacgcg cagaaaaaaa ggatctcaag aagatccttt   10020
gatcttttct acggggtctg acgctcagtg gaacgaaaac tcacgttaag ggattttggt   10080
catgagcttg cgccgtcccg tcaagtcagc gtaatgctct gccagtgtta caa          10133
```

<210> SEQ ID NO 80
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 80

```
gaggtgcagc tggtggagtc tgggggagcc ttggtgcagg ctgggggatc tctgagactc      60
tcctgtgaag cctctggaag cagcttcagc ctctatacca tggcctggta ccgccagact     120
ccaggaaagc agcgggagtt ggtcgcaacg attactagtg gttaccacac aaactatgcc     180
gactccgcga aggaccgatt caccatttct agagacaacg ccaagaacac ggcctatctg     240
caattgaaca gcctgaaacc tgaggacaca gccgtctatt actgtgcagc gaagagggtt     300
tggagcgcag agtataacta ctgggggccag gggaccctgg tcaccgtctc ctca          354
```

<210> SEQ ID NO 81
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 81

```
gaggtgcagc tggtggagtc tggggagga ttggtgcagg ctgggggctc tctgaaactc       60
tcctgtgcaa cctctggagg caccttcagt agctatcgtg taggctggtt ccgccaggct     120
ccagggaagc cgcgtgagac tgtagccact attagtagga atggtggagg cacacactat     180
gcggactccg tgaagggtcg attcaccatc tccagagaca cgccaagaa catggcgtat     240 ctacaaatga acggcctgaa acctgaggac acggccattt attactgtgc agcagattcc    300
ctcttctggc ctggcccagg ccattatgac aacttgggcc aggggaccca ggtcaccgtc    360
tcctca                                                                  366
```

<210> SEQ ID NO 82
<211> LENGTH: 369
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 82
gatgtgcagc tggtggagtc tgggggagga ttggtgcagg ctgggggctc tctgagactc      60
tcctgtgcag cctctggacg ctccttcaat agctatacct tgggctggtt ccgccaggct     120
ccaggaaagg agcgtgagtt tgtagcttat gccatttact atccagactc tgtgaagggc     180
cgattcacca tcgtcagaga caacgccagg aacacggtgt atctgcaaat gaatagcctc     240
aaatctgagg atacggccat ttattactgt gcagcagcgg acatacgtac taggcgctct     300
agtacctggt acagggagac gatggagtat gactactggg gccagggac cctggtcacc      360 gtctcctca                                                             369

<210> SEQ ID NO 83
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 83
gatgttcagc tggtggagtc tgggggagga ttggtgcagg ctgggggtc tctgagactc       60 tcctgtgcag cctctggaag catcttcgca gtcgatgcca tgggctggta ccgccaggct     120
ccagggaagc agcgcgagtt ggtcgcacgt attagtcgta ctaatttggg agcaagctat     180
ttagactccg tgaagggccg attcaccatc tccagagaca ccggcaagaa cacggtgtat     240
ctgcaaatgg tcagcctgga acctgaggac acagccgttt attactgtgc agcagcgaca     300
agaccgaccc tcgcgctcgt ggactactgg ggccagggga cccaggtcac cgtctcctca     360

<210> SEQ ID NO 84
<211> LENGTH: 384
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 84
gatgtccagc tggtggagtc tgggggaggc ttggtgcagc ctgggggtc tctgagactc       60 tcctgtgcag cctctggatt cacttcggat tattatgtca taggctggtt ccgccaggcc     120
ccagggaagg agcgcgaggg ggtatcatgt attagtagta ggtatgcgaa cacaaactat     180
gcagactccg tgaagggccg attcacccag tccagaggtg ctgctaagaa cacggtgtat     240
ctgcaaatga cgccctgaa acctgaggac acgccgttt attactgcgc ggcagatacg      300
aggcggtata catgcccgga tatagcgact atgagagga actttgattc ctggggccag     360
gggacccagg tcaccgtctc ctca                                            384

<210> SEQ ID NO 85
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 85

```
gatgtgcagc tggtggagtc tgggggagga ttggtgcagg ctggggactc tctgagactc    60
tcctgtgcag cctctggacg caccttcagt agctatgcca tggcctggtt ccgccaggct   120
ccagggaagg agcgtgagtt agtagcagct ttgagcagta gtggtgctag cacatcgtat   180
ccagactccg tgaagggccg attcaccatc tccagagaca acgccaagaa cacggtgtat   240
ctgcaaatga acagcctgaa acctgaggac acggccgttt attactgtgc agcgagactt   300
tatacctacg ggttgacaga aagagcgtat gactactggg gccaggggac ccaggtcacc   360
gtctcctca                                                           369
```

<210> SEQ ID NO 86
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 86

```
gatgtccagc tggtggagtc tgggggagga ttggtgcagg ctggggactc tctgaggctc    60
tcctgtgcag cctctggacg caccttcaga gactatgcca tggcctggtt ccgccaggct   120
ccagggaagg agcgtgggat tgtagcagct ttgagcaaga gtggtggtag tacatcgtat   180
ctagactccg tgaagggccg attcaccatc tccagagaca acgccaagaa cacggtgtat   240
ctgcaaatga acagcctgaa acctgaggac acggccgttt attactgtgc agcgagattg   300
tatacctacg ggttgacaga aagggcgtat gactactggg gccaggggac ccaggtcacc   360
gtctcctca                                                           369
```

<210> SEQ ID NO 87
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 87

```
gaggtgcagc tggtggagtc tgggggagga ttggtgcagg ctgggggctc tctgagactc    60
tcctgtgcag cctctacgga caccttcact ggctatacca tggctggtt ccgccagact   120 ccagggaagg agcgacaatt tgtagcgtcc atgagctgga atggtggttt cataaagtat   180
gcagactctg tgaagggccg attcaccatc tccagggaca acgccgagaa catggtgtat   240
cttgaaatga acaacctgaa atctgaggac acggccgttt attcctgtgc agcagacaac   300
atctattgga ctgcgtccga gcgccccgga gactataact actggggcca ggggacccag   360
gtcaccgtct cctca                                                    375
```

<210> SEQ ID NO 88
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

```
<400> SEQUENCE: 88
gaggtccagc tggtggagtc tgggggaggc ttggtgcagc ctgggggtc tctgagactc      60 tcctgcactg cctctggaac catgtccacc atcaacgcca tggcctggta ccgccaggct     120
ccagagaagc agcgcgagtt ggtcgctcgc atttggaatg atggagagac taactatgca    180
gactccgtga ggggccgatt cgccgtctct agagacaacg caaagaacac ggtgtatctg    240
caaatgaaca gcctgaaacc tgaggacacg gccgtctatt actgtaatgc gtatatacct    300
actactcagc gtatgaataa aatagctagt tattggggcc aggggaccct ggtcaccgtc    360
tcctca                                                                366

<210> SEQ ID NO 89
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 89
gaggtgcagc tggtggagtc tgggggagga ttggtgcagg ctggggactc tctgagggtc     60
tcctgtgcag cctctggacg caccttcagt agctatgcca tggcctggtt ccgccaggct    120
ccagggaagg agcgtgagtt tgtagcagct ttgagcagta gtggtgttag cacatcgtat    180
tcagactccg tgaagggccg attcaccatc tccagagaca cggccaagaa cacggtgtat    240
ctgcaaatga acagcctgaa acccgaggac acggccgttt attactgtgc agcgagacta    300
tatacctacg ggttgacaga aagggcgtat gactactggg gccaggggac ccaggtcacc    360
gtctcctca                                                             369

<210> SEQ ID NO 90
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 90
gaggtgcagc tggtggagtc tgggggaggc ttggtgcagc ctgggggtc tctgagactc      60 tcctgtgcag cctctggaag cttcctcgac atcaatgcca tggctggta ccgccaggct     120 ccaggaaagc agcgcgagtt ggtcgcaatg atgcctagtg gtggccgcac aaactatcat    180
gactccgttg agggccgatt caccatctcc agagacaacg ccaagaacac agtgtatctg    240
caaatggaca gcctgaaacc tgaggacacg gccgtctatt actgtgttgc agatgcgacc    300
cggtactccg gtttccgtac taacttctgg ggccggggaa cccaggtcac cgtctcctca    360

<210> SEQ ID NO 91
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 91
gaggtgcagc tggtggagtc tgggggaggc acggtgcagg ctggggggtc tctgcgactc     60
```

```
tcctgtgcag cctctggcgg tatcttcagc atctatgtca tgggctggca tcgccaggct    120
ccagggaagc agcgcgaatt ggtcgcagct attactcctg gttttaacac aaactatgca    180
gaccccgtga agggccgatt caccatctca agagacaacg ccaagagcac ggtgtacctg    240
gaaatgaaca gcctcgaacc tgaggatacg gccgtttatt actgttcagc taaacgaatc    300
tatgagtacg agtactatta ttggggccag gggacccagg tcaccgtctc ctca          354
```

<210> SEQ ID NO 92
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 92

```
gatgttcagc tggtggagtc tgggggagga ttggtgcagg ctggggactc tctgagactc     60
tcctgtgcag cctctggacg caccttcagt gaatatgcca tggcctggtt ccgccaggct    120
ccagggaagg agcgtgagtt tgtagcagct atgagcaaga gtggtgctag cacatcgtat    180
agtgactccg taaagggccg attcaccatc tccagagcca cgccaagaa cacggtgtat     240 ctcgaaatga acagcctgaa acctgaggac acggccggtt actactgtgc agcgagacta    300
tacacctacg ggttgacaga aagggcgtat gactactggg gccaggggac ccaggtcacc    360
gtctcctca                                                            369
```

<210> SEQ ID NO 93
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 93

```
gatgtgcagc tggtggagtc tgggggagga ttggtgcagg ctggggactc tctgagactc     60
tcctgtgcag cctctggacg caccttcagt gactatgcca tggcctggtt ccgccagggt    120
ccagggaagg agcgtgagct tgtagcagct ttgagcaaga gtggtgctag cacatcgtat    180
gcagactccg tgaagggccg attcaccatc tccagagaca cgccaagaa cacggtgtat     240 ctgcatatga acagcctgaa acctgaggac acgccatttt attactgtgc agcgagactt    300
tatacctacg ggttgacaga aagggcgtat gactactggg gccaggggac ccaggtcacc    360
gtctcctca                                                            369
```

<210> SEQ ID NO 94
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 94

```
gatgtgcagc tggtggagtc tgggggagga ttggtgcagg ctgggggctc tctgagcctc     60
tcctgtgcat cctctggacg caccttccagt atctatggca tgggctggtt ccgccaggct   120
```

```
ccagggaagg agcgtgagtt tgtagcggct attaggtgga gtgatagtaa cacaaactat    180
gcagactccg tgaagggccg attcaccatc tccggagaca acgccaagaa cgcggtgcat    240
ctgcaaatgc acagcctgaa acctgaggac acggccgttt attactgtgc agccaaaggg    300
accccttatt attataccga cttccggacg tatccgtact ggggccaggg gaccctggtc    360
accgtctcct ca                                                        372
```

<210> SEQ ID NO 95
<211> LENGTH: 384
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 95

```
gatgtccagc tggtggagtc tgggggaggc ttggtgcagc ctgggggtc tctgagactc       60 acctgtgcag cctctggatt cacttcggat tattatgtca taggctggtt ccgccaggcc     120
ccagggaagg agcgcgaggg ggtatcatgt attagtagta ggtatgcgaa cacaaactat     180
gcagactccg tgaagggccg attcacccag tccagaggtg ctgctaagaa cacggtgtat     240
ctgcaaatga acgccctgaa acctggggac acggccgttt attactgcgc ggcagatacg     300
aggcggtata catgcccgga tatagcgact atgcacagga actttgattc ctggggccag     360
gggacccagg tcaccgtctc ctca                                            384
```

<210> SEQ ID NO 96
<211> LENGTH: 384
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 96

```
gatgtccagc tggtggagtc tgggggaggc ttggtgcagc ctgggggtc tctgagactc       60 acctgtgcag cctctggatt cacttcggat tattatgtca taggctggtt ccgccaggcc     120
ccagggaagg agcgcgaggg ggtatcatgt attagtagta ggtatgcgaa cacaaactat     180
gcagactccg tgaagggccg attcacccag tccagaggtg ctgctaagaa cacggtgtat     240
ctgcaaatga acgccctgaa acctggggac acggccgttt attactgcgc ggcagatacg     300
aggcggtata catgcccgga tatagcgact atgcacagga actttgattc ctggggccag     360
gggacccagg tcaccgtctc ctca                                            384
```

<210> SEQ ID NO 97
<211> LENGTH: 185
<212> TYPE: PRT
<213> ORGANISM: Homo sapiens

<400> SEQUENCE: 97

Asp Gly Asn Glu Glu Met Gly Gly Ile Thr Gln Thr Pro Tyr Lys Val
 1               5                  10                  15

Ser Ile Ser Gly Thr Thr Val Ile Leu Thr Cys Pro Gln Tyr Pro Gly
                20                  25                  30

Ser Glu Ile Leu Trp Gln His Asn Asp Lys Asn Ile Gly Gly Asp Glu
            35                  40                  45

```
Asp Asp Lys Asn Ile Gly Ser Asp Glu Asp His Leu Ser Leu Lys Glu
    50                  55                  60

Phe Ser Glu Leu Glu Gln Ser Gly Tyr Tyr Val Cys Tyr Pro Arg Gly
 65                  70                  75                  80

Ser Lys Pro Glu Asp Ala Asn Phe Tyr Leu Tyr Leu Arg Ala Arg Val
                 85                  90                  95

Cys Glu Asn Cys Met Glu Met Asp Val Met Ser Val Ala Thr Ile Val
            100                 105                 110

Ile Val Asp Ile Cys Ile Thr Gly Gly Leu Leu Leu Val Tyr Tyr
            115                 120                 125

Trp Ser Lys Asn Arg Lys Ala Lys Ala Lys Pro Val Thr Arg Gly Ala
130                 135                 140

Gly Ala Gly Gly Arg Gln Arg Gly Gln Asn Lys Glu Arg Pro Pro Pro
145                 150                 155                 160

Val Pro Asn Pro Asp Tyr Glu Pro Ile Arg Lys Gly Gln Arg Asp Leu
                165                 170                 175

Tyr Ser Gly Leu Asn Gln Arg Arg Ile
                180                 185

<210> SEQ ID NO 98
<211> LENGTH: 261
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Asn Ser Leu Phe Asn Gln Glu Val Gln Ile Pro Leu Thr Glu Ser Tyr
 1               5                  10                  15

Cys Gly Pro Cys Pro Lys Asn Trp Ile Cys Tyr Lys Asn Asn Cys Tyr
                 20                  25                  30

Gln Phe Phe Asp Glu Ser Lys Asn Trp Tyr Glu Ser Gln Ala Ser Cys
             35                  40                  45

Met Ser Gln Asn Ala Ser Leu Leu Lys Val Tyr Ser Lys Glu Asp Gln
 50                  55                  60

Asp Leu Leu Lys Leu Val Lys Ser Tyr His Trp Met Gly Leu Val His
 65                  70                  75                  80

Ile Pro Thr Asn Gly Ser Trp Gln Trp Glu Asp Gly Ser Ile Leu Ser
                 85                  90                  95

Pro Asn Leu Leu Thr Ile Ile Glu Met Gln Lys Gly Asp Cys Ala Leu
            100                 105                 110

Tyr Ala Ser Ser Phe Lys Gly Tyr Ile Glu Asn Cys Ser Thr Pro Asn
            115                 120                 125

Thr Tyr Ile Cys Met Gln Arg Thr Val Gly Gly Gly Ser Gly Gly
130                 135                 140

Gly Gly Ser Gly Gly Gly Ser Leu Glu Asp Gly Asn Glu Glu Met
145                 150                 155                 160

Gly Gly Ile Thr Gln Thr Pro Tyr Lys Val Ser Ile Ser Gly Thr Thr
                165                 170                 175

Val Ile Leu Thr Cys Pro Gln Tyr Pro Gly Ser Glu Ile Leu Trp Gln
            180                 185                 190

His Asn Asp Lys Asn Ile Gly Gly Asp Glu Asp Lys Asn Ile Gly
            195                 200                 205

Ser Asp Glu Asp His Leu Ser Leu Lys Glu Phe Ser Glu Leu Glu Gln
```

Ser Gly Tyr Tyr Val Cys Tyr Pro Arg Gly Ser Lys Pro Glu Asp Ala
225                 230                 235                 240

Asn Phe Tyr Leu Tyr Leu Arg Ala Arg Val Cys Glu Asn Cys Met Glu
            245                 250                 255

Met Asp Val Met Ser
            260

<210> SEQ ID NO 99
<211> LENGTH: 7696
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 99

| | | | |
|---|---|---|---|
| acgcgtgtag tcttatgcaa tactctgtag tcttgcaaca tggtaacgat gagttagcaa | 60 |
| catgccttac aaggagagaa aaagcaccgt gcatgccgat tggtggaagt aaggtggtac | 120 |
| gatcgtgcct tattaggaag gcaacagacg ggtctgacat ggattggacg aaccactgaa | 180 |
| ttgccgcatt gcagagatat tgtatttaag tgcctagctc gatacataaa cgggtctctc | 240 |
| tggttagacc agatctgagc ctgggagctc tctggctaac tagggaaccc actgcttaag | 300 |
| cctcaataaa gcttgccttg agtgcttcaa gtagtgtgtg cccgtctgtt gtgtgactct | 360 |
| ggtaactaga gatccctcag acccttttag tcagtgtgga aaatctctag cagtggcgcc | 420 |
| cgaacaggga cttgaaagcg aaagggaaac cagaggagct ctctcgacgc aggactcggc | 480 |
| ttgctgaagc gcgcacggca agaggcgagg ggcggcgact ggtgagtacg ccaaaaattt | 540 |
| tgactagcgg aggctagaag agagagatg ggtgcgagag cgtcagtatt aagcggggga | 600 |
| gaattagatc gcgatgggaa aaaattcggt taaggccagg gggaagaaa aaatataaat | 660 |
| taaaacatat agtatgggca agcagggagc tagaacgatt cgcagttaat cctggcctgt | 720 |
| tagaaacatc agaaggctgt agacaaatac tgggacagct acaaccatcc cttcagacag | 780 |
| gatcagaaga acttagatca ttatataata cagtagcaac cctctattgt gtgcatcaaa | 840 |
| ggatagagat aaaagacacc aaggaagctt tagacaagat agaggaagag caaaacaaaa | 900 |
| gtaagaccac cgcacagcaa gcggccactg atcttcagac ctggaggagg agatatgagg | 960 |
| gacaattgga gaagtgaatt atataaatat aaagtagtaa aaattgaacc attaggagta | 1020 |
| gcacccacca aggcaaagag aagagtggtg cagagagaaa aaagagcagt gggaatagga | 1080 |
| gctttgttcc ttgggttctt gggagcagca ggaagcacta tgggcgcagc gtcaatgacg | 1140 |
| ctgacggtac aggccagaca attattgtct ggtatagtgc agcagcagaa caatttgctg | 1200 |
| agggctattg aggcgcaaca gcatctgttg caactcacag tctgggcat caagcagctc | 1260 |
| caggcaagaa tcctggctgt ggaaagatac ctaaaggatc aacagctcct ggggatttgg | 1320 |
| ggttgctctg gaaaactcat ttgcaccact gctgtgcctt ggaatgctag ttggagtaat | 1380 |
| aaatctctgg aacagatttg gaatcacacg acctggatgg agtgggacag agaaattaac | 1440 |
| aattacacaa gcttaataca ctccttaatt gaagaatcgc aaaaccagca agaaaagaat | 1500 |
| gaacaagaat tattggaatt agataaatgg gcaagtttgt ggaattggtt taacataaca | 1560 |
| aattggctgt ggtatataaa attattcata atgatagtag gaggcttggt aggtttaaga | 1620 |
| atagtttttg ctgtactttc tatagtgaat agagttaggc agggatattc accattatcg | 1680 |

```
tttcagaccc acctcccaac cccgagggga cccgacaggc ccgaaggaat agaagaagaa    1740
ggtggagaga gagacagaga cagatccatt cgattagtga acggatctcg acggtatcgg    1800
ttaactttta aaagaaaagg ggggattggg gggtacagtg caggggaaag aatagtagac    1860
ataatagcaa cagacataca aactaaagaa ttacaaaaac aaattacaaa attcaaaatt    1920
ttatcgatac tagtggatct gcgatcgctc cggtgcccgt cagtgggcag agcgcacatc    1980
gcccacagtc cccgagaagt tgggggaggg ggtcggcaat tgaacgggtg cctagagaag    2040
gtggcgcggg gtaaactggg aaagtgatgt cgtgtactgg ctccgccttt ttcccgaggg    2100
tgggggagaa ccgtatataa gtgcagtagt cgccgtgaac gttcttttc gcaacgggtt    2160
tgccgccaga acacagctga agcttcgagg ggctcgcatc tctccttcac gcgcccgccg    2220
ccctacctga ggccgccatc cacgccggtt gagtcgcgtt ctgccgcctc cgcctgtgg    2280
tgcctcctga actgcgtccg ccgtctaggt aagtttaaag ctcaggtcga gacgggcct    2340
ttgtccggcg ctcccttgga gcctacctag actcagccgg ctctccacgc tttgcctgac    2400
cctgcttgct caactctacg tctttgtttc gttttctgtt ctgcgccgtt acagatccaa    2460
gctgtgaccg gcgcctactc tagagccgcc accatggccc tgcctgtgac agctctgctg    2520
ctgcctctgg ccctgctgct ccatgccgcc agaccccca aggctgtagt attcctcgaa    2580
ccgcagtggt atcgggtact cgaaaaagac agtgtaacgc tgaagtgcca gggggcctat    2640
agtcccgagg ataactcaac ccaatggttc cacaatgaaa gcctcatctc ttcacaagca    2700
agttcttatt tcatagatgc cgccactgta gatgactccg agaatatcg tgtcaaacg    2760
aatttgtcta ctctgagcga cccggttcag cttgaggtac atagggtg ttgcttctc    2820
caagcccccc ggtgggtatt taaggaggaa gatccaatcc acttgcggtg tcacagctgg    2880
aagaacacag cccttcacaa ggtaacatac ttgcaaaacg gcaagggtag gaaatacttc    2940
catcacaaca gcgatttcta catacccaaaa gcaaccctca aggactccgg gagttatttc    3000
tgccgcgggc tcttcggttc taagaatgta agcagtgaaa cggtcaatat aaccattaca    3060
cagggtctcg cggtttctac catctcaagt ttcttccctc ccggttatca agcggccgcg    3120
ggcggtggtg gttctggggg cggggggtct ggaggagggg gaagtctcga ggatggaaat    3180
gaagaaatgg gagggataac ccaaactcca tacaaggtct ctatcagcgg tacgaccgta    3240
attttgacct gtcccccagta tcctggttcc gaaatacttt ggcaacacaa tgataagaat    3300
atcggtggag acgaggatga taagaacatt gggtctgatg aagaccacct ctctctcaag    3360
gaatttagcg agcttgaaca gtcaggttac tacgtgtgtt acccacgggg cagcaagccc    3420
gaggatgcca acttttacct gtacctgcgg gcaagggtct gtgaaaactg tatggagatg    3480
gatgtgatga gcgtagctac gattgtaata gtggacatct gcatcaccgg ggtttgttg    3540
ttgcttgttt actactggag taaaaacaga aaagcgaaag ctaagcctgt tacccgggga    3600
gccgggctg gcgaaggca gagggtcaa aataaagagc gcccccgcc tgttccgaat    3660
ccagactacg aacccatccg gaaagggcaa cgggatctct actccggctt gaatcagcga    3720
agaatttagt aagaattcga atttaaatcg gatccgcggc cgcgtcgaca atcaacctct    3780
ggattacaaa atttgtgaaa gattgactgg tattcttaac tatgttgctc cttttacgct    3840
atgtggatac gctgctttaa tgcctttgta tcatgctatt gcttcccgta tggctttcat    3900
tttctcctcc ttgtataaat cctggttgct gtctctttat gaggagttgt ggcccgttgt    3960
caggcaacgt ggcgtggtgt gcactgtgtt tgctgacgca accccactg gttgggcat    4020
tgccaccacc tgtcagctcc tttccgggac tttcgctttc cccctcccta ttgccacggc    4080
```

```
ggaactcatc gccgcctgcc ttgcccgctg ctggacaggg gctcggctgt tgggcactga   4140
caattccgtg gtgttgtcgg ggaaatcatc gtcctttcct tggctgctcg cctgtgttgc   4200
cacctggatt ctgcgcggga cgtccttctg ctacgtccct tcggccctca atccagcgga   4260
ccttccttcc cgcggcctgc tgccggctct gcggcctctt ccgcgtcttc gccttcgccc   4320
tcagacgagt cggatctccc tttgggccgc ctccccgcct ggtaccttta agaccaatga   4380
cttacaaggc agctgtagat cttagccact ttttaaaaga aaaggggggga ctggaagggc   4440
taattcactc ccaacgaaga taagatctgc tttttgcttg tactgggtct ctctggttag   4500
accagatctg agcctgggag ctctctggct aactagggaa cccactgctt aagcctcaat   4560
aaagcttgcc ttgagtgctt caagtagtgt gtgcccgtct gttgtgtgac tctggtaact   4620
agagatccct cagacccttt tagtcagtgt ggaaaatctc tagcagtagt agttcatgtc   4680
atcttattat tcagtattta aacttgcaa agaaatgaat atcagagagt gagaggaact   4740
tgtttattgc agcttataat ggttacaaat aaagcaatag catcacaaat ttcacaaata   4800
aagcattttt ttcactgcat tctagttgtg gtttgtccaa actcatcaat gtatcttatc   4860
atgtctggct ctagctatcc cgcccctaac tccgcccatc ccgcccctaa ctccgcccag   4920
ttccgcccat tctccgcccc atggctgact aattttttttt atttatgcag aggccgaggc   4980
cgcctcggcc tctgagctat tccagaagta gtgaggaggc ttttttggag gcctagactt   5040
ttgcagagac ggcccaaatt cgtaatcatg gtcatagctg tttcctgtgt gaaattgtta   5100
tccgctcaca attccacaca acatacgagc cggaagcata aagtgtaaag cctggggtgc   5160
ctaatgagtg agctaactca cattaattgc gttgcgctca ctgcccgctt tccagtcggg   5220
aaacctgtcg tgccagctgc attaatgaat cggccaacgc gcggggagag gcggtttgcg   5280
tattgggcgc tcttccgctt cctcgctcac tgactcgctg cgctcggtcg ttcggctgcg   5340
gcgagcggta tcagctcact caaaggcggt aatacggtta tccacagaat caggggataa   5400
cgcaggaaag aacatgtgag caaaaggcca gcaaaaggcc aggaaccgta aaaaggccgc   5460
gttgctggcg tttttccata ggctccgccc ccctgacgag catcacaaaa atcgacgctc   5520
aagtcagagg tggcgaaacc cgacaggact ataaagatac caggcgtttc ccctggaag   5580
ctccctcgtg cgctctcctg ttccgaccct gccgcttacc ggatacctgt ccgcctttct   5640
cccttcggga agcgtggcgc tttctcatag ctcacgctgt aggtatctca gttcggtgta   5700
ggtcgttcgc tccaagctgg gctgtgtgca cgaaccccc gttcagcccg accgctgcgc   5760
cttatccggt aactatcgtc ttgagtccaa cccggtaaga cacgacttat cgccactggc   5820
agcagccact ggtaacagga ttagcagagc gaggtatgta ggcggtgcta cagagttctt   5880
gaagtggtgg cctaactacg gctacactag aaggacagta tttggtatct gcgctctgct   5940
gaagccagtt accttcggaa aaagagttgg tagctcttga tccggcaaac aaaccaccgc   6000
tggtagcggt ggtttttttg tttgcaagca gcagattacg cgcagaaaaa aaggatctca   6060
agaagatcct ttgatctttt ctacggggtc tgacgctcag tggaacgaaa actcacgtta   6120
agggattttg gtcatgagat tatcaaaaag gatcttcacc tagatccttt taaattaaaa   6180
atgaagtttt aaatcaatct aaagtatata tgagtaaact tggtctgaca gttaccaatg   6240
cttaatcagt gaggcaccta tctcagcgat ctgtctattt cgttcatcca tagttgcctg   6300
actccccgtc gtgtagataa ctacgatacg ggagggctta ccatctggcc ccagtgctgc   6360
aatgataccg cgagacccac gctcaccggc tccagattta tcagcaataa accagccagc   6420
```

| | |
|---|---|
| cggaagggcc gagcgcagaa gtggtcctgc aactttatcc gcctccatcc agtctattaa | 6480 |
| ttgttgccgg gaagctagag taagtagttc gccagttaat agtttgcgca acgttgttgc | 6540 |
| cattgctaca ggcatcgtgg tgtcacgctc gtcgtttggt atggcttcat tcagctccgg | 6600 |
| ttcccaacga tcaaggcgag ttacatgatc ccccatgttg tgcaaaaaag cggttagctc | 6660 |
| cttcggtcct ccgatcgttg tcagaagtaa gttggccgca gtgttatcac tcatggttat | 6720 |
| ggcagcactg cataattctc ttactgtcat gccatccgta agatgctttt ctgtgactgg | 6780 |
| tgagtactca accaagtcat tctgagaata gtgtatgcgg cgaccgagtt gctcttgccc | 6840 |
| ggcgtcaata cggataata ccgcgccaca tagcagaact ttaaaagtgc tcatcattgg | 6900 |
| aaaacgttct cgggggcgaa aactctcaag gatcttaccg ctgttgagat ccagttcgat | 6960 |
| gtaacccact cgtgcaccca actgatcttc agcatctttt actttcacca gcgtttctgg | 7020 |
| gtgagcaaaa acaggaaggc aaaatgccgc aaaaaaggga ataagggcga cacggaaatg | 7080 |
| ttgaatactc atactcttcc tttttcaata ttattgaagc atttatcagg gttattgtct | 7140 |
| catgagcgga tacatatttg aatgtattta gaaaaataaa caaatagggg ttccgcgcac | 7200 |
| atttccccga aaagtgccac ctgacgtcta agaaaccatt attatcatga cattaaccta | 7260 |
| taaaaatagg cgtatcacga ggccctttcg tctcgcgcgt ttcggtgatg acggtgaaaa | 7320 |
| cctctgacac atgcagctcc cggagacggt cacagcttgt ctgtaagcgg atgccgggag | 7380 |
| cagacaagcc cgtcagggcg cgtcagcggg tgttggcggg tgtcggggct ggcttaacta | 7440 |
| tgcggcatca gagcagattg tactgagagt gcaccatatg cggtgtgaaa taccgcacag | 7500 |
| atgcgtaagg agaaaatacc gcatcaggcg ccattcgcca ttcaggctgc gcaactgttg | 7560 |
| ggaagggcga tcggtgcggg cctcttcgct attacgccag ctggcgaaag ggggatgtgc | 7620 |
| tgcaaggcga ttaagttggg taacgccagg ttttcccag tcacgacgtt gtaaaacgac | 7680 |
| ggccagtgcc aagctg | 7696 |

<210> SEQ ID NO 100
<211> LENGTH: 7882
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 100

| | |
|---|---|
| acgcgtgtag tcttatgcaa tactctgtag tcttgcaaca tggtaacgat gagttagcaa | 60 |
| catgccttac aaggagagaa aaagcaccgt gcatgccgat tggtggaagt aaggtggtac | 120 |
| gatcgtgcct tattaggaag gcaacagacg ggtctgacat ggattggacg aaccactgaa | 180 |
| ttgccgcatt gcagagatat tgtatttaag tgcctagctc gatacataaa cgggtctctc | 240 |
| tggttagacc agatctgagc ctgggagctc tctggctaac tagggaaccc actgcttaag | 300 |
| cctcaataaa gcttgccttg agtgcttcaa gtagtgtgtg cccgtctgtt gtgtgactct | 360 |
| ggtaactaga tccctcag acccttttag tcagtgtgga aaatctctag cagtggcgcc | 420 |
| cgaacaggga cttgaaagcg aaagggaaac cagaggagct ctctcgacgc aggactcggc | 480 |
| ttgctgaagc gcgcacggca agaggcgagg ggcggcgact ggtgagtacg ccaaaaattt | 540 |
| tgactagcgg aggctagaag gagagagatg ggtgcgagag cgtcagtatt aagcggggga | 600 |
| gaattagatc gcgatgggaa aaaattcggt taaggccagg gggaagaaa aatataaat | 660 |
| taaaacatat agtatgggca agcagggagc tagaacgatt cgcagttaat cctggcctgt | 720 |

```
tagaaacatc agaaggctgt agacaaatac tgggacagct acaaccatcc cttcagacag    780
gatcagaaga acttagatca ttatataata cagtagcaac cctctattgt gtgcatcaaa    840
ggatagagat aaaagacacc aaggaagctt tagacaagat agaggaagag caaaacaaaa    900
gtaagaccac cgcacagcaa gcggccactg atcttcagac ctggaggagg agatatgagg    960
gacaattgga gaagtgaatt atataaatat aaagtagtaa aaattgaacc attaggagta   1020
gcacccacca aggcaaagag aagagtggtg cagagagaaa aaagagcagt gggaatagga   1080
gctttgttcc ttgggttctt gggagcagca ggaagcacta tgggcgcagc gtcaatgacg   1140
ctgacggtac aggccagaca attattgtct ggtatagtgc agcagcagaa caatttgctg   1200
agggctattg aggcgcaaca gcatctgttg caactcacag tctggggcat caagcagctc   1260
caggcaagaa tcctggctgt ggaaagatac ctaaaggatc aacagctcct ggggatttgg   1320
ggttgctctg gaaaactcat ttgcaccact gctgtgcctt ggaatgctag ttggagtaat   1380
aaatctctgg aacagatttg gaatcacacg acctggatgg agtgggacag agaaattaac   1440
aattacacaa gcttaataca ctccttaatt gaagaatcgc aaaaccagca agaaaagaat   1500
gaacaagaat tattggaatt agataaatgg gcaagtttgt ggaattggtt taacataaca   1560
aattggctgt ggtatataaa attattcata atgatagtag gaggcttggt aggtttaaga   1620
atagtttttg ctgtactttc tatagtgaat agagttaggc agggatattc accattatcg   1680
tttcagaccc acctcccaac cccgagggga cccgacaggc ccgaaggaat agaagaagaa   1740
ggtggagaga gagacagaga cagatccatt cgattagtga acggatctcg acggtatcgg   1800
ttaactttta aagaaaagg ggggattggg gggtacagtg caggggaaag aatagtagac   1860
ataatagcaa cagacataca aactaaagaa ttacaaaaac aaattacaaa attcaaaatt   1920
ttatcgatac tagtggatct gcgatcgctc cggtgcccgt cagtgggcag agcgcacatc   1980
gcccacagtc cccgagaagt tggggggagg ggtcggcaat tgaacgggtg cctagagaag   2040
gtggcgcggg gtaaactggg aaagtgatgt cgtgtactgg ctccgccttt ttcccgaggg   2100
tgggggagaa ccgtatataa gtgcagtagt cgccgtgaac gttcttttc gcaacgggtt   2160 tgccgccaga acacagctga agcttcgagg ggctcgcatc tctccttcac gcgcccgccg   2220
ccctacctga ggccgccatc cacgccggtt gagtcgcgtt ctgccgcctc ccgcctgtgg   2280
tgcctcctga actgcgtccg ccgtctaggt aagtttaaag ctcaggtcga gaccgggcct   2340
ttgtccggcg ctcccttgga gcctacctag actcagccgg ctctccacgc tttgcctgac   2400
cctgcttgct caactctacg tctttgtttc gttttctgtt ctgcgccgtt acagatccaa   2460
gctgtgaccg cgcctactc tagagccgcc accatgcttc tcctggtgac aagccttctg   2520
ctctgtgagt taccacaccc agcattcctc ctgatcccac aggtccaact tcaacaatca   2580
ggaccagggc tcgtgaagcc gtcccaaacg cttagtctca catgcgccat tagtggggac   2640
tccgtgagtt caaattccgc cgcctggaat tggattaggc aaagtccatc tagggtctt   2700 gagtggctcg gccgcactta ctacagatcc aagtggtata acgactacgc agtatccgta   2760
aaatcaagaa taacaattaa tccagatact tctaagaacc aatttagtct tcaactgaac   2820
agcgtgaccc ggaggatac agcggtgtat tattgtgcgc gagaagttac cggggatctg   2880
gaggatgctt ttgatatctg gggccaagga acaatggtaa ccgttagttc aggcggtggt   2940
ggttctgggg gcggggggtc tggaggaggg ggaagtgata tacaaatgac acagagcccc   3000
agttccctta gtgcctcagt tggggatagg gtaacaatca cttgccgagc atcacagacg   3060
```

```
atatggtcct atctcaactg gtatcaacaa cgccctggca aggcacccaa cctgctgatc    3120
tacgccgcta gtagtttgca aagtggggta cctagtagat tctccggcag aggttctggc    3180
actgacttta ccttgacaat cagcagcctc aagcagaag acttcgcgac atactactgt    3240
cagcaaagtt actctatacc tcagacgttc ggtcagggga ccaagctcga gatcaaggcg    3300
gccgcgggcg gtggaggcag tggtggtggc ggctctggcg gtggtggtag cctcgaggac    3360
gggaacgaag agatgggagg cataactcaa acgccgtata agttagtat aagtggaaca    3420 acggttatat tgacgtgccc acaatatcca ggatcagaga tcctttggca gcataacgat    3480
aaaaacatcg gcggcgacga agacgacaaa aacattggca gcgacgaaga ccacctcagc    3540
cttaaagagt tctctgagtt ggaacaaagc gggtactacg tctgctatcc acggggggtct    3600 aaacccgagg atgcaaattt ctacctgtat ctcagagcta gggtatgcga aaactgtatg    3660
gaaatggacg tgatgagcgt ggcgactatc gtcatagtag atatttgtat taccgggggg    3720
cttctccttc tggtttatta ttggtctaag aatcggaaag cgaaagcgaa acccgtaaca    3780 cgagggggctg gtgctggggg caggcaaagg ggtcaaaata aggaaggcc cctccagtc    3840 cctaatcctg attacgagcc gataaggaaa ggtcagcggg acttgtacag cggtttgaac    3900
cagcggagga tctgataaga attcgaattt aaatcggatc cgcggccgcg tcgacaatca    3960
acctctggat tacaaaattt gtgaaagatt gactggtatt cttaactatg ttgctccttt    4020
tacgctatgt ggatacgctg ctttaatgcc tttgtatcat gctattgctt cccgtatggc    4080
tttcattttc tcctccttgt ataaatcctg gttgctgtct ctttatgagg agttgtggcc    4140
cgttgtcagg caacgtggcg tggtgtgcac tgtgtttgct gacgcaaccc ccactggttg    4200
gggcattgcc accacctgtc agctcctttc cgggactttc gctttccccc tccctattgc    4260
cacggcggaa ctcatcgccg cctgccttgc ccgctgctgg acaggggctc ggctgttggg    4320
cactgacaat tccgtggtgt tgtcggggaa atcatcgtcc tttccttggc tgctcgcctg    4380
tgttgccacc tggattctgc gcgggacgtc cttctgctac gtcccttcgg ccctcaatcc    4440
agcggacctt ccttcccgcg gcctgctgcc ggctctgcgg cctcttccgc gtcttcgcct    4500
tcgccctcag acgagtcgga tctccctttg ggccgcctcc ccgcctggta cctttaagac    4560
caatgactta caaggcagct gtagatctta gccactttt aaaagaaaag ggggactgg    4620 aagggctaat tcactcccaa cgaagataag atctgctttt tgcttgtact gggtctctct    4680
ggttagacca gatctgagcc tgggagctct ctggctaact agggaaccca ctgcttaagc    4740
ctcaataaag cttgccttga gtgcttcaag tagtgtgtgc ccgtctgttg tgtgactctg    4800
gtaactagag atccctcaga cccttttagt cagtgtggaa aatctctagc agtagtagtt    4860
catgtcatct tattattcag tatttataac ttgcaaagaa atgaatatca gagagtgaga    4920
ggaacttgtt tattgcagct tataatggtt acaaataaag caatagcatc acaaatttca    4980
caaataaagc attttttca ctgcattcta gttgtggttt gtccaaactc atcaatgtat    5040
cttatcatgt ctggctctag ctatcccgcc cctaactccg cccatcccgc ccctaactcc    5100
gcccagttcc gcccattctc cgccccatgg ctgactaatt ttttttattt atgcagaggc    5160
cgaggccgcc tcggcctctg agctattcca aagtagtga ggaggctttt ttggaggcct    5220
agacttttgc agagacggcc caaattcgta atcatggtca tagctgtttc ctgtgtgaaa    5280
ttgttatccg ctcacaattc cacacaacat acgagccgga agcataaagt gtaaagcctg    5340
gggtgcctaa tgagtgagct aactcacatt aattgcgttg cgctcactgc ccgctttcca    5400
gtcgggaaac ctgtcgtgcc agctgcatta atgaatcggc caacgcgcgg ggagaggcgg    5460
```

```
tttgcgtatt gggcgctctt ccgcttcctc gctcactgac tcgctgcgct cggtcgttcg   5520
gctgcggcga gcggtatcag ctcactcaaa ggcggtaata cggttatcca cagaatcagg   5580
ggataacgca ggaaagaaca tgtgagcaaa aggccagcaa aaggccagga accgtaaaaa   5640
ggccgcgttg ctggcgtttt tccataggct ccgcccccct gacgagcatc acaaaaatcg   5700
acgctcaagt cagaggtggc gaaacccgac aggactataa agataccagg cgtttccccc   5760
tggaagctcc ctcgtgcgct ctcctgttcc gaccctgccg cttaccggat acctgtccgc   5820
ctttctccct tcgggaagcg tggcgctttc tcatagctca cgctgtaggt atctcagttc   5880
ggtgtaggtc gttcgctcca agctgggctg tgtgcacgaa ccccccgttc agcccgaccg   5940
ctgcgcctta tccggtaact atcgtcttga gtccaacccg gtaagacacg acttatcgcc   6000
actggcagca gccactggta acaggattag cagagcgagg tatgtaggcg gtgctacaga   6060
gttcttgaag tggtggccta actacggcta cactagaagg acagtatttg gtatctgcgc   6120
tctgctgaag ccagttacct tcggaaaaag agttggtagc tcttgatccg gcaaacaaac   6180
caccgctggt agcggtggtt tttttgtttg caagcagcag attacgcgca gaaaaaaagg   6240
atctcaagaa gatcctttga tcttttctac ggggtctgac gctcagtgga acgaaaactc   6300
acgttaaggg attttggtca tgagattatc aaaaaggatc ttcacctaga tccttttaaa   6360
ttaaaaatga agttttaaat caatctaaag tatatatgag taaacttggt ctgacagtta   6420
ccaatgctta atcagtgagg cacctatctc agcgatctgt ctatttcgtt catccatagt   6480
tgcctgactc cccgtcgtgt agataactac gatacgggag ggcttaccat ctggccccag   6540
tgctgcaatg ataccgcgag acccacgctc accggctcca gatttatcag caataaacca   6600
gccagccgga agggccgagc gcagaagtgg tcctgcaact ttatccgcct ccatccagtc   6660
tattaattgt tgccgggaag ctagagtaag tagttcgcca gttaatagtt tgcgcaacgt   6720
tgttgccatt gctacaggca tcgtggtgtc acgctcgtcg tttggtatgg cttcattcag   6780
ctccggttcc caacgatcaa ggcgagttac atgatccccc atgttgtgca aaaaagcggt   6840
tagctccttc ggtcctccga tcgttgtcag aagtaagttg gccgcagtgt tatcactcat   6900
ggttatggca gcactgcata attctcttac tgtcatgcca tccgtaagat gcttttctgt   6960
gactggtgag tactcaacca agtcattctg agaatagtgt atgcggcgac cgagttgctc   7020
ttgcccggcg tcaatacggg ataataccgc gccacatagc agaactttaa aagtgctcat   7080
cattggaaaa cgttcttcgg ggcgaaaact ctcaaggatc ttaccgctgt tgagatccag   7140
ttcgatgtaa cccactcgtg cacccaactg atcttcagca tcttttactt tcaccagcgt   7200
ttctgggtga gcaaaaacag gaaggcaaaa tgccgcaaaa aagggaataa gggcgacacg   7260
gaaatgttga atactcatac tcttcctttt tcaatattat tgaagcattt atcagggtta   7320
ttgtctcatg agcggataca tatttgaatg tatttagaaa aataaacaaa tagggttccc   7380
gcgcacattt ccccgaaaag tgccacctga cgtctaagaa accattatta tcatgacatt   7440
aacctataaa aataggcgta tcacgaggcc ctttcgtctc gcgcgtttcg gtgatgacgg   7500
tgaaaacctc tgacacatgc agctcccgga cggtcaca gcttgtctgt aagcggatgc   7560
cgggagcaga caagcccgtc agggcgcgtc agcgggtgtt ggcgggtgtc ggggctggct   7620
taactatgcg gcatcagagc agattgtact gagagtgcac catatgcggt gtgaaatacc   7680
gcacagatgc gtaaggagaa aataccgcat caggcgccat tcgccattca ggctgcgcaa   7740
ctgttgggaa gggcgatcgg tgcgggcctc ttcgctatta cgccagctgg cgaaaggggg   7800
```

```
atgtgctgca aggcgattaa gttgggtaac gccagggttt tcccagtcac gacgttgtaa    7860
aacgacggcc agtgccaagc tg                                             7882
```

<210> SEQ ID NO 101
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Gly Gly Gly Gly Ser Gly Gly Gly Gly Ser
1               5                   10

<210> SEQ ID NO 102
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
ggtggcggag gttctggagg tggaggttcc                                     30

<210> SEQ ID NO 103
<211> LENGTH: 184
<212> TYPE: PRT
<213> ORGANISM: Homo sapiens

<400> SEQUENCE: 103

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 104

-continued

```
<211> LENGTH: 556
<212> TYPE: PRT
<213> ORGANISM: Homo sapiens

<400> SEQUENCE: 104

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
```

```
385                 390                 395                 400
Pro Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
                420                 425                 430

Ser Gln Asp Gly Ser Gly Tyr Glu Asn Pro Glu Asp Glu Pro Leu Gly
                435                 440                 445

Pro Glu Asp Glu Asp Ser Phe Ser Asn Ala Glu Ser Tyr Glu Asn Glu
450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
                500                 505                 510

Leu Arg Ser Ile Arg Gly Gln Pro Gly Pro Asn His Glu Glu Asp Ala
                515                 520                 525

Asp Ser Tyr Glu Asn Met Asp Asn Pro Asp Gly Pro Asp Pro Ala Trp
                530                 535                 540

Gly Gly Gly Gly Arg Met Gly Thr Trp Ser Thr Arg
545                 550                 555
```

<210> SEQ ID NO 105
<211> LENGTH: 847
<212> TYPE: PRT
<213> ORGANISM: Homo sapiens

<400> SEQUENCE: 105

```
Met His Leu Leu Gly Pro Trp Leu Leu Leu Val Leu Glu Tyr Leu
1               5                   10                  15

Ala Phe Ser Asp Ser Ser Lys Trp Val Phe Glu His Pro Glu Thr Leu
                20                  25                  30

Tyr Ala Trp Glu Gly Ala Cys Val Trp Ile Pro Cys Thr Tyr Arg Ala
            35                  40                  45

Leu Asp Gly Asp Leu Glu Ser Phe Ile Leu Phe His Asn Pro Glu Tyr
    50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
                85                  90                  95

Asp Lys Asn Lys Asn Cys Thr Leu Ser Ile His Pro Val His Leu Asn
                100                 105                 110

Asp Ser Gly Gln Leu Gly Leu Arg Met Glu Ser Lys Thr Glu Lys Trp
            115                 120                 125

Met Glu Arg Ile His Leu Asn Val Ser Glu Arg Pro Phe Pro Pro His
    130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175

Leu Leu Glu Gly Val Pro Met Arg Gln Ala Ala Val Thr Ser Thr Ser
                180                 185                 190

Leu Thr Ile Lys Ser Val Phe Thr Arg Ser Glu Leu Lys Phe Ser Pro
            195                 200                 205
```

```
Gln Trp Ser His His Gly Lys Ile Val Thr Cys Gln Leu Gln Asp Ala
210                 215                 220

Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
                245                 250                 255

Glu Gly Asp Ser Val Thr Met Thr Cys Glu Val Ser Ser Asn Pro
            260                 265                 270

Glu Tyr Thr Thr Val Ser Trp Leu Lys Asp Gly Thr Ser Leu Lys Lys
            275                 280                 285

Gln Asn Thr Phe Thr Leu Asn Leu Arg Glu Val Thr Lys Asp Gln Ser
290                 295                 300

Gly Lys Tyr Cys Cys Gln Val Ser Asn Asp Val Gly Pro Gly Arg Ser
305                 310                 315                 320

Glu Glu Val Phe Leu Gln Val Gln Tyr Ala Pro Glu Pro Ser Thr Val
                325                 330                 335

Gln Ile Leu His Ser Pro Ala Val Glu Gly Ser Gln Val Glu Phe Leu
                340                 345                 350

Cys Met Ser Leu Ala Asn Pro Leu Pro Thr Asn Tyr Thr Trp Tyr His
                355                 360                 365

Asn Gly Lys Glu Met Gln Gly Arg Thr Glu Glu Lys Val His Ile Pro
370                 375                 380

Lys Ile Leu Pro Trp His Ala Gly Thr Tyr Ser Cys Val Ala Glu Asn
385                 390                 395                 400

Ile Leu Gly Thr Gly Gln Arg Gly Pro Gly Ala Glu Leu Asp Val Gln
                405                 410                 415

Tyr Pro Pro Lys Lys Val Thr Thr Val Ile Gln Asn Pro Met Pro Ile
                420                 425                 430

Arg Glu Gly Asp Thr Val Thr Leu Ser Cys Asn Tyr Asn Ser Ser Asn
                435                 440                 445

Pro Ser Val Thr Arg Tyr Glu Trp Lys Pro His Gly Ala Trp Glu Glu
450                 455                 460

Pro Ser Leu Gly Val Leu Lys Ile Gln Asn Val Gly Trp Asp Asn Thr
465                 470                 475                 480

Thr Ile Ala Cys Ala Ala Cys Asn Ser Trp Cys Ser Trp Ala Ser Pro
                485                 490                 495

Val Ala Leu Asn Val Gln Tyr Ala Pro Arg Asp Val Arg Val Arg Lys
                500                 505                 510

Ile Lys Pro Leu Ser Glu Ile His Ser Gly Asn Ser Val Ser Leu Gln
                515                 520                 525

Cys Asp Phe Ser Ser Ser His Pro Lys Glu Val Gln Phe Phe Trp Glu
530                 535                 540

Lys Asn Gly Arg Leu Leu Gly Lys Glu Ser Gln Leu Asn Phe Asp Ser
545                 550                 555                 560

Ile Ser Pro Glu Asp Ala Gly Ser Tyr Ser Cys Trp Val Asn Asn Ser
                565                 570                 575

Ile Gly Gln Thr Ala Ser Lys Ala Trp Thr Leu Glu Val Leu Tyr Ala
                580                 585                 590

Pro Arg Arg Leu Arg Val Ser Met Ser Pro Gly Asp Gln Val Met Glu
                595                 600                 605

Gly Lys Ser Ala Thr Leu Thr Cys Glu Ser Asp Ala Asn Pro Pro Val
610                 615                 620

Ser His Tyr Thr Trp Phe Asp Trp Asn Asn Gln Ser Leu Pro Tyr His
```

```
                625                 630                 635                 640
Ser Gln Lys Leu Arg Leu Glu Pro Val Lys Val Gln His Ser Gly Ala
                    645                 650                 655

Tyr Trp Cys Gln Gly Thr Asn Ser Val Gly Lys Gly Arg Ser Pro Leu
                660                 665                 670

Ser Thr Leu Thr Val Tyr Tyr Ser Pro Glu Thr Ile Gly Arg Arg Val
            675                 680                 685

Ala Val Gly Leu Gly Ser Cys Leu Ala Ile Leu Ile Leu Ala Ile Cys
        690                 695                 700

Gly Leu Lys Leu Gln Arg Arg Trp Lys Arg Thr Gln Ser Gln Gln Gly
705                 710                 715                 720

Leu Gln Glu Asn Ser Ser Gly Gln Ser Phe Phe Val Arg Asn Lys Lys
                725                 730                 735

Val Arg Arg Ala Pro Leu Ser Glu Gly Pro His Ser Leu Gly Cys Tyr
            740                 745                 750

Asn Pro Met Met Glu Asp Gly Ile Ser Tyr Thr Thr Leu Arg Phe Pro
        755                 760                 765

Glu Met Asn Ile Pro Arg Thr Gly Asp Ala Glu Ser Ser Glu Met Gln
    770                 775                 780

Arg Pro Pro Pro Asp Cys Asp Asp Thr Val Thr Tyr Ser Ala Leu His
785                 790                 795                 800

Lys Arg Gln Val Gly Asp Tyr Glu Asn Val Ile Pro Asp Phe Pro Glu
                805                 810                 815

Asp Glu Gly Ile His Tyr Ser Glu Leu Ile Gln Phe Gly Val Gly Glu
            820                 825                 830

Arg Pro Gln Ala Gln Glu Asn Val Asp Tyr Val Ile Leu Lys His
        835                 840                 845

<210> SEQ ID NO 106
<211> LENGTH: 555
<212> TYPE: DNA
<213> ORGANISM: Unknown
<220> FEATURE:
<221> NAME/KEY: source
<223> OTHER INFORMATION: /note="Description of Unknown:
      CD16 ECD sequence"

<400> SEQUENCE: 106
cccaaggctg tagtattcct cgaaccgcag tggtatcggg tactcgaaaa agacagtgta      60
acgctgaagt gccagggggc ctatagtccc gaggataact caacccaatg gttccacaat     120
gaaagcctca tctcttcaca agcaagttct tatttcatag atgccgccac tgtagatgac     180
tccggagaat atcggtgtca aacgaatttg tctactctga gcgacccggt tcagcttgag     240
gtacacatag gtggttgct tctccaagcc ccccggtggg tatttaagga ggaagatcca     300
atccacttgc ggtgtcacag ctggaagaac acagcccttc acaaggtaac atacttgcaa     360
aacggcaagg gtaggaaata cttccatcac aacagcgatt tctacatacc aaaagcaacc     420
ctcaaggact ccgggagtta tttctgccgc gggctcttcg gttctaagaa tgtaagcagt     480
gaaacggtca atataaccat tacacagggt ctcgcggttt ctaccatctc aagtttcttc     540
cctcccggtt atcaa                                                     555

<210> SEQ ID NO 107
<211> LENGTH: 160
<212> TYPE: PRT
<213> ORGANISM: Homo sapiens
```

-continued

```
<400> SEQUENCE: 107

Gln Ser Ile Lys Gly Asn His Leu Val Lys Val Tyr Asp Tyr Gln Glu
1               5                   10                  15

Asp Gly Ser Val Leu Leu Thr Cys Asp Ala Glu Ala Lys Asn Ile Thr
            20                  25                  30

Trp Phe Lys Asp Gly Lys Met Ile Gly Phe Leu Thr Glu Asp Lys Lys
        35                  40                  45

Lys Trp Asn Leu Gly Ser Asn Ala Lys Asp Pro Arg Gly Met Tyr Gln
50                  55                  60

Cys Lys Gly Ser Gln Asn Lys Ser Lys Pro Leu Gln Val Tyr Tyr Arg
65                  70                  75                  80

Met Cys Gln Asn Cys Ile Glu Leu Asn Ala Ala Thr Ile Ser Gly Phe
                85                  90                  95

Leu Phe Ala Glu Ile Val Ser Ile Phe Val Leu Ala Val Gly Val Tyr
            100                 105                 110

Phe Ile Ala Gly Gln Asp Gly Val Arg Gln Ser Arg Ala Ser Asp Lys
        115                 120                 125

Gln Thr Leu Leu Pro Asn Asp Gln Leu Tyr Gln Pro Leu Lys Asp Arg
    130                 135                 140

Glu Asp Asp Gln Tyr Ser His Leu Gln Gly Asn Gln Leu Arg Arg Asn
145                 150                 155                 160

<210> SEQ ID NO 108
<211> LENGTH: 150
<212> TYPE: PRT
<213> ORGANISM: Homo sapiens

<400> SEQUENCE: 108

Phe Lys Ile Pro Ile Glu Glu Leu Glu Asp Arg Val Phe Val Asn Cys
1               5                   10                  15

Asn Thr Ser Ile Thr Trp Val Glu Gly Thr Val Gly Thr Leu Leu Ser
            20                  25                  30

Asp Ile Thr Arg Leu Asp Leu Gly Lys Arg Ile Leu Asp Pro Arg Gly
        35                  40                  45

Ile Tyr Arg Cys Asn Gly Thr Asp Ile Tyr Lys Asp Lys Glu Ser Thr
50                  55                  60

Val Gln Val His Tyr Arg Met Cys Gln Ser Cys Val Glu Leu Asp Pro
65                  70                  75                  80

Ala Thr Val Ala Gly Ile Ile Val Thr Asp Val Ile Ala Thr Leu Leu
                85                  90                  95

Leu Ala Leu Gly Val Phe Cys Phe Ala Gly His Glu Thr Gly Arg Leu
            100                 105                 110

Ser Gly Ala Ala Asp Thr Gln Ala Leu Leu Arg Asn Asp Gln Val Tyr
        115                 120                 125

Gln Pro Leu Arg Asp Arg Asp Asp Ala Gln Tyr Ser His Leu Gly Gly
    130                 135                 140

Asn Trp Ala Arg Asn Lys
145                 150

<210> SEQ ID NO 109
<211> LENGTH: 113
<212> TYPE: PRT
<213> ORGANISM: Homo sapiens

<400> SEQUENCE: 109

Arg Val Lys Phe Ser Arg Ser Ala Asp Ala Pro Ala Tyr Gln Gln Gly
```

```
                1               5                   10                  15
Gln Asn Gln Leu Tyr Asn Glu Leu Asn Leu Gly Arg Arg Glu Glu Tyr
            20                  25                  30
Asp Val Leu Asp Lys Arg Arg Gly Arg Asp Pro Glu Met Gly Gly Lys
        35                  40                  45
Pro Gln Arg Arg Lys Asn Pro Gln Glu Gly Leu Tyr Asn Glu Leu Gln
    50                  55                  60
Lys Asp Lys Met Ala Glu Ala Tyr Ser Glu Ile Gly Met Lys Gly Glu
65                  70                  75                  80
Arg Arg Arg Gly Lys Gly His Asp Gly Leu Tyr Gln Gly Leu Ser Thr
                85                  90                  95
Ala Thr Lys Asp Thr Tyr Asp Ala Leu His Met Gln Ala Leu Pro Pro
            100                 105                 110
Arg
```

<210> SEQ ID NO 110
<211> LENGTH: 137
<212> TYPE: PRT
<213> ORGANISM: Homo sapiens

<400> SEQUENCE: 110

```
Asn Ser Leu Phe Asn Gln Glu Val Gln Ile Pro Leu Thr Glu Ser Tyr
1               5                   10                  15
Cys Gly Pro Cys Pro Lys Asn Trp Ile Cys Tyr Lys Asn Asn Cys Tyr
            20                  25                  30
Gln Phe Phe Asp Glu Ser Lys Asn Trp Tyr Glu Ser Gln Ala Ser Cys
        35                  40                  45
Met Ser Gln Asn Ala Ser Leu Leu Lys Val Tyr Ser Lys Glu Asp Gln
    50                  55                  60
Asp Leu Leu Lys Leu Val Lys Ser Tyr His Trp Met Gly Leu Val His
65                  70                  75                  80
Ile Pro Thr Asn Gly Ser Trp Gln Trp Glu Asp Gly Ser Ile Leu Ser
                85                  90                  95
Pro Asn Leu Leu Thr Ile Ile Glu Met Gln Lys Gly Asp Cys Ala Leu
            100                 105                 110
Tyr Ala Ser Ser Phe Lys Gly Tyr Ile Glu Asn Cys Ser Thr Pro Asn
        115                 120                 125
Thr Tyr Ile Cys Met Gln Arg Thr Val
    130                 135
```

<210> SEQ ID NO 111
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 111

```
Ala Ala Ile Glu Val Met Tyr Pro Pro Pro Tyr Leu Gly Gly Gly Gly
1               5                   10                  15
Ser Gly Gly Gly Gly Ser Gly Gly Gly Gly Ser Leu Glu
            20                  25
```

<210> SEQ ID NO 112
<211> LENGTH: 171
<212> TYPE: PRT

<213> ORGANISM: Homo sapiens

<400> SEQUENCE: 112

```
Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170
```

<210> SEQ ID NO 113
<211> LENGTH: 280
<212> TYPE: PRT
<213> ORGANISM: Homo sapiens

<400> SEQUENCE: 113

```
Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
```

180                 185                 190
Ser His Arg Leu His Pro Ala Thr Glu Thr Gly Gly Arg Glu Ala Thr
                195                 200                 205

Ser Ser Pro Arg Pro Gln Pro Arg Asp Arg Arg Trp Gly Asp Thr Pro
            210                 215                 220

Pro Gly Arg Lys Pro Gly Ser Pro Val Trp Gly Glu Ser Tyr Leu
225                 230                 235                 240

Ser Ser Tyr Pro Thr Cys Pro Ala Gln Ala Trp Cys Ser Arg Ser Ala
                245                 250                 255

Leu Arg Ala Pro Ser Ser Ser Leu Gly Ala Phe Phe Ala Gly Asp Leu
            260                 265                 270

Pro Pro Pro Leu Gln Ala Gly Ala
        275                 280

<210> SEQ ID NO 114
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ile Tyr
            20                  25                  30

Asp Met Ser Trp Val Arg Gln Thr Pro Glu Lys Arg Leu Glu Trp Val
        35                  40                  45

Ala Tyr Ile Ser Ser Gly Gly Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Ser Gly Tyr Gly Thr His Trp Gly Val Leu Phe Ala Tyr
            100                 105                 110

Trp Gln Gly Thr Leu Val Thr Val Ser Ala
        115                 120

<210> SEQ ID NO 115
<211> LENGTH: 345
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 115

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
        35                  40                  45

Ala Arg Leu Ser Trp Asn Gln Val Asp Gln Val Ile Arg Asn Ala Leu
    50                  55                  60

```
Ala Ser Pro Gly Ser Gly Gly Asp Leu Gly Glu Ala Ile Arg Glu Gln
 65                  70                  75                  80

Pro Glu Gln Ala Arg Leu Ala Leu Thr Leu Ala Ala Glu Ser Glu
                 85                  90                  95

Arg Phe Val Arg Gln Gly Thr Gly Asn Asp Glu Ala Gly Ala Ala Asn
                100                 105                 110

Gly Pro Ala Asp Ser Gly Asp Ala Leu Leu Glu Arg Asn Tyr Pro Thr
                115                 120                 125

Gly Ala Glu Phe Leu Gly Asp Gly Asp Val Ser Phe Ser Thr Arg
130                 135                 140

Gly Thr Gln Asn Trp Thr Val Glu Arg Leu Leu Gln Ala His Arg Gln
145                 150                 155                 160

Leu Glu Glu Arg Gly Tyr Val Phe Val Gly Tyr His Gly Thr Phe Leu
                165                 170                 175

Glu Ala Ala Gln Ser Ile Val Phe Gly Gly Val Arg Ala Arg Ser Gln
                180                 185                 190

Asp Leu Asp Ala Ile Trp Arg Gly Phe Tyr Ile Ala Gly Asp Pro Ala
                195                 200                 205

Leu Ala Tyr Gly Tyr Ala Gln Asp Gln Glu Pro Asp Ala Ala Gly Arg
210                 215                 220

Ile Arg Asn Gly Ala Leu Leu Arg Val Tyr Val Pro Arg Ser Ser Leu
225                 230                 235                 240

Pro Gly Phe Tyr Arg Thr Ser Leu Thr Leu Ala Ala Pro Glu Ala Ala
                245                 250                 255

Gly Glu Val Glu Arg Leu Ile Gly His Pro Leu Pro Leu Arg Leu Asp
                260                 265                 270

Ala Ile Thr Gly Pro Glu Glu Glu Gly Gly Arg Leu Glu Thr Ile Leu
                275                 280                 285

Gly Trp Pro Leu Ala Glu Arg Thr Val Val Ile Pro Ser Ala Ile Pro
290                 295                 300

Thr Asp Pro Arg Asn Val Gly Gly Asp Leu Asp Pro Ser Ser Ile Pro
305                 310                 315                 320

Asp Lys Glu Gln Ala Ile Ser Ala Leu Pro Asp Tyr Ala Ser Gln Pro
                325                 330                 335

Gly Lys Pro Pro Arg Glu Asp Leu Lys
                340                 345

<210> SEQ ID NO 116
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MISC_FEATURE
<222> LOCATION: (1)..(20)
<223> OTHER INFORMATION: /note="This sequence may encompass 1-4 'Gly Gly
      Gly Gly Ser' repeating units"

<400> SEQUENCE: 116

Gly Gly Gly Gly Ser Gly Gly Gly Ser Gly Gly Gly Ser Gly
1               5                   10                  15

Gly Gly Gly Ser
            20
```

```
<210> SEQ ID NO 117
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Gly Gly Gly Gly Ser
1               5

<210> SEQ ID NO 118
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MISC_FEATURE
<222> LOCATION: (1)..(20)
<223> OTHER INFORMATION: /note="This sequence may encompass 2-4 'Gly Gly
      Gly Gly Ser' repeating units"

<400> SEQUENCE: 118

Gly Gly Gly Gly Ser Gly Gly Gly Gly Ser Gly Gly Gly Gly Ser Gly
1               5                   10                  15

Gly Gly Gly Ser
            20

<210> SEQ ID NO 119
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MISC_FEATURE
<222> LOCATION: (1)..(15)
<223> OTHER INFORMATION: /note="This sequence may encompass 1-3 'Gly Gly
      Gly Gly Ser' repeating units"

<400> SEQUENCE: 119

Gly Gly Gly Gly Ser Gly Gly Gly Gly Ser Gly Gly Gly Gly Ser
1               5                   10                  15

<210> SEQ ID NO 120
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Gly Gly Gly Gly Ser Gly Gly Gly Gly Ser Gly Gly Gly Gly Ser Gly
1               5                   10                  15

Gly Gly Gly Ser
            20

<210> SEQ ID NO 121
<211> LENGTH: 15
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Gly Gly Gly Gly Ser Gly Gly Gly Gly Ser Gly Gly Gly Gly Ser
1               5                   10                  15

<210> SEQ ID NO 122
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

Gly Gly Gly Ser
1

<210> SEQ ID NO 123
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(5000)
<223> OTHER INFORMATION: /note="This sequence may encompass 50-5000
      nucleotides"
<220> FEATURE:
<221> NAME/KEY: source
<223> OTHER INFORMATION: /note="See specification as filed for detailed
      description of substitutions and preferred embodiments"

<400> SEQUENCE: 123
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
aaaaaaaaaa aaaaaaaaaa aaaaaaaaaa aaaaaaaaaa aaaaaaaaaa aaaaaaaaaa     360
aaaaaaaaaa aaaaaaaaaa aaaaaaaaaa aaaaaaaaaa aaaaaaaaaa aaaaaaaaaa     420
aaaaaaaaaa aaaaaaaaaa aaaaaaaaaa aaaaaaaaaa aaaaaaaaaa aaaaaaaaaa     480
aaaaaaaaaa aaaaaaaaaa aaaaaaaaaa aaaaaaaaaa aaaaaaaaaa aaaaaaaaaa     540
aaaaaaaaaa aaaaaaaaaa aaaaaaaaaa aaaaaaaaaa aaaaaaaaaa aaaaaaaaaa     600
aaaaaaaaaa aaaaaaaaaa aaaaaaaaaa aaaaaaaaaa aaaaaaaaaa aaaaaaaaaa     660
aaaaaaaaaa aaaaaaaaaa aaaaaaaaaa aaaaaaaaaa aaaaaaaaaa aaaaaaaaaa     720
aaaaaaaaaa aaaaaaaaaa aaaaaaaaaa aaaaaaaaaa aaaaaaaaaa aaaaaaaaaa     780
aaaaaaaaaa aaaaaaaaaa aaaaaaaaaa aaaaaaaaaa aaaaaaaaaa aaaaaaaaaa     840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaaaaaaaa aaaaaaaaaa     960
```

```
aaaaaaaaaa aaaaaaaaaa aaaaaaaaaa aaaaaaaaaa aaaaaaaaaa aaaaaaaaaa    1020
aaaaaaaaaa aaaaaaaaaa aaaaaaaaaa aaaaaaaaaa aaaaaaaaaa aaaaaaaaaa    1080
aaaaaaaaaa aaaaaaaaaa aaaaaaaaaa aaaaaaaaaa aaaaaaaaaa aaaaaaaaaa    1140
aaaaaaaaaa aaaaaaaaaa aaaaaaaaaa aaaaaaaaaa aaaaaaaaaa aaaaaaaaaa    1200
aaaaaaaaaa aaaaaaaaaa aaaaaaaaaa aaaaaaaaaa aaaaaaaaaa aaaaaaaaaa    1260
aaaaaaaaaa aaaaaaaaaa aaaaaaaaaa aaaaaaaaaa aaaaaaaaaa aaaaaaaaaa    1320
aaaaaaaaaa aaaaaaaaaa aaaaaaaaaa aaaaaaaaaa aaaaaaaaaa aaaaaaaaaa    1380
aaaaaaaaaa aaaaaaaaaa aaaaaaaaaa aaaaaaaaaa aaaaaaaaaa aaaaaaaaaa    1440
aaaaaaaaaa aaaaaaaaaa aaaaaaaaaa aaaaaaaaaa aaaaaaaaaa aaaaaaaaaa    1500
aaaaaaaaaa aaaaaaaaaa aaaaaaaaaa aaaaaaaaaa aaaaaaaaaa aaaaaaaaaa    1560
aaaaaaaaaa aaaaaaaaaa aaaaaaaaaa aaaaaaaaaa aaaaaaaaaa aaaaaaaaaa    1620
aaaaaaaaaa aaaaaaaaaa aaaaaaaaaa aaaaaaaaaa aaaaaaaaaa aaaaaaaaaa    1680
aaaaaaaaaa aaaaaaaaaa aaaaaaaaaa aaaaaaaaaa aaaaaaaaaa aaaaaaaaaa    1740
aaaaaaaaaa aaaaaaaaaa aaaaaaaaaa aaaaaaaaaa aaaaaaaaaa aaaaaaaaaa    1800
aaaaaaaaaa aaaaaaaaaa aaaaaaaaaa aaaaaaaaaa aaaaaaaaaa aaaaaaaaaa    1860
aaaaaaaaaa aaaaaaaaaa aaaaaaaaaa aaaaaaaaaa aaaaaaaaaa aaaaaaaaaa    1920
aaaaaaaaaa aaaaaaaaaa aaaaaaaaaa aaaaaaaaaa aaaaaaaaaa aaaaaaaaaa    1980
aaaaaaaaaa aaaaaaaaaa aaaaaaaaaa aaaaaaaaaa aaaaaaaaaa aaaaaaaaaa    2040
aaaaaaaaaa aaaaaaaaaa aaaaaaaaaa aaaaaaaaaa aaaaaaaaaa aaaaaaaaaa    2100
aaaaaaaaaa aaaaaaaaaa aaaaaaaaaa aaaaaaaaaa aaaaaaaaaa aaaaaaaaaa    2160
aaaaaaaaaa aaaaaaaaaa aaaaaaaaaa aaaaaaaaaa aaaaaaaaaa aaaaaaaaaa    2220
aaaaaaaaaa aaaaaaaaaa aaaaaaaaaa aaaaaaaaaa aaaaaaaaaa aaaaaaaaaa    2280
aaaaaaaaaa aaaaaaaaaa aaaaaaaaaa aaaaaaaaaa aaaaaaaaaa aaaaaaaaaa    2340
aaaaaaaaaa aaaaaaaaaa aaaaaaaaaa aaaaaaaaaa aaaaaaaaaa aaaaaaaaaa    2400
aaaaaaaaaa aaaaaaaaaa aaaaaaaaaa aaaaaaaaaa aaaaaaaaaa aaaaaaaaaa    2460
aaaaaaaaaa aaaaaaaaaa aaaaaaaaaa aaaaaaaaaa aaaaaaaaaa aaaaaaaaaa    2520
aaaaaaaaaa aaaaaaaaaa aaaaaaaaaa aaaaaaaaaa aaaaaaaaaa aaaaaaaaaa    2580
aaaaaaaaaa aaaaaaaaaa aaaaaaaaaa aaaaaaaaaa aaaaaaaaaa aaaaaaaaaa    2640
aaaaaaaaaa aaaaaaaaaa aaaaaaaaaa aaaaaaaaaa aaaaaaaaaa aaaaaaaaaa    2700
aaaaaaaaaa aaaaaaaaaa aaaaaaaaaa aaaaaaaaaa aaaaaaaaaa aaaaaaaaaa    2760
aaaaaaaaaa aaaaaaaaaa aaaaaaaaaa aaaaaaaaaa aaaaaaaaaa aaaaaaaaaa    2820
aaaaaaaaaa aaaaaaaaaa aaaaaaaaaa aaaaaaaaaa aaaaaaaaaa aaaaaaaaaa    2880
aaaaaaaaaa aaaaaaaaaa aaaaaaaaaa aaaaaaaaaa aaaaaaaaaa aaaaaaaaaa    2940
aaaaaaaaaa aaaaaaaaaa aaaaaaaaaa aaaaaaaaaa aaaaaaaaaa aaaaaaaaaa    3000
aaaaaaaaaa aaaaaaaaaa aaaaaaaaaa aaaaaaaaaa aaaaaaaaaa aaaaaaaaaa    3060
aaaaaaaaaa aaaaaaaaaa aaaaaaaaaa aaaaaaaaaa aaaaaaaaaa aaaaaaaaaa    3120
aaaaaaaaaa aaaaaaaaaa aaaaaaaaaa aaaaaaaaaa aaaaaaaaaa aaaaaaaaaa    3180
aaaaaaaaaa aaaaaaaaaa aaaaaaaaaa aaaaaaaaaa aaaaaaaaaa aaaaaaaaaa    3240
aaaaaaaaaa aaaaaaaaaa aaaaaaaaaa aaaaaaaaaa aaaaaaaaaa aaaaaaaaaa    3300
aaaaaaaaaa aaaaaaaaaa aaaaaaaaaa aaaaaaaaaa aaaaaaaaaa aaaaaaaaaa    3360
```

```
aaaaaaaaaa aaaaaaaaaa aaaaaaaaaa aaaaaaaaaa aaaaaaaaaa aaaaaaaaaa    3420
aaaaaaaaaa aaaaaaaaaa aaaaaaaaaa aaaaaaaaaa aaaaaaaaaa aaaaaaaaaa    3480
aaaaaaaaaa aaaaaaaaaa aaaaaaaaaa aaaaaaaaaa aaaaaaaaaa aaaaaaaaaa    3540
aaaaaaaaaa aaaaaaaaaa aaaaaaaaaa aaaaaaaaaa aaaaaaaaaa aaaaaaaaaa    3600
aaaaaaaaaa aaaaaaaaaa aaaaaaaaaa aaaaaaaaaa aaaaaaaaaa aaaaaaaaaa    3660
aaaaaaaaaa aaaaaaaaaa aaaaaaaaaa aaaaaaaaaa aaaaaaaaaa aaaaaaaaaa    3720
aaaaaaaaaa aaaaaaaaaa aaaaaaaaaa aaaaaaaaaa aaaaaaaaaa aaaaaaaaaa    3780
aaaaaaaaaa aaaaaaaaaa aaaaaaaaaa aaaaaaaaaa aaaaaaaaaa aaaaaaaaaa    3840
aaaaaaaaaa aaaaaaaaaa aaaaaaaaaa aaaaaaaaaa aaaaaaaaaa aaaaaaaaaa    3900
aaaaaaaaaa aaaaaaaaaa aaaaaaaaaa aaaaaaaaaa aaaaaaaaaa aaaaaaaaaa    3960
aaaaaaaaaa aaaaaaaaaa aaaaaaaaaa aaaaaaaaaa aaaaaaaaaa aaaaaaaaaa    4020
aaaaaaaaaa aaaaaaaaaa aaaaaaaaaa aaaaaaaaaa aaaaaaaaaa aaaaaaaaaa    4080
aaaaaaaaaa aaaaaaaaaa aaaaaaaaaa aaaaaaaaaa aaaaaaaaaa aaaaaaaaaa    4140
aaaaaaaaaa aaaaaaaaaa aaaaaaaaaa aaaaaaaaaa aaaaaaaaaa aaaaaaaaaa    4200
aaaaaaaaaa aaaaaaaaaa aaaaaaaaaa aaaaaaaaaa aaaaaaaaaa aaaaaaaaaa    4260
aaaaaaaaaa aaaaaaaaaa aaaaaaaaaa aaaaaaaaaa aaaaaaaaaa aaaaaaaaaa    4320
aaaaaaaaaa aaaaaaaaaa aaaaaaaaaa aaaaaaaaaa aaaaaaaaaa aaaaaaaaaa    4380
aaaaaaaaaa aaaaaaaaaa aaaaaaaaaa aaaaaaaaaa aaaaaaaaaa aaaaaaaaaa    4440
aaaaaaaaaa aaaaaaaaaa aaaaaaaaaa aaaaaaaaaa aaaaaaaaaa aaaaaaaaaa    4500
aaaaaaaaaa aaaaaaaaaa aaaaaaaaaa aaaaaaaaaa aaaaaaaaaa aaaaaaaaaa    4560
aaaaaaaaaa aaaaaaaaaa aaaaaaaaaa aaaaaaaaaa aaaaaaaaaa aaaaaaaaaa    4620
aaaaaaaaaa aaaaaaaaaa aaaaaaaaaa aaaaaaaaaa aaaaaaaaaa aaaaaaaaaa    4680
aaaaaaaaaa aaaaaaaaaa aaaaaaaaaa aaaaaaaaaa aaaaaaaaaa aaaaaaaaaa    4740
aaaaaaaaaa aaaaaaaaaa aaaaaaaaaa aaaaaaaaaa aaaaaaaaaa aaaaaaaaaa    4800
aaaaaaaaaa aaaaaaaaaa aaaaaaaaaa aaaaaaaaaa aaaaaaaaaa aaaaaaaaaa    4860
aaaaaaaaaa aaaaaaaaaa aaaaaaaaaa aaaaaaaaaa aaaaaaaaaa aaaaaaaaaa    4920
aaaaaaaaaa aaaaaaaaaa aaaaaaaaaa aaaaaaaaaa aaaaaaaaaa aaaaaaaaaa    4980
aaaaaaaaaa aaaaaaaaaa                                                5000

<210> SEQ ID NO 124
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(30)
<223> OTHER INFORMATION: /note="This sequence may encompass 1-6 'Gly Gly
      Gly Gly Ser' repeating units"
<220> FEATURE:
<221> NAME/KEY: source
<223> OTHER INFORMATION: /note="See specification as filed for detailed
      description of substitutions and preferred embodiments"

<400> SEQUENCE: 124

Gly Gly Gly Gly Ser Gly Gly Gly Gly Ser Gly Gly Gly Gly Ser Gly
```

```
                1               5                   10                  15
            Gly Gly Gly Ser Gly Gly Gly Gly Ser Gly Gly Gly Gly Ser
                            20                  25                  30

<210> SEQ ID NO 125
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(2000)
<223> OTHER INFORMATION: /note="This sequence may encompass 50-2000
      nucleotides"

<400> SEQUENCE: 125
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
aaaaaaaaaa aaaaaaaaaa aaaaaaaaaa aaaaaaaaaa aaaaaaaaaa aaaaaaaaaa     360
aaaaaaaaaa aaaaaaaaaa aaaaaaaaaa aaaaaaaaaa aaaaaaaaaa aaaaaaaaaa     420
aaaaaaaaaa aaaaaaaaaa aaaaaaaaaa aaaaaaaaaa aaaaaaaaaa aaaaaaaaaa     480
aaaaaaaaaa aaaaaaaaaa aaaaaaaaaa aaaaaaaaaa aaaaaaaaaa aaaaaaaaaa     540
aaaaaaaaaa aaaaaaaaaa aaaaaaaaaa aaaaaaaaaa aaaaaaaaaa aaaaaaaaaa     600
aaaaaaaaaa aaaaaaaaaa aaaaaaaaaa aaaaaaaaaa aaaaaaaaaa aaaaaaaaaa     660
aaaaaaaaaa aaaaaaaaaa aaaaaaaaaa aaaaaaaaaa aaaaaaaaaa aaaaaaaaaa     720
aaaaaaaaaa aaaaaaaaaa aaaaaaaaaa aaaaaaaaaa aaaaaaaaaa aaaaaaaaaa     780
aaaaaaaaaa aaaaaaaaaa aaaaaaaaaa aaaaaaaaaa aaaaaaaaaa aaaaaaaaaa     840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaaaaaaaa aaaaaaaaaa     960
aaaaaaaaaa aaaaaaaaaa aaaaaaaaaa aaaaaaaaaa aaaaaaaaaa aaaaaaaaaa    1020
aaaaaaaaaa aaaaaaaaaa aaaaaaaaaa aaaaaaaaaa aaaaaaaaaa aaaaaaaaaa    1080
aaaaaaaaaa aaaaaaaaaa aaaaaaaaaa aaaaaaaaaa aaaaaaaaaa aaaaaaaaaa    1140
aaaaaaaaaa aaaaaaaaaa aaaaaaaaaa aaaaaaaaaa aaaaaaaaaa aaaaaaaaaa    1200
aaaaaaaaaa aaaaaaaaaa aaaaaaaaaa aaaaaaaaaa aaaaaaaaaa aaaaaaaaaa    1260
aaaaaaaaaa aaaaaaaaaa aaaaaaaaaa aaaaaaaaaa aaaaaaaaaa aaaaaaaaaa    1320
aaaaaaaaaa aaaaaaaaaa aaaaaaaaaa aaaaaaaaaa aaaaaaaaaa aaaaaaaaaa    1380
aaaaaaaaaa aaaaaaaaaa aaaaaaaaaa aaaaaaaaaa aaaaaaaaaa aaaaaaaaaa    1440
aaaaaaaaaa aaaaaaaaaa aaaaaaaaaa aaaaaaaaaa aaaaaaaaaa aaaaaaaaaa    1500
aaaaaaaaaa aaaaaaaaaa aaaaaaaaaa aaaaaaaaaa aaaaaaaaaa aaaaaaaaaa    1560
aaaaaaaaaa aaaaaaaaaa aaaaaaaaaa aaaaaaaaaa aaaaaaaaaa aaaaaaaaaa    1620
aaaaaaaaaa aaaaaaaaaa aaaaaaaaaa aaaaaaaaaa aaaaaaaaaa aaaaaaaaaa    1680
aaaaaaaaaa aaaaaaaaaa aaaaaaaaaa aaaaaaaaaa aaaaaaaaaa aaaaaaaaaa    1740
```

| | |
|---|---|
| aaaaaaaaaa aaaaaaaaaa aaaaaaaaaa aaaaaaaaaa aaaaaaaaaa aaaaaaaaaa | 1800 |
| aaaaaaaaaa aaaaaaaaaa aaaaaaaaaa aaaaaaaaaa aaaaaaaaaa aaaaaaaaaa | 1860 |
| aaaaaaaaaa aaaaaaaaaa aaaaaaaaaa aaaaaaaaaa aaaaaaaaaa aaaaaaaaaa | 1920 |
| aaaaaaaaaa aaaaaaaaaa aaaaaaaaaa aaaaaaaaaa aaaaaaaaaa aaaaaaaaaa | 1980 |
| aaaaaaaaaa aaaaaaaaaa | 2000 |

<210> SEQ ID NO 126
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 126

| | |
|---|---|
| tttttttttt tttttttttt tttttttttt tttttttttt tttttttttt tttttttttt | 60 |
| tttttttttt tttttttttt tttttttttt tttttttttt | 100 |

<210> SEQ ID NO 127
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (1)..(5000)
<223> OTHER INFORMATION: /note="This sequence may encompass 50-5000 nucleotides"

<400> SEQUENCE: 127

| | |
|---|---|
| tttttttttt tttttttttt tttttttttt tttttttttt tttttttttt tttttttttt | 60 |
| tttttttttt tttttttttt tttttttttt tttttttttt tttttttttt tttttttttt | 120 |
| tttttttttt tttttttttt tttttttttt tttttttttt tttttttttt tttttttttt | 180 |
| tttttttttt tttttttttt tttttttttt tttttttttt tttttttttt tttttttttt | 240 |
| tttttttttt tttttttttt tttttttttt tttttttttt tttttttttt tttttttttt | 300 |
| tttttttttt tttttttttt tttttttttt tttttttttt tttttttttt tttttttttt | 360 |
| tttttttttt tttttttttt tttttttttt tttttttttt tttttttttt tttttttttt | 420 |
| tttttttttt tttttttttt tttttttttt tttttttttt tttttttttt tttttttttt | 480 |
| tttttttttt tttttttttt tttttttttt tttttttttt tttttttttt tttttttttt | 540 |
| tttttttttt tttttttttt tttttttttt tttttttttt tttttttttt tttttttttt | 600 |
| tttttttttt tttttttttt tttttttttt tttttttttt tttttttttt tttttttttt | 660 |
| tttttttttt tttttttttt tttttttttt tttttttttt tttttttttt tttttttttt | 720 |
| tttttttttt tttttttttt tttttttttt tttttttttt tttttttttt tttttttttt | 780 |
| tttttttttt tttttttttt tttttttttt tttttttttt tttttttttt tttttttttt | 840 |
| tttttttttt tttttttttt tttttttttt tttttttttt tttttttttt tttttttttt | 900 |
| tttttttttt tttttttttt tttttttttt tttttttttt tttttttttt tttttttttt | 960 |
| tttttttttt tttttttttt tttttttttt tttttttttt tttttttttt tttttttttt | 1020 |
| tttttttttt tttttttttt tttttttttt tttttttttt tttttttttt tttttttttt | 1080 |

-continued

| | | | | | | |
|---|---|---|---|---|---|---|
| tttttttttt | tttttttttt | tttttttttt | tttttttttt | tttttttttt | tttttttttt | 1140 |
| tttttttttt | tttttttttt | tttttttttt | tttttttttt | tttttttttt | tttttttttt | 1200 |
| tttttttttt | tttttttttt | tttttttttt | tttttttttt | tttttttttt | tttttttttt | 1260 |
| tttttttttt | tttttttttt | tttttttttt | tttttttttt | tttttttttt | tttttttttt | 1320 |
| tttttttttt | tttttttttt | tttttttttt | tttttttttt | tttttttttt | tttttttttt | 1380 |
| tttttttttt | tttttttttt | tttttttttt | tttttttttt | tttttttttt | tttttttttt | 1440 |
| tttttttttt | tttttttttt | tttttttttt | tttttttttt | tttttttttt | tttttttttt | 1500 |
| tttttttttt | tttttttttt | tttttttttt | tttttttttt | tttttttttt | tttttttttt | 1560 |
| tttttttttt | tttttttttt | tttttttttt | tttttttttt | tttttttttt | tttttttttt | 1620 |
| tttttttttt | tttttttttt | tttttttttt | tttttttttt | tttttttttt | tttttttttt | 1680 |
| tttttttttt | tttttttttt | tttttttttt | tttttttttt | tttttttttt | tttttttttt | 1740 |
| tttttttttt | tttttttttt | tttttttttt | tttttttttt | tttttttttt | tttttttttt | 1800 |
| tttttttttt | tttttttttt | tttttttttt | tttttttttt | tttttttttt | tttttttttt | 1860 |
| tttttttttt | tttttttttt | tttttttttt | tttttttttt | tttttttttt | tttttttttt | 1920 |
| tttttttttt | tttttttttt | tttttttttt | tttttttttt | tttttttttt | tttttttttt | 1980 |
| tttttttttt | tttttttttt | tttttttttt | tttttttttt | tttttttttt | tttttttttt | 2040 |
| tttttttttt | tttttttttt | tttttttttt | tttttttttt | tttttttttt | tttttttttt | 2100 |
| tttttttttt | tttttttttt | tttttttttt | tttttttttt | tttttttttt | tttttttttt | 2160 |
| tttttttttt | tttttttttt | tttttttttt | tttttttttt | tttttttttt | tttttttttt | 2220 |
| tttttttttt | tttttttttt | tttttttttt | tttttttttt | tttttttttt | tttttttttt | 2280 |
| tttttttttt | tttttttttt | tttttttttt | tttttttttt | tttttttttt | tttttttttt | 2340 |
| tttttttttt | tttttttttt | tttttttttt | tttttttttt | tttttttttt | tttttttttt | 2400 |
| tttttttttt | tttttttttt | tttttttttt | tttttttttt | tttttttttt | tttttttttt | 2460 |
| tttttttttt | tttttttttt | tttttttttt | tttttttttt | tttttttttt | tttttttttt | 2520 |
| tttttttttt | tttttttttt | tttttttttt | tttttttttt | tttttttttt | tttttttttt | 2580 |
| tttttttttt | tttttttttt | tttttttttt | tttttttttt | tttttttttt | tttttttttt | 2640 |
| tttttttttt | tttttttttt | tttttttttt | tttttttttt | tttttttttt | tttttttttt | 2700 |
| tttttttttt | tttttttttt | tttttttttt | tttttttttt | tttttttttt | tttttttttt | 2760 |
| tttttttttt | tttttttttt | tttttttttt | tttttttttt | tttttttttt | tttttttttt | 2820 |
| tttttttttt | tttttttttt | tttttttttt | tttttttttt | tttttttttt | tttttttttt | 2880 |
| tttttttttt | tttttttttt | tttttttttt | tttttttttt | tttttttttt | tttttttttt | 2940 |
| tttttttttt | tttttttttt | tttttttttt | tttttttttt | tttttttttt | tttttttttt | 3000 |
| tttttttttt | tttttttttt | tttttttttt | tttttttttt | tttttttttt | tttttttttt | 3060 |
| tttttttttt | tttttttttt | tttttttttt | tttttttttt | tttttttttt | tttttttttt | 3120 |
| tttttttttt | tttttttttt | tttttttttt | tttttttttt | tttttttttt | tttttttttt | 3180 |
| tttttttttt | tttttttttt | tttttttttt | tttttttttt | tttttttttt | tttttttttt | 3240 |
| tttttttttt | tttttttttt | tttttttttt | tttttttttt | tttttttttt | tttttttttt | 3300 |
| tttttttttt | tttttttttt | tttttttttt | tttttttttt | tttttttttt | tttttttttt | 3360 |
| tttttttttt | tttttttttt | tttttttttt | tttttttttt | tttttttttt | tttttttttt | 3420 |

| | |
|---|---:|
| tttttttttt tttttttttt tttttttttt tttttttttt tttttttttt tttttttttt | 3480 |
| tttttttttt tttttttttt tttttttttt tttttttttt tttttttttt tttttttttt | 3540 |
| tttttttttt tttttttttt tttttttttt tttttttttt tttttttttt tttttttttt | 3600 |
| tttttttttt tttttttttt tttttttttt tttttttttt tttttttttt tttttttttt | 3660 |
| tttttttttt tttttttttt tttttttttt tttttttttt tttttttttt tttttttttt | 3720 |
| tttttttttt tttttttttt tttttttttt tttttttttt tttttttttt tttttttttt | 3780 |
| tttttttttt tttttttttt tttttttttt tttttttttt tttttttttt tttttttttt | 3840 |
| tttttttttt tttttttttt tttttttttt tttttttttt tttttttttt tttttttttt | 3900 |
| tttttttttt tttttttttt tttttttttt tttttttttt tttttttttt tttttttttt | 3960 |
| tttttttttt tttttttttt tttttttttt tttttttttt tttttttttt tttttttttt | 4020 |
| tttttttttt tttttttttt tttttttttt tttttttttt tttttttttt tttttttttt | 4080 |
| tttttttttt tttttttttt tttttttttt tttttttttt tttttttttt tttttttttt | 4140 |
| tttttttttt tttttttttt tttttttttt tttttttttt tttttttttt tttttttttt | 4200 |
| tttttttttt tttttttttt tttttttttt tttttttttt tttttttttt tttttttttt | 4260 |
| tttttttttt tttttttttt tttttttttt tttttttttt tttttttttt tttttttttt | 4320 |
| tttttttttt tttttttttt tttttttttt tttttttttt tttttttttt tttttttttt | 4380 |
| tttttttttt tttttttttt tttttttttt tttttttttt tttttttttt tttttttttt | 4440 |
| tttttttttt tttttttttt tttttttttt tttttttttt tttttttttt tttttttttt | 4500 |
| tttttttttt tttttttttt tttttttttt tttttttttt tttttttttt tttttttttt | 4560 |
| tttttttttt tttttttttt tttttttttt tttttttttt tttttttttt tttttttttt | 4620 |
| tttttttttt tttttttttt tttttttttt tttttttttt tttttttttt tttttttttt | 4680 |
| tttttttttt tttttttttt tttttttttt tttttttttt tttttttttt tttttttttt | 4740 |
| tttttttttt tttttttttt tttttttttt tttttttttt tttttttttt tttttttttt | 4800 |
| tttttttttt tttttttttt tttttttttt tttttttttt tttttttttt tttttttttt | 4860 |
| tttttttttt tttttttttt tttttttttt tttttttttt tttttttttt tttttttttt | 4920 |
| tttttttttt tttttttttt tttttttttt tttttttttt tttttttttt tttttttttt | 4980 |
| tttttttttt tttttttttt | 5000 |

```
<210> SEQ ID NO 128
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(5000)
<223> OTHER INFORMATION: /note="This sequence may encompass 100-5000
      nucleotides"

<400> SEQUENCE: 128
```

| | |
|---|---:|
| aaaaaaaaaa aaaaaaaaaa aaaaaaaaaa aaaaaaaaaa aaaaaaaaaa aaaaaaaaaa | 60 |
| aaaaaaaaaa aaaaaaaaaa aaaaaaaaaa aaaaaaaaaa aaaaaaaaaa aaaaaaaaaa | 120 |
| aaaaaaaaaa aaaaaaaaaa aaaaaaaaaa aaaaaaaaaa aaaaaaaaaa aaaaaaaaaa | 180 |
| aaaaaaaaaa aaaaaaaaaa aaaaaaaaaa aaaaaaaaaa aaaaaaaaaa aaaaaaaaaa | 240 |

-continued

```
aaaaaaaaaa aaaaaaaaaa aaaaaaaaaa aaaaaaaaaa aaaaaaaaaa aaaaaaaaaa        300
aaaaaaaaaa aaaaaaaaaa aaaaaaaaaa aaaaaaaaaa aaaaaaaaaa aaaaaaaaaa        360
aaaaaaaaaa aaaaaaaaaa aaaaaaaaaa aaaaaaaaaa aaaaaaaaaa aaaaaaaaaa        420
aaaaaaaaaa aaaaaaaaaa aaaaaaaaaa aaaaaaaaaa aaaaaaaaaa aaaaaaaaaa        480
aaaaaaaaaa aaaaaaaaaa aaaaaaaaaa aaaaaaaaaa aaaaaaaaaa aaaaaaaaaa        540
aaaaaaaaaa aaaaaaaaaa aaaaaaaaaa aaaaaaaaaa aaaaaaaaaa aaaaaaaaaa        600
aaaaaaaaaa aaaaaaaaaa aaaaaaaaaa aaaaaaaaaa aaaaaaaaaa aaaaaaaaaa        660
aaaaaaaaaa aaaaaaaaaa aaaaaaaaaa aaaaaaaaaa aaaaaaaaaa aaaaaaaaaa        720
aaaaaaaaaa aaaaaaaaaa aaaaaaaaaa aaaaaaaaaa aaaaaaaaaa aaaaaaaaaa        780
aaaaaaaaaa aaaaaaaaaa aaaaaaaaaa aaaaaaaaaa aaaaaaaaaa aaaaaaaaaa        840
aaaaaaaaaa aaaaaaaaaa aaaaaaaaaa aaaaaaaaaa aaaaaaaaaa aaaaaaaaaa        900
aaaaaaaaaa aaaaaaaaaa aaaaaaaaaa aaaaaaaaaa aaaaaaaaaa aaaaaaaaaa        960
aaaaaaaaaa aaaaaaaaaa aaaaaaaaaa aaaaaaaaaa aaaaaaaaaa aaaaaaaaaa       1020
aaaaaaaaaa aaaaaaaaaa aaaaaaaaaa aaaaaaaaaa aaaaaaaaaa aaaaaaaaaa       1080
aaaaaaaaaa aaaaaaaaaa aaaaaaaaaa aaaaaaaaaa aaaaaaaaaa aaaaaaaaaa       1140
aaaaaaaaaa aaaaaaaaaa aaaaaaaaaa aaaaaaaaaa aaaaaaaaaa aaaaaaaaaa       1200
aaaaaaaaaa aaaaaaaaaa aaaaaaaaaa aaaaaaaaaa aaaaaaaaaa aaaaaaaaaa       1260
aaaaaaaaaa aaaaaaaaaa aaaaaaaaaa aaaaaaaaaa aaaaaaaaaa aaaaaaaaaa       1320
aaaaaaaaaa aaaaaaaaaa aaaaaaaaaa aaaaaaaaaa aaaaaaaaaa aaaaaaaaaa       1380
aaaaaaaaaa aaaaaaaaaa aaaaaaaaaa aaaaaaaaaa aaaaaaaaaa aaaaaaaaaa       1440
aaaaaaaaaa aaaaaaaaaa aaaaaaaaaa aaaaaaaaaa aaaaaaaaaa aaaaaaaaaa       1500
aaaaaaaaaa aaaaaaaaaa aaaaaaaaaa aaaaaaaaaa aaaaaaaaaa aaaaaaaaaa       1560
aaaaaaaaaa aaaaaaaaaa aaaaaaaaaa aaaaaaaaaa aaaaaaaaaa aaaaaaaaaa       1620
aaaaaaaaaa aaaaaaaaaa aaaaaaaaaa aaaaaaaaaa aaaaaaaaaa aaaaaaaaaa       1680
aaaaaaaaaa aaaaaaaaaa aaaaaaaaaa aaaaaaaaaa aaaaaaaaaa aaaaaaaaaa       1740
aaaaaaaaaa aaaaaaaaaa aaaaaaaaaa aaaaaaaaaa aaaaaaaaaa aaaaaaaaaa       1800
aaaaaaaaaa aaaaaaaaaa aaaaaaaaaa aaaaaaaaaa aaaaaaaaaa aaaaaaaaaa       1860
aaaaaaaaaa aaaaaaaaaa aaaaaaaaaa aaaaaaaaaa aaaaaaaaaa aaaaaaaaaa       1920
aaaaaaaaaa aaaaaaaaaa aaaaaaaaaa aaaaaaaaaa aaaaaaaaaa aaaaaaaaaa       1980
aaaaaaaaaa aaaaaaaaaa aaaaaaaaaa aaaaaaaaaa aaaaaaaaaa aaaaaaaaaa       2040
aaaaaaaaaa aaaaaaaaaa aaaaaaaaaa aaaaaaaaaa aaaaaaaaaa aaaaaaaaaa       2100
aaaaaaaaaa aaaaaaaaaa aaaaaaaaaa aaaaaaaaaa aaaaaaaaaa aaaaaaaaaa       2160
aaaaaaaaaa aaaaaaaaaa aaaaaaaaaa aaaaaaaaaa aaaaaaaaaa aaaaaaaaaa       2220
aaaaaaaaaa aaaaaaaaaa aaaaaaaaaa aaaaaaaaaa aaaaaaaaaa aaaaaaaaaa       2280
aaaaaaaaaa aaaaaaaaaa aaaaaaaaaa aaaaaaaaaa aaaaaaaaaa aaaaaaaaaa       2340
aaaaaaaaaa aaaaaaaaaa aaaaaaaaaa aaaaaaaaaa aaaaaaaaaa aaaaaaaaaa       2400
aaaaaaaaaa aaaaaaaaaa aaaaaaaaaa aaaaaaaaaa aaaaaaaaaa aaaaaaaaaa       2460
aaaaaaaaaa aaaaaaaaaa aaaaaaaaaa aaaaaaaaaa aaaaaaaaaa aaaaaaaaaa       2520
aaaaaaaaaa aaaaaaaaaa aaaaaaaaaa aaaaaaaaaa aaaaaaaaaa aaaaaaaaaa       2580
aaaaaaaaaa aaaaaaaaaa aaaaaaaaaa aaaaaaaaaa aaaaaaaaaa aaaaaaaaaa       2640
```

-continued

```
aaaaaaaaaa aaaaaaaaaa aaaaaaaaaa aaaaaaaaaa aaaaaaaaaa aaaaaaaaaa    2700
aaaaaaaaaa aaaaaaaaaa aaaaaaaaaa aaaaaaaaaa aaaaaaaaaa aaaaaaaaaa    2760
aaaaaaaaaa aaaaaaaaaa aaaaaaaaaa aaaaaaaaaa aaaaaaaaaa aaaaaaaaaa    2820
aaaaaaaaaa aaaaaaaaaa aaaaaaaaaa aaaaaaaaaa aaaaaaaaaa aaaaaaaaaa    2880
aaaaaaaaaa aaaaaaaaaa aaaaaaaaaa aaaaaaaaaa aaaaaaaaaa aaaaaaaaaa    2940
aaaaaaaaaa aaaaaaaaaa aaaaaaaaaa aaaaaaaaaa aaaaaaaaaa aaaaaaaaaa    3000
aaaaaaaaaa aaaaaaaaaa aaaaaaaaaa aaaaaaaaaa aaaaaaaaaa aaaaaaaaaa    3060
aaaaaaaaaa aaaaaaaaaa aaaaaaaaaa aaaaaaaaaa aaaaaaaaaa aaaaaaaaaa    3120
aaaaaaaaaa aaaaaaaaaa aaaaaaaaaa aaaaaaaaaa aaaaaaaaaa aaaaaaaaaa    3180
aaaaaaaaaa aaaaaaaaaa aaaaaaaaaa aaaaaaaaaa aaaaaaaaaa aaaaaaaaaa    3240
aaaaaaaaaa aaaaaaaaaa aaaaaaaaaa aaaaaaaaaa aaaaaaaaaa aaaaaaaaaa    3300
aaaaaaaaaa aaaaaaaaaa aaaaaaaaaa aaaaaaaaaa aaaaaaaaaa aaaaaaaaaa    3360
aaaaaaaaaa aaaaaaaaaa aaaaaaaaaa aaaaaaaaaa aaaaaaaaaa aaaaaaaaaa    3420
aaaaaaaaaa aaaaaaaaaa aaaaaaaaaa aaaaaaaaaa aaaaaaaaaa aaaaaaaaaa    3480
aaaaaaaaaa aaaaaaaaaa aaaaaaaaaa aaaaaaaaaa aaaaaaaaaa aaaaaaaaaa    3540
aaaaaaaaaa aaaaaaaaaa aaaaaaaaaa aaaaaaaaaa aaaaaaaaaa aaaaaaaaaa    3600
aaaaaaaaaa aaaaaaaaaa aaaaaaaaaa aaaaaaaaaa aaaaaaaaaa aaaaaaaaaa    3660
aaaaaaaaaa aaaaaaaaaa aaaaaaaaaa aaaaaaaaaa aaaaaaaaaa aaaaaaaaaa    3720
aaaaaaaaaa aaaaaaaaaa aaaaaaaaaa aaaaaaaaaa aaaaaaaaaa aaaaaaaaaa    3780
aaaaaaaaaa aaaaaaaaaa aaaaaaaaaa aaaaaaaaaa aaaaaaaaaa aaaaaaaaaa    3840
aaaaaaaaaa aaaaaaaaaa aaaaaaaaaa aaaaaaaaaa aaaaaaaaaa aaaaaaaaaa    3900
aaaaaaaaaa aaaaaaaaaa aaaaaaaaaa aaaaaaaaaa aaaaaaaaaa aaaaaaaaaa    3960
aaaaaaaaaa aaaaaaaaaa aaaaaaaaaa aaaaaaaaaa aaaaaaaaaa aaaaaaaaaa    4020
aaaaaaaaaa aaaaaaaaaa aaaaaaaaaa aaaaaaaaaa aaaaaaaaaa aaaaaaaaaa    4080
aaaaaaaaaa aaaaaaaaaa aaaaaaaaaa aaaaaaaaaa aaaaaaaaaa aaaaaaaaaa    4140
aaaaaaaaaa aaaaaaaaaa aaaaaaaaaa aaaaaaaaaa aaaaaaaaaa aaaaaaaaaa    4200
aaaaaaaaaa aaaaaaaaaa aaaaaaaaaa aaaaaaaaaa aaaaaaaaaa aaaaaaaaaa    4260
aaaaaaaaaa aaaaaaaaaa aaaaaaaaaa aaaaaaaaaa aaaaaaaaaa aaaaaaaaaa    4320
aaaaaaaaaa aaaaaaaaaa aaaaaaaaaa aaaaaaaaaa aaaaaaaaaa aaaaaaaaaa    4380
aaaaaaaaaa aaaaaaaaaa aaaaaaaaaa aaaaaaaaaa aaaaaaaaaa aaaaaaaaaa    4440
aaaaaaaaaa aaaaaaaaaa aaaaaaaaaa aaaaaaaaaa aaaaaaaaaa aaaaaaaaaa    4500
aaaaaaaaaa aaaaaaaaaa aaaaaaaaaa aaaaaaaaaa aaaaaaaaaa aaaaaaaaaa    4560
aaaaaaaaaa aaaaaaaaaa aaaaaaaaaa aaaaaaaaaa aaaaaaaaaa aaaaaaaaaa    4620
aaaaaaaaaa aaaaaaaaaa aaaaaaaaaa aaaaaaaaaa aaaaaaaaaa aaaaaaaaaa    4680
aaaaaaaaaa aaaaaaaaaa aaaaaaaaaa aaaaaaaaaa aaaaaaaaaa aaaaaaaaaa    4740
aaaaaaaaaa aaaaaaaaaa aaaaaaaaaa aaaaaaaaaa aaaaaaaaaa aaaaaaaaaa    4800
aaaaaaaaaa aaaaaaaaaa aaaaaaaaaa aaaaaaaaaa aaaaaaaaaa aaaaaaaaaa    4860
aaaaaaaaaa aaaaaaaaaa aaaaaaaaaa aaaaaaaaaa aaaaaaaaaa aaaaaaaaaa    4920
aaaaaaaaaa aaaaaaaaaa aaaaaaaaaa aaaaaaaaaa aaaaaaaaaa aaaaaaaaaa    4980
aaaaaaaaaa aaaaaaaaaa                                                5000
```

```
<210> SEQ ID NO 129
<211> LENGTH: 400
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(400)
<223> OTHER INFORMATION: /note="This sequence may encompass 100-400
      nucleotides"
<220> FEATURE:
<221> NAME/KEY: source
<223> OTHER INFORMATION: /note="See specification as filed for detailed
      description of substitutions and preferred embodiments"

<400> SEQUENCE: 129
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
aaaaaaaaaa aaaaaaaaaa aaaaaaaaaa aaaaaaaaaa aaaaaaaaaa aaaaaaaaaa     360
aaaaaaaaaa aaaaaaaaaa aaaaaaaaaa aaaaaaaaaa                           400
```

COMPOSITIONS AND METHODS FOR TCR REPROGRAMMING USING FUSION PROTEINS

CROSS REFERENCE

This application claims the benefit of U.S. Provisional Application No. 62/425,407, filed Nov. 22, 2016, U.S. Provisional Application No. 62/425,535, filed Nov. 22, 2016, U.S. Provisional Application No. 62/425,697, filed Nov. 23, 2016, and U.S. Provisional Application No. 62/425,884, filed Nov. 23, 2016, each of which is incorporated herein by reference in their entirety.

BACKGROUND OF THE INVENTION

Most patients with hematological malignancies or with late-stage solid tumors are incurable with standard therapy. In addition, traditional treatment options often have serious side effects. Numerous attempts have been made to engage a patient's immune system for rejecting cancerous cells, an approach collectively referred to as cancer immunotherapy. However, several obstacles make it rather difficult to achieve clinical effectiveness. Although hundreds of so-called tumor antigens have been identified, these are often derived from self and thus can direct the cancer immunotherapy against healthy tissue, or are poorly immunogenic. Furthermore, cancer cells use multiple mechanisms to render themselves invisible or hostile to the initiation and propagation of an immune attack by cancer immunotherapies.

Recent developments using chimeric antigen receptor (CAR) modified autologous T-cell therapy, which relies on redirecting genetically engineered T cells to a suitable cell-surface molecule on cancer cells, show promising results in harnessing the power of the immune system to treat cancers. For example, the clinical results from an ongoing trial with B-cell maturation antigen (BCMA)-specific CAR T cells have shown partial remission in some multiple myeloma patients (one such trial may be found via clinicaltrials.gov identifier NCT02215967). An alternative approach is the use of T-cell receptor (TCR) alpha and beta chains selected for a tumor-associated peptide antigen for genetically engineering autologous T cells. These TCR chains will form complete TCR complexes and provide the T cells with a TCR for a second defined specificity. Encouraging results were obtained with engineered autologous T cells expressing NY-ESO-1-specific TCR alpha and beta chains in patients with synovial carcinoma. Most patients with late-stage solid tumors are incurable with standard therapy. In addition, traditional treatment options often have serious side effects. Numerous attempts have been made to engage a patient's immune system for rejecting cancerous cells, an approach collectively referred to as cancer immunotherapy. However, several obstacles make it rather difficult to achieve clinical effectiveness. Although hundreds of so-called tumor antigens have been identified, these are often derived from self and thus can direct the cancer immunotherapy against healthy tissue, or are poorly immunogenic. Furthermore, cancer cells use multiple mechanisms to render themselves invisible or hostile to the initiation and propagation of an immune attack by cancer immunotherapies.

NKG2D functions as an activating and costimulatory receptor involved in immunosurveillance upon binding to various cellular stress-inducible ligands displayed at the surface of autologous tumor cells and virus-infected cells. NKG2D provides both stimulatory and costimulatory innate immune responses on activated killer (NK) cells, leading to cytotoxic activity. NKG2D acts as a costimulatory receptor for T-cell receptor (TCR) in CD8+ T-cell-mediated adaptive immune responses by amplifying T-cell activation. Stimulates perforin-mediated elimination of ligand-expressing tumor cells. NKG2D signaling involves calcium influx, culminating in the expression of TNF-alpha. NKG2D participates in NK cell-mediated bone marrow graft rejection and may play a regulatory role in differentiation and survival of NK cells. NKG2D binds to ligands belonging to various subfamilies of MHC class I-related glycoproteins including MICA, MICB, RAET1E, RAET1G, ULBP1, ULBP2, ULBP3 (ULBP2>ULBP1>ULBP3) and ULBP4.

ROR1 is expressed on the cell surface of malignant B-cells (B-CLL) and mantle cell lymphoma (MCL). It has also been reported that ROR1 is expressed in certain other cancer cell lines, including Burkett's lymphoma, renal cell carcinoma, colon cancer and breast cancer cell lines.

CD16 is a low affinity Fc receptor. It is a cluster of differentiation molecule found on the surface of natural killer cells, neutrophil polymorphonuclear leukocytes, monocytes and macrophages. It has been identified as Fc receptors FcγRIIIa (CD16a) and FcγRIIIb (CD16b). These receptors bind to the Fc portion of IgG antibodies, which then activates the NK cell for antibody-dependent cell-mediated cytotoxicity.

Besides the ability of genetically modified T cells expressing a CAR or a second TCR to recognize and destroy respective target cells in vitro/ex vivo, successful patient therapy with engineered T cells requires the T cells to be capable of strong activation, expansion, persistence over time, and, in case of relapsing disease, to enable a 'memory' response. High and manageable clinical efficacy of CAR T cells is currently limited to mesothelin-positive B cell malignancies and to NY-ESO-1-peptide-expressing synovial sarcoma patients expressing HLA-A2. There is a clear need to improve genetically engineered T cells to more broadly act against various human malignancies. Described herein are novel fusion proteins of TCR subunits, including CD3 epsilon, CD3gamma and CD3 delta, and of TCR alpha and TCR beta chains with binding domains specific for cell surface antigens that have the potential to overcome limitations of existing approaches. Described herein are novel fusion proteins that more efficiently kill target cells than CARs, but release comparable or lower levels of pro-inflammatory cytokines. These fusion proteins and methods of their use represent an advantage for T-cell receptor (TCR) fusion proteins (TFPs) relative to CARs because elevated levels of these cytokines have been associated with dose-limiting toxicities for adoptive CAR-T therapies.

BRIEF SUMMARY OF THE INVENTION

In some aspects, provided herein is an isolated recombinant nucleic acid molecule encoding a T-cell receptor (TCR) fusion protein (TFP) comprising: a TCR subunit comprising at least a portion of a TCR extracellular domain, and a TCR intracellular domain comprising a stimulatory domain from an intracellular signaling domain selected from the group consisting of CD3 epsilon, CD3 gamma, CD3 delta, TCR alpha, and TCR beta; and a binding ligand or a fragment thereof that is capable of binding to an antibody or fragment thereof; wherein the TCR subunit and the binding ligand are operatively linked, and wherein the TFP incorporates into a TCR when expressed in a T-cell.

In some embodiments, the binding ligand is capable of binding an Fc domain of the antibody. In some embodiments, the binding ligand is capable of selectively binding an IgG1 antibody. In some embodiments, the binding ligand is capable of specifically binding an IgG1 antibody. In some embodiments, the antibody or fragment thereof binds to a cell surface antigen. In some embodiments, the antibody or fragment thereof binds to a cell surface antigen on the surface of a tumor cell. In some embodiments, the binding ligand comprises a monomer, a dimer, a trimer, a tetramer, a pentamer, a hexamer, a heptamer, an octomer, a nonamer, or a decamer. In some embodiments, the binding ligand does not comprise an antibody or fragment thereof. In some embodiments, the binding ligand comprises a CD16 polypeptide or fragment thereof. In some embodiments, the binding ligand comprises a CD16-binding polypeptide. In some embodiments, the binding ligand is human or humanized. In some embodiments, the isolated nucleic acid molecule further comprises a nucleic acid sequence encoding an antibody or fragment thereof capable of being bound by the binding ligand. In some embodiments, the antibody or fragment thereof is capable of being secreted from a cell.

In some aspects, provided herein is an isolated recombinant nucleic acid molecule encoding a T-cell receptor (TCR) fusion protein (TFP) comprising: a TCR subunit comprising at least a portion of a TCR extracellular domain, and a TCR intracellular domain comprising a stimulatory domain from an intracellular signaling domain selected from the group consisting of CD3 epsilon, CD3 gamma, CD3 delta, TCR alpha, and TCR beta; and an antigen domain comprising a ligand or a fragment thereof that binds to a receptor or polypeptide expressed on a surface of a cell; wherein the TCR subunit and the antigen domain are operatively linked, and wherein the TFP incorporates into a TCR when expressed in a T-cell.

In some embodiments, the antigen domain comprises a ligand. In some embodiments, the ligand binds to the receptor of a cell. In some embodiments, the ligand binds to the polypeptide expressed on a surface of a cell. In some embodiments, the receptor or polypeptide expressed on a surface of a cell comprises a stress response receptor or polypeptide. In some embodiments, the receptor or polypeptide expressed on a surface of a cell is an MHC class I-related glycoprotein. In some embodiments, the MHC class I-related glycoprotein is selected from the group consisting of MICA, MICB, RAET1E, RAET1G, ULBP1, ULBP2, ULBP3, ULBP4 and combinations thereof. In some embodiments, the antigen domain comprises a monomer, a dimer, a trimer, a tetramer, a pentamer, a hexamer, a heptamer, an octomer, a nonamer, or a decamer. In some embodiments, the antigen domain comprises a monomer or a dimer of the ligand or fragment thereof. In some embodiments, the ligand or fragment thereof is a monomer, a dimer, a trimer, a tetramer, a pentamer, a hexamer, a heptamer, an octomer, a nonamer, or a decamer. In some embodiments, the ligand or fragment thereof is a monomer or a dimer. In some embodiments, the antigen domain does not comprise an antibody or fragment thereof. In some embodiments, the antigen domain does not comprise a variable region. In some embodiments, the antigen domain does not comprise a CDR. In some embodiments, the ligand or fragment thereof is a Natural Killer Group 2D (NKG2D) ligand or a fragment thereof. In some embodiments, the TCR subunit comprises a first TCR subunit and a second TCR subunit, wherein the antigen domain comprises a first antigen domain and a second antigen domain, wherein the first TCR subunit is operatively linked to the first antigen domain, and wherein the second TCR subunit is operatively linked to the second antigen domain. In some embodiments, the antigen domain is human or humanized.

In some aspects, provided herein is an isolated recombinant nucleic acid molecule encoding a T-cell receptor (TCR) fusion protein (TFP) comprising: a TCR subunit comprising at least a portion of a TCR extracellular domain, and a TCR intracellular domain comprising a stimulatory domain from an intracellular signaling domain of CD3 epsilon; and a binding ligand comprising a CD16 polypeptide or a fragment thereof; wherein the TCR subunit and the binding ligand are operatively linked, and wherein the TFP incorporates into a TCR when expressed in a T-cell.

In some aspects, provided herein is an isolated recombinant nucleic acid molecule encoding a T-cell receptor (TCR) fusion protein (TFP) comprising: a TCR subunit comprising at least a portion of a TCR extracellular domain, and a TCR intracellular domain comprising a stimulatory domain from an intracellular signaling domain of CD3 gamma; and a binding ligand comprising a CD16 polypeptide or a fragment thereof; wherein the TCR subunit and the binding ligand are operatively linked, and wherein the TFP incorporates into a TCR when expressed in a T-cell.

In some aspects, provided herein is an isolated recombinant nucleic acid molecule encoding a T-cell receptor (TCR) fusion protein (TFP) comprising: a TCR subunit comprising at least a portion of a TCR extracellular domain, and a TCR intracellular domain comprising a stimulatory domain from an intracellular signaling domain of CD3 delta; and a binding ligand comprising a CD16 polypeptide or a fragment thereof; wherein the TCR subunit and the binding ligand are operatively linked, and wherein the TFP incorporates into a TCR when expressed in a T-cell.

In some aspects, provided herein is an isolated recombinant nucleic acid molecule encoding a T-cell receptor (TCR) fusion protein (TFP) comprising: a TCR subunit comprising at least a portion of a TCR extracellular domain, and a TCR intracellular domain comprising a stimulatory domain from an intracellular signaling domain of TCR alpha; and a binding ligand comprising a CD16 polypeptide or a fragment thereof; wherein the TCR subunit and the binding ligand are operatively linked, and wherein the TFP incorporates into a TCR when expressed in a T-cell.

In some aspects, provided herein is an isolated recombinant nucleic acid molecule encoding a T-cell receptor (TCR) fusion protein (TFP) comprising: a TCR subunit comprising at least a portion of a TCR extracellular domain, and a TCR intracellular domain comprising a stimulatory domain from an intracellular signaling domain of TCR beta; and a binding ligand comprising a CD16 polypeptide or a fragment thereof; wherein the TCR subunit and the binding ligand are operatively linked, and wherein the TFP incorporates into a TCR when expressed in a T-cell.

In some aspects, provided herein is an isolated recombinant nucleic acid molecule encoding a T-cell receptor (TCR) fusion protein (TFP) comprising a TCR subunit and a binding ligand capable of binding to an antibody or fragment thereof.

In some aspects, provided herein is an isolated recombinant nucleic acid molecule encoding a T-cell receptor (TCR) fusion protein (TFP) comprising a TCR subunit and a binding ligand comprising a CD16 polypeptide or a fragment thereof.

In some aspects, provided herein is an isolated recombinant nucleic acid molecule encoding a T cell receptor (TCR) fusion protein (TFP) comprising: a TCR subunit comprising at least a portion of a TCR extracellular domain, and a TCR intracellular domain comprising a stimulatory domain from an intracellular signaling domain of CD3 epsilon; and a human or humanized antibody domain comprising an antigen binding domain that is an anti-Receptor Tyrosine Kinase Like Orphan Receptor 1 (ROR1) binding domain; wherein the TCR subunit and the antibody domain are operatively linked, and wherein the TFP incorporates into a TCR when expressed in a T cell.

In some aspects, provided herein is an isolated recombinant nucleic acid molecule encoding a T cell receptor (TCR) fusion protein (TFP) comprising: a TCR subunit comprising at least a portion of a TCR extracellular domain, and a TCR intracellular domain comprising a stimulatory domain from an intracellular signaling domain of CD3 gamma; and a human or humanized antibody domain comprising an antigen binding domain that is an anti-Receptor Tyrosine Kinase Like Orphan Receptor 1 (ROR1) binding domain; wherein the TCR subunit and the antibody domain are operatively linked, and wherein the TFP incorporates into a TCR when expressed in a T cell.

In some aspects, provided herein is an isolated recombinant nucleic acid molecule encoding a T cell receptor (TCR) fusion protein (TFP) comprising: a TCR subunit comprising at least a portion of a TCR extracellular domain, and a TCR intracellular domain comprising a stimulatory domain from an intracellular signaling domain of CD3 delta; and a human or humanized antibody domain comprising an antigen binding domain that is an anti-Receptor Tyrosine Kinase Like Orphan Receptor 1 (ROR1) binding domain; wherein the TCR subunit and the antibody domain are operatively linked, and wherein the TFP incorporates into a TCR when expressed in a T cell.

In some aspects, provided herein is an isolated recombinant nucleic acid molecule encoding a T cell receptor (TCR) fusion protein (TFP) comprising: a TCR subunit comprising at least a portion of a TCR extracellular domain, and a TCR intracellular domain comprising a stimulatory domain from an intracellular signaling domain of TCR alpha; and a human or humanized antibody domain comprising an antigen binding domain that is an anti-Receptor Tyrosine Kinase Like Orphan Receptor 1 (ROR1) binding domain; wherein the TCR subunit and the antibody domain are operatively linked, and wherein the TFP incorporates into a TCR when expressed in a T cell.

In some aspects, provided herein is an isolated recombinant nucleic acid molecule encoding a T cell receptor (TCR) fusion protein (TFP) comprising: a TCR subunit comprising at least a portion of a TCR extracellular domain, and a TCR intracellular domain comprising a stimulatory domain from an intracellular signaling domain of TCR beta; and a human or humanized antibody domain comprising an antigen binding domain that is an anti-Receptor Tyrosine Kinase Like Orphan Receptor 1 (ROR1) binding domain; wherein the TCR subunit and the antibody domain are operatively linked, and wherein the TFP incorporates into a TCR when expressed in a T cell.

In some aspects, provided herein is an isolated recombinant nucleic acid molecule encoding a T-cell receptor (TCR) fusion protein (TFP) comprising a TCR subunit and a human or humanized antibody domain comprising an antigen binding domain that is an anti-ROR1 binding domain.

In some aspects, provided herein is an isolated recombinant nucleic acid molecule encoding a T-cell receptor (TCR) fusion protein (TFP) comprising: a TCR subunit comprising at least a portion of a TCR extracellular domain, and a TCR intracellular domain comprising a stimulatory domain from an intracellular signaling domain of CD3 epsilon; and an antigen domain comprising a ligand that is a Natural Killer Group 2D (NKG2D) ligand or a fragment thereof; wherein the TCR subunit and the antigen domain are operatively linked, and wherein the TFP incorporates into a TCR when expressed in a T-cell.

In some aspects, provided herein is an isolated recombinant nucleic acid molecule encoding a T-cell receptor (TCR) fusion protein (TFP) comprising: a TCR subunit comprising at least a portion of a TCR extracellular domain, and a TCR intracellular domain comprising a stimulatory domain from an intracellular signaling domain of CD3 gamma; and an antigen domain comprising a ligand that is a Natural Killer Group 2D (NKG2D) ligand or a fragment thereof; wherein the TCR subunit and the antigen domain are operatively linked, and wherein the TFP incorporates into a TCR when expressed in a T-cell.

In some aspects, provided herein is an isolated recombinant nucleic acid molecule encoding a T-cell receptor (TCR) fusion protein (TFP) comprising: a TCR subunit comprising at least a portion of a TCR extracellular domain, and a TCR intracellular domain comprising a stimulatory domain from an intracellular signaling domain of CD3 delta; and an antigen domain comprising a ligand that is a Natural Killer Group 2D (NKG2D) ligand or a fragment thereof; wherein the TCR subunit and the antigen domain are operatively linked, and wherein the TFP incorporates into a TCR when expressed in a T-cell.

In some aspects, provided herein is an isolated recombinant nucleic acid molecule encoding a T-cell receptor (TCR) fusion protein (TFP) comprising: a TCR subunit comprising at least a portion of a TCR extracellular domain, and a TCR intracellular domain comprising a stimulatory domain from an intracellular signaling domain of TCR alpha; and an antigen domain comprising a ligand that is a Natural Killer Group 2D (NKG2D) ligand or a fragment thereof; wherein the TCR subunit and the antigen domain are operatively linked, and wherein the TFP incorporates into a TCR when expressed in a T-cell.

In some aspects, provided herein is an isolated recombinant nucleic acid molecule encoding a T-cell receptor (TCR) fusion protein (TFP) comprising: a TCR subunit comprising at least a portion of a TCR extracellular domain, and a TCR intracellular domain comprising a stimulatory domain from an intracellular signaling domain of TCR beta; and an antigen domain comprising a ligand that is a Natural Killer Group 2D (NKG2D) ligand or a fragment thereof; wherein the TCR subunit and the antigen domain are operatively linked, and wherein the TFP incorporates into a TCR when expressed in a T-cell.

In some aspects, provided herein is an isolated recombinant nucleic acid molecule encoding a T-cell receptor (TCR) fusion protein (TFP) comprising a TCR subunit and an antigen domain.

In some aspects, provided herein is an isolated recombinant nucleic acid molecule encoding a T-cell receptor (TCR) fusion protein (TFP) comprising a TCR subunit and an antigen domain comprising a ligand that is a Natural Killer Group 2D (NKG2D) ligand or a fragment thereof.

In some embodiments, the TCR subunit and the antigen domain are operatively linked. In some embodiments, the TFP incorporates into a TCR when expressed in a T-cell. In some embodiments, the antigen domain is human or humanized. In some embodiments, the Natural Killer Group 2D (NKG2D) ligand or a fragment thereof binds to the receptor of a cell. In some embodiments, the Natural Killer Group 2D (NKG2D) ligand or a fragment thereof binds to the polypeptide expressed on a surface of a cell. In some embodiments, the Natural Killer Group 2D (NKG2D) ligand or a fragment thereof binds to stress response receptor or polypeptide. In some embodiments, the Natural Killer Group 2D (NKG2D) ligand or a fragment thereof binds to an MHC class I-related glycoprotein. In some embodiments, the MHC class I-related glycoprotein is selected from the group consisting of MICA, MICB, RAET1E, RAET1G, ULBP1, ULBP2, ULBP3, ULBP4 and combinations thereof. In some embodiments, the antigen domain comprises a monomer, a dimer, a trimer, a tetramer, a pentamer, a hexamer, a heptamer, an octomer, a nonamer, or a decamer of the Natural Killer Group 2D (NKG2D) ligand or a fragment thereof. In some embodiments, the antigen domain comprises a monomer or a dimer of the Natural Killer Group 2D (NKG2D) ligand or a fragment thereof. In some embodiments, the Natural Killer Group 2D (NKG2D) ligand or a fragment thereof is a monomer, a dimer, a trimer, a tetramer, a pentamer, a hexamer, a heptamer, an octomer, a nonamer, or a decamer. In some embodiments, the Natural Killer Group 2D (NKG2D) ligand or a fragment thereof is a monomer or a dimer. In some embodiments, the antigen domain does not comprise an antibody or fragment thereof. In some embodiments, the antigen domain does not comprise a variable region. In some embodiments, the antigen domain does not comprise a CDR. In some embodiments, the TCR subunit comprises a first TCR subunit and a second TCR subunit, wherein the antigen domain comprises a first antigen domain and a second antigen domain, wherein the first TCR subunit is operatively linked to the first antigen domain, and wherein the second TCR subunit is operatively linked to the second antigen domain. In some embodiments, the encoded ligand is connected to the TCR extracellular domain by a linker sequence.

In some aspects, provided herein is an isolated recombinant nucleic acid molecule encoding a first T-cell receptor (TCR) fusion protein (TFP) comprising: a TCR subunit comprising at least a portion of a TCR extracellular domain, and a TCR intracellular domain comprising a stimulatory domain from an intracellular signaling domain of CD3 epsilon; and a first human or humanized antibody domain comprising a first antigen binding domain; and a second T-cell receptor (TCR) fusion protein (TFP) comprising a TCR subunit comprising at least a portion of a TCR extracellular domain, and a second human or humanized antibody domain comprising a second antigen binding domain; wherein the TCR subunit of the first TFP and the first antibody domain are operatively linked and the TCR subunit of the second TFP and the second antibody domain are operatively linked, and wherein the first TFP and the second TFP incorporate into a TCR when expressed in a T-cell.

In some aspects, provided herein is an isolated recombinant nucleic acid molecule encoding a first T-cell receptor (TCR) fusion protein (TFP) comprising: a TCR subunit comprising at least a portion of a TCR extracellular domain, and a TCR intracellular domain comprising a stimulatory domain from an intracellular signaling domain of CD3 gamma; and a first human or humanized antibody domain comprising a first antigen binding domain; and a second T-cell receptor (TCR) fusion protein (TFP) comprising a TCR subunit comprising at least a portion of a TCR extracellular domain, and a second human or humanized antibody domain comprising a second antigen binding domain; wherein the TCR subunit of the first TFP and the first antibody domain are operatively linked and the TCR subunit of the second TFP and the second antibody domain are operatively linked, and wherein the first TFP and the second TFP incorporate into a TCR when expressed in a T-cell.

In some aspects, provided herein is an isolated recombinant nucleic acid molecule encoding a first T-cell receptor (TCR) fusion protein (TFP) comprising: a TCR subunit comprising at least a portion of a TCR extracellular domain, and a TCR intracellular domain comprising a stimulatory domain from an intracellular signaling domain of CD3 delta; and a first human or humanized antibody domain comprising a first antigen binding domain; and a second T-cell receptor (TCR) fusion protein (TFP) comprising a TCR subunit comprising at least a portion of a TCR extracellular domain, and a second human or humanized antibody domain comprising a second antigen binding domain; wherein the TCR subunit of the first TFP and the first antibody domain are operatively linked and the TCR subunit of the second TFP and the second antibody domain are operatively linked, and wherein the first TFP and the second TFP incorporate into a TCR when expressed in a T-cell.

In some aspects, provided herein is an isolated recombinant nucleic acid molecule encoding a first T-cell receptor (TCR) fusion protein (TFP) comprising: a TCR subunit comprising at least a portion of a TCR extracellular domain, and a TCR intracellular domain comprising a stimulatory domain from an intracellular signaling domain of TCR alpha; and a first human or humanized antibody domain comprising a first antigen binding domain; and a second T-cell receptor (TCR) fusion protein (TFP) comprising a TCR subunit comprising at least a portion of a TCR extracellular domain, and a second human or humanized antibody domain comprising a second antigen binding domain; wherein the TCR subunit of the first TFP and the first antibody domain are operatively linked and the TCR subunit of the second TFP and the second antibody domain are operatively linked, and wherein the first TFP and the second TFP incorporate into a TCR when expressed in a T-cell.

In some aspects, provided herein is an isolated recombinant nucleic acid molecule encoding a first T-cell receptor (TCR) fusion protein (TFP) comprising: a TCR subunit comprising at least a portion of a TCR extracellular domain, and a TCR intracellular domain comprising a stimulatory domain from an intracellular signaling domain of TCR beta; and a first human or humanized antibody domain comprising a first antigen binding domain; and a second T-cell receptor (TCR) fusion protein (TFP) comprising a TCR subunit comprising at least a portion of a TCR extracellular domain, and a second human or humanized antibody domain comprising a second antigen binding domain; wherein the TCR subunit of the first TFP and the first antibody domain are operatively linked and the TCR subunit of the second TFP and the second antibody domain are operatively linked, and wherein the first TFP and the second TFP incorporate into a TCR when expressed in a T-cell.

In some embodiments, the TCR subunit of the second TFP further comprises a TCR intracellular domain comprising a stimulatory domain from an intracellular signaling domain or a functional fragment thereof a selected from the group consisting of a TCR alpha, a TCR beta, a CD3 epsilon, a CD3 gamma, and a CD3 delta.

In some aspects, provided herein is an isolated recombinant nucleic acid molecule encoding a first T-cell receptor (TCR) fusion protein (TFP) comprising a TCR subunit comprising at least a portion of a TCR extracellular domain, and a TCR intracellular domain comprising a stimulatory domain from an intracellular signaling domain of CD3 epsilon; and a first human or humanized antibody domain comprising a first antigen binding domain and a second human or humanized antibody domain comprising a second antigen binding domain; wherein the TCR subunit, the first antibody domain, and the second antibody domain are operatively linked, and wherein the first TFP incorporates into a TCR when expressed in a T-cell.

In some aspects, provided herein is an isolated recombinant nucleic acid molecule encoding a first T-cell receptor (TCR) fusion protein (TFP) comprising a TCR subunit comprising at least a portion of a TCR extracellular domain, and a TCR intracellular domain comprising a stimulatory domain from an intracellular signaling domain of CD3 gamma; and a first human or humanized antibody domain comprising a first antigen binding domain and a second human or humanized antibody domain comprising a second antigen binding domain; wherein the TCR subunit, the first antibody domain, and the second antibody domain are operatively linked, and wherein the first TFP incorporates into a TCR when expressed in a T-cell.

In some aspects, provided herein is an isolated recombinant nucleic acid molecule encoding a first T-cell receptor (TCR) fusion protein (TFP) comprising a TCR subunit comprising at least a portion of a TCR extracellular domain, and a TCR intracellular domain comprising a stimulatory domain from an intracellular signaling domain of CD3 delta; and a first human or humanized antibody domain comprising a first antigen binding domain and a second human or humanized antibody domain comprising a second antigen binding domain; wherein the TCR subunit, the first antibody domain, and the second antibody domain are operatively linked, and wherein the first TFP incorporates into a TCR when expressed in a T-cell.

In some aspects, provided herein is an isolated recombinant nucleic acid molecule encoding a first T-cell receptor (TCR) fusion protein (TFP) comprising a TCR subunit comprising at least a portion of a TCR extracellular domain, and a TCR intracellular domain comprising a stimulatory domain from an intracellular signaling domain of TCR alpha; and a first human or humanized antibody domain comprising a first antigen binding domain and a second human or humanized antibody domain comprising a second antigen binding domain; wherein the TCR subunit, the first antibody domain, and the second antibody domain are operatively linked, and wherein the first TFP incorporates into a TCR when expressed in a T-cell.

In some aspects, provided herein is an isolated recombinant nucleic acid molecule encoding a first T-cell receptor (TCR) fusion protein (TFP) comprising a TCR subunit comprising at least a portion of a TCR extracellular domain, and a TCR intracellular domain comprising a stimulatory domain from an intracellular signaling domain of TCR beta; and a first human or humanized antibody domain comprising a first antigen binding domain and a second human or humanized antibody domain comprising a second antigen binding domain; wherein the TCR subunit, the first antibody domain, and the second antibody domain are operatively linked, and wherein the first TFP incorporates into a TCR when expressed in a T-cell.

In some embodiments, the first antigen binding domain or the second antigen binding domain is an anti-CD19 binding domain. In some embodiments, the first antigen binding domain or the second antigen binding domain is an anti-B-cell maturation antigen (BCMA) binding domain In some embodiments, the first antigen binding domain or the second antigen binding domain is an anti-CD22 binding domain.

In some aspects, provided herein is an isolated recombinant nucleic acid molecule encoding: a first T-cell receptor (TCR) fusion protein (TFP) comprising a TCR subunit, a first human or humanized antibody domain comprising a first antigen binding domain that is an anti-CD19 binding domain; and a second T-cell receptor (TCR) fusion protein (TFP) comprising a TCR subunit, a second human or humanized antibody domain comprising a second antigen binding domain that is an anti-BCMA binding domain.

In some aspects, provided herein is an isolated recombinant nucleic acid molecule encoding: a first T-cell receptor (TCR) fusion protein (TFP) comprising a TCR subunit, a first human or humanized antibody domain comprising a first antigen binding domain that is an anti-CD19 binding domain; and a second T-cell receptor (TCR) fusion protein (TFP) comprising a TCR subunit, a second human or humanized antibody domain comprising a second antigen binding domain that is an anti-CD22 binding domain.

In some embodiments, the TCR subunit of the first TFP and the first antibody domain are operatively linked and the TCR subunit of the second TFP and the second antibody domain are operatively linked. In some embodiments, the first TFP, the second TFP, or both incorporate into a TCR when expressed in a T-cell. In some embodiments, the encoded first antigen binding domain is connected to the TCR extracellular domain of the first TFP by a first linker sequence, the encoded second antigen binding domain is connected to the TCR extracellular domain of the second TFP by a second linker sequence, or both the first antigen binding domain is connected to the TCR extracellular domain of the first TFP by the first linker sequence and the encoded second antigen binding domain is connected to the TCR extracellular domain of the second TFP by the second linker sequence. In some embodiments, the first linker sequence and the second linker sequence comprise (G4S)n, wherein n=1 to 4. In some embodiments, the TCR subunit of the first TFP, the TCR subunit of the second TFP, or both comprise a TCR extracellular domain. In some embodiments, the TCR subunit of the first TFP, the TCR subunit of the second TFP, or both comprise a TCR transmembrane domain. In some embodiments, the TCR subunit of the first TFP, the TCR subunit of the second TFP, or both comprise a TCR intracellular domain. In some embodiments, the TCR subunit of the first TFP, the TCR subunit of the second TFP, or both comprise (i) a TCR extracellular domain, (ii) a TCR transmembrane domain, and (iii) a TCR intracellular domain, wherein at least two of (i), (ii), and (iii) are from the same TCR subunit. In some embodiments, the TCR subunit of the first TFP, the TCR subunit of the second TFP, or both comprise a TCR intracellular domain comprising a stimulatory domain selected from an intracellular signaling domain of CD3 epsilon, CD3 gamma or CD3 delta, or an amino acid sequence having at least one modification thereto. In some embodiments, the TCR subunit of the first TFP, the TCR subunit of the second TFP, or both comprise an intracellular domain comprising a stimulatory domain selected from a functional signaling domain of 4-1BB and/or a functional signaling domain of CD3 zeta, or an amino acid sequence having at least one modification thereto. In some embodiments, the first human or humanized antibody domain, the second human or humanized antibody domain, or both comprise an antibody fragment. In some embodiments, the first human or humanized antibody domain, the second human or humanized antibody domain, or both comprise a scFv or a VH domain.

In some embodiments, the isolated nucleic acid molecule encodes (i) a light chain (LC) CDR1, LC CDR2 and LC CDR3 of an anti-CD19 light chain binding domain amino acid sequence with 70-100% sequence identity to SEQ ID NO: 25, SEQ ID NO: 27 and SEQ ID NO: 29, respectively, and/or (ii) a heavy chain (HC) CDR1, HC CDR2 and HC CDR3 of an anti-CD19 heavy chain binding domain amino acid sequence with 70-100% sequence identity to SEQ ID NO: 31, SEQ ID NO: 33 and SEQ ID NO: 35, respectively. In some embodiments, the isolated nucleic acid molecule encodes a light chain variable region, wherein the light chain variable region comprises an amino acid sequence having at least one but not more than 30 modifications of a light chain variable region amino acid sequence of SEQ ID NO: 49, or a sequence with 95-99% identity to a light chain variable region amino acid sequence of SEQ ID NO: 49. In some embodiments, the isolated nucleic acid molecule encodes a heavy chain variable region, wherein the heavy chain variable region comprises an amino acid sequence having at least one but not more than 30 modifications of a heavy chain variable region amino acid sequence of SEQ ID NO: 51, or a sequence with 95-99% identity to a heavy chain variable region amino acid sequence of SEQ ID NO: 51. In some embodiments, the isolated nucleic acid molecule encodes (i) a light chain (LC) CDR1, LC CDR2 and LC CDR3 of an anti-BCMA light chain binding domain amino acid sequence with 70-100% sequence identity to SEQ ID NO: 37, SEQ ID NO: 39 and SEQ ID NO: 41, respectively, and/or (ii) a heavy chain (HC) CDR1, HC CDR2 and HC CDR3 of an anti-BCMA heavy chain binding domain amino acid sequence with 70-100% sequence identity to SEQ ID NO: 43, SEQ ID NO: 45 and SEQ ID NO: 47, respectively. In some embodiments, the isolated nucleic acid molecule encodes a light chain variable region, wherein the light chain variable region comprises an amino acid sequence having at least one but not more than 30 modifications of a light chain variable region amino acid sequence of SEQ ID NO: 53, or a sequence with 95-99% identity to a light chain variable region amino acid sequence of SEQ ID NO: 53. In some embodiments, the isolated nucleic acid molecule encodes a heavy chain variable region, wherein the heavy chain variable region comprises an amino acid sequence having at least one but not more than 30 modifications of a heavy chain variable region amino acid sequence of SEQ ID NO: 55, or a sequence with 95-99% identity to a heavy chain variable region amino acid sequence of SEQ ID NO: 55. In some embodiments, the anti-CD22 antigen binding domain comprises a variable region as described herein or one or more CDRs as described herein.

In some embodiments, the encoded first TFP, the encoded second TFP, or both include an extracellular domain of a TCR subunit that comprises an extracellular domain or portion thereof of a protein selected from the group consisting of a TCR alpha chain, a TCR beta chain, a CD3 epsilon TCR subunit, a CD3 gamma TCR subunit, a CD3 delta TCR subunit, functional fragments thereof, and amino acid sequences thereof having at least one but not more than 20 modifications. In some embodiments, the encoded first TFP and the encoded second TFP include a transmembrane domain that comprises a transmembrane domain of a protein selected from the group consisting of a TCR alpha chain, a TCR beta chain, a CD3 epsilon TCR subunit, a CD3 gamma TCR subunit, a CD3 delta TCR subunit, functional fragments thereof, and amino acid sequences thereof having at least one but not more than 20 modifications. In some embodiments, the encoded first TFP and the encoded second TFP include a transmembrane domain that comprises a transmembrane domain of a protein selected from the group consisting of a TCR alpha chain, a TCR beta chain, a TCR zeta chain, a CD3 epsilon TCR subunit, a CD3 gamma TCR subunit, a CD3 delta TCR subunit, CD45, CD4, CD5, CD8, CD9, CD16, CD22, CD33, CD28, CD37, CD64, CD80, CD86, CD134, CD137, CD154, functional fragments thereof, and amino acid sequences thereof having at least one but not more than 20 modifications. In some embodiments, the TCR subunit and the binding ligand are operatively linked. In some embodiments, the TCR subunit and the antibody domain are operatively linked. In some embodiments, the TFP incorporates into a TCR when expressed in a T-cell. In some embodiments, the binding ligand is connected to the TCR extracellular domain by a linker sequence. In some embodiments, the encoded antigen binding domain is connected to the TCR extracellular domain by a linker sequence. In some embodiments, the linker sequence comprises (G4S)n, wherein n=1 to 4. In some embodiments, the TCR subunit comprises a TCR extracellular domain. In some embodiments, the TCR subunit comprises a TCR transmembrane domain. In some embodiments, the TCR subunit comprises a TCR intracellular domain. In some embodiments, the TCR subunit comprises (i) a TCR extracellular domain, (ii) a TCR transmembrane domain, and (iii) a TCR intracellular domain, and wherein at least two of (i), (ii), and (iii) are from the same TCR subunit. In some embodiments, the TCR subunit comprises a TCR intracellular domain comprising a stimulatory domain selected from an intracellular signaling domain of CD3 epsilon, CD3 gamma, CD3 delta, or an amino acid sequence having at least one modification thereto. In some embodiments, the TCR subunit comprises an intracellular domain comprising a stimulatory domain selected from a functional signaling domain of 4-1BB and/or a functional signaling domain of CD3 zeta, or an amino acid sequence having at least one modification thereto. In some embodiments, the binding ligand comprises a CD16-binding antibody or antibody fragment. In some embodiments, the human or humanized antibody domain comprises an antibody fragment. In some embodiments, the human or humanized antibody domain comprises a scFv or a VH domain.

In some embodiments, the isolated nucleic acid molecule encodes an NKG2D amino acid sequence with 70-100% sequence identity to an NKG2D ligand provided herein.

In some embodiments, the isolated nucleic acid molecule encodes a CD16 amino acid sequence with about 70 to about 100% sequence identity to a CD16 polypeptide provided herein. In some embodiments, the isolated nucleic acid molecule encodes (i) a light chain (LC) CDR1, LC CDR2 and LC CDR3 of an anti-ROR1 light chain binding domain amino acid sequence with 70-100% sequence identity to a light chain (LC) CDR1, LC CDR2 and LC CDR3 of an anti-ROR1 light chain binding domain provided herein, respectively, and/or (ii) a heavy chain (HC) CDR1, HC CDR2 and HC CDR3 of an anti-ROR1 heavy chain binding domain amino acid sequence with 70-100% sequence identity to a heavy chain (HC) CDR1, HC CDR2 and HC CDR3 of an anti-ROR1 heavy chain binding domain provided herein, respectively. In some embodiments, the isolated nucleic acid molecule encodes a light chain variable region, wherein the light chain variable region comprises an amino acid sequence having at least one but not more than 30 modifications of a light chain variable region amino acid sequence of a light chain variable region provided herein, or a sequence with 95-99% identity to a light chain variable region amino acid sequence of a light chain variable region provided herein. In some embodiments, the isolated nucleic acid molecule encodes a heavy chain variable region, wherein the heavy chain variable region comprises an amino acid sequence having at least one but not more than 30 modifications of a heavy chain variable region amino acid sequence of a heavy chain variable region provided herein, or a sequence with 95-99% identity to a heavy chain variable region amino acid sequence of a heavy chain variable region provided herein.

In some embodiments, the TFP includes an extracellular domain of a TCR subunit that comprises an extracellular domain or portion thereof of a protein selected from the group consisting of a TCR alpha chain, a TCR beta chain, a CD3 epsilon TCR subunit, a CD3 gamma TCR subunit, a CD3 delta TCR subunit, functional fragments thereof, and amino acid sequences thereof having at least one but not more than 20 modifications. In some embodiments, the encoded TFP includes a transmembrane domain that comprises a transmembrane domain of a protein selected from the group consisting of a TCR alpha chain, a TCR beta chain, a CD3 epsilon TCR subunit, a CD3 gamma TCR subunit, a CD3 delta TCR subunit, functional fragments thereof, and amino acid sequences thereof having at least one but not more than 20 modifications. In some embodiments, the encoded TFP includes a transmembrane domain that comprises a transmembrane domain of a protein selected from the group consisting of a TCR alpha chain, a TCR beta chain, a TCR zeta chain, a CD3 epsilon TCR subunit, a CD3 gamma TCR subunit, a CD3 delta TCR subunit, CD45, CD4, CD5, CD8, CD9, CD16, CD22, CD33, CD28, CD37, CD64, CD80, CD86, CD134, CD137, CD154, functional fragments thereof, and amino acid sequences thereof having at least one but not more than 20 modifications. In some embodiments, the isolated nucleic acid molecule further comprises a sequence encoding a costimulatory domain. In some embodiments, the costimulatory domain is a functional signaling domain obtained from a protein selected from the group consisting of OX40, CD2, CD27, CD28, CD5, ICAM-1, LFA-1 (CD11a/CD18), ICOS (CD278), and 4-1BB (CD137), and amino acid sequences thereof having at least one but not more than 20 modifications thereto. In some embodiments, the at least one but not more than 20 modifications thereto comprise a modification of an amino acid that mediates cell signaling or a modification of an amino acid that is phosphorylated in response to a ligand binding to the TFP. In some embodiments, the isolated nucleic acid molecule further comprises a sequence encoding an intracellular signaling domain In some embodiments, the isolated nucleic acid molecule further comprises a leader sequence. In some embodiments, the isolated nucleic acid molecule further comprises a protease cleavage site. In some embodiments, the at least one but not more than 20 modifications thereto comprise a modification of an amino acid that mediates cell signaling or a modification of an amino acid that is phosphorylated in response to a ligand binding to the first TFP, the second TFP, or both.

In some embodiments, the isolated nucleic acid molecule is mRNA.

In some embodiments, the TFP includes an immunoreceptor tyrosine-based activation motif (ITAM) of a TCR subunit that comprises an ITAM or portion thereof of a protein selected from the group consisting of CD3 zeta TCR subunit, CD3 epsilon TCR subunit, CD3 gamma TCR subunit, CD3 delta TCR subunit, TCR zeta chain, Fc epsilon receptor 1 chain, Fc epsilon receptor 2 chain, Fc gamma receptor 1 chain, Fc gamma receptor 2a chain, Fc gamma receptor 2b1 chain, Fc gamma receptor 2b2 chain, Fc gamma receptor 3a chain, Fc gamma receptor 3b chain, Fc beta receptor 1 chain, TYROBP (DAP12), CD5, CD16a, CD16b, CD22, CD23, CD32, CD64, CD79a, CD79b, CD89, CD278, CD66d, functional fragments thereof, and amino acid sequences thereof having at least one but not more than 20 modifications thereto. In some embodiments, the first TFP, the second TFP, or both include an immunoreceptor tyrosine-based activation motif (ITAM) of a TCR subunit that comprises an ITAM or portion thereof of a protein selected from the group consisting of CD3 zeta TCR subunit, CD3 epsilon TCR subunit, CD3 gamma TCR subunit, CD3 delta TCR subunit, TCR zeta chain, Fc epsilon receptor 1 chain, Fc epsilon receptor 2 chain, Fc gamma receptor 1 chain, Fc gamma receptor 2a chain, Fc gamma receptor 2b1 chain, Fc gamma receptor 2b2 chain, Fc gamma receptor 3a chain, Fc gamma receptor 3b chain, Fc beta receptor 1 chain, TYROBP (DAP12), CD5, CD16a, CD16b, CD22, CD23, CD32, CD64, CD79a, CD79b, CD89, CD278, CD66d, functional fragments thereof, and amino acid sequences thereof having at least one but not more than 20 modifications thereto. In some embodiments, the ITAM replaces an ITAM of CD3 gamma, CD3 delta, or CD3 epsilon. In some embodiments, the ITAM is selected from the group consisting of CD3 zeta TCR subunit, CD3 epsilon TCR subunit, CD3 gamma TCR subunit, and CD3 delta TCR subunit and replaces a different ITAM selected from the group consisting of CD3 zeta TCR subunit, CD3 epsilon TCR subunit, CD3 gamma TCR subunit, and CD3 delta TCR subunit.

In some embodiments, the isolated nucleic acid molecule further comprises a leader sequence.

In some aspects, provided herein is an isolated polypeptide molecule encoded by a nucleic acid molecule described herein. In some embodiments, the isolated polypeptide comprises a first polypeptide encoded by a first nucleic acid molecule and a second polypeptide encoded by a second nucleic acid molecule.

In some aspects, provided herein is an isolated recombinant TFP molecule comprising a human or humanized CD16 polypeptide or a fragment thereof, a TCR extracellular domain, a transmembrane domain, and an intracellular domain.

In some aspects, provided herein is an isolated recombinant TFP molecule comprising a human or humanized CD16 polypeptide or a fragment thereof, a TCR extracellular domain, a transmembrane domain, and an intracellular signaling domain, wherein the TFP molecule is capable of functionally interacting with an endogenous TCR complex and/or at least one endogenous TCR polypeptide.

In some aspects, provided herein is an isolated recombinant TFP molecule comprising a human or humanized CD16 polypeptide or a fragment thereof, a TCR extracellular domain, a transmembrane domain, and an intracellular signaling domain, wherein the TFP molecule is capable of functionally integrating into an endogenous TCR complex.

In some aspects, provided herein is an isolated recombinant TFP molecule comprising a human or humanized anti-Receptor Tyrosine Kinase Like Orphan Receptor 1 (ROR1) binding domain, a TCR extracellular domain, a transmembrane domain, and an intracellular domain.

In some aspects, provided herein is an isolated recombinant TFP molecule comprising a human or humanized anti-Receptor Tyrosine Kinase Like Orphan Receptor 1 (ROR1) binding domain, a TCR extracellular domain, a transmembrane domain, and an intracellular signaling domain, wherein the TFP molecule is capable of functionally interacting with an endogenous TCR complex and/or at least one endogenous TCR polypeptide.

In some aspects, provided herein is an isolated recombinant TFP molecule comprising a human or humanized anti-Receptor Tyrosine Kinase Like Orphan Receptor 1 (ROR1) binding domain, a TCR extracellular domain, a transmembrane domain, and an intracellular signaling domain, wherein the TFP molecule is capable of functionally integrating into an endogenous TCR complex.

In some aspects, provided herein is an isolated recombinant TFP molecule comprising a human NKG2D polypeptide or a fragment thereof, a TCR extracellular domain, a transmembrane domain, and an intracellular domain.

In some aspects, provided herein is an isolated recombinant TFP molecule comprising a human NKG2D polypeptide or a fragment thereof, a TCR extracellular domain, a transmembrane domain, and an intracellular signaling domain, wherein the TFP molecule is capable of functionally interacting with an endogenous TCR complex and/or at least one endogenous TCR polypeptide.

In some aspects, provided herein is an isolated recombinant TFP molecule comprising a human NKG2D polypeptide or a fragment thereof, a TCR extracellular domain, a transmembrane domain, and an intracellular signaling domain, wherein the TFP molecule is capable of functionally integrating into an endogenous TCR complex.

In some aspects, provided herein is an isolated recombinant TFP molecule comprising a first TFP molecule comprising a human or humanized anti-CD19 binding domain, a TCR extracellular domain, a transmembrane domain, and an intracellular domain, and a second TFP molecule comprising a human or humanized anti-BCMA binding domain, a TCR extracellular domain, a transmembrane domain, and an intracellular domain.

In some aspects, provided herein is an isolated recombinant TFP molecule comprising a first TFP molecule comprising a human or humanized anti-CD19 binding domain, a TCR extracellular domain, a transmembrane domain, and an intracellular domain, and a second TFP molecule comprising a human or humanized anti-BCMA binding domain, a TCR extracellular domain, a transmembrane domain, and an intracellular domain, wherein the first TFP molecule is capable of functionally interacting with an endogenous TCR complex and/or at least one endogenous TCR polypeptide.

In some aspects, provided herein is an isolated recombinant TFP molecule comprising a first TFP molecule comprising a human or humanized anti-CD19 binding domain, a TCR extracellular domain, a transmembrane domain, and an intracellular domain, and a second TFP molecule comprising a human or humanized anti-BCMA binding domain, a TCR extracellular domain, a transmembrane domain, and an intracellular domain, wherein the first TFP molecule is capable of functionally integrating into an endogenous TCR complex. In some embodiments the isolated recombinant TFP molecule comprises an antibody or antibody fragment comprising a human or humanized anti-CD19 binding domain, a humanized anti-BCMA binding domain, a TCR extracellular domain, a transmembrane domain, and an intracellular domain.

In some aspects, provided herein is an isolated recombinant TFP molecule comprising a first TFP molecule comprising a human or humanized anti-CD19 binding domain, a TCR extracellular domain, a transmembrane domain, and an intracellular domain, and a second TFP molecule comprising a human or humanized anti-CD22 binding domain, a TCR extracellular domain, a transmembrane domain, and an intracellular domain.

In some aspects, provided herein is an isolated recombinant first TFP molecule comprising a human or humanized anti-CD19 binding domain, a humanized anti-CD22 binding domain, a TCR extracellular domain, a transmembrane domain, and an intracellular signaling domain, wherein the first TFP molecule is capable of functionally interacting with an endogenous TCR complex and/or at least one endogenous TCR polypeptide.

In some aspects, provided herein is an isolated recombinant first TFP molecule comprising a human or humanized anti-CD19 binding domain, a humanized anti-CD22 binding domain, a TCR extracellular domain, a transmembrane domain, and an intracellular signaling domain, wherein the first TFP molecule is capable of functionally integrating into an endogenous TCR complex.

In some embodiments, the isolated TFP molecule comprises an antibody or antibody fragment comprising a human or humanized anti-ROR1 binding domain, a TCR extracellular domain, a transmembrane domain, and an intracellular domain. In some embodiments, the anti-ROR1 binding domain is a scFv or a VH domain. In some embodiments, the anti-ROR1 binding domain comprises a heavy chain with 95-100% identity to an amino acid sequence of an anti-ROR1 light chain provided herein, a functional fragment thereof, or an amino acid sequence thereof having at least one but not more than 30 modifications. In some embodiments, the anti-ROR1 binding domain comprises a light chain with 95-100% identity to an amino acid sequence of an anti-ROR1 heavy chain provided herein, a functional fragment thereof, or an amino acid sequence thereof having at least one but not more than 30 modifications. In some embodiments, the isolated TFP molecule comprises a TCR extracellular domain that comprises an extracellular domain or portion thereof of a protein selected from the group consisting of a TCR alpha chain, a TCR beta chain, a CD3 epsilon TCR subunit, a CD3 gamma TCR subunit, a CD3 delta TCR subunit, functional fragments thereof, and amino acid sequences thereof having at least one but not more than 20 modifications. In some embodiments, the TCR extracellular domain is operably connected by a linker sequence. In some embodiments, the linker region comprises (G4S)n, wherein n=1 to 4. In some embodiments, the isolated TFP molecule further comprises a sequence encoding a costimulatory domain. In some embodiments, the isolated TFP molecule further comprises a sequence encoding an intracellular signaling domain. In some embodiments, the isolated TFP molecule further comprises comprising a leader sequence.

In some aspects, provided herein is a nucleic acid comprising a sequence encoding a TFP described herein. In some embodiments, the isolated recombinant TFP molecule comprises an antibody or antibody fragment comprising a human or humanized anti-CD19 binding domain, a humanized anti-CD22 binding domain, a TCR extracellular domain, a transmembrane domain, and an intracellular domain. In some embodiments, the isolated TFP molecule further comprises the anti-CD19 binding domain, the anti-BCMA binding domain, the anti-CD22 binding domain, or a combination thereof are a scFv or a VH domain.

In some embodiments, the anti-CD19 binding domain comprises a heavy chain with 95-100% identity to an amino acid sequence of SEQ ID NO: 51, a functional fragment thereof, or an amino acid sequence thereof having at least one but not more than 30 modifications. In some embodiments, the anti-CD19 binding domain comprises a light chain with 95-100% identity to an amino acid sequence of SEQ ID NO: 49, a functional fragment thereof, or an amino acid sequence thereof having at least one but not more than 30 modifications. In some embodiments, the anti-BCMA binding domain comprises a heavy chain with 95-100% identity to an amino acid sequence of SEQ ID NO: 55, a functional fragment thereof, or an amino acid sequence thereof having at least one but not more than 30 modifications. In some embodiments, the anti-BCMA binding domain comprises a light chain with 95-100% identity to an amino acid sequence of SEQ ID NO: 53, a functional fragment thereof, or an amino acid sequence thereof having at least one but not more than 30 modifications.

In some embodiments, the anti-CD22 binding domain comprises a variable region as described herein or one or more CDRs as described herein. In some embodiments, the isolated recombinant TFP molecule comprises a TCR extracellular domain that comprises an extracellular domain or portion thereof of a protein selected from the group consisting of a TCR alpha chain, a TCR beta chain, a CD3 epsilon TCR subunit, a CD3 gamma TCR subunit, a CD3 delta TCR subunit, functional fragments thereof, and amino acid sequences thereof having at least one but not more than 20 modifications. In some embodiments, the anti-CD19 binding domain is connected to the TCR extracellular domain of the first TFP molecule by a first linker sequence and the anti-BCMA binding domain is connected to the TCR extracellular domain of the first TFP molecule by a second linker sequence. In some embodiments, the anti-CD19 binding domain is connected to the TCR extracellular domain of the first TFP molecule by a first linker sequence and the anti-CD22 binding domain is connected to the TCR extracellular domain of the first TFP molecule by a second linker sequence. In some embodiments, the first linker sequence and the second linker sequence comprise (G4S)n, wherein n=1 to 4. In some embodiments, the isolated recombinant TFP molecule further comprises a costimulatory domain. In some embodiments, the isolated recombinant TFP molecule further comprises an intracellular signaling domain. In some embodiments, the isolated recombinant TFP molecule further comprises a leader sequence.

In some aspects, provided herein is a nucleic acid comprising a sequence encoding an isolated recombinant TFP described herein.

In some embodiments, the nucleic acid comprises a first nucleic acid encoding the first TFP molecule and a second nucleic acid encoding the second TFP molecule. In some embodiments, the nucleic acid is selected from the group consisting of a DNA and a RNA. In some embodiments, the nucleic acid is a mRNA. In some embodiments, the nucleic acid further comprises a promoter. In some embodiments, the nucleic acid is an in vitro transcribed nucleic acid. In some embodiments, the nucleic acid further comprises a sequence encoding a poly(A) tail. In some embodiments, the nucleic acid further comprises a 3' UTR sequence. In some embodiments, the nucleic acid further comprises a sequencing encoding a protease cleavage site.

In some aspects, provided herein is a vector comprising a nucleic acid molecule encoding a TFP described herein.

In some aspects, provided herein is a vector comprising a nucleic acid molecule encoding the isolated recombinant TFP molecule described herein.

In some embodiments, the vector comprises a) a first vector comprising a first nucleic acid molecule encoding the first TFP; and b) a second vector comprising a second nucleic acid molecule encoding the second TFP.

In some embodiments, the vector is selected from the group consisting of a DNA, a RNA, a plasmid, a lentivirus vector, adenoviral vector, a Rous sarcoma viral (RSV) vector, or a retrovirus vector. In some embodiments, the vector further comprises a promoter. In some embodiments, the vector is an in vitro transcribed vector. In some embodiments, the nucleic acid molecule in the vector further encodes a poly(A) tail. In some embodiments, the nucleic acid molecule in the vector further encodes a 3' UTR. In some embodiments, the nucleic acid molecule in the vector further encodes a protease cleavage site.

In some aspects, provided herein is a cell comprising an isolated nucleic acid molecule described herein, a polypeptide molecule described herein, a TFP molecule described herein, a nucleic acid described herein, or a vector described herein.

In some aspects, provided herein is a cell comprising an isolated nucleic acid molecule described herein, a polypeptide molecule described herein, an isolated recombinant TFP molecule described herein, a nucleic acid described herein, or a vector described herein.

In some embodiments, the cell is a human T cell. In some embodiments, the T cell is a $CD8^+$ or $CD4^+$ T cell. In some embodiments, the cell further comprises a nucleic acid encoding an inhibitory molecule that comprises a first polypeptide that comprises at least a portion of an inhibitory molecule, associated with a second polypeptide that comprises a positive signal from an intracellular signaling domain. In some embodiments, the inhibitory molecule comprises a first polypeptide that comprises at least a portion of PD1 and a second polypeptide comprising a costimulatory domain and primary signaling domain.

In some aspects, provided herein is a human $CD8^+$ or $CD4^+$ T-cell comprising at least two TFP molecules, the TFP molecules comprising a human or humanized CD16 polypeptide or a fragment thereof, a TCR extracellular domain, a transmembrane domain, and an intracellular domain, wherein the TFP molecule is capable of functionally interacting with an endogenous TCR complex and/or at least one endogenous TCR polypeptide in, at and/or on the surface of the human $CD8^+$ or $CD4^+$ T-cell.

In some aspects, provided herein is a protein complex comprising: a TFP molecule comprising a human or humanized CD16 polypeptide or a fragment thereof, a TCR extracellular domain, a transmembrane domain, and an intracellular domain; and at least one endogenous TCR subunit or endogenous TCR complex.

In some aspects, provided herein is a human $CD8^+$ or $CD4^+$ T cell comprising at least two TFP molecules, the TFP molecules comprising a human or humanized anti-Receptor Tyrosine Kinase Like Orphan Receptor 1 (ROR1) binding domain, a TCR extracellular domain, a transmembrane domain, and an intracellular domain, wherein the TFP molecule is capable of functionally interacting with an endogenous TCR complex and/or at least one endogenous TCR polypeptide in, at and/or on the surface of the human $CD8^+$ or $CD4^+$ T cell.

In some aspects, provided herein is a protein complex comprising: a TFP molecule comprising a human or humanized anti-Receptor Tyrosine Kinase Like Orphan Receptor 1 (ROR1) binding domain, a TCR extracellular domain, a transmembrane domain, and an intracellular domain; and at least one endogenous TCR subunit or endogenous TCR complex.

In some aspects, provided herein is a human $CD8^+$ or $CD4^+$ T-cell comprising at least two TFP molecules, the TFP molecules comprising a human NKG2D polypeptide or a fragment thereof, a TCR extracellular domain, a transmembrane domain, and an intracellular domain, wherein the TFP molecule is capable of functionally interacting with an endogenous TCR complex and/or at least one endogenous TCR polypeptide in, at and/or on the surface of the human $CD8^+$ or $CD4^+$ T-cell.

In some aspects, provided herein is a protein complex comprising: a TFP molecule comprising a human NKG2D polypeptide or a fragment thereof, a TCR extracellular domain, a transmembrane domain, and an intracellular domain; and at least one endogenous TCR subunit or endogenous TCR complex.

In some aspects, provided herein is a human CD8+ or CD4+ T-cell comprising an isolated recombinant TFP molecule, the isolated recombinant TFP molecule comprising a) a first TFP molecule comprising a human or humanized anti-CD19 binding domain, a TCR extracellular domain, a transmembrane domain, and an intracellular domain, and b) second TFP molecule comprising a human or humanized anti-BCMA binding domain, a TCR extracellular domain, a transmembrane domain, and an intracellular domain, wherein the TFP molecule is capable of functionally interacting with an endogenous TCR complex and/or at least one endogenous TCR polypeptide in, at and/or on the surface of the human CD8+ or CD4+ T-cell.

In some aspects, provided herein is a human CD8+ or CD4+ T-cell comprising an isolated recombinant TFP molecule, the isolated recombinant TFP molecule comprising a) a first TFP molecule comprising a human or humanized anti-CD19 binding domain, a TCR extracellular domain, a transmembrane domain, and an intracellular domain, and b) second TFP molecule comprising a human or humanized anti-CD22 binding domain, a TCR extracellular domain, a transmembrane domain, and an intracellular domain, wherein the TFP molecule is capable of functionally interacting with an endogenous TCR complex and/or at least one endogenous TCR polypeptide in, at and/or on the surface of the human CD8+ or CD4+ T-cell.

In some aspects, provided herein is a protein complex comprising: a first TFP molecule comprising a human or humanized CD19 binding domain, a TCR extracellular domain, a transmembrane domain, and an intracellular domain; a second TFP molecule comprising a human or humanized anti-BCMA binding domain, a TCR extracellular domain, a transmembrane domain, and an intracellular domain; and at least one endogenous TCR subunit or endogenous TCR complex.

In some aspects, provided herein is a protein complex comprising: a first TFP molecule comprising a human or humanized CD19 binding domain, a TCR extracellular domain, a transmembrane domain, and an intracellular domain; a second TFP molecule comprising a human or humanized anti-CD22 binding domain, a TCR extracellular domain, a transmembrane domain, and an intracellular domain; and at least one endogenous TCR subunit or endogenous TCR complex.

In some embodiments, the TCR comprises an extracellular domain or portion thereof of a protein selected from the group consisting of TCR alpha chain, a TCR beta chain, a CD3 epsilon TCR subunit, a CD3 gamma TCR subunit, and a CD3 delta TCR subunit. In some embodiments, the NKG2D ligand or a fragment thereof is connected to the TCR extracellular domain by a linker sequence. In some embodiments, the CD16 polypeptide or a fragment thereof is connected to the TCR extracellular domain by a linker sequence. In some embodiments, the anti-ROR1 binding domain is connected to the TCR extracellular domain by a linker sequence. In some embodiments, the linker region comprises (G4S)n, wherein n=1 to 4.

In some aspects, provided herein is a protein complex comprising a TFP encoded by an isolated nucleic acid molecule described herein, and at least one endogenous TCR subunit or endogenous TCR complex.

In some aspects, provided herein is a human CD8+ or CD4+ T-cell comprising at least two different TFP proteins per a protein complex described herein.

In some aspects, provided herein is a human CD8+ or CD4+ T-cell comprising at least two different TFP molecules encoded by an isolated nucleic acid molecule described herein.

In some embodiments, the TFP comprises an extracellular domain or portion thereof of a protein selected from the group consisting of TCR alpha chain, a TCR beta chain, a CD3 epsilon TCR subunit, a CD3 gamma TCR subunit, and a CD3 delta TCR subunit. In some embodiments, the human or humanized anti-CD19 binding domain is connected to the TCR extracellular domain of the first TFP molecule by a first linker sequence and the human or humanized anti-BCMA binding domain is connected to the TCR extracellular domain of the second TFP molecule by a second linker sequence. In some embodiments, the human or humanized anti-CD19 binding domain is connected to the TCR extracellular domain of the first TFP molecule by a first linker sequence and the human or humanized anti-CD20 binding domain is connected to the TCR extracellular domain of the second TFP molecule by a second linker sequence. In some embodiments, the first linker sequence and the second linker sequence comprise (G4S)n, wherein n=1 to 4.

In some aspects, provided herein is a protein complex comprising a first TFP and a second TFP encoded by an isolated nucleic acid molecule described herein, and at least one endogenous TCR subunit or endogenous TCR complex.

In some aspects, provided herein is a human CD8+ or CD4+ T-cell comprising the first TFP molecule and the second TFP molecule per a protein complex described herein.

In some aspects, provided herein is a human CD8+ or CD4+ T-cell comprising the first TFP molecule and the second TFP molecule encoded by an isolated nucleic acid molecule described herein.

In some aspects, provided herein is a population of human CD8+ or CD4+ T-cells, wherein the T-cells of the population individually or collectively comprise at least two TFP molecules, the TFP molecules comprising a human or humanized CD16 polypeptide or a fragment thereof, a TCR extracellular domain, a transmembrane domain, and an intracellular domain, wherein the TFP molecule is capable of functionally interacting with an endogenous TCR complex and/or at least one endogenous TCR polypeptide in, at and/or on the surface of the human CD8+ or CD4+ T-cell.

In some aspects, provided herein is a population of human CD8+ or CD4+ T cells, wherein the T cells of the population individually or collectively comprise at least two TFP molecules, the TFP molecules comprising a human or humanized anti-Receptor Tyrosine Kinase Like Orphan Receptor 1 (ROR1) binding domain, a TCR extracellular domain, a transmembrane domain, and an intracellular domain, wherein the TFP molecule is capable of functionally interacting with an endogenous TCR complex and/or at least one endogenous TCR polypeptide in, at and/or on the surface of the human CD8+ or CD4+ T cell.

In some aspects, provided herein is a population of human CD8+ or CD4+ T-cells, wherein the T-cells of the population individually or collectively comprise at least two TFP molecules, the TFP molecules comprising a human NKG2D polypeptide or a fragment thereof, a TCR extracellular domain, a transmembrane domain, and an intracellular domain, wherein the TFP molecule is capable of functionally interacting with an endogenous TCR complex and/or at least one endogenous TCR polypeptide in, at and/or on the surface of the human CD8⁺ or CD4⁺ T-cell.

In some aspects, provided herein is a population of human CD8⁺ or CD4⁺ T-cells, wherein the T-cells of the population individually or collectively comprise a first TFP molecule and a second TFP molecule, the first TFP molecule comprising a human or humanized anti-CD19 binding domain, a TCR extracellular domain, a transmembrane domain, and an intracellular domain and the second TFP molecule comprising a human or humanized anti-BCMA binding domain, a TCR extracellular domain, a transmembrane domain, and an intracellular domain, wherein the first TFP molecule and the second TFP molecule are capable of functionally interacting with an endogenous TCR complex and/or at least one endogenous TCR polypeptide in, at and/or on the surface of the human CD8⁺ or CD4⁺ T-cell.

In some aspects, provided herein is a population of human CD8⁺ or CD4⁺ T-cells, wherein the T-cells of the population individually or collectively comprise a first TFP molecule and a second TFP molecule, the first TFP molecule comprising a human or humanized anti-CD19 binding domain, a TCR extracellular domain, a transmembrane domain, and an intracellular domain and the second TFP molecule comprising a human or humanized anti-CD22 binding domain, a TCR extracellular domain, a transmembrane domain, and an intracellular domain, wherein the first TFP molecule and the second TFP molecule are capable of functionally interacting with an endogenous TCR complex and/or at least one endogenous TCR polypeptide in, at and/or on the surface of the human CD8⁺ or CD4⁺ T-cell.

In some aspects, provided herein is a population of human CD8⁺ or CD4⁺ T-cells, wherein the T-cells of the population individually or collectively comprise the first TFP molecule and the second TFP molecule encoded by an isolated nucleic acid molecule described herein.

In some aspects, provided herein is a population of human CD8⁺ or CD4⁺ T-cells, wherein the T-cells of the population individually or collectively comprise at least two TFP molecules encoded by an isolated nucleic acid molecule described herein.

In some aspects, provided herein is a method of making a cell comprising transducing a T-cell with an isolated nucleic acid molecule described herein, a nucleic acid described herein, or a vector described herein.

In some aspects, provided herein is a method of generating a population of RNA-engineered cells comprising introducing an in vitro transcribed RNA or synthetic RNA into a cell, where the RNA comprises a nucleic acid encoding a TFP molecule described herein.

In some aspects, provided herein is a method of generating a population of RNA-engineered cells comprising introducing an in vitro transcribed RNA or synthetic RNA into a cell, where the RNA comprises a nucleic acid encoding an isolated recombinant TFP molecule described herein.

In some aspects, provided herein is a method of providing an anti-tumor immunity in a mammal comprising administering to the mammal an effective amount of an isolated nucleic acid molecule described herein, a polypeptide molecule described herein, a cell expressing a polypeptide molecule described herein, a TFP molecule described herein, a nucleic acid described herein, a vector described herein, or a cell described herein.

In some aspects, provided herein is a method of providing an anti-tumor immunity in a mammal comprising administering to the mammal an effective amount of an isolated nucleic acid molecule described herein, a polypeptide molecule described herein, a cell expressing a polypeptide molecule described herein, a TFP molecule described herein, a nucleic acid described herein, a vector described herein, or a cell described herein.

In some embodiments, the cell is an autologous T-cell. In some embodiments, the cell is an allogeneic T-cell. In some embodiments, the mammal is a human.

In some aspects, provided herein is a method of treating a mammal having a disease associated with expression of a tumor-associated antigen, comprising administering to the mammal an effective amount of an isolated nucleic acid molecule described herein, a polypeptide molecule described herein, a cell expressing a polypeptide molecule described herein, a TFP molecule described herein, a nucleic acid described herein, a vector described herein, or a cell described herein.

In some aspects, provided herein is a method of treating a mammal having a disease associated with expression of a ROR1, comprising administering to the mammal an effective amount of an isolated nucleic acid molecule described herein, a polypeptide molecule described herein, a cell expressing a polypeptide molecule described herein, a TFP molecule described herein, a nucleic acid described herein, a vector described herein, or a cell described herein.

In some aspects, provided herein is a method of treating a mammal having a disease associated with expression of a NKG2D receptor, comprising administering to the mammal an effective amount of an isolated nucleic acid molecule described herein, a polypeptide molecule described herein, a cell expressing a polypeptide molecule described herein, a TFP molecule described herein, a nucleic acid described herein, a vector described herein, or a cell described herein.

In some embodiments, the disease associated with expression of an anti-NKG2D receptor is selected from the group consisting of a dysplasia, a proliferative disease, a cancer, a malignancy, a non-cancer related indication associated with expression of an anti-NKG2D receptor, inflammatory disease, rheumatoid arthritis, colitis, celiac disease, intestinal inflammation, multiple sclerosis, alopecia areata, type 1 diabetes, chronic obstructive pulmonary disease, atherosclerosis, and metabolic syndrome associated with type 2 diabetes. In some embodiments, the disease associated with expression of an anti-NKG2D receptor is an infectious disease.

In some aspects, provided herein is a method of treating a mammal having a disease associated with expression of CD19, BCMA, or CD22 comprising administering to the mammal an effective amount of an isolated nucleic acid molecule described herein, a polypeptide molecule described herein, a cell expressing a polypeptide molecule described herein, a TFP molecule described herein, a nucleic acid described herein, a vector described herein, or a cell described herein.

In some embodiments, the disease associated with CD19, BCMA, or CD22 expression is selected from the group consisting of a proliferative disease, a cancer, a malignancy, myelodysplasia, a myelodysplastic syndrome, a preleukemia, a non-cancer related indication associated with expression of CD19, a non-cancer related indication associated with expression of BCMA, and a non-cancer related indication associated with expression of CD22. In some embodiments, the disease associated with ROR1 expression is selected from the group consisting of a dysplasia, a proliferative disease, a cancer, a malignancy, and a non-cancer related indication associated with expression of ROR1.

In some embodiments, the disease is a cancer selected from the group consisting of mesothelioma, papillary serous ovarian adenocarcinoma, clear cell acute lymphoid leukemia (T-ALL), acute lymphoblastic leukemia (ALL); chronic myelogenous leukemia (CML), chronic lymphocytic leukemia (CLL), B cell chronic lymphocytic leukemia, B cell prolymphocytic leukemia, blastic plasmacytoid dendritic cell neoplasm, Burkitt's lymphoma, diffuse large B cell lymphoma, follicular lymphoma, hairy cell leukemia, small cell-follicular lymphoma, large cell-follicular lymphoma, malignant lymphoproliferative conditions, MALT lymphoma, mantle cell lymphoma, Marginal zone lymphoma, multiple myeloma, myelodysplasia, myelodysplastic syndrome, non-Hodgkin's lymphoma, plasmablastic lymphoma, plasmacytoid dendritic cell neoplasm, Waldenstrom macroglobulinemia, pre-leukemia, ovarian carcinoma, mixed Mullerian ovarian carcinoma, endometroid mucinous ovarian carcinoma, pancreatic adenocarcinoma, ductal pancreatic adenocarcinoma, uterine serous carcinoma, lung adenocarcinoma, extrahepatic bile duct carcinoma, gastric adenocarcinoma, esophageal adenocarcinoma, colorectal adenocarcinoma, breast adenocarcinoma, renal cancer, colon cancer, gastric cancer, autoimmune disease, and combinations thereof. In some embodiments, the disease is a cancer selected from the group consisting of mesothelioma, papillary serous ovarian adenocarcinoma, clear cell acute lymphoid leukemia (T-ALL), acute lymphoblastic leukemia (ALL); chronic myelogenous leukemia (CML), chronic lymphocytic leukemia (CLL), B cell chronic lymphocytic leukemia, B cell prolymphocytic leukemia, blastic plasmacytoid dendritic cell neoplasm, Burkitt's lymphoma, diffuse large B cell lymphoma, follicular lymphoma, hairy cell leukemia, small cell-follicular lymphoma, large cell-follicular lymphoma, malignant lymphoproliferative conditions, MALT lymphoma, mantle cell lymphoma, Marginal zone lymphoma, multiple myeloma, myelodysplasia, myelodysplastic syndrome, non-Hodgkin's lymphoma, plasmablastic lymphoma, plasmacytoid dendritic cell neoplasm, Waldenstrom macroglobulinemia, pre-leukemia, ovarian carcinoma, mixed Mullerian ovarian carcinoma, endometroid mucinous ovarian carcinoma, pancreatic adenocarcinoma, ductal pancreatic adenocarcinoma, uterine serous carcinoma, lung adenocarcinoma, extrahepatic bile duct carcinoma, gastric adenocarcinoma, esophageal adenocarcinoma, colorectal adenocarcinoma, breast adenocarcinoma, renal cancer, colon cancer, gastric cancer, a disease associated with ROR1 expression, and combinations thereof. In some embodiments, the disease is a cancer selected from the group consisting of Ewing's sarcoma, glioma, neuroblastoma, multiple myeloma, melanoma, leukemia (e.g., AML, CML, ad CLL), ovarian carcinoma, bladder carcinoma, breast carcinoma, lung carcinoma, hepatocellular carcinoma, colon carcinoma, renal carcinoma, and prostate carcinoma. In some embodiments, the disease is a hematologic cancer selected from the group consisting of B-cell acute lymphoid leukemia (B-ALL), T-cell acute lymphoid leukemia (T-ALL), acute lymphoblastic leukemia (ALL); chronic myelogenous leukemia (CML), chronic lymphocytic leukemia (CLL), B cell prolymphocytic leukemia, blastic plasmacytoid dendritic cell neoplasm, Burkitt's lymphoma, diffuse large B cell lymphoma, follicular lymphoma, hairy cell leukemia, small cell-follicular lymphoma, large cell-follicular lymphoma, malignant lymphoproliferative conditions, MALT lymphoma, mantle cell lymphoma, Marginal zone lymphoma, multiple myeloma, myelodysplasia, myelodysplastic syndrome, non-Hodgkin's lymphoma, plasmablastic lymphoma, plasmacytoid dendritic cell neoplasm, Waldenstrom macroglobulinemia, preleukemia, a disease associated with CD19, BCMA, or CD22 expression, and combinations thereof.

In some embodiments, the cells expressing a TFP molecule are administered in combination with an agent that increases the efficacy of a cell expressing a TFP molecule. In some embodiments, the cells expressing a TFP molecule are administered in combination with an antibody or fragment thereof that specifically binds to a cell surface-associated antigen on a tumor cell. In some embodiments, the cells expressing a first TFP molecule and a second TFP molecule are administered in combination with an agent that increases the efficacy of a cell expressing the first TFP molecule and the second TFP molecule. In some embodiments, less cytokines are released in the mammal compared a mammal administered an effective amount of a T-cell expressing a chimeric antigen receptor (CAR) having the antigen domain. In some embodiments, less cytokines are released in the mammal compared a mammal administered an effective amount of a T-cell expressing a chimeric antigen receptor (CAR) having the antigen domain comprising the ligand NKG2D. In some embodiments, less cytokines are released in the mammal compared to a mammal administered an effective amount of a T-cell expressing a chimeric antigen receptor (CAR) capable of binding to the cell surface-associated antigen. In some embodiments, less cytokines are released in the mammal compared to a mammal administered an effective amount of a T-cell expressing an anti-ROR1 chimeric antigen receptor (CAR). In some embodiments, less cytokines are released in the mammal compared a mammal administered an effective amount of a T-cell expressing: an anti-CD19 chimeric antigen receptor (CAR); an anti-BCMA CAR; an anti-CD22 CAR; an anti-CD19 CAR and an anti-BCMA CAR; an anti-CD19CAR and an anti-CD22CAR; or a combination thereof. In some embodiments, the cells expressing a TFP molecule are administered in combination with an agent that ameliorates one or more side effects associated with administration of a cell expressing a TFP molecule. In some embodiments, the cells expressing a TFP molecule are administered in combination with a second therapeutic agent. In some embodiments, the cells expressing a TFP molecule are administered in combination with an agent that treats the disease associated with ROR1. In some embodiments, the cells expressing a TFP molecule are administered in combination with an agent that treats the disease associated with an anti-NKG2D receptor. In some embodiments, the cells expressing the first TFP molecule and a second TFP molecule are administered in combination with an agent that ameliorates one or more side effects associated with administration of a cell expressing the first TFP molecule and the second TFP molecule. In some embodiments, the cells expressing the first TFP molecule and a second TFP molecule are administered in combination with an agent that treats the disease associated with CD19, BCMA, or CD22.

In some aspects, provided herein is an isolated nucleic acid molecule described herein, a polypeptide molecule described herein, a cell expressing a polypeptide molecule described herein, a TFP molecule described herein, a nucleic acid described herein, a vector described herein, or a cell described herein, for use as a medicament.

In some aspects, provided herein is an isolated nucleic acid molecule described herein, for use as a medicament.

In some aspects, provided herein is a method of treating a mammal having a disease associated with expression of ROR1 comprising administering to the mammal an effective amount of an isolated nucleic acid molecule described herein, a polypeptide molecule described herein, a cell expressing a polypeptide molecule described herein, a TFP molecule described herein, a nucleic acid described herein, a vector described herein, or a cell described herein, wherein less cytokines are released in the mammal compared a mammal administered an effective amount of a T cell expressing an anti-ROR1 chimeric antigen receptor (CAR).

In some aspects, provided herein is a method of treating a mammal having a disease associated with expression of an anti-NKG2D receptor comprising administering to the mammal an effective amount of an isolated nucleic acid molecule described herein, a polypeptide molecule described herein, a cell expressing a polypeptide molecule described herein, a TFP molecule described herein, a nucleic acid described herein, a vector described herein, or a cell described herein, wherein less cytokines are released in the mammal compared a mammal administered an effective amount of a T-cell expressing a chimeric antigen receptor (CAR) having the antigen domain comprising the ligand NKG2D.

In some aspects, provided herein is a method of treating a mammal having a disease associated with expression of CD19, BCMA, or CD22 comprising administering to the mammal an effective amount of an isolated nucleic acid molecule described herein, a polypeptide molecule described herein, a cell expressing a polypeptide molecule described herein, a TFP molecule described herein, a nucleic acid described herein, a vector described herein, or a cell described herein, wherein less cytokines are released in the mammal compared to a mammal administered an effective amount of a T-cell expressing: an anti-CD19 chimeric antigen receptor (CAR); an anti-BCMA CAR; an anti-CD22 CAR; an anti-CD19 CAR and an anti-BCMA CAR; an anti-CD19CAR and an anti-CD22CAR; or a combination thereof.

In some aspects, provided herein is an isolated recombinant nucleic acid molecule encoding a first T-cell receptor (TCR) fusion protein (TFP) comprising: a TCR subunit comprising at least a portion of a TCR extracellular domain, and a TCR intracellular domain comprising a stimulatory domain from an intracellular signaling domain of CD3 epsilon; and a first human or humanized antibody domain comprising a first antigen binding domain; and a second T-cell receptor (TCR) fusion protein (TFP) comprising a TCR subunit comprising at least a portion of a TCR extracellular domain, and a second human or humanized antibody domain comprising a second antigen binding domain; wherein the TCR subunit of the first TFP and the first antibody domain are operatively linked and the TCR subunit of the second TFP and the second antibody domain are operatively linked, and wherein the first TFP and the second TFP incorporate into a TCR when expressed in a T-cell.

In some aspects, provided herein is an isolated recombinant nucleic acid molecule encoding a first T-cell receptor (TCR) fusion protein (TFP) comprising: a TCR subunit comprising at least a portion of a TCR extracellular domain, and a TCR intracellular domain comprising a stimulatory domain from an intracellular signaling domain of CD3 gamma; and a first human or humanized antibody domain comprising a first antigen binding domain; and a second T-cell receptor (TCR) fusion protein (TFP) comprising a TCR subunit comprising at least a portion of a TCR extracellular domain, and a second human or humanized antibody domain comprising a second antigen binding domain; wherein the TCR subunit of the first TFP and the first antibody domain are operatively linked and the TCR subunit of the second TFP and the second antibody domain are operatively linked, and wherein the first TFP and the second TFP incorporate into a TCR when expressed in a T-cell.

In some aspects, provided herein is an isolated recombinant nucleic acid molecule encoding a first T-cell receptor (TCR) fusion protein (TFP) comprising: a TCR subunit comprising at least a portion of a TCR extracellular domain, and a TCR intracellular domain comprising a stimulatory domain from an intracellular signaling domain of CD3 delta; and a first human or humanized antibody domain comprising a first antigen binding domain; and a second T-cell receptor (TCR) fusion protein (TFP) comprising a TCR subunit comprising at least a portion of a TCR extracellular domain, and a second human or humanized antibody domain comprising a second antigen binding domain; wherein the TCR subunit of the first TFP and the first antibody domain are operatively linked and the TCR subunit of the second TFP and the second antibody domain are operatively linked, and wherein the first TFP and the second TFP incorporate into a TCR when expressed in a T-cell.

In some aspects, provided herein is an isolated recombinant nucleic acid molecule encoding a first T-cell receptor (TCR) fusion protein (TFP) comprising: a TCR subunit comprising at least a portion of a TCR extracellular domain, and a TCR intracellular domain comprising a stimulatory domain from an intracellular signaling domain of TCR alpha; and a first human or humanized antibody domain comprising a first antigen binding domain; and a second T-cell receptor (TCR) fusion protein (TFP) comprising a TCR subunit comprising at least a portion of a TCR extracellular domain, and a second human or humanized antibody domain comprising a second antigen binding domain; wherein the TCR subunit of the first TFP and the first antibody domain are operatively linked and the TCR subunit of the second TFP and the second antibody domain are operatively linked, and wherein the first TFP and the second TFP incorporate into a TCR when expressed in a T-cell.

In some aspects, provided herein is an isolated recombinant nucleic acid molecule encoding a first T-cell receptor (TCR) fusion protein (TFP) comprising: a TCR subunit comprising at least a portion of a TCR extracellular domain, and a TCR intracellular domain comprising a stimulatory domain from an intracellular signaling domain of TCR beta; and a first human or humanized antibody domain comprising a first antigen binding domain; and a second T-cell receptor (TCR) fusion protein (TFP) comprising a TCR subunit comprising at least a portion of a TCR extracellular domain, and a second human or humanized antibody domain comprising a second antigen binding domain; wherein the TCR subunit of the first TFP and the first antibody domain are operatively linked and the TCR subunit of the second TFP and the second antibody domain are operatively linked, and wherein the first TFP and the second TFP incorporate into a TCR when expressed in a T-cell.

In some embodiments, the TCR subunit of the second TFP further comprises a TCR intracellular domain comprising a stimulatory domain from an intracellular signaling domain or a functional fragment thereof a selected from the group consisting of a TCR alpha, a TCR beta, a CD3 epsilon, a CD3 gamma, and a CD3 delta. In some embodiments, the first antigen binding domain or the second antigen binding domain is an anti-CD19 binding domain. In some embodiments, the first antigen binding domain or the second antigen binding domain is an anti-B-cell maturation antigen (BCMA) binding domain. In some embodiments, the first antigen binding domain or the second antigen binding domain is an anti-CD22 binding domain.

In some aspects, provided herein is an isolated recombinant nucleic acid molecule encoding: a first T-cell receptor (TCR) fusion protein (TFP) comprising a TCR subunit, a first human or humanized antibody domain comprising a first antigen binding domain that is an anti-CD19 binding domain; and a second T-cell receptor (TCR) fusion protein (TFP) comprising a TCR subunit, a second human or humanized antibody domain comprising a second antigen binding domain that is an anti-BCMA binding domain.

In some aspects, provided herein is an isolated recombinant nucleic acid molecule encoding: a first T-cell receptor (TCR) fusion protein (TFP) comprising a TCR subunit, a first human or humanized antibody domain comprising a first antigen binding domain that is an anti-CD19 binding domain; and a second T-cell receptor (TCR) fusion protein (TFP) comprising a TCR subunit, a second human or humanized antibody domain comprising a second antigen binding domain that is an anti-CD22 binding domain.

In some embodiments, the TCR subunit of the first TFP and the first antibody domain are operatively linked and the TCR subunit of the second TFP and the second antibody domain are operatively linked. In some embodiments, the first TFP, the second TFP, or both incorporate into a TCR when expressed in a T-cell. In some embodiments, the encoded first antigen binding domain is connected to the TCR extracellular domain of the first TFP by a first linker sequence, the encoded second antigen binding domain is connected to the TCR extracellular domain of the second TFP by a second linker sequence, or both the first antigen binding domain is connected to the TCR extracellular domain of the first TFP by the first linker sequence and the encoded second antigen binding domain is connected to the TCR extracellular domain of the second TFP by the second linker sequence. In some embodiments, the first linker sequence and the second linker sequence comprise (G4S)n, wherein n=1 to 4. In some embodiments, the TCR subunit of the first TFP, the TCR subunit of the second TFP, or both comprise a TCR extracellular domain. In some embodiments, the TCR subunit of the first TFP, the TCR subunit of the second TFP, or both comprise a TCR transmembrane domain. In some embodiments, the TCR subunit of the first TFP, the TCR subunit of the second TFP, or both comprise a TCR intracellular domain. In some embodiments, the TCR subunit of the first TFP, the TCR subunit of the second TFP, or both comprise (i) a TCR extracellular domain, (ii) a TCR transmembrane domain, and (iii) a TCR intracellular domain, wherein at least two of (i), (ii), and (iii) are from the same TCR subunit. In some embodiments, the TCR subunit of the first TFP, the TCR subunit of the second TFP, or both comprise a TCR intracellular domain comprising a stimulatory domain selected from an intracellular signaling domain of CD3 epsilon, CD3 gamma or CD3 delta, or an amino acid sequence having at least one modification thereto. In some embodiments, the TCR subunit of the first TFP, the TCR subunit of the second TFP, or both comprise an intracellular domain comprising a stimulatory domain selected from a functional signaling domain of 4-1BB and/or a functional signaling domain of CD3 zeta, or an amino acid sequence having at least one modification thereto. In some embodiments, the first human or humanized antibody domain, the second human or humanized antibody domain, or both comprise an antibody fragment. In some embodiments, the first human or humanized antibody domain, the second human or humanized antibody domain, or both comprise a scFv or a VH domain.

In some embodiments, the isolated nucleic acid molecule encodes (i) a light chain (LC) CDR1, LC CDR2 and LC CDR3 of an anti-CD19 light chain binding domain amino acid sequence with 70-100% sequence identity to SEQ ID NO: 25, SEQ ID NO: 27 and SEQ ID NO: 29, respectively, and/or (ii) a heavy chain (HC) CDR1, HC CDR2 and HC CDR3 of an anti-CD19 heavy chain binding domain amino acid sequence with 70-100% sequence identity to SEQ ID NO: 31, SEQ ID NO: 33 and SEQ ID NO: 35, respectively. In some embodiments, the isolated nucleic acid molecule encodes a light chain variable region, wherein the light chain variable region comprises an amino acid sequence having at least one but not more than 30 modifications of a light chain variable region amino acid sequence of SEQ ID NO: 49, or a sequence with 95-99% identity to a light chain variable region amino acid sequence of SEQ ID NO: 49. In some embodiments, the isolated nucleic acid molecule encodes a heavy chain variable region, wherein the heavy chain variable region comprises an amino acid sequence having at least one but not more than 30 modifications of a heavy chain variable region amino acid sequence of SEQ ID NO: 51, or a sequence with 95-99% identity to a heavy chain variable region amino acid sequence of SEQ ID NO: 51. In some embodiments, the isolated nucleic acid molecule encodes (i) a light chain (LC) CDR1, LC CDR2 and LC CDR3 of an anti-BCMA light chain binding domain amino acid sequence with 70-100% sequence identity to SEQ ID NO: 37, SEQ ID NO: 39 and SEQ ID NO: 41, respectively, and/or (ii) a heavy chain (HC) CDR1, HC CDR2 and HC CDR3 of an anti-BCMA heavy chain binding domain amino acid sequence with 70-100% sequence identity to SEQ ID NO: 43, SEQ ID NO: 45 and SEQ ID NO: 47, respectively. In some embodiments, the isolated nucleic acid molecule encodes a light chain variable region, wherein the light chain variable region comprises an amino acid sequence having at least one but not more than 30 modifications of a light chain variable region amino acid sequence of SEQ ID NO: 53, or a sequence with 95-99% identity to a light chain variable region amino acid sequence of SEQ ID NO: 53. In some embodiments, the isolated nucleic acid molecule encodes a heavy chain variable region, wherein the heavy chain variable region comprises an amino acid sequence having at least one but not more than 30 modifications of a heavy chain variable region amino acid sequence of SEQ ID NO: 55, or a sequence with 95-99% identity to a heavy chain variable region amino acid sequence of SEQ ID NO: 55. In some embodiments, the anti-CD22 antigen binding domain comprises a variable region as described herein or one or more CDRs as described herein.

In some embodiments, the encoded first TFP, the encoded second TFP, or both include an extracellular domain of a TCR subunit that comprises an extracellular domain or portion thereof of a protein selected from the group consisting of a TCR alpha chain, a TCR beta chain, a CD3 epsilon TCR subunit, a CD3 gamma TCR subunit, a CD3 delta TCR subunit, functional fragments thereof, and amino acid sequences thereof having at least one but not more than 20 modifications. In some embodiments, the encoded first TFP and the encoded second TFP include a transmembrane domain that comprises a transmembrane domain of a protein selected from the group consisting of a TCR alpha chain, a TCR beta chain, a CD3 epsilon TCR subunit, a CD3 gamma TCR subunit, a CD3 delta TCR subunit, functional fragments thereof, and amino acid sequences thereof having at least one but not more than 20 modifications. In some embodiments, the encoded first TFP and the encoded second TFP include a transmembrane domain that comprises a transmembrane domain of a protein selected from the group consisting of a TCR alpha chain, a TCR beta chain, a TCR zeta chain, a CD3 epsilon TCR subunit, a CD3 gamma TCR subunit, a CD3 delta TCR subunit, CD45, CD4, CD5, CD8, CD9, CD16, CD22, CD33, CD28, CD37, CD64, CD80, CD86, CD134, CD137, CD154, functional fragments thereof, and amino acid sequences thereof having at least one but not more than 20 modifications. In some embodiments, the isolated nucleic acid molecule further comprises a sequence encoding a costimulatory domain. In some embodiments, the costimulatory domain is a functional signaling domain obtained from a protein selected from the group consisting of OX40, CD2, CD27, CD28, CD5, ICAM-1, LFA-1 (CD11a/CD18), ICOS (CD278), and 4-1BB (CD137), and amino acid sequences thereof having at least one but not more than 20 modifications thereto. In some embodiments, the isolated nucleic acid molecule further comprises a sequence encoding an intracellular signaling domain. In some embodiments, the isolated nucleic acid molecule further comprises a leader sequence. In some embodiments, the isolated nucleic acid molecule further comprises a protease cleavage site. In some embodiments, the at least one but not more than 20 modifications thereto comprise a modification of an amino acid that mediates cell signaling or a modification of an amino acid that is phosphorylated in response to a ligand binding to the first TFP, the second TFP, or both. In some embodiments, the isolated nucleic acid molecule is an mRNA. In some embodiments, the first TFP, the second TFP, or both include an immunoreceptor tyrosine-based activation motif (ITAM) of a TCR subunit that comprises an ITAM or portion thereof of a protein selected from the group consisting of CD3 zeta TCR subunit, CD3 epsilon TCR subunit, CD3 gamma TCR subunit, CD3 delta TCR subunit, TCR zeta chain, Fc epsilon receptor 1 chain, Fc epsilon receptor 2 chain, Fc gamma receptor 1 chain, Fc gamma receptor 2a chain, Fc gamma receptor 2b1 chain, Fc gamma receptor 2b2 chain, Fc gamma receptor 3a chain, Fc gamma receptor 3b chain, Fc beta receptor 1 chain, TYROBP (DAP12), CD5, CD16a, CD16b, CD22, CD23, CD32, CD64, CD79a, CD79b, CD89, CD278, CD66d, functional fragments thereof, and amino acid sequences thereof having at least one but not more than 20 modifications thereto. In some embodiments, the ITAM replaces an ITAM of CD3 gamma, CD3 delta, or CD3 epsilon. In some embodiments, the ITAM is selected from the group consisting of CD3 zeta TCR subunit, CD3 epsilon TCR subunit, CD3 gamma TCR subunit, and CD3 delta TCR subunit and replaces a different ITAM selected from the group consisting of CD3 zeta TCR subunit, CD3 epsilon TCR subunit, CD3 gamma TCR subunit, and CD3 delta TCR subunit. In some embodiments, the isolated nucleic acid molecule further comprises a leader sequence.

In some aspects, provided herein is an isolated polypeptide molecule encoded by a nucleic acid molecule described herein. In some embodiments, the isolated polypeptide comprises a first polypeptide encoded by a first nucleic acid molecule and a second polypeptide encoded by a second nucleic acid molecule.

In some aspects, provided herein is an isolated recombinant TFP molecule comprising a first TFP molecule comprising a human or humanized anti-CD19 binding domain, a TCR extracellular domain, a transmembrane domain, and an intracellular domain, and a second TFP molecule comprising a human or humanized anti-BCMA binding domain, a TCR extracellular domain, a transmembrane domain, and an intracellular domain.

In some aspects, provided herein is an isolated recombinant TFP molecule comprising a first TFP molecule comprising a human or humanized anti-CD19 binding domain, a TCR extracellular domain, a transmembrane domain, and an intracellular domain, and a second TFP molecule comprising a human or humanized anti-BCMA binding domain, a TCR extracellular domain, a transmembrane domain, and an intracellular domain, wherein the first TFP molecule is capable of functionally interacting with an endogenous TCR complex and/or at least one endogenous TCR polypeptide.

In some aspects, provided herein is an isolated recombinant TFP molecule comprising a first TFP molecule comprising a human or humanized anti-CD19 binding domain, a TCR extracellular domain, a transmembrane domain, and an intracellular domain, and a second TFP molecule comprising a human or humanized anti-BCMA binding domain, a TCR extracellular domain, a transmembrane domain, and an intracellular domain, wherein the first TFP molecule is capable of functionally integrating into an endogenous TCR complex. In some embodiments, the isolated recombinant TFP molecule comprises an antibody or antibody fragment comprising a human or humanized anti-CD19 binding domain, a humanized anti-BCMA binding domain, a TCR extracellular domain, a transmembrane domain, and an intracellular domain.

In some aspects, provided herein is an isolated recombinant TFP molecule comprising a first TFP molecule comprising a human or humanized anti-CD19 binding domain, a TCR extracellular domain, a transmembrane domain, and an intracellular domain, and a second TFP molecule comprising a human or humanized anti-CD22 binding domain, a TCR extracellular domain, a transmembrane domain, and an intracellular domain.

In some aspects, provided herein is an isolated recombinant first TFP molecule comprising a human or humanized anti-CD19 binding domain, a humanized anti-CD22 binding domain, a TCR extracellular domain, a transmembrane domain, and an intracellular signaling domain, wherein the first TFP molecule is capable of functionally interacting with an endogenous TCR complex and/or at least one endogenous TCR polypeptide.

In some aspects, provided herein is an isolated recombinant first TFP molecule comprising a human or humanized anti-CD19 binding domain, a humanized anti-CD22 binding domain, a TCR extracellular domain, a transmembrane domain, and an intracellular signaling domain, wherein the first TFP molecule is capable of functionally integrating into an endogenous TCR complex.

In some embodiments, the isolated recombinant TFP molecule comprises an antibody or antibody fragment comprising a human or humanized anti-CD19 binding domain, a humanized anti-CD22 binding domain, a TCR extracellular domain, a transmembrane domain, and an intracellular domain.

In some embodiments, the anti-CD19 binding domain, the anti-BCMA binding domain, the anti-CD22 binding domain, or a combination thereof are a scFv or a VH domain. In some embodiments, the anti-CD19 binding domain comprises a heavy chain with 95-100% identity to an amino acid sequence of SEQ ID NO: 51, a functional fragment thereof, or an amino acid sequence thereof having at least one but not more than 30 modifications. In some embodiments, the anti-CD19 binding domain comprises a light chain with 95-100% identity to an amino acid sequence of SEQ ID NO: 49, a functional fragment thereof, or an amino acid sequence thereof having at least one but not more than 30 modifications. In some embodiments, the anti-BCMA binding domain comprises a heavy chain with 95-100% identity to an amino acid sequence of SEQ ID NO: 55, a functional fragment thereof, or an amino acid sequence thereof having at least one but not more than 30 modifications. In some embodiments, the anti-BCMA binding domain comprises a light chain with 95-100% identity to an amino acid sequence of SEQ ID NO: 53, a functional fragment thereof, or an amino acid sequence thereof having at least one but not more than 30 modifications. In some embodiments, the anti-CD22 binding domain comprises a variable region as described herein or one or more CDRs as described herein. In some embodiments, the isolated recombinant TFP molecule comprises a TCR extracellular domain that comprises an extracellular domain or portion thereof of a protein selected from the group consisting of a TCR alpha chain, a TCR beta chain, a CD3 epsilon TCR subunit, a CD3 gamma TCR subunit, a CD3 delta TCR subunit, functional fragments thereof, and amino acid sequences thereof having at least one but not more than 20 modifications. In some embodiments, the anti-CD19 binding domain is connected to the TCR extracellular domain of the first TFP molecule by a first linker sequence and the anti-BCMA binding domain is connected to the TCR extracellular domain of the first TFP molecule by a second linker sequence. In some embodiments, the anti-CD19 binding domain is connected to the TCR extracellular domain of the first TFP molecule by a first linker sequence and the anti-CD22 binding domain is connected to the TCR extracellular domain of the first TFP molecule by a second linker sequence. In some embodiments, the first linker sequence and the second linker sequence comprise (G4S)n, wherein n=1 to 4. In some embodiments, the isolated recombinant TFP molecule further comprises a costimulatory domain. In some embodiments, an isolated recombinant TFP molecule described herein, further comprises an intracellular signaling domain. In some embodiments, an isolated recombinant TFP molecule described herein, further comprises a leader sequence. In some aspects, provided herein is a nucleic acid comprising a sequence encoding an isolated recombinant TFP described herein. In some embodiments, the nucleic acid comprises a first nucleic acid encoding the first TFP molecule and a second nucleic acid encoding the second TFP molecule. In some embodiments, the nucleic acid is selected from the group consisting of a DNA and an RNA. In some embodiments, the nucleic acid is an mRNA. In some embodiments, the nucleic acid described herein, further comprises a promoter. In some embodiments, the nucleic acid is an in vitro transcribed nucleic acid. In some embodiments, the nucleic acid further comprises a sequence encoding a poly(A) tail. In some embodiments, the nucleic acid further comprises a 3' UTR sequence. In some embodiments, the nucleic acid further comprises a sequencing encoding a protease cleavage site.

In some aspects, provided herein is a vector comprising a nucleic acid molecule encoding an isolated recombinant TFP molecule described herein.

In some embodiments, the vector comprises a) a first vector comprising a first nucleic acid molecule encoding the first TFP; and b) a second vector comprising a second nucleic acid molecule encoding the second TFP. In some embodiments, the vector is selected from the group consisting of a DNA, an RNA, a plasmid, a lentivirus vector, adenoviral vector, a Rous sarcoma viral (RSV) vector, or a retrovirus vector. In some embodiments, the vector described herein, further comprises a promoter. In some embodiments, the vector is an in vitro transcribed vector. In some embodiments, the nucleic acid molecule in the vector further encodes a poly(A) tail. In some embodiments, the nucleic acid molecule in the vector further encodes a 3' UTR. In some embodiments, the nucleic acid molecule in the vector further encodes a protease cleavage site.

In some aspects, provided herein is a cell comprising ab isolated nucleic acid molecule described herein, a polypeptide molecule described herein, an isolated recombinant TFP molecule described herein, a nucleic acid described herein, or a vector described herein.

In some embodiments, the cell is a human T-cell. In some embodiments, the T-cell is a $CD8^+$ or $CD4^+$ T-cell. In some embodiments, a cell described herein further comprises a nucleic acid encoding an inhibitory molecule that comprises a first polypeptide that comprises at least a portion of an inhibitory molecule, associated with a second polypeptide that comprises a positive signal from an intracellular signaling domain. In some embodiments, the inhibitory molecule comprises a first polypeptide that comprises at least a portion of PD1 and a second polypeptide comprising a costimulatory domain and primary signaling domain.

In some aspects, provided herein is a human $CD8^+$ or $CD4^+$ T-cell comprising an isolated recombinant TFP molecule, the isolated recombinant TFP molecule comprising a first TFP molecule comprising a human or humanized anti-CD19 binding domain, a TCR extracellular domain, a transmembrane domain, and an intracellular domain, and second TFP molecule comprising a human or humanized anti-BCMA binding domain, a TCR extracellular domain, a transmembrane domain, and an intracellular domain, wherein the TFP molecule is capable of functionally interacting with an endogenous TCR complex and/or at least one endogenous TCR polypeptide in, at and/or on the surface of the human $CD8^+$ or $CD4^+$ T-cell.

In some aspects, provided herein is a human $CD8^+$ or $CD4^+$ T-cell comprising an isolated recombinant TFP molecule, the isolated recombinant TFP molecule comprising a first TFP molecule comprising a human or humanized anti-CD19 binding domain, a TCR extracellular domain, a transmembrane domain, and an intracellular domain, and second TFP molecule comprising a human or humanized anti-CD22 binding domain, a TCR extracellular domain, a transmembrane domain, and an intracellular domain, wherein the TFP molecule is capable of functionally interacting with an endogenous TCR complex and/or at least one endogenous TCR polypeptide in, at and/or on the surface of the human $CD8^+$ or $CD4^+$ T-cell.

In some aspects, provided herein is a protein complex comprising: a first TFP molecule comprising a human or humanized CD19 binding domain, a TCR extracellular domain, a transmembrane domain, and an intracellular domain; a second TFP molecule comprising a human or humanized anti-BCMA binding domain, a TCR extracellular domain, a transmembrane domain, and an intracellular domain; and at least one endogenous TCR subunit or endogenous TCR complex.

In some aspects, provided herein is a protein complex comprising: a first TFP molecule comprising a human or humanized CD19 binding domain, a TCR extracellular domain, a transmembrane domain, and an intracellular domain; a second TFP molecule comprising a human or humanized anti-CD22 binding domain, a TCR extracellular domain, a transmembrane domain, and an intracellular domain; and at least one endogenous TCR subunit or endogenous TCR complex.

In some embodiments, the TFP comprises an extracellular domain or portion thereof of a protein selected from the group consisting of TCR alpha chain, a TCR beta chain, a CD3 epsilon TCR subunit, a CD3 gamma TCR subunit, and a CD3 delta TCR subunit. In some embodiments, the human or humanized anti-CD19 binding domain is connected to the TCR extracellular domain of the first TFP molecule by a first linker sequence and the human or humanized anti-BCMA binding domain is connected to the TCR extracellular domain of the second TFP molecule by a second linker sequence. In some embodiments, the human or humanized anti-CD19 binding domain is connected to the TCR extracellular domain of the first TFP molecule by a first linker sequence and the human or humanized anti-CD20 binding domain is connected to the TCR extracellular domain of the second TFP molecule by a second linker sequence. In some embodiments, the first linker sequence and the second linker sequence comprise (G4S)n, wherein n=1 to 4.

In some aspects, provided herein is a protein complex comprising a first TFP and a second TFP encoded by the isolated nucleic acid molecule described herein, and at least one endogenous TCR subunit or endogenous TCR complex.

In some aspects, provided herein is a human $CD8^+$ or $CD4^+$ T-cell comprising the first TFP molecule and the second TFP molecule per the protein complex described herein.

In some aspects, provided herein is a human $CD8^+$ or $CD4^+$ T-cell comprising the first TFP molecule and the second TFP molecule encoded by an isolated nucleic acid molecule described herein.

In some aspects, provided herein is a population of human $CD8^+$ or $CD4^+$ T-cells, wherein the T-cells of the population individually or collectively comprise a first TFP molecule and a second TFP molecule, the first TFP molecule comprising a human or humanized anti-CD19 binding domain, a TCR extracellular domain, a transmembrane domain, and an intracellular domain and the second TFP molecule comprising a human or humanized anti-BCMA binding domain, a TCR extracellular domain, a transmembrane domain, and an intracellular domain, wherein the first TFP molecule and the second TFP molecule are capable of functionally interacting with an endogenous TCR complex and/or at least one endogenous TCR polypeptide in, at and/or on the surface of the human $CD8^+$ or $CD4^+$ T-cell.

In some aspects, provided herein is a population of human $CD8^+$ or $CD4^+$ T-cells, wherein the T-cells of the population individually or collectively comprise a first TFP molecule and a second TFP molecule, the first TFP molecule comprising a human or humanized anti-CD19 binding domain, a TCR extracellular domain, a transmembrane domain, and an intracellular domain and the second TFP molecule comprising a human or humanized anti-CD22 binding domain, a TCR extracellular domain, a transmembrane domain, and an intracellular domain, wherein the first TFP molecule and the second TFP molecule are capable of functionally interacting with an endogenous TCR complex and/or at least one endogenous TCR polypeptide in, at and/or on the surface of the human $CD8^+$ or $CD4^+$ T-cell.

In some aspects, provided herein is a population of human $CD8^+$ or $CD4^+$ T-cells, wherein the T-cells of the population individually or collectively comprise the first TFP molecule and the second TFP molecule encoded by the isolated nucleic acid molecule described herein.

In some aspects, provided herein is a method of making a cell comprising transducing a T-cell with an isolated nucleic acid molecule described herein, a nucleic acid described herein, or a vector described herein.

In some aspects, provided herein is a method of generating a population of RNA-engineered cells comprising introducing an in vitro transcribed RNA or synthetic RNA into a cell, where the RNA comprises a nucleic acid encoding the isolated recombinant TFP molecule described herein.

In some aspects, provided herein is a method of providing an anti-tumor immunity in a mammal comprising administering to the mammal an effective amount of an isolated nucleic acid molecule described herein, a polypeptide molecule described herein, a cell expressing a polypeptide molecule described herein, a TFP molecule described herein, a nucleic acid described herein, a vector described herein, or a cell or cell population described herein.

In some embodiments, the cell is an autologous T-cell. In some embodiments, the cell is an allogeneic T-cell. In some embodiments, the mammal is a human.

In some aspects, provided herein is a method of treating a mammal having a disease associated with expression of CD19, BCMA, or CD22 comprising administering to the mammal an effective amount of an isolated nucleic acid molecule described herein, a polypeptide molecule described herein, a cell expressing a polypeptide molecule described herein, a TFP molecule described herein, a nucleic acid described herein, a vector described herein, or a cell or cell population described herein.

In some embodiments, the disease associated with CD19, BCMA, or CD22 expression is selected from the group consisting of a proliferative disease, a cancer, a malignancy, myelodysplasia, a myelodysplastic syndrome, a preleukemia, a non-cancer related indication associated with expression of CD19, a non-cancer related indication associated with expression of BCMA, and a non-cancer related indication associated with expression of CD22. In some embodiments, the disease is a hematologic cancer selected from the group consisting of B-cell acute lymphoid leukemia (B-ALL), T-cell acute lymphoid leukemia (T-ALL), acute lymphoblastic leukemia (ALL); chronic myelogenous leukemia (CML), chronic lymphocytic leukemia (CLL), B cell prolymphocytic leukemia, blastic plasmacytoid dendritic cell neoplasm, Burkitt's lymphoma, diffuse large B cell lymphoma, follicular lymphoma, hairy cell leukemia, small cell-follicular lymphoma, large cell-follicular lymphoma, malignant lymphoproliferative conditions, MALT lymphoma, mantle cell lymphoma, Marginal zone lymphoma, multiple myeloma, myelodysplasia, myelodysplastic syndrome, non-Hodgkin's lymphoma, plasmablastic lymphoma, plasmacytoid dendritic cell neoplasm, Waldenstrom macroglobulinemia, preleukemia, a disease associated with CD19, BCMA, or CD22 expression, and combinations thereof. In some embodiments, the cells expressing a first TFP molecule and a second TFP molecule are administered in combination with an agent that increases the efficacy of a cell expressing the first TFP molecule and the second TFP molecule. In some embodiments, less cytokines are released in the mammal compared a mammal administered an effective amount of a T-cell expressing: an anti-CD19 chimeric antigen receptor (CAR); an anti-BCMA CAR; an anti-CD22 CAR; an anti-CD19 CAR and an anti-BCMA CAR; an anti-CD19 CAR and an anti-CD22 CAR; or a combination thereof. In some embodiments, the cells expressing the first TFP molecule and a second TFP molecule are administered in combination with an agent that ameliorates one or more side effects associated with administration of a cell expressing the first TFP molecule and the second TFP molecule. In some embodiments, the cells expressing the first TFP molecule and a second TFP molecule are administered in combination with an agent that treats the disease associated with CD19, BCMA, or CD22.

In some aspects, provided herein is an isolated nucleic acid molecule described herein, a polypeptide molecule described herein, a cell expressing a polypeptide molecule described herein, a TFP molecule described herein, a nucleic acid described herein, a vector described herein, or a cell or cell population described herein, for use as a medicament.

In some aspects, provided herein is a method of treating a mammal having a disease associated with expression of CD19, BCMA, or CD22 comprising administering to the mammal an effective amount of an isolated nucleic acid molecule described herein, a polypeptide molecule described herein, a cell expressing a polypeptide molecule described herein, a TFP molecule described herein, a nucleic acid described herein, a vector described herein, or a cell or cell population described herein, wherein less cytokines are released in the mammal compared to a mammal administered an effective amount of a T-cell expressing: an anti-CD19 chimeric antigen receptor (CAR); an anti-BCMA CAR; an anti-CD22 CAR; an anti-CD19 CAR and an anti-BCMA CAR; an anti-CD19CAR and an anti-CD22CAR; or a combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 2 shows surface expression of TFP T cells as measured by FACS.

FIG. 11 is two graphs showing that CD16-positive T cells were efficient in CD20-positive tumor lysis in the presence of 1 μg/ml of anti-CD20 (rituximab) and not in the presence of non-glycosylated CD20.

FIG. 14 shows NKG2D ligand expression on multiple solid tumor cell lines and in vitro tumor cell lysis by NKG2D E-TFP T cells.

FIG. 15 is a series of graphs showing in vivo efficacy of NKG2D ε-TFP T cells in mesothelin expressing tumor xenografts in NSG mice.

DETAILED DESCRIPTION

Figure 1A:
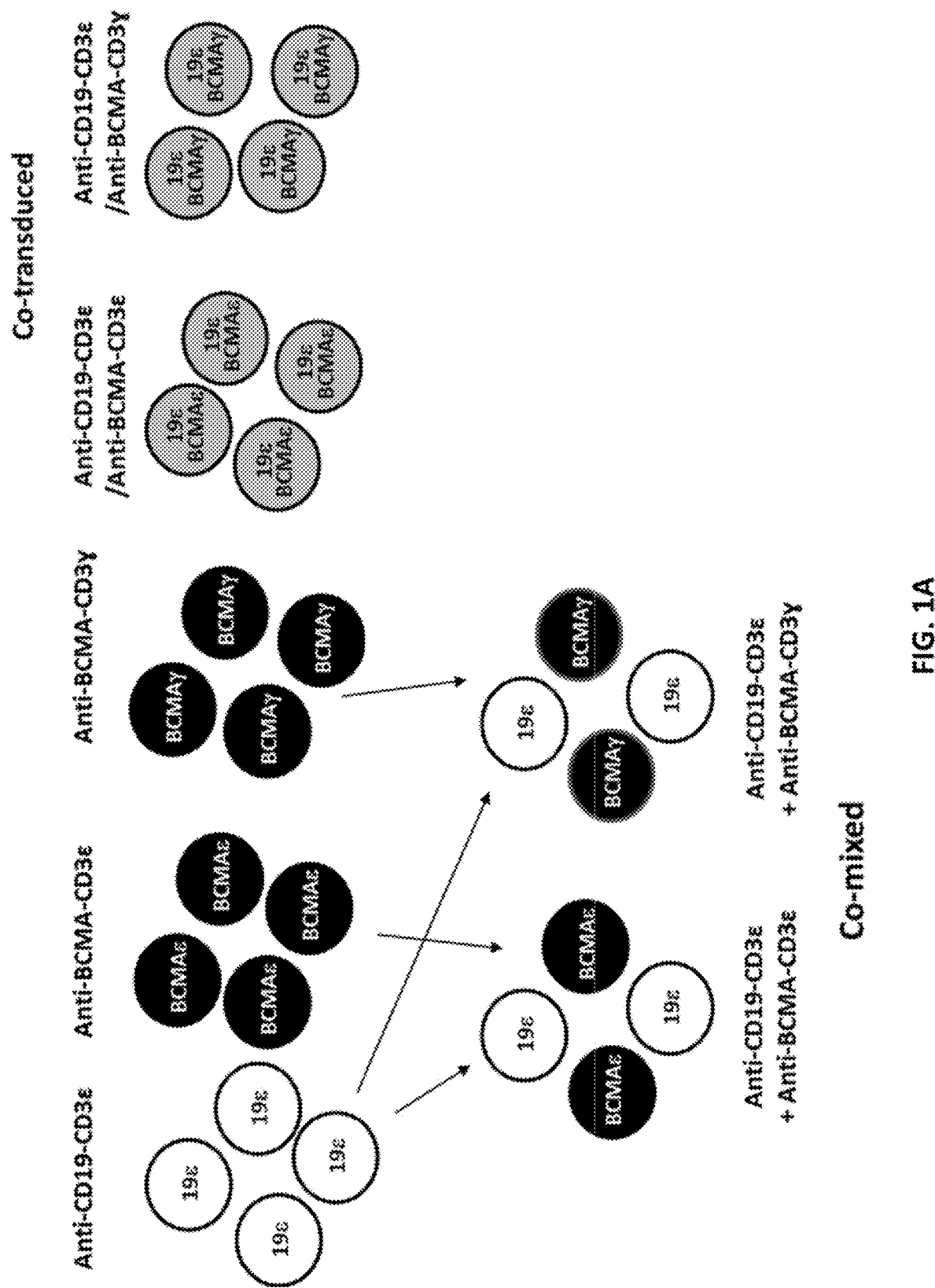
FIG. 1A is a drawing showing some of the methods of dual targeting of cancer cells disclosed herein. Tumor cell antigen targets BCMA and CD19 are exemplary antigens. The figure shows T cells as circles. White circles show examples of T cells transduced with a TFP having an anti-CD19 TFP attached to the CD3 epsilon subunit. Black circles show examples of T cells transduced with a TFP having an anti-BCMA TFP attached to the CD3 epsilon (ε) or gamma (γ) subunit. The 'black' and 'white' cells are mixed to create a T cell population that comprises both anti-BCMA TFPs and anti-CD19 TFPs. The grey cells show examples of co-transduced T cell populations that have been made by either transducing a single T cell population with two types of lentivirus (i.e., each having specificity for (i.e., an scFv) a different anti-tumor-antigen) or by transducing a single T cell population with (a) a lentivirus having the first anti-tumor-antigen scFv on one TCR subunit and a second anti-tumor antigen scFv on a second TCR subunit, or (b) a lentivirus having the first anti-tumor antigen scFv and the second anti-tumor antigen scFv operatively linked (e.g., by a G4S linker) and attached to a single TCR subunit.

Provided herein are compositions of matter and methods of use for the treatment of a disease such as cancer, using T-cell receptor (TCR) fusion proteins or T cell populations. As used herein, a "T-cell receptor (TCR) fusion protein" or "TFP" includes a recombinant polypeptide derived from the various polypeptides comprising the TCR that is generally capable of i) binding to a surface antigen on target cells and ii) interacting with other polypeptide components of the intact TCR complex, typically when co-located in or on the surface of a T-cell. As provided herein, TFPs provide substantial benefits as compared to Chimeric Antigen Receptors. The term "Chimeric Antigen Receptor," or alternatively, a "CAR," refers to a recombinant polypeptide comprising an extracellular antigen binding domain in the form of a scFv, a transmembrane domain, and cytoplasmic signaling domains (also referred to herein as "an intracellular signaling domains") comprising a functional signaling domain derived from a stimulatory molecule as defined below. Generally, the central intracellular signaling domain of a CAR is derived from the CD3 zeta chain that is normally found associated with the TCR complex. The CD3 zeta signaling domain can be fused with one or more functional signaling domains derived from at least one co-stimulatory molecule such as 4-1BB (i.e., CD137), CD27 and/or CD28.

In one aspect, described herein are isolated nucleic acid molecules encoding a T-cell Receptor (TCR) fusion protein (TFP) that comprise a TCR subunit and a human or humanized antibody domain comprising an anti-tumor antigen binding domain, such as anti-BCMA, anti-CD19, anti CD20, anti-CD22, etc. In some embodiments, the TCR subunit comprises a TCR extracellular domain. In other embodiments, the TCR subunit comprises a TCR transmembrane domain. In yet other embodiments, the TCR subunit comprises a TCR intracellular domain. In further embodiments, the TCR subunit comprises (i) a TCR extracellular domain, (ii) a TCR transmembrane domain, and (iii) a TCR intracellular domain, wherein at least two of (i), (ii), and (iii) are from the same TCR subunit. In yet further embodiments, the TCR subunit comprises a TCR intracellular domain comprising a stimulatory domain selected from an intracellular signaling domain of CD3 epsilon, CD3 gamma or CD3 delta, or an amino acid sequence having at least one, two or three modifications thereto. In yet further embodiments, the TCR subunit comprises an intracellular domain comprising a stimulatory domain selected from a functional signaling domain of 4-1BB and/or a functional signaling domain of CD3 zeta, or an amino acid sequence having at least one, two or three modifications thereto.

In some embodiments, the human or humanized antibody domain comprises an antibody fragment. In some embodiments, the human or humanized antibody domain comprises a scFv or a $V_H$ domain.

In some embodiments, the isolated nucleic acid molecules comprise (i) a light chain (LC) CDR1, LC CDR2 and LC CDR3 of any anti-tumor-associated antigen light chain binding domain amino acid sequence provided herein, and/or (ii) a heavy chain (HC) CDR1, HC CDR2 and HC CDR3 of any anti-tumor-associated antigen heavy chain binding domain amino acid sequence provided herein.

In some embodiments, the light chain variable region comprises an amino acid sequence having at least one, two or three modifications but not more than 30, 20 or 10 modifications of an amino acid sequence of a light chain variable region provided herein, or a sequence with 95-99% identity to an amino acid sequence provided herein. In other embodiments, the heavy chain variable region comprises an amino acid sequence having at least one, two or three modifications but not more than 30, 20 or 10 modifications of an amino acid sequence of a heavy chain variable region provided herein, or a sequence with 95-99% identity to an amino acid sequence provided herein.

In some embodiments, the TFP includes an extracellular domain of a TCR subunit that comprises an extracellular domain or portion thereof of a protein selected from the group consisting of the alpha or beta chain of the T-cell receptor, CD3 delta, CD3 epsilon, or CD3 gamma, or a functional fragment thereof, or an amino acid sequence having at least one, two or three modifications but not more than 20, 10 or 5 modifications thereto. In other embodiments, the encoded TFP includes a transmembrane domain that comprises a transmembrane domain of a protein selected from the group consisting of the alpha, beta chain of the TCR or TCR subunits CD3 epsilon, CD3 gamma and CD3 delta, or a functional fragment thereof, or an amino acid sequence having at least one, two or three modifications but not more than 20, 10 or 5 modifications thereto.

In some embodiments, the encoded TFP includes a transmembrane domain that comprises a transmembrane domain of a protein selected from the group consisting of a TCR alpha chain, a TCR beta chain, a TCR zeta chain, a CD3 epsilon TCR subunit, a CD3 gamma TCR subunit, a CD3 delta TCR subunit, CD45, CD2, CD4, CD5, CD8, CD9, CD16, CD22, CD33, CD28, CD37, CD64, CD80, CD86, CD134, CD137 and CD154, functional fragment(s) thereof, and amino acid sequences thereof having at least one, two or three modifications but not more than 20 modifications thereto.

In some instances, the isolated nucleic acid molecule further comprises a sequence encoding a costimulatory domain. In some instances, the costimulatory domain is a functional signaling domain obtained from a protein selected from the group consisting of DAP10, DAP12, CD30, LIGHT, OX40, CD2, CD27, CD28, CDS, ICAM-1, LFA-1 (CD11a/CD18), ICOS (CD278), and 4-1BB (CD137), and amino acid sequences thereof having at least one but not more than 20 modifications thereto. In some instances, the isolated nucleic acid molecule further comprises a leader sequence. In some instances, the isolated nucleic acid molecule is mRNA.

In some instances, the TFP includes an immunoreceptor tyrosine-based activation motif (ITAM) of a TCR subunit that comprises an ITAM or portion thereof of a protein selected from the group consisting of CD3 zeta TCR subunit, CD3 epsilon TCR subunit, CD3 gamma TCR subunit, CD3 delta TCR subunit, TCR zeta chain, Fc epsilon receptor 1 chain, Fc epsilon receptor 2 chain, Fc gamma receptor 1 chain, Fc gamma receptor 2a chain, Fc gamma receptor 2b1 chain, Fc gamma receptor 2b2 chain, Fc gamma receptor 3a chain, Fc gamma receptor 3b chain, Fc beta receptor 1 chain, TYROBP (DAP12), CD5, CD16a, CD16b, CD22, CD23, CD32, CD64, CD79a, CD79b, CD89, CD278, CD66d, functional fragments thereof, and amino acid sequences thereof having at least one but not more than 20 modifications thereto. In some instances, the ITAM replaces an ITAM of CD3 gamma, CD3 delta, or CD3 epsilon. In some instances, the ITAM is selected from the group consisting of CD3 zeta TCR subunit, CD3 epsilon TCR subunit, CD3 gamma TCR subunit, and CD3 delta TCR subunit and replaces a different ITAM selected from the group consisting of CD3 zeta TCR subunit, CD3 epsilon TCR subunit, CD3 gamma TCR subunit, and CD3 delta TCR subunit.

In some instances, the nucleic acid comprises a nucleotide analog. In some instances, the nucleotide analog is selected from the group consisting of 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2'-O-NMA) modified, a locked nucleic acid (LNA), an ethylene nucleic acid (ENA), a peptide nucleic acid (PNA), a 1',5'-anhydrohexitol nucleic acid (HNA), a morpholino, a methylphosphonate nucleotide, a thiolphosphonate nucleotide, and a 2'-fluoro N3-P5'-phosphoramidite.

In some embodiments, the encoded anti-tumor-associated antigen binding domain is connected to the TCR extracellular domain by a linker sequence. In some instances, the encoded linker sequence comprises $(G_4S)_n$, wherein n=1 to 4. In some instances, the encoded linker sequence comprises a long linker (LL) sequence. In some instances, the encoded long linker sequence comprises $(G_4S)_n$, wherein n=2 to 4. In some instances, the encoded linker sequence comprises a short linker (SL) sequence. In some instances, the encoded short linker sequence comprises $(G_4S)_n$, wherein n=1 to 3.

In some embodiments, the isolated nucleic acid molecules further comprise a leader sequence.

Also provided herein are isolated polypeptide molecules encoded by any of the previously described nucleic acid molecules.

Also provided herein in another aspect, are isolated T-cell receptor fusion protein (TFP) molecules that comprise a human or humanized anti-tumor-associated antigen binding domain, a TCR extracellular domain, a transmembrane domain, and an intracellular domain. In some embodiments, the isolated TFP molecules comprises an antibody or antibody fragment comprising a human or humanized anti-tumor-associated antigen binding domain, a TCR extracellular domain, a transmembrane domain, and an intracellular domain.

In some embodiments, the anti-tumor-associated antigen binding domain is a scFv or a $V_H$ domain. In other embodiments, the anti-tumor-associated antigen binding domain comprises a light chain and a heavy chain of an amino acid sequence provided herein, or a functional fragment thereof, or an amino acid sequence having at least one, two or three modifications but not more than 30, 20 or 10 modifications of an amino acid sequence of a light chain variable region provided herein, or a sequence with 95-99% identity with an amino acid sequence provided herein. In some embodiments, the isolated TFP molecules comprise a TCR extracellular domain that comprises an extracellular domain or portion thereof of a protein selected from the group consisting of the alpha or beta chain of the T-cell receptor, CD3 delta, CD3 epsilon, or CD3 gamma, or an amino acid sequence having at least one, two or three modifications but not more than 20, 10 or 5 modifications thereto.

In some embodiments, the anti-tumor-associated antigen binding domain is connected to the TCR extracellular domain by a linker sequence. In some instances, the linker region comprises $(G_4S)_n$, wherein n=1 to 4. In some instances, the linker sequence comprises a long linker (LL) sequence. In some instances, the long linker sequence comprises $(G_4S)_n$, wherein n=2 to 4. In some instances, the linker sequence comprises a short linker (SL) sequence. In some instances, the short linker sequence comprises $(G_4S)_n$, wherein n=1 to 3.

In some embodiments, the isolated TFP molecules further comprise a sequence encoding a costimulatory domain. In other embodiments, the isolated TFP molecules further comprise a sequence encoding an intracellular signaling domain. In yet other embodiments, the isolated TFP molecules further comprise a leader sequence.

Also provided herein are vectors that comprise a nucleic acid molecule encoding any of the previously described TFP molecules. In some embodiments, the vector is selected from the group consisting of a DNA, an RNA, a plasmid, a lentivirus vector, adenoviral vector, or a retrovirus vector. In some embodiments, the vector further comprises a promoter. In some embodiments, the vector is an in vitro transcribed vector. In some embodiments, a nucleic acid sequence in the vector further comprises a poly(A) tail. In some embodiments, a nucleic acid sequence in the vector further comprises a 3′UTR.

Also provided herein are cells that comprise any of the described vectors. In some embodiments, the cell is a human T-cell. In some embodiments, the cell is a CD8$^+$ or CD4$^+$ T-cell. In one embodiment, the CD8$^+$ cell is a gamma-delta T cells. In another embodiment, the CD8$^+$ cell is an NK-T cell. In other embodiments, the cells further comprise a nucleic acid encoding an inhibitory molecule that comprises a first polypeptide that comprises at least a portion of an inhibitory molecule, associated with a second polypeptide that comprises a positive signal from an intracellular signaling domain. In some instances, the inhibitory molecule comprises a first polypeptide that comprises at least a portion of PD1 and a second polypeptide comprising a costimulatory domain and primary signaling domain.

In another aspect, provided herein are isolated TFP molecules that comprise a human or humanized anti-tumor-associated antigen (TAA) binding domain, a TCR extracellular domain, a transmembrane domain, and an intracellular signaling domain, wherein the TFP molecule is capable of functionally interacting with an endogenous TCR complex and/or at least one endogenous TCR polypeptide.

In another aspect, provided herein are isolated TFP molecules that comprise a human or humanized anti-TAA binding domain, a TCR extracellular domain, a transmembrane domain, and an intracellular signaling domain, wherein the TFP molecule is capable of functionally integrating into an endogenous TCR complex.

In another aspect, provided herein are human CD8$^+$ or CD4$^+$ T cells that comprise one or more TFP molecules, the TFP molecules comprising a human or humanized anti-tumor-associated antigen binding domain, a TCR extracellular domain, a transmembrane domain, and an intracellular domain, wherein the TFP molecule is capable of functionally interacting with an endogenous TCR complex and/or at least one endogenous TCR polypeptide in, at and/or on the surface of the human CD8$^+$ or CD4$^+$ T-cell. In another aspect, the cells comprise at least two non-identical TFP molecules.

In another aspect, provided herein are protein complexes that comprise i) a TFP molecule comprising a human or humanized anti-tumor-associated antigen binding domain, a TCR extracellular domain, a transmembrane domain, and an intracellular domain; and ii) at least one endogenous TCR complex.

In some embodiments, the TCR comprises an extracellular domain or portion thereof of a protein selected from the group consisting of the alpha or beta chain of the T-cell receptor, CD3 delta, CD3 epsilon, or CD3 gamma. In some embodiments, the anti-tumor-associated antigen binding domain is connected to the TCR extracellular domain by a linker sequence. In some instances, the linker region comprises $(G_4S)_n$, wherein n=1 to 4. In some instances, the linker sequence comprises a long linker (LL) sequence. In some instances, the long linker sequence comprises $(G_4S)_n$, wherein n=2 to 4. In some instances, the linker sequence comprises a short linker (SL) sequence. In some instances, the short linker sequence comprises $(G_4S)_n$, wherein n=1 to 3.

Also provided herein are human CD8$^+$ or CD4$^+$ T cells that comprise at least two different TFP proteins per any of the described protein complexes.

In another aspect, provided herein is a population of human CD8$^+$ or CD4$^+$ T cells, wherein the T cells of the population individually or collectively comprise at least two TFP molecules, the TFP molecules comprising a human or humanized anti-tumor-associated antigen binding domain, a TCR extracellular domain, a transmembrane domain, and an intracellular domain, wherein the TFP molecule is capable of functionally interacting with an endogenous TCR complex and/or at least one endogenous TCR polypeptide in, at and/or on the surface of the human CD8$^+$ or CD4$^+$ T-cell.

In another aspect, provided herein is a population of human CD8$^+$ or CD4$^+$ T cells, wherein the T cells of the population individually or collectively comprise at least two TFP molecules encoded by an isolated nucleic acid molecule provided herein.

In another aspect, provided herein are methods of making a cell comprising transducing a T-cell with any of the described vectors.

In another aspect, provided herein are methods of generating a population of RNA-engineered cells that comprise introducing a in vitro transcribed RNA or synthetic RNA into a cell, where the RNA comprises nucleic acid encoding one or more of the described TFP molecules.

In another aspect, provided herein are methods of providing an anti-tumor immunity in a mammal that comprise administering to the mammal an effective amount of a cell expressing any of the described TFP molecules. In some embodiments, the cell is an autologous T-cell. In some embodiments, the cell is an allogeneic T-cell. In some embodiments, the mammal is a human.

In another aspect, provided herein are methods of treating a mammal having a disease associated with expression of tumor-associated antigen that comprise administering to the mammal an effective amount of the cell comprising any of the described TFP molecules. In some embodiments, the disease associated with tumor-associated antigen expression is selected from a proliferative disease such as a cancer or malignancy or a precancerous condition such as a myelodysplasia, a myelodysplastic syndrome or a preleukemia, or is a non-cancer related indication associated with expression of tumor-associated antigen.

In some embodiments, the disease is a hematologic cancer selected from the group consisting of one or more acute leukemias including but not limited to B-cell acute lymphoid leukemia ("B-ALL"), T-cell acute lymphoid leukemia ("T-ALL"), acute lymphoblastic leukemia (ALL); one or more chronic leukemias including but not limited to chronic myelogenous leukemia (CML), chronic lymphocytic leukemia (CLL); additional hematologic cancers or hematologic conditions including, but not limited to B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, smoldering multiple myeloma, solitary plasmacytoma, lymphoplasmacytic lymphoma, plasma cell leukemia, myelodysplasia and myelodysplastic syndrome, non-Hodgkin's lymphoma, plasmablastic lymphoma, plasmacytoid dendritic cell neoplasm, Waldenstrom's macroglobulinemia, and "preleukemia" which are a diverse collection of hematological conditions united by ineffective production (or dysplasia) of myeloid blood cells, and to disease associated with tumor-associated antigen expression include, but not limited to atypical and/or non-classical cancers, malignancies, precancerous conditions or proliferative diseases expressing tumor-associated antigen; and combinations thereof.

In some embodiments, the cells expressing any of the described TFP molecules are administered in combination with an agent that ameliorates one or more side effects associated with administration of a cell expressing a TFP molecule. In some embodiments, the cells expressing any of the described TFP molecules are administered in combination with an agent that treats the disease associated with tumor-associated antigen.

Also provided herein are any of the described isolated nucleic acid molecules, any of the described isolated polypeptide molecules, any of the described isolated TFPs, any of the described protein complexes, any of the described vectors or any of the described cells for use as a medicament.

Definitions

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

As used herein, "about" can mean plus or minus less than 1 or 1, 2, 3, 4, 5, 6, 7, 8, 9, 10, 11, 12, 13, 14, 15, 16, 17, 18, 19, 20, 25, 30, or greater than 30 percent, depending upon the situation and known or knowable by one skilled in the art. The term "about" or "approximately" can mean within an acceptable error range for the particular value as determined by one of ordinary skill in the art, which will depend in part on how the value is measured or determined, i.e. the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term "about" or "approximately" can mean within an order of magnitude, within 5-fold, and more preferably within 2-fold, of a value. Where particular values are described in the application and claims, unless otherwise stated the term "about" meaning within an acceptable error range for the particular value should be assumed. The term "about" can have the meaning as commonly understood by one of ordinary skill in the art. The term "about" can refer to ±10%. The term "about" can refer to ±5%.

As used herein the specification, "subject" or "subjects" or "individuals" may include, but are not limited to, mammals such as humans or non-human mammals, e.g., domesticated, agricultural or wild, animals, as well as birds, and aquatic animals. "Patients" are subjects suffering from or at risk of developing a disease, disorder or condition or otherwise in need of the compositions and methods provided herein.

As used herein, "treating" or "treatment" refers to any indicia of success in the treatment or amelioration of the disease or condition. Treating can include, for example, reducing, delaying or alleviating the severity of one or more symptoms of the disease or condition, or it can include reducing the frequency with which symptoms of a disease, defect, disorder, or adverse condition, and the like, are experienced by a patient. As used herein, "treat or prevent" is sometimes used herein to refer to a method that results in some level of treatment or amelioration of the disease or condition, and contemplates a range of results directed to that end, including but not restricted to prevention of the condition entirely.

As used herein, "preventing" refers to the prevention of the disease or condition, e.g., tumor formation, in the patient. For example, if an individual at risk of developing a tumor or other form of cancer is treated with the methods of the present invention and does not later develop the tumor or other form of cancer, then the disease has been prevented, at least over a period of time, in that individual.

As used herein, a "therapeutically effective amount" is the amount of a composition or an active component thereof sufficient to provide a beneficial effect or to otherwise reduce a detrimental non-beneficial event to the individual to whom the composition is administered. By "therapeutically effective dose" herein is meant a dose that produces one or more desired or desirable (e.g., beneficial) effects for which it is administered, such administration occurring one or more times over a given period of time. The exact dose will depend on the purpose of the treatment, and will be ascertainable by one skilled in the art using known techniques (see, e.g. Lieberman, Pharmaceutical Dosage Forms (vols. 1-3, 1992); Lloyd, *The Art, Science and Technology of Pharmaceutical Compounding* (1999); and Pickar, *Dosage Calculations* (1999))

As used herein, a "T-cell receptor (TCR) fusion protein" or "TFP" includes a recombinant polypeptide derived from the various polypeptides comprising the TCR that is generally capable of i) binding to a surface antigen on target cells and ii) interacting with other polypeptide components of the intact TCR complex, typically when co-located in or on the surface of a T-cell.

As used herein, the term the term "BCMA" refers to the B-cell maturation antigen" or "BCMA" or "BCM," also known as tumor necrosis factor receptor superfamily member 17 (TNFRSF17) and Cluster of Differentiation 269 protein (CD269), or TNFRSF13A, is a protein that in humans is encoded by the TNFRSF17 gene. BCMA is a cell surface receptor of the TNF receptor superfamily which recognizes B-cell activating factor (BAFF). The receptor is preferentially expressed in mature B lymphocytes, and may be important for B cell development and autoimmune response. This receptor has been shown to specifically bind to the tumor necrosis factor (ligand) superfamily, member 13b (TNFSF13B/TALL-1/BAFF), and to lead to NF-κB and MAPK8/JNK activation. It is a non-glycosylated integral membrane receptor for the ligands BAFF and APRIL. BCMA's ligands can also bind additional receptors: TACI (Transmembrane Activator and Calcium modulator and cyclophilin ligand Interactor), which binds APRIL and BAFF; as well as BAFF-R (BAFF Receptor or BR3), which shows restricted but high affinity for BAFF. Together, these receptors and their corresponding ligands regulate different aspects of humoral immunity, B-cell development and homeostasis.

BCMA's expression is typically restricted to the B-cell lineage and is reported to increase in terminal B-cell differentiation. BCMA is expressed by human plasma blasts, plasma cells from tonsils, spleen and bone marrow, but also by tonsillar memory B cells and by germinal center B cells, which have a TACI-BAFFR low phenotype (Darce et al, 2007). BCMA is virtually absent on naive and memory B-cells (Novak et al., 2004a and b). The BCMA antigen is expressed on the cell surface so is accessible to the antibody, but is also expressed in the golgi. As suggested by its expression profile, BCMA signaling, typically linked with B-cell survival and proliferation, is important in the late stages of B-cell differentiation, as well as the survival of long lived bone marrow plasma cells (O'Connor et al., 2004) and plasmablasts (Avery et al., 2003). Furthermore, as BCMA binds APRIL with high affinity, the BCMA-APRIL signaling axis is suggested to predominate at the later stages of B-cell differentiation, perhaps being the most physiologically relevant interaction.

The human and murine amino acid and nucleic acid sequences can be found in a public database, such as GenBank, UniProt and Swiss-Prot. For example, the amino acid sequence of human BCMA can be found as UniProt/Swiss-Prot Accession No. Q02223. The human BCMA polypeptide canonical sequence is UniProt Accession No. Q02223-1:

(SEQ ID NO: 103)
MLQMAGQCSQNEYFDSLLHACIPCQLRCSSNTPPLTCQRYCNASVTNSVK

GTNAILWTCLGLSLIISLAVFVLMFLLRKINSEPLKDEFKNTGSGLLGMA

NIDLEKSRTGDEIILPRGLEYTVEECTCEDCIKSKPKVDSDHCFPLPAME

EGATILVTTKTNDYCKSLPAALSATEIEKSISAR.

The human CD19 polypeptide canonical sequence is UniProt Accession No. P15391 (or P15391-2:

(SEQ ID NO: 104)
MPPPRLLFFLLFLTPMEVRPEEPLVVKVEEGDNAVLQCLKGTSDGPTQQL

TWSRESPLKPFLKLSLGLPGLGIHMRPLAIWLFIFNVSQQMGGFYLCQPG

PPSEKAWQPGWTVNVEGSGELFRWNVSDLGGLGCGLKNRSSEGPSSPSGK

LMSPKLYVWAKDRPEIWEGEPPCLPPRDSLNQSLSQDLTMAPGSTLWLSC

GVPPDSVSRGPLSWTHVHPKGPKSLLSLELKDDRPARDMWVMETGLLLPR

ATAQDAGKYYCHRGNLTMSFHLEITARPVLWHWLLRTGGWKVSAVTLAYL

IFCLCSLVGILHLQRALVLRRKRKRMTDPTRRFFKVTPPPGSGPQNQYGN

VLSLPTPTSGLGRAQRWAAGLGGTAPSYGNPSSDVQADGALGSRSPPGVG

PEEEEGEGYEEPDSEEDSEFYENDSNLGQDQLSQDGSGYENPEDEPLGPE

DEDSFSNAESYENEDEELTQPVARTMDFLSPHGSAWDPSREATSLGSQSY

EDMRGILYAAPQLRSIRGQPGPNHEEDADSYENMDNPDGPDPAWGGGGRM

GTWSTR.

The nucleotide sequence encoding of the human CD19 can be found at Accession No. NM001178098. CD19 is expressed on most B lineage cancers, including, e.g., ALL, CLL and non-Hodgkin's lymphoma (NHL). Other cells that express CD19 are provided below in the definition of "disease associated with expression of CD19." It is also an early marker of normal B cell progenitors. See, e.g., Nicholson et al. Mol. Immun. 34 (16-17): 1157-1165 (1997). In one example, the antigen-binding portion of TFPs recognizes and binds an epitope within the extracellular domain of the CD19 protein as expressed on a malignant and normal B cell.

As used herein, the term "CD22" refers to B-cell receptor CD22, also known as B-lymphocyte cell adhesion molecule (BL-CAM), Sialic acid-binding Ig-like lectin 2 (Siglec-2), and T-cell surface antigen Leu-14. CD22 mediates B-cell-to-B-cell interactions and may be involved in the localization of B-cells in lymphoid tissues. It binds sialylated glycoproteins, one of which is CD45, and preferentially binds to alpha-2,6-linked sialic acid. The sialic acid recognition site can be masked by cis interactions with sialic acids on the same cell surface. Upon ligand-induced tyrosine phosphorylation, the immune response seems to be involved in regulation of B-cell antigen receptor signaling. CD22 plays a role in positive regulation through interaction with Src family tyrosine kinases and may also act as an inhibitory receptor by recruiting cytoplasmic phosphatases via their SH2 domains that block signal transduction through dephosphorylation of signaling molecules.

The CD22 canonical sequence is the beta isoform (one of five isoforms) and can be found at UniProt Accession Number P20273-1, and corresponds to the sequence:

(SEQ ID NO: 105)
MHLLGPWLLLLVLEYLAFSDSSKWVFEHPETLYAWEGACVWIPCTYRALD

GDLESFILFHNPEYNKNTSKFDGTRLYESTKDGKVPSEQKRVQFLGDKNK

NCTLSIHPVHLNDSGQLGLRMESKTEKWMERIELNVSERPFPPHIQLPPH

QESQEVTLTCLLNFSCYGYPIQLQWLLEGVPMRQAAVTSTSLTIKSVFTR

SELKFSPQWSHHGKIVTCQLQDADGKFLSNDTVQLNVKHTPKLEIKVTPS

DAIVREGDSVTMTCEVSSSNPEYTTVSWLKDGTSLKKQNTFTLNLREVTK

DQSGKYCCQVSNDVGPGRSEEVFLQVQYAPEPSTVQILHSPAVEGSQVEF

LCMSLANPLPTNYTWYHNGKEMQGRTEEKVHIPKILPWHAGTYSCVAENI

LGTGQRGPGAELDVQYPPKKVTTVIQNPMPIREGDTVTLSCNYNSSNPSV

TRYEWKPHGAWEEPSLGVLKIQNVGWDNTTIACAACNSWCSWASPVALNV

QYAPRDVRVRKIKPLSEIHSGNSVSLQCDFSSSHPKEVQFFWEKNGRLLG

KESQLNFDSISPEDAGSYSCWVNNSIGQTASKAWTLEVLYAPRRLRVSMS

PGDQVMEGKSATLTCESDANPPVSHYTWFDWNNQSLPYHSQKLRLEPVKV

QHSGAYWCQGTNSVGKGRSPLSTLTVYYSPETIGRRVAVGLGSCLAILIL

AICGLKLQRRWKRTQSQQGLQENSSGQSFFVRNKKVRRAPLSEGPHSLGC

YNPMMEDGISYTTLRFPEMNIPRTGDAESSEMQRPPPDCDDTVTYSALHK

RQVGDYENVIPDFPEDEGIHYSELIQFGVGERPQAQENVDYVILKH.

As used herein, the term "ROR1" may refer to tyrosine-protein kinase transmembrane receptor ROR1, also known as neurotrophic tyrosine kinase, receptor-related 1 (NTRKR1) or dJ537F10.1. It is a protein that in mice and humans is encoded by the ROR1 gene and is a member of the receptor tyrosine kinase-like orphan receptor (ROR) family along with ROR2. ROR1 is a glycosylated type I membrane protein; it is a pseudokinase that lacks catalytic activity and may interact with the non-canonical Wnt signaling pathway. RORs contain two distinct extracellular cysteine-rich domains and one transmembrane domain. Within the intracellular portion, ROR1 possesses a tyrosine kinase domain, two serine/threonine-rich domains and a proline-rich domain. This gene is highly expressed during early embryonic development but expressed at very low levels in normal (i.e., non-cancerous) adult tissues. Increased expression of this gene is associated with B-cell chronic lymphocytic leukemia. Alternative splicing results in multiple transcript variants encoding different isoforms.

The human and murine amino acid and nucleic acid sequences can be found in a public database, such as GenBank, UniProt and Swiss-Prot. For example, the human ROR1 polypeptide canonical sequence is UniProt Accession No. Q01973-1:

(SEQ ID NO: 20)
MHRPRRGTRPPLLALLAALLLAARGAAAQETELSVSAELVPTSSWNISS

ELNKDSYLTLDEPMNNITTSLGQTAELHCKVSGNPPPTIRWFKNDAPVVQ

EPRRLSFRSTIYGSRLRIRNLDTTDTGYFQCVATNGKEVVSSTGVLFVKF

GPPPTASPGYSDEYEEDGFCQPYRGIACARFIGNRTVYMESLHMQGEIEN

QITAAFTMIGTSSHLSDKCSQFAIPSLCHYAFPYCDETSSVPKPRDLCRD

ECEILENVLCQTEYIFARSNPMILMRLKLPNCEDLPQPESPEAANCIRIG

IPMADPINKNHKCYNSTGVDYRGTVSVTKSGRQCQPWNSQYPHTHTFTAL

RFPELNGGHSYCRNPGNQKEAPWCFTLDENFKSDLCDIPACDSKDSKEKN

KMEILYILVPSVAIPLAIALLFFFICVCRNNQKSSSAPVQRQPKHVRGQN

VEMSMLNAYKPKSKAKELPLSAVRFMEELGECAFGKIYKGHLYLPGMDHA

QLVAIKTLKDYNNPQQWTEFQQEASLMAELHHPNIVCLLGAVTQEQPVCM

LFEYINQGDLHEFLIMRSPHSDVGCSSDEDGTVKSSLDHGDFLHIAIQIA

AGMEYLSSHFFVHKDLAARNILIGEQLHVKISDLGLSREIYSADYYRVQS

KSLLPIRWMPPEAIMYGKFSSDSDIWSFGVVLWEIFSFGLQPYYGFSNQE

VIEMVRKRQLLPCSEDCPPRMYSLMTECWNEIPSRRPRFKDIHVRLRSWE

GLSSHTSSTTPSGGNATTQTTSLSASPVSNLSNPRYPNYMFPSQGITPQG

QIAGFIGPPIPQNQRFIPINGYPIPPGYAAFPAAHYQPTGPPRVIQHCPP

PKSRSPSSASGSTSTGHVTSLPSSGSNQEANIPLLPHMSIPNHPGGMGIT

VFGNKSQKPYKIDSKQASLLGDANIHGHTESMISAEL.

The nucleotide sequence encoding human ROR1 transcript variant 1 can be found at Accession No. XM_017001376. The nucleotide sequence encoding human ROR1 transcript variant 2 can be found at Accession No. XM_011541526. The nucleotide sequence encoding human ROR1 transcript variant 3 can be found at Accession No. XM_017001377. A low level of ROR1 expression is seen in adipose tissue and to a lesser degree in the pancreas, lung, and a subset of intermediate B cells.

As used herein, the term "NKG2D" refers to NKG2-D type II integral membrane protein, NKG2-D, Killer cell lectin-like receptor subfamily K member 1 (KLRK), NK cell receptor D, NKG2-D-activating NK receptor, and CD314. Many immune receptors are composed of separate ligand-binding and signal-transducing subunits. In natural killer (NK) and T cells, DAP10 was identified as a cell surface adaptor protein in an activating receptor complex with NKG2D, a receptor for the stress-inducible and tumor-associated major histocompatibility complex molecule MICA. Within the DAP10 cytoplasmic domain, an Src homology 2 (SH2) domain-binding site was capable of recruiting the p85 subunit of the phosphatidylinositol 3-kinase (PI 3-kinase), providing for NKG2D-dependent signal transduction. Thus, NKG2D-DAP10 receptor complexes activate NK and T cell responses against MICA-bearing tumors.

NKG2D is a homo dimer with C-type, lectin-like, type II transmembrane glycoprotein signals through a positively charged arginine in the transmembrane domain which associates with a negatively charged aspartic acid in the transmembrane domain of the adaptor DAP10 (Charles L. Sentman, Cancer Immunity (1 May 2013) Vol. 13, p. 8). Increase in NKG2D was observed with higher levels of gamma-chain cytokines such as IL-2, IL-7, IL-12, and IL-15 in human NK and CD8 T cells. IL-21, IFN-γ, and TGF-β have been shown to decrease NKG2D expression.

NKG2D Ligands (NKG2DL) include MHC region encoded MICA/B and a second family of MHC class I-related proteins, the ULBPs, also known as retinoic acid early transcripts (RAETs) (Bahram et al., 1994, Proc. Natl. Acad. Sci. USA 91, 6259-6263; Bauer et al., 1999, Science, July 30; 285(5428):727-9). Although MICA/B proteins are part of MHC family, they do not present antigen and do not associate with 132-microglobulin. To date six genes, ULBP1-6, have been identified as belonging to the ULBP family (Cosman et al., 2001, Immunity February; 14(2):123-33). These molecules are 55-60% homologous in their amino-acid sequences, and are equally distantly related to MICs or MHC. Functionally, the ULBPs do not bind 12-microglobulin or present antigenic peptides and lack an a3 domain (Eagle et al., PLoS One 4:1-14, 2009; Eagle et al., Eur J Immunol 39:3207-30164:1-14, 2009). ULBPs are attached to the cell membrane via a GPI-anchor.

NKG2D ligands are expressed on surface of tumor cells originating from colon, liver, gastric, breasts, ovary and lung. They are also expressed on non-solid tumors including AML, ALL, CML, CLL. An increase in NKG2DL expression correlates to higher relapse rate among breast cancer patients.

The human and murine amino acid and nucleic acid sequences can be found in a public database, such as GenBank, UniProt and Swiss-Prot. For example, the human canonical NKG2D sequence (isoform 1) corresponds to UniProt Accession No. P26718-1 and has the sequence MGWIRGRRSRHSWEMSEFHNYNLDLKKSDF-STRWQKQRCPVVKSKCRENASPFFFCCFIAVAMG IRFIIMVAIWSAVFLNSLFNQEVQIPLTESYCGPCPKN-WICYKNNCYQFFDESKNWYESQASCMSQ-NASLLKVYSKEDQDLLKLVKSYHWMGLVHIPTNG-SWQWEDGSILSPNLLTIIEMQKGDCALYASS FKGYIENCSTPNTYICMQRTV (SEQ ID NO: 14). In one embodiment, the fragment used in TFPs comprises the extracellular domain sequence (SEQ ID NO: 110)
NSLFNQEVQIPLTESYCGPCPKNWICYKNNCYQFFDESKNWYESQASCMS

QNASLLKVYSKEDQDLLKLVKSYHWMGLVHIPTNGSWQWEDGSILSPNLL

TIIEMQKGDCALYASSFKGYIENCSTPNTYICMQRTV

As used herein, the term "CD16" may refer to a 50-80 kDa glycoprotein that is expressed in two different isoforms: Fc gamma receptor IIIa (known as CD16, CD16a, CD16, CD16A, FcG3, FcGR3, FcGRIII, FcR-10, FcRIII, FcRIIIA, IGFR3, IMD20) and Fc-gamma receptor IIIb (FCGR3B, UniProtKB Q9ULV2). The transmembrane form is found on human NK cells, macrophages, and mast cells, while the glycosylphosphatidylinositol (GPI)-linked form is present on neutrophils. The human CD16 antigen is a low-affinity receptor for aggregated IgG. The transmembrane form plays a role in signal transduction, NK cell activation, and antibody-dependent cellular cytotoxicity.

By "V158 allele" or "V158 variant" is meant a CD16 polypeptide with valine at residue 158. In human populations, there are two naturally occurring CD16 alleles, one with phenylalanine (F) or valine (V) at residue 158. The V158 allele has a higher affinity for the Fc region of IgG1 antibodies, and thus in one embodiment the TFPs disclosed herein comprises the V158 CD16 polypeptide. Patients having two "V" alleles respond better to antibody-based cancer therapies than do patients having a VF or FF genotype. The methods disclosed herein provide a way to enhance a patient's response to IgG1 therapeutics in patients with a VF or FF genotype. See, e.g., Kudo et al. (2013) Cancer Res; 74(1); 1-11, herein incorporated by reference.

The human and murine amino acid and nucleic acid sequences can be found in a public database, such as GenBank, UniProt and Swiss-Prot. For example, the human CD16 isoform A is UniProt Accession No. P08637 and has the sequence:

(SEQ ID NO: 23)
MWQLLLPTALLLLVSAGMRTEDLPKAVVFLEPQWYRVLEKDSVTLKCQGA

YSPEDNSTQWFHNESLISSQASSYFIDAATVDDSGEYRCQTNLSTLSDPV

QLEVHIGWLLLQAPRWVFKEEDPIHLRCHSWKNTALHKVTYLQNGKGRKY

FHHNSDFYIPKATLKDSGSYFCRGLFGSKNVSSETVNITITQGLAVSTIS

SFFPPGYQVSFCLVMVLLFAVDTGLYFSVKTNIRSSTRDWKDHKFKWRKD

PQDK.

In one embodiment, the CD16 TFP composition comprises SEQ ID NO:23. In another embodiment, the CD16 TFP composition comprises SEQ ID NO:24, which is a V158 variation of the sequence set forth in SEQ ID NO:23 and has the sequence MWQLLLPTALLLLVSAGM-RTEDLPKAVVFLEPQWYRVLEKDSVTLKCQGAYSP EDNSTQWFHNESLISSQASSYFIDAATVDDSGEY-RCQTNLSTLSDPVQLEVHIGWLLLQAPRWVF-KEEDPIHLRCHSWKNTALHKVTYLQNGKG RKYFHHNSDFYIPKATLKDSGSYFCRGLVGSKNVS-SETVNITITQGLAVSTISSFFPPGYQVSFCLVMVLLFA VDTGLYFSVKTNIRSSTRDWKDHKFKWRKDPQDK (SEQ ID NO:24). The V158 polymorphism of FCRG3A (CD16) encodes a high-affinity immunoglobulin Fc receptor and is associated with favorable responses to antibody therapy (see, e.g., Kudo et al., *Cancer Res;* 74(1); 93-103 (2013), herein incorporated by reference).

The portion of the TFP composition comprising an antibody or antibody fragment thereof may exist in a variety of forms where the antigen binding domain is expressed as part of a contiguous polypeptide chain including, for example, a single domain antibody fragment (sdAb), a single chain antibody (scFv) derived from a murine, humanized or human antibody (Harlow et al., 1999, In: Using Antibodies: A Laboratory Manual, Cold Spring Harbor Laboratory Press, N.Y.; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In one aspect, the antigen binding domain of a TFP composition comprises an antibody fragment. In a further aspect, the TFP comprises an antibody fragment that comprises a scFv or a sdAb.

The term "antigen" or "Ag" may refer to a molecule that is capable of being bound specifically by an antibody, or otherwise provokes an immune response. This immune response may involve either antibody production, or the activation of specific immunologically-competent cells, or both. As used herein, the term "cancer antigen" or "cancer-related antigen" may refer to any cancer cell marker expressed on the surface of a malignant or tumor cell that can be treated with the combination therapy described herein, including, but not limited to: described herein include, but are not limited to, 5T4, 8H9, αvβθ integrin, αvβ6 integrin, alphafetoprotein (AFP), B7-H6, CA-125 carbonic anhydrase 9 (CA9), CD19, CD20, CD22, CD30, CD33, CD38, CD44, CD44v6, CD44v7/8, CD52, CD123, CD171, carcinoembryonic antigen (CEA), EpCAM (epithelial cell adhesion molecule), E-cadherin, EMA (epithelial membrane antigen), EGFRvlll, epithelial glycoprotein-2 (EGP-2), epithelial glycoprotein-40 (EGP-40), ErbB1/EGFR, ErbB2/HER2/neu/EGFR2, ErbB3/HER3, ErbB4, epithelial tumor antigen (ETA), folate binding protein (FBP), fetal acetylcholine receptor (AchR), folate receptor-α, G250/CAIX, ganglioside 2 (GD2), ganglioside 3 (GD3), HLA-A1, HLA-A2, high molecular weight melanoma-associated antigen (HMW-MAA), IL-13 receptor α2 (IL-13Ru2), kinase insert domain receptor (KDR), k-light chain, Lewis Y (LeY), L1 cell adhesion molecule, melanoma-associated antigen (MAGE-A1), mesothelin, mucin-1 (MUC1), mucin-16 (MUC16), natural killer group 2 member D (NKG2D) ligands, nerve cell adhesion molecule (NCAM), NY-ESO-1, oncofetal antigen (h5T4), prostate stem cell antigen (PSCA), prostate-specific membrane antigen (PSMA), receptor-tyrosine kinase-like orphan receptor 1 (ROR1), TAA targeted by mAb IgE, tumor-associated glycoprotein-72 (TAG-72), tyrosinase, and vascular endothelial growth factor (VEGF) receptors.

The term "antibody," as used herein, refers to a protein, or polypeptide sequences derived from an immunoglobulin molecule, which specifically binds to an antigen. Antibodies can be intact immunoglobulins of polyclonal or monoclonal origin, or fragments thereof and can be derived from natural or from recombinant sources.

The terms "antibody fragment" or "antibody binding domain" refer to at least one portion of an antibody, or recombinant variants thereof, that contains the antigen binding domain, i.e., an antigenic determining variable region of an intact antibody, that is sufficient to confer recognition and specific binding of the antibody fragment to a target, such as an antigen and its defined epitope. Examples of antibody fragments include, but are not limited to, Fab, Fab', F(ab')$_2$, and Fv fragments, single-chain (sc)Fv ("scFv") antibody fragments, linear antibodies, single domain antibodies (abbreviated "sdAb") (either V$_L$ or V$_H$), camelid V$_{HH}$ domains, and multi-specific antibodies formed from antibody fragments.

The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single polypeptide chain, and wherein the scFv retains the specificity of the intact antibody from which it is derived.

"Heavy chain variable region" or "$V_H$" (or, in the case of single domain antibodies, e.g., nanobodies, "$V_{HH}$") with regard to an antibody refers to the fragment of the heavy chain that contains three CDRs interposed between flanking stretches known as framework regions, these framework regions are generally more highly conserved than the CDRs and form a scaffold to support the CDRs.

Unless specified, as used herein an scFv may have the $V_L$ and $V_H$ regions in either order, e.g., with respect to the N-terminal and C-terminal ends of the polypeptide, the scFv may comprise $V_L$-linker-$V_H$ or may comprise $V_H$-linker-$V_L$.

The portion of the TFP composition of the invention comprising an antibody or antibody fragment thereof may exist in a variety of forms where the antigen binding domain is expressed as part of a contiguous polypeptide chain including, for example, a single domain antibody fragment (sdAb) or heavy chain antibodies HCAb 242:423-426). In one aspect, the antigen binding domain of a TFP composition of the invention comprises an antibody fragment. In a further aspect, the TFP comprises an antibody fragment that comprises a scFv or a sdAb.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa ("κ") and lambda ("λ") light chains refer to the two major antibody light chain isotypes.

The term "recombinant antibody" refers to an antibody that is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art. The term "antigen" or "Ag" refers to a molecule that is capable of being bound specifically by an antibody, or otherwise provokes an immune response. This immune response may involve either antibody production, or the activation of specific immunologically-competent cells, or both.

The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full-length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

The term "anti-tumor effect" refers to a biological effect which can be manifested by various means, including but not limited to, e.g., a decrease in tumor volume, a decrease in the number of tumor cells, a decrease in the number of metastases, an increase in life expectancy, decrease in tumor cell proliferation, decrease in tumor cell survival, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "autologous" refers to any material derived from the same individual to whom it is later to be re-introduced into the individual.

The term "allogeneic" refers to any material derived from a different animal of the same species or different patient as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "xenogeneic" refers to a graft derived from an animal of a different species.

The term "cancer" may refer to a disease characterized by the rapid and uncontrolled growth of aberrant cells. Cancer cells can spread locally or through the bloodstream and lymphatic system to other parts of the body. Examples of various cancers are described herein and include, but are not limited to, prostate cancer, breast cancer, melanoma, sarcoma, colorectal cancer, pancreatic cancer, uterine cancer, ovarian cancer, stomach cancer, gastric cancer, small cell lung cancer, non-small cell lung cancer, bladder cancer, cholangiocarcinoma, squamous cell lung cancer, mesothelioma, adrenocortico carcinoma, esophageal cancer, head & neck cancer, liver cancer, nasopharyngeal carcinoma, neuroepithelial cancer, adenoid cystic carcinoma, thymoma, chronic lymphocytic leukemia, glioma, glioblastoma multiforme, neuroblastoma, papillary renal cell carcinoma, mantle cell lymphoma, lymphoblastic leukemia, acute myeloid leukemia, and the like.

The term "conservative sequence modifications" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a TFP of the invention can be replaced with other amino acid residues from the same side chain family and the altered TFP can be tested using the functional assays described herein.

The term "stimulation" refers to a primary response induced by binding of a stimulatory domain or stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, and/or reorganization of cytoskeletal structures, and the like.

The term "stimulatory molecule" or "stimulatory domain" refers to a molecule or portion thereof expressed by a T-cell that provides the primary cytoplasmic signaling sequence(s) that regulate primary activation of the TCR complex in a stimulatory way for at least some aspect of the T-cell signaling pathway. In one aspect, the primary signal is initiated by, for instance, binding of a TCR/CD3 complex with an MHC molecule loaded with peptide, and which leads to mediation of a T-cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or "ITAM". Examples of an ITAM containing primary cytoplasmic signaling sequence that is of particular use in the invention includes, but is not limited to, those derived from TCR zeta, FcR gamma, FcR beta, CD3 gamma, CD3 delta, CD3 epsilon, CD5, CD22, CD79a, CD79b, CD278 (also known as "ICOS") and CD66d.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T cells may recognize these complexes using their T-cell receptors (TCRs). APCs process antigens and present them to T cells.

An "intracellular signaling domain," as the term is used herein, refers to an intracellular portion of a molecule. The intracellular signaling domain generates a signal that promotes an immune effector function of the TFP containing cell, e.g., a TFP-expressing T-cell. Examples of immune effector function, e.g., in a TFP-expressing T-cell, include cytolytic activity and T helper cell activity, including the secretion of cytokines. In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation.

A primary intracellular signaling domain can comprise an ITAM ("immunoreceptor tyrosine-based activation motif"). Examples of ITAM containing primary cytoplasmic signaling sequences include, but are not limited to, those derived from CD3 zeta, FcR gamma, FcR beta, CD3 gamma, CD3 delta, CD3 epsilon, CD5, CD22, CD79a, CD79b, and CD66d DAP10 and DAP12.

The term "costimulatory molecule" refers to the cognate binding partner on a T-cell that specifically binds with a costimulatory ligand, thereby mediating a costimulatory response by the T-cell, such as, but not limited to, proliferation. Costimulatory molecules are cell surface molecules other than antigen receptors or their ligands that are required for an efficient immune response. Costimulatory molecules include, but are not limited to an MHC class 1 molecule, BTLA and a Toll ligand receptor, as well as OX40, CD2, CD27, CD28, CDS, ICAM-1, LFA-1 (CD11a/CD18) and 4-1BB (CD137). A costimulatory intracellular signaling domain can be the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, lymphocyte function-associated antigen-1 (LFA-1), CD2, CD7, LIGHT, NKG2C, SLAMF7, NKp80, CD160, B7-H3, and a ligand that specifically binds with CD83, and the like. The intracellular signaling domain can comprise the entire intracellular portion, or the entire native intracellular signaling domain, of the molecule from which it is derived, or a functional fragment thereof. The term "4-1BB" refers to a member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank Acc. No. AAA62478.2, or equivalent residues from non-human species, e.g., mouse, rodent, monkey, ape and the like.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain one or more introns.

The term "effective amount" or "therapeutically effective amount" are used interchangeably herein, and refer to an amount of a compound, formulation, material, or composition, as described herein effective to achieve a particular biological or therapeutic result.

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence driven by a promoter.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic include, but are not limited to, e.g., the LENTIVECTOR™ gene delivery technology from Oxford BioMedica, the LENTIMAX™ vector system from Lentigen, and the like. Nonclinical types of lentiviral vectors are also available and would be known to one skilled in the art.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Human" or "fully human" refers to an immunoglobulin, such as an antibody or antibody fragment, where the whole molecule is of human origin or consists of an amino acid sequence identical to a human form of the antibody or immunoglobulin.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

The term "parenteral" administration of an immunogenic composition includes, e.g., subcutaneous (s.c.), intravenous (i.v.), intramuscular (i.m.), or intrasternal injection, intratumoral, or infusion techniques.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter" refers to a DNA sequence recognized by the transcription machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "constitutive" promoter refers to a nucleotide sequence which, when operably linked with a polynucleotide which encodes or specifies a gene product, causes the gene product to be produced in a cell under most or all physiological conditions of the cell.

The term "inducible" promoter refers to a nucleotide sequence which, when operably linked with a polynucleotide which encodes or specifies a gene product, causes the gene product to be produced in a cell substantially only when an inducer which corresponds to the promoter is present in the cell.

The term "tissue-specific" promoter refers to a nucleotide sequence which, when operably linked with a polynucleotide encodes or specified by a gene, causes the gene product to be produced in a cell substantially only if the cell is a cell of the tissue type corresponding to the promoter.

The terms "linker" and "flexible polypeptide linker" as used in the context of a scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence (Gly-Gly-Gly-Ser)$_n$, where n is a positive integer equal to or greater than 1. For example, n=1, n=2, n=3, n=4, n=5, n=6, n=7, n=8, n=9 and n=10. In one embodiment, the flexible polypeptide linkers include, but are not limited to, (Gly$_4$Ser)$_4$ or (Gly$_4$Ser)$_3$. In another embodiment, the linkers include multiple repeats of (Gly$_2$Ser), (GlySer) or (Gly$_3$Ser). Also included within the scope of the invention are linkers described in WO2012/138475 (incorporated herein by reference). In some instances, the linker sequence comprises a long linker (LL) sequence. In some instances, the long linker sequence comprises (G$_4$S)$_n$, wherein n=2 to 4. In some instances, the linker sequence comprises a short linker (SL) sequence. In some instances, the short linker sequence comprises (G$_4$S)$_n$, wherein n=1 to 3.

As used herein, a 5' cap (also termed an RNA cap, an RNA 7-methylguanosine cap or an RNA m7G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA, preferably mRNA, which has been synthesized in vitro. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In the preferred embodiment of a construct for transient expression, the polyA is between 50 and 5000, preferably greater than 64, more preferably greater than 100, most preferably greater than 300 or 400. Poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

The term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (e.g., mammals, human).

The term, a "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

In the context of the present invention, "tumor antigen" or "hyperproliferative disorder antigen" or "antigen associated with a hyperproliferative disorder" refers to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, NHL, leukemias, uterine cancer, cervical cancer, bladder cancer, kidney cancer and adenocarcinomas such as breast cancer, prostate cancer, ovarian cancer, pancreatic cancer, and the like.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "specifically binds," refers to an antibody, an antibody fragment or a specific ligand, which recognizes and binds a cognate binding partner (e.g., BCMA, NKG2D, ROR1, etc.) present in a sample, but which does not necessarily and substantially recognize or bind other molecules in the sample.

The term "binding ligand" may generally refer to a polypeptide (e.g., a protein), a polynucleotide (e.g., DNA, RNA, or a hybrid of DNA and RNA), a molecule, a chemical compound, a fragment thereof, and/or a hybrid thereof. In some embodiments, the binding ligand can comprise a polynucleotide, and the polynucleotide can be single stranded, double stranded, or a combination thereof. In some embodiments, a binding ligand can comprise a biological molecule or a non-biological molecule. In some embodiments, a biological molecule or non-biological molecule can be a naturally occurring molecule or an artificial molecule. Non-limiting examples of a binding ligand include a protein, a carbohydrate, a lipid, or a nucleic acid. In some embodiments, the binding ligand may associate, bind, and/or couple with an antibody or fragment thereof (e.g., an IgA isotype antibody, an IgD isotype antibody, an IgE isotype antibody, an IgG isotype antibody, an IgM isotype antibody, an IgW isotype antibody, an IgY isotype antibody). In some embodiments the antibody or fragment thereof may be an Fc domain of the antibody (e.g., the binding ligand is an Fc receptor). For example, in some embodiments the binding ligand can specifically bind to an IgG1 antibody. In some embodiments, the binding ligand may be capable of associating, capable of binding, and/or capable of coupling with an antibody or fragment thereof. In one embodiment, the binding ligand may comprise a CD16 polypeptide, or a fragment thereof. In another embodiment, the binding ligand may comprise a CD16 polynucleotide, or a fragment thereof. In some embodiments, the binding ligand can comprise a CD16 polypeptide, and the CD16 polypeptide comprises at least about 10%, 20%, 30%, 40%, 50%, 60%, 70%, 80%, 90%, or 95% sequence homology the native CD16 polypeptide sequence. In some embodiments, the binding ligand can comprise a CD16 polypeptide, and the CD16 polypeptide comprises at most about 99%, 95%, 90%, 80%, 70%, 60%, 50%, 40%, 30%, 20%, or 10%, sequence homology the native CD16 polypeptide sequence. In some embodiments, the binding ligand can comprise a CD16 polynucleotide, and the CD16 polynucleotide comprises at least about 10%, 20%, 30%, 40%, 50%, 60%, 70%, 80%, 90%, or 95% sequence homology the native CD16 polynucleotide sequence. In some embodiments, the binding ligand can comprise a CD16 polynucleotide, and the CD16 polynucleotide comprises at most about 99%, 95%, 90%, 80%, 70%, 60%, 50%, 40%, 30%, 20%, or 10%, sequence homology the native CD16 polynucleotide sequence. In some embodiments, the binding ligand can comprise multiple subunits. In some embodiments, a binding ligand can comprise multiple subunits, and the subunits can be the same. In some embodiments, a binding ligand can comprise multiple different subunits. In some embodiments, a binding ligand can comprise multiple subunits, and at least two of the subunits can be different. In some embodiments, a binding ligand can comprise a dimer, trimer, tetramer, pentamer, hexamer, heptamer, nonamer, or decamer. In some embodiments, a binding ligand can comprise greater than about ten subunits. In some embodiments, a binding ligand can comprise a polymer. In some embodiments, the binding ligand may be non-human (e.g., primate), human, or humanized.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

T-Cell Receptor (TCR) Fusion Proteins (TFP)

The present invention encompasses recombinant DNA constructs encoding TFPs, wherein the TFP in one aspect comprises an antibody fragment that binds specifically to one or more tumor associated antigens ("TAA"), e.g., a human TAA, wherein the sequence of the antibody fragment is contiguous with and in the same reading frame as a nucleic acid sequence encoding a TCR subunit or portion thereof. The TFPs provided herein are able to associate with one or more endogenous (or alternatively, one or more exogenous, or a combination of endogenous and exogenous) TCR subunits in order to form a functional TCR complex. In another aspect, the TFP comprises a CD16 fragment that binds specifically to the Tc region of an IgG1 or IgG4 antibody.

In one aspect, the TFP of the invention comprises a target-specific binding element otherwise referred to as an antigen binding domain. The choice of moiety depends upon the type and number of target antigen that define the surface of a target cell. For example, the antigen binding domain may be chosen to recognize a target antigen that acts as a cell surface marker on target cells associated with a particular disease state. Thus, examples of cell surface markers that may act as target antigens for the antigen binding domain in a TFP of the invention include those associated with viral, bacterial and parasitic infections; autoimmune diseases; and cancerous diseases (e.g., malignant diseases).

In one aspect, the TFP-mediated T-cell response can be directed to an antigen of interest by way of engineering an antigen-binding domain into the TFP that specifically binds a desired antigen.

In one aspect, the portion of the TFP comprising the antigen binding domain comprises an antigen binding domain that targets BCMA. In another aspect, the antigen binding domain targets human ROR1. In another aspect, the antigen binding domain targets human NKG2D. In another aspect, the TFP comprises a CD16 polypeptide as the antigen binding domain, and the target is an anti-TAA antibody that is in turn targeted to a TAA.

TFP comprises a CD16 moiety, e.g., a human CD16 moiety, wherein the sequence of the CD16 protein or fragment thereof is contiguous with and in the same reading frame as a nucleic acid sequence encoding a TCR subunit or portion thereof. The TFPs provided herein are able to associate with one or more endogenous (or alternatively, one or more exogenous, or a combination of endogenous and exogenous) TCR subunits in order to form a functional TCR complex. In one aspect, the CD16 TFP comprises a target-specific binding element otherwise referred to as an Fcγ receptor. The CD16 TFP may be chosen to work with approved anti-cancer monoclonal (IgG) antibodies, thus combining the specificity of the antibody with immune cells that mediate antibody-triggered effector functions. The Fc domain acts as a bridge between the specificity dictated by the Fab region and the CD16 TFP. For example, the CD16 TFP may be combined with the standard of care anti-CD20 antibody rituximab. CD20 is primarily found on the surface of immune system B cells. Rituximab destroys B cells and is therefore used to treat diseases which are characterized by overactive, dysfunctional, or excessive numbers of B cells. This can include many lymphomas, leukemias, transplant rejection, and autoimmune disorders. Thus, examples of cell surface markers that may act as target antigens for the antibody combined with a TFP include those associated with viral, bacterial and parasitic infections; autoimmune diseases; and cancerous diseases (e.g., malignant diseases). The CD16 moiety may be attached to the TFP via a linker. In another embodiment, the linker sequence comprises sets of glycine and serine repeats such as $(Gly_4Ser)_n$, where n is a positive integer equal to or greater than 1. In one embodiment, the linker can be $(Gly_4Ser)_4$ or $(Gly_4Ser)_3$. In some instances, the linker sequence comprises a long linker (LL) sequence. In some instances, the long linker sequence comprises $(G_4S)_n$, wherein n=2 to 4. In some instances, the linker sequence comprises a short linker (SL) sequence. In some instances, the short linker sequence comprises $(G_4S)_n$, wherein n=1 to 3.

The antigen binding domain can be any domain that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain ($V_H$), a light chain variable domain ($V_L$) and a variable domain ($V_{HH}$) of a camelid derived nanobody, and to an alternative scaffold known in the art to function as antigen binding domain, such as a recombinant fibronectin domain, anticalin, DARPIN and the like. Likewise, a natural or synthetic ligand specifically recognizing and binding the target antigen can be used as antigen binding domain for the TFP. In some instances, it is beneficial for the antigen binding domain to be derived from the same species in which the TFP will ultimately be used in. For example, for use in humans, it may be beneficial for the antigen binding domain of the TFP to comprise human or humanized residues for the antigen binding domain of an antibody or antibody fragment.

Thus, in one aspect, the antigen-binding domain comprises a humanized or human antibody or an antibody fragment, or a murine antibody or antibody fragment. In one embodiment, the humanized or human anti-TAA binding domain comprises one or more (e.g., all three) light chain complementary determining region 1 (LC CDR1), light chain complementary determining region 2 (LC CDR2), and light chain complementary determining region 3 (LC CDR3) of a humanized or human anti-TAA binding domain described herein, and/or one or more (e.g., all three) heavy chain complementary determining region 1 (HC CDR1), heavy chain complementary determining region 2 (HC CDR2), and heavy chain complementary determining region 3 (HC CDR3) of a humanized or human anti-TAA binding domain described herein, e.g., a humanized or human anti-TAA binding domain comprising one or more, e.g., all three, LC CDRs and one or more, e.g., all three, HC CDRs. In one embodiment, the humanized or human anti-TAA binding domain comprises one or more (e.g., all three) heavy chain complementary determining region 1 (HC CDR1), heavy chain complementary determining region 2 (HC CDR2), and heavy chain complementary determining region 3 (HC CDR3) of a humanized or human anti-TAA binding domain described herein, e.g., the humanized or human anti-tumor-associated antigen binding domain has two variable heavy chain regions, each comprising a HC CDR1, a HC CDR2 and a HC CDR3 described herein. In one embodiment, the humanized or human anti-tumor-associated antigen binding domain comprises a humanized or human light chain variable region described herein and/or a humanized or human heavy chain variable region described herein. In one embodiment, the humanized or human anti-tumor-associated antigen binding domain comprises a humanized heavy chain variable region described herein, e.g., at least two humanized or human heavy chain variable regions described herein. In one embodiment, the anti-tumor-associated antigen binding domain is a scFv comprising a light chain and a heavy chain of an amino acid sequence provided herein. In an embodiment, the anti-tumor-associated antigen binding domain (e.g., an scFv or $V_H$H nb) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided herein, or a sequence with 95-99% identity with an amino acid sequence provided herein; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided herein, or a sequence with 95-99% identity to an amino acid sequence provided herein. In one embodiment, the humanized or human anti-tumor-associated antigen binding domain is a scFv, and a light chain variable region comprising an amino acid sequence described herein, is attached to a heavy chain variable region comprising an amino acid sequence described herein, via a linker, e.g., a linker described herein. In one embodiment, the humanized anti-tumor-associated antigen binding domain includes a $(Gly_4\text{-}Ser)_n$ linker, wherein n is 1, 2, 3, 4, 5, or 6, preferably 3 or 4. The light chain variable region and heavy chain variable region of a scFv can be, e.g., in any of the following orientations: light chain variable region-linker-heavy chain variable region or heavy chain variable region-linker-light chain variable region. In some instances, the linker sequence comprises a long linker (LL) sequence. In some instances, the long linker sequence comprises $(G_4S)_n$, wherein n=2 to 4. In some instances, the linker sequence comprises a short linker (SL) sequence. In some instances, the short linker sequence comprises $(G_4S)_n$, wherein n=1 to 3.

In some aspects, a non-human antibody is humanized, where specific sequences or regions of the antibody are modified to increase similarity to an antibody naturally produced in a human or fragment thereof. In one aspect, the antigen binding domain is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions (see, e.g., Queen et al., U.S. Pat. No. 5,585,089; and Riechmann et al., 1988, Nature, 332:323, which are incorporated herein by reference in their entireties.)

A humanized antibody or antibody fragment has one or more amino acid residues remaining in it from a source which is nonhuman. These nonhuman amino acid residues are often referred to as "import" residues, which are typically taken from an "import" variable domain. As provided herein, humanized antibodies or antibody fragments comprise one or more CDRs from nonhuman immunoglobulin molecules and framework regions wherein the amino acid residues comprising the framework are derived completely or mostly from human germline. Multiple techniques for humanization of antibodies or antibody fragments are well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference in their entirety). In such humanized antibodies and antibody fragments, substantially less than an intact human variable domain has been substituted by the corresponding sequence from a nonhuman species. Humanized antibodies are often human antibodies in which some CDR residues and possibly some framework (FR) residues are substituted by residues from analogous sites in rodent antibodies. Humanization of antibodies and antibody fragments can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (see, e.g., Nicholson et al. Mol. Immun. 34 (16-17): 1157-1165 (1997); Carter et al., Proc. Natl. Acad. Sci. USA, 89:4285 (1992); Presta et al., J. Immunol., 151:2623 (1993), the contents of which are incorporated herein by reference herein in their entirety). In some embodiments, the framework region, e.g., all four framework regions, of the heavy chain variable region are derived from a $V_H4\text{-}4\text{-}59$ germline sequence. In one embodiment, the framework region can comprise, one, two, three, four or five modifications, e.g., substitutions, e.g., from the amino acid at the corresponding murine sequence.

In one embodiment, the framework region, e.g., all four framework regions of the light chain variable region are derived from a VK3-1.25 germline sequence. In one embodiment, the framework region can comprise, one, two, three, four or five modifications, e.g., substitutions, e.g., from the amino acid at the corresponding murine sequence.

In some aspects, the portion of a TFP composition of the invention that comprises an antibody fragment is humanized with retention of high affinity for the target antigen and other favorable biological properties. According to one aspect of the invention, humanized antibodies and antibody fragments are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind the target antigen. In this way, FR residues can be selected and combined from the recipient and import sequences so that the desired antibody or antibody fragment characteristic, such as increased affinity for the target antigen, is achieved. In general, the CDR residues are directly and most substantially involved in influencing antigen binding.

In one aspect, the anti-tumor-associated antigen binding domain is a fragment, e.g., a single chain variable fragment (scFv) or a camelid heavy chain ($V_HH$). In one aspect, the anti-tumor-associated antigen binding domain is a Fv, a Fab, a (Fab')$_2$, or a bi-functional (e.g. bi-specific) hybrid antibody (e.g., Lanzavecchia et al., Eur. J. Immunol. 17, 105 (1987)). In one aspect, the antibodies and fragments thereof of the invention binds a tumor-associated antigen protein with wild-type or enhanced affinity.

Also provided herein are methods for obtaining an antibody antigen binding domain specific for a target antigen (e.g., BCMA or any target antigen described elsewhere herein for targets of fusion moiety binding domains), the method comprising providing by way of addition, deletion, substitution or insertion of one or more amino acids in the amino acid sequence of a $V_H$ (or $V_HH$) domain set out herein a $V_H$ domain which is an amino acid sequence variant of the $V_H$ domain, optionally combining the $V_H$ domain thus provided with one or more $V_L$ domains, and testing the $V_H$ domain or $V_H/V_L$ combination or combinations to identify a specific binding member or an antibody antigen binding domain specific for a target antigen of interest (e.g., BCMA, NKG2D, ROR1, or a TAA target of the combination of a CD16 TFP+an anti-TAA antibody) and optionally with one or more desired properties.

In some instances, $V_H$ domains and scFvs can be prepared according to method known in the art (see, for example, Bird et al., (1988) Science 242:423-426 and Huston et al., (1988) Proc. Natl. Acad. Sci. USA 85:5879-5883). scFv molecules can be produced by linking $V_H$ and $V_L$ regions together using flexible polypeptide linkers. The scFv molecules comprise a linker (e.g., a Ser-Gly linker) with an optimized length and/or amino acid composition. The linker length can greatly affect how the variable regions of a scFv fold and interact. In fact, if a short polypeptide linker is employed (e.g., between 5-10 amino acids) intra-chain folding is prevented. Inter-chain folding is also required to bring the two variable regions together to form a functional epitope binding site. In some instances, the linker sequence comprises a long linker (LL) sequence. In some instances, the long linker sequence comprises $(G_4S)_n$, wherein n=2 to 4. In some instances, the linker sequence comprises a short linker (SL) sequence. In some instances, the short linker sequence comprises $(G_4S)_n$, wherein n=1 to 3. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

A scFv can comprise a linker of about 10, 11, 12, 13, 14, 15 or greater than 15 residues between its $V_L$ and $V_H$ regions. The linker sequence may comprise any naturally occurring amino acid. In some embodiments, the linker sequence comprises amino acids glycine and serine. In another embodiment, the linker sequence comprises sets of glycine and serine repeats such as $(Gly_4Ser)_n$, where n is a positive integer equal to or greater than 1. In one embodiment, the linker can be $(Gly_4Ser)_4$ or $(Gly_4Ser)_3$. Variation in the linker length may retain or enhance activity, giving rise to superior efficacy in activity studies. In some instances, the linker sequence comprises a long linker (LL) sequence. In some instances, the long linker sequence comprises $(G_4S)_n$, wherein n=2 to 4. In some instances, the linker sequence comprises a short linker (SL) sequence. In some instances, the short linker sequence comprises $(G_4S)_n$, wherein n=1 to 3.

Stability and Mutations

The stability of an anti-tumor-associated antigen binding domain, e.g., scFv molecules (e.g., soluble scFv) can be evaluated in reference to the biophysical properties (e.g., thermal stability) of a conventional control scFv molecule or a full-length antibody. In one embodiment, the humanized or human scFv has a thermal stability that is greater than about 0.1, about 0.25, about 0.5, about 0.75, about 1, about 1.25, about 1.5, about 1.75, about 2, about 2.5, about 3, about 3.5, about 4, about 4.5, about 5, about 5.5, about 6, about 6.5, about 7, about 7.5, about 8, about 8.5, about 9, about 9.5, about 10 degrees, about 11 degrees, about 12 degrees, about 13 degrees, about 14 degrees, or about 15 degrees Celsius than a parent scFv in the described assays.

The improved thermal stability of the anti-tumor-associated antigen binding domain, e.g., scFv is subsequently conferred to the entire tumor-associated antigen-TFP construct, leading to improved therapeutic properties of the anti-tumor-associated antigen TFP construct. The thermal stability of the anti-tumor-associated antigen binding domain, e.g., scFv can be improved by at least about 2° C. or 3° C. as compared to a conventional antibody. In one embodiment, the anti-tumor-associated antigen binding domain, e.g., scFv has a 1° C. improved thermal stability as compared to a conventional antibody. In another embodiment, the anti-tumor-associated antigen binding domain, e.g., scFv has a 2° C. improved thermal stability as compared to a conventional antibody. In another embodiment, the scFv has a 4° C., 5° C., 6° C., 7° C., 8° C., 9° C., 10° C., 11° C., 12° C., 13° C., 14° C., or 15° C. improved thermal stability as compared to a conventional antibody. Comparisons can be made, for example, between the scFv molecules disclosed herein and scFv molecules or Fab fragments of an antibody from which the scFv $V_H$ and $V_L$ were derived. Thermal stability can be measured using methods known in the art. For example, in one embodiment, $T_M$ can be measured. Methods for measuring $T_M$ and other methods of determining protein stability are described below.

Mutations in scFv (arising through humanization or mutagenesis of the soluble scFv) alter the stability of the scFv and improve the overall stability of the scFv and the anti-tumor-associated antigen TFP construct. Stability of the humanized scFv is compared against the murine scFv using measurements such as $T_M$, temperature denaturation and temperature aggregation. In one embodiment, the anti-tumor-associated antigen binding domain, e.g., a scFv, comprises at least one mutation arising from the humanization process such that the mutated scFv confers improved stability to the anti-tumor-associated antigen TFP construct. In another embodiment, the anti-tumor-associated antigen binding domain, e.g., scFv comprises at least 1, 2, 3, 4, 5, 6, 7, 8, 9, 10 mutations arising from the humanization process such that the mutated scFv confers improved stability to the tumor-associated antigen-TFP construct.

In one aspect, the antigen binding domain of the TFP comprises an amino acid sequence that is homologous to an antigen binding domain amino acid sequence described herein, and the antigen binding domain retains the desired functional properties of the anti-tumor-associated antigen antibody fragments described herein. In one specific aspect, the TFP composition of the invention comprises an antibody fragment. In a further aspect, that antibody fragment comprises a scFv.

In various aspects, the antigen binding domain of the TFP is engineered by modifying one or more amino acids within one or both variable regions (e.g., $V_H$ and/or $V_L$), for example within one or more CDR regions and/or within one or more framework regions. In one specific aspect, the TFP composition of the invention comprises an antibody fragment. In a further aspect, that antibody fragment comprises a scFv.

It will be understood by one of ordinary skill in the art that the antibody or antibody fragment of the invention may further be modified such that they vary in amino acid sequence (e.g., from wild-type), but not in desired activity. For example, additional nucleotide substitutions leading to amino acid substitutions at "non-essential" amino acid residues may be made to the protein. For example, a nonessential amino acid residue in a molecule may be replaced with another amino acid residue from the same side chain family. In another embodiment, a string of amino acids can be replaced with a structurally similar string that differs in order and/or composition of side chain family members, e.g., a conservative substitution, in which an amino acid residue is replaced with an amino acid residue having a similar side chain, may be made.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Percent identity in the context of two or more nucleic acids or polypeptide sequences refers to two or more sequences that are the same. Two sequences are "substantially identical" if two sequences have a specified percentage of amino acid residues or nucleotides that are the same (e.g., 60% identity, optionally 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., (2003) Current Protocols in Molecular Biology). Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

In one aspect, the present invention contemplates modifications of the starting antibody or fragment (e.g., scFv) amino acid sequence that generate functionally equivalent molecules. For example, the $V_H$ or $V_L$ of an anti-tumor-associated antigen binding domain, e.g., scFv, comprised in the TFP can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting $V_H$ or $V_L$ framework region of the anti-tumor-associated antigen binding domain, e.g., scFv. The present invention contemplates modifications of the entire TFP construct, e.g., modifications in one or more amino acid sequences of the various domains of the TFP construct in order to generate functionally equivalent molecules. The TFP construct can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity of the starting TFP construct.

Extracellular Domain

The extracellular domain may be derived either from a natural or from a recombinant source. Where the source is natural, the domain may be derived from any protein, but in particular a membrane-bound or transmembrane protein. In one aspect, the extracellular domain is capable of associating with the transmembrane domain. An extracellular domain of particular use in this invention may include at least the extracellular region(s) of e.g., the alpha, beta or zeta chain of the T-cell receptor, or CD3 epsilon, CD3 gamma, or CD3 delta, or in alternative embodiments, CD28, CD45, CD2, CD4, CD5, CD8, CD9, CD16, CD22, CD33, CD37, CD64, CD80, CD86, CD134, CD137, CD154.

Transmembrane Domain

In general, a TFP sequence contains an extracellular domain and a transmembrane domain encoded by a single genomic sequence. In alternative embodiments, a TFP can be designed to comprise a transmembrane domain that is heterologous to the extracellular domain of the TFP. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 or up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 or up to 15 amino acids of the intracellular region). In one aspect, the transmembrane domain is one that is associated with one of the other domains of the TFP is used. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another TFP on the TFP-T-cell surface. In a different aspect, the amino acid sequence of the transmembrane domain may be modified or substituted so as to minimize interactions with the binding domains of the native binding partner present in the same TFP.

The transmembrane domain may be derived either from a natural or from a recombinant source. Where the source is natural, the domain may be derived from any membrane-bound or transmembrane protein. In one aspect, the transmembrane domain is capable of signaling to the intracellular domain(s) whenever the TFP has bound to a target. A transmembrane domain of particular use in this invention may include at least the transmembrane region(s) of e.g., the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154.

In some instances, the transmembrane domain can be attached to the extracellular region of the TFP, e.g., the antigen binding domain of the TFP, via a hinge, e.g., a hinge from a human protein. For example, in one embodiment, the hinge can be a human immunoglobulin (Ig) hinge, e.g., an IgG4 hinge, or a CD8a hinge.

Linkers

Optionally, a short oligo- or polypeptide linker, between 2 and 20 amino acids in length may form the linkage between the transmembrane domain and the cytoplasmic region of the TFP. A glycine-serine doublet provides a particularly suitable linker. For example, in one aspect, the linker comprises the amino acid sequence of GGGGSGGGGS (SEQ ID NO: 101). In some embodiments, the linker is encoded by a nucleotide sequence of GGTGGCGGAGGTTCTGGAGGTGGAGGTTCC (SEQ ID NO: 102). In some embodiments, the linker comprises the amino acid sequence of GGGGSGGGGSGGGGSLE (SEQ ID NO: 1). In other embodiments, the linker comprises the amino acid sequence of AAAGGGGSGGGGSGGGGSLE (SEQ ID NO:2). In other embodiments, the linker is a long linker having the sequence AAIEVMYPPPYLGGGGSGGGGSGGGGSLE (SEQ ID NO:3). In some embodiments, the linker is encoded by a nucleotide sequence of GGTGGAGGCGGTTCTGGTG-GAGGCGGTTCGGATGGCGGAGGTTCA (SEQ ID NO:66). In other embodiments, the linker is encoded by a nucleotide sequence of (SEQ ID NO: 73)
GGAGAGGGTAAATCTTCCGGATCTGGTTCCGAAAGCAAGGCTAGC.

Cytoplasmic Domain

The cytoplasmic domain of the TFP can include an intracellular signaling domain, if the TFP contains CD3 gamma, delta or epsilon polypeptides; TCR alpha and TCR beta subunits are generally lacking in a signaling domain. An intracellular signaling domain is generally responsible for activation of at least one of the normal effector functions of the immune cell in which the TFP has been introduced. The term "effector function" refers to a specialized function of a cell. Effector function of a T-cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the TFP of the invention include the cytoplasmic sequences of the T-cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of naive T cells and that a secondary and/or costimulatory signal is required. Thus, naïve T-cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain).

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs (ITAMs).

Examples of ITAMs containing primary intracellular signaling domains that are of particular use in the invention include those of CD3 zeta, FcR gamma, FcR beta, CD3 gamma, CD3 delta, CD3 epsilon, CD5, CD22, CD79a, CD79b, and CD66d. In one embodiment, a TFP of the invention comprises an intracellular signaling domain, e.g., a primary signaling domain of CD3-epsilon. In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

The intracellular signaling domain of the TFP can comprise the CD3 zeta signaling domain by itself or it can be combined with any other desired intracellular signaling domain(s) useful in the context of a TFP of the invention. For example, the intracellular signaling domain of the TFP can comprise a CD3 epsilon chain portion and a costimulatory signaling domain. The costimulatory signaling domain refers to a portion of the TFP comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD1, ICOS, lymphocyte function-associated antigen-1 (LFA-1), CD2, CD7, LIGHT, NKG2C, B7-H3, and a ligand that specifically binds with CD83, and the like. For example, CD27 costimulation has been demonstrated to enhance expansion, effector function, and survival of human TFP-T cells in vitro and augments human T-cell persistence and antitumor activity in vivo (Song et al. Blood. 2012; 119(3):696-706).

The intracellular signaling sequences within the cytoplasmic portion of the TFP of the invention may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequences.

In one embodiment, a glycine-serine doublet can be used as a suitable linker. In one embodiment, a single amino acid, e.g., an alanine, a glycine, can be used as a suitable linker.

In one aspect, the TFP-expressing cell described herein can further comprise a second TFP, e.g., a second TFP that includes a different antigen binding domain, e.g., to the same target (e.g., CD22) or a different target (e.g., CD123). In one embodiment, when the TFP-expressing cell comprises two or more different TFPs, the antigen binding domains of the different TFPs can be such that the antigen binding domains do not interact with one another. For example, a cell expressing a first and second TFP can have an antigen binding domain of the first TFP, e.g., as a fragment, e.g., a scFv, that does not associate with the antigen binding domain of the second TFP, e.g., the antigen binding domain of the second TFP is a $V_{HH}$.

In another aspect, the TFP-expressing cell described herein can further express another agent, e.g., an agent which enhances the activity of a TFP-expressing cell. For example, in one embodiment, the agent can be an agent which inhibits an inhibitory molecule. Inhibitory molecules, e.g., PD1, can, in some embodiments, decrease the ability of a TFP-expressing cell to mount an immune effector response. Examples of inhibitory molecules include PD1, PD-L1, CTLA4, TIM3, LAG3, VISTA, BTLA, TIGIT, LAIR1, CD160, 2B4 and TGFR beta. In one embodiment, the agent that inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, LAG3, CTLA4, CD160, BTLA, LAIR1, TIM3, 2B4 and TIGIT, or a fragment of any of these (e.g., at least a portion of an extracellular domain of any of these), and a second polypeptide which is an intracellular signaling domain described herein (e.g., comprising a costimulatory domain (e.g., 4-1BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of an extracellular domain of PD1), and a second polypeptide of an intracellular signaling domain described herein (e.g., a CD28 signaling domain described herein and/or a CD3 zeta signaling domain described herein). PD1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD1, PD-L1 and PD-L2 have been shown to downregulate T-cell activation upon binding to PD1 (Freeman et al. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD1 with PD-L1.

In one embodiment, the agent comprises the extracellular domain (ECD) of an inhibitory molecule, e.g., Programmed Death 1 (PD1) can be fused to a transmembrane domain and optionally an intracellular signaling domain such as 41BB and CD3 zeta (also referred to herein as a PD1 TFP). In one embodiment, the PD1 TFP, when used in combinations with an anti-tumor antigen TFP described herein, improves the persistence of the T-cell. In one embodiment, the TFP is a PD1 TFP comprising the extracellular domain of PD1. Alternatively, provided are TFPs containing an antibody or antibody fragment such as a scFv that specifically binds to the Programmed Death-Ligand 1 (PD-L1) or Programmed Death-Ligand 2 (PD-L2).

In another aspect, the present invention provides a population of TFP-expressing T cells, e.g., TFP-T cells. In some embodiments, the population of TFP-expressing T cells comprises a mixture of cells expressing different TFPs. For example, in one embodiment, the population of TFP-T cells can include a first cell expressing a TFP having an anti-tumor-associated antigen binding domain described herein, and a second cell expressing a TFP having a different anti-tumor-associated antigen binding domain, e.g., an anti-tumor-associated antigen binding domain described herein that differs from the anti-tumor-associated antigen binding domain in the TFP expressed by the first cell. As another example, the population of TFP-expressing cells can include a first cell expressing a TFP that includes an anti-tumor-associated antigen binding domain, e.g., as described herein, and a second cell expressing a TFP that includes an antigen binding domain to a target other than tumor-associated antigen (e.g., another tumor-associated antigen).

In another aspect, the present invention provides a population of cells wherein at least one cell in the population expresses a TFP having an anti-tumor-associated antigen domain described herein, and a second cell expressing another agent, e.g., an agent which enhances the activity of a TFP-expressing cell. For example, in one embodiment, the agent can be an agent which inhibits an inhibitory molecule. Inhibitory molecules, e.g., can, in some embodiments, decrease the ability of a TFP-expressing cell to mount an immune effector response. Examples of inhibitory molecules include PD1, PD-L1, PD-L2, CTLA4, TIM3, LAG3, VISTA, BTLA, TIGIT, LAIR1, CD160, 2B4 and TGFR beta. In one embodiment, the agent that inhibits an inhibitory molecule comprises a first polypeptide, e.g., an inhibitory molecule, associated with a second polypeptide that provides a positive signal to the cell, e.g., an intracellular signaling domain described herein.

Disclosed herein are methods for producing in vitro transcribed RNA encoding TFPs. The present invention also includes a TFP encoding RNA construct that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length. RNA so produced can efficiently transfect different kinds of cells. In one aspect, the template includes sequences for the TFP.

In one aspect, the anti-tumor-associated antigen TFP is encoded by a messenger RNA (mRNA). In one aspect, the mRNA encoding the anti-tumor-associated antigen TFP is introduced into a T-cell for production of a TFP-T-cell. In one embodiment, the in vitro transcribed RNA TFP can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is a TFP of the present invention. In one embodiment, the DNA to be used for PCR contains an open reading frame. The DNA can be from a naturally occurring DNA sequence from the genome of an organism. In one embodiment, the nucleic acid can include some or all of the 5' and/or 3' untranslated regions (UTRs). The nucleic acid can include exons and introns. In one embodiment, the DNA to be used for PCR is a human nucleic acid sequence. In another embodiment, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In one embodiment, the primers are designed to amplify the coding region of a human cDNA, including all or portions of the 5' and 3' UTRs. Primers useful for PCR can be generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between one and 3,000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3'UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments, the 5' UTR can be 5'UTR of an RNA virus whose RNA genome is stable in cells. In other embodiments, various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However, polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100 T tail (size can be 50-5000 Ts), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Nucleic Acid Constructs Encoding a TFP

The present invention also provides nucleic acid molecules encoding one or more TFP constructs described herein. In one aspect, the nucleic acid molecule is provided as a messenger RNA transcript. In one aspect, the nucleic acid molecule is provided as a DNA construct. Exemplary DNA sequences encoding binders, linkers, and TFPs in their expression plasmids are disclosed in Appendix A.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In another embodiment, the vector comprising the nucleic acid encoding the desired TFP of the invention is an adenoviral vector (A5/35).

In another embodiment, one or more domains of the TFP construct (e.g., extracellular, transmembrane, and intracellular signaling domain) are engineered using a gene editing technique such as clustered regularly interspaced short palindromic repeats (CRISPR®, see, e.g., U.S. Pat. No. 8,697,359), transcription activator-like effector nucleases (TALEN, see, e.g., U.S. Pat. No. 9,393,257), meganucleases (naturally occurring endodeoxyribonucleases having large recognition sites comprising double-stranded DNA sequences of 12 to 40 base pairs), or zinc finger nuclease (ZFN, see, e.g., Urnov et al., Nat. Rev. Genetics (2010) v11, 636-646) methods. In this way, a chimeric construct may be engineered to combine desirable characteristics of each subunit, such as conformation or signaling capabilities. See also Sander & Joung, Nat. Biotech. (2014) v32, 347-55; and June et al., 2009 Nature Reviews Immunol. 9.10: 704-716, each incorporated herein by reference. In some embodiments, one or more of the extracellular domain, the transmembrane domain, or the cytoplasmic domain of a TFP subunit are engineered to have aspects of more than one natural TCR subunit domain (i.e., are chimeric).

The expression constructs of the present invention may also be used for nucleic acid immunization and gene therapy, using standard gene delivery protocols. Methods for gene delivery are known in the art (see, e.g., U.S. Pat. Nos. 5,399,346, 5,580,859, 5,589,466, incorporated by reference herein in their entireties). In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, e.g., in Sambrook et al., 2012, Molecular Cloning: A Laboratory Manual, volumes 1-4, Cold Spring Harbor Press, N.Y.), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (e.g., WO 01/96584; WO 01/29058; and U.S. Pat. No. 6,326,193).

A number of virally based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter that is capable of expressing a TFP transgene in a mammalian T-cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving TFP expression from transgenes cloned into a lentiviral vector (see, e.g., Milone et al., Mol. Ther. 17(8): 1453-1464 (2009)). Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1a promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline-regulated promoter.

In order to assess the expression of a TFP polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art (see, e.g., Sambrook et al., 2012, Molecular Cloning: A Laboratory Manual, volumes 1-4, Cold Spring Harbor Press, N.Y.). One method for the introduction of a polynucleotide into a host cell is calcium phosphate transfection Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like (see, e.g., U.S. Pat. Nos. 5,350,674 and 5,585,362).

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

The present invention further provides a vector comprising a TFP encoding nucleic acid molecule. In one aspect, a TFP vector can be directly transduced into a cell, e.g., a T-cell. In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the TFP construct in mammalian T cells. In one aspect, the mammalian T-cell is a human T-cell.

Sources of T Cells

Prior to expansion and genetic modification, a source of T cells is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain aspects of the present invention, any number of T-cell lines available in the art, may be used. In certain aspects of the present invention, T cells can be obtained from a unit of blood collected from a subject using any number of techniques known to the skilled artisan, such as Ficoll® separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and to place the cells in an appropriate buffer or media for subsequent processing steps. In one aspect of the invention, the cells are washed with phosphate buffered saline (PBS). In an alternative aspect, the wash solution lacks calcium and may lack magnesium or may lack many if not all divalent cations. Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the COBE® 2991 cell processor, the Baxter CytoMate®, or the Haemonetics® Cell Saver® 5) according to the manufacturer's instructions. After washing, the cells may be resuspended in a variety of biocompatible buffers, such as, for example, Ca-free, Mg-free PBS, PlasmaLyte® A, or other saline solution with or without buffer. Alternatively, the undesirable components of the apheresis sample may be removed and the cells directly resuspended in culture media.

In one aspect, T cells are isolated from peripheral blood lymphocytes by lysing the red blood cells and depleting the monocytes, for example, by centrifugation through a Percoll® gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one aspect, T cells are isolated by incubation with anti-CD3/anti-CD28 (e.g., 3×28)-conjugated beads, such as Dynabeads® M-450 CD3/CD28 T, for a time period sufficient for positive selection of the desired T cells. In one aspect, the time period is about 30 minutes. In a further aspect, the time period ranges from 30 minutes to 36 hours or longer and all integer values there between. In a further aspect, the time period is at least 1, 2, 3, 4, 5, or 6 hours. In yet another preferred aspect, the time period is 10 to 24 hours. In one aspect, the incubation time period is 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of $CD8^+$ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain aspects, it may be desirable to perform the selection procedure and use the "unselected" cells in the activation and expansion process. "Unselected" cells can also be subjected to further rounds of selection.

Enrichment of a T-cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain aspects, it may be desirable to enrich for or positively select for regulatory T cells which typically express CD4+, CD25+, CD62Lhi, $GITR^+$, and $FoxP3^+$. Alternatively, in certain aspects, T regulatory cells are depleted by anti-C25 conjugated beads or other similar method of selection.

In one embodiment, a T-cell population can be selected that expresses one or more of IFN-γ, TNF-alpha, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO2013/126712.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 2 billion cells/mL is used. In one aspect, a concentration of 1 billion cells/mL is used. In a further aspect, greater than 100 million cells/mL is used. In a further aspect, a concentration of cells of 10, 15, 20, 25, 30, 35, 40, 45, or 50 million cells/mL is used. In yet one aspect, a concentration of cells from 75, 80, 85, 90, 95, or 100 million cells/mL is used. In further aspects, concentrations of 125 or 150 million cells/mL can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related aspect, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one aspect, the concentration of cells used is $5\times10^6$/mL. In other aspects, the concentration used can be from about $1\times10^5$/mL to $1\times10^6$/mL, and any integer value in between. In other aspects, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan® and PlasmaLyte® A, the cells then are frozen to −80° C. at a rate of 1 per minute and stored in the vapor phase of a liquid nitrogen storage tank. Other methods of controlled freezing may be used as well as uncontrolled freezing immediately at −20° C. or in liquid nitrogen. In certain aspects, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T-cell therapy for any number of diseases or conditions that would benefit from T-cell therapy, such as those described herein. In one aspect, a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and tacrolimus (FK506), antibodies, or other immunoablative agents such as alemtuzumab, anti-CD3 antibodies, cyclophosphamide, fludarabine, cyclosporin, rapamycin, mycophenolic acid, steroids, romidepsin (formerly FR901228), and irradiation.

In a further aspect of the present invention, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and 7,572,631.

Generally, the T cells of the invention may be expanded by contact with a surface having attached thereto an agent that stimulates a CD3/TCR complex associated signal and a ligand that stimulates a costimulatory molecule on the surface of the T cells. In particular, T-cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4$^+$ T cells or CD8$^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol. Meth. 227(1-2):53-63, 1999).

T cells that have been exposed to varied stimulation times may exhibit different characteristics. For example, typical blood or apheresed peripheral blood mononuclear cell products have a helper T-cell population (TH, CD4$^+$) that is greater than the cytotoxic or suppressor T-cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T-cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T-cell product for specific purposes.

Once an anti-tumor-associated antigen TFP is constructed, various assays can be used to evaluate the activity of the molecule, such as but not limited to, the ability to expand T cells following antigen stimulation, sustain T-cell expansion in the absence of re-stimulation, and anti-cancer activities in appropriate in vitro and animal models. Assays to evaluate the effects of an anti-tumor-associated antigen TFP are described in further detail below Western blot analysis of TFP expression in primary T cells can be used to detect the presence of monomers and dimers (see, e.g., Milone et al., Molecular Therapy 17(8): 1453-1464 (2009)). Very briefly, T cells (1:1 mixture of CD4$^+$ and CD8$^+$ T cells) expressing the TFPs are expanded in vitro for more than 10 days followed by lysis and SDS-PAGE under reducing conditions. TFPs are detected by Western blotting using an antibody to a TCR chain. The same T-cell subsets are used for SDS-PAGE analysis under non-reducing conditions to permit evaluation of covalent dimer formation.

In vitro expansion of TFP+ T cells following antigen stimulation can be measured by flow cytometry. For example, a mixture of CD4$^+$ and CD8$^+$ T cells are stimulated with alphaCD3/alphaCD28 and APCs followed by transduction with lentiviral vectors expressing GFP under the control of the promoters to be analyzed. Exemplary promoters include the CMV IE gene, EF-1alpha, ubiquitin C, or phosphoglycerokinase (PGK) promoters. GFP fluorescence is evaluated on day 6 of culture in the CD4$^+$ and/or CD8$^+$ T-cell subsets by flow cytometry (see, e.g., Milone et al., Molecular Therapy 17(8): 1453-1464 (2009)). Alternatively, a mixture of CD4$^+$ and CD8$^+$ T cells are stimulated with alphaCD3/alphaCD28 coated magnetic beads on day 0, and transduced with TFP on day 1 using a bicistronic lentiviral vector expressing TFP along with eGFP using a 2A ribosomal skipping sequence.

Sustained TFP+ T-cell expansion in the absence of re-stimulation can also be measured (see, e.g., Milone et al., Molecular Therapy 17(8): 1453-1464 (2009)). Briefly, mean T-cell volume (fl) is measured on day 8 of culture using a Coulter Multisizer III particle counter following stimulation with alphaCD3/alphaCD28 coated magnetic beads on day 0, and transduction with the indicated TFP on day 1.

Animal models can also be used to measure a TFP-T activity. For example, xenograft model using human BCMA-specific TFP$^+$ T cells to treat a cancer in immunodeficient mice (see, e.g., Milone et al., Molecular Therapy 17(8): 1453-1464 (2009)). Very briefly, after establishment of cancer, mice are randomized as to treatment groups. Different numbers of engineered T cells are coinjected at a 1:1 ratio into NOD/SCID/γ-/- mice bearing cancer. The number of copies of each vector in spleen DNA from mice is evaluated at various times following T-cell injection. Animals are assessed for cancer at weekly intervals. Peripheral blood tumor-associated antigen$^+$ cancer cell counts are measured in mice that are injected with alpha tumor-associated antigen-zeta TFP$^+$ T cells or mock-transduced T cells. Survival curves for the groups are compared using the log-rank test. In addition, absolute peripheral blood CD4$^+$ and CD8$^+$ T-cell counts 4 weeks following T-cell injection in NOD/SCID/γ-/- mice can also be analyzed. Mice are injected with cancer cells and 3 weeks later are injected with T cells engineered to express TFP by a bicistronic lentiviral vector that encodes the TFP linked to eGFP. T cells are normalized to 45-50% input GFP+ T cells by mixing with mock-transduced cells prior to injection, and confirmed by flow cytometry. Animals are assessed for cancer at 1-week intervals. Survival curves for the TFP+ T-cell groups are compared using the log-rank test.

Dose dependent TFP treatment response can be evaluated (see, e.g., Milone et al., Molecular Therapy 17(8): 1453-1464 (2009)). For example, peripheral blood is obtained 35-70 days after establishing cancer in mice injected on day 21 with TFP T cells, an equivalent number of mock-transduced T cells, or no T cells. Mice from each group are randomly bled for determination of peripheral blood+cancer cell counts and then killed on days 35 and 49. The remaining animals are evaluated on days 57 and 70.

Assessment of cell proliferation and cytokine production has been previously described, e.g., at Milone et al., Molecular Therapy 17(8): 1453-1464 (2009). Briefly, assessment of TFP-mediated proliferation is performed in microtiter plates by mixing washed T cells with cells expressing BCMA or CD32 and CD137 (KT32-BBL) for a final T-cell:cell expressing BCMA ratio of 2:1. Cells expressing BCMA cells are irradiated with gamma-radiation prior to use. Anti-CD3ε (clone OKT3) and anti-CD28 (clone 9.3) monoclonal antibodies are added to cultures with KT32-BBL cells to serve as a positive control for stimulating T-cell proliferation since these signals support long-term CD8$^+$ T-cell expansion ex vivo. T cells are enumerated in cultures using Count-Bright™ fluorescent beads (Invitrogen) and flow cytometry as described by the manufacturer. TFP+ T cells are identified by GFP expression using T cells that are engineered with eGFP-2A linked TFP-expressing lentiviral vectors. For TFP+ T cells not expressing GFP, the TFP+ T cells are detected with biotinylated recombinant BCMA protein and a secondary avidin-PE conjugate. CD4$^+$ and CD8$^+$ expression on T cells are also simultaneously detected with specific monoclonal antibodies (BD Biosciences). Cytokine measurements are performed on supernatants collected 24 hours following re-stimulation using the human TH1/TH2 cytokine cytometric bead array kit (BD Biosciences) according the manufacturer's instructions. Fluorescence is assessed using a FACScalibur™ flow cytometer, and data is analyzed according to the manufacturer's instructions.

Cytotoxicity can be assessed by a standard $^{51}$Cr-release assay (see, e.g., Milone et al., Molecular Therapy 17(8): 1453-1464 (2009)). Briefly, target cells are loaded with $^{51}$Cr (as NaCrO$_4$, New England Nuclear) at 37° C. for 2 hours with frequent agitation, washed twice in complete RPMI and plated into microtiter plates. Effector T cells are mixed with target cells in the wells in complete RPMI at varying ratios of effector cell:target cell (E:T). Additional wells containing media only (spontaneous release, SR) or a 1% solution of triton-X 100 detergent (total release, TR) are also prepared. After 4 hours of incubation at 37° C., supernatant from each well is harvested. Released $^{51}$Cr is then measured using a gamma particle counter (Packard Instrument Co., Waltham, Mass.). Each condition is performed in at least triplicate, and the percentage of lysis is calculated using the formula: % Lysis=(ER−SR)/(TR−SR), where ER represents the average $^{51}$Cr released for each experimental condition.

Imaging technologies can be used to evaluate specific trafficking and proliferation of TFPs in tumor-bearing animal models. Such assays have been described, e.g., in Barrett et al., Human Gene Therapy 22:1575-1586 (2011). Briefly, NOD/SCID/γc-/- (NSG) mice are injected IV with cancer cells followed 7 days later with T cells 4 hour after electroporation with the TFP constructs. The T cells are stably transfected with a lentiviral construct to express firefly luciferase, and mice are imaged for bioluminescence. Alternatively, therapeutic efficacy and specificity of a single injection of TFP+ T cells in a cancer xenograft model can be measured as follows: NSG mice are injected with cancer cells transduced to stably express firefly luciferase, followed by a single tail-vein injection of T cells electroporated with BCMA TFP 7 days later. Animals are imaged at various time points post injection. For example, photon-density heat maps of firefly luciferase positive cancer in representative mice at day 5 (2 days before treatment) and day 8 (24 hours post TFP+PBLs) can be generated.

Other assays, including those described in the Example section herein as well as those that are known in the art can also be used to evaluate the anti-TAA TFP constructs disclosed herein.

Therapeutic Applications
Tumor Antigen Associated Diseases or Disorders

While examples and embodiments have been provided herein, additional techniques and embodiments related to, e.g., ROR1-associated diseases and/or anti-ROR1 antibodies and uses therefor, may be found in U.S. Pat. No. 9,217,040, filed Jan. 13, 2013; U.S. Pat. No. 9,758,586, filed Nov. 30, 2011; International Publication No. WO 2012076066, filed Jun. 17, 2011; Mato, A. & Porter, D. (2015) Blood 126(4), 478-485; Choi, M., et al. (2015) Clinical Lymphoma, Myeloma & Leukemia 15(S1), S167-S169; Cui, B., et al. (2015) Cancer Research 73(12), 3649-3660; Yu, J., et al. (2015) Journal of Clinical Investigation 10(1172), 1-34; Borcherding, N., et al. (2014) Protein Cell 5(7), 496-502; Zhang, S., et al. (2012) The American Journal of Pathology 181(6), 1903-1910; Hudecek, M., et al. (2010) Blood 116(22), 4532-4541; and Deniger, D., et al. (2015) PLoS ONE 10(6), 1-19, which are entirely incorporated herein by reference.

In one aspect, the invention provides methods for treating a disease associated with a TAA, e.g., ROR1 or NKG2D ligand (NKG2DL) expression. In one aspect, the invention provides methods for treating a disease wherein part of the tumor is negative for NKG2DL and part of the tumor is positive for NKG2DL. For example, the TFP is useful for treating subjects that have undergone treatment for a disease associated with elevated expression of NKG2DL, wherein the subject that has undergone treatment for elevated levels of NKG2DL exhibits a disease associated with elevated levels of NKG2DL.

In one aspect, the invention pertains to a vector comprising a TAA-binding TFP operably linked to promoter for expression in mammalian T cells. In one aspect, the invention provides a recombinant T-cell expressing the, e.g., NKG2D TFP for use in treating NKG2DL-expressing tumors, wherein the recombinant T-cell expressing the NKG2D TFP is termed a NKG2D TFP-T. In one aspect, the NKG2D TFP-T is capable of contacting a tumor cell with at least one NKG2DL expressed on its surface such that the TFP-T targets the tumor cell and growth of the tumor is inhibited.

Dual Specificity TFPs

Many patients treated with cancer therapeutics that are directed to one target on a tumor cell, e.g., BCMA, CD19, CD20, CD22, CD123, etc., become resistant over time as escape mechanisms such as alternate signaling pathways and feedback loops become activated. Dual specificity therapeutics attempt to address this by combining targets that often substitute for each other as escape routes. Therapeutic T cell populations having TCRs specific to more than one tumor-associated antigen are promising combination therapeutics. Tumor Associated Antigen Targets for Anti-TAA TFP-T Cells, Dual Specificity Anti-TAA TFP T Cells, Or for CD-16 TFP T Cells in Combination with an Anti-TAA Antibody Exemplary tumor-associated antigens include, but are not limited to, oncofetal antigens (e.g., those expressed in fetal tissues and in cancerous somatic cells), oncoviral antigens (e.g., those encoded by tumorigenic transforming viruses), overexpressed/accumulated antigens (e.g., those expressed by both normal and neoplastic tissue, with the level of expression highly elevated in neoplasia), cancer-testis antigens (e.g., those expressed only by cancer cells and adult reproductive tissues such as testis and placenta), lineage-restricted antigens (e.g., those expressed largely by a single cancer histotype), mutated antigens (e.g., those expressed by cancer as a result of genetic mutation or alteration in transcription), post-translationally altered antigens (e.g., those tumor-associated alterations in glycosylation, etc.), and idiotypic antigens (e.g., those from highly polymorphic genes where a tumor cell expresses a specific clonotype, e.g., as in B cell, T cell lymphoma/leukemia resulting from clonal aberrancies). Exemplary tumor-associated antigens include, but are not limited to, antigens of alpha-actinin-4, ARTC1, BCR-ABL fusion protein (b3a2), B-RAF, CASP-5, CASP-8, beta-catenin, Cdc27, CDK4, CDK12, CDKN2A, CLPP, COA-1, CSNKiA1, dek-can fusion protein, EFTUD2, Elongation factor 2, ETV6-AML1 fusion protein, FLT3-ITD, FNDC3B, FN1, GAS7, GPNMB, HAUS3, HSDL1, LDLR-fucosyltransferase AS fusion protein, HLA-A2d, HLA-AIId, hsp70-2, MART2, MATN, ME1, MUM-if, MUM-2, MUM-3, neo-PAP, Myosin class I, NFYC, OGT, OS-9, p53, pml-RARalpha fusion protein, PPP1R3B, PRDX5, PTPRK, K-ras, N-ras, RBAF600, SIRT2, SNRPD1, SYT-SSX1 or -SSX2 fusion protein, TGF-betaRII, triosephosphate isomerase, BAGE-1, D393-CD20n, Cyclin-A1, GAGE-1, GAGE-2, GAGE-8, GAGE-3, GAGE-4, GAGE-5, GAGE-6, GAGE-7, GnTVf, HERV-K-MEL, KK-LC-1, KM-HN-1, LAGE-1, LY6K, MAGE-A1, MAGE-A2, MAGE-A3, MAGE-A4, MAGE-A6, MAGE-A9, MAGE-A10, MAGE-A12 m, MAGE-C1, MAGE-C2, mucink, NA88-A, NY-ESO-1/LAGE-2, SAGE, Spl7, SSX-2, SSX-4, TAG-1, TAG-2, TRAG-3, TRP2-INT2g, XAGE-1b/GAGED2a, Gene/protein, CEA, gp100/Pmel17, mamaglobin-A, Melan-A/MART-1, NY-BR-1, OA1, PAP, PSA, RAB38/NY-MEL-1, TRP-1/gp75, TRP-2, tyrosinase, adipophilin, AIM-2, ALDH1A1, BCLX (L), BING-4, CALCA, CD45, CD274, CPSF, cyclin D1, DKKi, ENAH (hMena), EpCAM, EphA3, EZH2, FGF5, glypican-3, G250/MN/CAIX, HER-2/neu, HLA-DOB, Hepsin, IDO1, IGF2B3, ILi3Ralpha2, Intestinal carboxyl esterase, alpha-foetoprotein, Kallikrein 4, KIF20A, Lengsin, M-CSF, MCSP, mdm-2, Meloe, Midkine, MMP-2, MMP-7, MUC1, MUC5AC, p53, PAX5, PBF, PRAME, PSMA, RAGE-1, RGS5, RhoC, RNF43, RU2AS, secernin 1, SOX10, STEAP1, survivin, Telomerase, TPBG, VEGF, and WT1.

In one aspect, the invention provides methods for treating a disease associated with at least one tumor-associated antigen expression. In one aspect, the invention provides methods for treating a disease wherein part of the tumor is negative for the tumor associated antigen and part of the tumor is positive for the tumor associated antigen. For example, the antibody or TFP of the invention is useful for treating subjects that have undergone treatment for a disease associated with elevated expression of said tumor antigen, wherein the subject that has undergone treatment for elevated levels of the tumor associated antigen exhibits a disease associated with elevated levels of the tumor associated antigen.

In one aspect, the invention pertains to a vector comprising an anti-tumor-associated antigen antibody or TFP operably linked to promoter for expression in mammalian T cells. In one aspect, the invention provides a recombinant T-cell expressing a tumor-associated antigen TFP for use in treating tumor-associated antigen-expressing tumors, wherein the recombinant T-cell expressing the tumor-associated antigen TFP is termed a tumor-associated antigen TFP-T. In one aspect, the tumor-associated antigen TFP-T of the invention is capable of contacting a tumor cell with at least one tumor-associated antigen TFP of the invention expressed on its surface such that the TFP-T targets the tumor cell and growth of the tumor is inhibited.

In one aspect, the invention pertains to a method of inhibiting growth of a tumor-associated antigen-expressing tumor cell, comprising contacting the tumor cell with a tumor-associated antigen antibody or TFP T-cell of the present invention such that the TFP-T is activated in response to the antigen and targets the cancer cell, wherein the growth of the tumor is inhibited.

In one aspect, the invention pertains to a method of treating cancer in a subject. The method comprises administering to the subject a tumor-associated antigen antibody, bispecific antibody, or TFP T-cell of the present invention such that the cancer is treated in the subject. An example of a cancer that is treatable by the tumor-associated antigen TFP T-cell of the invention is a cancer associated with expression of tumor-associated antigen. In one aspect, the cancer is a myeloma. In one aspect, the cancer is a lymphoma. In one aspect, the cancer is colon cancer.

In some embodiments, tumor-associated antigen antibodies or TFP therapy can be used in combination with one or more additional therapies. In some instances, such additional therapies comprise a chemotherapeutic agent, e.g., cyclophosphamide. In some instances, such additional therapies comprise surgical resection or radiation treatment.

In one aspect, disclosed herein is a method of cellular therapy wherein T cells are genetically modified to express a TFP and the TFP-expressing T-cell is infused to a recipient in need thereof. The infused cell is able to kill tumor cells in the recipient. Unlike antibody therapies, TFP-expressing T cells are able to replicate in vivo resulting in long-term persistence that can lead to sustained tumor control. In various aspects, the T cells administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T-cell to the patient.

In some instances, disclosed herein is a type of cellular therapy where T cells are modified, e.g., by in vitro transcribed RNA, to transiently express a TFP and the TFP-expressing T-cell is infused to a recipient in need thereof. The infused cell is able to kill tumor cells in the recipient. Thus, in various aspects, the T cells administered to the patient, is present for less than one month, e.g., three weeks, two weeks, or one week, after administration of the T-cell to the patient.

Without wishing to be bound by any particular theory, the anti-tumor immunity response elicited by the TFP-expressing T cells may be an active or a passive immune response, or alternatively may be due to a direct vs indirect immune response. In one aspect, the TFP transduced T cells exhibit specific proinflammatory cytokine secretion and potent cytolytic activity in response to human cancer cells expressing the tumor-associated antigen, resist soluble tumor-associated antigen inhibition, mediate bystander killing and/or mediate regression of an established human tumor. For example, antigen-less tumor cells within a heterogeneous field of tumor-associated antigen-expressing tumor may be susceptible to indirect destruction by tumor-associated antigen-redirected T cells that has previously reacted against adjacent antigen-positive cancer cells.

In one aspect, the human TFP-modified T cells of the invention may be a type of vaccine for ex vivo immunization and/or in vivo therapy in a mammal. In one aspect, the mammal is a human.

With respect to ex vivo immunization, at least one of the following occurs in vitro prior to administering the cell into a mammal: i) expansion of the cells, ii) introducing a nucleic acid encoding a TFP to the cells or iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing a TFP disclosed herein. The TFP-modified cell can be administered to a mammalian recipient to provide a therapeutic benefit. The mammalian recipient may be a human and the TFP-modified cell can be autologous with respect to the recipient. Alternatively, the cells can be allogeneic, syngeneic or xenogeneic with respect to the recipient.

The procedure for ex vivo expansion of hematopoietic stem and progenitor cells is described, e.g., in U.S. Pat. No. 5,199,942, incorporated herein by reference, can be applied to the cells of the present invention. Other suitable methods are known in the art; therefore, the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the TFP-modified T cells of the invention are used in the treatment of diseases, disorders and conditions associated with expression of tumor-associated antigens. In certain aspects, the cells of the invention are used in the treatment of patients at risk for developing diseases, disorders and conditions associated with expression of tumor-associated antigens. Thus, the present invention provides methods for the treatment or prevention of diseases, disorders and conditions associated with expression of tumor-associated antigens comprising administering to a subject in need thereof, a therapeutically effective amount of the TFP-modified T cells of the invention.

In one aspect, the antibodies or TFP-T cells of the inventions may be used to treat a proliferative disease such as a cancer or malignancy or is a precancerous condition. In one aspect, the cancer is a myeloma. In one aspect, the cancer is a lymphoma. In one aspect, the cancer is a colon cancer. Further, a disease associated with tumor-associated antigen expression includes, but is not limited to, e.g., atypical and/or non-classical cancers, malignancies, precancerous conditions or proliferative diseases expressing tumor-associated antigens. Non-cancer related indications associated with expression of tumor-associated antigens vary depending on the antigen, but are not limited to, e.g., infectious disease, autoimmune disease, (e.g., lupus), inflammatory disorders (allergy and asthma) and transplantation.

The antibodies or TFP-modified T cells of the present invention may be administered either alone, or as a pharmaceutical composition in combination with diluents and/or with other components such as IL-2, IL-7, IL-12, IL-15 or other cytokines or cell populations.

The present invention also provides methods for inhibiting the proliferation or reducing a tumor-associated antigen-expressing cell population, the methods comprising contacting a population of cells comprising a tumor-associated antigen-expressing cell with an anti-tumor-associated antigen TFP-T-cell of the invention that binds to the tumor-associated antigen-expressing cell. In a specific aspect, the present invention provides methods for inhibiting the proliferation or reducing the population of cancer cells expressing tumor-associated antigen, the methods comprising contacting the tumor-associated antigen-expressing cancer cell population with an anti-tumor-associated antigen antibody or TFP-T-cell of the invention that binds to the tumor-associated antigen-expressing cell. In one aspect, the present invention provides methods for inhibiting the proliferation or reducing the population of cancer cells expressing tumor-associated antigen, the methods comprising contacting the tumor-associated antigen-expressing cancer cell population with an anti-tumor-associated antigen antibody or TFP-T-cell of the invention that binds to the tumor-associated antigen-expressing cell. In certain aspects, the anti-tumor-associated antigen antibody or TFP-T-cell of the invention reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model for multiple myeloma or another cancer associated with tumor-associated antigen-expressing cells relative to a negative control. In one aspect, the subject is a human.

The present invention also provides methods for preventing, treating and/or managing a disease associated with tumor-associated antigen-expressing cells (e.g., a cancer expressing tumor-associated antigen), the methods comprising administering to a subject in need an anti-tumor-associated antigen antibody or TFP-T-cell of the invention that binds to the tumor-associated antigen-expressing cell. In one aspect, the subject is a human. Non-limiting examples of disorders associated with tumor-associated antigen-expressing cells include autoimmune disorders (such as lupus), inflammatory disorders (such as allergies and asthma) and cancers (such as hematological cancers or atypical cancers expressing tumor-associated antigen).

The present invention also provides methods for preventing, treating and/or managing a disease associated with tumor-associated antigen-expressing cells, the methods comprising administering to a subject in need an anti-tumor-associated antigen antibody or TFP-T-cell of the invention that binds to the tumor-associated antigen-expressing cell. In one aspect, the subject is a human.

The present invention provides methods for preventing relapse of cancer associated with tumor-associated antigen-expressing cells, the methods comprising administering to a subject in need thereof an anti-tumor-associated antigen antibody and/or TFP-T-cell of the invention that binds to the tumor-associated antigen-expressing cell. In one aspect, the methods comprise administering to the subject in need thereof an effective amount of an anti-tumor-associated antigen antibody or TFP-T-cell described herein that binds to the tumor-associated antigen-expressing cell in combination with an effective amount of another therapy.

Combination Therapies

An antibody or TFP-expressing cell described herein may be used in combination with other known agents and therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

Anti-Cancer Antibodies for Combination Therapies with CD16 TFP T Cells

The CD16 TFPs disclosed herein are administered in combination with an anti-cancer antibody. Any IgG1 or IgG4 anti-cancer antibody against a tumor-associated antigen expressed on the surface of a tumor cell is suitable for use in the combinations and methods disclosed herein. Such antibodies include, but are not limited to, antibodies against 5T4, 8H9, $\alpha v \beta \theta$ integrin, $\alpha v \beta \theta$ integrin, alphafetoprotein (AFP), B7-H6, CA-125 carbonic anhydrase 9 (CA9), CD19, CD20, CD22, CD30, CD33, CD38, CD44, CD44v6, CD44v7/8, CD52, CD123, CD171, carcinoembryonic antigen (CEA), EpCAM (epithelial cell adhesion molecule), E-cadherin, EMA (epithelial membrane antigen), EGFRvIII, epithelial glycoprotein-2 (EGP-2), epithelial glycoprotein-40 (EGP-40), ErbB1/EGFR, ErbB2/HER2/neu/EGFR2, ErbB3/HER3, ErbB4, epithelial tumor antigen (ETA), folate binding protein (FBP), fetal acetylcholine receptor (AchR), folate receptor-$\alpha$, G250/CAIX, ganglioside 2 (GD2), ganglioside 3 (GD3), HLA-A1, HLA-A2, high molecular weight melanoma-associated antigen (HMW-MAA), IL-13 receptor $\alpha 2$ (IL-13Ru2), kinase insert domain receptor (KDR), k-light chain, Lewis Y (LeY), L1 cell adhesion molecule, melanoma-associated antigen (MAGE-A1), mesothelin, mucin-1 (MUC1), mucin-16 (MUC16), natural killer group 2 member D (NKG2D) ligands, nerve cell adhesion molecule (NCAM), CTLA-4, PD-1, PD-L1, NY-ESO-1, oncofetal antigen (h5T4), prostate stem cell antigen (PSCA), prostate-specific membrane antigen (PSMA), receptor-tyrosine kinase-like orphan receptor 1 (ROR1), TAA targeted by mAb IgE, tumor-associated glycoprotein-72 (TAG-72), tyrosinase, and vascular endothelial growth factor (VEGF) receptors. In one embodiment, the tumor-associated antigen is an antigen not expressed on the cell surface of cells of normal (i.e., non-cancerous) tissue. In another embodiment, the tumor-associated antigen is expressed on the cell surface of cells of normal tissue at a much lower level (e.g., fewer receptors per cell) than the antigen is expressed on tumor cells.

Other Combinations

In some embodiments, the "at least one additional therapeutic agent" includes a TFP-expressing cell. Also provided are T cells that express multiple TFPs, which bind to the same or different target antigens, or same or different epitopes on the same target antigen. Also provided are populations of T cells in which a first subset of T cells expresses a first TFP and a second subset of T cells express a second TFP.

A TFP-expressing cell described herein and the at least one additional therapeutic agent can be administered simultaneously, in the same or in separate compositions, or sequentially. For sequential administration, the TFP-expressing cell described herein can be administered first, and the additional agent can be administered second, or the order of administration can be reversed.

In further aspects, a TFP-expressing cell described herein may be used in a treatment regimen in combination with surgery, chemotherapy, radiation, immunosuppressive agents, such as cyclosporin, azathioprine, methotrexate, mycophenolate, antibodies, or other immunoablative agents such as alemtuzumab, anti-CD3 antibodies or other antibody therapies, cyclophosphamide, fludarabine, cyclosporin, tacrolimus (fujimycin), rapamycin, mycophenolic acid, steroids, romidepsin (also known as FR901228), cytokines, and irradiation. peptide vaccine, such as that described in Izumoto et al. 2008 J Neurosurg 108:963-971.

In one embodiment, the subject can be administered an agent which reduces or ameliorates a side effect associated with the administration of a TFP-expressing cell. Side effects associated with the administration of a TFP-expressing cell include, but are not limited to cytokine release syndrome (CRS), and hemophagocytic lymphohistiocytosis (HLH), also termed Macrophage Activation Syndrome (MAS). Symptoms of CRS include high fevers, nausea, transient hypotension, hypoxia, and the like. Accordingly, the methods described herein can comprise administering a TFP-expressing cell described herein to a subject and further administering an agent to manage elevated levels of a soluble factor resulting from treatment with a TFP-expressing cell. In one embodiment, the soluble factor elevated in the subject is one or more of IFN-γ, TNFα, IL-2, IL-6, and IL-8. Therefore, an agent administered to treat this side effect can be an agent that neutralizes one or more of these soluble factors. Such agents include, but are not limited to a steroid, an inhibitor of TNFα, and an inhibitor of IL-6. An example of a TNFα inhibitor is etanercept (marketed under the name ENBREL®). An example of an IL-6 inhibitor is tocilizumab (marketed under the name ACTEMRA®).

In one embodiment, the subject can be administered an agent which enhances the activity of a TFP-expressing cell. For example, in one embodiment, the agent can be an agent which inhibits an inhibitory molecule. Inhibitory molecules, e.g., Programmed Death 1 (PD1), can, in some embodiments, decrease the ability of a TFP-expressing cell to mount an immune effector response. Examples of inhibitory molecules include PD1, PD-L1, CTLA4, TIM3, LAG3, VISTA, BTLA, TIGIT, LAIR1, CD160, 2B4 and TGFR beta. Inhibition of an inhibitory molecule, e.g., by inhibition at the DNA, RNA or protein level, can optimize a TFP-expressing cell performance. In embodiments, an inhibitory nucleic acid, e.g., an inhibitory nucleic acid, e.g., a dsRNA, e.g., an siRNA or shRNA, can be used to inhibit expression of an inhibitory molecule in the TFP-expressing cell. In an embodiment, the inhibitor is a shRNA. In an embodiment, the inhibitory molecule is inhibited within a TFP-expressing cell. In these embodiments, a dsRNA molecule that inhibits expression of the inhibitory molecule is linked to the nucleic acid that encodes a component, e.g., all of the components, of the TFP. In one embodiment, the inhibitor of an inhibitory signal can be, e.g., an antibody or antibody fragment that binds to an inhibitory molecule. For example, the agent can be an antibody or antibody fragment that binds to PD1, PD-L1, PD-L2 or CTLA4 (e.g., ipilimumab (also referred to as MDX-010 and MDX-101, and marketed as YERVOY®); Bristol-Myers Squibb; tremelimumab (IgG2 monoclonal antibody available from Pfizer, formerly known as ticilimumab, CP-675,206)). In an embodiment, the agent is an antibody or antibody fragment that binds to T-cell immunoglobulin and mucin-domain containing-3 (TIM3). In an embodiment, the agent is an antibody or antibody fragment that binds to Lymphocyte-activation gene 3 (LAG3).

In some embodiments, an agent suitable for use in combination with the TFP T cells disclosed herein is an agent that modulates myeloid suppressor cells, e.g., CCR2 antibodies. Other therapeutics, e.g, nanoparticle therapeutics, are known in the art.

In some embodiments, the agent which enhances the activity of a TFP-expressing cell can be, e.g., a fusion protein comprising a first domain and a second domain, wherein the first domain is an inhibitory molecule, or fragment thereof, and the second domain is a polypeptide that is associated with a positive signal, e.g., a polypeptide comprising an intracellular signaling domain as described herein. In some embodiments, the polypeptide that is associated with a positive signal can include a costimulatory domain of CD28, CD27, ICOS, e.g., an intracellular signaling domain of CD28, CD27 and/or ICOS, and/or a primary signaling domain, e.g., of CD3 zeta, e.g., described herein.

In one embodiment, the fusion protein is expressed by the same cell that expressed the TFP. In another embodiment, the fusion protein is expressed by a cell, e.g., a T-cell that does not express an anti-tumor-associated antigen TFP.

Pharmaceutical Compositions

Pharmaceutical compositions of the present invention may comprise a TFP-expressing cell, e.g., a plurality of TFP-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one embodiment, the pharmaceutical composition is substantially free of, e.g., there are no detectable levels of a contaminant, e.g., selected from the group consisting of endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, in some instances $10^5$ to $10^6$ cells/kg body weight, including all integer values within those ranges. T-cell compositions may also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain aspects, T cells can be activated from blood draws of from 10 cc to 400 cc. In certain aspects, T cells are activated from blood draws of 20 cc, 30 cc, 40 cc, 50 cc, 60 cc, 70 cc, 80 cc, 90 cc, or 100 cc.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, by intravenous (i.v.) injection, or intraperitoneally. In one aspect, the T-cell compositions of the present invention are administered to a patient by intradermal or subcutaneous injection. In one aspect, the T-cell compositions of the present invention are administered by i.v. injection. The compositions of T cells may be injected directly into a tumor, lymph node, or site of infection.

In a particular exemplary aspect, subjects may undergo leukapheresis, wherein leukocytes are collected, enriched, or depleted ex vivo to select and/or isolate the cells of interest, e.g., T cells. These T-cell isolates may be expanded by methods known in the art and treated such that one or more TFP constructs of the invention may be introduced, thereby creating a TFP-expressing T-cell of the invention. Subjects in need thereof may subsequently undergo standard treatment with high dose chemotherapy followed by peripheral blood stem cell transplantation. In certain aspects, following or concurrent with the transplant, subjects receive an infusion of the expanded TFP T cells of the present invention. In an additional aspect, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for alemtuzumab (CAMPATH®), for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

In one embodiment, the TFP is introduced into T cells, e.g., using in vitro transcription, and the subject (e.g., human) receives an initial administration of TFP T cells of the invention, and one or more subsequent administrations of the TFP T cells of the invention, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the TFP T cells of the invention are administered to the subject (e.g., human) per week, e.g., 2, 3, or 4 administrations of the TFP T cells of the invention are administered per week. In one embodiment, the subject (e.g., human subject) receives more than one administration of the TFP T cells per week (e.g., 2, 3 or 4 administrations per week) (also referred to herein as a cycle), followed by a week of no TFP T cells administrations, and then one or more additional administration of the TFP T cells (e.g., more than one administration of the TFP T cells per week) is administered to the subject. In another embodiment, the subject (e.g., human subject) receives more than one cycle of TFP T cells, and the time between each cycle is less than 10, 9, 8, 7, 6, 5, 4, or 3 days. In one embodiment, the TFP T cells are administered every other day for 3 administrations per week. In one embodiment, the TFP T cells of the invention are administered for at least two, three, four, five, six, seven, eight or more weeks.

In one aspect, tumor-associated antigen TFP T cells are generated using lentiviral viral vectors, such as lentivirus. TFP-T cells generated that way will have stable TFP expression.

In one aspect, TFP T cells transiently express TFP vectors for 4, 5, 6, 7, 8, 9, 10, 11, 12, 13, 14, 15 days after transduction. Transient expression of TFPs can be effected by RNA TFP vector delivery. In one aspect, the TFP RNA is transduced into the T-cell by electroporation.

A potential issue that can arise in patients being treated using transiently expressing TFP T cells (particularly with murine scFv bearing TFP T cells) is anaphylaxis after multiple treatments.

Without being bound by this theory, it is believed that such an anaphylactic response might be caused by a patient developing humoral anti-TFP response, i.e., anti-TFP antibodies having an anti-IgE isotype. It is thought that a patient's antibody producing cells undergo a class switch from IgG isotype (that does not cause anaphylaxis) to IgE isotype when there is a ten- to fourteen-day break in exposure to antigen.

If a patient is at high risk of generating an anti-TFP antibody response during the course of transient TFP therapy (such as those generated by RNA transductions), TFP T-cell infusion breaks should not last more than ten to fourteen days.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein. Without further description, it is believed that one of ordinary skill in the art can, using the preceding description and the following illustrative examples, make and utilize the compounds of the present invention and practice the claimed methods. The following working examples specifically point out various aspects of the present invention, and are not to be construed as limiting in any way the remainder of the disclosure.

Example 1: TFP Constructs

Anti-TAA TFP constructs are engineered by cloning one or more anti-TAA scFv DNA fragment or CD16 fragment linked to a CD3 or TCR DNA fragment by either a DNA sequence encoding a short linker (SL): AAA GGGGSGGGGSGGGGSLE (SEQ ID NO:2) or a long linker (LL): AAAIEVMYPPPYLGGGGSGG GGSGGGGSLE (SEQ ID NO:3) into, e.g., p510 vector ((System Biosciences (SBI)) at XbaI and EcoR1 sites. CAR constructs are generated by cloning synthesized DNA encoding an anti-TAA antibody (e.g., NKG2D or anti-ROR1), partial CD28 extracellular domain, CD28 transmembrane domain, CD28 intracellular domain and CD3 zeta into, e.g., a p510 vector at XbaI and EcoR1 sites. CD3ε TFP constructs disclosed herein comprise the sequence set forth in SEQ ID NO:97, which has an N-terminal truncation in reference to the full sequence (SEQ ID NO:4).

The anti-ROR1, NKG2D, etc. TFPs are generated as described above. For example, the anti-ROR1TFP constructs generated are p510_antiROR1_LL_TCRα (anti- ROR1 scFv-long linker-human full length T cell receptor α chain), p510_antiROR1_LL_TCR αC (anti-ROR1 scFv-long linker-human T cell receptor α constant domain chain), p510_antiROR1 LL_TCRβ (anti-ROR1 scFv-long linker-human full length T cell receptor β chain), p510_antiROR1LL_TCRβC (anti-ROR1 scFv-long linker-human T cell receptor β constant domain chain), p510_antiROR1_LL_CD3γ (anti-ROR1 scFv-long linker-human CD3γ chain), p510_antiROR1_LL_CD3☐ (anti-ROR1 scFv-long linker-human CD3☐ chain), p510_antiROR1_LL_CD3ε (anti-ROR1 scFv-long linker-human CD3ε chain), p510_antiROR1_SL_TCRβ (anti-ROR1 scFv-short linker-human full length T cell receptor β chain), p510_antiROR1_SL_CD3γ (anti-ROR1 scFv-short linker-human CD3γ chain), p510_antiROR1_SL_CD3☐ (anti-ROR1 scFv-short linker-human CD3☐ chain), p510_antiROR1_SL_CD3ε (anti-ROR1 scFv-short linker-human CD3β chain).

The anti-ROR1 CAR construct, p510_antiROR1_28 is generated by cloning synthesized DNA encoding anti-ROR1, partial CD28 extracellular domain, CD28 transmembrane domain, CD28 intracellular domain and CD3 zeta into p510 vector at XbaI and EcoR1 sites.

Dual specificity TFP constructs wherein both scFvs are expressed in the same TCR are engineered. In one embodiment, a first anti-tumor antigen scFv DNA fragment is linked to a CD3 or TCR DNA fragment by either a DNA sequence encoding a short linker (SL): AAAGGGGSGGGGSGGGGSLE or a long linker (LL): AAAIEVMYPPPYLGGGGSGGGGSGGGGSLE into p510 vector ((System Biosciences (SBI)) at XbaI and EcoR1 sites. In another embodiment, a second anti-tumor antigen scFv DNA fragment is operatively linked to the first anti-tumor antigen fragment by a SL or LL.

In another embodiment, a first anti-tumor antigen scFv DNA fragment is linked to a first CD3 or TCR fragment by either a DNA sequence encoding a SL or an LL in a first expression construct, and a second anti-tumor antigen scFv DNA fragment is linked to a first CD3 or TCR fragment by either a DNA sequence encoding a SL or an LL in a second expression construct. For example, an anti-CD20 or anti-CD22 antigen scFv DNA fragment is operatively connected to a CD3β DNA fragment, and an anti-CD19 scFv DNA fragment is operatively connected to a CD3γ scFv DNA fragment, each in its own viral expression construct. Any combination of CD3 subunits may be used, such as CD3ε/CD3ε, CD3ε/CD3β, CD3ε/CD3δ, CD3ε/CD3α and the like.

Figure 1B:
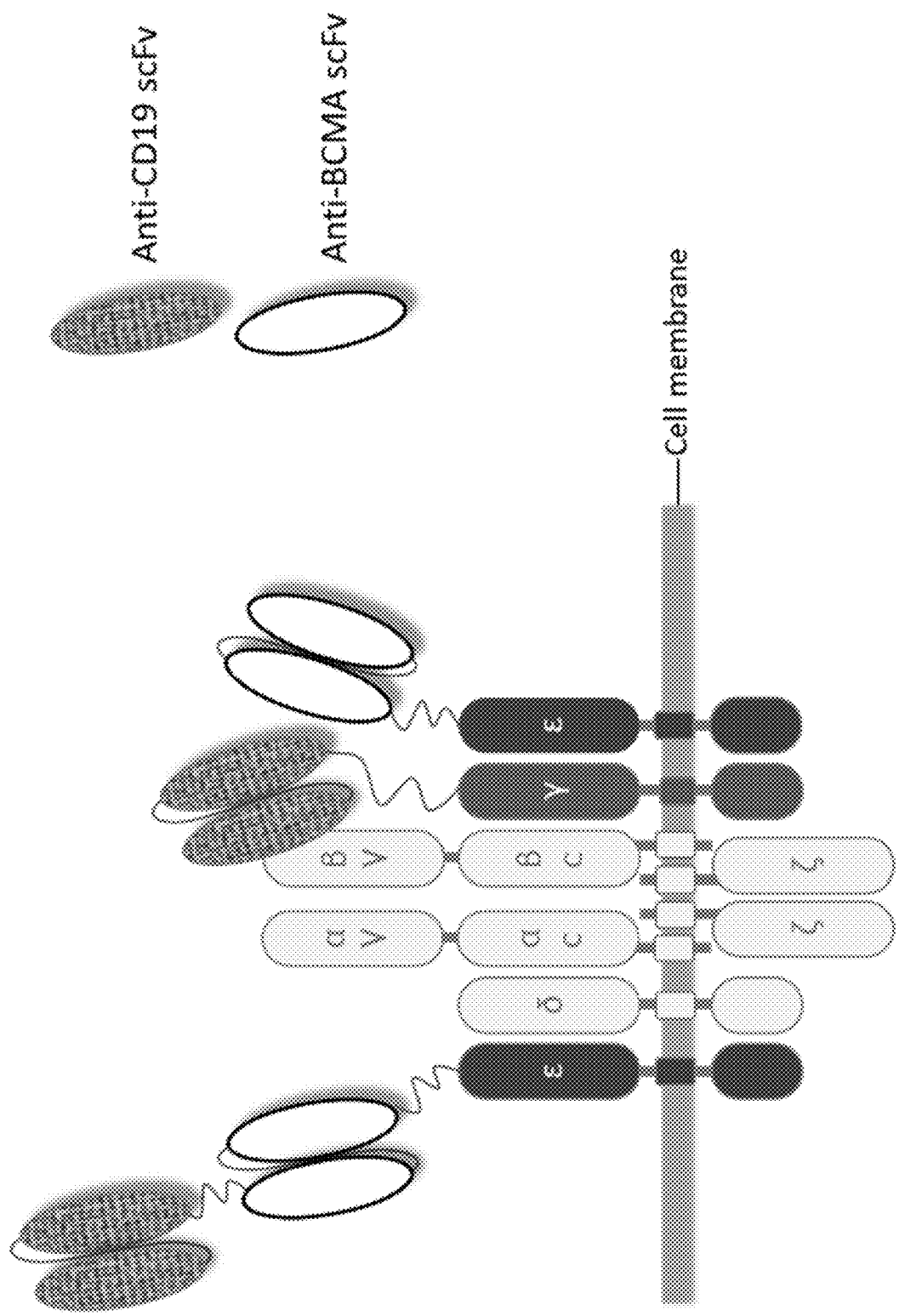
FIG. 1B is a drawing showing two exemplary ways a single TCR is engineered to have dual specificity. The TCR subunits, epsilon, delta, alpha, beta, gamma, and epsilon are shown from left to right along the cell membrane. White ovals represent anti-BCMA scFvs, and textured ovals represent anti-CD19 scFvs. In one embodiment, the scFvs are operatively connected to each other via a first linker and operatively connected to the TCR via a second linker connected to, e.g., an epsilon subunit (shown on left epsilon subunit in the figure). In another embodiment, the scFvs are each operatively connected to a TCR subunit; shown in this example are an anti-CD19 scFv operatively connected via a linker to the gamma subunit, and an anti-BCMA scFv operatively connected via a linker to an epsilon subunit (shown on the gamma and right epsilon in the figure).

In one embodiment, both viral expression constructs are used to transduce the same population of T cells such that one population of T cells will have TFPs specific to more than one tumor-associated antigen. In another embodiment, the viral expression constructs are each used to transduce a separate population of T cells, and the two populations of transduced T cells are then mixed before using. Exemplary strategies of producing dual specificity T cell populations are shown in FIGS. 1A and 1B.

In one embodiment, an anti-tumor-associated antigen CAR construct is generated as a comparator. A p510_antitumor-associated antigen_28ζ CAR is generated by cloning synthesized DNA encoding anti-tumor-associated antigen, partial CD28 extracellular domain, CD28 transmembrane domain, CD28 intracellular domain and CD3 zeta into p510 vector at XbaI and EcoR1 sites.

Anti-BCMA TFP constructs were engineered by cloning an anti-BCMA scFv DNA fragment linked to a CD3 DNA fragment by a DNA sequence encoding the linker: GGGGSGGGGSGGGGSLE (SEQ ID NO: 1) into p510 vector (SBI) at XbaI and EcoR1 sites. The anti-BCMA TFP constructs generated were p510_antiBCMA_CD3γ (anti-BCMA scFv (or $V_H$H)-linker-human CD3γ chain) and p510_anti-BCMA_CD3ε (anti-BCMA scFv (or $V_H$H)-linker-human CD3ε chain).

Full length BCMA was synthesized and cloned into p514 (SBI) at BamHI and NheI sites to generate the construct p514BCMA, used to generate stable target cell lines.

Anti-CD19 TFP constructs were engineered by cloning an anti-CD19 scFv DNA fragment linked to a CD3 or TCR DNA fragment by either a DNA sequence encoding a short linker (SL): AAAGGGGSGGGGSGGGGSLE (SEQ ID NO:2) or a long linker (LL): AAAIEVMYPP-PYLGGGGSGGGGSGGGGSLE (SEQ ID NO:3) into p510 vector ((System Biosciences (SBI)) at XbaI and EcoR1 sites.

The anti-CD19 TFP constructs generated were p510_antiCD19_LL_TCRα (anti-CD19 scFv-long linker-human full length T cell receptor α chain), p510_antiCD19_LL_TCR αC (anti-CD19 scFv-long linker-human T cell receptor α constant domain chain), p510_antiCD19 LL_TCRβ (anti-CD19 scFv-long linker-human full length T cell receptor β chain), p510_antiCD19_LL_TCRβC (anti-CD19 scFv-long linker-human T cell receptor β constant domain chain), p510_antiCD19_LL_CD3γ (anti-CD19 scFv-long linker-human CD3γ chain), p510_antiCD19_LL_CD3δ (anti-CD19 scFv-long linker-human CD3δ chain), p510_antiCD19_LL_CD3ε (anti-CD19 scFv-long linker-human CD3ε chain), p510_antiCD19_SL_TCRβ (anti-CD19 scFv-short linker-human full length T cell receptor β chain), p510_antiCD19_SL_CD3γ (anti-CD19 scFv-short linker-human CD3γ chain), p510_antiCD19_SL_CD3γ (anti-CD19 scFv-short linker-human CD3γ chain), p510_antiCD19_SL_CD3ε (anti-CD19 scFv-short linker-human CD3ε chain).

The anti-CD19 CAR construct, p510_antiCD19_28 was generated by cloning synthesized DNA encoding anti-CD19, partial CD28 extracellular domain, CD28 transmembrane domain, CD28 intracellular domain and CD3 zeta into p510 vector at XbaI and EcoR1 sites.

Exemplary construct sequences encoding anti-BCMA, anti-CD19, anti-CAIX, and anti-FAP constructs are disclosed in co-pending International Patent Application No. PCT/US2016/033416, incorporated herein by reference.

Anti-CD22 TFP constructs were engineered by cloning an anti-CD22 scFv DNA fragment linked to a CD3 or TCR DNA fragment by either a DNA sequence encoding a short linker (SL): AAAGGGGSGGGGSGGGGSLE or a long linker (LL): AAAIEVMYPP-PYLGGGGSGGGGSGGGGSLE into p510 vector ((System Biosciences (SBI)) at XbaI and EcoR1 sites.

Example 2: Antibody Sequences

Generation of Antibody Sequences

Provided are antibody polypeptides that are capable of specifically binding to the human TAA polypeptide(s), and fragments or domains thereof. Anti-TAA antibodies can be generated using diverse technologies (see, e.g., (Nicholson et al, 1997). Where murine anti-TAA antibodies are used as a starting material, humanization of murine anti-TAA antibodies is desired for the clinical setting, where the mouse-specific residues may induce a human-anti-mouse antigen (HAMA) response in subjects who receive T-cell receptor (TCR) fusion protein (TFP) treatment, i.e., treatment with T cells transduced with the TFP.TAA construct. Humanization is accomplished by grafting CDR regions from murine anti-TAA antibody onto appropriate human germline acceptor frameworks, optionally including other modifications to CDR and/or framework regions. As provided herein, antibody and antibody fragment residue numbering follows Kabat (Kabat E. A. et al, 1991; Chothia et al, 1987).

The human BCMA polypeptide canonical sequence is UniProt Accession No. Q02223. The human ROR1 polypeptide canonical sequence is UniProt Accession No. Q01973-1. The human NKG2D polypeptide canonical sequence is UniProt Accession No. P26718-1 (isoform 1). Provided are polypeptides that are capable of specifically binding to the Fc portion of human IgGs, and fragments or domains thereof.

Generation of scFvs

Human or humanized anti-TAA IgGs are used to generate scFv sequences for TFP constructs. DNA sequences coding for human or humanized $V_L$ and $V_H$ domains are obtained, and the codons for the constructs are, optionally, optimized for expression in cells from Homo sapiens. The order in which the $V_L$ and $V_H$ domains appear in the scFv is varied (i.e., $V_L$-$V_H$, or $V_H$-$V_L$ orientation), and three copies of the "G4S" or "G$_4$S" subunit (G$_4$S)$_3$ connect the variable domains to create the scFv domain. Anti-BCMA scFv plasmid constructs can have optional Flag, His or other affinity tags, and are electroporated into HEK-293 or other suitable human or mammalian cell lines and purified. Validation assays include binding analysis by FACS, kinetic analysis using Proteon, and staining of TAA-expressing cells.

Exemplary anti-ROR1 VL and VH domains, CDRs, and the nucleotide sequences encoding them, can be those described in U.S. Pat. No. 9,316,646, U.S. Patent Publication No. 2016/0208018, and international Patent Publication No. WO2016016344, each of which is entirely incorporated herein by reference. Other exemplary anti-ROR1 VL and VH domains, CDRs, and the nucleotide sequences encoding them, respectively, can be those of the following monoclonal antibodies: mouse anti-ROR1 antibody 2H6, mouse anti-ROR1 antibody 2A2, and the following polyclonal antibodies: anti-ROR1 goat anti-ROR1 antibody Catalog Number: AF2000 (R&D Systems), Antibody No. ABIN2869437, mouse anti-ROR1 Antibody No. ABIN969385, anti-ROR1 Antibody No. ABIN1108893, and rabbit polyclonal anti-ROR1 antibody Cat. No. ABIN359929 (Antibodies Online).

Exemplary anti-BMCA and anti-CD19 antibodies are disclosed in co-pending International Patent Publication No. WO/2016/187349, herein incorporated by reference. Exemplary anti-BMCA and anti-CD19 CDRs of $V_L$ and $V_H$ domains and the nucleotide sequences encoding them, respectively, are shown below:

CD16 Binders

In some embodiments, CD16 TFPs disclosed herein comprise the amino acid sequence set forth in SEQ ID NO:23. In other embodiments, CD16 TFPs disclosed herein comprise the extracellular domain of CD16 only, as set forth in SEQ ID NO: 106.

Anti-ROR1

In some embodiments, the antibodies or fragments thereof disclosed herein comprise single domain antibodies (sdAbs) such as camelids. In one embodiment, the anti-ROR1 sdAbs for use in the TFP constructs disclosed herein are encoded by any one of SEQ ID Nos: 80-96. In other embodiments, the anti-ROR1 antibodies or fragments thereof are scFvs. An exemplary anti-ROR1 binder is encoded by SEQ ID NO:65, which encodes scFv "2-7" in the orientation VH_linker_VL. Another exemplary binder is encoded by NO:69, which encodes scFv "2-9" in the orientation VH_linker_VL. Another exemplary binder is encoded by NO:79, which encodes scFv "3-6" in the orientation VL linker VH.

NKG2D Binders of NKG2D Ligand (NKG2DL)

In some embodiments, the NKG2DL binder is a monomer, e.g., one that is encoded by the sequence set forth in SEQ ID NO: 107. In other embodiments, the NKG2DL binder is a dimer, e.g., one that is encoded by the sequence set forth in SEQ ID NO:108.

Anti-CD19

Anti-CD19 light chain CDR1
Coding Sequence:
(SEQ ID NO: 25)
AGGGCAAGTCAGGACATTAGTAAA Amino acid sequence:
(SEQ ID NO: 26)
RASQDISK Anti-CD19 light chain CDR2
Coding Sequence:
(SEQ ID NO: 27)
ATCTACCATACATCAAGATTA Amino acid sequence:
(SEQ ID NO: 28)
IYHTSRL Anti-CD19 light chain CDR3
Coding Sequence:
(SEQ ID NO: 29)
CAACAGGGTAATACGCTTCCGTACACG Amino acid sequence:
(SEQ ID NO: 30)
QQGNTLPYT Anti-CD19 heavy chain CDR1
Coding Sequence:
(SEQ ID NO: 31)
GGGGTCTCATTACCCGACTATGGTGTAAGC Amino acid sequence:
(SEQ ID NO: 32)
GVSLPDYGVS Anti-CD19 heavy chain CDR2
Coding Sequence:
(SEQ ID NO: 33)
GTAATATGGGGTAGTGAAACCACATACTATAATTCAGCTCTC Amino acid sequence:
(SEQ ID NO: 34)
VIWGSETTYYNSAL Anti-CD19 heavy chain CDR3
Coding Sequence:
(SEQ ID NO: 35)
CATTATTACTACGGTGGTAGCTATGCTATGGACTAC Amino acid sequence:
(SEQ ID NO: 36)
HYYYGGSYAMDY Anti-CD19 light chain variable region
Coding Sequence:
(SEQ ID NO: 37)
GACATCCAGATGACACAGACTACATCCTCCCTGTCTGCCTCTCTGGGAGA

CAGAGTCACCATCAGTTGCAGGGCAAGTCAGGACATTAGTAAATATTTAA

ATTGGTATCAGCAGAAACCAGATGGAACTGTTAAACTCCTGATCTACCAT

ACATCAAGATTACACTCAGGAGTCCCATCAAGGTTCAGTGGCAGTGGGTC

TGGAACAGATTATTCTCTCACCATTAGCAACCTGGAGCAAGAAGATATTG

CCACTTACTTTTGCCAACAGGGTAATACGCTTCCGTACACGTTCGGAGGG

GGGACTAAGTTGGAAATAACA

-continued

Amino acid sequence:
(SEQ ID NO: 38)
DIQMTQTTSSLSASLGDRVTISCRASQDISKYLNWYQQKPDGTVKLLIYH

TSRLHSGVPSRFSGSGSGTDYSLTISNLEQEDIATYFCQQGNTLPYTFGG

GTKLEIT

Anti-CD19 heavy chain variable region
Coding Sequence:
(SEQ ID NO: 39)
GAGGTGAAACTGCAGGAGTCAGGACCTGGCCTGGTGGCGCCCTCACAGAG

CCTGTCCGTCACATGCACTGTCTCAGGGGTCTCATTACCCGACTATGGTG

TAAGCTGGATTCGCCAGCCTCCACGAAAGGGTCTGGAGTGGCTGGGAGTA

ATATGGGGTAGTGAAACCACATACTATAATTCAGCTCTCAAATCCAGACT

GACCATCATCAAGGACAACTCCAAGAGCCAAGTTTTCTTAAAAATGAACA

GTCTGCAAACTGATGACACAGCCATTTACTACTGTGCCAAACATTATTAC

TACGGTGGTAGCTATGCTATGGACTACTGGGGTCAAGGAACCTCAGTCAC

CGTCTCCTCA

Amino acid sequence:
(SEQ ID NO: 40)
EVKLQESGPGLVAPSQSLSVTCTVSGVSLPDYGVSWIRQPPRKGLEWLGV

IWGSETTYYNSALKSRLTIIKDNSKSQVFLKMNSLQTDDTAIYYCAKHYY

YGGSYAMDYWGQGTSVTVSS

Anti-BCMA

Anti-BCMA light chain CDR1
Coding Sequence:
(SEQ ID NO: 41)
AAAAGCAGCCAGAGCCTGGTGCATAGCAACGGCAACACCTATCTGCAT Amino acid sequence:
(SEQ ID NO: 42)
KSSQSLVHSNGNTYLH Anti-BCMA light chain CDR2
Coding Sequence:
(SEQ ID NO: 43)
AAAGTGAGCAACCGCTTTAGC Amino acid sequence:
(SEQ ID NO: 44)
KVSNRFS Anti-BCMA light chain CDR3
Coding Sequence:
(SEQ ID NO: 45)
GCGGAAACCAGCCATGTGCCGTGGACC Amino acid sequence:
(SEQ ID NO: 46)
AETSHVPWT Anti-BCMA heavy chain CDR1
Coding Sequence:
(SEQ ID NO: 47)
AAAGCGAGCGGCTATAGCTTTCCGGATTATTATATTAAC Amino acid sequence:
(SEQ ID NO: 48)
KASGYSFPDYYIN Anti-BCMA heavy chain CDR2
Coding Sequence:
(SEQ ID NO: 49)
TGGATTTATTTTGCGAGCGGCAACAGCGAATATAACCAGAAATTTACCGG
C -continued Amino acid sequence:
(SEQ ID NO: 50)
WIYFASGNSEYNQKFTG Anti-BCMA heavy chain CDR3
Coding Sequence:
(SEQ ID NO: 51)
CTGTATGATTATGATTGGTATTTTGATGTG Amino acid sequence:
(SEQ ID NO: 52)
LYDYDWYFDV Anti-BCMA heavy chain variable region
Coding Sequence:
(SEQ ID NO: 53)
CAGGTGCAGCTGGTGCAGAGCGGCGCGGAAGTGAAAAAACCGGGCGCGAG

CGTGAAAGTGAGCTGCAAAGCGAGCGGCTATAGCTTTCCGGATTATTATA

TTAACTGGGTGCGCCAGGCGCCGGGCCAGGGCCTGGAATGGATGGGCTGG

ATTTATTTTGCGAGCGGCAACAGCGAATATAACCAGAAATTTACCGGCCG

CGTGACCATGACCCGCGATACCAGCAGCAGCACCGCGTATATGGAACTGA

GCAGCCTGCGCAGCGAAGATACCGCGGTGTATTTTTGCGCGAGCCTGTAT

GATTATGATTGGTATTTTGATGTGTGGGGCCAGGGCACCATGGTGACCGT

GAGCAGC

Amino acid sequence:
(SEQ ID NO: 54)
QVQLVQSGAEVKKPGASVKVSCKASGYSFPDYYINWVRQAPGQGLEWMGW

IYFASGNSEYNQKFTGRVTMTRDTSSSTAYMELSSLRSEDTAVYFCASLY

DYDWYFDVWGQGTMVTVSS

Anti-BCMA light chain variable region
Coding Sequence:
(SEQ ID NO: 55)
GATATTGTGATGACCCAGACCCCGCTGAGCCTGAGCGTGACCCCGGGCGA

ACCGGCGAGCATTAGCTGCAAAAGCAGCCAGAGCCTGGTGCATAGCAACG

GCAACACCTATCTGCATTGGTATCTGCAGAAACCGGGCCAGAGCCCGCAG

CTGCTGATTTATAAAGTGAGCAACCGCTTTAGCGGCGTGCCGGATCGCTT

TAGCGGCAGCGGCAGCGGCGCGGATTTTACCCTGAAAATTAGCCGCGTGG

AAGCGGAAGATGTGGGCGTGTATTATTGCGCGGAAACCAGCCATGTGCCG

TGGACCTTTGGCCAGGGCACCAAACTGGAAATTAAAAGC

Amino acid sequence:
(SEQ ID NO: 56)
DIVMTQTPLSLSVTPGEPASISCKSSQSLVHSNGNTYLHWYLQKPGQSPQ

LLIYKVSNRFSGVPDRFSGSGSGADFTLKISRVEAEDVGVYYCAETSHVP

WTFGQGTKLEIKS

Anti-CD22 Exemplary Sequences

Anti-CD22 light chain CDR1
Amino acid sequence:
(SEQ ID NO: 57)
QDIHGY

Anti-CD22 light chain CDR2
Amino acid sequence:
(SEQ ID NO: 58)
YTS

Anti-CD22 light chain CDR3
Amino acid sequence:
(SEQ ID NO: 59)
QQGNTLPWT

Anti-CD22 heavy chain CDR1
Amino acid sequence:
(SEQ ID NO: 60)
GFAFSIYD

Anti-CD22 heavy chain CDR2
Amino acid sequence:
(SEQ ID NO: 61)
ISSGGGTT

Anti-CD22 heavy chain CDR3
Amino acid sequence:
(SEQ ID NO: 62)
ARHSGYGTHWGVLFAY Anti-CD22 light chain variable region
Amino acid sequence:
(SEQ ID NO: 63)
EVQLVESGGGLVKPGGSLKLSCAASGFAFSIYDMSWVRQTPEKRLEWVAY

ISSGGGTTYYPDTVKGRFTISRDNAKNTLYLQMSSLKSEDTAMYYCARHS

GYGTHWGVLFAYWQGTLVTVSA

Anti-CD22 heavy chain variable region
Amino acid sequence:
(SEQ ID NO: 64)
GGSLAALTAHQACHLPLETFTRHRQPRGWEQLEQCGYPVQRLVALYLAAR

LSWNQVDQVIRNALASPGSGGDLGEAIREQPEQARLALTLAAAESERFVR

QGTGNDEAGAANGPADSGDALLERNYPTGAEFLGDGGDVSFSTRGTQNWT

VERLLQAHRQLEERGYVFVGYHGTFLEAAQSIVFGGVRARSQDLDAIWRG

FYIAGDPALAYGYAQDQEPDAAGRIRNGALLRVYVPRSSLPGFYRTSLTL

AAPEAAGEVERLIGHPLPLRLDAITGPEEEGGRLETILGWPLAERTVVIP

SAIPTDPRNVGGDLDPSSIPDKEQAISALPDYASQPGKPPREDLK

Source of TCR Subunits

Subunits of the human T Cell Receptor (TCR) complex all contain an extracellular domain, a transmembrane domain, and an intracellular domain. A human TCR complex contains the CD3-epsilon polypeptide, the CD3-gamma polypeptide, the CD3-delta polypeptide, the CD3-zeta polypeptide, the TCR alpha chain polypeptide and the TCR beta chain polypeptide. The human CD3-epsilon polypeptide canonical sequence is UniProt Accession No. P07766. The human CD3-gamma polypeptide canonical sequence is Uni-Prot Accession No. P09693. The human CD3-delta polypeptide canonical sequence is UniProt Accession No. P043234. The human CD3-zeta polypeptide canonical sequence is UniProt Accession No. P20963. The human TCR alpha chain canonical sequence is UniProt Accession No. Q6ISU1. The human TCR beta chain C region canonical sequence is UniProt Accession No. P01850, a human TCR beta chain V region sequence is P04435.

The human CD3-epsilon polypeptide canonical sequence is: MQSGTHWRVLGLCLLSVGVWGQDGNEEMG-GITQTPYKVSISGTTVILTCPQYPGSEILWQH NDKNIGGDEDDKNIGSD-EDHLSLKEFSELEQSGYYVCYPRGSKPEDANFYLYL-RARVCENC MEMDVMSVATIVIVDICITGGLLLL-VYYWSKNRKAKAKPVTRGAGAGGRQRGQNKERPPP VPNPDYEPIRKGQRDLYSGLNQRRI (SEQ ID NO:4). In one embodiment, the human CD3-epsilon fragment used in the TFPs is (SEQ ID NO: 97)
DGNEEMGGITQTPYKVSISGTTVILTCPQYPGSEILWQHNDKNIGGDEDD

KNIGSDEDHLSLKEFSELEQSGYYVCYPRGSKPEDANFYLYLRARVCENC

MEMDVMSVATIVIVDICITGGLLLLVYYWSKNRKAKAKPVTRGAGAGGRQ

RGQNKERPPPVPNPDYEPIRKGQRDLYSGLNQRRI

The human CD3-gamma polypeptide canonical sequence is: MEQGKGLAVLILAIILLQGT-LAQSIKGNHLVKVYDYQEDGSVLLTCDAEAKNIT-WFKDGKM IGFLTEDKKKWNLGSNAKDPRG-MYQCKGSQNKSKPLQVYYRMCQNCIELNAATISGFL-FA EIVSIFVLAVGVYFIAGQDGVRQSR-ASDKQTLLPNDQLYQPLK-DREDDQYSHLQGNQLRRN (SEQ ID NO:5). In one embodiment, the human CD3-gamma fragment used in the TFPs is:

(SEQ ID NO: 107)
QSIKGNHLVKVYDYQEDGSVLLTCDAEAKNITWFKDGKMIGFLTEDKKKWN

LGSNAKDPRGMYQCKGSQNKSKPLQVYYRMCQNCIELNAATISGFLFAEIV

SIFVLAVGVYFIAGQDGVRQSRASDKQTLLPNDQLYQPLKDREDDQYSHLQ

GNQLRRN.

The human CD3-delta polypeptide canonical sequence is: MEHSTFLSGLVLATLLSQVSPFKIPIEELEDRVFVNCN-TSITWVEGTVGTLLSDITRLDLGKRI LDPRGIYRC-NGTDIYKDKESTVQVHYRMCQSCVELD-PATVAGIIVTDVIATLLLALGVFCFA GHETGRLSGAADTQALLRNDQVYQPLRDRD-DAQYSHLGGNWARNK (SEQ ID NO:6). In one embodiment, the human CD3-delta fragment used in the TFPs is:

(SEQ ID NO: 108)
FKIPIEELEDRVFVNCNTSITWVEGTVGTLLSDITRLDLGKRILDPRGIYR

CNGTDIYKDKESTVQVHYRMCQSCVELDPATVAGIIVTDVIATLLLALGVF

CFAGHETGRLSGAADTQALLRNDQVYQPLRDRDDAQYSHLGGNWARNK

The human CD3-zeta polypeptide canonical sequence is: MKWKALFTAAILQAQLPITEAQSFGLLDPKLCYLL-DGILFIYGVLTALFLRVKFSRSADAPA YQQGGQNQLY-NELNLGRREEYDVLDKRR-GRDPEMGGKPQRRKNPQEGLYNELQKDKMAE AYSEIGMKGERRRGKGHDGLYQGLSTATKDTY-DALHMQALPPR (SEQ ID NO:7). In one embodiment, the human CD3-zeta fragment used in the TFPs is:

(SEQ ID NO: 109)
RVKFSRSADAPAYQQGQNQLYNELNLGRREEYDVLDKRRGRDPEMGGKPQR

RKNPQEGLYNELQKDKMAEAYSEIGMKGERRRGKGHDGLYQGLSTATKDTY

DALHMQALPPR

The human TCR alpha chain canonical sequence is:

(SEQ ID NO: 8)
MAGTWLLLLLALGCPALPTGVGGTPFPSLAPPIMLLVDGKQQMVVVCLVL

DVAPPGLDSPIWFSAGNGSALDAFTYGPSPATDGTWTNLAHLSLPSEELA

SWEPLVCHTGPGAEGHSRSTQPMHLSGEASTARTCPQEPLRGTPGGALWL

-continued

GVLRLLLFKLLLFDLLLTCSCLCDPAGPLPSPATTTRLRALGSHRLHPAT

ETGGREATSSPRPQPRDRRWGDTPPGRKPGSPVWGEGSYLSSYPTCPAQA

WCSRSALRAPSSSLGAFFAGDLPPPLQAGAA.

The human TCR alpha chain C region canonical sequence is:

(SEQ ID NO: 9)
PNIQNPDPAVYQLRDSKSSDKSVCLFTDFDSQTNVSQSKDSDVYITDKTV

LDMRSMDFKSNSAVAWSNKSDFACANAFNNSIIPEDTFFPSPESSCDVKL

VEKSFETDTNLNFQNLSVIGFRILLLKVAGFNLLMTLRLWSS

The human TCR alpha chain V region CTL-L17 canonical sequence is:

(SEQ ID NO: 10)
MAMLLGASVLILWLQPDWVNSQQKNDDQQVKQNSPSLSVQEGRISILNCD

YTNSMFDYFLWYKKYPAEGPTFLISISSIKDKNEDGRFTVFLNKSAKEIL

SLEIIVPSQPGDSAVYFCAAKGAGTASKLTFGTGTRLQVTL.

The human TCR beta chain C region canonical sequence is:

(SEQ ID NO: 11)
EDLNKVFPPEVAVFEPSEAEISHTQKATLVCLATGFFPDHVELSWWVNGK

EVHSGVSTDPQPLKEQPALNDSRYCLSSRLRVSATFWQNPRNHFRCQVQF

YGLSENDEWTQDRAKPVTQIVSAEAWGRADCGFTSVSYQQGVLSATILYE

ILLGKATLYAVLVSALVLMAMVKRKDF.

The human TCR beta chain V region CTL-L17 canonical sequence is:

(SEQ ID NO: 12)
MGTSLLCWMALCLLGADHADTGVSQNPREINITKRGQNVTFRCDPISEHN

RLYWYRQTLGQGPEFLTYFQNEAQLEKSRLLSDRFSAERPKGSFSTLEIQ

RTEQGDSAMYLCASSLAGLNQPQHFGDGTRLSIL.

The human TCR beta chain V region YT35 canonical sequence is:

(SEQ ID NO: 13)
MDSWTFCCVSLCILVAKHTDAGVIQSPREIEVTEMGQEVTLRCKPISGHN

SLFWYRQTMMRGLELLIYFNNNVPIDDSGMPEDRFSAKMPNASFSTLKIQ

PSEPRDSAVYFCASSFSTCSANYGYTFGSGTRLTVV.

Generation of TFPs from TCR Domains and scFvs

An exemplary dual specificity TFP is a TFP with scFvs with binding specificity to BCMA and CD19. Another exemplary dual specificity TFP is a TFP with scFvs with binding specificity to BCMA and CD20. Another exemplary dual specificity TFP is a TFP with scFvs with binding specificity to BCMA and CD22. Another exemplary dual specificity TFP is a TFP with scFvs with binding specificity to CD19 and CD22.

Anti-TAA scFvs (e.g., NKG2D, ROR1, etc.) are recombinantly linked to CD3-epsilon or other TCR subunits (see 1C) using a linker sequence, such as $G_4S$, $(G_4S)_2$ $(G_4S)_3$ or $(G_4S)_4$. Various linkers and scFv configurations are used. TCR alpha and TCR beta chains are used for generation of TFPs either as full-length polypeptides or as only their constant domains. Any variable sequence of TCR alpha and TCR beta chains is suitable for making TFPs.

CD19 scFvs are recombinantly linked to a second CD3-epsilon or other TCR subunit using a linker sequence as described above.

CD16 peptides are recombinantly linked to CD3-epsilon or other TCR subunits (see 1C) using a linker sequence, such as $G_4S$, $(G_4S)_2$ $(G_4S)_3$ or $(G_4S)_4$. Various linkers and scFv configurations are utilized. TCR alpha and TCR beta chains were used for generation of TFPs either as full-length polypeptides or only their constant domains. Any variable sequence of TCR alpha and TCR beta chains is allowed for making TFPs.

TFP Expression Vectors

Expression vectors are provided that include: a promoter (Cytomegalovirus (CMV) enhancer-promoter), a signal sequence to enable secretion, a polyadenylation signal and transcription terminator (Bovine Growth Hormone (BGH) gene), an element allowing episomal replication and replication in prokaryotes (e.g., SV40 origin and ColE1 or others known in the art) and elements to allow selection (ampicillin resistance gene and zeocin marker).

Preferably, the TFP-encoding nucleic acid construct or constructs is/are cloned into one or more lentiviral expression vectors and expression validated based on the quantity and quality of the effector T-cell response of transduced T cells in response to TAA+target cells. Effector T-cell responses include, but are not limited to, cellular expansion, proliferation, doubling, cytokine production and target cell lysis or cytolytic activity (i.e., degranulation).

The single or dual specificity TFP lentiviral transfer vectors are used to produce the genomic material packaged into the VSVg pseudotyped lentiviral particles. Lentiviral transfer vector DNA is mixed with the three packaging components of VSVg, gag/pol and rev in combination with Lipofectamine® reagent to transfect them together into 293 cells. After 24 and 48 hours, the media is collected, filtered and concentrated by ultracentrifugation. The resulting viral preparation is stored at −80° C. The number of transducing units is determined by titration on SupT1 cells (T cell lymphoblastic lymphoma, (ATCC® CRL-1942™). Redirected dual specificity TFP T cells are produced by activating fresh naive T cells with anti-CD3x anti-CD28 beads for 24 hrs and then adding the appropriate number of transducing units to obtain the desired percentage of transduced T cells. These modified T cells are allowed to expand until they become rested and come down in size at which point they are cryopreserved for later analysis. The cell numbers and sizes are measured using a Coulter Counter® Multisizer™ 3 (Beckman Coulter). Before cryopreserving, percentage of cells transduced (expressing TFP.BCMA on the cell surface) and their relative fluorescence intensity of that expression are determined by flow cytometric analysis. From the histogram plots, the relative expression levels of the TFPs are examined by comparing percentage transduced with their relative fluorescent intensity.

In some embodiments, multiple TFPs are introduced by T-cell transduction with multiple viral vectors.

CD16 Viral Preparation

A high titer on viral preparation predicts higher CD16 TFP expression on the T cell surfaces. Table 1 shows viral titer for various constructs isolated form HEK-293 cells.

TABLE 1

HEK-293 titer values

| Construct | Titer* |
|---|---|
| 19CD3ε | 7.29E+07 |
| CD16 CD3ε | 2.74E+07 |
| CD16 CD3γ | 8.37E+07 |
| CD16 CD3δ | 4.00E+07 |
| CD16 CD28-CD3ζ | 5.23E+07 |
| CD16 41BB CD3ζ | 5.21E+07 |
| CD16 TCRβ | 1.05E+08 |

*Infectious units per ml (IFU/ml)

Evaluating Cytolytic Activity, Proliferation Capabilities and Cytokine Secretion of Humanized TFP Redirected T Cells The functional abilities of TFP.TAA T cells to produce cell-surface-expressed TFPs, and to kill target tumor cells, proliferate and secrete cytokines are determined using assays known in the art.

Human PBMCs (e.g., blood from a normal apheresed donor whose naive T cells are obtained by negative selection for T cells, CD4$^+$ and CD8$^+$ lymphocytes) are treated with human interleukin-2 (IL-2) then activated with anti-CD3x anti-CD28 beads, e.g., in 10% RPMI at 37° C., 5% $CO_2$ prior to transduction with the TFP-encoding lentiviral vectors. Flow cytometry assays are utilized to confirm cell surface presence of a TFP, such as by an anti-FLAG antibody or an anti-murine variable domain antibody. Cytokine (e.g., IFN-γ) production is measured using ELISA or other assays.

Example 3: Human TFP T-Cell Efficacy in a Human ALL Mouse Model

Primary human ALL cells can be grown in immune compromised mice (e.g., NSG or NOD) without having to culture them in vitro. Likewise, cultured human ALL cell lines can induce leukemia in such mice. ALL-bearing mice can be used to test the efficacy of human TFP.TAA T cells, for instance, in the model HALLX5447. The readout in this model is the survival of mice after intravenous (i.v.) infusion of ALL cells in the absence and presence of i.v. administered human TFP.TAA T cells.

Example 4: Human TFP T-Cell Treatment in an In Vivo Solid Tumor Xenograft Mouse Model The efficacy of human TFP.TAA T cells can also be tested in immune compromised mouse models bearing subcutaneous solid tumors derived from human TAA-expressing human cell lines. Tumor shrinkage in response to human TFP.TAA T-cell treatment can be either assessed by caliper measurement of tumor size, or by following the intensity of a GFP fluorescence signal emitted by GFP-expressing tumor cells.

Primary human solid tumor cells can be grown in immune compromised mice without having to culture them in vitro. Exemplary solid cancer cells include solid tumor cell lines, such as provided in The Cancer Genome Atlas (TCGA) and/or the Broad Cancer Cell Line Encyclopedia (CCLE, see Barretina et al., Nature 483:603 (2012)). Exemplary solid cancer cells include primary tumor cells isolated from mesothelioma, renal cell carcinoma, stomach cancer, breast cancer, lung cancer, ovarian cancer, prostate cancer, colon cancer, cervical cancer, brain cancer, liver cancer, pancreatic cancer, kidney, endometrial, or stomach cancer. In some embodiments, the cancer to be treated is selected from the group consisting of mesotheliomas, papillary serous ovarian adenocarcinomas, clear cell ovarian carcinomas, mixed Mullerian ovarian carcinomas, endometroid mucinous ovarian carcinomas, pancreatic adenocarcinomas, ductal pancreatic adenocarcinomas, uterine serous carcinomas, lung adenocarcinomas, extrahepatic bile duct carcinomas, gastric adenocarcinomas, esophageal adenocarcinomas, colorectal adenocarcinomas and breast adenocarcinomas. These mice can be used to test the efficacy of TFP.tumor-associated antigen T cells in the human tumor xenograft models (see, e.g., Morton et al., Nat. Procol. 2:247 (2007)). Following an implant or injection of $1 \times 10^6$-$1 \times 10^7$ primary cells (collagenase-treated bulk tumor suspensions in EC matrix material) or tumor fragments (primary tumor fragments in EC matrix material) subcutaneously, tumors are allowed to grow to 200-500 mm$^3$ prior to initiation of treatment.

Example 5: Preparation of T Cells Transduced with TFPs

Lentiviral Production

Lentivirus encoding the appropriate constructs are prepared as follows. $5 \times 10^6$ HEK-293FT cells are seeded into a 100 mm dish and allowed to reach 70-90% confluency overnight. 2.5 µg of the indicated DNA plasmids and 20 µL Lentivirus Packaging Mix (ALSTEM, cat #VP100) are diluted in 0.5 mL DMEM or Opti-MEM® I Medium without serum and mixed gently. In a separate tube, 30 µL of NanoFect® transfection reagent (ALSTEM, cat #NF100) is diluted in 0.5 mL DMEM or Opti-MEM I Medium without serum and mixed gently. The NanoFect/DMEM and DNA/DMEM solutions are then mixed together and vortexed for 10-15 seconds prior to incubation of the DMEM-plasmid-NanoFect mixture at room temperature for 15 minutes. The complete transfection complex from the previous step is added dropwise to the plate of cells and rocked to disperse the transfection complex evenly in the plate. The plate is then incubated overnight at 37° C. in a humidified 5% CO2 incubator. The following day, the supernatant is replaced with 10 mL fresh media and supplemented with 20 µL of ViralBoost™ (500×, ALSTEM, cat #VB100). The plates are then incubated at 37° C. for an additional 24 hours. The lentivirus containing supernatant is then collected into a 50 mL sterile, capped conical centrifuge tube and put on ice. After centrifugation at 3000 rpm for 15 minutes at 4° C., the cleared supernatant is filtered with a low-protein binding 0.45 m sterile filter and virus is subsequently isolated by ultracentrifugation at 25,000 rpm (Beckmann, L8-70M) for 1.5 hours, at 4° C. The pellet is removed and re-suspended in DMEM media and lentivirus concentrations/titers are established by quantitative RT-PCR, using the Lenti-X™ qRT-PCR Titration kit (Clontech®; catalog number 631235). Any residual plasmid DNA is removed by treatment with DNaseI. The virus stock preparation is either used for infection immediately or aliquoted and stored at −80° C. for future use.

Lentivirus titers were established by transducing Jurkat cells with different amount of virus preparation. The DNA was then isolated from the transduced Jurkat cells 24 hours after transduction. The virus titer was determined by quantitative real-time PCR, with in-house designed primers/probe specific for Woodchuck Hepatitis Virus (WHP) Post-transcriptional Regulatory Element (WPRE) as well for albumin (internal quantitation control).

T Cell Isolation

Peripheral Blood Mononuclear Cells (PBMCs) are prepared from either whole blood or buffy coat. Whole blood is collected in 10 mL Heparin vacutainers and either processed immediately or stored overnight at 4° C. Approximately 10 mL of whole anti-coagulated blood is mixed with sterile phosphate buffered saline (PBS) buffer for a total volume of 20 mL in a 50 mL conical centrifuge tube (PBS, pH 7.4, without $Ca^{2+}/Mg^{2+}$). 20 mL of this blood/PBS mixture is then gently overlaid onto the surface of 15 mL of Ficoll-Paque® PLUS (GE Healthcare, 17-1440-03) prior to centrifugation at 400 g for 30-40 min at room temperature with no brake application.

Buffy coat is purchased from Research Blood Components (Boston, MA). LeucoSep™ tubes (Greiner bio-one) are prepared by adding 15 mL Ficoll-Paque® (GE Health Care) and centrifuged at 1000 g for 1 minute. Buffy coat is diluted 1:3 in PBS (pH 7.4, without $Ca^{2+}$ or $Mg^{2+}$). The diluted buffy coat is transferred to LeucoSep tube and centrifuged at 1000 g for 15 minutes with no brake application. The layer of cells containing PBMCs, seen at the diluted plasma/Ficoll interface, is removed carefully to minimize contamination by Ficoll®. Residual Ficoll, platelets, and plasma proteins are then removed by washing the PBMCs three times with 40 mL of PBS by centrifugation at 200 g for 10 minutes at room temperature. The cells are then counted with a hemocytometer. $CD4^+$ and $CD8^+$ T cells are then frozen down in freezing medium (90% FBS+10% DMSO at a concentration of $30-50 \times 10^6$ cells per vial.

T-Cell Activation

PBMCs prepared from either whole blood or buffy coat are stimulated with anti-human CD28 and CD3 antibody-conjugated magnetic beads for 24 hours prior to viral transduction. Freshly isolated PBMCs are washed once in CAR-T medium (AIM V-AlbuMAX (BSA, Life Technologies), with 5% AB serum and 1.25 jag/mL amphotericin B (Gemini Bioproducts), 100 U/mL penicillin, and 100 µg/mL streptomycin) without huIL-2, before being re-suspended at a final concentration of $1 \times 10^6$ cells/mL in CAR-T medium with 300 IU/mL human IL-2, IL-7, or IL-15 (from a 1000× stock; Invitrogen).

Alternatively, frozen CD4+/CD8+ T cells are thawed in pre-warmed DMEM+10% FBS, spun down, and then resuspended in complete T cell expansion medium supplemented with 300 IU/mL huIL2 (Thermo Fisher®) at a final concentration of 1×106 cells/mL. Prior to being used to activate T cells, anti-human CD28 and anti-human CD3 antibody-conjugated magnetic beads (Dynabeads®, Thermo Fisher) are washed three times with sterile 1×PBS (pH7.4), using a magnetic rack to isolate beads from the solution. The T cells were then mixed with the beads at 1:1 ratio, by transferring 25 µL ($1 \times 10^6$ beads) of beads to 1 mL of T cell suspension. The beads/cells mixture is then dispensed to single wells of a non-TC treated 12-well plate, and incubated at 37° C. with 5% CO2 for 24 hrs.

Prior to activation, anti-human CD28 and CD3 antibody-conjugated magnetic beads (available from, e.g., Invitrogen, Life Technologies) are washed three times with 1 mL of sterile 1×PBS (pH 7.4), using a magnetic rack to isolate beads from the solution, before re-suspension in CAR-T medium, with 300 IU/mL human IL-2, to a final concentration of $4 \times 10^7$ beads/mL. PBMC and beads are then mixed at a 1:1 bead-to-cell ratio, by transferring 25 µL ($1 \times 10^6$ beads) of beads to 1 mL of PBMC. The desired number of aliquots are then dispensed to single wells of a 12-well low-attachment or non-treated cell culture plate, and incubated at 37° C., with 5% CO2, for 24 hours before viral transduction.

T-Cell Transduction and Expansion

Following activation of PBMCs, cells are incubated for 24 hours at 37° C., 5% $CO_2$. Lentivirus was thawed on ice and then added to activated T cells at indicated MOI in the presence of g/ml Polybrene (Sigma). Cells were spinoculated with the lentivirus at 200 g for 100 minutes at room temperature. The transduced T cells were incubated for an additional 24 hr before an additional lentivirus transduction. After the 2nd round of lentivirus transduction, the T cells were expanded in T cell expansion medium supplemented with 300 IU/mL of hIL-2 and sub-cultured every other day at $5 \times 10^5$ cells/mL.

In some instances, activated PBMCs are electroporated with in vitro transcribed (IVT) mRNA. Human PBMCs are stimulated with Dynabeads® (Thermo Fisher®) at 1-to-1 ratio for 3 days in the presence of 300 IU/ml recombinant human IL-2 (R&D System). The beads are removed before electroporation. The cells are washed and re-suspended in OPTI-MEM® medium (Thermo Fisher) or AimV medium (Invitrogen) in 5% hAB serum (Gemini Bio-Products) and 1% antibiotics at the concentration of $2.5 \times 10^7$ cells/mL. 200 µL of the cell suspension ($5 \times 10^6$ cells) are transferred to the 2 mm gap Electroporation Cuvettes Plus™ (Harvard Apparatus BTX) and prechilled on ice. 10 µg of IVT TFP mRNA is added to the cell suspension. The mRNA/cell mixture is then electroporated at 200 V for 20 milliseconds using ECM830 Electro Square Wave Porator (Harvard Apparatus BTX). Immediately after the electroporation, the cells are transferred to fresh cell culture medium (AIM V AlbuMAX® (BSA) serum free medium+5% human AB serum+ 300 IU/ml IL-2) and incubated at 37° C.

Verification of TFP Expression by Cell Staining

Following lentiviral transduction or mRNA electroporation, expression of TFPs, e.g., ROR1, NKG2D, CD16, or dual specificity TFPs, is confirmed by flow cytometry. T cells are stained using anti-CD3 APC (Clone, UCHT1), anti-CD4-Pacific blue (Clone, RPAT4), anti-CD8-APCCY7 (Clone), and e.g., human NKG2D/CD314-APC (R&D systems, LOT #LCO061321) and their respective isotype controls (BD biosciences).

NKG2D TFP T Cell Populations

T cells are washed three times in 3 mL staining buffer (PBS, 4% BSA) and re-suspended in PBS at $1 \times 10^6$ cells per well. For dead cell exclusion, cells are incubated with LIVE/DEAD® Fixable Aqua Dead Cell Stain (Invitrogen) for 30 minutes on ice. Cells are washed twice with PBS and re-suspended in 50 µL staining buffer. To block Fc receptors, 1 µL of 1:100 diluted normal goat IgG (BD Bioscience) is added to each tube and incubated in ice for 10 minutes. 1.0 mL FACS buffer is added to each tube, mixed well, and cells are pelleted by centrifugation at 300 g for 5 min. Surface expression of scFv TFPs is detected by Zenon® R-Phycoerythrin-labeled human NKG2D IgG1 Fc or human IgG1 isotype control. 1 µg antibodies are added to the respective samples and incubated for 30 minutes on ice. Cells are then washed twice, and stained for surface markers using Anti-CD3 APC (clone, UCHT1), anti-CD4-Pacific blue (Clone RPA-T4), anti-CD8 APCCy7 (Clone SK1), from BD bioscience. Flow cytometry is performed using BD-LSRII Fortessa® X20 (BD Biosciences) and data are acquired using FACS diva software and are analyzed with FlowJo® (Treestar, Inc. Ashland, OR).

Figure 2A:
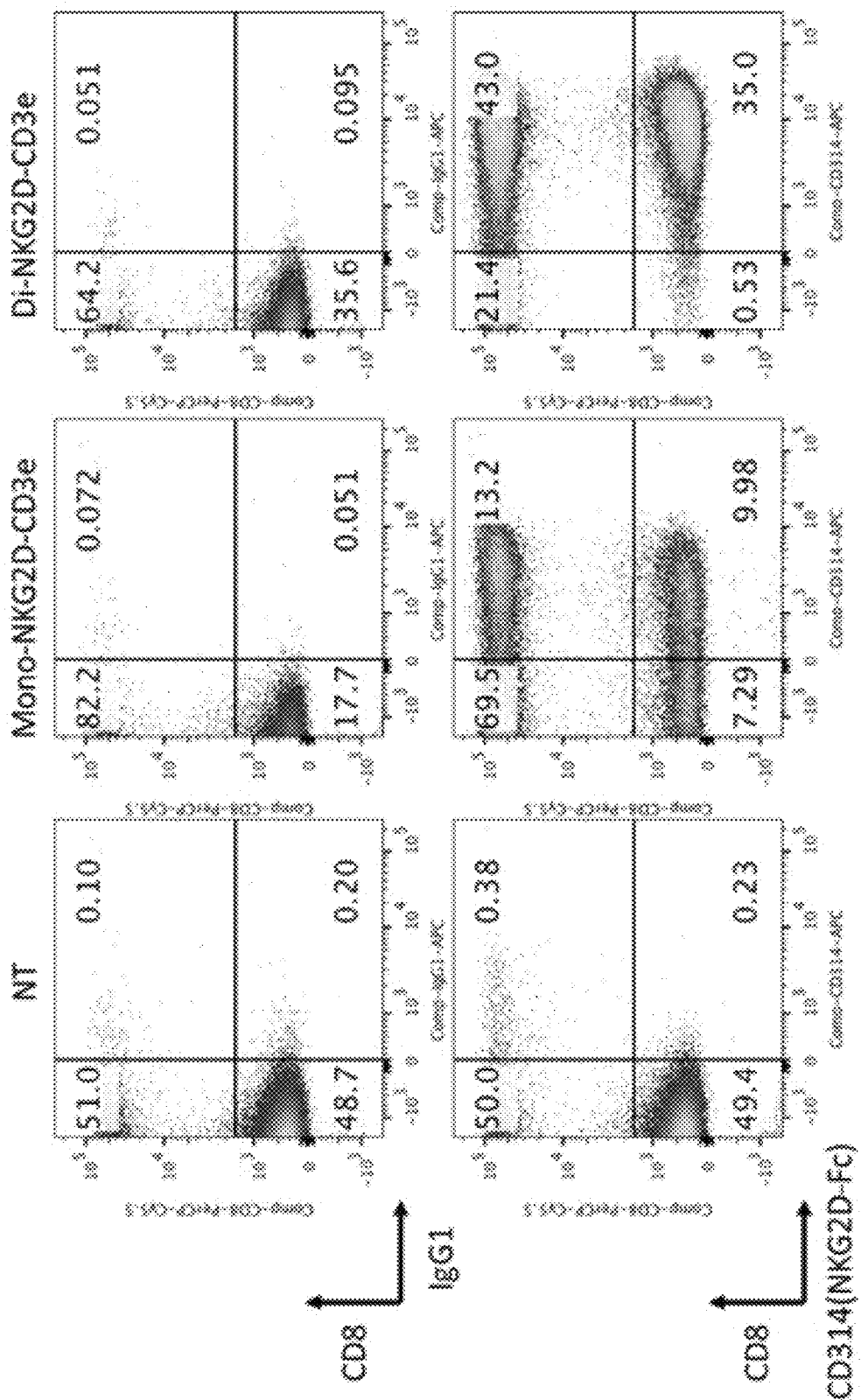
FIG. 2A shows surface expression of NKG2D-specific TFP-T cells, as described in Example 5. Both monomeric and dimeric NKG2D CD3ε TFP T cells showed expression compared to the non-transduced ("NT"); dimeric NKG2D TFP T cells were the most highly expressed.

Exemplary results are shown in FIG. 2A, which shows the surface expression analysis of activated PBMC cells stained for CD8 (anti-CD8 APCCy7, y-axes) and NKG2D ("NKG2D") (Zenon® R-Phycoerythrin-labeled hNKG2D IgG, x-axes). Shown from left to right are cells that were either non-transduced or transduced with NKG2D-CD3ε, NKG2D-CD28ζ, and NKG2D-41BBζ constructs. The proportion of $CD8^+$, $NKG2D^+$ cells is shown in the top right corner of each panel.

Dual Specificity TFP T Cell Populations

Surface expression of TFP carrying anti-CD19 or anti-BCMA scFv is detected with biotinylated goat anti-mouse F(ab')$_2$ (Thermo Fisher) at 4.5 µg per sample for 30 minutes at 4° C. After 3 washes with staining buffer, the cells are stained with PE-conjugated streptavidin (BD Biosciences, at 1:1000 dilution). The surface expression of TFP bearing an anti-tumor-associated antigen (Ag) scFv is also detected by staining with Ag Fc fusion protein. The Ag Fc fusion protein, e.g., a BCMA-Fc fusion protein, is expressed in-house and labelled with Zenon®-PE (Thermo Fisher) according to manufacturer's protocol. The T cells are stained with LIVE/DEAD® Fixable Aqua Dead Cell Stain, blocked with Human BD Fc Block™ and then stained with 1 µg of labelled BCMA_Fc fusion sample per sample.

The T cell markers (CD3, CD4, CD8) are stained with APC mouse anti-human CD3 antibody (Clone-UCHT1, BD Biosciences, at 1:100 dilution), PerCP/Cy5.5 mouse anti-human CD8 antibody (Clone-SKI, BD Biosciences, at 1:100 dilution) and Pacific Blue™ mouse anti-human CD4 antibody (Clone-RPA-T4, BD Biosciences, at 1:1000 dilution) for 30 minutes at 4° C. After 2 washes with staining buffer, the cells are then run on LSRFortessa™ X20 (BD Biosciences). The data are acquired using FACSDiva® and analyzed with FlowJo® (Treestar, Inc. Ashland, OR).

Figure 2B:
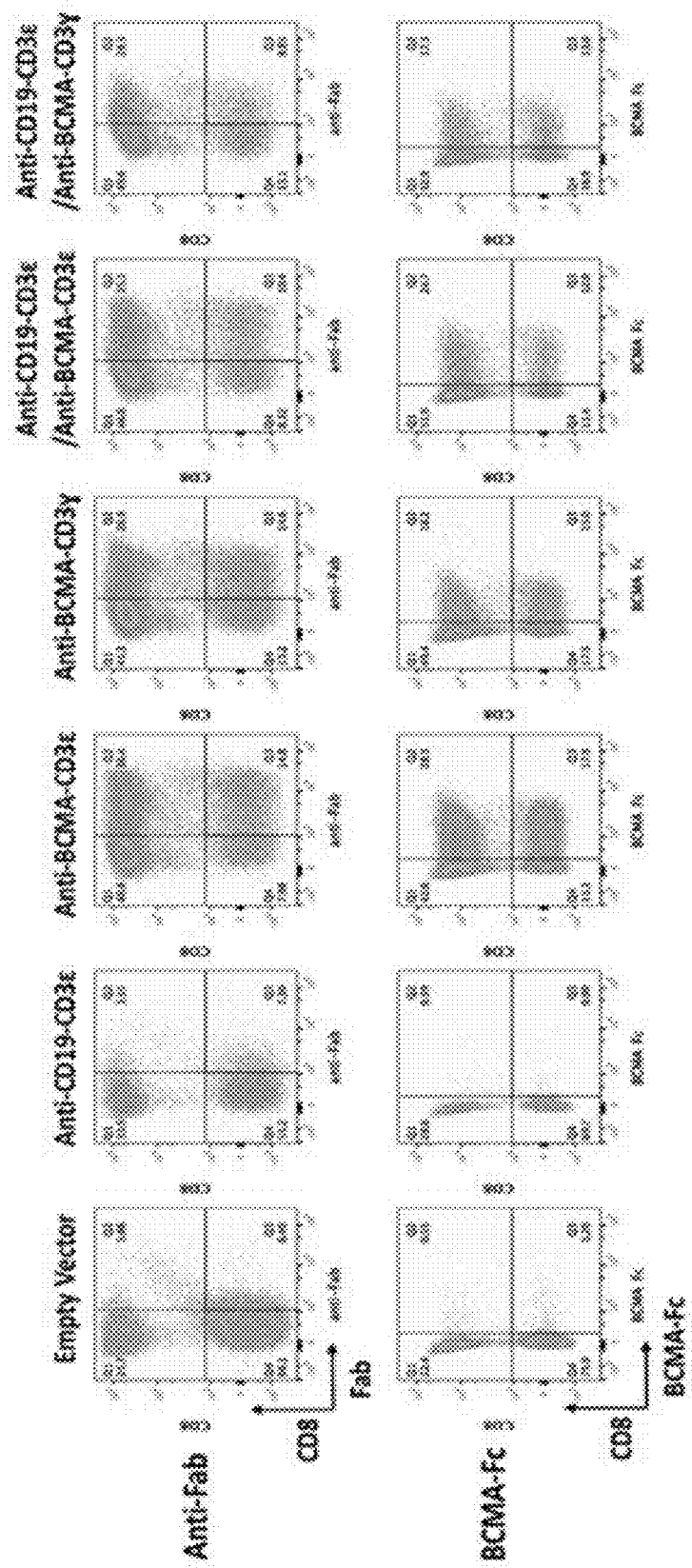
FIG. 2B is a series of images showing FACS analysis of anti-BCMA and/or anti-CD19-transduced T cells. The cells were sorted by surface expression of CD8 (y-axes) and either anti-Fab (top row) or BCMA-Fc (bottom row) (x-axes). Shown are results from cells transduced with empty vector, anti-CD19-CD3ε, anti-BCMA-CD3ε, anti-BCMA-CD3γ, both anti-CD19-CD3ε and anti-BCMA-CD3ε, or anti-CD19-CD3ε+ anti-BCMA-CD3γ.

Results are shown in FIG. 2B, which confirmed expression of the TCRs. The cells were sorted by surface expression of CD8 (y-axes) and either anti-Fab (top row) or BCMA-Fc (bottom row) (x-axes). Shown are results from cells transduced with empty vector, anti-CD19-CD3ε, anti-BCMA-CD3ε, anti-BCMA-CD3γ, both anti-CD19-CD3ε and anti-BCMA-CD3ε, or anti-CD19-CD3ε+ anti-BCMA-CD3γ.

CD16 TFP T Cell Populations

CD16 (FcγRIIIa) is present mostly on NK cells, neutrophils, monocytes, macrophages and leukocytes. However, unlike T cells, NK cells represent only a minor fraction (5-15%) of circulating lymphocytes. In addition, NK cells are resistant to most conventional gene-transfection/transduction techniques, although short-term transient transduction has been achieved with vaccinia virus. Exogenous T cells, however, are more easily transduced and can be expanded by the methods disclosed herein, making them much more suitable for boosting a patient's immune response to anti-cancer therapeutics in combination therapy.

Following lentiviral transduction or mRNA electroporation, expression of CD16 TFPs is confirmed by flow cytometry, using an anti-CD16-PE antibody and an IgG1k-PE antibody (Catalog Nos. 555407 and 555749, respectively, both from BD Pharmingen). T cells are washed three times in 3 mL staining buffer (PBS, 4% BSA) and re-suspended in PBS at 1×10$^6$ cells per well. For dead cell exclusion, cells are incubated with LIVE/DEAD® Fixable Aqua Dead Cell Stain (Invitrogen) for 30 minutes on ice. Cells are washed twice with PBS and re-suspended in 50 µL staining buffer. To block Fc receptors, 1 µL of 1:100 diluted normal goat IgG (BD Bioscience) is added to each tube and incubated in ice for 10 minutes. 1.0 mL FACS buffer is added to each tube, mixed well, and cells are pelleted by centrifugation at 300 g for 5 min.

Figures 3A, 3B:
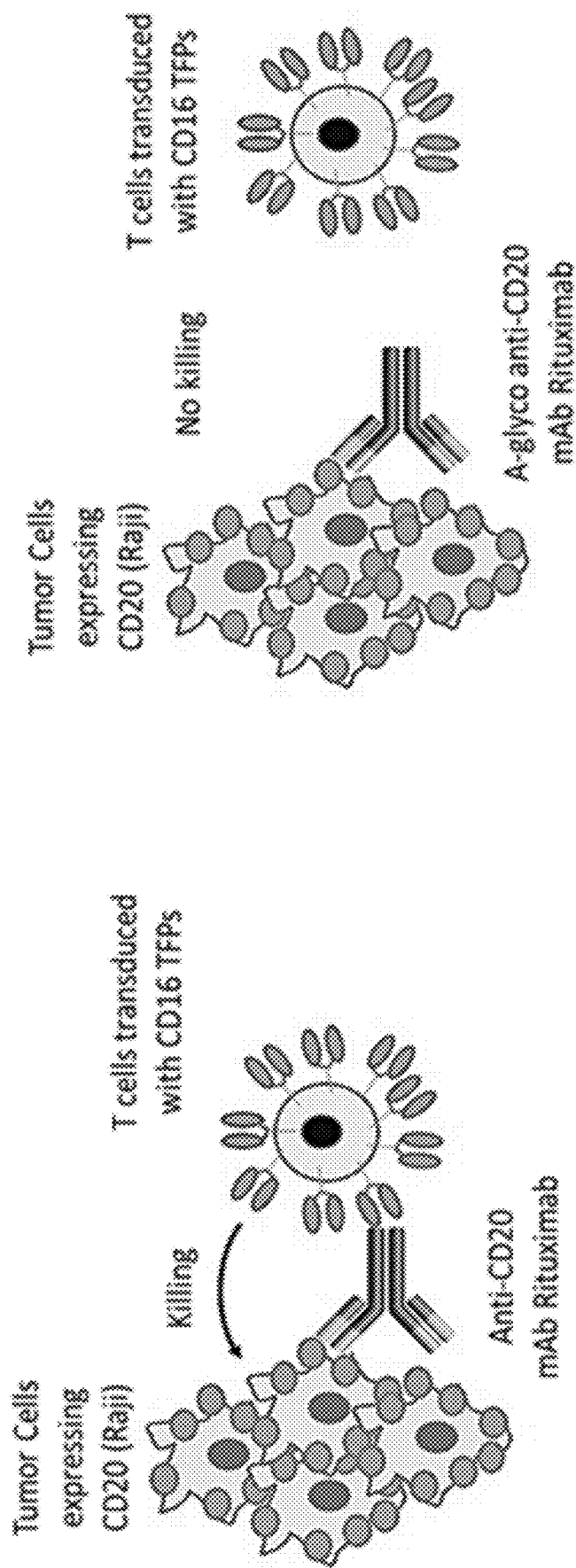
FIG. 3A shows a schematic of CD20$^+$ Raji cells being bound by the anti-CD20 antibody rituximab, that is bound in turn by T cells transduced with CD16 TFPs, resulting in the induction of cell lysis (FIG. 3A). When non-glycosylated rituximab is used, CD16 TFPs cannot bind to the antibody and thus do not induce lysis in the target cell (FIG. 3B).

FIG. 3 shows a schematic of CD20+ Raji cells being bound by the anti-CD20 antibody rituximab, that is bound in turn by T cells transduced with CD16 TFPs, resulting in the induction of cell lysis (FIG. 3A). When non-glycosylated rituximab is used, CD16 TFPs cannot bind to the antibody and thus do not induce lysis in the target cell (FIG. 3B).

Surface expression of cancer antigens detected by CD16 TFPs is detected by Zenon® R-Phycoerythrin-labeled human anti-CD20 IgG1 Fc (e.g., rituximab) or an a-glycosylated form of an anti-CD20 antibody. The a-glycosylated form of CD20 has a functional scFv that binds to the CD20 antigen on tumor cell surface but will not engage CD16TFPs or CARs due to N-glycosylation mutation with N to G substitution on its Fc portion. 1 µg of each anti-CD20 or anti-CD20 a-glycosylated or Zenon R-Phycoerythrin alone was incubated with Raji cells for 30 minutes on ice. Cells are then washed twice with PBS, Flow cytometry is performed using LSRFortessa® X20 (BD Biosciences) and data is acquired using FACS diva software and is analyzed with FlowJo® (Treestar, Inc. Ashland, OR).

Figure 4A:
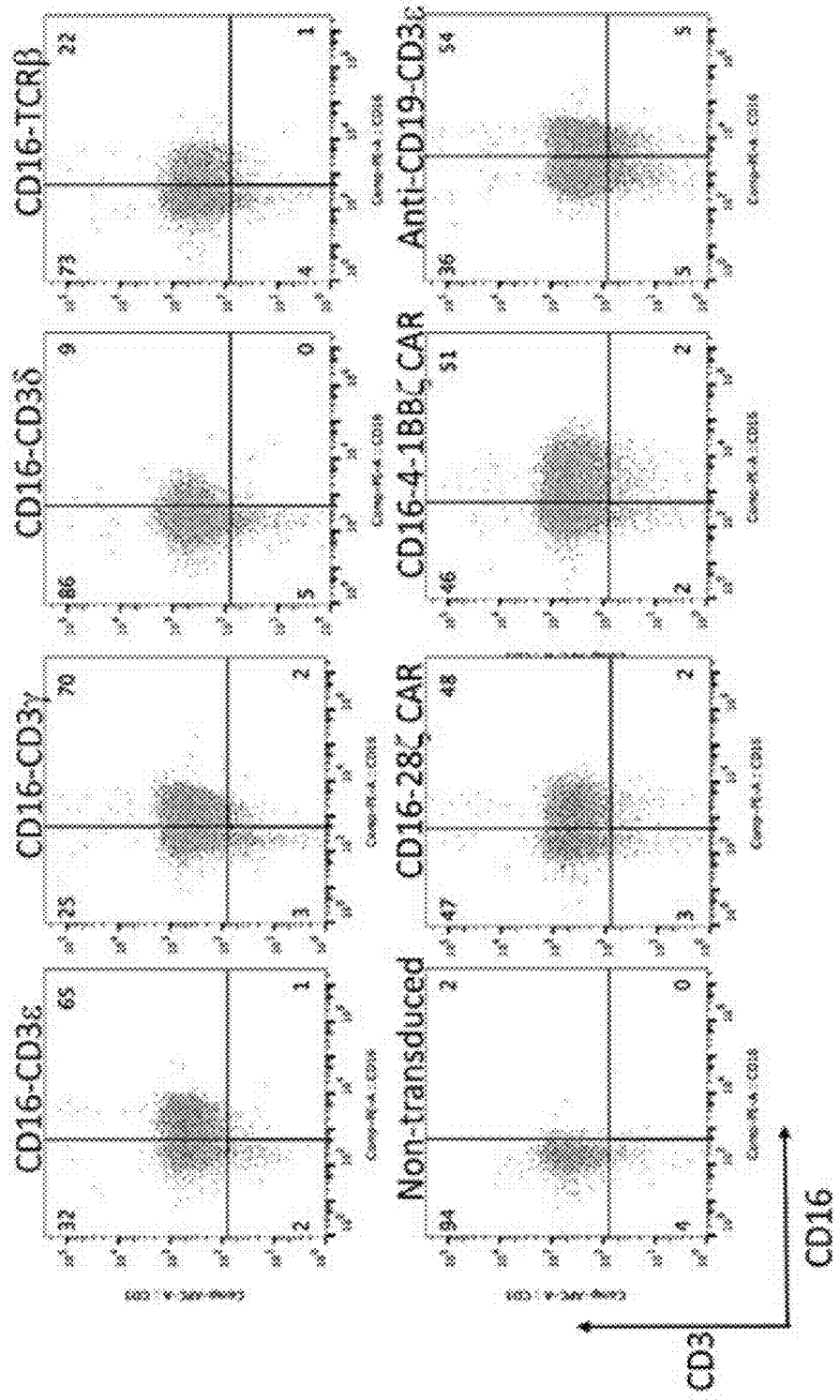
FIG. 4A shows confirmation of surface expression of TFPs in cells stained for CD16 (anti-CD16, x-axis) and CD3ε (y-axis). Shown from left to right are cells that were either non-transduced or transduced with: CD16-CD3ε TFP, CD16-CD3γ TFP, CD16-CD3δ TFP, and CD16-CD3β constructs (top row); and non-transduced, CD16-CD28ζ CAR, CD16-41BBζ CAR, and an anti-CD19-CD3ε TFP as a positive control. The proportion of CD3$^+$, CD16$^+$ cells is shown in the top right corner of each panel. Exemplary results of Zenon staining are shown in FIG. 4B. To demonstrate the accuracy of the method, Raji cells (that express both CD19 and CD20) that have been are either unstained or stained with anti-CD19 were treated according to the methods above using anti-CD19 TFPs.

Exemplary results of FACS confirmation are shown in FIG. 4A, showing cells stained for CD16 (anti-CD16, x-axis) and CD3ε (y-axis). Shown from left to right are cells that were either non-transduced or transduced with: CD16-CD3ε TFP, CD16-CD3γ TFP, CD16-CD3δ TFP, and CD16-CD3β constructs (top row); and non-transduced, CD16-CD28ζ CAR, CD16-41BBζ CAR, and an anti-CD19-CD3ε TFP as a positive control. The proportion of CD3$^+$, CD16$^+$ cells is shown in the top right corner of each panel.

Figure 4C:
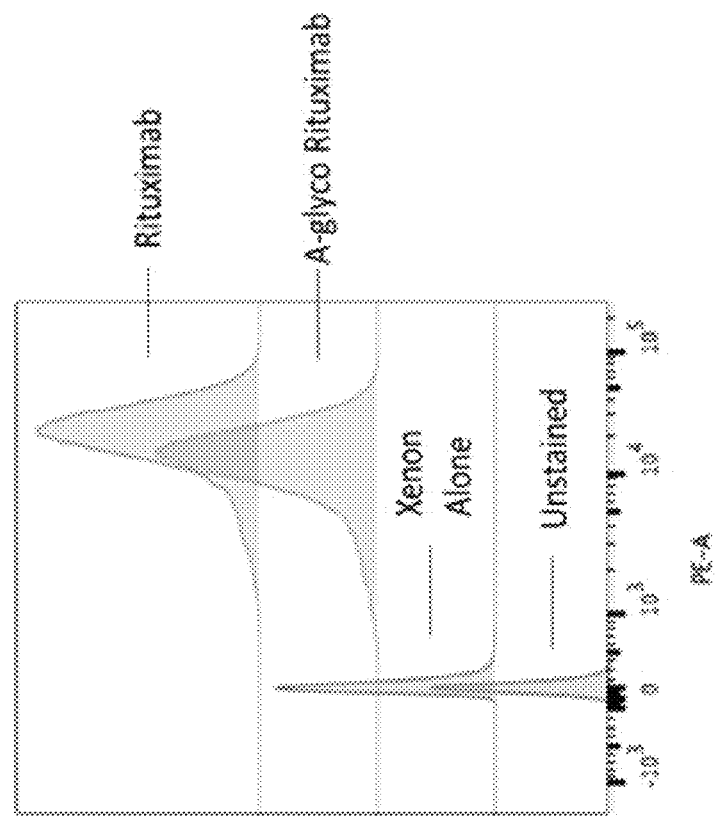
FIG. 4C shows that both rituximab and a-glycosylated rituximab was able to bind to CD19$^+$ Raji cells.
Figure 4B:
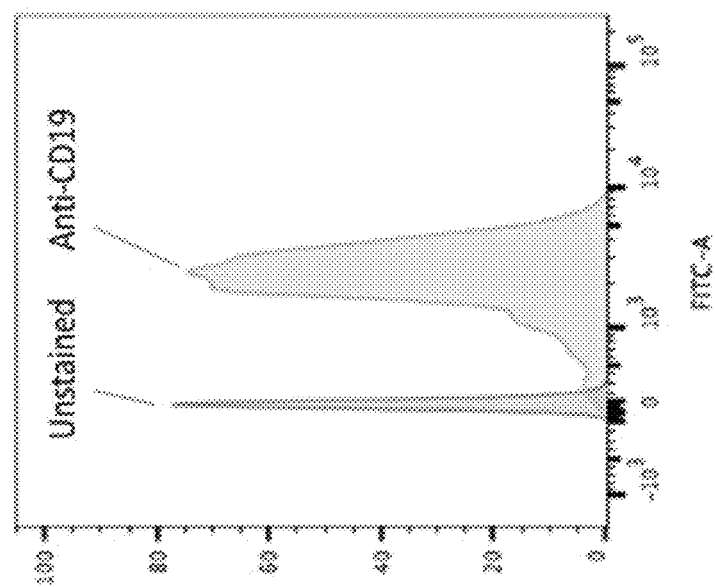

Exemplary results of Zenon staining are shown in FIG. 4B. To demonstrate the accuracy of the method, Raji cells (that express both CD19 and CD20) that have been are either unstained or stained with anti-CD19 were treated according to the methods above using anti-CD19 TFPs. FIG. 4C shows that both rituximab and a-glycosylated rituximab was able to bind to CD19+ Raji cells.

Example 6: Cytotoxicity Assay by Flow Cytometry

Target cells that are either positive or negative for anti-tumor antigen targets are labelled with the fluorescent dye, carboxyfluorescein diacetate succinimidyl ester (CFSE). These target cells are mixed with effector T cells that are either un-transduced, transduced with control CAR-T constructs, or transduced with TFPs. After the indicated incubation period, the percentage of dead to live CFSE-labeled target cells and negative control target cells is determined for each effector/target cell culture by flow cytometry. The percent survival of target cells in each T-cell+target cell culture is calculated relative to wells containing target cells alone.

The cytotoxic activity of effector T cells, or the combination of an anti-cancer agent and the effector T cells (e.g., an anti-cancer antibody and a CD16 TFP) is measured by comparing the number of surviving target cells in target cells without or with effector T cells, following co-incubation of effector and target cells, using flow cytometry. In experiments with anti-tumor antigen TFPs or CAR-T cells, the target cells are tumor-antigen-positive cells, while cells used as a negative control are tumor-antigen-negative cells.

Target cells are washed once, and re-suspended in PBS at 1×10$^6$ cells/mL. The fluorescent dye carboxyfluorescein diacetate succinimidyl ester (CFSE) (Thermo Fisher®) is added to the cell suspension at a concentration of 0.03 µM and the cells are incubated for 20 minutes at room temperature. The labeling reaction is stopped, by adding to the cell suspension with complete cell culture medium (RPMI-1640+10% HI-FBS) at the volume 5 times of the reaction volume, and the cells are incubated for an additional 2 minutes at room temperature. The cells are pelleted by centrifugation and re-suspended in cytotoxicity medium (Phenol red-free RPMI1640 (Invitrogen) plus 5% AB serum (Gemini Bioproducts) at 2×10$^5$ cells/mL. Fifty microliters of CFSE labelled-target cell suspension (equivalent to 10,000 cells) are added to each well of the 96-well U-bottom plate (Corning).

Effector T cells transduced with anti-tumor-antigen-TFP constructs, together with non-transduced T cells as negative controls, are washed and suspended at $2\times10^6$ cells/mL, or $1\times10^6$ cells/mL in cytotoxicity medium. 50 μL of effector T-cell suspensions (equivalent to 100,000 or 50,000 cells) are added to the plated target cells to reach the effector-to-target ratio of 10-to-1 or 5-to-1, respectively, in a total volume of 100 μL. The cultures are then mixed, spin down, and incubated for 4 hours at 37° C., 5% $CO_2$. Immediately following this incubation, 7AAD (7-aminoactinomycin D) (BioLegend) is added to the cultured cells as recommended by the manufacturer, and flow cytometry is performed with a BD Fortessa X-20 (BD Biosciences). Analysis of flow cytometric data is performed using FlowJo® software (Tree-Star, Inc.).

The percentage of survival for RPMI-8226 target cells is calculated by dividing the number of alive RPMI-8226 target cells (CFSE+7-AAD−) in sample with effector T cells and target cells, by the number of alive RPMI-8226 (CFSE+7-AAD−) cells in the sample with target cells alone. The cytotoxicity for effector cells is calculated as the percentage of killing for RPMI-8226=100%−percentage of survival for RPMI-8226 cells.

T cells transduced with an anti-tumor-antigen-28ζ CAR construct may demonstrate cytotoxicity against tumor-antigen-expressing cells, when compared to T cells that are either non-transduced or are transduced with a non-tumor-associated antigen-specific CAR control. However, T cells transduced with anti-tumor-associated antigen-CD3ε may induce more efficient cytotoxicity against the targets than the anti-tumor-associated antigen CAR control. Anti-tumor-associated antigen-CD3γ TFPs may also mediate robust cytotoxicity that is greater than that observed with anti-tumor-associated antigen-CAR at effector:target ratios between 5 and 10:1. Some cytotoxicity may be observed with anti-tumor-associated antigen-TCRα and anti-tumor-associated antigen-TCRβ TFPs. Similar results may be obtained with anti-tumor-associated antigen TFPs constructed with an alternative hinge region. Once again, cytotoxicity against tumor-associated antigen-expressing target cells may be greater with anti-tumor-associated antigen-CD3ε or anti-tumor-associated antigen-CD3γ TFP-transduced T cells than with anti-tumor-associated antigen-CAR-transduced T cells.

Example 7: Cytotoxicity by Real Time Cytotoxicity Assay: NKG2D TFP T Cells

NKG2D TFPs may also demonstrate superior cytotoxicity over NKG2D CARs in the real-time cytotoxicity assay (RTCA) format. The RTCA assay measures the electrical impedance of an adherent target cell monolayer, in each well of a specialized 96-well plate, in real time and presents the final readout as a value called the cell index. Changes in cell index indicate disruption of the target cell monolayer as a result of killing of target cells by co-incubated T-cell effectors. Thus, the cytotoxicity of the effector T cells can be evaluated as the change in cell index of wells with both target cells and effector T cells compared to that of wells with target cells alone.

Adherent target cells are cultured in DMEM, 10% FBS, 1% Antibiotic-Antimycotic (Life Technologies). To prepare the RTCA, 50 μL of, e.g., DMEM medium is added into the appropriate wells of an E-plate (ACEA Biosciences, Inc, Catalog #: JL-10-156010-1A). The plate is then placed into a RTCA MP instrument (ACEA Biosciences, Inc.) and the appropriate plate layout and assay schedule entered into the RTCA 2.0 software as described in the manufacturers manual. Baseline measurement is performed every 15 minutes for 100 measurements. $1\times10^4$ target cells in a 100 μL volume are then added to each assay well and the cells are allowed to settle for 15 minutes. The plate is returned to the reader and readings are resumed.

The next day, effector T cells are washed and re-suspended in cytotoxicity media (Phenol red-free RPMI1640 (Invitrogen) plus 5% AB serum (Gemini Bioproducts; 100-318)). The plate is then removed from the instrument and the effector T cells, suspended in cytotoxicity medium (Phenol red-free RPMI1640+5% AB serum), are added to each well at 100,000 cells or 50,000 cells to reach the effector-to-target ratio of 10-to-1 or 5-to-1, respectively. The plate is then placed back to the instrument. The measurement is carried out for every 2 minutes for 100 measurements, and then every 15 minutes for 1,000 measurements.

In the RTCA assay, killing of NKG2D-transduced cells may be observed by T cells transduced with NKG2D-28ζ CAR-transduced T cells, as demonstrated by a time-dependent decrease in the cell index following addition of the effector cells relative to cells alone or cells co-incubated with T cells transduced with a control CAR construct. However, target cell killing by NKG2D-CD3ε TFP-expressing T cells may be deeper and more rapid than that observed with the NKG2D CAR. For example, within 4 hours of addition of T cells transduced with NKG2D-CD3ε TFP, killing of the NKG2DL-expressing target cells may be essentially complete. Little or no killing may be observed with T cells transduced with a number of TFP constructs comprising other CD3 and TCR constructs. Similar results may be obtained with NKG2D TFPs constructed with an alternative hinge region. Cytotoxicity against NKG2D-transduced target cells may be greater with NKG2D-CD3ε or NKG2D-CD3γ TFP-transduced T cells than with NKG2D-CAR-transduced T cells.

The cytotoxic activity of TFP-transduced T cells may be dose-dependent with respect to the amount of virus (MOI) used for transduction. Increased killing of NKG2DL-positive cells may be observed with increasing MOI of NKG2D-CD3ε TFP lentivirus, further reinforcing the relationship between TFP transduction and cytotoxic activity.

An NKG2D TFP construct is engineered by cloning a NKG2D scFv DNA fragment linked to a CD3ε DNA fragment by a DNA sequence coding the linker: GGGGSGGGGSGGGGSLE (SEQ ID NO: 1) into a p510 vector (from SBI) at XbaI and EcoRI sites. The NKG2D TFP construct generated is, e.g., p510_antiNKG2D_SS1_CD3ε (NKG2D SS1 scFv-linker-human CD3ε chain).

Full length NKG2D is PCR amplified from pCMV6_XL4_NKG2D (Origene) and the monomer, or a dimer comprising a linker, is cloned into XbaI and EcoRI restriction digested p527a (pCDH-EF1-MCS-T2A-Puro) (SBI) via Gibson Recombination reaction.

Target cells for the RTCA are, e.g., NKG2D⁺ HeLa cells (cervical adenocarcinoma, ATCC® CCL-2™) and NKG2D-negative PC-3 cells (prostate adenocarcinoma, ATCC® CRL-1435™) are used as negative controls. Adherent target cells are cultured in DMEM with 10% FBS and 1% Antibiotic-Antimycotic (Life Technologies).

The normalized cell index, indicative of cytotoxicity, is then determined. Activated PBMCs are untreated, non-transduced, or transduced with empty vector, a NKG2D TFP), a NKG2D CAR with the CD28ζ, or 41BBζ signaling domain.

The target NKG2D-positive HeLa cells are efficiently killed by the anti-NKG2D TFP-transduced T cells, compared to the negative controls. In contrast, the NKG2D-negative PC-3 cells are not efficiently killed by any of the constructs.

Activation of the T cells expressing anti-NKG2D CAR and TFP constructs is performed using NKG2D$^+$ and NKG2D$^-$ K562 cells. As described above, activated PBMCs are transduced with 50 MOI LVs for two consecutive days and expanded. Day 8 post transduction, co-cultures of PBMCs were set up with target cells (K562 cells overexpressing NKG2D) at E:T, 1:1 ratio ($0.2 \times 10^6$ each cell type) in cytotoxicity medium (Phenol red-free RPMI1640 (Invitrogen) plus 5% AB serum (Gemini Bioproducts; 100-318). K562 cells overexpressing BCMA were used as negative controls. 24 hours after the beginning of co-culturing, cells are harvested, washed with PBS three times and stained with Live/Dead Aqua for 30 min on ice. To block Fc receptors, human Fc block (BD) is added and incubated for 10 minutes at room temperature. Cells are subsequently stained with anti-CD3 APC (clone, UCHT1), anti-CD8 APCcy7 (Clone SK1), anti-CD69-Alexa Fluor® 700 (clone FN50) from BD Biosciences and anti-CD25-PE (Clone BC96, eBioscience). Cells are washed twice and analyzed by BD LSRII-Fortessa. Data are analyzed as above using FlowJo® analysis software (Tree star, Inc.).

T cells are either non-transduced, transduced with empty vector, transduced with anti-NKG2D-CD3ε TFP, anti-NKG2D-28ζ CAR, or anti-NKG2D-41BBζ CAR. As will be shown, T cells expressing anti-NKG2D CAR and TFP constructs are activated by culturing with NKG2D$^+$ cells, but not the NKG2D– cells. The data will demonstrate the ability of NKG2D-expressing cells to specifically activate T cells.

Activation of T cells may be similarly assessed by analysis of granzyme B production. T cells are cultured and expanded as described above, and intracellular staining for granzyme B is done according to the manufacturer's kit instructions (Gemini Bioproducts; 100-318). Cells are harvested, washed with PBS three times and blocked with human Fc block for 10 min. Cells are stained for surface antigens with anti-CD3 APC (clone, UCHT1), and anti-CD8 APCcy7 (Clone SK1) for 30 min at 4° C. Cells were then fixed with Fixation/Permeabilization solution (BD Cytofix/Cytoperm Fixation/Permeabilization kit cat #554714) for 20 min at 4 C, flowed by washing with BD Perm/Wash buffer. Cells are subsequently stained with anti-Granzyme B Alexafluor700 (Clone GB11), washed with BD Perm/Wash buffer twice and resuspended in FACS buffer. Data are acquired on BD LSRII-Fortessa and analyzed using FlowJo® (Tree star Inc.).

T cells are either non-transduced, transduced with empty vector, transduced with anti-NKG2D-CD3ε TFP, anti-NKG2D-28ζ CAR, or anti-NKG2D-41BBζ CAR. T cells expressing anti-NKG2D CAR and TFP constructs are activated by culturing with NKG2D$^+$ cells, but not the NKG2D– cells. The percentage of granzyme B-positive cells for each construct in NKG2D ligand-cells and NKG2D ligand$^+$ cells is determined.

Example 8: Cytotoxicity by Real Time Cytotoxicity Assay: CD16 TFP T Cells

Preparation of target cells and transduced T cells is performed as described above for NKG2D.

In the RTCA assay, killing of Ag-transduced cells may be observed by T cells transduced with CD16-28ζ CAR-transduced T cells, as demonstrated by a time-dependent decrease in the cell index following addition of the effector cells relative to cells alone or cells co-incubated with T cells transduced with a control CAR construct. However, target cell killing by CD16-CD3ε TFP-expressing T cells may be deeper and more rapid than that observed with the CD16 CAR. For example, within 4 hours of addition of T cells transduced with CD16-CD3ε TFP and an anti-TAA antibody, killing of the Ag-expressing target cells may be essentially complete. Little or no killing may be observed with T cells transduced with a number of TFP constructs comprising other CD3 and TCR constructs. Similar results may be obtained with CD16 TFPs constructed with an alternative hinge region. Cytotoxicity against Ag-transduced target cells may be greater with CD16-CD3ε or CD16-CD3γ TFP-transduced T cells than with CD16-CAR-transduced T cells.

The cytotoxic activity of CD16 TFP-transduced T cells, in combination with an anti-TAA antibody, may be dose-dependent with respect to the amount of virus (MOI) used for transduction. Increased killing of Ag-positive cells may be observed with increasing MOI of CD16-CD3ε TFP lentivirus and increased dose of the anti-Ag antibody, further reinforcing the relationship between TFP transduction and cytotoxic activity.

A CD16 TFP construct is engineered by cloning a CD16 DNA fragment linked to a CD3ε DNA fragment by a DNA sequence coding the linker: GGGGSGGGGSGGGGSLE (SEQ ID NO: 1) into a p510 vector (from SBI) at XbaI and EcoRI sites.

Target cells for the RTCA are, e.g., Ag-positive HeLa cells (cervical adenocarcinoma, ATCC® CCL-2™) and Ag-negative cells, e.g., PC-3 cells (prostate adenocarcinoma, ATCC® CRL-1435™) are used as negative controls. Adherent target cells are cultured in DMEM with 10% FBS and 1% Antibiotic-Antimycotic (Life Technologies).

The normalized cell index, indicative of cytotoxicity, is then determined. Activated PBMCs are untreated, non-transduced, or transduced with empty vector, a CD16 TFP, a CD16 CAR with the CD28ζ, or 41BBζ signaling domain.

The target Ag-positive HeLa cells are efficiently killed by the anti-Ag antibody in combination with the CD16 TFP-transduced T cells, compared to the negative controls. In contrast, the Ag-negative PC-3 cells are not efficiently killed by any of the constructs.

Activation of the T cells expressing anti-CD16 CAR and TFP constructs is performed using CD16$^+$ and CD16$^-$ K562 cells. As described above, activated PBMCs are transduced with 50 MOI LVs for two consecutive days and expanded. Day 8 post transduction, co-cultures of PBMCs were set up with target cells (K562 cells overexpressing CD16) at E:T, 1:1 ratio ($0.2 \times 10^6$ each cell type) in cytotoxicity medium (Phenol red-free RPMI1640 (Invitrogen) plus 5% AB serum (Gemini Bioproducts; 100-318). K562 cells overexpressing BCMA were used as negative controls. 24 hours after the beginning of co-culturing, cells are harvested, washed with PBS three times and stained with Live/Dead Aqua for 30 min on ice. To block Fc receptors, human Fc block (BD) is added and incubated for 10 minutes at room temperature. Cells are subsequently stained with anti-CD3 APC (clone, UCHT1), anti-CD8 APCcy7 (Clone SK1), anti-CD69-Alexa Fluor® 700 (clone FN50) from BD Biosciences and anti-CD25-PE (Clone BC96, eBioscience). Cells are washed twice and analyzed by BD LSRII-Fortessa. Data are analyzed as above using FlowJo® analysis software (Tree star, Inc.).

T cells are either non-transduced, transduced with empty vector, transduced with CD16-CD3ε TFP, CD16-28ζ CAR, or CD16-41BBζ CAR. As will be shown, T cells expressing CD16 CAR and TFP constructs are activated by culturing with Ag+ cells and an effective amount of an anti-Ag antibody, but not the Ag- cells. The data demonstrate the ability of Ag-expressing cells to specifically activate T cells in the presence of an anti-Ag antibody.

Activation of T cells may be similarly assessed by analysis of granzyme B production. T cells are cultured and expanded as described above, and intracellular staining for granzyme B is done according to the manufacturer's kit instructions (Gemini Bioproducts; 100-318). Cells are harvested, washed with PBS three times and blocked with human Fc block for 10 min. Cells are stained for surface antigens with anti-CD3 APC (clone, UCHT1), and anti-CD8 APCcy7 (Clone SK1) for 30 min at 4° C. Cells were then fixed with Fixation/Permeabilization solution (BD Cytofix/Cytoperm Fixation/Permeabilization kit cat #554714) for 20 min at 4 C, flowed by washing with BD Perm/Wash buffer. Cells are subsequently stained with anti-Granzyme B Alexafluor700 (Clone GB11), washed with BD Perm/Wash buffer twice and resuspended in FACS buffer. Data are acquired on BD LSRII-Fortessa and analyzed using FlowJo® (Tree star Inc.).

T cells are either non-transduced, transduced with empty vector, transduced with CD16-CD3ε TFP, CD16-28ζ CAR, or CD16-41BBζ CAR. T cells expressing CD16 CAR and TFP constructs are activated by culturing with Ag+ cells, but not the Ag- cells. The percentage of granzyme B-positive cells for each construct in Ag- cells and Ag+ cells is determined.

Figure 5:
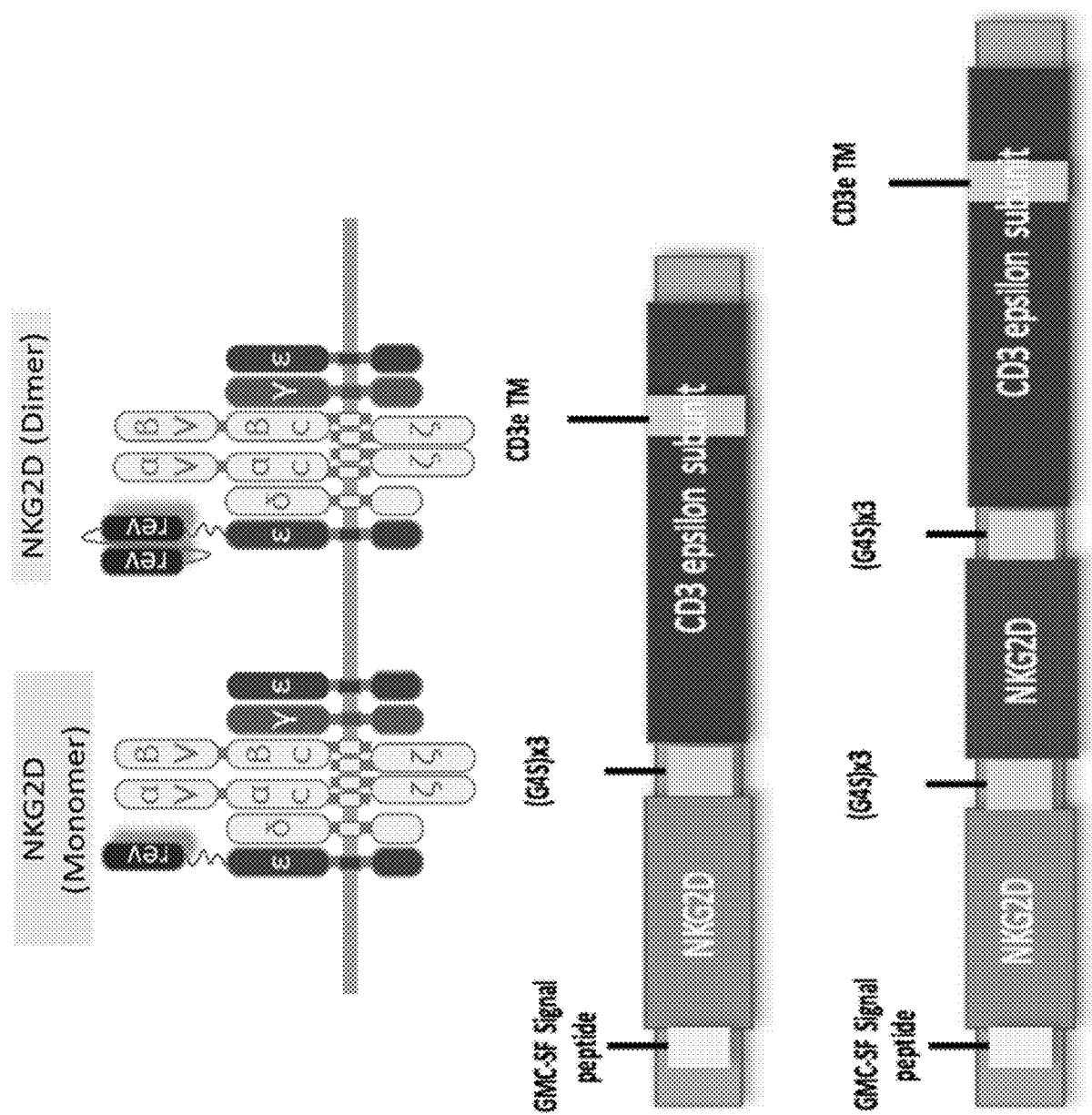
FIG. 5 shows an illustration of NKG2D ε-TFP T cell structures and lentiviral vectors bearing NKG2D ε-TFP constructs, both monomeric and dimeric. The top panel shows a complete T cell receptor with NKG2D-specific subunits, with either monomeric or dimeric NKG2D binders. The bottom panel shows a schematic of the layout of the constructs.

Example 9: NKG2D TFP-T Cells Proliferate in an Antigen-Specific Manner and Lyse NKG2D Ligand-Expressing Tumor Cells In Vitro In order to evaluate further the efficacy of NKG2D TFP T cells in vitro, three groups of TFP T cells were tested: monomeric NKG2D-CD3ε, dimeric NKG2D-CD3ε, and untransduced. A schematic of monomeric and dimeric NKG2D TFPs is shown in FIG. 5.

Materials and Methods

Lentivirus Generation

The lentivirus was prepared by transient transfection of 293TN Producer Cell Line (System Biosciences, Inc., LV900A-1) TFP and CAR constructs were generated using monomers or dimers of the NKG2D receptor sequence fused to a CD3 epsilon chain (see Appendix A).

T Cells Isolation and Lentivirus Transduction

CD4+ and CD8+ T cells were purified from Leukopack® sample (HemaCare, donor ID: W313716040891). The leukapheresis sample was subjected to CD4+ and CD8+ T cell enrichment using CD4 and CD8 MACS beads using automated cliniMACS® Prodigy automated system (Miltenyi) according to manufacturer's instructions.

T cells were activated using Dynabeads at 1:1 ratio and were maintained in AimV medium (Invitrogen) in 5% human AB serum (Gemini Bio Products, catalog #100-318), and 1% Penicillin-Streptomycin (Gibco, catalog #15240-062) in presence of 300 IU/ml IL-2 (Peprotech). Dynabead-activated T cells were transduced with lentivirus at 10 MOI (virus titered using Jurkat cells) respectively in presence of polybrene (5 μg/ml) and spinoculation at 100×G for 100 minutes once at 24-hour post-transduction.

Transduction Efficiency Determination

Transduction efficiency was determined by flow cytometry. T cells were stained using anti-CD3 APC (Clone, UCHT1), anti-CD4-Pacific blue (Clone, RPAT4), anti-CD8-APCCY7 (Clone), Human NKG2D/CD314-APC (R&D systems, LOT #LC0061321) and their respective isotype controls (BD biosciences). Cells were analyzed using BD-LSRII Fortessa® X20.

Cell Lines and Antigen Expression on Tumor Cell Surface:

Ovarian cancer cell lines OVCAR3 and OVCAR5 were purchased from ATCC. AE17 mesothelioma cell line was purchased from Sigma. All cell lines were grown according to manufacturer's instructions. Antigen expression on tumor cell surface was determined using anti-MIC A/B-R-phycoerythrin (PE) (BD Pharmingen™, Lot #6049687), anti-ULBP-2/5/6-PE (R&D systems, Lot #LWE0716091), IgG1 k isotype control-PE (BD Pharmingen, Lot #6070641). Cell surface staining was performed using the standard protocol and analyzed using BD-LSRII Fortessa® X20.

Determination of Antigen Specific T Cell Proliferation:

Proliferation assay was performed as following: 100 μg/well of ULBP2-Fc (R&D systems, Lot #GMI0316041) or IgG control in 100 μl 1×PBS was coated on 96-well high-binding plates at 4° C. overnight. The plate was washed with 1×PBS and blocked with 1% BSA for 20 mins at 4° C. and washed again with 1×PBS. Five thousand CFSC-labelled T cells were plated per well and incubated at 37° C. for 3 days. Live/Dead staining was performed on the cells on the day 4 according to established protocol and analyzed using BD-LSRII Fortessa® X20.

Determination of Antigen-Specific Tumor Lysis:

Ovarian cancer cell lines OVCAR3 or OVCAR5, or mesothelioma cell line AE17 were co-cultured with NKG2D CD3e TFP or untransduced T cells at 1:5, 1:1 and 5:1 E:T ratio on a 96-well RTCA plate. The presence of live, adherent tumor cells was recorded as electrical impulse captured by electrode at the bottom of the RTCA plate. Dead cells that are non-adherent are not recorded by the electrodes and hence the cell count drops following the standard established protocol.

Results

Figure 6A:
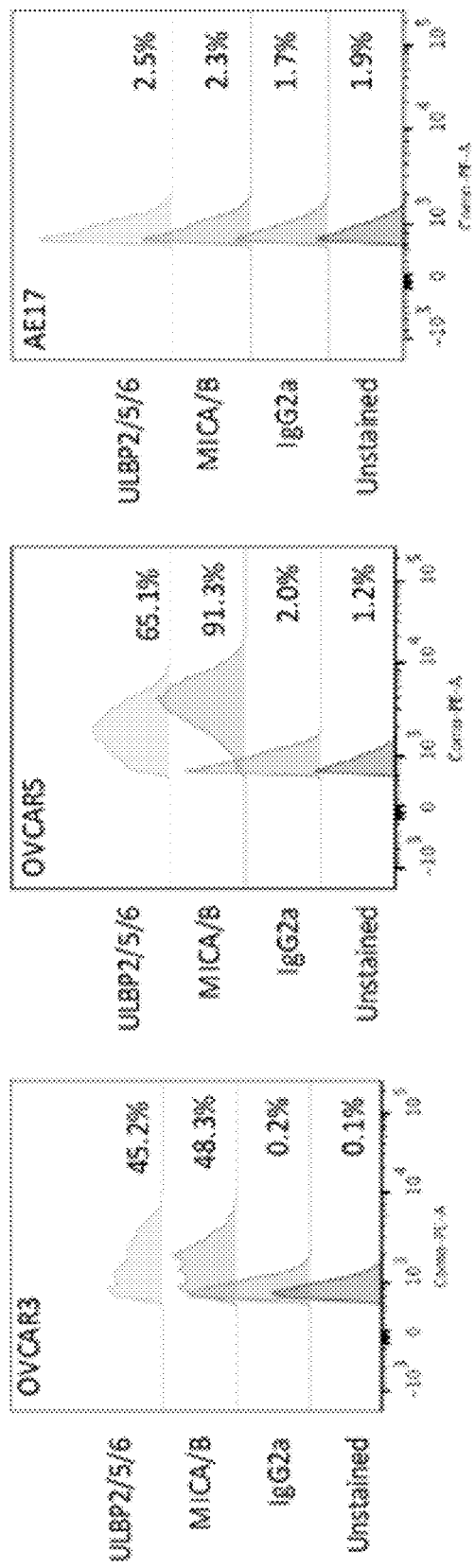
FIG. 6A is traces of Zenon staining that shows NKG2D-CD3ε TFP-T cells proliferate upon ULBP2 peptide stimulation.
Figure 6B:
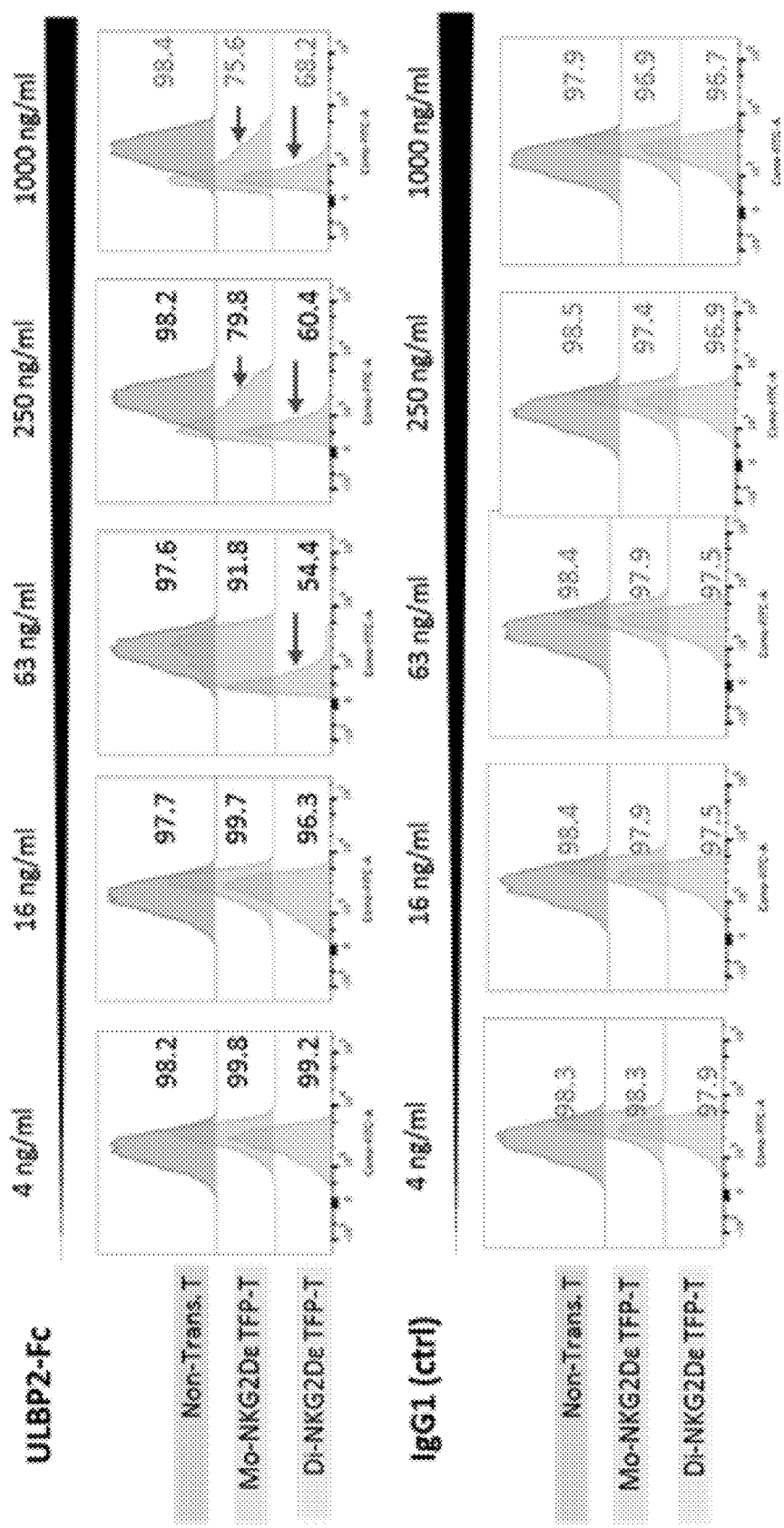
FIG. 6B shows NKG2DL antigen expression on tumor cells: OVCAR3 and OVCAR5 cells have varying levels of NKGD2L expression on the cell surface, while the AE17 mouse cell line was negative for NKG2DL expression. Arrows indicate TFP-T cell proliferation (dilution of CFSE dye after 72 hrs).
Figure 7A:
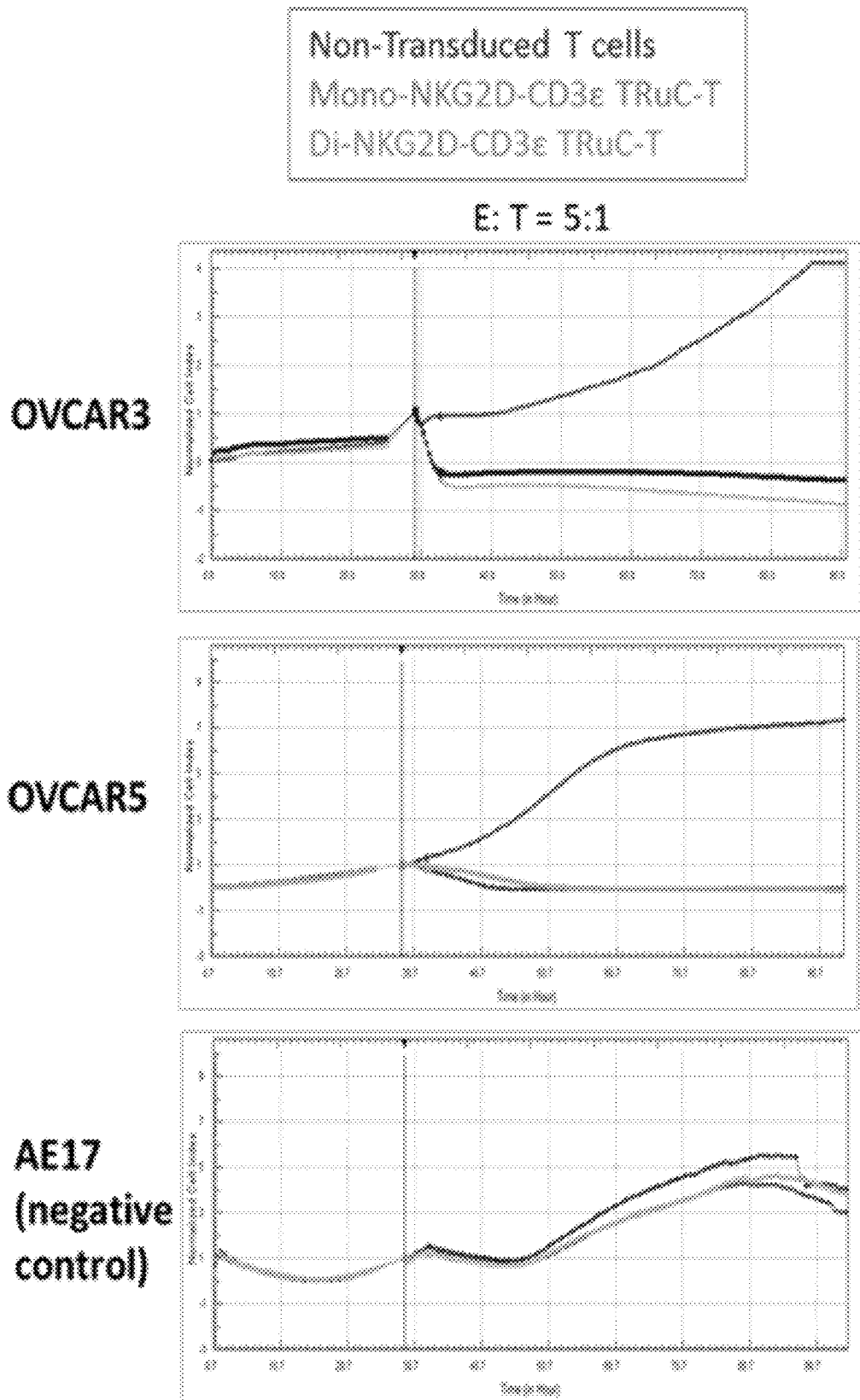
FIGS. 7A-C shows traces of RTCA analysis of monomer and dimer NKG2D ε-TFP T cell activity against NKG2D-ligand positive cells, at a 5:1 (FIG. 7A), 1:1 (FIG. 7B), or 1:5 (FIG. 7C) effector cell:target cell ratio in ovarian cancer cells lines OVCAR3 and OVCAR5, and AE17 mesothelin$^+$ cell line as a negative control. The figure shows that NKG2D ε-TFP T cells do not effectively kill non-transduced T cells (NT) but specifically kill NKG2DL$^+$ ovarian cancer cells in vitro, most particularly at a higher ratio of effector cells: target cells.
Figure 7B:
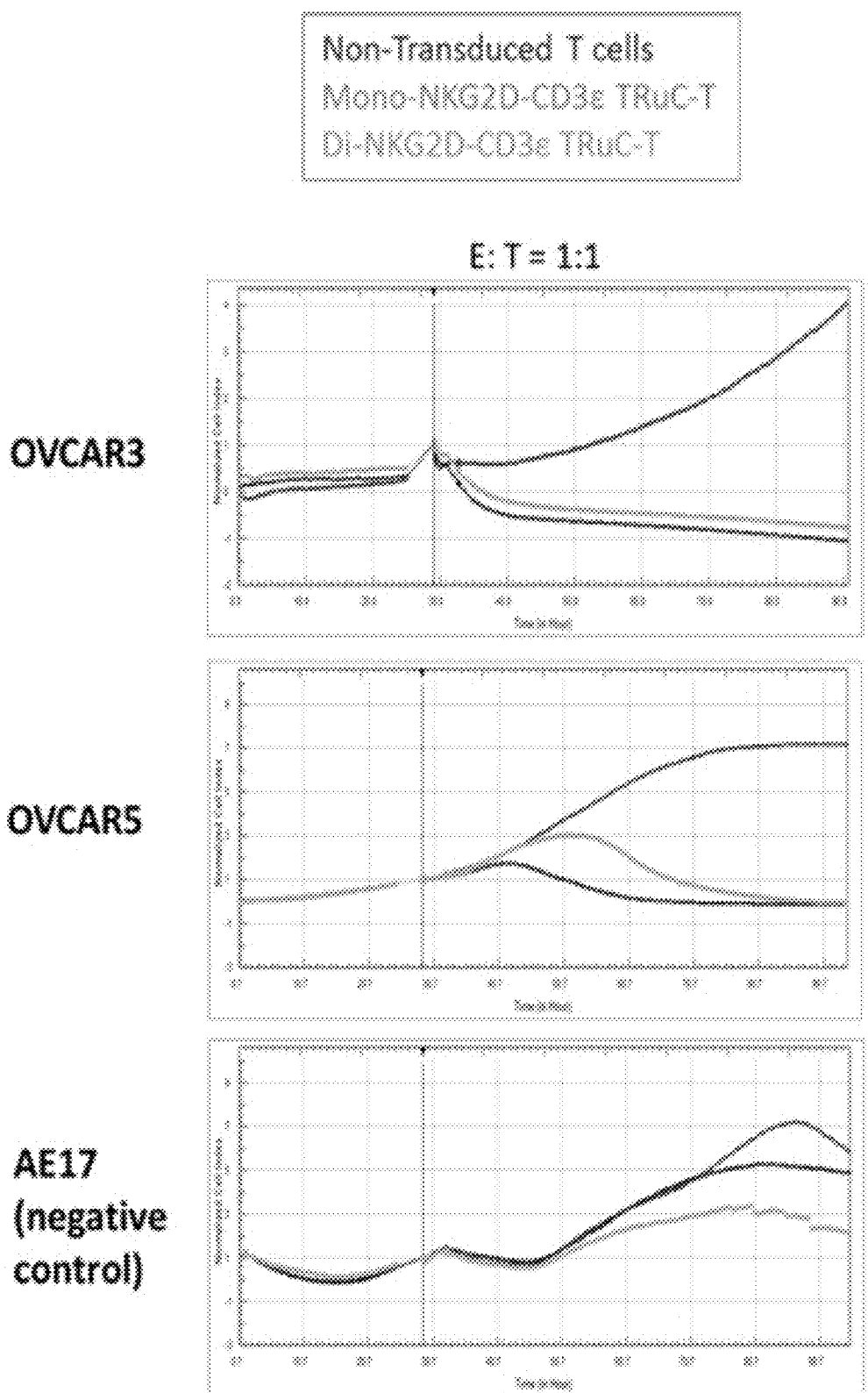
Figure 7C:
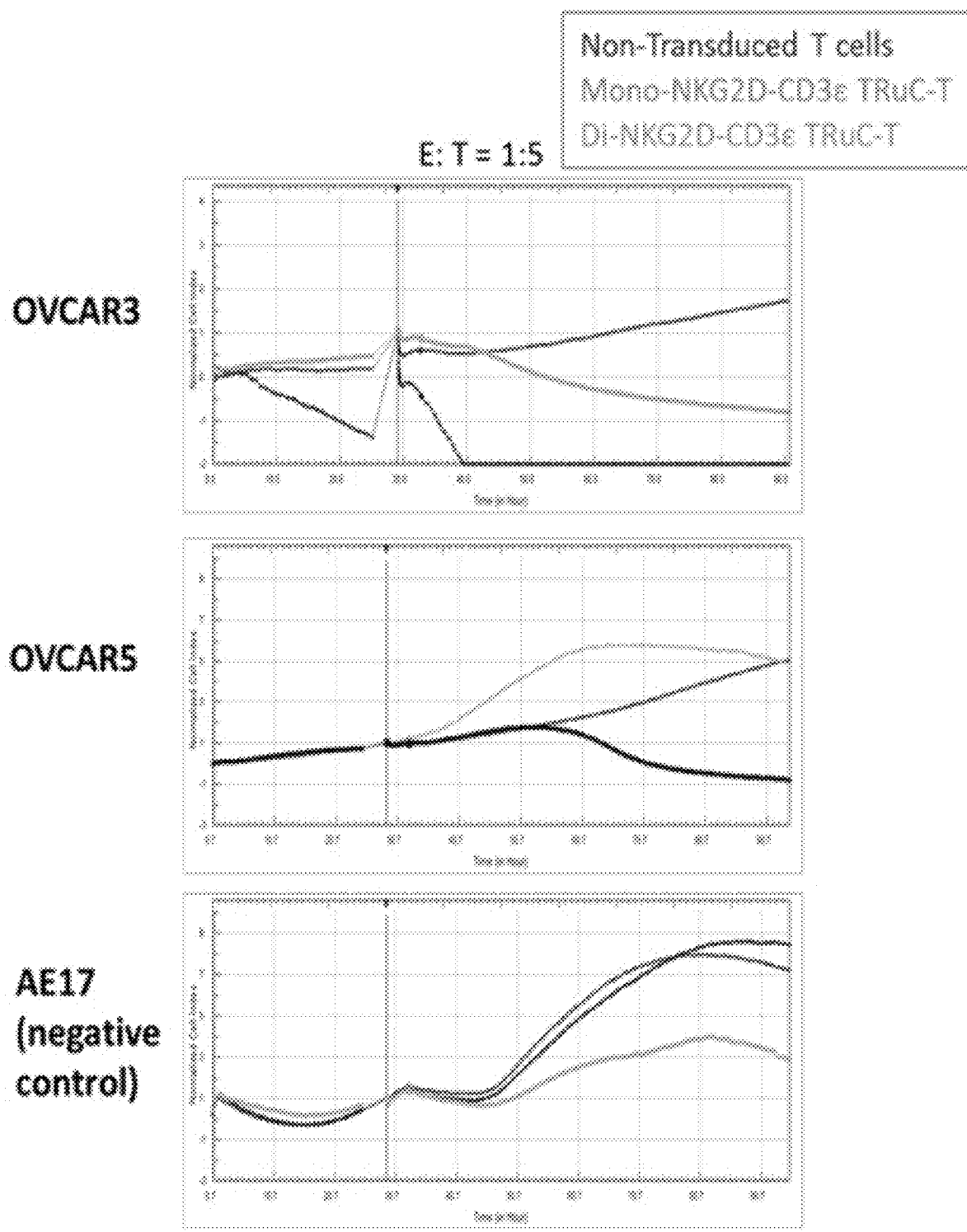

T cells were enriched for CD4+ and CD8+ T cells and transduced with indicated lentivirus vectors (FIG. 6). T cells were stimulated using CD3 and CD28 Dynabeads and cultured in the presence of IL-2 as mentioned above. FIGS. 7A-C shows Zenon staining against NKG2D ligands using (from left to right) anti-ULBP1, anti-ULBP2/5/6, anti-ULBP3, anti-ULBP4, and anti-MICA/B on MSTO-MSLN-Luc cells, OVCAR3-Luc, SaOS2-Luc, and SKOV3-Luc cells. In each graph, the top trace is anti-NKG2D ligand, the middle trace is an isotype control or secondary antibody alone, and the bottom trace is unstained cells.

Mono and di NKG2D CD3ε TFP formats were evaluated by anti-NKG2D surface staining. Our data revealed the di NKG2D CD3ε TFP variant is most efficiently expressed on the surface when compared to mono NKG2D CD3ε TFP variants, while the isotype control was negative for all T cell groups (see FIG. 2A).

To determine the antigen specificity of NKG2D CD3ε TFP T cells, CFSC-labelled T cells were cocultured with ULBP-2 coated onto a plate for three-day culture period. The dimer NKG2D CD3ε TFP T cell proliferate in the presence of antigen at concentrations as low as 60 ng/ml (indicated by red arrow in FIG. 6A) unlike untransduced T cells. The mono NKG2D CD3 F TFP T cells proliferate to antigen concentrations up to 250 ng/ml (indicated by arrows on FIG. 6A). The increased proliferation capacity of di NKG2D CD3ε TFPs could be due to increase expression of di NKG2D CD3e on T cell surface compared to mono NKG2D CD3e TFPs. None of the transduced or untransduced condition proliferate in the presence of isotype control bound to a plate.

To assess the antigen-specific tumor lysis capacity of NKG2D CD3ε TFP T cells, effector and tumor cells were co-cultured at 1:5, 1:1, and 5:1 E:T ratio. Ovarian cancer cells that expressed NKG2DL on its surfaced were evaluated by flow cytometry analysis for NKG2DL expression. OVCAR3 and OVCAR5 were both positive for MICA/B and ULBP2/5/6 compared to isotype control or unstained samples. AE17 mouse tumor cell line was negative for NKG2DL antigen expression and had a similar profile to isotype control or unstained sample in the PE channel when evaluated by flow cytometry (FIG. 6B).

Antigen-specific tumor lysis capacity evaluated by RTCA assay showed that dimeric NKG2D CD3ε TFP T cells and mono NKG2D CD3ε TFP T cells lysed antigen positive tumor cells to similar extent at 1:5 ratio, while at 1:1 and 5:1 ratio mono NKG2D CD3ε TFP showed delayed tumor lysis due to lower TFP expression compared to di NKH2D CD3ε T cells (FIGS. 7A-C). No tumor lysis was observed with antigen negative AE17 mouse tumor cell line or with untransduced T cell conditions.

These results show antigen-specific proliferation and tumor lysis of mono and di NKG2D CD3ε TFP T cells compared to untransduced T cells.

Example 10: Luciferase-Based Cytotoxicity Assay-Dual Specificity TFP T Cells

The luciferase based cytotoxicity assay ("Luc-Cyto" assay) assesses the cytotoxicity of TFP T cells by indirectly measuring the luciferase enzymatic activity in the residual live target cells after co-culture. The target cells used in Luc-Cyto assay were HeLa-BCMAt and HeLa-CD19t cells stably transduced to express firefly luciferase. The DNA encoding firefly luciferase was synthesized by GeneArt® (Thermo Fisher®) and inserted into the multiple cloning site of single-promoter lentiviral vector pCDH527A-1 (System Bioscience). The lentivirus carrying the firefly luciferase was packaged with the same procedure as mentioned in section 1.1. The HeLa-BCMAt and HeLa-CD19t cells were then transduced with the firefly luciferase construct carrying lentivirus for 24 hours and then selected with puromycin (5 µg/mL). The generation of HeLa-BCMAt-luciferase or HeLa-CD19t-luciferase cells was confirmed by measuring the luciferase enzymatic activity in the cells with Bright-Glo™ Luciferase Assay System (Promega).

Figures 8A, 8B:
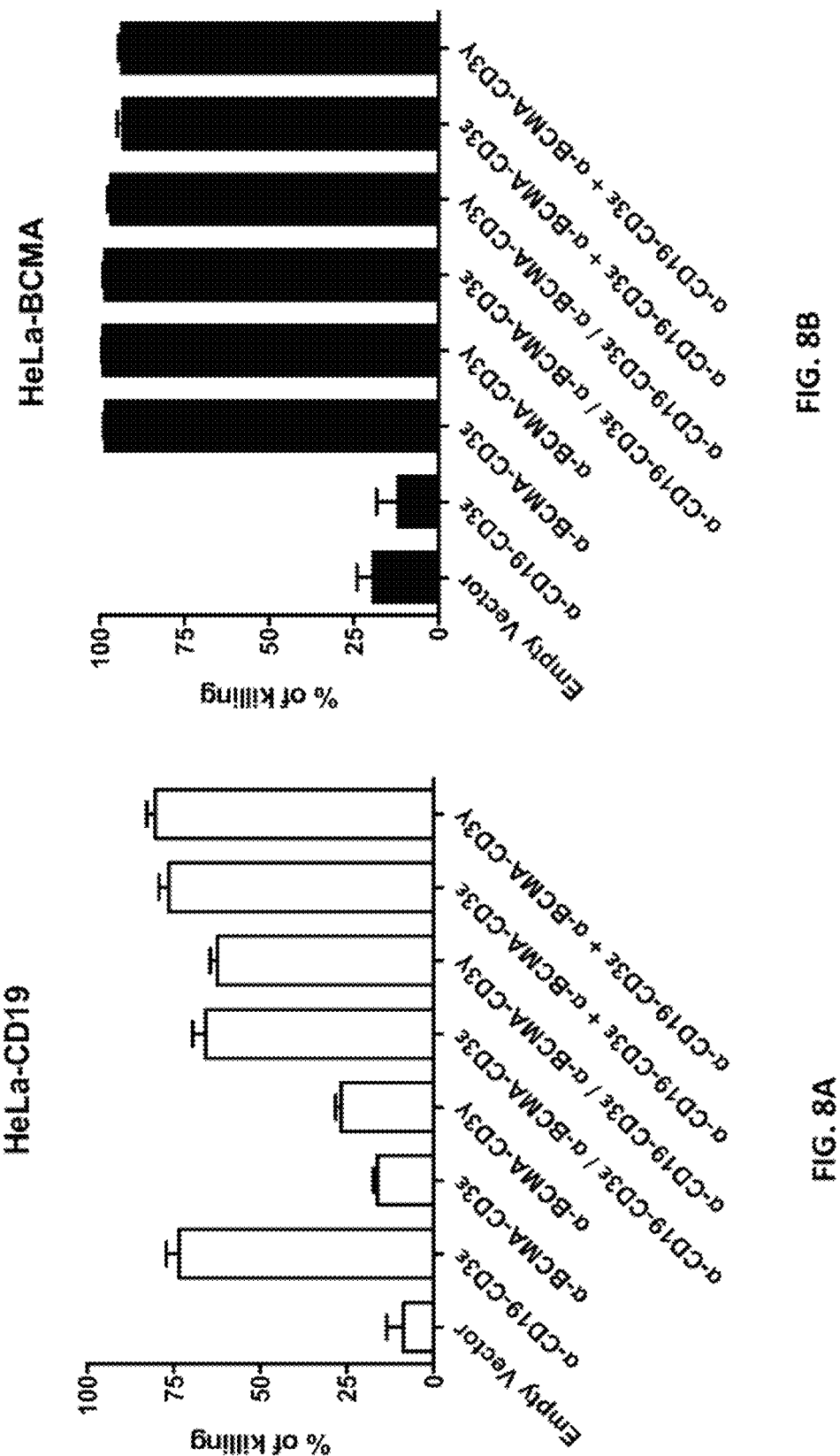
FIGS. 8A-C is a series of graphs showing tumor cell lysis as measured in a luciferase assay. T cells were transduced with an empty expression vector, or the following TFPs: anti-CD19-CD3ε, anti-BCMA-CD3ε, anti-BCMA-CD3γ, anti-CD19-CD3ε, anti-BCMA-CD3ε, anti-CD19-CD3ε/ anti-BCMA-CD3γ, anti-CD19-CD3ε, anti-BCMA-CD3ε, or anti-CD19-CD3ε, anti-BCMA-CD3γ. The transduced T cells were incubated with HeLa cells that stably express CD19 (FIG. 8A), HeLa cells that stably express BCMA (FIG. 8B), or HeLa cells that stably express both CD19 and BCMA (FIG. 8C). "T" refers to assays with a T cell population transduced with two viruses, one with an anti-BCMA TFP and one with an anti-CD19 TFP; "+" refers to the use of two populations of T cells, one transduced with an anti-BCMA TFPs and one transduced with anti-CD19 TFPs, that have been combined. The T cells were mixed with the target HeLa cells and incubated together for 24 hours. The cells were spun into a pellet and resuspended in medium containing the luciferase substrate. Luciferase is released by cell lysis; thus, higher luciferase activity corresponds to a greater percentage of cell death.
Figures 8C, 9A:
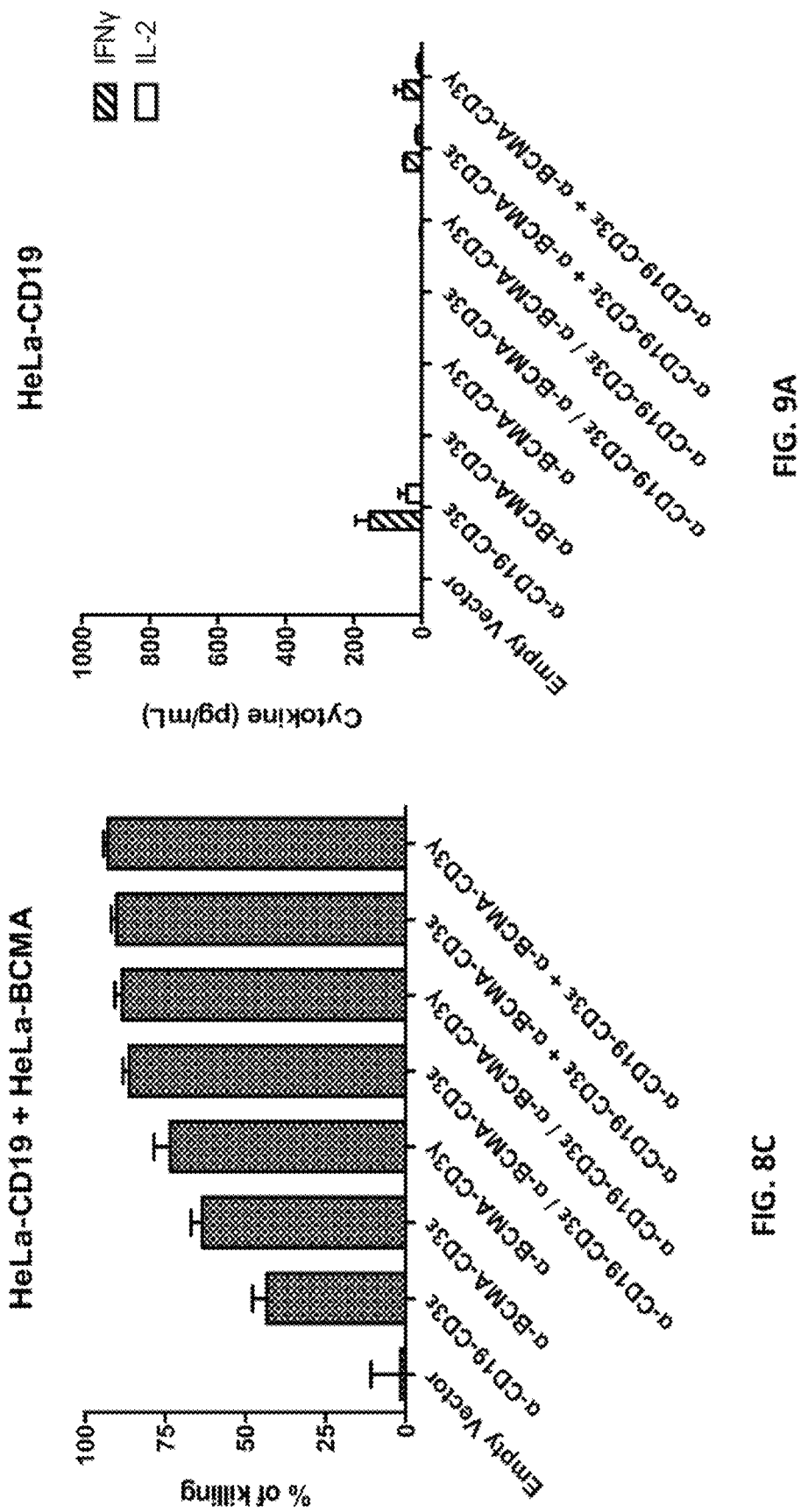
FIGS. 9A-C is a series of graphs showing cytokine production as measured in the supernatant of the cells that were pelleted in the analysis shown in FIG. 8. A Luminex® ELISA assay was performed to detect and quantify the amount of IFNγ (hatched bars) and IL-2 (solid bars). As above, the transduced T cells were incubated with HeLa cells that stably express CD19 (FIG. 9A), HeLa cells that stably express BCMA (FIG. 9B), or HeLa cells that stably express both CD19 and BCMA (FIG. 9C). "/" refers to assays with a T cell population transduced with two viruses, one with an anti-BCMA TFP and one with an anti-CD19 TFP; "+" refers to the use of two populations of T cells, one transduced with an anti-BCMA TFPs and one transduced with anti-CD19 TFPs, that have been combined. Total cytokine production is shown on the Y axis.

Results are shown in FIG. 8. T cells were transduced with an empty expression vector, or the following TFPs: anti-CD19-CD3ε, anti-BCMA-CD3ε, anti-BCMA-CD3γ, anti-CD19-CD3ε/anti-BCMA-CD3ε, anti-CD19-CD3ε/anti-BCMA-CD3γ, anti-CD19-CD3ε+ anti-BCMA-CD3ε, or anti-CD19-CD3ε+ anti-BCMA-CD3γ. The transduced T cells were incubated with HeLa cells that stably express CD19 (FIG. 8A), HeLa cells that stably express BCMA (FIG. 8B), or HeLa cells that stably express both CD19 and BCMA (FIG. 8C). "/" refers to assays with a T cell population transduced with two viruses, one with an anti-BCMA TFP and one with an anti-CD19 TFP; "+" refers to the use of two populations of T cells, one transduced with an anti-BCMA TFPs and one transduced with anti-CD19 TFPs, that have been combined. The target cells (in this assay, HeLa-BCMAt-luciferase or HeLa-CD19t-luciferase) were plated at 5000 cells per well in 96-well plate. TFP T cells were added to the target cells at desired effector-to-target ratios. The mixture of cells was then cultured for 24 hours at 37° C. with 5% $CO_2$ before the luciferase enzymatic activity in the live target cells was measured by the Bright-Glo® Luciferase Assay System. The cells were spun into a pellet and resuspended in medium containing the luciferase substrate. Luciferase is released by cell lysis, thus, higher luciferase activity corresponds to a greater percentage of cell death. As shown in the figure, the dual-specificity TFP T cell populations killed a higher percentage of cells than any of the single constructs alone.

Example 11: IL-2 and IFN-γ Secretion by Luminex®: Dual Specificity TFP T Cells

To detect the levels of cytokine release by effector cells in contact with target cells, 2-Plex assays were performed using the Human Cytokine Magnetic Buffer Reagent Kit (Invitrogen, LHB0001M) with the Human IL-2 Magnetic Bead Kit (Invitrogen, LHC0021M) and the Human IFN-γ Magnetic Bead Kit (Invitrogen, LHC4031M). Cytokine production was measured in the supernatant of the cells that were pelleted in the analysis shown in FIG. 8.

Figure 9C:
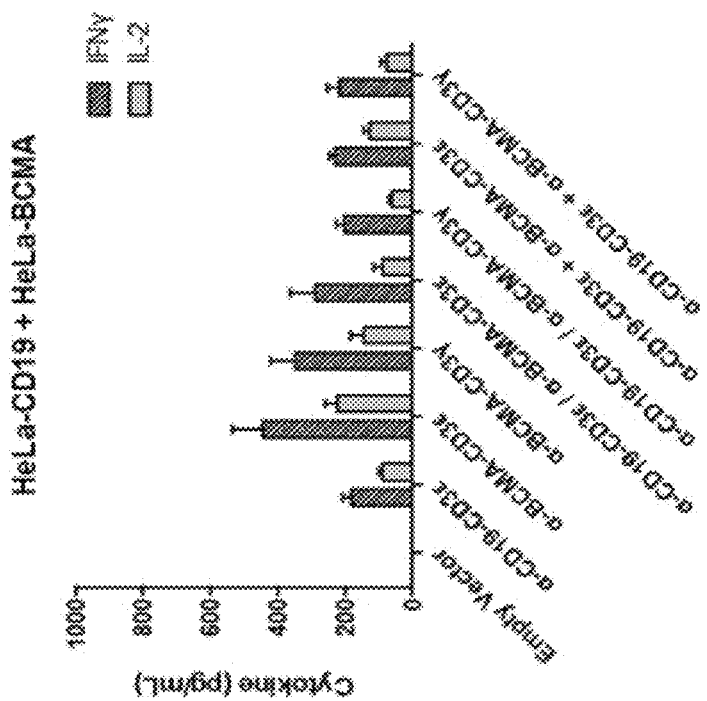
Figure 9B:
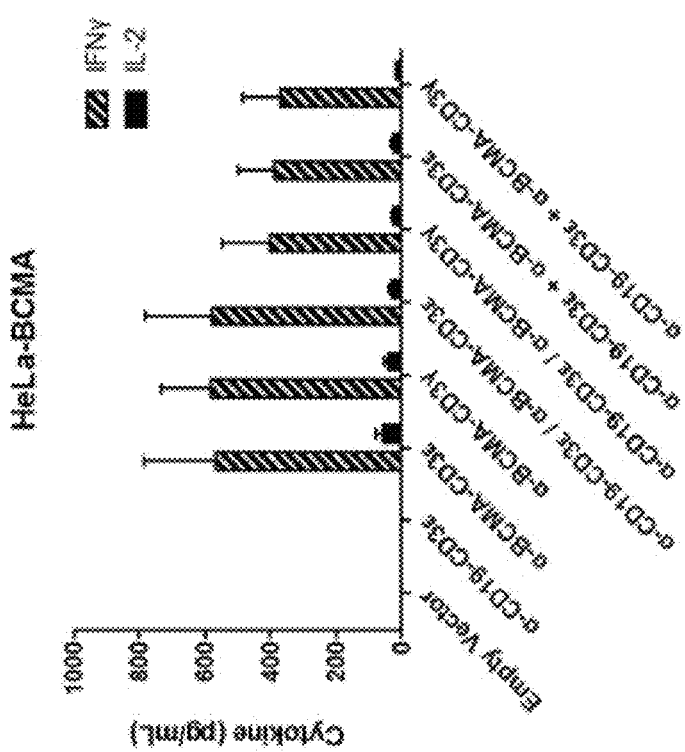

Results are shown in FIG. 9 and the amount of IFNγ (hatched bars) and IL-2 (solid bars) is shown. As above, the transduced T cells were incubated with HeLa cells that stably express CD19 (FIG. 9A), HeLa cells that stably express BCMA (FIG. 9B), or HeLa cells that stably express both CD19 and BCMA (FIG. 9C). "/" refers to assays with a T cell population transduced with two viruses, one with an anti-BCMA TFP and one with an anti-CD19 TFP; "+" refers to the use of two populations of T cells, one transduced with an anti-BCMA TFPs and one transduced with anti-CD19 TFPs, that have been combined. Total cytokine production is shown on the Y axis. As shown in the figure, cytokine production from cells treated with the dual specificity TFP was not higher than that of the single specificity TFPs. In most cases production of cytokines was lower, indicating that there may be no increase in toxicity for patients receiving treatment with the engineered T cells described herein.

Example 12: IL-2 and IFN-γ Secretion by ELISA: NKG2D TFP T Cells

Another measure of effector T-cell activation and proliferation associated with the recognition of cells bearing cognate antigen is the production of effector cytokines such as interleukin-2 (IL-2) and interferon-gamma (IFN-γ).

ELISA assays for human IL-2 (catalog #EH2IL2, Thermo Scientific®) and IFN-γ catalog #KHC4012, Invitrogen) are performed as described in the product inserts. In one example, 50 µL of reconstituted standards or samples in duplicate are added to each well of a 96-well plate followed by 50 µL of Biotinylated Antibody Reagent. Samples are mixed by gently tapping the plate several times. 50 µL of Standard Diluent is then added to all wells that did not contain standards or samples and the plate is carefully sealed with an adhesive plate cover prior to incubation for 3 hours at room temperature (20-25° C.). The plate cover is then removed, plate contents are emptied, and each well is filled with Wash Buffer. This wash procedure is repeated a total of 3 times and the plate is blotted onto paper towels or other absorbent material. 100 µL of prepared Streptavidin-HRP Solution is added to each well and a new plate cover is attached prior to incubation for 30 minutes at room temperature. The plate cover is again removed, the plate contents are discarded, and 100 µL of TMB Substrate Solution is added into each well. The reaction is allowed to develop at room temperature in the dark for 30 minutes, after which 100 μL of Stop Solution is added to each well. Evaluate the plate. Absorbance is measured on an ELISA plate reader set at 450 nm and 550 nm within 30 minutes of stopping the reaction. 550 nm values are subtracted from 450 nm values and IL-2 amounts in unknown samples are calculated relative to values obtained from an IL-2 standard curve.

Alternatively, 2-Plex assays are performed using the Human Cytokine Magnetic Buffer Reagent Kit (Invitrogen, LHB0001M) with the Human IL-2 Magnetic Bead Kit (Invitrogen, LHC0021M) and the Human IFN-γ Magnetic Bead Kit (Invitrogen, LHC4031M). Briefly, 25 μL of Human IL-2 and IFN-γ antibody beads are added to each well of a 96-well plate and washed using the following guidelines: two washes of 200 μL 1× wash solution, placing the plate in contact with a Magnetic 96-well plate Separator (Invitrogen, A14179), letting the beads settle for 1 minute and decanting the liquid. Then, 50 μL of Incubation Buffer is added to each well of the plate with 100 μL of reconstituted standards in duplicates or 50 μL of samples (supernatants from cytotoxicity assays) and 50 μL of Assay Diluent, in triplicate, for a total volume of 150 μL. Samples are mixed in the dark at 600 rpm with an orbital shaker with a 3 mm orbital radius for 2 hours at room temperature. The plate is washed following the same washing guidelines and 100 μL of human IL-2 and IFN-γ biotinylated detector antibody is added to each well. Samples are mixed in the dark at 600 rpm with an orbital shaker with a 3 mm orbital radius for 1 hour at room temperature. The plate is washed following the same washing guidelines and 100 μL of Streptavidin-R-Phycoerythrin is added to each well. Samples are mixed in the dark at 600 rpm with an orbital shaker with a 3 mm orbital radius for 30 minutes at room temperature. The plate is washed 3 times using the same washing guidelines and after decanting the liquid the samples are re-suspended in 150 μL of 1× wash solution. The samples are mixed at 600 rpm with an orbital shaker with a 3 mm orbital radius for 3 minutes and stored over night at 4° C. Afterwards, the plate is washed following the same washing guidelines and the samples are re-suspended in 150 μL of 1× wash solution.

The plate is read using the MAGPIX System (Luminex) and xPONENT software. Analysis of the data is performed using MILLIPLEX Analyst software, which provides the standard curve and cytokine concentrations.

Relative to non-transduced or control CAR-transduced T cells, T cells transduced with NKG2D TFPs may produce higher levels of both IL-2 and IFN-γ when co-cultured with either cells that endogenously express NKG2D or NKG2D-transduced cells. In contrast, co-culture with NKG2D negative cells or non-transduced cells, may result in little or no cytokine release from TFP-transduced T cells. Consistent with the previous cytotoxicity data, NKG2D TFPs constructed with an alternative hinge region may generate similar results upon co-culture with NKG2D-bearing target cells.

In agreement with the previous cytotoxicity data, NKG2D-CD3ε and NKG2D-CD3γ may produce the highest IL-2 and IFN-γ levels of the TFP constructs. However, cytokine production by T cells transduced with NKG2D-CD3ε and NKG2D-CD3γ TFPs may be comparable to that of T cells expressing NKG2D-28ζ CAR, despite the TFPs demonstrating much higher levels of target cell killing. The possibility that TFPs may more efficiently kill target cells than CARs, but release comparable or lower levels of pro-inflammatory cytokines, represents a potential advantage for TFPs relative to CARs since elevated levels of these cytokines have been associated with dose-limiting toxicities for adoptive CAR-T therapies.

Activated PBMCs are transduced with 50 MOI lentiviruses for two consecutive days and expanded. Day 8 post transduction, co-cultures of PBMCs were set up with target cells (K562 cells overexpressing NKG2D) at E:T, 1:1 ratio ($0.2\times10^6$ each cell type) in cytotoxicity medium (Phenol red-free RPMI1640 (Invitrogen) plus 5% AB serum (Gemini Bioproducts; 100-318). K562 cells overexpressing BCMA were used as negative controls. After 24 hours, cells are analyzed for IFN-γ and IL-2 expression by ELISA as described above. T cells expressing NKG2D CAR and TFP constructs are activated, as evidenced by both IFN-γ and IL-2 production, by co-culturing with $NKG2D^+$ cells, but not the $NKG2D^-$ cells, further demonstrating the ability of NKG2D-expressing cells to specifically activate T cells.

Example 13: Cytotoxicity by Real Time Cytotoxicity Assay: Dual Specificity TFP T Cells The RTCA measures the electrical impedance of an adherent target cell monolayer, in each well of a specialized 96-well plate, in real time and presents the final readout as a value called the cell index. Changes in cell index indicate disruption of the target cell monolayer as a result of killing of target cells by co-incubated T-cell effectors. Thus, the cytotoxicity of the effector T-cells can be evaluated as the change in cell index of wells with both target cells and effector T-cells compared to that of wells with target cells alone.

The target cells used in this Example were HeLa cells expressing truncated BCMA (HeLa-BCMAt, intracellular domain deleted) or HeLa cells expressing truncated CD19 (HeLa-CD19t, intracellular domain deleted). The DNA encoding human BCMAt or CD19t was synthesized by GeneArt® (Thermo Fisher) and inserted into the multiple cloning site of dual-promoter lentiviral vector pCDH514B (System Bioscience) carrying neomycin as selection marker, which is under the control of EF1a promoter. The lentivirus carrying the BCMAt or CD19t encoding vector was then packaged with the same procedure as described above. The HeLa cells were then transduced with the BCMAt or CD19t construct carrying lentivirus for 24 hours and then selected with G418 (1 mg/mL). The expression of BCMAt or CD19t by the selected HeLa-BCMAt or HeLa-CD19t cells was confirmed by FACS analysis with anti-human BCMA antibodies (BioLegend, clone #19A2; Miltenyi, clone #REA315) or anti-human CD19 antibodies (BD Biosciences), respectively.

For the RTCA, target cells (HeLa-BCMAt or HeLa-CD19t) were plated at 10,000 cells per well in the 96-well polyethylene terephthalate (PET) E-Plate® (ACEA Biosciences, Inc.). In order to test the dual-specific TFP T cells, HeLa-BCMAt and HeLa-CD19t cells were mixed at 1:1 ratio to reach final number 10,000 cells per well. The plate was then placed into the xCELLigence® RTCA MP instrument (ACEA Biosciences, Inc.) and the baseline measurement was done every 15 minutes for 100 measurements. The plate was then removed from the instrument and the effector T cells, suspended in cytotoxicity medium (Phenol red-free RPMI1640+5% AB serum), were added to each well at 60,000 cells to reach the effector-to-target ratio of 6-to-1. The plate was then placed back to the instrument. The measurement was carried out for every 2 minutes for 100 measurements, and then every 15 minutes for 1000 measurements.

Results are shown in FIG. 10. A key to FIG. 10 is presented in the Table below.

TABLE 2

Constructs used in RTCA assay.

| FIGURE | Trace Number | Target Cells | Construct |
|---|---|---|---|
| 5A | 1 | HeLa-CD19 | Target only |
|  | 2 |  | α-BCMA-CD3ε |
|  | 3 |  | α-BCMA-CD3γ |
|  | 4 |  | Non-transduced |
|  | 5 |  | Empty Vector |
|  | 6 |  | α-CD19-CD3ε/α-BCMA-CD3γ |
|  | 7 |  | α-CD19-CD3ε/α-BCMA-CD3ε |
|  | 8 |  | α-CD19-CD3ε + α-BCMA-CD3γ |
|  | 9 |  | α-CD19-CD3ε + α-BCMA-CD3ε |
|  | 10 |  | α-CD19-CD3ε |
| 5B | 1 | HeLa-BCMA | Target only |
|  | 2 |  | Non-transduced |
|  | 3 |  | Empty Vector |
|  | 4 |  | α-CD19-CD3ε |
|  | 5 |  | α-CD19-CD3ε + α-BCMA-CD3ε |
|  | 6 |  | α-CD19-CD3ε + α-BCMA-CD3γ |
|  | 7 |  | α-CD19-CD3ε/α-BCMA-CD3γ |
|  | 8 |  | α-CD19-CD3ε/α-BCMA-CD3ε |
|  | 9 |  | α-BCMA-CD3ε |
|  | 10 |  | α-BCMA-CD3γ |
| 5C | 1 | HeLa-CD19 + | Target only |
|  | 2 | HeLa-BCMA | Non-transduced |
|  | 3 | (εε) | Empty Vector |
|  | 4 |  | α-CD19-CD3ε |
|  | 5 |  | α-BCMA-CD3ε |
|  | 6 |  | α-CD19-CD3ε/α-BCMA-CD3ε |
|  | 7 |  | α-CD19-CD3ε + α-BCMA-CD3ε |
| 5D | 1 | HeLa-CD19 + | Target only |
|  | 2 | HeLa-BCMA | Non-transduced |
|  | 3 | (εγ) | Empty Vector |
|  | 4 |  | α-CD19-CD3ε |
|  | 5 |  | α-BCMA-CD3γ |
|  | 6 |  | α-CD19-CD3ε/α-BCMA-CD3γ |
|  | 7 |  | α-CD19-CD3ε + α-BCMA-CD3γ |

In the table in the right-hand column, "/" refers to assays with a T cell population transduced with two viruses, one with an anti-BCMA TFP and one with an anti-CD19 TFP; "+" refers to the use of two populations of T cells, one transduced with an anti-BCMA TFPs and one transduced with anti-CD19 TFPs, that have been combined.

Figure 10A:
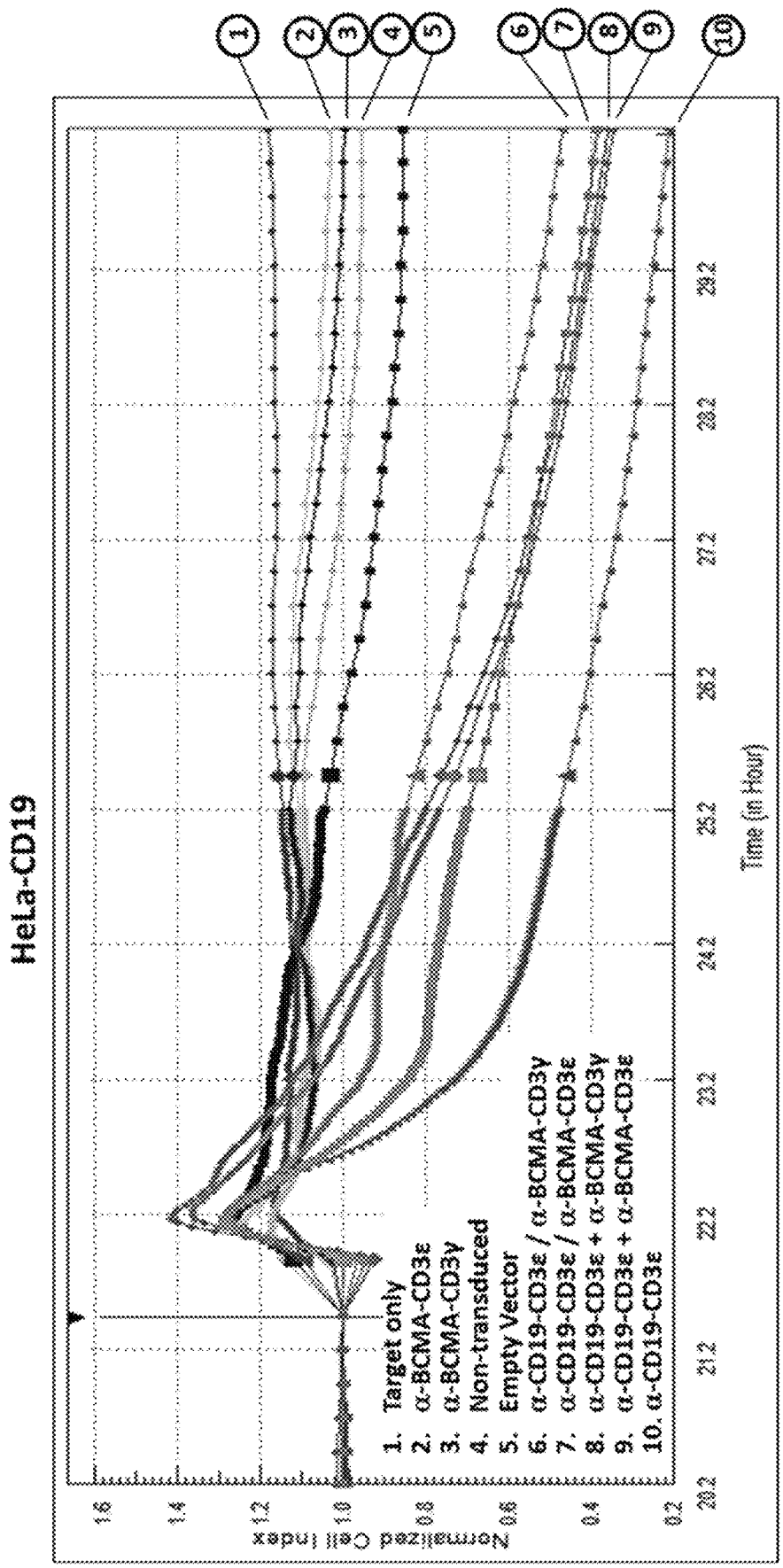
FIGS. 10A-D is a series of images showing the results of a Real Time Cytotoxicity Assay (RTCA) as described in Example 9. The normalized cell index, indicative of cytotoxicity, was determined in a real time cell analyzer (RTCA) assay. Table 2 summarizes the constructs used in the Example.

FIG. 10A shows CD19-expressing HeLa cells, and shows that dual constructs comprising anti-BCMA and anti-CD19 TFP T cells killed cells better and faster than cells with anti-BCMA TFP T cells alone. The monospecific anti-CD19 TFP control had comparable activity to the dual specificity TFP T cells.

Figure 10B:
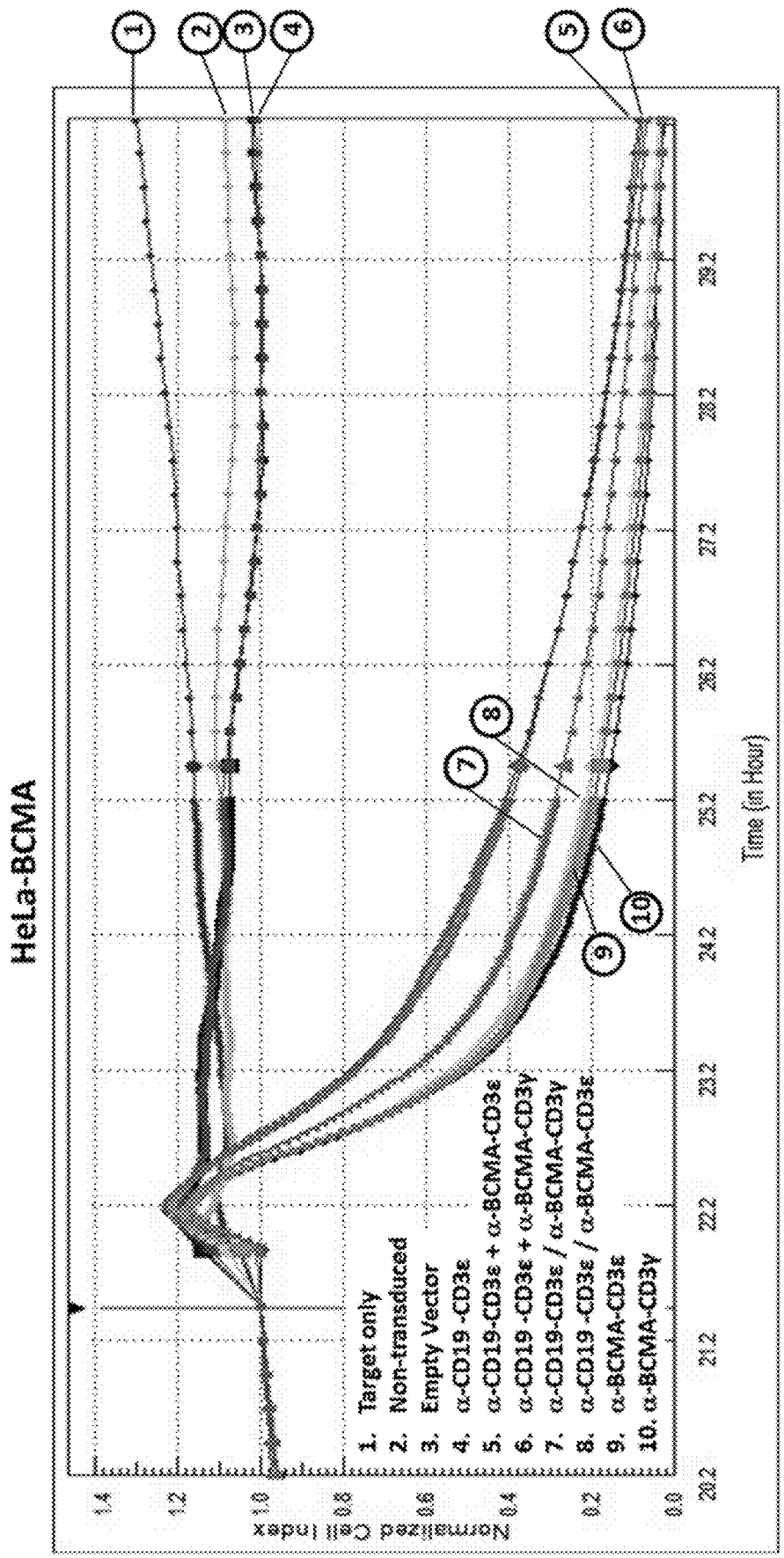

FIG. 10B shows BCMA-expressing HeLa cells, and shows that dual constructs comprising anti-BCMA and anti-CD19 TFP T cells killed cells better and faster than cells with anti-CD19 TFP T cells alone. The monospecific anti-BCMA TFP control had comparable activity to the dual specificity TFP T cells.

Figure 10C:
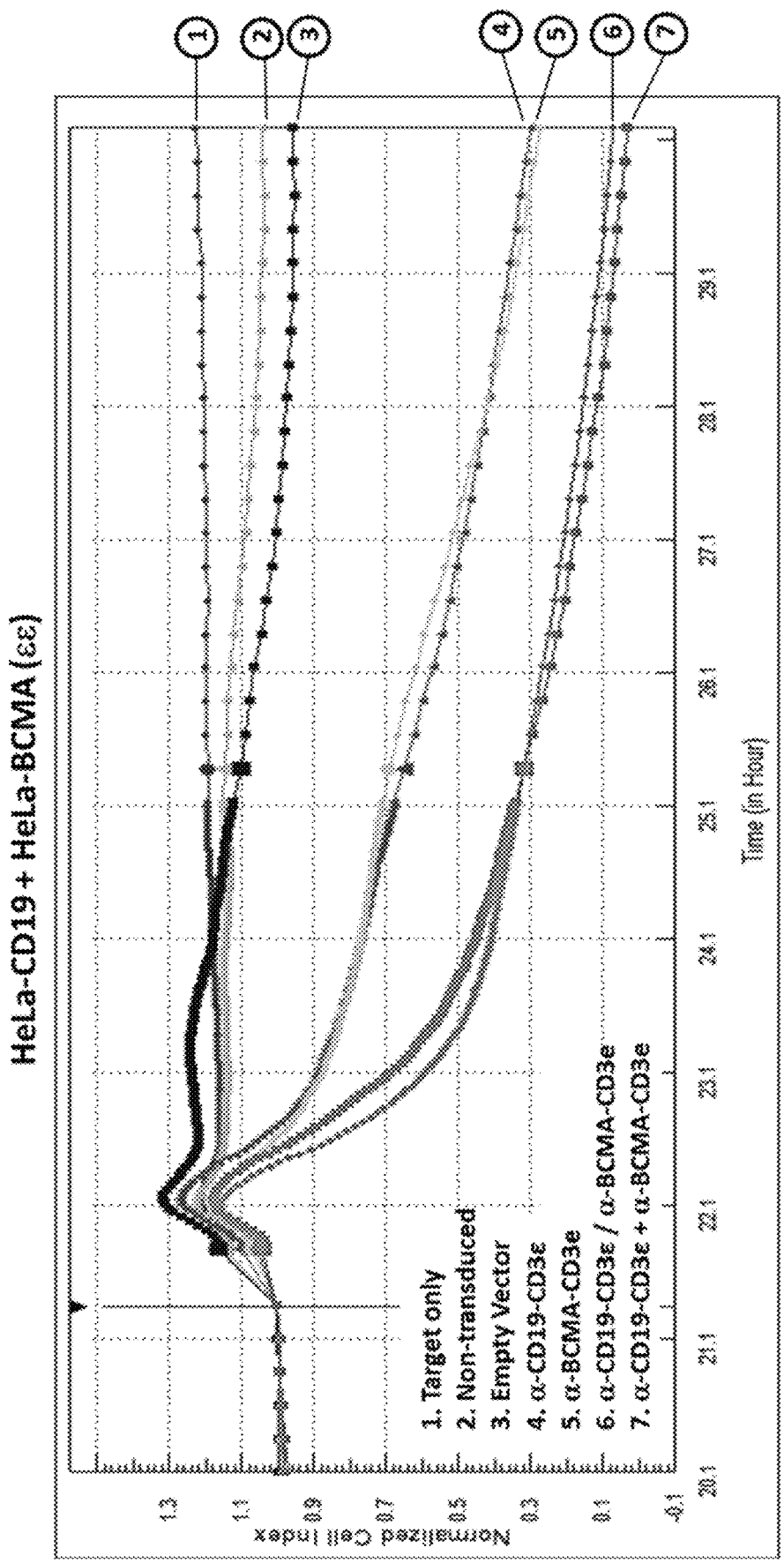

FIG. 10C shows BCMA- and CD19-expressing HeLa cells and measures the ability of the "εε" dual specificity construct, compared to the single specificity TFPs. As shown, the dual-specificity TFP T cells, whether transduced with two viruses or two T cell populations mixed, had significantly greater activity than either single specificity TFP T cell population alone.

Figure 10D:
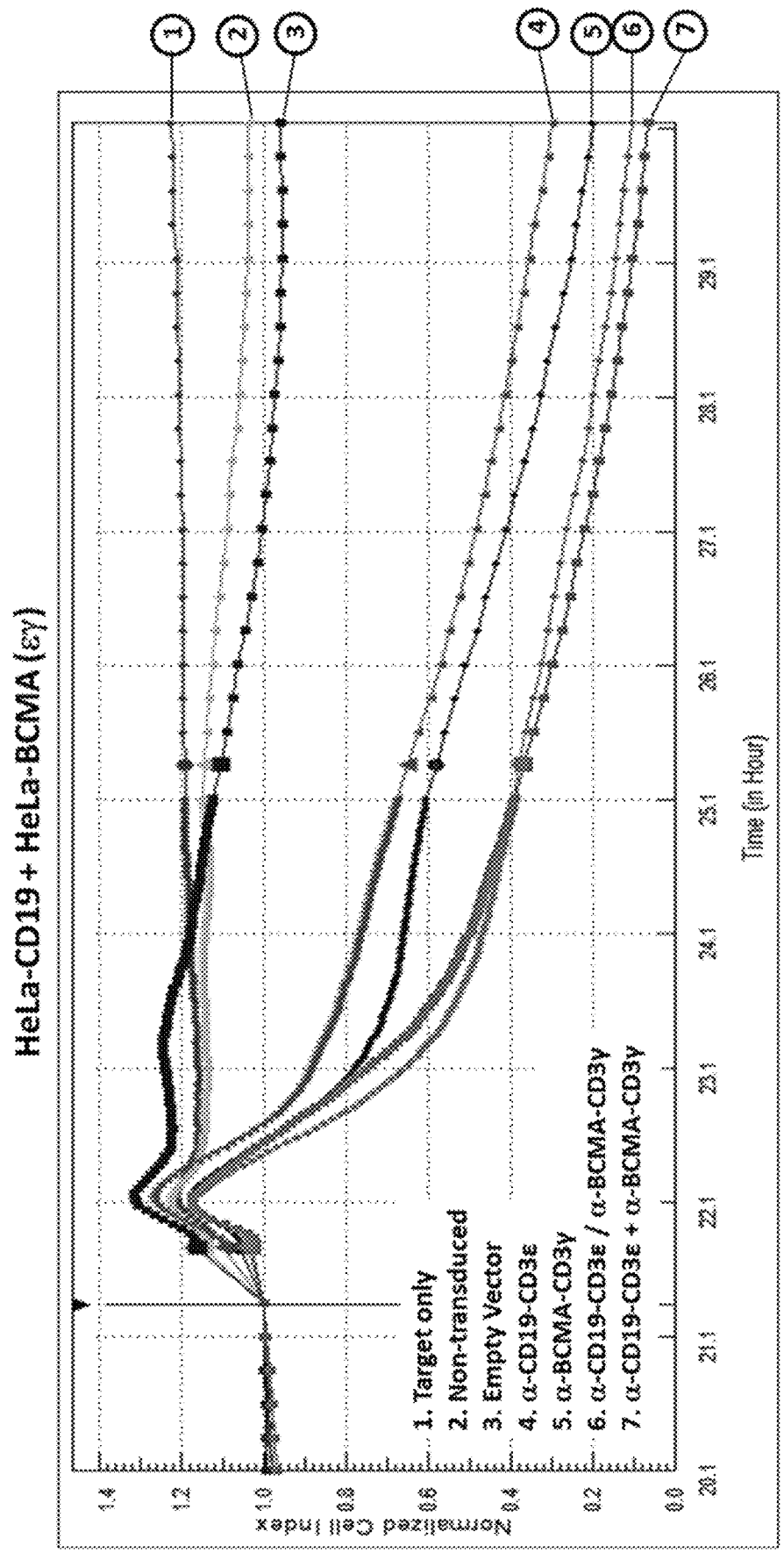

FIG. 10D shows BCMA- and CD19-expressing HeLa cells and measures the ability of the "εγ" dual specificity construct, compared to the single specificity TFPs. As shown, the dual-specificity TFP T cells, whether transduced with two viruses or two T cell populations mixed, had significantly greater activity than either single specificity TFP T cell population alone.

Example 14: CD107a Exposure by Flow Cytometry

An additional assay for T-cell activation is surface expression of CD107a, a lysosomal associated membrane protein (LAMP-1) that is located in the membrane of cytoplasmic cytolytic granules in resting cells. Degranulation of effector T cells, a prerequisite for cytolytic activity, results in mobilization of CD107a to the cell surface following activation-induced granule exocytosis. Thus, CD107a exposure provides an additional measure of T-cell activation, in addition to cytokine production, that correlates closely with cytotoxicity.

Target and effector cells are separately washed and re-suspended in cytotoxicity medium (RPMI+5% human AB serum+1% antibiotic antimycotic). The assay is performed by combining $2\times10^5$ effectors cells with $2\times10^5$ target cells in a 100 µL final volume in U-bottom 96-well plates (Corning), in the presence of 0.5 µL/well of PE/Cy7-labelled anti-human CD107a (LAMP-1) antibody (Clone-H4A3, BD Biosciences). The cultures are then incubated for an hour at 37° C., 5% $CO_2$. Immediately following this incubation, 10 µL of a 1:10 dilution of the secretion inhibitor monensin (1000× solution, BD GolgiStop™) is carefully added to each well without disturbing the cells. The plates are then incubated for a further 2.5 hours at 37° C., 5% $CO_2$. Following this incubation, the cells are stained with APC anti-human CD3 antibody (Clone-UCHT1, BD Biosciences), PerCP/Cy5.5 anti-human CD8 antibody (Clone-SKI, BD Biosciences) and Pacific Blue anti-human CD4 antibody (Clone-RPA-T4, BD Biosciences) and then incubated for 30 minutes at 37° C., 5% $CO_2$. The cells are then washed 2× with FACS buffer (and resuspended in 100 µL FACS buffer and 100 ul IC fix buffer prior to analysis.

Exposure of CD107a on the surface of T cells is detected by flow cytometry. Flow cytometry is performed with a LSRFortessa™ X20 (BD Biosciences) and analysis of flow cytometric data is performed using FlowJo software (Treestar, Inc. Ashland, OR). The percentage of $CD8^+$ effector cells, within the CD3 gate, that are $CD107^+$ is determined for each effector/target cell culture.

Consistent with the previous cytotoxicity and cytokine data, co-culture of tumor-associated antigen-expressing target cells with effector T cells transduced with anti-tumor-associated antigen-28ζ CAR may induce an increase in surface CD107a expression relative to effectors incubated with tumor-associated antigen negative target cells. In comparison, under the same conditions, anti-tumor-associated antigen-CD3ε LL or anti-tumor-associated antigen-CD3γ LL TFP-expressing effectors may exhibit a 5 to 7-fold induction of CD107a expression. Anti-tumor-associated antigen TFPs constructed with an alternative hinge region may generate similar results upon co-culture with tumor-associated antigen-bearing target cells.

Example 15: In Vivo Mouse Efficacy Studies

To assess the ability of effector T cells transduced with anti-tumor-associated antigen TFPs to achieve anti-tumor responses in vivo, effector T cells transduced with either anti-tumor-associated antigen-28ζ CAR, anti-tumor-associated antigen-CD3ε LL TFP or anti-tumor-associated anti-gen-CD3γ LL TFP are adoptively transferred into NOD/

SCID/IL-2Rγ−/− (NSG-JAX) mice that had previously been inoculated with tumor-associated antigen+ human cancer cell lines.

Female NOD/SCID/IL-2Rγ−/− (NSG-JAX) mice, at least 6 weeks of age prior to the start of the study, are obtained from The Jackson Laboratory (stock number 005557) and acclimated for 3 days before experimental use. Human tumor-associated antigen-expressing cell lines for inoculation are maintained in log-phase culture prior to harvesting and counting with trypan blue to determine a viable cell count. On the day of tumor challenge, the cells are centrifuged at 300 g for 5 minutes and re-suspended in pre-warmed sterile PBS at either 0.5-1×10$^6$ cells/100 μL. T cells for adoptive transfer, either non-transduced or transduced with anti-tumor-associated antigen-28ζ CAR, anti-tumor-associated antigen-CD3ε LL TFP or anti-CD3γ LL TFP constructs are prepared. On day 0 of the study, 10 animals per experimental group are challenged intravenously with 0.5-1×10$^6$ tumor-associated antigen-expressing cells. 3 days later, 5×10$^6$ of effector T-cell populations are intravenously transferred to each animal in 100 μL of sterile PBS. Detailed clinical observations on the animals are recorded daily until euthanasia. Body weight measurements are made on all animals weekly until death or euthanasia. All animals are euthanized 35 days after adoptive transfer of test and control articles. Any animals appearing moribund during the study are euthanized at the discretion of the study director in consultation with a veterinarian.

Relative to non-transduced T cells, adoptive transfer of T-cell transduced with either anti-tumor-associated antigen-28ζ CAR, anti-tumor-associated antigen-CD3ε LL TFP or anti-tumor-associated antigen-CD3γ LL TFP may prolong survival mesothelin-expressing cell line tumor-bearing mice, and may indicate that both anti-tumor-associated antigen CAR and TFP-transduced T cells are capable of mediating target cell killing with corresponding increased survival in these mouse models. Collectively, these data may indicate that TFPs represent an alternative platform for engineering chimeric receptors that demonstrate superior antigen-specific killing to first generation CARs both in vitro and in vivo.

Example 16: CD16 TFPs Induce Tumor Cell Lysis and Cytokine Production in the Presence of a Tumor Cell Antigen and an Anti-Tumor Antigen Antibody Luciferase-labeled Raji cells (Raji-FFLuc tumor cells that have been stably transduced with firefly luciferase) were combined with CD16 TFP T cells at a 1:10 ratio, e.g., 5000 tumor cells+50,000 TFP T cells). Rituximab or non-glycosylated rituximab was added at 1 μg/ml and the combination of cells and antibody was incubated at 37° C. for 24 hours. Cells were spun, and the supernatant and pellet were harvested. The pellets were resuspended and incubated with luciferin substrate and read on a SpectraMax® plate reader. Luciferase signal equates with lysis as the luciferase is available from the lysed cells only.

Figure 11A:
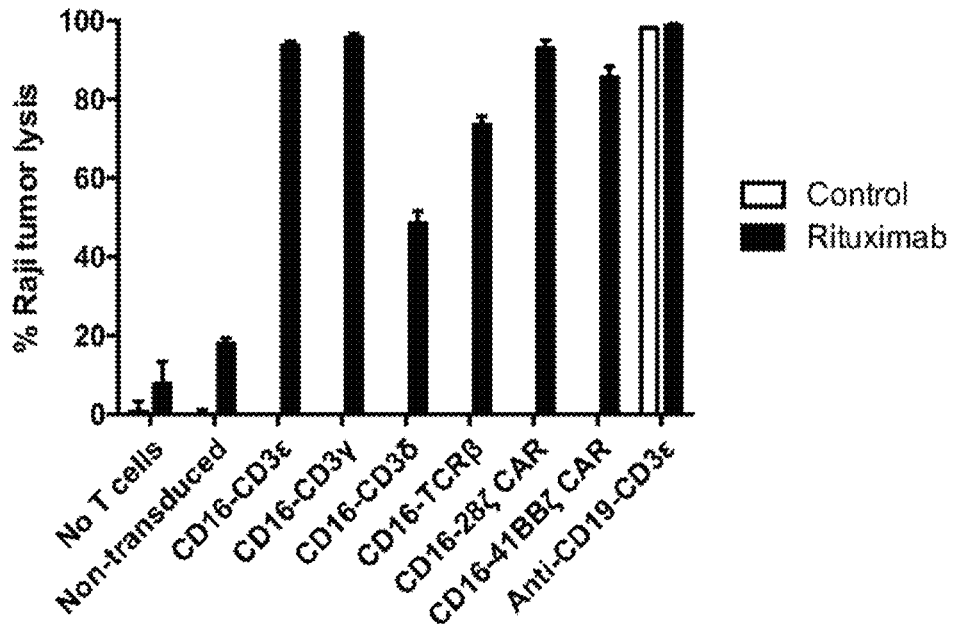
FIG. 11A shows Raji cell lysis with the combination of rituximab, and various transduced T cells.

FIG. 11 shows the results of this assay with T cells transduced with various constructs, as compared to a no-antibody control. Raji cells were incubated with rituximab and the following T cells: medium alone (no antibody, white bars), Raji cells with no T cells as a negative control, non-transduced T cells as a negative control, CD16-CD3ε TFP, CD16-CD3γ TFP, CD16-CD3δ TFP, CD16-CD3β TFP, CD16-CD28ζ CAR, CD16-41BBζ CAR, and an anti-CD19-CD3ε TFP with known activity as a positive control. As can be seen in FIG. 11A, the TFPs and CARs were all able to induce lysis in the target cell population to varying degrees. The negative controls had minimal lysis, if any. CD16-CD3ε TFP and CD16-CD3γ were the most potent of the CD16 TFPs. The positive control anti-CD19 TFP induced lysis in the "no antibody" control group (white bars), as this TFP binds directly to the target cells.

Figure 11B:
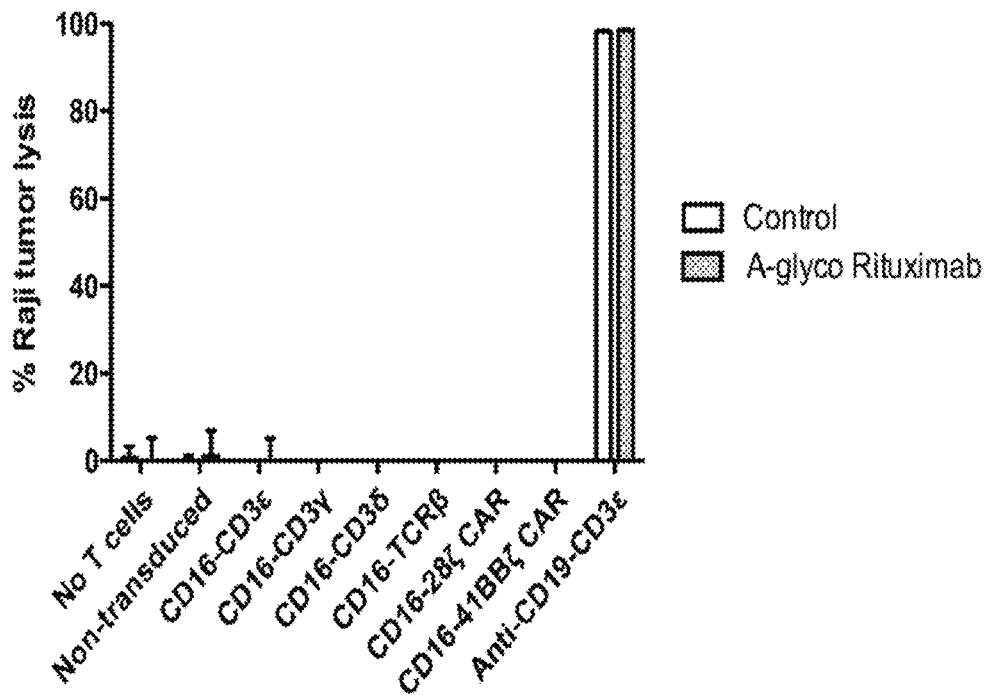
FIG. 11B shows the same combinations with non-glycosylated rituximab.

FIG. 11B shows the same assay but with non-glycosylated rituximab antibody. As expected, since CD16 will not bind the non-glycosylated form, very little cell lysis was detected for any of the T cell constructs other than with the anti-CD19 TFP positive control which functions independently of rituximab.

Figure 12A:
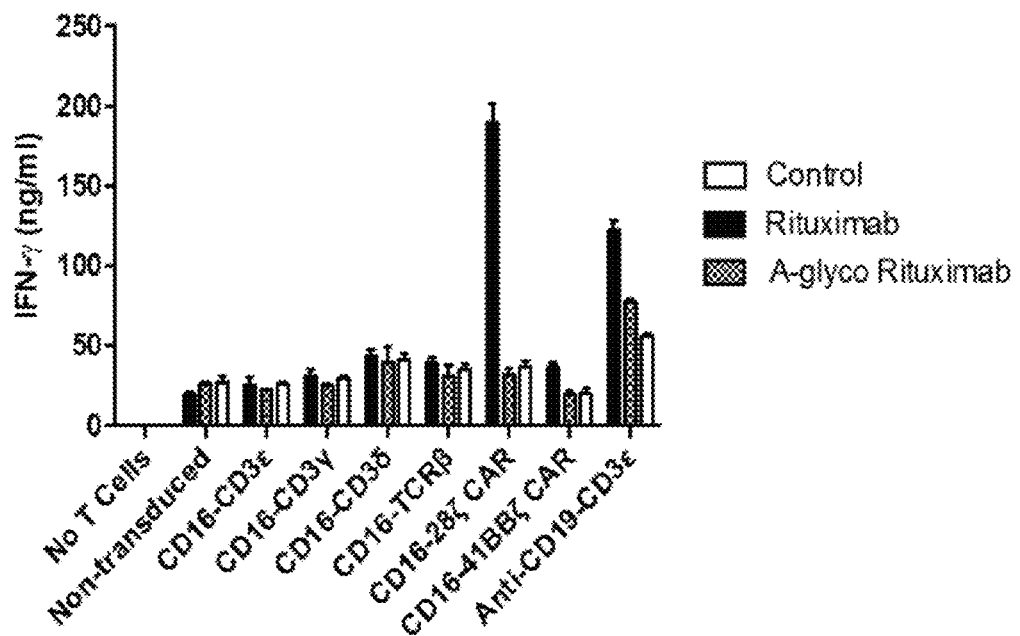
FIG. 12 is two graphs showing that low levels of interferon gamma (IFN-γ, FIG. 12A) and interleukin 2 (IL-2, FIG. 12B) were produced by TFP-transduced T cells in combination with Raji cells and rituximab, as compared to higher levels of cytokines produced by CAR-transduced T cells.
Figure 12B:
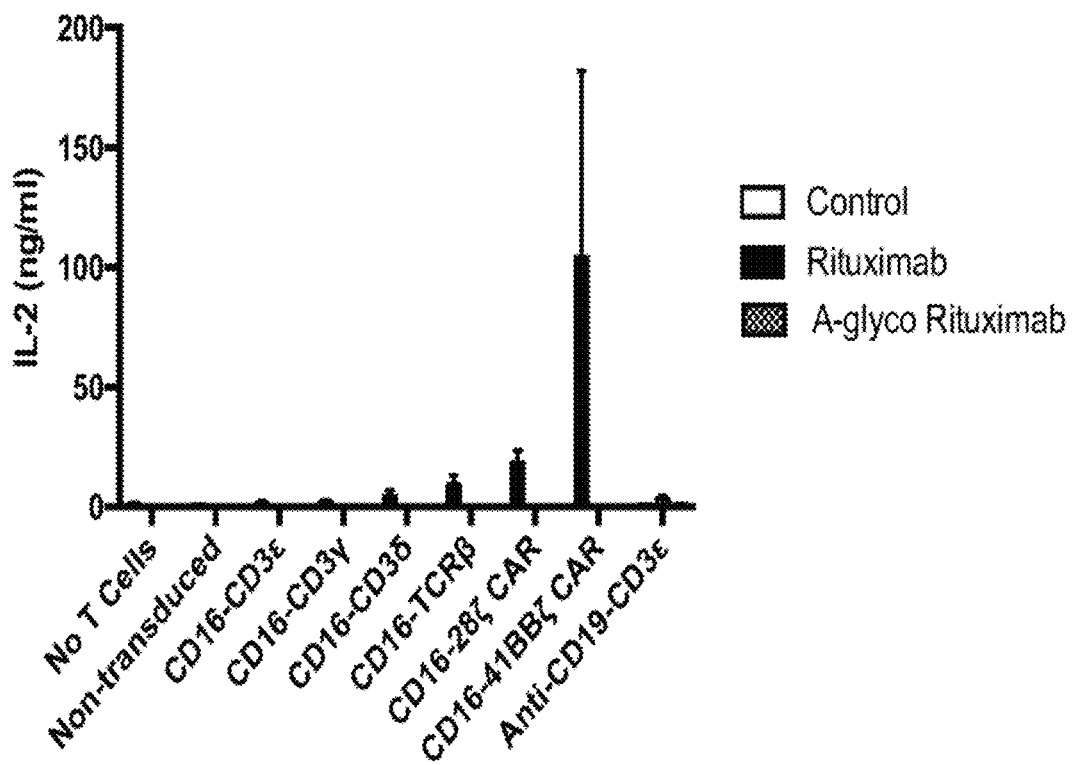

The supernatant collected from the method above was used in a Luminex® ELISA assay to detect and quantify the amount of IFNγ and IL-2. As shown in FIG. 12A (IFNγ) and FIG. 12B (IL-2), the TFP T cells induced much lower cytokine concentrations than their CAR T cell counterparts, making them attractive as therapeutics, since excess cytokine production induces undesirable side-effects in patients.

Example 17: In Vitro and In Vivo Efficacy of NKG2D+-TFP T Cells Against Multiple Malignancies NKG2D ε-TFP T cells from a normal donor were prepared to test the in vitro and in vivo anti-tumor efficacy of NKG2D ε-TFP T cells against multiple solid tumor cell lines expressing an NKG2D ligand. Purified normal donor CD4 and CD8 T cells were collected by prodigy and NKG2D CD3ε-TFP T cells were ex vivo expanded and transduced in presence of DynaBeads+IL-2 or TransAct+IL-7/15 condition for 10 days. In vitro and in vivo anti-tumor activities were analyzed using multiple NKG2D ligand-expressing tumor cell lines. Lentiviral vectors and lentivirus was prepared as described in the examples above.

NKG2D Monomer or Dimer CD3ε-TFP T Cell Preparation

Frozen CD4$^+$ or CD8$^+$ T cells from ND13 (HemaCare, donor ID: W313716040891) or ND15 (HemaCare, donor ID: W313717041459) were re-suspended in either T cell expansion medium (AIM-V®+AlbuMAX® (BSA) (1×) (Gibco, 31035-025) supplemented with 5% human AB serum (Gemini Products, 100-318) 300 IU/mL rhIL-2 (Peprotech, 200-02) and 1% antibiotics (Invitrogen, lot #1734036) or in TexMACS™ medium (Miltenyi, lot #5151126094) with 3% human AB serum (Gemini Products, 100-318), 12.5 ng/mL of IL-7 (Miltenyi, Catalog #130-095-363) and 12.5 ng/ml of IL-15 (Miltenyi, Catalog #130-095-765) and 1% antibiotics (Invitrogen) on day 0. For T cell activated in Dynabeads+IL-2 condition, Dynabeads Human T-activator CD3/CD28 (Gibco, 00415447, lot 1785079) were washed three times with sterile 1×PBS. The beads were then added to the T cells at 1:1 ratio, by transferring 50 μL (1×10$^6$ beads) of beads suspension to 1 mL of T cell suspension (1×10$^6$ cells/mL). The 1 mL beads/cells mixture were then dispensed to single well of a 48-well plate, and incubated at 37° C. with 5% CO$_2$. For T cell activated in TransAct+IL-7/15 condition, the beads were added to the T cells directly at 1:1 ratio, by transferring 40 μL (1×10$^6$ beads) of beads suspension to 1 mL of T cell suspension (1×10$^6$ cells/mL). Lentivirus transduction is performed on day 1 at indicated MOI, T cells without lentivirus added were served as un-transduced group (NT). Plates were put back into the 37° C. incubator, without disturbing the cells in the well. Transduced T cells were maintained in T cell expansion medium supplemented with 300 IU/mL rhIL-2 or TexMACS™ supplemented with 12.5 ng/ml of IL-7 and 12.5 ng/ml of IL-15. Transduced T cells were sub-cultured every 48 hours to the concentration of $5\times10^5$ cells/mL. On day 10 post activation, SD1 (anti-mesothelin) CD3ε-TFP T cells and untransduced T cells were counted, phenotyped, and frozen in liquid nitrogen for further analysis.

Tumor Cells

The MSLN+ cell line MSTO-211H (ATCC® CRL-2081™) was obtained from ATCC. High MSLN-expressing cell line MSTO-211H-FL MSLN was generated by stably transducing MSTO-211H (ATCC, CRL-2081™) with lentiviral vectors encoding full-length MSLN. OVCAR3 (ATCC HTB-161™), SaOS2 (ATCC HTB-85™), SKOV3 (ATCC HTB-77™), A549 (ATCC-CCL 185™), A431 (ATCC CRL-1555™), U373 (ATCC HTB-17™), PC-3 (ATCC CRL-1435™). Luciferase expressing cell lines were generated by transducing the cells with lentiviral vectors encoding firefly luciferase. After transduction, stable expressers were selected by adding puromycin (5 µg/mL) or G418 (5 mg/mL). All cell lines as well as their derivatives were maintained medium recommended by ATCC.

FACS-Based Transduction Efficiency and T Cell Activation Determination

For more details, refer to SOP 005 T cell phenotype staining panel short. Briefly, the T cells were de-beaded (if expanded in Dynabeads+IL-2 condition) and washed with PBS 2 times before the staining with fixable live/dead aqua (at 1:1000 dilution with PBS). After washing 2 times with PBS, the cells pellet was re-suspended in 100 µL of antibody staining mix, prepare antibody staining mix with the following antibody in 100 µL/sample FACS buffer: human Fc block (1 µL/sample), CD4-Pacific blue (Biolegend, cat #300521, lot #B231611, 1 µL/sample), CD8-PerCPcy5.5 (Biolegend, cat #344710, lot #B226362, 1 µL/sample), NKG2D-APC (R&D, cat #: FAB139A, lot #LC00613121, 1 µL/sample), ULBP1-APC (R&D, cat #: FAB139A, lot #LC00613121, 1 µL/sample). ULBP2/5/6-PE (R&D, FAB1298P, Lot #LWE0716091, 1 µL/sample), ULBP4-APC (R&D, cat #: FAB6285A, lot #ADXO0117041, 1 µL/sample), MICA/B-AF488 (ebioscience, cat #: 53-5788-42, Lot #: E10683-1633, 1 µL/sample) Prepare isotype control mix with the match isotype control antibodies (1 µL/sample). Incubate for at least 30 minutes at 4° C. in the dark. Centrifuge at 600×g for 2 minutes at RT, discard the supernatant and resuspend cell pellet in 200 µL FACS buffer. Repeat wash for 2 times and run samples on a BD LSR Fortessa X-20 Cell Analyzer.

Tumor Cell Lysis—the Luciferase Reporter (Luc) Assay

NKG2D ligand expression was confirmed on target cells, and expression of NKG2D monomer or dimer ε-TFP T cells was confirmed by flow cytometry on the day of Luc assay as quality control. The single suspension of target cells were prepared in R10 medium. $1\times10^4$ cells in 100 µL was added to 96-well round-bottom plate. TFP T cells were thawed, de-beaded (if ex vivo expanded in Dynabeads+IL-2 conditions), washed, and then re-suspended in with T cell culture media without cytokines. The desired number of T cells (in 100 µL) was added to reach effector-to-target ratio at 5-to-1, 1-to-1 and 1-to-5, respectively. Three replicates were prepared for each type of T cell at tested ratio. The cells were then cultured for 24 hours at 37° C. with 5% $CO_2$. After 24 hour co-culture, the plate was centrifuged at 300×g for 2 minutes to pellet down the cells. 100 µL of culture supernatant from each well were removed carefully for Luminex® assay. 100 µL of assay buffer from Bright-Glo™ Luciferase Assay System (Promega, E2650, lot 0000223852) were added to each well. The content in each well was mixed by gently pipetting up and down. The cell-reagent mixture was left at room temperature in dark for 3 minutes for complete lysis of the cells. 200 µL of cell lysate from each well were transferred to Greiner-One white walled 96 well plate. The luminescence was measured relative luminescence unit (RLU) by SpectraMax® M5 plate reader (Molecular Devices).

The percent (%) of tumor lysis was calculated by the formula listed below:

$$\% \text{ Tumor Lysis} = 100 * \left[1 - \frac{\text{Luminescence (Tumor} + T \text{ cell)}}{\text{Luminescence(Tumor)}}\right]$$

Subcutaneous Xenograft Mouse Model with MSTO-FL MSLN and In Vivo Assessments

The mouse model was carried out at Abpro (Wobum, MA). Female 6-week-old NSG mice (The Jackson Laboratory, stock number 005557) were acclimated for minimum 3 days under the same conditions as were used for the study below ND. The MSTO-211H-FLMSLN-Luc cells were suspended in sterile PBS at a concentration of $1\times10^6$ cells/100 µL. The PBS cell suspension was then mixed 1-to-1 with ice cold Matrigel® for a final injection volume of 200 µL for each mouse. The resulting PBS/Matrigel cell suspension was kept on ice until subcutaneous administration in the dorsal hind flank of the mouse. Tumor growth was monitored as tumor volume with Caliper measurement. The volume of tumor was calculated as:

Tumor volume=½(length×width²)

Thirteen days after tumor cell injection, the animals were randomized according to tumor volume (200-300 mm³) and divided into 3 groups to receive injection of NKG2D dimer ε-TFP T cells from ND13 ex vivo expanded in dynabeads+ IL-2 condition. The T cell injection day was considered as the day 0 of the study. The T cells were prepared in sterile PBS at a concentration of $1\times10^6$ or $5\times10^6$ cells/100 µL twice on day 0 and day 20 respectively. The cell suspension was then injected intravenously into the mouse via tail vein.

CD4 and CD8 Ratio, NKG2D Ligand Expression During NKG2D Dimer CD3ε-TFP T Cells Ex Vivo Expansion with TransAct+IL-7/15 Condition and During Antigen Engagement For NKG2D dimer CD3ε-TFP T cells generated using TransAct+IL-7/15 conditions, cells were counted and stained with CD3, CD4, CD8, and NKG2D ligand (NKG2DL) at day 3, 6, 8, 10 days post-expansion. For NKG2D ligand expression upon antigen engagement, EGFRvIII-TFP T cells and K562 parental or K562-EGFRvIII cells were co-cultured at 1:1 ratio for 24 hrs. NKG2D ligand expression was then measured by flow cytometry and analyzed by gating on CD4+ and CD8+ T cells.

Figure 13A:
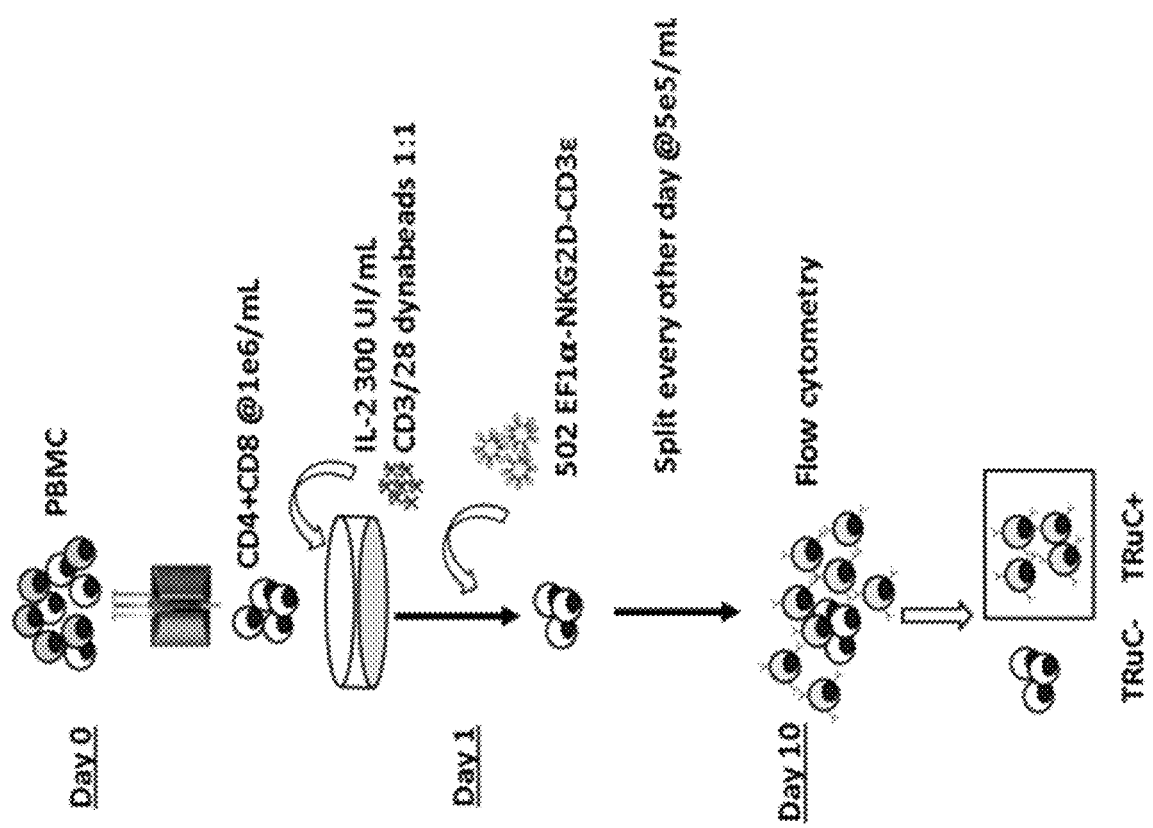
FIG. 13 is a schematic diagram of ex vivo expansion experimental design and transduction efficiency of NKG2D ε-TFP T cells by flow cytometry with Dynabeads™+IL-2 condition (FIG. 13A) and corresponding transduction efficiency of the monomer and dimer NKG2D ε-TFP T cells (FIG. 13B). An isotype match was used as a negative control.
Figure 13B:
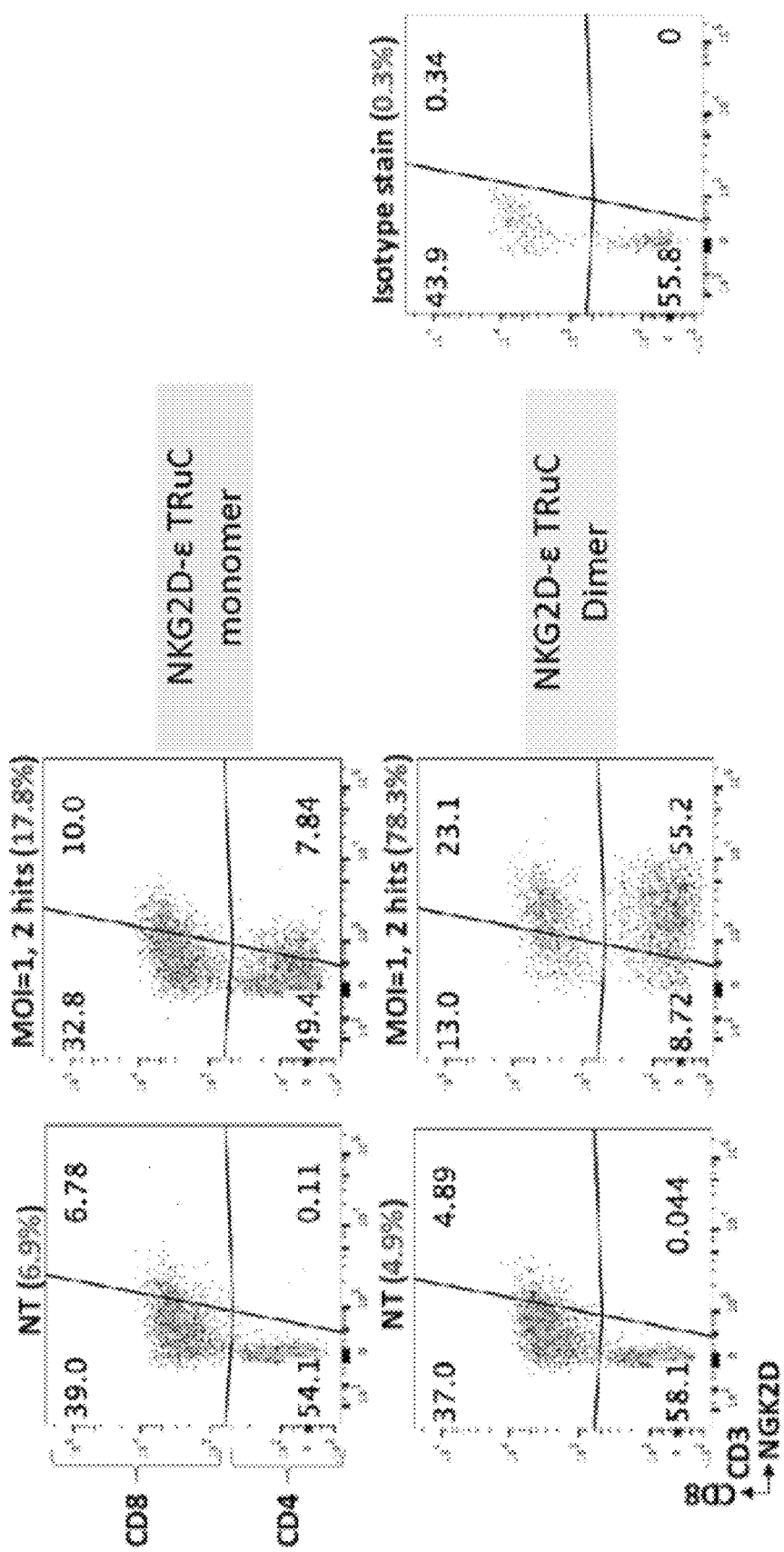

Ex Vivo Expansion of NKG2D Monomer and Dimer ε-TFP™ T Cells in Dynabeads+IL-2 Condition NKG2D ligand-specific TFP T cells were prepared with lentivirus encoding NKG2D extracellular domain (ECD) in reverse order with the CD3β formats of the TFP, because NKG2D dimerizes on cell surface, monomer and dimer fusions were generated, the NKG2D monomer and dimer CD3ε-TFP structure and plasmid design were shown in FIG. 5 above. The experimental plan for ex vivo expansion with Dynabeads+IL-2 condition is shown in FIG. 13A. ND13 (W313716040891 from HemaCare™, Van Nuys, CA) was used to produce both NKG2D monomer and dimer CD3ε-TFP T cells. The transduction efficiency for the NKG2D monomer and dimer ε-TFP was determined on day 10 of expansion by surface stain for presence of NGK2D on CD4+ and CD8+ populations (FIG. 13B). Transduction efficiency for NKG2D monomer was around 18% and dimer was around 78%. NKG2D dimer CD3ε-TFP show higher transduction efficiency compared to NKG2D monomer CD3ε-TFP.

Figure 14A:
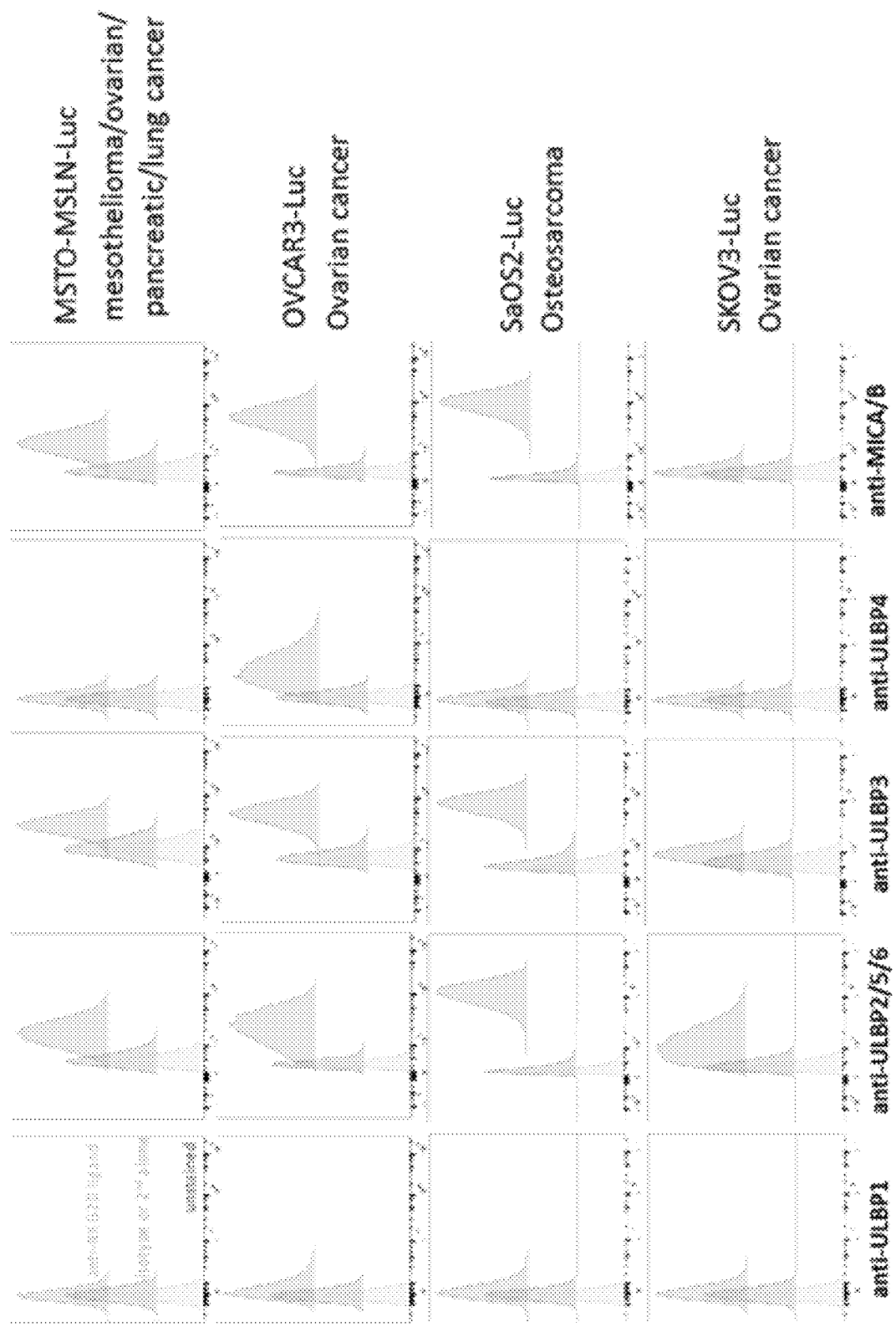
FIG. 14A shows Zenon staining against NKG2D ligands was performed using (from left to right) anti-ULBP1, anti-ULBP2/5/6, anti-ULBP3, anti-ULBP4, and anti-MICA/B on MSTO-MSLN-Luc cells, OVCAR3-Luc, SaOS2-Luc, and SKOV3-Luc cells. In each graph, the top trace is NKG2D ligand, the middle trace is an isotype control or secondary antibody alone, and the bottom trace is unstained cells.
Figure 14B:
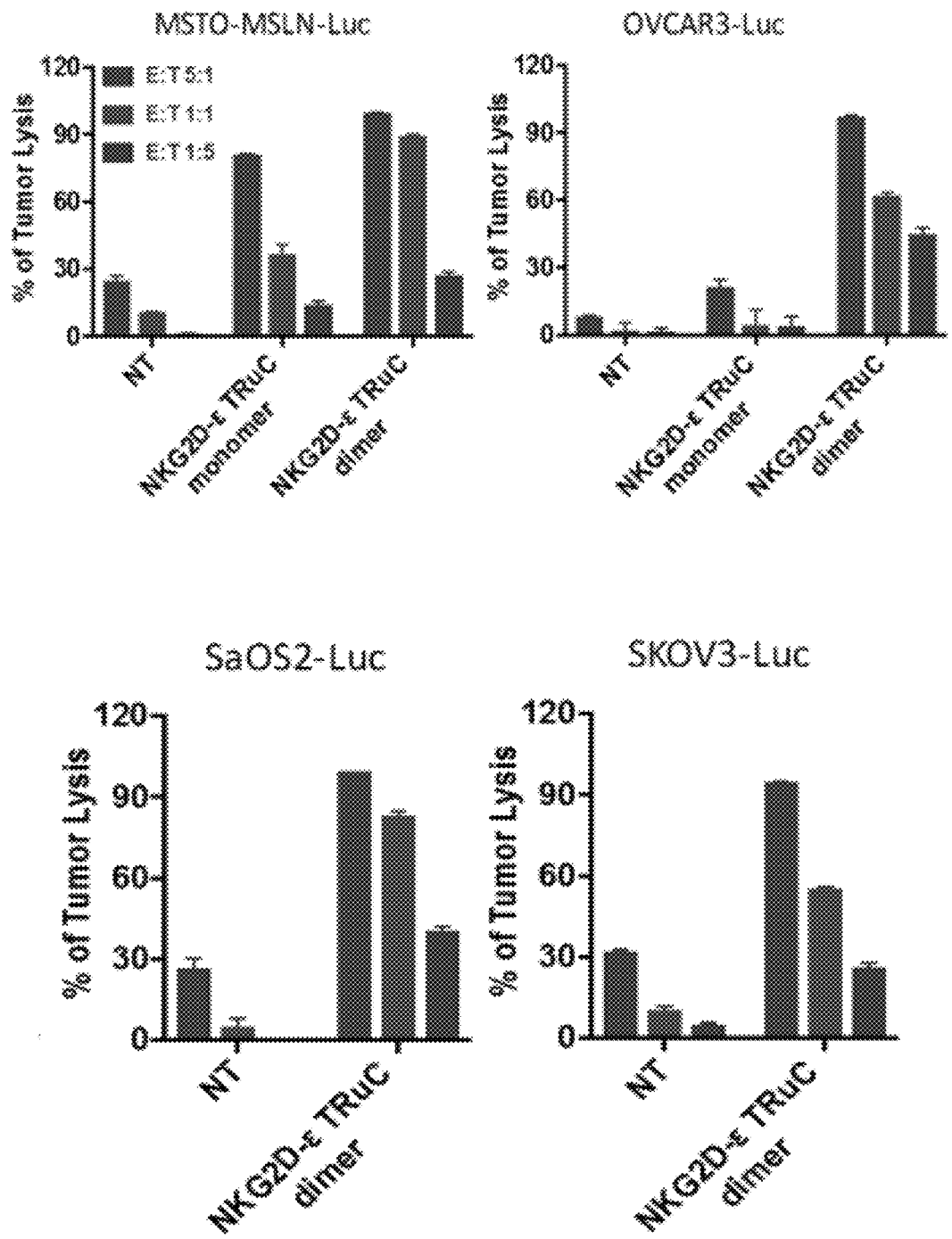
FIG. 14B shows in vitro tumor lysis by NKG2D monomer and/or dimer E-TFP T cells using luciferase assay for 24 h co-culture.
Figure 14C:
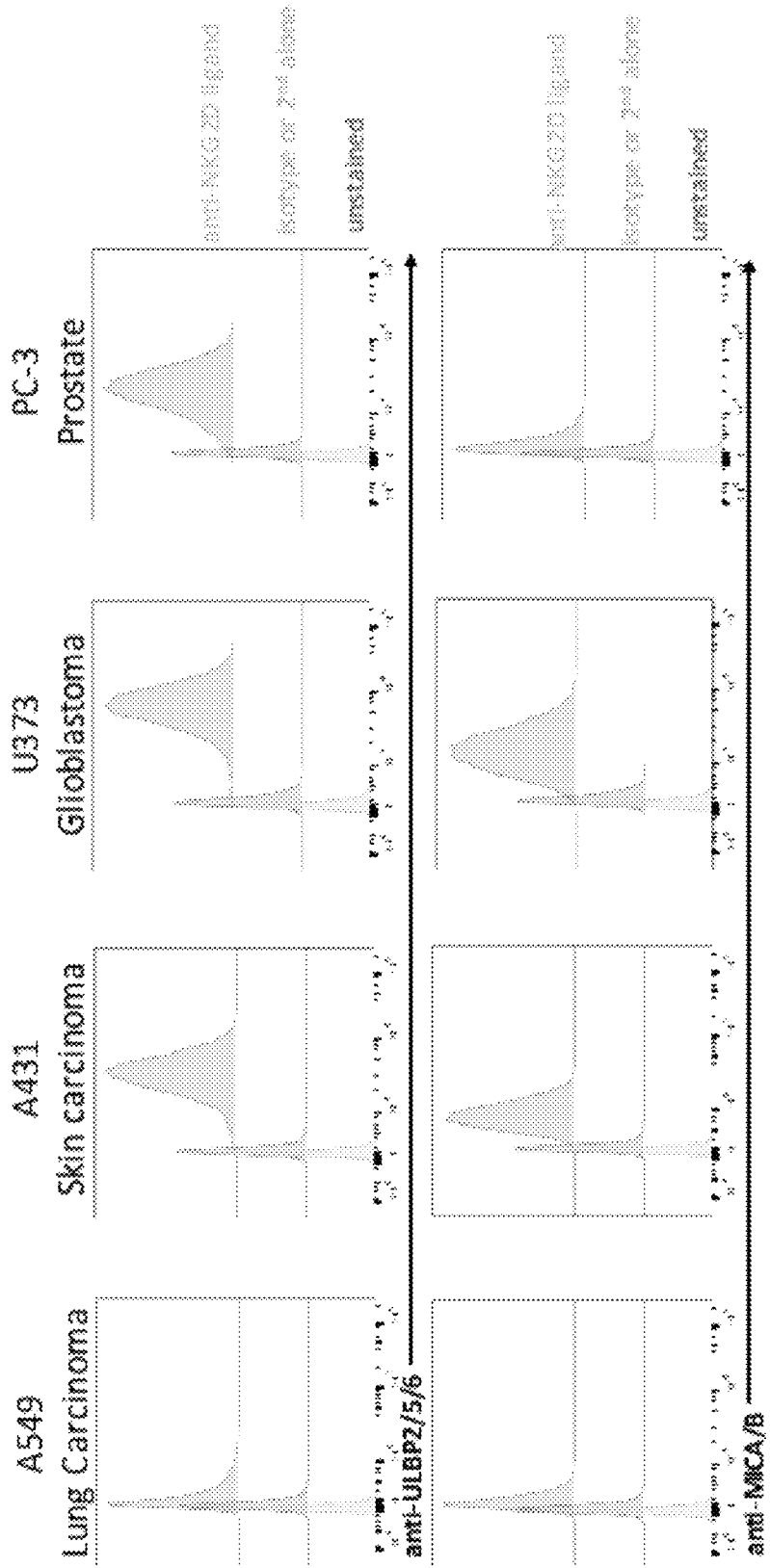
FIG. 14C shows ULBP2/5/6 and MICA/B expression on A549, A431, U373, and PC-3 tumor cell lines and tumor lysis by NKG2D dimer E-TFP T cells using luciferase assay for 24 h co-culture.
Figure 14D:
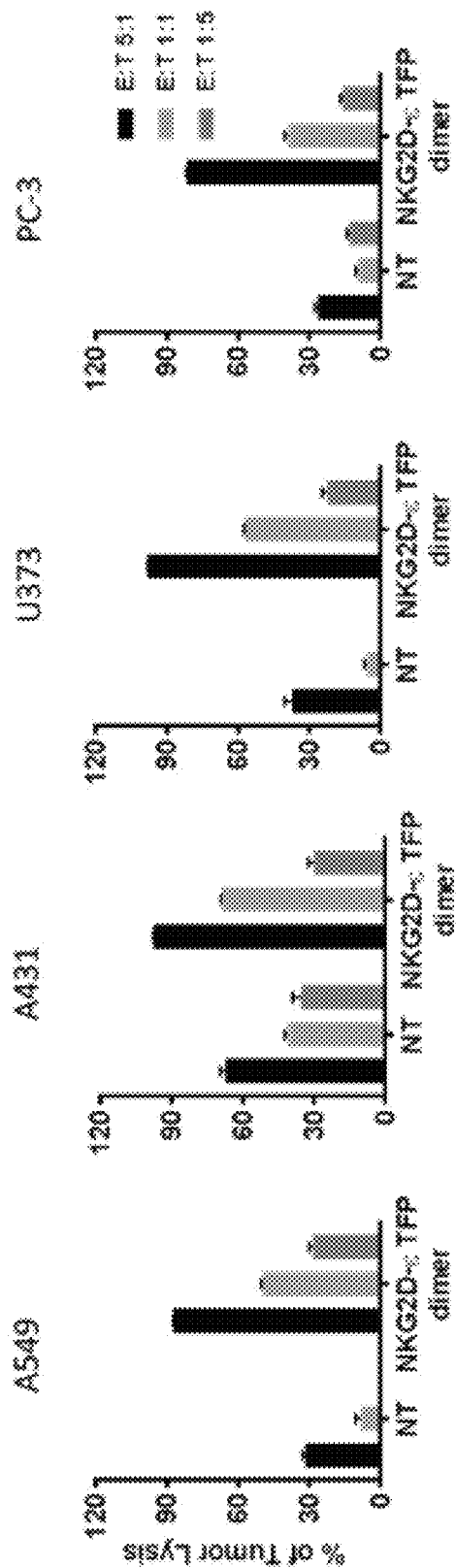
FIG. 14D shows graphs of the results shown in FIG. 14C.

The in vitro efficacy of NKG2D monomer or dimer CD3ε-TFP cells were tested using luciferase reporter tumor cell lysis assays. Ligands expression (ULBP-1, ULBP2/5/6, ULBP-3, ULBP-4, MICA/B) were confirmed on MSTO-211H-FLMSLN-Luc (mesothelioma/ovarian/pancreatic/lung cancer), OVCAR3-Luc and SKOV3-Luc (ovarian cancer), SaOS2 (osteosarcoma) cell lines (FIG. 14A), ULBP2/5/6 and MICA/B were confirmed on A549-Luc (lung carcinoma), A431 (skin carcinoma), U373 (glioblastoma), and PC-3 (prostate cancer) cell lines on the day of assay (FIG. 14C), both NKG2D monomer and dimer CD3ε-TFP T cells showed different levels of tumor killing. Robust tumor cell lysis was observed for NKG2D dimer CD3ε-TFP T cells when co-cultured with all the cell lines at 5-to-1 effector to target ratio, NKG2D dimer CD3ε-TFP T cells when co-cultured with all the cell lines at 1-to-1 effector to target ratio or NKG2D monomer CD3ε-TFP T cells when co-cultured with all the cell lines at 5-to-1 effector to target ratio show 30-50% of killing after 24 hr. No tumor lysis was observed for both NT T cells when co-cultured with those cell lines (FIGS. 14B and 14C).

Figure 15A:
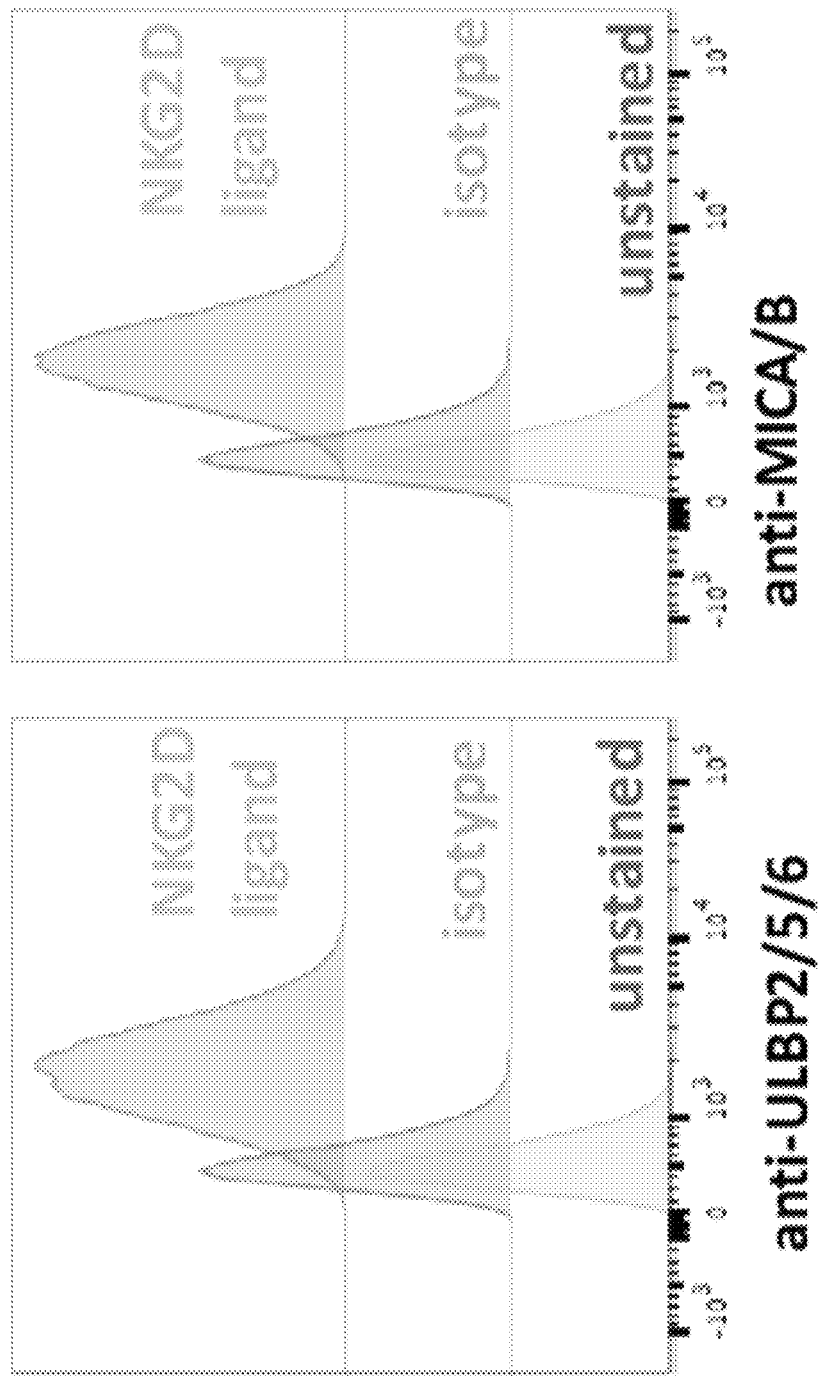
FIG. 15A shows NKG2D ligand (ULBP2/5/6 and MICA/B) expression on MSTO-MLSN cells on the day of injection (tumor QC).
Figure 15B:
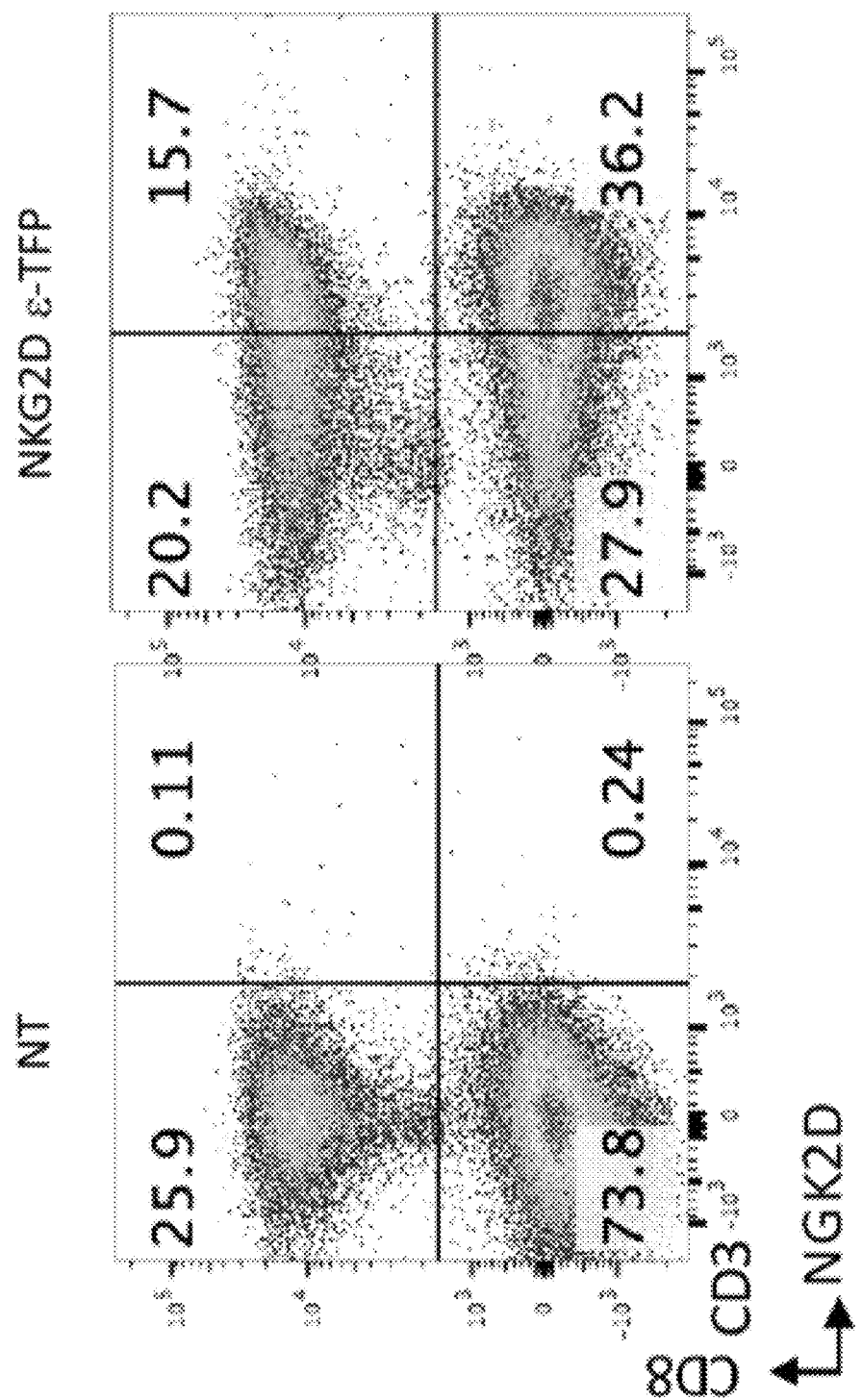
FIG. 15B shows NKG2D expression on NT and NKG2D dimer ε-TFP T cells on the day of injection (T cell QC).
Figure 15C:
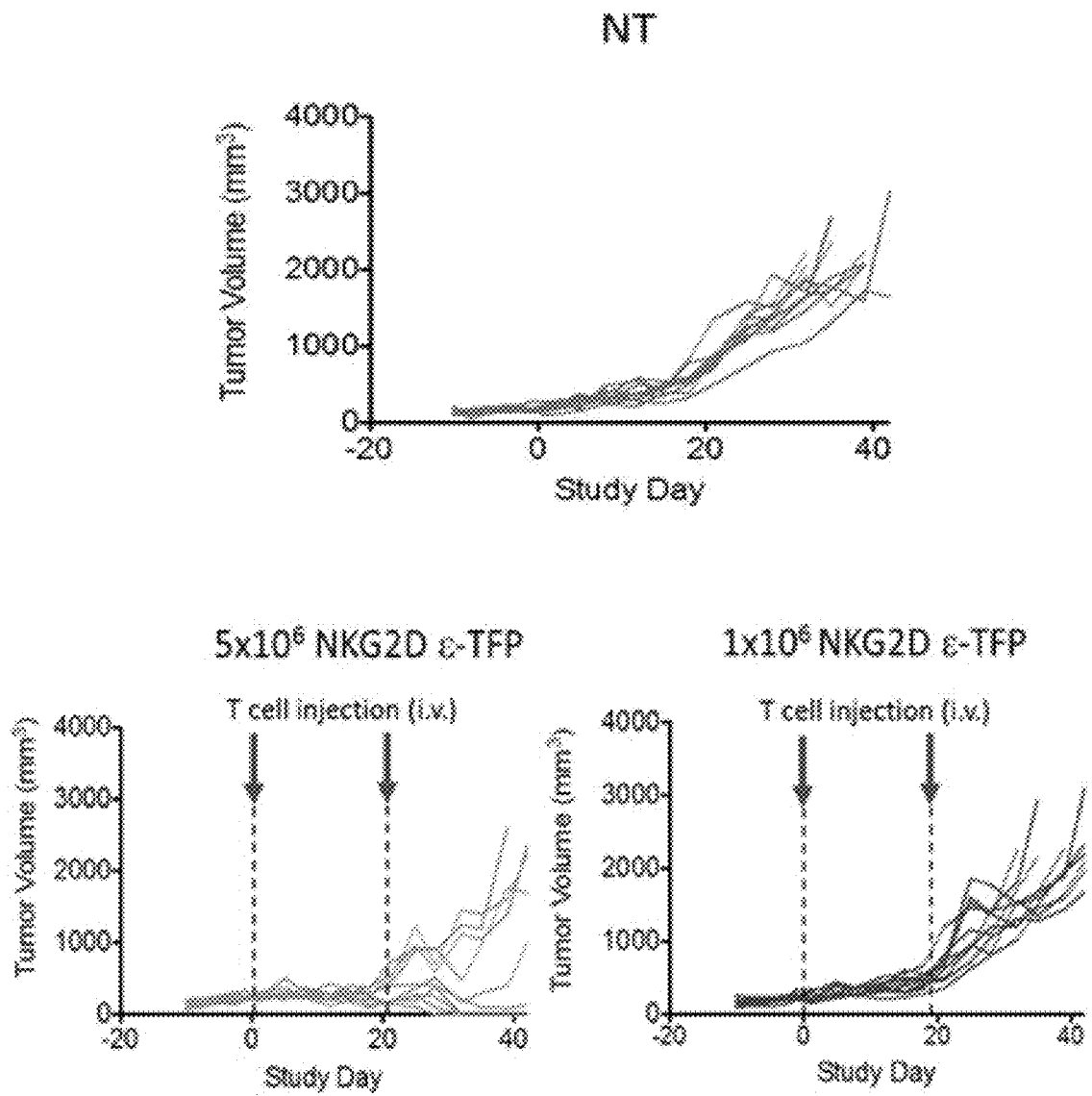
FIG. 15C shows tumor volumes of mice treated with two doses of non-transduced ("NT", left panel) or NKG2D dimer e-TFP T cells at two doses: $5 \times 10^6$ NKG2D ε-TFP cells and $1 \times 10^6$ NKG2D ε-TFP cells. T cells were injected on study days zero and 20. Each line in the graph represents one mouse.
Figure 15D:
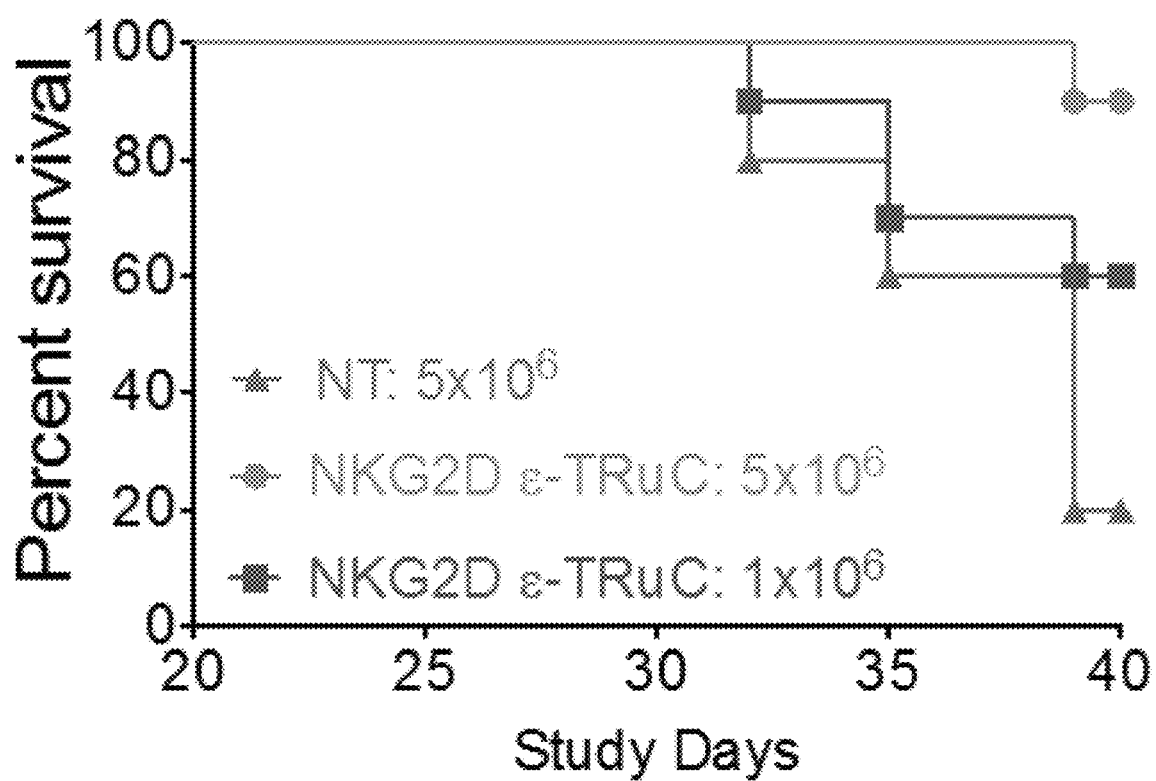
FIG. 15D shows survival of mice treated with two doses of NT or NKG2D dimer ε-TFP T cells, NT vs NKG2D dimer ε-TFP T, $P<0.05$.

In Vivo Efficacy of NKG2D Dimer ε-TFP T Cells in Xenografted Ligand-Expressing Tumor Mouse Model MSTO-211H-FLMSLN-Luc was used to establish s.c. xenografted NKG2D ligand-expressing tumor mouse model, tumor volume was measured twice a week. QC of target expression on tumors and TFP expression on T cells were performed on the day of injection, respectively (FIGS. 15A and 15B). Day 13 post tumor injection, average tumor volume reached 200-300 mm$^3$. On day 10, Dynabeads+IL-2-expanded NKG2D dimer ε-TFP T cells from ND13 (W313716040891 from HemaCare™, Van Nuys, CA) were thawed and transduction efficiency was confirmed. $1 \times 10^6$ or $5 \times 10^6$ per mouse NKG2D dimer ε-TFP T cells or matching un-transduced T cells were i.v. injected twice on day 0 and day 20 and tumor volumes were monitored thereafter. Treatment with NKG2D dimer ε-TFP T cells at a dose of $5 \times 10^6$ cells shows partial protection over 42 days of observation. 4 out of 10 mice cleared the tumor and remained tumor free till day 42; 1 out of 10 mice retained tumor volume around 100 mm$^3$. A significant difference in survival was shown between mice treated with NT cells and mice treated with $5 \times 10^6$ NKG2D dimer ε-TFP T cells. Treatment with the NKG2D dimer ε-TFP at a dose of $1 \times 10^6$ could not control tumor growth. (FIGS. 15C and 15D).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

APPENDIX A

SEQUENCE SUMMARY

| SEQ ID NO. | Name | Sequence |
|---|---|---|
| 1 | Short Linker 1 | GGGGSGGGGSGGGGSLE |
| 2 | Short Linker 2 | AAAGGGGSGGGGSGGGGSLE |
| 3 | Long Linker | AAAIEVMYPPPYLGGGGSGGGGSGGGGSLE |
| 4 | human CD3-ε | MQSGTHWRVLGLCLLSVGVWGQDGNEEMGGITQTPYKVSISGTT VILTCPQYPGSEILWQHNDKNIGGDEDDKNIGSDEDHLSLKEFSEL EQSGYYVCYPRGSKPEDANFYLYLRARVCENCMEMDVMSVATIV IVDICITGGLLLLVYYWSKNRKAKAKPVTRGAGAGGRQRGQNKE RPPPVPNPDYEPIRKGQRDLYSGLNQRRI |
| 5 | human CD3-γ | MEQGKGLAVLILAIILLQGTLAQSIKGNHLVKVYDYQEDGSVLLT CDAEAKNITWFKDGKMIGFLTEDKKKWNLGSNAKDPRGMYQCK GSQNKSKPLQVYYRMCQNCIELNAATISGFLFAEIVSIFVLAVGVY FIAGQDGVRQSRASDKQTLLPNDQLYQPLKDREDDQYSHLQGNQ LRRN |
| 6 | human CD3-δ | MEHSTFLSGLVLATLLSQVSPFKIPIEELEDRVFVNCNTSITWVEGT VGTLLSDITRLDLGKRILDPRGIYRCNGTDIYKDKESTVQVHYRMC QSCVELDPATVAGIIVTDVIATLLLALGVFCFAGHETGRLSGAADT QALLRNDQVYQPLRDRDDAQYSHLGGNWARNKS |
| 7 | human CD3-ζ | MKWKALFTAAILQAQLPITEAQSFGLLDPKLCYLLDGILFIYGVILT ALFLRVKFSRSADAPAYQQGQNQLYNELNLGRREEYDVLDKRRG RDPEMGGKPQRRKNPQEGLYNELQKDKMAEAYSEIGMKGERRR GKGHDGLYQGLSTATKDTYDALHMQALPPR |
| 8 | human TCR α-chain | MAGTWLLLLLALGCPALPTGVGGTPFPSLAPPIMLLVDGKQQMV VVCLVLDVAPPGLDSPIWFSAGNGSALDAFTYGPSPATDGTWTNL AHLSLPSEELASWEPLVCHTGPGAEGHSRSTQPMHLSGEASTART CPQEPLRGTPGGALWLGVLRLLLFKLLLFDLLLTCSCLCDPAGPLP SPATTTRLRALGSHRLHPATETGGREATSSPRPQPRDRRWGDTPPG RKPGSPVWGEGSYLSSYPTCPAQAWCSRSALRAPSSSLGAFFAGD LPPPLQAGA |

APPENDIX A-continued

SEQUENCE SUMMARY

| SEQ ID NO. | Name | Sequence |
|---|---|---|
| 9 | human TCR α-chain C region | PNIQNPDPAVYQLRDSKSSDKSVCLFTDFDSQTNVSQSKDSDVYIT DKTVLDMRSMDFKSNSAVAWSNKSDFACANAFNNSIIPEDTFFPSP ESSCDVKLVEKSFETDTNLNFQNLSVIGFRILLLKVAGFNLLMTLR LWSS |
| 10 | human TCR α-chain V region CTL-L17 | MAMLLGASVLILWLQPDWVNSQQKNDDQQVKQNSPSLSVQEGRI SILNCDYTNSMFDYFLWYKKYPAEGPTFLISISSIKDKNEDGRFTVF LNKSAKHLSLHIVPSQPGDSAVYFCAAKGAGTASKLTFGTGTRLQ VTL |
| 11 | human TCR β-chain C region | EDLNKVFPPEVAVFEPSEAEISHTQKATLVCLATGFFPDHVELSWW VNGKEVHSGVSTDPQPLKEQPALNDSRYCLSSRLRVSATFWQNPR NHFRCQVQFYGLSENDEWTQDRAKPVTQIVSAEAWGRADCGFTS VSYQQGVLSATILYEILLGKATLYAVLVSALVLMAMVKRKDF |
| 12 | human TCR β-chain V region CTL-L17 | MGTSLLCWMALCLLGADHADTGVSQNPRHNITKRGQNVTFRCDP ISEHNRLYWYRQTLGQGPEFLTYFQNEAQLEKSRLLSDRFSAERPK GSFSTLEIQRTEQGDSAMYLCASSLAGLNQPQHFGDGTRLSIL |
| 13 | human TCR β-chain V region YT35 | MDSWTFCCVSLCILVAKHTDAGVIQSPRHEVTEMGQEVTLRCKPI SGHNSLFWYRQTMMRGLELLIYFNNNVPIDDSGMPEDRFSAKMP NASFSTLKIQPSEPRDSAVYFCASSFSTCSANYGYTFGSGTRLTVV |
| 14 | NKG2D type II integral membrane protein, UniProt Accession No. P26718-1 | MGWIRGRRSRHSWEMSEFHNYNLDLKKSDFSTRWQKQRCPVVKS KCRENASPFFFCCFIAVAMGIRFIIMVAIWSAVFLNSLFNQEVQIPLT ESYCGPCPKNWICYKNNCYQFFDESKNWYESQASCMSQNASLLK VYSKEDQDLLKLVKSYHWMGLVHIPTNGSWQWEDGSILSPNLLTI IEMQKGDCALYASSFKGYIENCSTPNTYICMQRTV |
| 15 | p502_NKG2D_ CD3epsilon extracellular domain dimer (ECD) | NSLFNQEVQIPLTESYCGPCPKNWICYKNNCYQFFDESKNWYE SQASCMSQNASLLKVYSKEDQDLLKLVKSYHWMGLVHIPTNG SWQWEDGSILSPNLLTIIEMQKGDCALYASSFKGYIENCSTPNT YICMQRTVGGGGSGGGGSGGGGSLENSLFNQEVQIPLTESYCG PCPKNWICYKNNCYQFFDESKNWYESQASCMSQNASLLKVYS KEDQDLLKLVKSYHWMGLVHIPTNGSWQWEDGSILSPNLLTII EMQKGDCALYASSFKGYIENCSTPNTYICMQRTVAAAGGGGS GGGGSGGGGSLEDGNEEMGGITQTPYKVSISGTTVILTCPQYPG SEILWQHNDKNIGGDEDDKNIGSDEDHLSLKEFSELEQ SGYYVC YPRGSKPEDANFYLYLRARVCENCMEMDVMS |
| 16 | p502_NKG2D_ CD3epsilon ORF, dimer (amino acid sequence) | NSLFNQEVQIPLTESYCGPCPKNWICYKNNCYQFFDESKNWYESQ ASCMSQNASLLKVYSKEDQDLLKLVKSYHWMGLVHIPTNGSWQ WEDGSILSPNLLTIIMMQKGDCALYASSFKGYIENCSTPNTYICMQR TVGGGGSGGGGSGGGGSLENSLFNQEVQIPLTESYCGPCPKNWIC YKNNCYQFFDESKNWYESQASCMSQNASLLKVYSKEDQDLLKLV KSYHWMGLVHIPTNGSWQWEDGSILSPNLLTIIEMQKGDCALYAS SKGYIENCSTPNTYICMQRTVAAAGGGGSGGGGSGGGGSLEDGN EEMGGITQTPYKVSISGTTVILTCPQYPGSEILWQHNDKNIGGDED DKNIGSDEDHLSLKEFSELEQSGYYVCYPRGSKPEDANFYLYLRA RVCENCMEMDVMSVATIVIVDICITGLLLLVYYWSKNRKAKAK PVTRGAGAGGRQRGQNKERPPPVPNPDYEPIRKGQRDLYSGLNQR RI* |
| 17 | p502 NKG2D monomer DNA Sequence | ACGCGTGTAGTCTTATGCAATACTCTGTAGTCTTGCAACATGGT AACGATGAGTTAGCAACATGCCTTACAAGGAGAGAAAAAGCAC CGTGCATGCCGATTGGTGGAAGTAAGGTGGTACGATCGTGCCT TATTAGGAAGGCAACAGACGGGTCTGACATGGATTGGACGAAC CACTGAATTGCCGCATTGCAGAGATATTGTATTTAAGTGCCTAG CTCGATACATAAACGGGTCTCTCTGGTTAGACCAGATCTGAGCC TGGGAGCTCTCTGGCTAACTAGGGAACCCACTGCTTAAGCCTCA ATAAAGCTTGCCTTGAGTGCTTCAAGTAGTGTGTGCCCGTCTGT TGTGTGACTCTGGTAACTAGAGATCCCTCAGACCCTTTTAGTCA GTGTGGAAAATCTCTAGCAGTGGCGCCCGAACAGGGACTTGAA AGCGAAAGGGAAACCAGAGGAGCTCTCTCGACGCAGGACTCG GCTTGCTGAAGCGCGCACGGCAAGAGGCGAGGGGCGGCGACT GGTGAGTACGCCAAAAATTTTGACTAGCGGAGGCTAGAAGGAG AGATGGGTGCGAGAGCGTCAGTATTAAGCGGGGGAGAATTA GATCGCGATGGGAAAAAATTCGGTTAAGGCCAGGGGGAAAGA AAAATATAAATTAAAACATATAGTATGGGCAAGCAGGGAGCT AGAACGATTCGCAGTTAATCCTGGCCTGTTAGAAACATCAGAA GGCTGTAGACAAATACTGGGACAGCTACAACCATCCCTTCAGA CAGGATCAGAAGAACTTAGATCATTATATAATACAGTAGCAAC |

APPENDIX A-continued

SEQUENCE SUMMARY

| SEQ ID NO. | Name | Sequence |
|---|---|---|
| | | CCTCTATTGTGTGCATCAAAGGATAGAGATAAAAGACACCAAG |
| | | GAAGCTTTAGACAAGATAGAGGAAGAGCAAAACAAAAGTAAG |
| | | ACCACCGCACAGCAAGCGGCCACTGATCTTCAGACCTGGAGGA |
| | | GGAGATATGAGGGACAATTGGAGAAGTGAATTATATAAATATA |
| | | AAGTAGTAAAAATTGAACCATTAGGAGTAGCACCCACCAAGGC |
| | | AAAGAGAAGAGTGGTGCAGAGAGAAAAAAGAGCAGTGGGAAT |
| | | AGGAGCTTTGTTCCTTGGGTTCTTGGGAGCAGCAGGAAGCACT |
| | | ATGGGCGCAGCGTCAATGACGCTGACGGTACAGGCCAGACAAT |
| | | TATTGTCTGGTATAGTGCAGCAGCAGAACAATTTGCTGAGGGCT |
| | | ATTGAGGCGCAACAGCATCTGTTGCAACTCACAGTCTGGGGCA |
| | | TCAAGCAGCTCCAGGCAAGAATCCTGGCTGTGGAAAGATACCT |
| | | AAAGGATCAACAGCTCCTGGGGATTTGGGGTTGCTCTGGAAAA |
| | | CTCATTTGCACCACTGCTGTGCCTTGGAATGCTAGTTGGAGTAA |
| | | TAAATCTCTGGAACAGATTTGGAATCACACGACCTGGATGGAG |
| | | TGGGACAGAGAAATTAACAATTACACAAGCTTAATACACTCCT |
| | | TAATTGAAGAATCGCAAAACCAGCAAGAAAAGAATGAACAAG |
| | | AATTATTGGAATTAGATAAATGGGCAAGTTTGTGGAATTGGTTT |
| | | AACATAACAAATTGGCTGTGGTATATAAAATTATTCATAATGAT |
| | | AGTAGGAGGCTTGGTAGGTTTAAGAATAGTTTTTGCTGTACTTT |
| | | CTATAGTGAATAGAGTTAGGCAGGGATATTCACCATTATCGTTT |
| | | CAGACCCACCTCCCAACCCCGAGGGGACCCGACAGGCCCGAAG |
| | | GAATAGAAGAAGAAGGTGGAGAGAGAGACAGAGACAGATCCA |
| | | TTCGATTAGTGAACGGATCTCGACGGTATCGGTTAACTTTTAAA |
| | | AGAAAAGGGGGGATTGGGGGGTACAGTGCAGGGGAAAGAATA |
| | | GTAGACATAATAGCAACAGACATACAAACTAAAGAATTACAAA |
| | | AACAAATTACAAAATTCAAATTTTATCGATACTAGTGGATCTG |
| | | CGATCGCTCCGGTGCCCGTCAGTGGGCAGAGCGCACATCGCCC |
| | | ACAGTCCCCGAGAAGTTGGGGGGAGGGGTCGGCAATTGAACGG |
| | | GTGCCTAGAGAAGGTGGCGCGGGGTAAACTGGGAAAGTGATGT |
| | | CGTGTACTGGCTCCGCCTTTTTCCCGAGGGTGGGGGAGAACCGT |
| | | ATATAAGTGCAGTAGTCGCCGTGAACGTTCTTTTTCGCAACGGG |
| | | TTTGCCGCCAGAACACAGCTGAAGCTTCGAGGGGCTCGCATCT |
| | | CTCCTTCACGCGCCCGCCGCCCTACCTGAGGCCGCCATCCACGC |
| | | CGGTTGAGTCGCGTTCTGCCGCCTCCCGCCTGTGGTGCCTCCTG |
| | | AACTGCGTCCGCCGTCTAGGTAAGTTTAAAGCTCAGGTCGAGA |
| | | CCGGGCCTTTGTCCGGCGCTCCCTTGGAGCCTACCTAGACTCAG |
| | | CCGGCTCTCCACGCTTTGCCTGACCCTGCTTGCTCAACTCTACG |
| | | TCTTTGTTTCGTTTTCTGTTCTGCGCCGTTACAGATCCAAGCTGT |
| | | GACCGGCGCCTACTCTAGAGCCGCCACCATGCTTCTCCTGGTGA |
| | | CAAGCCTTCTGCTCTGTGAGTTACCACACCCAGCATTCCTCCTG |
| | | ATCCCAAACTCCCTCTTCAACCAGGAGGTGCAGATCCCCCTCAC |
| | | AGAGAGCTACTGCGGGCCCTGTCCAAAGAATTGGATATGTTAC |
| | | AAGAACAATTGCTACCAGTTCTTCGATGAGTCAAAAAATTGGT |
| | | ATGAGAGCCAAGCTTCCTGCATGTCTCAGAATGCCAGCCTTCTG |
| | | AAGGTGTACTCAAAAGAAGACCAGGACTTGCTGAAACTGGTCA |
| | | AGTCTTACCACTGGATGGGGCTCGTGCACATTCCAACGAACGG |
| | | TAGCTGGCAGTGGGAAGATGGCTCCATATTGTCTCCTAACCTTC |
| | | TCACCATAATAGAGATGCAGAAGGGTGATTGCGCTCTGTACGC |
| | | TAGTAGCTTCAAGGGCTATATTGAGAATTGTAGTACACCCAAC |
| | | ACATACATTTGTATGCAGAGAACCGTGGGAGGTGGTGGCAGCG |
| | | GTGGCGGTGGAAGTGGTGGCGGCGGTTCTCTCGAGGATGGTAA |
| | | TGAAGAAATGGGTGGTATTACACAGACACCATATAAAGTCTCC |
| | | ATCTCTGGAACCACAGTAATATTGACATGCCCTCAGTATCCTGG |
| | | ATCTGAAATACTATGGCAACACAATGATAAAAACATAGGCGGT |
| | | GATGAGGATGATAAAAACATAGGCAGTGATGAGGATCACCTGT |
| | | CACTGAAGGAATTTTCAGAATTGGAGCAAAGTGGTTATTATGTC |
| | | TGCTACCCCAGAGGAAGCAAACCAGAAGATGCGAACTTTTATC |
| | | TCTACCTGAGGGCAAGAGTGTGTGAGAACTGCATGGAGATGGA |
| | | TGTGATGTCGGTGGCCACAATTGTCATAGTGGACATCTGCATCA |
| | | CTGGGGGCTTGCTGCTGCTGGTTTACTACTGGAGCAAGAATAG |
| | | AAAGGCCAAGGCCAAGCCTGTGACACGAGGAGCGGGTGCTGG |
| | | CGGCAGGCAAAGGGGACAAAACAAGGAGAGGCCACCACCTGT |
| | | TCCCAACCCAGACTATGAGCCCATCCGGAAAGGCCAGCGGGAC |
| | | CTGTATTCTGGCCTGAATCAGAGACGCATCTGATAAGAATTCGA |
| | | ATTTAAATCGGATCCGCGGCCGCGTCGACAATCAACCTCTGGAT |
| | | TACAAAATTTGTGAAAGATTGACTGGTATTCTTAACTATGTTGC |
| | | TCCTTTTACGCTATGTGGATACGCTGCTTTAATGCCTTTGTATCA |
| | | TGCTATTGCTTCCCGTATGGCTTTCATTTTCTCCTCCTTGTATAA |
| | | ATCCTGGTTGCTGTCTCTTTATGAGGAGTTGTGGCCCGTTGTCA |
| | | GGCAACGTGGCGTGGTGTGCACTGTGTTTGCTGACGCAACCCCC |
| | | ACTGGTTGGGGCATTGCCACCACCTGTCAGCTCCTTTCCGGGAC |
| | | TTTCGCTTTCCCCCTCCCTATTGCCACGGCGGAACTCATCGCCG |
| | | CCTGCCTTGCCCGCTGCTGGACAGGGGCTCGGCTGTTGGGCACT |
| | | GACAATTCCGTGGTGTTGTCGGGGAAATCATCGTCCTTTCCTTG |

APPENDIX A-continued

SEQUENCE SUMMARY

| SEQ ID NO. | Name | Sequence |
|---|---|---|
| | | GCTGCTCGCCTGTGTTGCCACCTGGATTCTGCGCGGGACGTCCT
TCTGCTACGTCCCTTCGGCCCTCAATCCAGCGGACCTTCCTTCC
CGCGGCCTGCTGCCGGCTCTGCGGCCTCTTCCGCGTCTTCGCCT
TCGCCCTCAGACGAGTCGGATCTCCCTTTGGGCCGCCTCCCCGC
CTGGTACCTTTAAGACCAATGACTTACAAGGCAGCTGTAGATCT
TAGCCACTTTTTAAAAGAAAAGGGGGACTGGAAGGGCTAATT
CACTCCCAACGAAGATAAGATCTGCTTTTTGCTTGTACTGGGTC
TCTCTGGTTAGACCAGATCTGAGCCTGGGAGCTCTCTGGCTAAC
TAGGGAACCCACTGCTTAAGCCTCAATAAAGCTTGCCTTGAGTG
CTTCAAGTAGTGTGTGCCCGTCTGTTGTGTGACTCTGGTAACTA
GAGATCCCTCAGACCCTTTTAGTCAGTGTGGAAAATCTCTAGCA
GTAGTAGTTCATGTCATCTTATTATTCAGTATTTATAACTTGCAA
AGAAATGAATATCAGAGAGTGAGAGGAACTTGTTTATTGCAGC
TTATAATGGTTACAAATAAAGCAATAGCATCACAAATTTCACA
AATAAAGCATTTTTTCACTGCATTCTAGTTGTGGTTTGTCCAA
ACTCATCAATGTATCTTATCATGTCTGGCTCTAGCTATCCCGCC
CCTAACTCCGCCCATCCCGCCCCTAACTCCGCCCAGTTCCGCCC
ATTCTCCGCCCCATGGCTGACTAATTTTTTTATTTATGCAGAGG
CCGAGGCCGCCTCGGCCTCTGAGCTATTCCAGAAGTAGTGAGG
AGGCTTTTTTGGAGGCCTAGACTTTTGCAGAGACGGCCCAAATT
CGTAATCATGGTCATAGCTGTTTCCTGTGTGAAATTGTTATCCG
CTCACAATTCCACACAACATACGAGCCGGAAGCATAAAGTGTA
AAGCCTGGGGTGCCTAATGAGTGAGCTAACTCACATTAATTGC
GTTGCGCTCACTGCCCGCTTTCCAGTCGGGAAACCTGTCGTGCC
AGCTGCATTAATGAATCGGCCAACGCGCGGGGAGAGGCGGTTT
GCGTATTGGGCGCTCTTCCGCTTCCTCGCTCACTGACTCGCTGC
GCTCGGTCGTTCGGCTGCGGCGAGCGGTATCAGCTCACTCAAA
GGCGGTAATACGGTTATCCACAGAATCAGGGGATAACGCAGGA
AAGAACATGTGAGCAAAAGGCCAGCAAAAGGCCAGGAACCGT
AAAAAGGCCGCGTTGCTGGCGTTTTTCCATAGGCTCCGCCCCCC
TGACGAGCATCACAAAAATCGACGCTCAAGTCAGAGGTGGCGA
AACCCGACAGGACTATAAAGATACCAGGCGTTTCCCCCTGGAA
GCTCCCTCGTGCGCTCTCCTGTTCCGACCCTGCCGCTTACCGGA
TACCTGTCCGCCTTTCTCCCTTCGGGAAGCGTGGCGCTTTCTCAT
AGCTCACGCTGTAGGTATCTCAGTTCGGTGTAGGTCGTTCGCTC
CAAGCTGGGCTGTGTGCACGAACCCCCCGTTCAGCCCGACCGC
TGCGCCTTATCCGGTAACTATCGTCTTGAGTCCAACCCGGTAAG
ACACGACTTATCGCCACTGGCAGCAGCCACTGGTAACAGGATT
AGCAGAGCGAGGTATGTAGGCGGTGCTACAGAGTTCTTGAAGT
GGTGGCCTAACTACGGCTACACTAGAAGGACAGTATTTGGTAT
CTGCGCTCTGCTGAAGCCAGTTACCTTCGGAAAAAGAGTTGGT
AGCTCTTGATCCGGCAAACAAACCACCGCTGGTAGCGGTGGTT
TTTTTGTTTGCAAGCAGCAGATTACGCGCAGAAAAAAAGGATC
TCAAGAAGATCCTTTGATCTTTTCTACGGGGTCTGACGCTCAGT
GGAACGAAAACTCACGTTAAGGGATTTTGGTCATGAGATTATC
AAAAAGGATCTTCACCTAGATCCTTTTAAATTAAAAATGAAGTT
TTAAATCAATCTAAAGTATATATGAGTAAACTTGGTCTGACAGT
TACCAATGCTTAATCAGTGAGGCACCTATCTCAGCGATCTGTCT
ATTTCGTTCATCCATAGTTGCCTGACTCCCCGTCGTGTAGATAA
CTACGATACGGGAGGGCTTACCATCTGGCCCCAGTGCTGCAAT
GATACCGCGAGACCCACGCTCACCGGCTCCAGATTTATCAGCA
ATAAACCAGCCAGCCGGAAGGGCCGAGCGCAGAAGTGGTCCTG
CAACTTTATCCGCCTCCATCCAGTCTATTAATTGTTGCCGGGAA
GCTAGAGTAAGTAGTTCGCCAGTTAATAGTTTGCGCAACGTTGT
TGCCATTGCTACAGGCATCGTGGTGTCACGCTCGTCGTTTGGTA
TGGCTTCATTCAGCTCCGGTTCCCAACGATCAAGGCGAGTTACA
TGATCCCCCATGTTGTGCAAAAAAGCGGTTAGCTCCTTCGGTCC
TCCGATCGTTGTCAGAAGTAAGTTGGCCGCAGTGTTATCACTCA
TGGTTATGGCAGCACTGCATAATTCTCTTACTGTCATGCCATCC
GTAAGATGCTTTTCTGTGACTGGTGAGTACTCAACCAAGTCATT
CTGAGAATAGTGTATGCGGCGACCGAGTTGCTCTTGCCCGGCGT
CAATACGGGATAATACCGCGCCACATAGCAGAACTTTAAAAGT
GCTCATCATTGGAAAACGTTCTTCGGGGCGAAAACTCTCAAGG
ATCTTACCGCTGTTGAGATCCAGTTCGATGTAACCCACTCGTGC
ACCCAACTGATCTTCAGCATCTTTTACTTTCACCAGCGTTTCTGG
GTGAGCAAAAACAGGAAGGCAAAATGCCGCAAAAAAGGGAAT
AAGGGCGACACGGAAATGTTGAATACTCATACTCTTCCTTTTTC
AATATTATTGAAGCATTTATCAGGGTTATTGTCTCATGAGCGGA
TACATATTTGAATGTATTTAGAAAAATAAACAAATAGGGGTTC
CGCGCACATTTCCCCGAAAAGTGCCACCTGACGTCTAAGAAAC
CATTATTATCATGACATTAACCTATAAAAATAGGCGTATCACGA
GGCCCTTTCGTCTCGCGCGTTTCGGTGATGACGGTGAAAACCTC
TGACACATGCAGCTCCCGGAGACGGTCACAGCTTGTCTGTAAG
CGGATGCCGGGAGCAGACAAGCCCGTCAGGGCGCGTCAGCGG |

APPENDIX A-continued

SEQUENCE SUMMARY

| SEQ ID NO. | Name | Sequence |
|---|---|---|
| | | GTGTTGGCGGGTGTCGGGGCTGGCTTAACTATGCGGCATCAGA GCAGATTGTACTGAGAGTGCACCATATGCGGTGTGAAATACCG CACAGATGCGTAAGGAGAAAATACCGCATCAGGCGCCATTCGC CATTCAGGCTGCGCAACTGTTGGGAAGGGCGATCGGTGCGGGC CTCTTCGCTATTACGCCAGCTGGCGAAAGGGGGATGTGCTGCA AGGCGATTAAGTTGGGTAACGCCAGGGTTTTCCCAGTCACGAC GTTGTAAAACGACGGCCAGTGCCAAGCTG |
| 18 | p502_NKG2D_ dimer_ CD3epsilon (DNA Sequence) | ACGCGTGTAGTCTTATGCAATACTCTGTAGTCTTGCAACATGGT AACGATGAGTTAGCAACATGCCTTACAAGGAGAGAAAAAGCAC CGTGCATGCCGATTGGTGGAAGTAAGGTGGTACGATCGTGCCT TATTAGGAAGGCAACAGACGGGTCTGACATGGATTGGACGAAC CACTGAATTGCCGCATTGCAGAGATATTGTATTTAAGTGCCTAG CTCGATACATAAACGGGTCTCTCTGGTTAGACCAGATCTGAGCC TGGGAGCTCTCTGGCTAACTAGGGAACCCACTGCTTAAGCCTCA ATAAAGCTTGCCTTGAGTGCTTCAAGTAGTGTGTGCCCGTCTGT TGTGTGACTCTGGTAACTAGAGATCCCTCAGACCCTTTTAGTCA GTGTGGAAAATCTCTAGCAGTGGCGCCCGAACAGGGACTTGAA AGCGAAAGGGAAACCAGAGGAGCTCTCTCGACGCAGGACTCG GCTTGCTGAAGCGCGCACGGCAAGAGGCGAGGGGCGGCGACT GGTGAGTACGCCAAAAATTTTGACTAGCGGAGGCTAGAAGGAG AGAGATGGGTGCGAGAGCGTCAGTATTAAGCGGGGGAGAATTA GATCGCGATGGGAAAAAATTCGGTTAAGGCCAGGGGGAAAGA AAAAATATAAATTAAAACATATAGTATGGGCAAGCAGGGAGCT AGAACGATTCGCAGTTAATCCTGGCCTGTTAGAAACATCAGAA GGCTGTAGACAAATACTGGGACAGCTACAACCATCCCTTCAGA CAGGATCAGAAGAACTTAGATCATTATATAATACAGTAGCAAC CCTCTATTGTGTGCATCAAAGGATAGAGATAAAAGACACCAAG GAAGCTTTAGACAAGATAGAGGAAGAGCAAAACAAAGTAAG ACCACCGCACAGCAAGCGGCCACTGATCTTCAGACCTGGAGGA GGAGATATGAGGGACAATTGGAGAAGTGAATTATATAAATATA AAGTAGTAAAAATTGAACCATTAGGAGTAGCACCCACCAAGGC AAAGAGAAGAGTGGTGCAGAGAGAAAAAAGAGCAGTGGGAAT AGGAGCTTTGTTCCTTGGGTTCTTGGGAGCAGCAGGAAGCACT ATGGGCGCAGCGTCAATGACGCTGACGGTACAGGCCAGACAAT TATTGTCTGGTATAGTGCAGCAGCAGAACAATTTGCTGAGGGCT ATTGAGGCGCAACAGCATCTGTTGCAACTCACAGTCTGGGGCA TCAAGCAGCTCCAGGCAAGAATCCTGGCTGTGGAAAGATACCT AAAGGATCAACAGCTCCTGGGGATTTGGGGTTGCTCTGGAAAA CTCATTTGCACCACTGCTGTGCCTTGGAATGCTAGTTGGAGTAA TAAATCTCTGGAACAGATTTGGAATCACACGACCTGGATGGAG TGGGACAGAGAAATTAACAATTACACAAGCTTAATACACTCCT TAATTGAAGAATCGCAAAACCAGCAAGAAAAGAATGAACAAG AATTATTGGAATTAGATAAATGGGCAAGTTTGTGGAATTGGTTT AACATAACAAATTGGCTGTGGTATATAAAATTATTCATAATGAT AGTAGGAGGCTTGGTAGGTTTAAGAATAGTTTTTGCTGTACTTT CTATAGTGAATAGAGTTAGGCAGGGATATTCACCATTATCGTTT CAGACCCACCTCCCAACCCCGAGGGGACCCGACAGGCCCGAAG GAATAGAAGAAGAAGGTGGAGAGAGAGACAGAGACAGATCCA TTCGATTAGTGAACGGATCTCGACGGTATCGGTTAACTTTTAAA AGAAAAGGGGGGATTGGGGGGTACAGTGCAGGGGAAAGAATA GTAGACATAATAGCAACAGACATACAAACTAAAGAATTACAAA AACAAATTACAAAATTCAAAATTTTATCGATACTAGTGGATCTG CGATCGCTCCGGTGCCCGTCAGTGGGCAGAGCGCACATCGCCC ACAGTCCCCGAGAAGTTGGGGGGAGGGGTCGGCAATTGAACGG GTGCCTAGAGAAGGTGGCGCGGGGTAAACTGGGAAAGTGATGT CGTGTACTGGCTCCGCCTTTTTCCCGAGGGTGGGGGAGAACCGT ATATAAGTGCAGTAGTCGCCGTGAACGTTCTTTTTCGCAACGGG TTTGCCGCCAGAACACAGCTGAAGCTTCGAGGGGCTCGCATCT CTCCTTCACGCGCCCGCCGCCCTACCTGAGGCCGCCATCCACGC CGGTTGAGTCGCGTTCTGCCGCCTCCCGCCTGTGGTGCCTCCTG AACTGCGTCCGCCGTCTAGGTAAGTTTAAAGCTCAGGTCGAGA CCGGGCCTTTGTCCGGCGCTCCCTTGGAGCCTACCTAGACTCAG CCGGCTCTCCACGCTTTGCCTGACCCTGCTTGCTCAACTCTACG TCTTTGTTTCGTTTTCTGTTCTGCGCCGTTACAGATCCAAGCTGT GACCGGCGCCTACTCTAGAGCCGCCACCATGCTTCTCCTGGTGA CAAGCCTTCTGCTCTGTGAGTTACCACACCCAGCATTCCTCCTG ATCCCAAACTCCCTCTTCAACCAGGAGGTGCAGATCCCCCTCAC AGAGAGCTACTGCGGGCCCTGTCCAAAGAATTGGATATGTTAC AAGAACAATTGCTACCAGTTCTTCGATGAGTCAAAAAATTGGT ATGAGAGCCAAGCTTCCTGCATGTCTCAGAATGCCAGCCTTCTG AAGGTGTACTCAAAAGAAGACCAGGACTTGCTGAAACTGGTCA AGTCTTACCACTGGATGGGCTCGTGCACATTCCAACGAACGG TAGCTGGCAGTGGGAAGATGGCTCCATATTGTCTCCTAACCTTC |

APPENDIX A-continued

SEQUENCE SUMMARY

| SEQ ID NO. | Name | Sequence |
|---|---|---|
| | | TCACCATAATAGAGATGCAGAAGGGTGATTGCGCTCTGTACGC
TAGTAGCTTCAAGGGCTATATTGAGAATTGTAGTACACCCAAC
ACATACATTTGTATGCAGAGAACCGTGGGAGGTGGTGGCAGCG
GTGGCGGTGGAAGTGGTGGCGGTGGCAGTCTCGAGAACTCATT
ATTCAACCAAGAAGTTCAAATTCCCTTGACCGAAAGTTACTGTG
GCCCATGTCCTAAAAACTGGATATGTTACAAAAATAACTGCTA
CCAATTTTTTGATGAGAGTAAAAACTGGTATGAGAGCCAGGCT
TCTTGTATGTCTCAAAATGCCAGCCTTCTGAAAGTATACAGCAA
AGAGGACCAGGATTTACTTAAACTGGTGAAGTCATATCATTGG
ATGGGACTAGTACACATTCCAACAAATGGATCTTGGCAGTGGG
AAGATGGCTCCATTCTCTCACCCAACCTACTAACAATAATTGAA
ATGCAGAAGGGAGACTGTGCACTCTATGCCTCTAGCTTTAAAG
GCTATATAGAAAACTGTTCAACTCCAAATACATACATCTGCATG
CAAAGGACTGTGGCGGCCGCAGGTGGCGGCGGTTCTGGTGGCG
GCGGTTCTGGTGGCGGCGGTTCTCTCGAGGATGGTAATGAAGA
AATGGGTGGTATTACACAGACACCCATATAAAGTCTCCATCTCTG
GAACCACAGTAATATTGACATGCCCTCAGTATCCTGGATCTGAA
ATACTATGGCAACACAATGATAAAAACATAGGCGGTGATGAGG
ATGATAAAAACATAGGCAGTGATGAGGATCACCTGTCACTGAA
GGAATTTTCAGAATTGGAGCAAAGTGGTTATTATGTCTGCTACC
CCAGAGGAAGCAAACCAGAAGATGCGAACTTTTATCTCTACCT
GAGGGCAAGAGTGTGTGAGAACTGCATGGAGATGGATGTGATG
TCGGTGGCCACAATTGTCATAGTGGACATCTGCATCACTGGGG
GCTTGCTGCTGCTGGTTTACTACTGGAGCAAGAATAGAAAGGC
CAAGGCCAAGCCTGTGACACGAGGAGCGGGTGCTGGCGGCAG
GCAAAGGGGACAAAACAAGGAGAGGCCACCACCTGTTCCCAA
CCCAGACTATGAGCCCATCCGGAAAGGCCAGCGGGACCTGTAT
TCTGGCCTGAATCAGAGACGCATCTGATAAGAATTCGAATTTA
AATCGGATCCGCGGCCGCGTCGACAATCAACCTCTGGATTACA
AAATTTGTGAAAGATTGACTGGTATTCTTAACTATGTTGCTCCT
TTTACGCTATGTGGATACGCTGCTTTAATGCCTTTGTATCATGCT
ATTGCTTCCCGTATGGCTTTCATTTTCTCCTCCTTGTATAAATCC
TGGTTGCTGTCTCTTTATGAGGAGTTGTGGCCCGTTGTCAGGCA
ACGTGGCGTGGTGTGCACTGTGTTTGCTGACGCAACCCCCACTG
GTTGGGGCATTGCCACCACCTGTCAGCTCCTTTCCGGGACTTTC
GCTTTCCCCCTCCCTATTGCCACGGCGGAACTCATCGCCGCCTG
CCTTGCCCGCTGCTGGACAGGGGCTCGGCTGTTGGGCACTGAC
AATTCCGTGGTGTTGTCGGGGAAATCATCGTCCTTTCCTTGGCT
GCTCGCCTGTGTTGCCACCTGGATTCTGCGCGGGACGTCCTTCT
GCTACGTCCCTTCGGCCCTCAATCCAGCGGACCTTCCTTCCCGC
GGCCTGCTGCCGGCTCTGCGGCCTCTTCCGCGTCTTCGCCTTCG
CCCTCAGACGAGTCGGATCTCCCTTTGGGCCGCCTCCCCGCCTG
GTACCTTTAAGACCAATGACTTACAAGGCAGCTGTAGATCTTAG
CCACTTTTTAAAAGAAAAGGGGGGACTGGAAGGGCTAATTCAC
TCCCAACGAAGATAAGATCTGCTTTTTGCTTGTACTGGGTCTCT
CTGGTTAGACCAGATCTGAGCCTGGGAGCTCTCTGGCTAACTAG
GGAACCCACTGCTTAAGCCTCAATAAAGCTTGCCTTGAGTGCTT
CAAGTAGTGTGTGCCCGTCTGTTGTGTGACTCTGGTAACTAGAG
ATCCCTCAGACCCTTTTAGTCAGTGTGGAAAATCTCTAGCAGTA
GTAGTTCATGTCATCTTATTATTCAGTATTTATAACTTGCAAAG
AAATGAATATCAGAGAGTGAGAGGAACTTGTTTATTGCAGCTT
ATAATGGTTACAAATAAAGCAATAGCATCACAAATTTCACAA
TAAAGCATTTTTTTCACTGCATTCTAGTTGTGGTTTGTCCAAACT
CATCAATGTATCTTATCATGTCTGGCTCTAGCTATCCCGCCCCT
AACTCCGCCCATCCCGCCCCTAACTCCGCCCAGTTCCGCCCATT
CTCCGCCCCATGGCTGACTAATTTTTTTTATTTATGCAGAGGCC
GAGGCCGCCTCGGCCTCTGAGCTATTCCAGAAGTAGTGAGGAG
GCTTTTTTGGAGGCCTAGACTTTTGCAGAGACGGCCCAAATTCG
TAATCATGGTCATAGCTGTTTCCTGTGTGAAATTGTTATCCGCT
CACAATTCCACACAACATACGAGCCGGAAGCATAAAGTGTAAA
GCCTGGGGTGCCTAATGAGTGAGCTAACTCACATTAATTGCGTT
GCGCTCACTGCCCGCTTTCCAGTCGGGAAACCTGTCGTGCCAGC
TGCATTAATGAATCGGCCAACGCGCGGGGAGAGGCGGTTTGCG
TATTGGGCGCTCTTCCGCTTCCTCGCTCACTGACTCGCTGCGCTC
GGTCGTTCGGCTGCGGCGAGCGGTATCAGCTCACTCAAAGGCG
GTAATACGGTTATCCACAGAATCAGGGGATAACGCAGGAAAGA
ACATGTGAGCAAAAGGCCAGCAAAAGGCCAGGAACCGTAAAA
AGGCCGCGTTGCTGGCGTTTTTCCATAGGCTCCGCCCCCCTGAC
GAGCATCACAAAAATCGACGCTCAAGTCAGAGGTGGCGAAACC
CGACAGGACTATAAAGATACCAGGCGTTTCCCCCTGGAAGCTC
CCTCGTGCGCTCTCCTGTTCCGACCCTGCCGCTTACCGGATACC
TGTCCGCCTTTCTCCCTTCGGGAAGCGTGGCGCTTTCTCATAGC
TCACGCTGTAGGTATCTCAGTTCGGTGTAGGTCGTTCGCTCCAA
GCTGGGCTGTGTGCACGAACCCCCCGTTCAGCCCGACCGCTGC |

APPENDIX A-continued

SEQUENCE SUMMARY

| SEQ ID NO. | Name | Sequence |
|---|---|---|
| | | GCCTTATCCGGTAACTATCGTCTTGAGTCCAACCCGGTAAGACA CGACTTATCGCCACTGGCAGCAGCCACTGGTAACAGGATTAGC AGAGCGAGGTATGTAGGCGGTGCTACAGAGTTCTTGAAGTGGT GGCCTAACTACGGCTACACTAGAAGGACAGTATTTGGTATCTG CGCTCTGCTGAAGCCAGTTACCTTCGGAAAAAGAGTTGGTAGC TCTTGATCCGGCAAACAAACCACCGCTGGTAGCGGTGGTTTTTT TGTTTGCAAGCAGCAGATTACGCGCAGAAAAAAAGGATCTCAA GAAGATCCTTTGATCTTTTCTACGGGGTCTGACGCTCAGTGGAA CGAAAACTCACGTTAAGGGATTTTGGTCATGAGATTATCAAAA AGGATCTTCACCTAGATCCTTTTAAATTAAAAATGAAGTTTTAA ATCAATCTAAAGTATATATGAGTAAACTTGGTCTGACAGTTACC AATGCTTAATCAGTGAGGCACCTATCTCAGCGATCTGTCTATTT CGTTCATCCATAGTTGCCTGACTCCCCGTCGTGTAGATAACTAC GATACGGGAGGGCTTACCATCTGGCCCCAGTGCTGCAATGATA CCGCGAGACCCACGCTCACCGGCTCCAGATTTATCAGCAATAA ACCAGCCAGCCGGAAGGGCCGAGCGCAGAAGTGGTCCTGCAAC TTTATCCGCCTCCATCCAGTCTATTAATTGTTGCCGGGAAGCTA GAGTAAGTAGTTCGCCAGTTAATAGTTTGCGCAACGTTGTTGCC ATTGCTACAGGCATCGTGGTGTCACGCTCGTCGTTTGGTATGGC TTCATTCAGCTCCGGTTCCCAACGATCAAGGCGAGTTACATGAT CCCCCATGTTGTGCAAAAAAGCGGTTAGCTCCTTCGGTCCTCCG ATCGTTGTCAGAAGTAAGTTGGCCGCAGTGTTATCACTCATGGT TATGGCAGCACTGCATAATTCTCTTACTGTCATGCCATCCGTAA GATGCTTTTCTGTGACTGGTGAGTACTCAACCAAGTCATTCTGA GAATAGTGTATGCGGCGACCGAGTTGCTCTTGCCCGGCGTCAAT ACGGGATAATACCGCGCCACATAGCAGAACTTTAAAAGTGCTC ATCATTGGAAAACGTTCTTCGGGGCGAAAACTCTCAAGGATCTT ACCGCTGTTGAGATCCAGTTCGATGTAACCCACTCGTGCACCCA ACTGATCTTCAGCATCTTTTACTTTCACCAGCGTTTCTGGGTGA GCAAAAACAGGAAGGCAAAATGCCGCAAAAAAGGGAATAAGG GCGACACGGAAATGTTGAATACTCATACTCTTCCTTTTTCAATA TTATTGAAGCATTTATCAGGGTTATTGTCTCATGAGCGGATACA TATTTGAATGTATTTAGAAAAATAAACAAATAGGGGTTCCGCG CACATTTCCCCGAAAAGTGCCACCTGACGTCTAAGAAACCATT ATTATCATGACATTAACCTATAAAAATAGGCGTATCACGAGGC CCTTTCGTCTCGCGCGTTTCGGTGATGACGGTGAAAACCTCTGA CACATGCAGCTCCCGGAGACGGTCACAGCTTGTCTGTAAGCGG ATGCCGGGAGCAGACAAGCCCGTCAGGGCGCGTCAGCGGGTGT TGGCGGGTGTCGGGGCTGGCTTAACTATGCGGCATCAGAGCAG ATTGTACTGAGAGTGCACCATATGCGGTGTGAAATACCGCACA GATGCGTAAGGAGAAAATACCGCATCAGGCGCCATTCGCCATT CAGGCTGCGCAACTGTTGGGAAGGGCGATCGGTGCGGGCCTCT TCGCTATTACGCCAGCTGGCGAAAGGGGGATGTGCTGCAAGGC GATTAAGTTGGGTAACGCCAGGGTTTTCCCAGTCACGACGTTGT AAAACGACGGCCAGTGCCAAGCTG |
| 20 | human ROR1, Isoform 1 (canonical) UniProt Acc # Q01973-1 | MHRPRRRGTRPPLLALLAALLLAARGAAAQETELSVSAELVPTSS WNISSELNKDSYLTLDEPMNNITTSLGQTAELHCKVSGNPPPTIRW FKNDAPVVQEPRRLSFRSTIYGSRLRIRNLDTTDTGYFQCVATNGK EVVSSTGVLFVKFGPPPTASPGYSDEYEEDGFCQPYRGIACARFIG NRTVYMESLHMQGEIENQITAAFTMIGTSSRLSDKCSQFAIPSLCH YAFPYCDETSSVPKPRDLCRDECEILENVLCQTEYIFARSNPMILMR LKLPNCEDLPQPESPEAANCIRIGIPMADPINKNHKCYNSTGVDYR GTVSVTKSGRQCQPWNSQYPHTHTFTALRFPELNGGHSYCRNPGN QKEAPWCFTLDENFKSDLCDIPACDSKDSKEKNKMEILYILVPSVA IPLAIALLFFFICVCRNNQKSSSAPVQRQPKHVRGQNVEMSMLNAY KPKSKAKELPLSAVRFMEELGECAFGKIYKGHLYLPGMDHAQLV AIKTLKDYNNPQQWTEFQQEASLMAELHHPNIVCLLGAVTQEQPV CMLFEYINQGDLHEFLIMRSPHSDVGCSSDEDGTVKSSLDHGDFLH IAIQIAAGMEYLSSHFFVHKDLAARNILIGEQLHVKISDLGLSREIYS ADYYRVQSKSLLPIRWMPPEAIMYGKFSSDSDIWSFGVVLWEIFSF GLQPYYGFSNQEVIEMVRKRQLLPCSEDCPPRMYSLMTECWNEIP SRRPRFKDIHVRLRSWEGLSSHTSSTTPSGGNATTQTTSLSASPVSN LSNPRYPNYMFPSQGITPQGQIAGFIGPPIPQNQRFIPINGYPIPPGYA AFPAAHYQPTGPPRVIQHCPPPKSRSPSSASGSTSTGHVTSLPSSGS NQEANIPLLPHMSIPNHPGGMGITVFGNKSQKPYKIDSKQASLLGD ANIHGHTESMISAEL |
| 21 | human ROR1 Isoform 2 | MHRPRRRGTRPPLLALLAALLLAARGAAAQETELSVSAELVPTSS WNISSELNKDSYLTLDEPMNNITTSLGQTAELHCKVSGNPPPTIRW FKNDAPVVQEPRRLSFRSTIYGSRLRIRNLDTTDTGYFQCVATNGK EVVSSTGVLFVKFGPPPTASPGYSDEYEEDGFCQPYRGIACARFIG NRTVYMESLHMQGEIENQITAAFTMIGTSSHLSDKCSQFAIPSLCH YAFPYCDETSSVPKPRDLCRDECEILENVLCQTEYIFARSNPMILMR |

APPENDIX A-continued

SEQUENCE SUMMARY

| SEQ ID NO. | Name | Sequence |
|---|---|---|
|  |  | LKLPNCEDLPQPESPEAANCIRIGIPMADPINKNHKCYNSTGVDYR GTVSVTKSGRQCQPWNSQYPHTHTFTALRFPELNGGHSYCRNPGN QKEAPWCFTLDENFKSDLCDIPACGK |
| 22 | human ROR1 Isoform 3 | MNNITTSLGQTAELHCKVSGNPPPTIRWFKNDAPVVQEPRRLSF RSTIYGSRLRIRNLDTTDTGYFQCVATNGKEVVSSTGVLFVKFGPP PTASPGYSDEYEEDGFCQPYRGIACARFIGNRTVYMESLHMQGEIE NQITAAFTMIGTSSRLSDKCSQFAIPSLCHYAFPYCDETSSVPKPRD LCRDECEILENVLCQTEYIFARSNPMILMRLKLPNCEDLPQPESPEA ANCIRIGIPMADPINKNHKCYNSTGVDYRGTVSVTKSGRQCQPWN SQYPHTHTFTALRFPELNGGHSYCRNPGNQKEAPWCFTLDENFKS DLCDIPACDSKDSKEKNKMEILYILVPSVAIPLAIALLFFFICVCRNN QKSSSAPVQRQPKHVRGQNVEMSMLNAYKPKSKAKELPLSAVRF MEELGECAFGKIYKGHLYLPGMDHAQLVAIKTLKDYNNPQQWTE FQQEASLMAELHHPNIVCLLGAVTQEQPVCMLFEYINQGDLHEFLI MRSPHSDVGCSSDEDGTVKSSLDHGDFLHIAIQIAAGMEYLSSHFF VHKDLAARNILIGEQLHVKISDLGLSREIYSADYYRVQSKSLLPIR WMPPEAIMYGKFSSDSDIWSFGVVLWEIFSFGLQPYYGFSNQEVIE MVRKRQLLPCSEDCPPRMYSLMTECWNEIPSRRPRFKDIHVRLRS WEGLSSHTSSTTPSGGNATTQTTSLSASPVSNLSNPRYPNYMFPSQ GITPQGQIAGFIGPPIPQNQRFIPINGYPIPPGYAAFPAAHYQPTGPPR VIQHCPPPKSRSPSSASGSTSTGHVTSLPSSGSNQEANIPLLPHMSIP NHPGGMGITVFGNKSQKPYKIDSKQASLLGDANIHGHTESMISAEL |
| 23 | CD16 Isoform A, UniProt Accession No. P08637 | MWQLLLPTALLLLVSAGMRTEDLPKAVVFLEPQWYRVLEKDSVT LKCQGAYSPEDNSTQWFHNESLISSQASSYFIDAATVDDSGEYRCQ TNLSTLSDPVQLEVHIGWLLLQAPRWVFKEEDPIYLRCHSWKNTA LHKVTYLQNGKGRKYFEIHNSDFYIPKATLKDSGSYFCRGLFGSKN VSSETVNITITQGLAVSTISSFFPPGYQVSFCLVMVLLFAVDTGLYF SVKTNIRSSTRDWKDHKFKWRKDPQDK |
| 24 | CD16 V158 variant of SEQ ID NO: 23 | MWQLLLPTALLLLVSAGMRTEDLPKAVVFLEPQWYRVLEKDSVT LKCQGAYSPEDNSTQWFHNESLISSQASSYFIDAATVDDSGEYRCQ TNLSTLSDPVQLEVHIGWLLLQAPRWVFKEEDPIHLRCHSWKNTA LHKVTYLQNGKGRKYFHEINSDFYIPKATLKDSGSYFCRGLVGSKN VSSETVNITITQGLAVSTISSFFPPGYQVSFCLVMVLLFAVDTGLYF SVKTNIRSSTRDWKDHKFKWRKDPQDK |
| 25 | Anti-CD19 light chain CDR1 (DNA) | AGGGCAAGTCAGGACATTAGTAAA |
| 26 | Anti-CD19 light chain CDR1 (protein) | RASQDISK |
| 27 | Anti-CD19 light chain CDR2 (DNA) | ATCTACCATACATCAAGATTA |
| 28 | Anti-CD19 light chain CDR2 (protein) | IYHTSRL |
| 29 | Anti-CD19 light chain CDR3 (DNA) | CAACAGGGTAATACGCTTCCGTACACG |
| 30 | Anti-CD19 light chain CDR3 (protein) | QQGNTLPYT |
| 31 | Anti-CD19 heavy chain CDR1 (DNA) | GGGGTCTCATTACCCGACTATGGTGTAAGC |
| 32 | Anti-CD19 heavy chain CDR1 (protein) | GVSLPDYGVS |
| 33 | Anti-CD19 heavy chain CDR2 (DNA) | GTAATATGGGGTAGTGAAACCACATACTATAATTCAGCTCTC |

APPENDIX A-continued

SEQUENCE SUMMARY

| SEQ ID NO. | Name | Sequence |
|---|---|---|
| 34 | Anti-CD19 heavy chain CDR2 (protein) | VIWGSETTYYNSAL |
| 35 | Anti-CD19 heavy chain CDR3 (DNA) | CATTATTACTACGGTGGTAGCTATGCTATGGACTAC |
| 36 | Anti-CD19 heavy chain CDR3 (protein) | HYYYGGSYAMDY |
| 37 | Anti-CD19 light chain variable region (DNA) | GACATCCAGATGACACAGACTACATCCTCCCTGTCTGCCTCTCT GGGAGACAGAGTCACCATCAGTTGCAGGGCAAGTCAGGACATT AGTAAATATTTAAATTGGTATCAGCAGAAACCAGATGGAACTG TTAAACTCCTGATCTACCATACATCAAGATTACACTCAGGAGTC CCATCAAGGTTCAGTGGCAGTGGGTCTGGAACAGATTATTCTCT CACCATTAGCAACCTGGAGCAAGAAGATATTGCCACTTACTTTT GCCAACAGGGTAATACGCTTCCGTACACGTTCGGAAC TAAGTTGGAAATAACA |
| 38 | Anti-CD19 light chain variable region (protein) | DIQMTQTTSSLSASLGDRVTISCRASQDISKYLNWYQQKPDGTVKL LIYHTSRLHSGVPSRFSGSGSGTDYSLTISNLEQEDIATYFCQQGNT LPYTFGGGTKLEIT |
| 39 | Anti-CD19 heavy chain variable region (DNA) | GAGGTGAAACTGCAGGAGTCAGGACCTGGCCTGGTGGCGCCCT CACAGAGCCTGTCCGTCACATGCACTGTCTCAGGGGTCTCATTA CCCGACTATGGTGTAAGCTGGATTCGCCAGCCTCCACGAAAGG GTCTGGAGTGGCTGGGAGTAATATGGGGTAGTGAAACCACATA CTATAATTCAGCTCTCAAATCCAGACTGACCATCATCAAGGACA ACTCCAAGAGCCAAGTTTTCTTAAAAATGAACAGTCTGCAAAC TGATGACACAGCCATTTACTACTGTGCCAAACATTATTACTACG GTGGTAGCTATGCTATGGACTACTGGGGTCAAGGAACCTCAGT CACCGTCTCCTCA |
| 40 | Anti-CD19 heavy chain variable region (protein) | EVKLQESGPGLVAPSQSLSVTCTVSGVSLPDYGVSWIRQPPRKGLE WLGVIWGSETTYYNSALKSRLTIIKDNSKSQVFLKMNSLQTDDTAI YYCAKHYYYGGSYAMDYWGQGTSVTVSS |
| 41 | Anti-BCMA light chain CDR1 (DNA) | AAAAGCAGCCAGAGCCTGGTGCATAGCAACGGCAACACCTATC TGCAT |
| 42 | Anti-BCMA light chain CDR1 (protein) | KSSQSLVHSNGNTYLH |
| 43 | Anti-BCMA light chain CDR2 (DNA) | AAAGTGAGCAACCGCTTTAGC |
| 44 | Anti-BCMA light chain CDR2 (protein) | KVSNRFS |
| 45 | Anti-BCMA light chain CDR3 (DNA) | GCGGAAACCAGCCATGTGCCGTGGACC |
| 46 | Anti-BCMA light chain CDR3 (protein) | AETSHVPWT |
| 47 | Anti-BCMA heavy chain CDR1 (DNA) | AAAGCGAGCGGCTATAGCTTTCCGGATTATTATATTAAC |
| 48 | Anti-BCMA heavy chain CDR1 (protein) | KASGYSFPDYYIN |

APPENDIX A-continued

SEQUENCE SUMMARY

| SEQ ID NO. | Name | Sequence |
|---|---|---|
| 49 | Anti-BCMA heavy chain CDR2 (DNA) | TGGATTTATTTTGCGAGCGGCAACAGCGAATATAACCAGAAAT TTACCGGC |
| 50 | Anti-BCMA heavy chain CDR2 (protein) | WIYFASGNSEYNQKFTG |
| 51 | Anti-BCMA heavy chain CDR3 (DNA) | CTGTATGATTATGATTGGTATTTTGATGTG |
| 52 | Anti-BCMA heavy chain CDR3 (protein) | LYDYDWYFDV |
| 53 | Anti-BCMA heavy chain variable region (DNA) | CAGGTGCAGCTGGTGCAGAGCGGCGCGGAAGTGAAAAAACCG GGCGCGAGCGTGAAAGTGAGCTGCAAAGCGAGCGGCTATAGCT TTCCGGATTATTATATTAACTGGGTGCGCCAGGCGCCGGGCCAG GGCCTGGAATGGATGGGCTGGATTTATTTTGCGAGCGGCAACA GCGAATATAACCAGAAATTTACCGGCCGCGTGACCATGACCCG CGATACCAGCAGCAGCACCGCGTATATGGAACTGAGCAGCCTG CGCAGCGAAGATACCGCGGTGTATTTTTGCGCGAGCCTGTATG ATTATGATTGGTATTTTGATGTGTGGGGCCAGGGCACCATGGTG ACCGTGAGCAGC |
| 54 | Anti-BCMA heavy chain variable region (protein) | QVQLVQSGAEVKKPGASVKVSCKASGYSFPDYYINWVRQAPGQG LEWMGWIYFASGNSEYNQKFTGRVTMTRDTSSSTAYMELSSLRSE DTAVYFCASLYDYDWYFDVWGQGTMVTVSS |
| 55 | Anti-BCMA light chain variable region (DNA) | GATATTGTGATGACCCAGACCCCGCTGAGCCTGAGCGTGACCC CGGGCGAACCGGCGAGCATTAGCTGCAAAAGCAGCCAGAGCCT GGTGCATAGCAACGGCAACACCTATCTGCATTGGTATCTGCAG AAAACCGGGCCAGAGCCCGCAGCTGCTGATTTATAAAGTGAGCA ACCGCTTTAGCGGCGTGCCGGATCGCTTTAGCGGCAGCGGCAG CGGCGCGGATTTTACCCTGAAAATTAGCCGCGTGGAAGCGGAA GATGTGGGCGTGTATTATTGCGCGGAAACCAGCCATGTGCCGT GGACCTTTGGCCAGGGCACCAAACTGGAAATTAAAAGC |
| 56 | Anti-BCMA light chain variable region (protein) | DIVMTQTPLSLSVTPGEPASISCKSSQSLVHSNGNTYLHWYLQKPG QSPQLLIYKVSNRFSGVPDRFSGSGSGADFTLKISRVEAEDVGVYY CAETSHVPWTFGQGTKLEIKS |
| 57 | Anti-CD22 light chain CDR1 | QDIHGY |
| 58 | Anti-CD22 light chain CDR2 | YTS |
| 59 | Anti-CD22 light chain CDR3 | QQGNTLPWT |
| 60 | Anti-CD22 heavy chain CDR1 | GFAFSIYD |
| 61 | Anti-CD22 heavy chain CDR2 | ISSGGGTT |
| 62 | Anti-CD22 heavy chain CDR3 | ARHSGYGTHWGVLFAY |

APPENDIX A-continued

SEQUENCE SUMMARY

| SEQ ID NO. | Name | Sequence |
|---|---|---|
| 63 | Anti-CD22 light chain variable region | DIQMTQSPSSLSASVGDRVTITCRASQTIWSYLNWYQQRPGKAP NLLIYAASSLQSGVPSRFSGRGSGTDFTLTISSLQAEDFATYYCQ QSYSIPQTFGQGTKLEIKEVQLVESGGGLVKPGGSLKLSCAASG FAFSIYDMSWVRQTPEKRLEWVAYISSGGGTTYYPDTVKGRFTI SRDNAKNTLYLQMSSLKSEDTAMYYCARHSGYGTHWGVLFA YWQGTLVTVSA |
| 64 | Anti-CD22 heavy chain variable region | QVQLQQSGPGLVKPSQTLSLTCAISGDSVSSNSAAWNWIRQSPS RGLEWLGRTYYRSKWYNDYAVSVKSRITINPDTSKNQFSLQLN SVTPEDTAVYYCAREVTGDLEDAFDIWGQGTMVTVSSGGSLA ALTAHQACHLPLETFTRHRQPRGWEQLEQCGYPVQRLVALYL AARLSWNQVDQVIRNALASPGSGGDLGEAIREQPEQARLALTL AAAESERFVRQGTGNDEAGAANGPADSGDALLERNYPTGAEF LGDGGDVSFSTRGTQNWTVERLLQAHRQLEERGYVFVGYHGT FLEAAQSIVFGGVRARSQDLDAIWRGFYIAGDPALAYGYAQDQ EPDAAGRIRNGALLRVYVPRSSLPGFYRTSLTLAAPEAAGEVER LIGHPLPLRLDAITGPEEEGGRLETILGWPLAERTVVIPSAIPTDP RNVGGDLDPSSIPDKEQAISALPDYASQPGKPPREDLK |
| 65 | Anti-ROR1 scFv 2-7 VH_linker4_ anti-ROR1 2-7 VL (DNA) | GAAGTGCAGCTGCTGGAAAGCGGCGGTGGTCTGGTTCAGCC GGGTGGCAGCCTGCGTCTGAGCTGTGCGGCGAGCGGCTTTA CCTTTAGCAGCTATGCCATGAGCTGGGTGCGTCAGGCACCGG GTAAAGGCCTGGAATGGGTGAGCGCGATTAGCGGCAGCGGC GGCAGCACCTATTATGCGGATAGCGTGAAAGGCCGTTTTACC ATTAGCCGTGATAACAGCAAAAACACCCTGTATCTGCAGAT GAACAGCCTGCGTGCGGAAGATACCGCGGTGTATTATTGCG CGAAAGATAAGGGTTGGTTTAACTGGCAATTCGATTATTGGG GCCAGGGCACCCTGGTTACCGTTAGCAGCGGTGGAGGCGGT TCTGGTGGAGGCGGTTCGGATGGCGGAGGTTCAGAAATTGT GCTGACCCAGAGCCCGGGCACGCTGTCTCTGAGCCCGGGTG AACGTGCGACCCTGAGCTGTCGTGCGAGCCAAAGCGTGAGC AGCAGCTATCTGGCCTGGTATCAgCAGAAACCGGGCCAGGC ACCGCGTCTGCTGATTTATGGCGCGAGCAGCCgTGCGACCGG CATTCCGGATCGTTTTAGCGGCAGCGGTAGCGGCACCGATTT TACCCTGACCATTAGCCGTCTGGAACCGGAAGATTTTGCGGT GTATTATTGCCAGCAGTATGGCAGCAGCCCGTGGACCTTTGG CCAGGGCACCAAAGTGGAAATTAAA |
| 66 | Linker 4 (DNA) | GGTGGAGGCGGTTCTGGTGGAGGCGGTTCGGATGGCGGAGG TTCA |
| 67 | anti-ROR1 scFv 2-7 VH (DNA) | GAAGTGCAACTTCTCGAGAGCGGTGGGGGACTCGTCCAGCC GGGGAGGTTCCCTGCGACTCAGCTGTGCAGCCTCAGGCTTTAC CTTTTCCAGTTACGCAATGAGTTGGGTCCGGCAGGCGCCTGG TAAAGGACTCGAGTGGGTGAGTGCAATCAGCGGAAGTGGCG GTCTACATACTATGCGGACTCTGTTAAAGGCAGGTTCACTA TTTCAAGGGACAATTCCAAGAACACGCTCTACCTGCAGATG AATAGCCTTAGAGCTGAAGACACGGCCGTGTACTATTGTGCC AAAGACAAGGGGATGGTTCAACTGGCAGTTCGACTACTGGGG GCAGGGAACTCTCGTCACCGTGAGCTCC |
| 68 | anti-ROR1 scFv 2-7 VL (DNA) | GAAATTGTTCTCACACAGTCACCCGGAACCCTTTCATTGTCC CCCGGCGAGCGCGCCACCCTCAGCTGTCGGGCCAGTCAGAG CGTGTCTAGCTCTTACCTGGCCTGGTACCAGCAGAAACCTGG GCAAGCTCCCAGACTCCTGATATATGGGGCCAGCAGCCGGG CCACTGGCATTCCGGACAGGTTTAGTGGATCAGGCTCTGGCA CTGATTTTACACTGACATTTCAAGGTTGAACCCGAAGACT TCGCAGTGTACTATTGTCAGCAGTATGGGTCTAGCCCGTGGA CTTTCGGGCAAGGCACCAAGGTGGAAATCAAG |
| 69 | anti-ROR1 2-9 VH_Linker4_ anti-ROR1 2-9 VL | GAAGTGCAGCTGCTGGAAAGCGGCGGTGGTCTGGTTCAGCC GGGTGGCAGCCTGCGTCTGAGCTGTGCGGCGAGCGGCTTTA CCTTTAGCAGCTATGCCATGAGCTGGGTGCGTCAGGCACCGG GTAAAGGCCTGGAATGGGTGAGCGCGATTAGCGGCAGCGGC GGCAGCACCTATTATGCGGATAGCGTGAAAGGCCGTTTTACC ATTAGCCGTGATAACAGCAAAAACACCCTGTATCTGCAGAT GAACAGCCTGCGTGCGGAAGATACCGCGGTGTATTATTGCG CGAAAAACAATATCACTTCGATTATTGGGGCCAGGGCACC CTGGTTACCGTTAGCAGCGGTGGAGGCGGTTCTGGTGGAGG CGGTTCGGTGGCGGAGGTTCAGAAATTGTGCTGACCCAGA GCCCGGGCACGCTGTCTCTGAGCCCGGGTGAACGTGCGACC CTGAGCTGTCGTGCGAGCCAGAGCGTGAGCAGCAGCTATCT GGCCTGGTATCAGCAGAAACCGGGCCAGGCACCGCGTCTGC TGATTTATGGCGCGAGCAGCCGTGCGACCGGCATTCCGGATC |

APPENDIX A-continued

SEQUENCE SUMMARY

| SEQ ID NO. | Name | Sequence |
|---|---|---|
| | | GTTTTAGCGGCAGCGGTAGCGGCACCGATTTTACCCTGACCA<br>TTAGCCGTCTGGAACCGGAAGATTTTGCGGTGTATTATTGCC<br>AGCAGTATGGCAGCAGCCCGTGGACCTTTGGCCAGGGCACC<br>AAAGTGGAAATTAAA |
| 70 | anti-ROR1 scFv 2-9 VH (DNA) | GAAGTGCAACTTCTCGAGAGCGGTGGGGGACTCGTCCAGCC<br>GGGGAGGTTCCCTGCGACTCAGCTGTGCAGCCTCAGGCTTTAC<br>CTTTTCCAGTTACGCAATGAGTTGGGTCCGGCAGGCGCCTGG<br>TAAAGGACTCGAGTGGGTGAGTGCAATCAGCGGAAGTGGCG<br>GTCTACATACTATGCGGACTCTGTTAAAGGCAGGTTCACTA<br>TTTCAAGGGACAATTCCAAGAACACGCTCTACCTGCAGATG<br>AATAGCCTTAGAGCTGAAGACACGGCCGTGTACTATTGTGCC<br>AAAAAGCAGTACCATTTCGACTACTGGGGCAGGGAACTCT<br>CGTCACCGTGAGCTCC |
| 71 | anti-ROR1 scFv 2-9 VL (DNA) | GAAATTGTTCTCACACAGTCACCCGGAACCCTTTCATTGTCC<br>CCCGGCGAGCGCGCCACCCTCAGCTGTCGGGCCAGTCAGAG<br>CGTGTCTAGCTCTTACCTGGCCTGGTACCAGCAGAAACCTGG<br>GCAAGCTCCCAGACTCCTGATATATGGGGCCAGCAGCCGGG<br>CCACTGGCATTCCGGACAGGTTTAGTGGATCAGGCTCTGGCA<br>CTGATTTTACACTGACGATTTCAAGGTTGGAACCCGAAGACT<br>TCGCAGTGTACTATTGTCAGCAGTATGGGTCTAGCCCGTGGA<br>CTTTCGGGCAAGGCACCAAGGTGGAAATCAAG |
| 72 | anti-ROR1 scFv 3-6 (DNA) | CAGTCTGCCCTGACTCAGCCTGCCTCCGTGTCTGGGTCTCCT<br>GGACAGTCGATCACCATCTCCTGCACTGGAACCAGCAGTGA<br>CGTTGGTGGTTATAACTATGTCTCCTGGTACCAACAGCACCC<br>AGGCAAAGCCCCCAAAGTCATGATTTATGATGTCAGTAATC<br>GGCCCTCAGGGGTTTCTGATCGCTTCTCTGGCTCCAAGTCTG<br>GCAACACGGCCTCCCTGACCATCTCTGGGCTCCAGGTTGAGG<br>ACGAGGCTGATTATTACTGCAGCTCATATTCAACCAGCATCA<br>CCCCAGTTTTCGGCGGGGGGACCAAGCTCACCGTCCTAGGA<br>GAGGGTAAATCTTCCGGATCTGGTTCCGAAAGCAAGGCTAG<br>CCAGGTCCAGCTGGTGCAGTCTGGAGCAGAGGTGAAAAAGC<br>CCGGGGAGTCTCTGAAGATCTCCTGTAGGCTTCTGGATACA<br>GCTTTACCAGCTACTGGATCGGCTGGGTGCGCCAGATGCCCG<br>GGAAAGGCCTGGAGTGGATGGGGATCATCTATCCTGGTGAC<br>TCTGATACCAGATACAGCCCGTCCTTCCAAGGCCAGGTCACC<br>ATCTCAGCCGACAAGTCCATCAGCACCGCCTACCTGCAGTGG<br>AGCAGCCTGAAGGCCTCGGACACCGCCATGTATTACTGTGC<br>GAGACTGGAACTCGGTTACTACTACTACGGTATGGACGTCTG<br>GGGCCAAGGAACCACGGTCACCGTCTCCTCA |
| 73 | Linker 5 (DNA) | GGAGAGGGTAAATCTTCCGGATCTGGTTCCGAAAGCAAGGC<br>TAGC |
| 74 | anti-ROR1 scFv 3-6 VL (DNA) | CAGTCAGCTCTGACCCAACCTGCCTCCGTCTCTGGGAGTCCA<br>GGCCAGAGTATCACAATTTCTTGTACAGGCACCTCATCTGAT<br>GTCGGCGGTTACAATTACGTTAGTTGGTATCAGCAACATCCA<br>GGTAAGGCTCCAAAGGTGATGATCTATGACGTCTCAAATAG<br>ACCCTCTGGCGTCAGCGACAGGTTTAGTGGTAGCAAATCCG<br>GGAACACAGCTTCACTTACAATTAGCGGCCTCCAAGTAGAA<br>GACGAAGCTGACTATTACTGCTCTAGTTATTCAACGTCAATT<br>ACCCCTGTGTTTGGTGGCGGTACAAAACTCACAGTGCTT |
| 75 | anti-ROR1 scFv 3-6 VH (DNA) | CAAGTGCAACTTGTGCAATCAGGAGCTGAAGTCAAAAAGCC<br>GGGAGAATCCCTGAAAATAAGCTGCGAAGCAAGTGGTTACT<br>CTTTTACTTCTTACTGGATTGGATGGGTTCGGCAGATGCCCG<br>GAAAGGGACTCGAGTGGATGGGAATTATTTACCCTGGAGAC<br>AGCGACACAAGATACAGCCCTTCATTCCAGGGGCAGGTGAC<br>CATTTCTGCTGACAAATCAATCAGTACAGCCTATCTGCAATG<br>GAGTTCCCTCAAAGCCAGTGACACTGCTATGTATTACTGCGC<br>GCGACTGGAACTGGATACTACTACTACGGAATGGACGTAT<br>GGGGACAGGGAACCACCGTTACTGTTAGTAGC |
| 76 | pLRPO_anti ROR1 2-7 CD3epsilon_ T2A-eGFP | CCAATTAACCAATTCTGAttagaaaaactcatcgagcatcaaatgaaactgcaattta<br>ttcacatcaggattatcaataccatattttgaaaaagccgtttctgtaatgaaggagaaaactcaccga<br>ggcagttccataggatggcaagatcctggtatcggtctgcgattccgactcgtccaacatcaatacaa<br>cctattaatttcccctcgtcaaaaataaggttatcaagtgagaaatcaccatgagtgacgactgaatcc<br>ggtgagaatggcaaaagtttatgcatttctttccagacttgttcaacaggccagccattacgctcgtcat<br>caaaatcactcgcatcaaccaaaccgttattcattcgtgattgcgcctgagcaagacgaaatacgcga<br>tcgctgttaaaaggacaattacaaacaggaatcgaatgcaaccggcgcaggaacactgccagcgca<br>tcaacaatattttcacctgaatcaggatattcttctaatacctggaatgctgttttttccggggatcgcagtg<br>gtgagtaaccatgcatcatcaggagtacggataaaatgatgatggtcggaagaggcataaattccgt

APPENDIX A-continued

SEQUENCE SUMMARY

| SEQ ID NO. | Name | Sequence |
|---|---|---|
| | | cagccagtttagtctgaccatctcatctgtaacatcattggcaacgctacctttgccatgtttcagaaaca |
| | | actctggcgcatcgggcttcccatacaagcgatagattgtcgcacctgattgcccgacattatcgcga |
| | | gcccatttatacccatataaatcagcatccatgttggaatttaatcgcggcctcgacgtttcccgttgaat |
| | | atggctcatAACACCCCTTGTATTACTGTTTATGTAAGCAGACAGT |
| | | TTTATTGTTCATGATGATATATTTTTATCTTGTGCAATGTAAC |
| | | ATCAGAGATTTTGAGACACAACGTGGCTTTCCCCCCCCCCCC |
| | | CATGACATTAACCTATAAAAATAGGCGTATCACGAGGCCAG |
| | | CTTGGGAAACCATAAGACCGAGATAGAGTTGAGTGTTGTTC |
| | | CAGTTTGGAACAAGAGTCCACTATTAAAGAACGTGGACTCC |
| | | AACGTCAAAGGGCGAAAAACCGTCTATCAGGGCGATGGCCC |
| | | ACTACGTGAACCATCACCCAAATCAAGTTTTTTGGGGTCGAG |
| | | GTGCCGTAAAGCACTAAATCGGAACCCTAAAGGGAGCCCCC |
| | | GATTTAGAGCTTGACGGGGAAAGCCGGCGAACGTGGCGAGA |
| | | AAGGAAGGGAAGAAAGCGAAAGGAGCGGGCGCTAAGGCGC |
| | | TGGCAAGTGTAGCGGTCACGCTGCGCGTAACCACCACACCC |
| | | GCCGCGCTTAATGCGCCGCTACAGGGCGCGTACTATGGTTGC |
| | | TTTGACGTATGCGGTGTGAAATACCGCACAGATGCGTAAGG |
| | | AGAAAATACCGCATCAGGCGccattcgccattcaggctgcgcaactgttgggaag |
| | | ggcgatcggtgcgggcctcttcgctattacgccaGCTGGCGAAAGGGGGATGTG |
| | | CTGCAAGGCGATTAAGTTGGGTAACGCCAGGGTTTTCCCAGT |
| | | CACGACGTTGTAAAACGACGGCCAGTGAATTGATCGAGATC |
| | | GTGATCCGGATCAAGATCCAGATCGAATTGGAGGCTACAGT |
| | | CAGTGGAGAGGACTTTCACTGACTGACTGACTGCGTCTCAAC |
| | | CTcctaggggacattgattattgactagttattaatagtaatcaattacggggtcattagttcatagccc |
| | | atatatggagttccgcgttacataacttacggtaaatggcccgcctggctgaccgcccaacgaccccc |
| | | gcccattgacgtcaataatgacgtatgttcccatagtaacgccaatagggactttccattgacgtcaatg |
| | | ggtggagtatttacggtaaactgcccacttggcagtacatcaagtgtatcatatgccaagtacgcccc |
| | | tattgacgtcaatgacggtaaatggcccgcctggcattatgcccagtacatgaccttatgggactttcct |
| | | acttggcagtacatctacgtattagtcatcgctattaccatggtgatgcggttttggcagtacatcaatgg |
| | | gcgtggatagcggtttgactcacggggatttccaagtctccaccccattgacgtcaatgggagtttgttt |
| | | tggcaccaaaatcaacgggactttccaaaatgtcgtaacaactccgccccattgacgcaaatgggcg |
| | | gtaggcgtgtacggtgggaggtctatataagcagagagctcgtttagtgaaccgtgtctctctggttaga |
| | | ccagatctgagcctgggagctctctggctaactagggaacccactgcttaagcctcaataaagcttgc |
| | | cttgagtgctcaaagtagtgtgtgcccgtctgttgtgtgactctggtaactagagatccctcagaccctt |
| | | tagtcagtgtggaaaatctctagcagtggcgcccgaacagggacttgaaagcgaaagtaaagccag |
| | | aggagatctctcgacgcaggactcggcttgctgaagcgcgcacgcacaaccatcccttcagacaggatca |
| | | gaagaacttagatcattatataatacaatagcagtcctctattgtgtgcatcaaaggatagatgtaaaag |
| | | acaccaaggaagccttagataagatagaggaagagcaaaacaaaagtaagaaaaaggcacagca |
| | | agcgatcttcagacctggaggaggcaggaggcgatatgagggacaattggagaagtgaattatata |
| | | aatataaagtagtaaaaattgaaccattaggagtagcacccaccaaggcaaagagaagagtggtgc |
| | | agagagaaaaaagagcagtgggaataggagctttgttccttgggttcttgggagcagcaggaagca |
| | | ctatgggcgcagcgtcaatgacgctgacggtacaggccagacaattattgtctgatatagtgcagca |
| | | gcagaacaatttgctgagggctattgaggcgcaacagcatctgttgcaactcacagtctggggcatc |
| | | aaacagctccaggcaagaatcctggctgtggaaagatacctaaaggatcaacagctcctggggattt |
| | | ggggttgctctggaaaaactcatttgcaccactgctgtgccttggaatgctagttggagtaataaatctct |
| | | ggaacagatttggaataacatgacctggatggagtgggacagagaaattaacaattacacaagctta |
| | | atacactccttaattgaagaatcgcaaaaccagcaagaaaagaatgaacaagaattattggaattaga |
| | | taaatgggcaagtttgtggaattggtttaacataacaaattggctgtggtatataaaattattcataatgat |
| | | agtaggaggcttggtaggtttaagaatagttttttgctgtacttttctatagtgaatagagttaggcagggat |
| | | attcaccattatcgtttcagacccacctcccaatcccgaggggaccacgcgtacaaatggcagtattc |
| | | atccacaattttaaaagaaaaggggggattggggggtacagtgcaggggaaagaatagtagacata |
| | | atagcaacagacatacaaactaaagaattacaaaaacaaattacaaaaattcaaaattttcgggttatt |
| | | acagggacagcagaaatccactttggaaagctggcatccggctccggtgcccgtcagtgggcag |
| | | agcgcacatcgcccacatccccgagaagttgggggggaggggtcggcaattgaaccggtgcctag |
| | | agaaggtggcgcggggtaaactgggaaagtgatgtcgtgtactggctccgccttttccgagggtg |
| | | ggggagaaccgtatataagtgcagtagtcgccgtgaacgttcttttttcgcaacgggtttgccgccaga |
| | | acacaggtaagtgccgtgtgtggttcccgcgggcctggcctctttacgggttatggccgttctcgtgcc |
| | | ttgaattacttccacgcccctggctgcagtacgtgattatgatcccgagatcgggttggaagtgggt |
| | | gggagagttcgaggccttgcgcttaaggagcccatcgcctcgtgatgagttgaggcctggcctgg |
| | | gcgctggggccgccgcgtgcgaatctggtggcaccttcgcgcctgtctcgctgctttcgataagtctc |
| | | tagccatttaaaattttttgatgacctgctgcgacgctttttttctggcaagatagtcttgtaaatgcgggcc |
| | | aagatctgcacactggtatttcggtttttggggccgcgggcggcgacggggcccgtgcgtcccagc |
| | | gcacatgttcggcgaggcgggggcctgcgagcgcggccaccgagaatcggacgggggtagtctca |
| | | agctggccggcctgctctggtgcctggcctcgcgccgccgtgtatcgccccgccctgggcggcaa |
| | | ggctgcccggtcggcaccagttgcgtgagcggaaagatggccgcttccgggccgctgggtcaggg |
| | | agctcaaaatggaggacgcggcgctcgggagagcgggcgggtgagtcacccacacaaaggaaa |
| | | agggcctttccgtcctcagccgtcgcttcatgtgactccacggagtaccgggcgccgtccaggcacc |
| | | tcgattagttctcgagcttttggagtacgtcgtctttaggttggggggagggggttttatgcgatggagttt |
| | | ccccacactgagtgggtggagactgaagttaggccagcttggcacttgatgtaattctccttggaattt |
| | | gccattttgagtttggatcttggttcattctcaagcctcagacagtggttcaaagttttttttcttccatttca |

APPENDIX A-continued

SEQUENCE SUMMARY

| SEQ ID NO. | Name | Sequence |
|---|---|---|
| | | ggtgtcgtgaaaactacccctctagagccgccaccATGCTCCTCCTCGTGACTAG<br>CCTTCTCCTGTGCGAGCTCCCACACCCTGCATTCCTCCTGATC<br>CCAGAAGTGCAACTTCTCGAGAGCGGTGGGGGACTCGTCCA<br>GCCGGGAGGTTCCCTGCGACTCAGCTGTGCAGCCTCAGGCTT<br>TACCTTTTCCAGTTACGCAATGAGTTGGGTCCGGCAGGCGCC<br>TGGTAAAGGACTCGAGTGGGTGAGTGCAATCAGCGGAAGTG<br>GCGGGTCTACATACTATGCGGACTCTGTTAAAGGCAGGTTCA<br>CTATTTCAAGGGACAATTCCAAGAACACGCTCTACCTGCAGA<br>TGAATAGCCTTAGAGCTGAAGACACGGCCGTGTACTATTGTG<br>CCAAAGACAAGGGATGGTTCAACTGGCAGTTCGACTACTGG<br>GGGCAGGGAACTCTCGTCACCGTGAGCTCCGGCGGAGGTGG<br>AAGCGGGGGAGGGGGCTCCGGTGGTGGGGGATCAGAAATTG<br>TTCTCACACAGTCACCCGGAACCCTTTCATTGTCCCCCGGCG<br>AGCGCGCCACCCTCAGCTGTCGGGCCAGTCAGAGCGTGTCT<br>AGCTCTTACCTGGCCTGGTACCAGCAGAAACCTGGGCAAGC<br>TCCCAGACTCCTGATATATGGGGCCAGCAGCCGGGCCACTG<br>GCATTCCGGACAGGTTTAGTGGATCAGGCTCTGGCACTGATT<br>TTACACTGACGATTTCAAGGTTGGAACCCGAAGACTTCGCAG<br>TGTACTATTGTCAGCAGTATGGGTCTAGCCCGTGGACTTTCG<br>GGCAAGGCACCAAGGTGGAAATCAAGGCAGCTGCTGGAGGT<br>GGGGGAAGTGGCGGTGGTGGCTCAGGCGGCGGGGGGAGCCT<br>CGAGGACGGTAATGAAGAGATGGGGGGCATTACACAAACCC<br>CGTACAAGGTCTCTATCAGTGGGACGACTGTGATTCTGACAT<br>GCCCACAGTATCCAGGTTCAGAAATCCTGTGGCAGCATAAT<br>GACAAGAACATCGGTGGGGATGAGGATGATAAGAATATCGG<br>AAGCGACGAAGACCACCTGTCTCTCAAAGAGTTTAGCGAGC<br>TGGAGCAGAGTGGGTATTATGTCTGCTATCCTAGAGGTAGCA<br>AGCCAGAGGACGCAAACTTTTACCTTTACCTCAGAGCCAGG<br>GTCTGCGAGAACTGCATGGAAATGGACGTGATGAGTGTTGC<br>AACTATAGTGATAGTTGACATTTGCATCACCGGGGGTCTGCT<br>CCTGCTGGTTTACTATTGGAGCAAGAACCGCAAGGCTAAAG<br>CCAAGCCAGTAACACGGGGCGCAGGCGCGGGAGGCAGGCA<br>GCGAGGGCAGAATAAGGAGCGCCCCCCACCCGTCCCGAATC<br>CGGATTACGAACCCATTCGGAAAGGCCAGAGGGACTTGTAC<br>TCAGGGCTCAACCAAAGACGGATCGAGGGGCGAGGATCCTT<br>GCTGACATGTGGTGACGTGGAGGAGAATCCTGGTCCTTCTCG<br>CgccgccaccATGGTGTCTAAAGGCGAAGAGCTGTTCACCGGTG<br>TGGTGCCGATTCTTGTAGAGCTGGATGGAGATGTTAATGGTC<br>ACAAGTTTTCAGTGTCTGGGGAGGGCGAAGGCGACGCGACC<br>TATGGTAAACTCACGCTTAAGTTTATCTGCACCACAGGGAAG<br>CTCCCTGTTCCATGGCCAACCCTTGTGACAACACTTACTTAC<br>GGCGTGCAGTGTTTCAGCAGGTATCCTGACCATATGAAGCA<br>GCACGATTTCTTCAAGTCTGCAATGCCCGAGGGGTACGTACA<br>AGAGCGGACAATTTTCTTCAAGGACGACGGAAATTACAAAA<br>CTAGGGCAGAGGTTAAGTTCGAAGGGGATACACTTGTTAAT<br>AGGATCGAACTGAAAGGCATTGATTTCAAGGAGGATGGAAA<br>CATACTCGGGCACAAACTGGAATATAACTACAATTCACATA<br>ATGTGTATATCATGGCTGATAAGCAGAAAAACGGTATCAAA<br>GTGAACTTTAAGATCCGGCATAACATTGAAGACGGTAGCGT<br>GCAGCTCGCTGACCACTACCAGCAGAACACTCCAATCGGGG<br>ACGGGCCGGTCCTCCTGCCCGACAACCACTACCTCAGCACCC<br>AGAGCGCACTTAGCAAAGACCCAAACGAGAAGAGAGACCA<br>TATGGTGCTGCTGGAGTTCGTTACCGCAGCCGGAATCACCTT<br>GGGCATGGACGAGCTCTATAAATGAgaattcgaacggatatcgagcatctta<br>ccgccatttatacccatatttgttctgttttttcttgatttgggtatacatttaaatgttaataaaacaaaatggt<br>ggggcaatcatttcacttttttagggatatgtaattactagttcaggtgtattgccacaagacaaacatgtt<br>aagaaactttcccgttaatttacgctctgttcctgttaatcaacctctggattacaaaatttgtgaaagattga<br>ctgatattcttaactatgttgctccttttacgctgtgtggatatgctgctttatagcctctgtatctagctattg<br>cttccccgtacggctttcgttttctcctccttgtataaatcctggttgctgtctctttagaggagttgtggcc<br>cgttgtccgtcaacgtggcgtggtgtgctctgtgtttgctgacgcaaccccactggctggggcattg<br>ccaccacctgtcaactccttttctgggactttcgctttccccctcccgatcgccacggcagaactcatcg<br>ccgcctgccttgccgctgctggacaggggctaggttgctgggcactgataattccgtggtgttgtca<br>gtactggtacctttaagaccaatgacttacaaggcagctgtagatcttagccactttttaaaagaaaagg<br>ggggactggaagggctaattcactcccaaagaagacaagatctgcttttttgcctgtactgggtctctct<br>ggttagaccagatctgagcctgggagctctctggctaactagggaacccactgcttaagcctcaataa<br>agcttgccttgagtgcttcaatgatcataatcaagccatatcacatctgtagagggtttacttgctttaaaaa<br>acctccacacctcccctgaacctgaaacataaaatgaatgcaattgttgttgttaacttgtttattgcag<br>cttataatggttacaaataaagcaatagcatcacaaatttcacaaataaagcattttttcactgcattcta<br>gttgtggtttgtccaaaactcatcaatgtatcttatcatgtctggatctgcgtcgacACGAAGAGA<br>CGACTGACTGACTGACTGGAAAGAGGAAGGGCTGGAAGAG<br>GAAGGAGCTTGATCCAGATCCCGATCTCGATCCAGATCCGG<br>ATCGCAGCTTGGCGTAATCATGGTCATAGCTGTTTCCTGTGT<br>GAAATTGTTATCCGCTCACAATTCCACACAACATACGAGCCG<br>GAAGCATAAAGTGTAAAGCCTGGGGTGCCTAATGAGTGAGC |

APPENDIX A-continued

SEQUENCE SUMMARY

| SEQ ID NO. | Name | Sequence |
|---|---|---|
| | | TAACTCACATTAATTGCGTTGCGCTCACTGCCCGCTTTCCAG<br>TCGGGAAACCTGTCGTGCCAGCTGCATTAATGAATCGGCCA<br>ACGCGCGGGGAGAGGCGGTTTGCGTATTGGGCGCTCTTCCG<br>CTTCCTCGCTCACTGACTCGCTGCGCTCGGTCGTTCGGCTGC<br>GGCGAGCGGTATCAGCTCACTCAAAGGCGGTAATACGGTTA<br>TCCACAGAATCAGGGGATAACGCAGGAAAGAACATGTGAGC<br>AAAAGGCCAGCAAAAGGCCAGGAACCGTAAAAAGGCCGCG<br>TTGCTGGCGTTTTTCCATAGGCTCCGCCCCCCTGACGAGCAT<br>CACAAAAATCGACGCTCAAGTCAGAGGTGGCGAAACCCGAC<br>AGGACTATAAAGATACCAGGCGTTTCCCCCTGGAAGCTCCCT<br>CGTGCGCTCTCCTGTTCCGACCCTGCCGCTTACCGGATACCT<br>GTCCGCCTTTCTCCCTTCGGGAAGCGTGGCGCTTTCTCATAG<br>CTCACGCTGTAGGTATCTCAGTTCGGTGTAGGTCGTTCGCTC<br>CAAGCTGGGCTGTGTGCACGAACCCCCCGTTCAGCCCGACC<br>GCTGCGCCTTATCCGGTAACTATCGTCTTGAGTCCAACCCGG<br>TAAGACACGACTTATCGCCACTGGCAGCAGCCACTGGTAAC<br>AGGATTAGCAGAGCGAGGTATGTAGGCGGTGCTACAGAGTT<br>CTTGAAGTGGTGGCCTAACTACGGCTACACTAGAAGAACAG<br>TATTTGGTATCTGCGCTCTGCTGAAGCCAGTTACCTTCGGAA<br>AAAGAGTTGGTAGCTCTTGATCCGGCAAACAAACCACCGCT<br>GGTAGCGGTGGTTTTTTTGTTTGCAAGCAGCAGATTACGCGC<br>AGAAAAAAAGGATCTCAAGAAGATCCTTTGATCTTTTCTACG<br>GGGTCTGACGCTCAGTGGAACGAAAACTCACGTTAAGGGAT<br>TTTGGTCATGAGATTATCAAAAAGGATCTTCACCTAGATCCT<br>TTTAAATTAAAAATGAAGTTTTAAATCAATCTAAAGTATATA<br>TGAGTAAACTTGGTCTGACAGTTACCAATGCTTAATCAGTGA<br>GGCACCTATCTCAGCGATCTGTCTATTTCGTTCATCCATAGTT<br>GCCTGACTCCCCGTCGTGTAGATAACTACGATACGGGAGGG<br>CTTACCATCTGGCCCCAGTGCTGCAATGATACCGCAGCTTGG<br>GAAACCATAAGAGCTGAAGCCAGTTACCTTCGGAAAAAGAG<br>TTGGTAGCTCTTGATCCGGCAAACAAACCACCGCTGGTAGCG<br>GTGGTTTTTTTGTTTGCAAGCAGCAGATTACGCGCAGAAAAA<br>AAGGATCTCAAGAAGATCCTTTGATCTTTTCTACGGGGTCTG<br>ACGCTCAGTGGAACGAAAACTCACGTTAAGGGATTTTGGTC<br>ATGAGCTTGCGCCGTCCCGTCAAGTCAGCGTAATGCTCTGCC<br>AGTGTTACAA |
| 77 | eGFP | ATGGTGTCTAAAGGCGAAGAGCTGTTCACCGGTGTGGTGCC<br>GATTCTTGTAGAGCTGGATGGAGATGTTAATGGTCACAAGTT<br>TTCAGTGTCTGGGGAGGGCGAAGGCGACGCGACCTATGGTA<br>AACTCACGCTTAAGTTTATCTGCACCACAGGGAAGCTCCCTG<br>TTCCATGGCCAACCCTTGTGACAACACTTACTTACGGCGTGC<br>AGTGTTTCAGCAGGTATCCTGACCATATGAAGCAGCACGATT<br>TCTTCAAGTCTGCAATGCCCGAGGGGTACGTACAAGAGCGG<br>ACAATTTTCTTCAAGGACGACGGAAATTACAAAACTAGGGC<br>AGAGGTTAAGTTCGAAGGGGATACACTTGTTAATAGGATCG<br>AACTGAAAGGCATTGATTTCAAGGAGGATGGAAACATACTC<br>GGGCACAAACTGGAATATAACTACAATTCACATAATGTGTA<br>TATCATGGCTGATAAGCAGAAAAACGGTATCAAAGTGAACT<br>TTAAGATCCGGCATAACATTGAAGACGGTAGCGTGCAGCTC<br>GCTGACCACTACCAGCAGAACACTCCAATCGGGGACGGGCC<br>GGTCCTCCTGCCCGACAACCACTACCTCAGCACCCAGAGCGC<br>ACTTAGCAAAGACCCAAACGAGAAGAGAGACCATATGGTGC<br>TGCTGGAGTTCGTTACCGCAGCCGGAATCACCTTGGGCATGG<br>ACGAGCTCTATAAATGA |
| 78 | pLRPO anti-ROR1 2-9 CD3epsilon T2A_eGFP | CCAATTAACCAATTCTGAttagaaaaactcatcgagcatcaaatgaaactgcaatttta<br>ttcacatcaggattatcaataccatatttttgaaaaagccgtttctgtaatgaaggagaaaactcaccga<br>ggcagttccataggatggcaagatcctggtatcggtctgcgattccgactcgtcaacatcaatacaa<br>cctattaatttcccctcgtcaaaaataaggttatcaagtgagaaatcaccatgagtgacgactgaatcc<br>ggtgagaatggcaaaagtttatgcatttctttccagacttgttcaacaggccagccattacgctcgtcat<br>caaaatcactcgcatcaaccaaaccgttattcattcgtgattgcgcctgagcaagacgaaatacgcga<br>tcgctgttaaaaggacaattacaaacaggaatcgaatgcaaccggcgcaggaacactgccagcgca<br>tcaacaatattttcacctgaatcaggatattcttctaatacctggaatgctgttttccggggatcgcagtg<br>gtgagtaaccatgcatcatcaggagtacggataaaatgatgatggtcggaagaggcataaattccgt<br>cagccagtttagtctgaccatctcatctgtaacatcattggcaacgtacctttgccatgtttcagaaaca<br>actctggcgcatcgggcttcccatacaagcgatagattgtcgcacctgattgcccgacattatcgcga<br>gcccatttatacccatataaatcagcatccatgttggaatttaatcgcggcctcgacgtttcccgttgaat<br>atggctcatAACACCCCTTGTATTACTGTTTATGTAAGCAGACAGT<br>TTATTGTTCATGATGATATATTTTTATCTTGTGCAATGTAAC<br>ATCAGAGATTTTGAGACACAACGTGGCTTTCCCCCCCCCCC<br>CATGACATTAACCTATAAAAATAGGCGTATCACGAGGCCAG<br>CTTGGGAAACCATAAGACCGAGATAGAGTTGAGTGTTGTTC<br>CAGTTTGGAACAAGAGTCCACTATTAAAGAACGTGGACTCC |

APPENDIX A-continued

SEQUENCE SUMMARY

| SEQ ID NO. | Name | Sequence |
|---|---|---|
| | | AACGTCAAAGGGCGAAAAACCGTCTATCAGGGCGATGGCCC<br>ACTACGTGAACCATCACCCAAATCAAGTTTTTTGGGGTCGAG<br>GTGCCGTAAAGCACTAAATCGGAACCCTAAAGGGAGCCCCC<br>GATTTAGAGCTTGACGGGGAAAGCCGGCGAACGTGGCGAGA<br>AAGGAAGGGAAGAAAGCGAAAGGAGCGGGCGCTAAGGCGC<br>TGGCAAGTGTAGCGGTCACGCTGCGCGTAACCACCACACCC<br>GCCGCGCTTAATGCGCCGCTACAGGGCGCGTACTATGGTTGC<br>TTTGACGTATGCGGTGTGAAATACCGCACAGATGCGTAAGG<br>AGAAAATACCGCATCAGGCGccattcgccattcaggctgcgcaactgttgggaag<br>ggcgatcggtgcgggcctcttcgctattacgccaGCTGGCGAAAGGGGGATGTG<br>CTGCAAGGCGATTAAGTTGGGTAACGCCAGGGTTTTCCCAGT<br>CACGACGTTGTAAAACGACGGCCAGTGAATTGATCGAGATC<br>GTGATCCGGATCAAGATCCAGATCGAATTGGAGGCTACAGT<br>CAGTGGAGAGGACTTTCACTGACTGACTGCGTCTCAAC<br>CTcctaggggacattgattattgactagttattaatagtaatcaattacggggtcattagttcatagccc<br>atatatggagttccgcgttacataacttacggtaaatggcccgcctggctgaccgcccaacgacccccc<br>gcccattgacgtcaataatgacgtatgttcccatagtaacgccaatagggactttccattgacgtcaatg<br>ggtggagtatttacggtaaactgcccacttggcagtacatcaagtgtatcatatgccaagtacgcccccc<br>tattgacgtcaatgacggtaaatggcccgcctggcattatgcccagtacatgaccttatgggactttcct<br>acttggcagtacatctacgtattagtcatcgctattaccatggtgatgcggttttggcagtacatcaatgg<br>gcgtggatagcggtttgactcacggggatttccaagtctccacccccattgacgtcaatgggagtttgttt<br>tggcaccaaaatcaacgggactttccaaaatgtcgtaacaactccgccccattgacgcaaatgggcg<br>gtaggcgtgtacggtggggaggtctatataagcagagctcgtttagtgaaccgggtctctctggttaga<br>ccagatctgagcctgggagctctctggctaactagggaacccactgcttaagcctcaataaagcttgc<br>cttgagtgctcaaagtagtgtgtgcccgtctgttgtgtgactctggtaactagagatccctcagacccttt<br>tagtcagtgtggaaaatctctagcagtggcgcccgaacagggacttgaaagcgaaagtaaagccag<br>aggagatctctcgacgcaggactcggcttgctgaagcgcgcacggcaagaggcgaggggcggc<br>gactggtgagtacgccaaaaattttgactagcggaggctagaaggagagagtagggtgcgagagc<br>gtcggtattaagcgggggagaattagatAaatgggaaaaaattcggttaaggccagggggaaagaa<br>acaatataaactaaaacatatagttagggcaagcagggagctagaacgattcgcagttaatcctggcc<br>ttttagagacatcagaaggctgtagacaaatactgggacagctacaaccatcccttcagacaggatca<br>gaagaacttagatcattatataatcaatagcagtcctctattgtgtgcatcaaaggatagatgtaaaag<br>acaccaaggaagccttagataagatagaggaagagcaaaacaaaagtaagaaaaaggcacagca<br>agcgatcttcagacctggaggaggcaggaggcgatatgagggacaattggagaagtgaattatata<br>aatataaagtagtaaaaattgaaccattaggagtagcacccaccaaggcaaagagaagagtggtgc<br>agagagaaaaaagagcagtgggaataggagctttgttccttgggttcttgggagcagcaggaagca<br>ctatgggcgcagcgtcaatgacgctgacggtacaggccagacaattattgtctgatatagtgcagca<br>gcagaacaatttgctgagggctattgaggcgcaacagcatctgttgcaactcacagtctggggcatc<br>aaacagctccaggcaagaatcctggctgtggaaagatacctaaaggatcaacagctcctggggattt<br>ggggttgctctggaaaactcatttgcaccactgctgtgccttggaatgctagttggagtaataaatctct<br>ggaacagatttggaataacatgacctggatggagtgggacagagaaattaacaattacacaagctta<br>atacactccttaattgaagaatcgcaaaaccagcaagaaaagaatgaacaagaattattggaattaga<br>taaatgggcaagtttgtggaattggtttaacataacaaattggctgtggtatataaaattattcataatgat<br>agtaggaggcttggtaggtttaagaatagttttttgctgtactttctatagtgaatagagttaggcagggat<br>attcaccattatcgtttcagacccacctcccaatcccgaggggaccacgcgtacaaatggcagtattc<br>atccacaatttttaaaagaaaaggggggattgggggggtacagtgcaggggaaagaatagtagacata<br>atagcaacagacatacaaactaaagaattacaaaaacaaattacaaaaattcaaaattttcgggtttatt<br>acaggggacagcagaaatccactttggaaagctgagcatccggctccggtgcccgtcagtgggcag<br>agcgcacatcgcccacagtccccgagaagttgggggggagggtcggcaattgaaccggtgcctag<br>agaaggtggcgcggggtaaactgggaaagtgatgtcgtgtactggctccgcctttttcccgagggtg<br>ggggagaaccgtatataagtgcagtagtcgccgtgaacgttcttttttcgcaacgggtttgccgccaga<br>acacaggtaagtgccgtgtgtggttcccgcgggcctggcctcttttacgggttatggcccttgcgtgcc<br>ttgaattacttccacgcccctggctgcagtacgtgattcttgatcccgagcttcgggttggaagtgggt<br>gggagagttcgaggccttgcgcttaaggagcccctttcgcctcgtgcttgagttgaggcctggcctgg<br>gcgctggggccgccgcgtgcgaatctggtggcaccttcgcgcctgtctcgctgcttttcgataagtctc<br>tagccattttaaaattttttgatgacctgctgcgacgctttttttctggcaagatagtcttgtaaatgcgggcc<br>aagatctgcacactggtatttcggtttttgggcccgcgggcggcgacggggcccgtgcgtcccagc<br>gcacatgttcggcgaggcgggccctgcgagcgcggccaccgagaatcggacggggtagtctca<br>agctggccggcctgctctggtgcctggcctcgcgccgccgtgtatcgccccgccctgggcggcaa<br>ggctggcccggtcggcaccagttgcgtgagcggaaagatggccgcttcccggccctgctgcaggg<br>agctcaaaatggaggacgcggcgctcgggacggcgggcgggtgagtcacccacacaaaggaaa<br>agggccttccgtcctcagccgtcgcttcatgtgactccacggagtaccgggcgccgtccaggcacc<br>tcgattagttctcgagcttttggagtacgtcgtctttaggttgggggagagggtttttatgcgatggagttt<br>ccccacactgagtgggtggagactgaagttaggccagcttggcacttgatgtaattctccttggaattt<br>gccattttgagtttggatcttggttcattctcaagcctcagacagtggttcaaagttttttttcttccatttca<br>ggtgtcgtgaaaactaccccctctagagccgccaccATGCTCCTCCTCGTGACTAG<br>CCTTCTCCTGTGCGAGCTCCCACACCCTGCATTCCTCCTGATC<br>CCAGAAGTGCAACTTCTCGAGAGCGGTGGGGACTCGTCCA<br>GCCGGGAGGTTCCCTGCGACTCAGCTGTGCAGCCTCAGGCTT<br>TACCTTTTCCAGTTACGCAATGAGTTGGGTCCGGCAGGCGCC<br>TGGTAAAGGACTCGAGTGGGTGAGTGCAATCAGCGGAAGTG<br>GCGGGTCTACATACTATGCGGACTCTGTTAAAGGCAGGTTCA<br>CTATTTCAAGGGACAATTCAAGAACACGCTCTACCTGCAGA<br>TGAATAGCCTTAGAGCTGAAGCACGGCCGTGTACTATTGTG |

APPENDIX A-continued

SEQUENCE SUMMARY

| SEQ ID NO. | Name | Sequence |
|---|---|---|
| | | CCAAAAAGCAGTACCATTTCGACTACTGGGGGCAGGGAACT |
| | | CTCGTCACCGTGAGCTCCGGCGGAGGTGGAAGCGGGGGAGG |
| | | GGGCTCCGGTGGTGGGGGATCAGAAATTGTTCTCACACAGT |
| | | CACCCGGAACCCTTTCATTGTCCCCCGGCGAGCGCGCCACCC |
| | | TCAGCTGTCGGGCCAGTCAGAGCGTGTCTAGCTCTTACCTGG |
| | | CCTGGTACCAGCAGAAACCTGGGCAAGCTCCCAGACTCCTG |
| | | ATATATGGGGCCAGCAGCCGGGCCACTGGCATTCCGGACAG |
| | | GTTTAGTGGATCAGGCTCTGGCACTGATTTTACACTGACGAT |
| | | TTCAAGGTTGGAACCCGAAGACTTCGCAGTGTACTATTGTCA |
| | | GCAGTATGGGTCTAGCCCGTGGACTTTCGGGCAAGGCACCA |
| | | AGGTGGAAATCAAGGCAGCTGCTGGAGGTGGGGGAAGTGGC |
| | | GGTGGTGGCTCAGGCGGCGGGGGGAGCCTCGAGGACGGTAA |
| | | TGAAGAGATGGGGGCATTACACAAACCCCGTACAAGGTCT |
| | | CTATCAGTGGGACGACTGTGATTCTGACATGCCCACAGTATC |
| | | CAGGTTCAGAAATCCTGTGGCAGCATAATGACAAGAACATC |
| | | GGTGGGGATGAGGATGATAAGAATATCGGAAGCGACGAAG |
| | | ACCACCTGTCTCTCAAAGAGTTTAGCGAGCTGGAGCAGAGT |
| | | GGGTATTATGTCTGCTATCCTAGAGGTAGCAAGCCAGAGGA |
| | | CGCAAACTTTTACCTTTACCTCAGAGCCAGGGTCTGCGAGAA |
| | | CTGCATGGAAATGGACGTGATGAGTGTTGCAACTATAGTGA |
| | | TAGTTGACATTTGCATCACCGGGGGTCTGCTCCTGCTGGTTT |
| | | ACTATTGGAGCAAGAACCGCAAGGCTAAAGCCAAGCCAGTA |
| | | ACACGGGGCGCAGGCGCGGGAGGCAGGCAGCGAGGGCAGA |
| | | ATAAGGAGCGCCCCCCACCCGTCCCGAATCCGGATTACGAA |
| | | CCCATTCGGAAAGGCCAGAGGGACTTGTACTCAGGGCTCAA |
| | | CCAAAGACGGATCGAGGGGCGAGGATCCTTGCTGACATGTG |
| | | GTGACGTGGAGGAGAATCCTGGTCCTTCTCGCgccgccaccATGG |
| | | TGTCTAAAGGCGAAGAGCTGTTCACCGGTGTGGTGCCGATTC |
| | | TTGTAGAGCTGGATGGAGATGTTAATGGTCACAAGTTTTCAG |
| | | TGTCTGGGGAGGGCGAAGGCGACGCGACCTATGGTAAACTC |
| | | ACGCTTAAGTTTATCTGCACCACAGGGAAGCTCCCTGTTCCA |
| | | TGGCCAACCCTTGTGACAACACTTACTTACGGCGTGCAGTGT |
| | | TTCAGCAGGTATCCTGACCATATGAAGCAGCACGATTTCTTC |
| | | AAGTCTGCAATGCCCGAGGGGTACGTACAAGAGCGGACAAT |
| | | TTTCTTCAAGGACGACGGAAATTACAAAACTAGGGCAGAGG |
| | | TTAAGTTCGAAGGGGATACACTTGTTAATAGGATCGAACTG |
| | | AAAGGCATTGATTTCAAGGAGGATGGAAACATACTCGGGCA |
| | | CAAACTGGAATATAACTACAATTCACATAATGTGTATATCAT |
| | | GGCTGATAAGCAGAAAAACGGTATCAAAGTGAACTTTAAGA |
| | | TCCGGCATAACATTGAAGACGGTAGCGTGCAGCTCGCTGAC |
| | | CACTACCAGCAGAACACTCCAATCGGGGACGGGCCGGTCCT |
| | | CCTGCCCGACAACCACTACCTCAGCACCCAGAGCGCACTTA |
| | | GCAAAGACCCAAACGAGAAGAGAGACCATATGGTGCTGCTG |
| | | GAGTTCGTTACCGCAGCCGGAATCACCTTGGGCATGGACGA |
| | | GCTCTATAAATGAgaattcgaacggatatcgagcatcttaccgccatttatacccatatttg |
| | | ttctgttttttcttgatttgggtatacatttaaatgttaataaaacaaaatggtggggcaatcatttacatttttta |
| | | gggatatgtaattactagttcaggtgtattgccacaagacaaacatgttaagaaactttcccgttatttac |
| | | gctctgttcctgttaatcaacctctggattacaaaatttgtgaaagattgactgatattcttaactatgttgct |
| | | ccttttacgctgtgtggatatgctgctttatagcctctgtatctagctattgcttcccgtacggctttcgtttt |
| | | ctcctccttgtataaatcctggttgctgtctcttttagaggagttgtggcccgttgtccgtcaacgtggcgt |
| | | ggtgtgctctgtgtttgctgacgcaacccccactggctggggcattgccaccacctgtcaactcctttct |
| | | gggactttcgctttcccctcccgatcgccacggcagaactcatcgccgcctgccttgcccgctgctg |
| | | gacagggctaggttgctgggcactgataattccgtggtgttgtcagtactggtacctttaagaccaat |
| | | gacttacaaggcagctgtagatcttagccacttttttaaaagaaaaggggggactggaagggctaattc |
| | | actcccaaagaagacaagatctgcttttttgcctgtactgggtctctctggttagaccagatctgagcctg |
| | | ggagctctctggctaactagggaacccactgcttaagcctcaataaagcttgccttgagtgcttcaatg |
| | | atcataatcaagccatatcacatctgtagagggtttacttgctttaaaaaacctccacacctccccctgaa |
| | | cctgaaacataaaatgaatgcaattgttgttgttaacttgtttattgcagcttataatggttacaaataaag |
| | | caatagcatcacaaatttcacaaataaagcattttttcactgcattctagttgtggtttgtccaaactcatc |
| | | aatgtatcttatcatgtctggatctgcgtcgacACGAAGAGACGACTGACTGACT |
| | | GACTGGAAAGAGGAAGGGCTGGAAGAGGAAGGAGCTTGAT |
| | | CCAGATCCCGATCTCGATCCAGATCCGGATCGCAGCTTGGCG |
| | | TAATCATGGTCATAGCTGTTTCCTGTGTGAAATTGTTATCCG |
| | | CTCACAATTCCACACAACATACGAGCCGGAAGCATAAAGTG |
| | | TAAAGCCTGGGGTGCCTAATGAGTGAGCTAACTCACATTAAT |
| | | TGCGTTGCGCTCACTGCCCGCTTTCCAGTCGGGAAACCTGTC |
| | | GTGCCAGCTGCATTAATGAATCGGCCAACGCGCGGGGAGAG |
| | | GCGGTTTGCGTATTGGGCGCTCTTCCGCTTCCTCGCTCACTG |
| | | ACTCGCTGCGCTCGGTCGTTCGGCTGCGGCGAGCGGTATCAG |
| | | CTCACTCAAAGGCGGTAATACGGTTATCCACAGAATCAGGG |
| | | GATAACGCAGGAAAGAACATGTGAGCAAAAGGCCAGCAAA |
| | | AGGCCAGGAACCGTAAAAAGGCCGCGTTGCTGGCGTTTTTC |
| | | CATAGGCTCCGCCCCCCTGACGAGCATCACAAAAATCGACG |
| | | CTCAAGTCAGAGGTGGCGAAACCCGACAGGACTATAAAGAT |

APPENDIX A-continued

SEQUENCE SUMMARY

| SEQ ID NO. | Name | Sequence |
|---|---|---|
| | | ACCAGGCGTTTCCCCCTGGAAGCTCCCTCGTGCGCTCTCCTG<br>TTCCGACCCTGCCGCTTACCGGATACCTGTCCGCCTTTCTCCC<br>TTCGGGAAGCGTGGCGCTTTCTCATAGCTCACGCTGTAGGTA<br>TCTCAGTTCGGTGTAGGTCGTTCGCTCCAAGCTGGGCTGTGT<br>GCACGAACCCCCCGTTCAGCCCGACCGCTGCGCCTTATCCGG<br>TAACTATCGTCTTGAGTCCAACCCGGTAAGACACGACTTATC<br>GCCACTGGCAGCAGCCACTGGTAACAGGATTAGCAGAGCGA<br>GGTATGTAGGCGGTGCTACAGAGTTCTTGAAGTGGTGGCCTA<br>ACTACGGCTACACTAGAAGAACAGTATTTGGTATCTGCGCTC<br>TGCTGAAGCCAGTTACCTTCGGAAAAAGAGTTGGTAGCTCTT<br>GATCCGGCAAACAAACCACCGCTGGTAGCGGTGGTTTTTTTG<br>TTTGCAAGCAGCAGATTACGCGCAGAAAAAAAGGATCTCAA<br>GAAGATCCTTTGATCTTTTCTACGGGGTCTGACGCTCAGTGG<br>AACGAAAACTCACGTTAAGGGATTTTGGTCATGAGATTATCA<br>AAAAGGATCTTCACCTAGATCCTTTTAAATTAAAAATGAAGT<br>TTTAAATCAATCTAAAGTATATATGAGTAAACTTGGTCTGAC<br>AGTTACCAATGCTTAATCAGTGAGGCACCTATCTCAGCGATC<br>TGTCTATTTCGTTCATCCATAGTTGCCTGACTCCCCGTCGTGT<br>AGATAACTACGATACGGGAGGGCTTACCATCTGGCCCCAGT<br>GCTGCAATGATACCGCAGCTTGGGAAACCATAAGAGCTGAA<br>GCCAGTTACCTTCGGAAAAAGAGTTGGTAGCTCTTGATCCGG<br>CAAACAAACCACCGCTGGTAGCGGTGGTTTTTTTGTTTGCAA<br>GCAGCAGATTACGCGCAGAAAAAAAGGATCTCAAGAAGATC<br>CTTTGATCTTTTCTACGGGTCTGACGCTCAGTGGAACGAAA<br>ACTCACGTTAAGGGATTTTGGTCATGAGCTTGCGCCGTCCCG<br>TCAAGTCAGCGTAATGCTCTGCCAGTGTTACAA |
| 79 | pLRPO_anti-<br>ROR1 3-6<br>CD3e T2A<br>eGFP | CCAATTAACCAATTCTGAttagaaaaactcatcgagcatcaaatgaaactgcaattta<br>ttcacatcaggattatcaataccatatttttgaaaaagccgtttctgtaatgaaggagaaaactcaccga<br>ggcagttccataggatggcaagatcctggtatcggtctgcgattccgactcgtccaacatcaatacaa<br>cctattaatttcccctcgtcaaaaataaggttatcaagtgagaaatcaccatgagtgacgactgaatcc<br>ggtgagaatggcaaaagtttatgcatttctttccagacttgttcaacaggccagccattacgctcgtcat<br>caaaatcactcgcatcaaccaaaccgttattcattcgtgattgcgcctgagcaagacgaaatacgcga<br>tcgctgttaaaaggacaattacaaacaggaatcgaatgcaaccggcgcaggaacactgccagcgca<br>tcaacaatattttcacctgaatcaggatattcttctaatacctggaatgctgttttccggggatcgcagtg<br>gtgagtaaccatgcatcatcaggagtacggataaaatgatgatggtcggaagaggcataaattccgt<br>cagccagtttagtctgaccatctcatctgtaacatcattggcaacgctacctttgccatgtttcagaaaca<br>actctgcgcatcgggcttcccatacaagcgatagattgtcgcacctgattgcccgacattatcgcga<br>gcccatttatacccatataaatcagcatccatgttggaatttaatcgcggcctcgacgtttcccgttgaat<br>atggctcatAACACCCCTTGTATTACTGTTTATGTAAGCAGACAGT<br>TTTATTGTTCATGATGATATATTTTTATCTTGTGCAATGTAAC<br>ATCAGAGATTTTGAGACACAACGTGGCTTTCCCCCCCCCCCC<br>CATGACATTAACCTATAAAAATAGGCGTATCACGAGGCCAG<br>CTTGGGAAACCATAAGACCGAGATAGAGTTGAGTGTTGTTC<br>CAGTTTGGAACAAGAGTCCACTATTAAAGAACGTGGACTCC<br>AACGTCAAAGGGCGAAAAACCGTCTATCAGGGCGATGGCCC<br>ACTACGTGAACCATCACCCAAATCAAGTTTTTTGGGGTCGAG<br>GTGCCGTAAAGCACTAAATCGGAACCCTAAAGGGAGCCCCC<br>GATTTAGAGCTTGACGGGGAAAGCCGGCGAACGTGGCGAGA<br>AAGGAAGGGAAGAAAGCGAAAGGAGCGGGCGCTAAGGCGC<br>TGGCAAGTGTAGCGGTCACGCTGCGCGTAACCACCACACCC<br>GCCGCGCTTAATGCGCCGCTACAGGGCGCGTACTATGGTTGC<br>TTTGACGTATGCGGTGTGAAATACCGCACAGATGCGTAAGG<br>AGAAAATACCGCATCAGGCGccattcgccattcaggctgcgcaactgttgggaag<br>ggcgatcggtgcgggcctcttcgctattacgccaGCTGGCGAAAGGGGGATGTG<br>CTGCAAGGCGATTAAGTTGGGTAACGCCAGGGTTTTCCCAGT<br>CACGACGTTGTAAAACGACGGCCAGTGAATTGATCGAGATC<br>GTGATCCGGATCAAGATCCAGATCGAATTGGAGGCTACAGT<br>CAGTGGAGAGGACTTTCACTGACTGACTGACTGCGTCTCAAC<br>CTcctagggacattgattattgactagttattaatagtaatcaattacggggtcattagttcatagccc<br>atatatggagttccgcgttacataacttacggtaaatggcccgcctggctgaccgcccaacgacccc<br>gcccattgacgtcaataatgacgtatgttcccatagtaacgccaatagggactttccattgacgtcaatg<br>ggtggagtatttacggtaaactgcccacttggcagtacatcaagtgtatcatatgccaagtacgcccc<br>tattgacgtcaatgacggtaaatggcccgcctggcattatgcccagtacatgaccttatgggactttcct<br>acttggcagtacatctacgtattagtcatcgctattaccatggtgatgcggttttggcagtacatcaatgg<br>gcgtggatagcggtttgactcacggggatttccaagtctccaccccattgacgtcaatgggagtttgttt<br>tggcaccaaaatcaacgggactttccaaaatgtcgtaacaactccgccccattgacgcaaatgggcg<br>gtaggcgtgtacggtgggaggtctatataagcagagctcgtttagtgaaccgggtctctctggttaga<br>ccagatctgagcctgggagctctctggctaactagggaacccactgcttaagcctcaataaagcttgc<br>cttgagtgctcaaagtagtgtgtgcccgtctgttgtgtgactctggtaactagagatccctcagacccttt<br>tagtcagtgtggaaaatctctagcagtggcgcccgaacagggacttgaaagcgaaagtaaagccag<br>aggagatctctcgacgcaggactcggcttgctgaagcgcgcacggcaagaggcgaggggcggc<br>gactggtgagtacgccaaaaatttttgactagcggaggctagaaggagagagtagggtgcgagagc<br>gtcggtattaagcggggggagaattagataaatgggaaaaaattcggttaaggccagggggaaagaa |

APPENDIX A-continued

SEQUENCE SUMMARY

| SEQ ID NO. | Name | Sequence |
|---|---|---|
| | | acaatataaactaaaacatatagttagggcaagcagggagctagaacgattcgcagttaatcctggcc |
| | | ttttagagacatcagaaggctgtagacaaatactgggacagctacaaccatcccttcagacaggatca |
| | | gaagaacttagatcattatataatacaatagcagtcctctattgtgtgcatcaaaggatagatgtaaaag |
| | | acaccaaggaagccttagataagatagaggaagagcaaaacaaaagtaagaaaaaggcacagca |
| | | agcgatcttcagacctggaggaggcaggaggcgatatgagggacaattggagaagtgaattatata |
| | | aatataaagtagtaaaaattgaaccattaggagtagcacccaccaaggcaaagagaagagtggtgc |
| | | agagagaaaaaagagcagtgggaataggagctttgttccttgggttcttgggagcagcaggaagca |
| | | ctatgggcgcagcgtcaatgacgctgacggtacaggccagacaattattgtctgatatagtgcagca |
| | | gcagaacaatttgctgagggctattgaggcgcaacagcatctgttgcaactcacagtctgggcatc |
| | | aaacagctccaggcaagaatcctggctgtggaaagatacctaaaggatcaacagctcctggggattt |
| | | ggggttgctctggaaaactcatttgcaccactgctgtgccttggaatgctagttggagtaataaatctct |
| | | ggaacagatttggaataacatgacctggatggagtgggacagagaaattaacaattacacaagctta |
| | | atacactccttaattgaagaatcgcaaaaccagcaagaaaagaatgaacaagaattattggaattaga |
| | | taaatgggcaagtttgtggaattggtttaacataacaaattggctgtggtatataaaattattcataatgat |
| | | agtaggaggcttggtaggtttaagaatagttttttgctgtactttctatagtgaatagagttaggcagggat |
| | | attcaccattatcgtttcagacccacctcccaatcccgaggggaccacgcgtacaaatggcagtattc |
| | | atccacaattttaaaagaaaaggggggattggggggtacagtgcaggggaaagaatagtagacata |
| | | atagcaacagacatacaaactaaagaattacaaaaacaaattacaaaaattcaaaattttcgggtttatt |
| | | acagggacagcagaaatccactttggaaagctgagcatccggtcgccgtcagtgggcag |
| | | agcgcacatcgcccacagtccccgagaagttgggggggagggtcggcaattgaaccggtgcctag |
| | | agaaggtggcgcggggtaaactgggaaagtgatgtcgtgtactggctccgccttttcccgagggtg |
| | | ggggagaaccgtatataagtgcagtagtcgccgtgaacgttcttttttcgcaacgggtttgccgccaga |
| | | acacaggtaagtgccgtgtgtggttcccgcgggcctggcctctttacgggttatggccctgcgtgcc |
| | | ttgaattacttccacgcccctggctgcagtacgtgattatgatcccgagatcgggttggaagtgggt |
| | | gggagagttcgaggccttgcgcttaaggagcccatcgcctcgtgatgagttgaggcctggcctgg |
| | | gcgctggggccgccgcgtgcgaatctggtggcaccttcgcgcctgtctcgctgctttcgataagtctc |
| | | tagccatttaaaattttttgatgacctgctgcgacgcttttttttctggcaagatagtcttgtaaatgcgggcc |
| | | aagatctgcacactggtatttcggttttttggggccgcgggcggcgacggggcccgtgcgtcccagc |
| | | gcacatgttcggcgaggcggggcctgcgagcgcggccaccgagaatcggacgggggtagtctca |
| | | agctggccggcctgctctggtgcctggcctcgcgccgccgtgtatcgccccgccctgggcggcaa |
| | | ggctggcccggtcggcaccagttgcgtgagcggaaagatggccgcttcccggccctgctgcaggg |
| | | agctcaaaatggaggacgcggcgctcgggagagcgggcgggtgagtcacccacacaaaggaaa |
| | | aggggcctttccgtcctcagccgtcgcttcatgtgactccacggagtaccgggcgccgtccaggcacc |
| | | tcgattagttctcgagatttggagtacgtcgtctttaggttggggggagggggttttatgcgatggagttt |
| | | ccccacactgagtgggtggagactgaagttaggccagcttggcacttgatgtaattctccttggaattt |
| | | gccattttgagtttggatcttggttcattctcaagcctcagacagttggttcaaagttttttttcttccatttca |
| | | ggtgtcgtgaaaactaccccctctagagccgccaccATGCTTCTCCTTGTTACATC |
| | | ACTGTTGCTTTGTGAACTGCCCCACCCCGCGTTTCTTTTGATC |
| | | CCTCAGTCAGCTCTGACCCAACCTGCCTCCGTCTCTGGGAGT |
| | | CCAGGCCAGAGTATCACAATTTCTTGTACAGGCACCTCATCT |
| | | GATGTCGGCGGTTACAATTACGTTAGTTGGTATCAGCAACAT |
| | | CCAGGTAAGGCTCCAAAGGTGATGATCTATGACGTCTCAAA |
| | | TAGACCCTCTGGCGTCAGCGACAGGTTTAGTGGTAGCAAATC |
| | | CGGGAACACAGCTTCACTTACAATTAGCGGCCTCCAAGTAG |
| | | AAGACGAAGCTGACTATTACTGCTCTAGTTATTCAACGTCAA |
| | | TTACCCCTGTGTTTGGTGGCGGTACAAAACTCACAGTGCTTG |
| | | GCGGAGGCGGGTCTGGAGGTGGAGGTTCTGGAGGCGGAGGT |
| | | TCCCAAGTGCAACTTGTGCAATCAGGAGCTGAAGTCAAAAA |
| | | GCCGGGAGAATCCCTGAAAATAAGCTGCGAAGCAAGTGGTT |
| | | ACTCTTTTACTTCTTACTGGATTGGATGGGTTCGGCAGATGC |
| | | CCGGAAAGGGACTCGAGTGGATGGGAATTATTTACCCTGGA |
| | | GACAGCGACACAAGATACAGCCCTTCATTCCAGGGGCAGGT |
| | | GACCATTTCTGCTGACAAATCAATCAGTACAGCCTATCTGCA |
| | | ATGGAGTTCCCTCAAAGCCAGTGACACTGCTATGTATTACTG |
| | | CGCGCGACTGGAACTGGGATACTACTACTACGGAATGGACG |
| | | TATGGGGACAGGGAACCACCGTTACTGTTAGTAGCGCCGCC |
| | | GCTGGAGGGGGAGGATCCGGAGGAGGGGGGAGCGGAGGAG |
| | | GAGGATCATTGGAGGATGGAAATGAAGAGATGGCGGCATC |
| | | ACTCAGACACCGTACAAAGTGAGTATTTCTGGAACCACCGTC |
| | | ATTTTGACTTGTCCTCAGTACCCAGGAAGCGAGATTCTGTGG |
| | | CAGCATAACGACAAGAACATCGGGGGCGACGAGGACGATA |
| | | AAAATATAGGGTCTGACGAGGACCACCTTAGCCTTAAGGAG |
| | | TTTAGCGAGCTGGAACAGTCCGGATACTATGTATGCTATCCA |
| | | CGCGGCAGCAAACCCGAGGATGCTAACTTTTACTTGTACTTG |
| | | AGGGCGCGCGTTTGTGAGAACTGCATGGAGATGGATGTTAT |
| | | GTCCGTAGCTACCATTGTTATCGTCGACATTTGTATTACCGG |
| | | TGGATTGCTGCTGTTGGTCTACTATTGGTCCAAAAATCGGAA |
| | | AGCCAAGGCCAAACCCGTAACGAGAGGTGCCGGCGCTGGAG |
| | | GAAGACAGAGGGGCCAGAATAAAGAGAGGCCGCGCCAGT |
| | | TCCCAATCCTGATTATGAACCCATTCGAAAAGGGCAGAGGG |
| | | ACCTCTATTCCGGGCTCAACCAGAGGAGGATCGAAGGAAGG |
| | | GGATCCTTGCTTACCTGTGGCGACGTAGAAGAGAATCCAGG |
| | | CCCCTCAAGGgccgccaccATGGTGTCAAAGGGCGAAGAGTTGT |
| | | TTACTGGAGTCGTACCCATCCTGGTGGAATTGGACGGGGAC |

APPENDIX A-continued

SEQUENCE SUMMARY

| SEQ ID NO. | Name | Sequence |
|---|---|---|
| | | GTGAACGGCCACAAGTTCTCTGTGTCTGGAGAAGGCGAGGG<br>CGACGCTACTTATGGAAAACTGACTCTGAAATTTATTTGCAC<br>TACAGGAAAACTGCCTGTCCCATGGCCCACGCTGGTTACAAC<br>CCTCACATATGGTGTTCAATGTTTCTCTCGCTACCCCGACCA<br>CATGAAGCAGCATGACTTTTTCAAGTCCGCGATGCCCGAAG<br>GGTACGTTCAAGAACGCACTATATTTTTCAAGGATGATGGCA<br>ACTACAAGACAAGAGCTGAGGTGAAATTCGAAGGTGATACA<br>CTTGTAAACAGAATCGAACTCAAGGGAATCGACTTCAAGGA<br>AGACGGAAATATCCTCGGGCACAAACTGGAATATAACTACA<br>ATAGCCACAACGTATATATCATGGCCGACAAACAGAAGAAT<br>GGGATCAAGGTAAATTTTAAGATAAGACACAATATAGAAGA<br>CGGATCTGTGCAATTGGCCGACCATTATCAGCAGAATACCCC<br>CATTGGAGATGGCCCAGTGCTCCTTCCAGACAATCACTACCT<br>TTCAACACAGTCCGCGTTGTCTAAAGACCCCAATGAGAAGA<br>GGGACCACATGGTGTTGCTCGAATTTGTTACTGCCGCTGGGA<br>TCACTCTGGGCATGGATGAGTTGTATAAATGAgaattcgaacggatat<br>cgagcatcttaccgccatttatacccatatttgttctgttttcttgatttgggtatacatttaaatgttaataa<br>aacaaaatggtggggcaatcatttacattttagggatatgtaattactagttcaggtgtattgccacaag<br>acaaacatgttaagaaactttcccgttatttacgctctgttcctgttaatcaacctctggattacaaaatttg<br>tgaaagattgactgatattcttaactatgttgctccttttacgctgtgtggatatgctgctttatagcctctgt<br>atctagctattgatcccgtacggctttcgttttctcctccttgtataaatcctggttgctgtctcttttagag<br>gagttgtggcccgttgtccgtcaacgtggcgtggtgtgctctgtgtttgctgacgcaaccccactgg<br>ctggggcattgccaccacctgtcaactccttttctgggactttcgctttcccccctcccgatcgccacggc<br>agaactcatcgccgcctgccttgcccgctgctggacaggggctaggttgctgggcactgataattcc<br>gtggtgttgtcagtactggtacctttaagaccaatgacttacaaggcagctgtagatcttagccacttttt<br>aaaagaaaaggggggactggaagggctaattcactcccaaagaagacaagatctgcttttttgcctgt<br>actgggtctctctggttagaccagatctgagcctgggagctctctggctaactagggaacccactgctt<br>aagcctcaataaagcttgccttgagtgcttcaatgatcataatcaagccatatcacatctgtagaggttta<br>cttgattaaaaaacctccacacctcccctgaacctgaaacataaaatgaatgcaattgttgttgttaac<br>ttgtttattgcagcttataatggttacaaataaagcaatagcatcacaaatttcacaaataaagcattttttt<br>cactgcattctagttgtggtttgtccaaactcatcaatgtatcttatcatgtaggatctgcgtcgacAC<br>GAAGAGACGACTGACTGACTGGAAAGAGGAAGGGCT<br>GGAAGAGGAAGGAGCTTGATCCAGATCCCGATCTCGATCCA<br>GATCCGGATCGCAGCTTGGCGTAATCATGGTCATAGCTGTTT<br>CCTGTGTGAAATTGTTATCCGCTCACAATTCCACACAACATA<br>CGAGCCGGAAGCATAAAGTGTAAAGCCTGGGGTGCCTAATG<br>AGTGAGCTAACTCACATTAATTGCGTTGCGCTCACTGCCCGC<br>TTTCCAGTCGGGAAACCTGTCGTGCCAGCTGCATTAATGAAT<br>CGGCCAACGCGCGGGGAGAGGCGGTTTGCGTATTGGGCGCT<br>CTTCCGCTTCCTCGCTCACTGACTCGCTGCGCTCGGTCGTTCG<br>GCTGCGGCGAGCGGTATCAGCTCACTCAAAGGCGGTAATAC<br>GGTTATCCACAGAATCAGGGGATAACGCAGGAAAGAACATG<br>TGAGCAAAAGGCCAGCAAAAGGCCAGGAACCGTAAAAAGG<br>CCGCGTTGCTGGCGTTTTTCCATAGGCTCCGCCCCCCTGACG<br>AGCATCACAAAAATCGACGCTCAAGTCAGAGGTGGCGAAAC<br>CCGACAGGACTATAAAGATACCAGGCGTTTCCCCCTGGAAG<br>CTCCCTCGTGCGCTCTCCTGTTCCGACCCTGCCGCTTACCGG<br>ATACCTGTCCGCCTTTCTCCCTTCGGGAAGCGTGGCGCTTTCT<br>CATAGCTCACGCTGTAGGTATCTCAGTTCGGTGTAGGTCGTT<br>CGCTCCAAGCTGGGCTGTGTGCACGAACCCCCCGTTCAGCCC<br>GACCGCTGCGCCTTATCCGGTAACTATCGTCTTGAGTCCAAC<br>CCGGTAAGACACGACTTATCGCCACTGGCAGCAGCCACTGG<br>TAACAGGATTAGCAGAGCGAGGTATGTAGGCGGTGCTACAG<br>AGTTCTTGAAGTGGTGGCCTAACTACGGCTACACTAGAAGA<br>ACAGTATTTGGTATCTGCGCTCTGCTGAAGCCAGTTACCTTC<br>GGAAAAAGAGTTGGTAGCTCTTGATCCGGCAAACAAACCAC<br>CGCTGGTAGCGGTGGTTTTTTGTTTGCAAGCAGCAGATTAC<br>GCGCAGAAAAAAAGGATCTCAAGAAGATCCTTTGATCTTTTC<br>TACGGGGTCTGACGCTCAGTGGAACGAAAACTCACGTTAAG<br>GGATTTTGGTCATGAGATTATCAAAAAGGATCTTCACCTAGA<br>TCCTTTTAAATTAAAAATGAAGTTTTAAATCAATCTAAAGTA<br>TATATGAGTAAACTTGGTCTGACAGTTACCAATGCTTAATCA<br>GTGAGGCACCTATCTCAGCGATCTGTCTATTTCGTTCATCCA<br>TAGTTGCCTGACTCCCCGTCGTGTAGATAACTACGATACGGG<br>AGGGCTTACCATCTGGCCCCAGTGCTGCAATGATACCGCAGC<br>TTGGGAAACCATAAGAGCTGAAGCCAGTTACCTTCGGAAAA<br>AGAGTTGGTAGCTCTTGATCCGGCAAACAAACCACCGCTGG<br>TAGCGGTGGTTTTTTTGTTTGCAAGCAGCAGATTACGCGCAG<br>AAAAAAAGGATCTCAAGAAGATCCTTTGATCTTTTCTACGGG<br>GTCTGACGCTCAGTGGAACGAAAACTCACGTTAAGGGATTTT<br>GGTCATGAGCTTGCGCCGTCCCGTCAAGTCAGCGTAATGCTC<br>TGCCAGTGTTACAA |

APPENDIX A-continued

SEQUENCE SUMMARY

| SEQ ID NO. | Name | Sequence |
|---|---|---|
| 80 | ROR1 sdAb1 (DNA) | GAGGTGCAGCTGGTGGAGTCTGGGGGAGCCTTGGTGCAGGC<br>TGGGGGATCTCTGAGACTCTCCTGTGAAGCCTCTGGAAGCAG<br>CTTCAGCCTCTATACCATGGCCTGGTACCGCCAGACTCCAGG<br>AAAGCAGCGGGAGTTGGTCGCAACGATTACTAGTGGTTACC<br>ACACAAACTATGCCGACTCCGCGAAGGACCGATTCACCATTT<br>CTAGAGACAACGCCAAGAACACGGCCTATCTGCAATTGAAC<br>AGCCTGAAACCTGAGGACACAGCCGTCTATTACTGTGCAGC<br>GAAGAGGGTTTGGAGCGCAGAGTATAACTACTGGGGCCAGG<br>GGACCCTGGTCACCGTCTCCTCA |
| 81 | ROR1 sdAb4 (DNA) | GAGGTGCAGCTGGTGGAGTCTGGGGGAGGATTGGTGCAGGC<br>TGGGGGCTCTCTGAAACTCTCCTGTGCAACCTCTGGAGGCAC<br>CTTCAGTAGCTATCGTGTAGGCTGGTTCCGCCAGGCTCCAGG<br>GAAGCCGCGTGAGACTGTAGCCACTATTAGTAGGAATGGTG<br>GAGGCACACACTATGCGGACTCCGTGAAGGGTCGATTCACC<br>ATCTCCAGAGACAACGCCAAGAACATGGCGTATCTACAAAT<br>GAACGGCCTGAAACCTGAGGACACGGCCATTTATTACTGTG<br>CAGCAGATTCCCTCTTCTGGCCTGGCCCAGGCCATTATGACA<br>ACTTGGGCCAGGGGACCCAGGTCACCGTCTCCTCA |
| 82 | ROR1 sdAb5 (DNA) | GATGTGCAGCTGGTGGAGTCTGGGGGAGGATTGGTGCAGGC<br>TGGGGGCTCTCTGAGACTCTCCTGTGCAGCCTCTGGACGCTC<br>CTTCAATAGCTATACCTTGGGCTGGTTCCGCCAGGCTCCAGG<br>AAAGGAGCGTGAGTTTGTAGCTTATGCCATTTACTATCCAGA<br>CTCTGTGAAGGGCCGATTCACCATCGTCAGAGACAACGCCA<br>GGAACACGGTGTATCTGCAAATGAATAGCCTCAAATCTGAG<br>GATACGGCCATTTATTACTGTGCAGCAGCGGACATACGTACT<br>AGGCGCTCTAGTACCTGGTACAGGGAGACGATGGAGTATGA<br>CTACTGGGGCCAGGGGACCCTGGTCACCGTCTCCTCA |
| 83 | ROR1 sdAb10 (DNA) | GATGTTCAGCTGGTGGAGTCTGGGGGAGGATTGGTGCAGGC<br>TGGGGGGGTCTCTGAGACTCTCCTGTGCAGCCTCTGGAAGCAT<br>CTTCGCAGTCGATGCCATGGGCTGGTACCGCCAGGCTCCAGG<br>GAAGCAGCGCGAGTTGGTCGCACGTATTAGTCGTACTAATTT<br>GGGAGCAAGCTATTTAGACTCCGTGAAGGGCCGATTCACCA<br>TCTCCAGAGACACCGGCAAGAACACGGTGTATCTGCAAATG<br>GTCAGCCTGGAACCTGAGGACACAGCCGTTTATTACTGTGCA<br>GCAGCCGACAAGACCGACCCTCGCGCTCGTGGACTACTGGGG<br>CCAGGGGACCCAGGTCACCGTCTCCTCA |
| 84 | ROR1 sdAb11 (DNA) | GATGTCCAGCTGGTGGAGTCTGGGGGAGGCTTGGTGCAGCC<br>TGGGGGGTCTCTGAGACTCTCCTGTGCAGCCTCTGGATTCAC<br>TTCGGATTATTATGTCATAGGCTGGTTCCGCCAGGCCCCAGG<br>GAAGGAGCGCGAGGGGGTATCATGTATTAGTAGTAGGTATG<br>CGAACACAAACTATGCAGACTCCGTGAAGGGCCGATTCACC<br>CAGTCCAGAGGTGCTGCTAAGAACACGGTGTATCTGCAAAT<br>GAACGCCCTGAAACCTGAGGACACGGCCGTTTATTACTGCG<br>CGGCAGATACGAGGCGGTATACATGCCCGGATATAGCGACT<br>ATGGAGAGGAACTTTGATTCCTGGGGCCAGGGGACCCAGGT<br>CACCGTCTCCTCA |
| 85 | ROR1 sdAb12 (DNA) | GATGTGCAGCTGGTGGAGTCTGGGGGAGGATTGGTGCAGGC<br>TGGGGACTCTCTGAGACTCTCCTGTGCAGCCTCTGGACGCAC<br>CTTCAGTAGCTATGCCATGGCCTGGTTCCGCCAGGCTCCAGG<br>GAAGGAGCGTGAGTTAGTAGCAGCTTTGAGCAGTAGTGGTG<br>CTAGCACATCGTATCCAGACTCCGTGAAGGGCCGATTCACCA<br>TCTCCAGAGACAACGCCAAGAACACGGTGTATCTGCAAATG<br>AACAGCCTGAAACCTGAGGACACGGCCGTTTATTACTGTGC<br>AGCGAGACTTTATACCTACGGGTTGACAGAAAGAGCGTATG<br>ACTACTGGGGCCAGGGGACCCAGGTCACCGTCTCCTCA |
| 86 | ROR1 sdAb13 (DNA) | GATGTCCAGCTGGTGGAGTCTGGGGGAGGATTGGTGCAGGC<br>TGGGGACTCTCTGAGGCTCTCCTGTGCAGCCTCTGGACGCAC<br>CTTCAGAGACTATGCCATGGCCTGGTTCCGCCAGGCTCCAGG<br>GAAGGAGCGTGGGATTGTAGCAGCTTTGAGCAAGAGTGGTG<br>GTAGTACATCGTATCTAGACTCCGTGAAGGGCCGATTCACCA<br>TCTCCAGAGACAACGCCAAGAACACGGTGTATCTGCAAATG<br>AACAGCCTGAAACCTGAGGACACGGCCGTTTATTACTGTGC<br>AGCGAGATTGTATACCTACGGGTTGACAGAAAGGGCGTATG<br>ACTACTGGGGCCAGGGGACCCAGGTCACCGTCTCCTCA |
| 87 | ROR1 sdAb14 (DNA) | GAGGTGCAGCTGGTGGAGTCTGGGGGAGGATTGGTGCAGGC<br>TGGGGGCTCTCTGAGACTCTCCTGTGCAGCCTCTACGGACAC<br>CTTCACTGGCTATACCATGGGCTGGTTCCGCCAGACTCCAGG |

APPENDIX A-continued

SEQUENCE SUMMARY

| SEQ ID NO. | Name | Sequence |
|---|---|---|
| | | GAAGGAGCGACAATTTGTAGCGTCCATGAGCTGGAATGGTG GTTTCATAAAGTATGCAGACTCTGTGAAGGGCCGATTCACCA TCTCCAGGGACAACGCCGAGAACATGGTGTATCTTGAAATG AACAACCTGAAATCTGAGGACACGGCCGTTTATTCCTGTGCA GCAGACAACATCTATTGGACTGCGTCCGAGCGCCCCGGAGA CTATAACTACTGGGGCCAGGGGACCCAGGTCACCGTCTCCTC A |
| 88 | ROR1 sdAb19 (DNA) | GAGGTCCAGCTGGTGGAGTCTGGGGGAGGCTTGGTGCAGCC TGGGGGGTCTCTGAGACTCTCCTGCACTGCCTCTGGAACCAT GTCCACCATCAACGCCATGGGCTGGTACCGCCAGGCTCCAG AGAAGCAGCGCGAGTTGGTCGCTCGCATTTGGAATGATGGA GAGACTAACTATGCAGACTCCGTGAGGGGCCGATTCGCCGT CTCTAGAGACAACGCAAAGAACACGGTGTATCTGCAAATGA ACAGCCTGAAACCTGAGGACACGGCCGTCTATTACTGTAAT GCGTATATACCTACTACTCAGCGTATGAATAAAATAGCTAGT TATTGGGGCCAGGGGACCCTGGTCACCGTCTCCTCA |
| 89 | ROR1 sdAb20 (DNA) | GAGGTGCAGCTGGTGGAGTCTGGGGGAGGATTGGTGCAGGC TGGGGACTCTCTGAGGGTCTCCTGTGCAGCCTCTGGACGCAC CTTCAGTAGCTATGCCATGGCCTGGTTCCGCCAGGCTCCAGG GAAGGAGCGTGAGTTTGTAGCAGCTTTGAGCAGTAGTGGTG TTAGCACATCGTATTCAGACTCCGTGAAGGGCCGATTCACCA TCTCCAGAGACACGGCCAAGAACACGGTGTATCTGCAAATG AACAGCCTGAAACCCGAGGACACGGCCGTTTATTACTGTGC AGCGAGACTATATACCTACGGGTTGACAGAAAGGGCGTATG ACTACTGGGGCCAGGGGACCCAGGTCACCGTCTCCTCA |
| 90 | ROR1 sdAb22 (DNA) | GAGGTGCAGCTGGTGGAGTCTGGGGGAGGCTTGGTGCAGCC TGGGGGGTCTCTGAGACTCTCCTGTGCAGCCTCTGGAAGCTT CCTCGACATCAATGCCATGGGCTGGTACCGCCAGGCTCCAG GAAAGCAGCGCGAGTTGGTCGCAATGATGCCTAGTGGTGGC CGCACAAACTATCATGACTCCGTTGAGGGCCGATTCACCATC TCCAGAGACAACGCCAAGAACACAGTGTATCTGCAAATGGA CAGCCTGAAACCTGAGGACACGGCCGTCTATTACTGTTGC AGATGCGACCCGGTACTCCGGTTTCCGTACTAACTTCTGGGG CCGGGGAACCCAGGTCACCGTCTCCTCA |
| 91 | ROR1 sdAb26 (DNA) | GAGGTGCAGCTGGTGGAGTCTGGGGGAGGCACGGTGCAGGC TGGGGGGTCTCTGCGACTCTCCTGTGCAGCCTCTGGCGGTAT CTTCAGCATCTATGTCATGGGCTGGCATCGCCAGGCTCCAGG GAAGCAGCGCGAATTGGTCGCAGCTATTACTCCTGGTTTTAA CACAAACTATGCAGACCCCGTGAAGGGCCGATTCACCATCT CAAGAGACAACGCCAAGAGCACGGTGTACCTGGAAATGAAC AGCCTCGAACCTGAGGATACGGCCGTTTATTACTGTTCAGCT AAACGAATCTATGAGTACGAGTACTATTATTGGGGCCAGGG GACCCAGGTCACCGTCTCCTCA |
| 92 | ROR1 sdAb27 (DNA) | GATGTTCAGCTGGTGGAGTCTGGGGGAGGATTGGTGCAGGC TGGGGACTCTCTGAGACTCTCCTGTGCAGCCTCTGGACGCAC CTTCAGTGAATATGCCATGGCCTGGTTCCGCCAGGCTCCAGG GAAGGAGCGTGAGTTTGTAGCAGCTATGAGCAAGAGTGGTG CTAGCACATCGTATAGTGACTCCGTAAAGGGCCGATTCACCA TCTCCAGAGCCAACGCCAAGAACACGGTGTATCTCGAAATG AACAGCCTGAAACCTGAGGACACGGCCGGTTACTACTGTGC AGCGAGACTATACACCTACGGGTTGACAGAAAGGGCGTATG ACTACTGGGGCCAGGGGACCCAGGTCACCGTCTCCTCA |
| 93 | ROR1 sdAb29 (DNA) | GATGTGCAGCTGGTGGAGTCTGGGGGAGGATTGGTGCAGGC TGGGGACTCTCTGAGACTCTCCTGTGCAGCCTCTGGACGCAC CTTCAGTGACTATGCCATGGCCTGGTTCCGCCAGGGTCCAGG GAAGGAGCGTGAGCTTGTAGCAGCTTTGAGCAAGAGTGGTG CTAGCACATCGTATGCAGACTCCGTGAAGGGCCGATTCACC ATCTCCAGAGACAACGCCAAGAACACGGTGTATCTGCATAT GAACAGCCTGAAACCTGAGGACACGGCCTTTATTACTGTG CAGCGAGACTTTATACCTACGGGTTGACAGAAAGGGCGTAT GACTACTGGGGCCAGGGGACCCAGGTCACCGTCTCCTCA |
| 94 | ROR1 sdAb30 (DNA) | GATGTGCAGCTGGTGGAGTCTGGGGGAGGATTGGTGCAGGC TGGGGGCTCTCTGAGCCTCTCCTGTGCATCCTCTGGACGCAC CTCCAGTATCTATGGCATGGGCTGGTTCCGCCAGGCTCCAGG GAAGGAGCGTGAGTTTGTAGCGGCTATTAGGTGGAGTGATA GTAACACAAACTATGCAGACTCCGTGAAGGGCCGATTCACC ATCTCCGGAGACAACGCCAAGAACGCGGTGCATCTGCAAAT |

APPENDIX A-continued

SEQUENCE SUMMARY

| SEQ ID NO. | Name | Sequence |
|---|---|---|
| | | GCACAGCCTGAAACCTGAGGACACGGCCGTTTATTACTGTGC<br>AGCCAAAGGGACCCCTTATTATTATACCGACTTCCGGACGTA<br>TCCGTACTGGGGCCAGGGGACCCTGGTCACCGTCTCCTCA |
| 95 | ROR1 sdAb31 (DNA) | GATGTCCAGCTGGTGGAGTCTGGGGGAGGCTTGGTGCAGCC<br>TGGGGGGTCTCTGAGACTCACCTGTGCAGCCTCTGGATTCAC<br>TTCGGATTATTATGTCATAGGCTGGTTCCGCCAGGCCCCAGG<br>GAAGGAGCGCGAGGGGGTATCATGTATTAGTAGTAGGTATG<br>CGAACACAAACTATGCAGACTCCGTGAAGGGCCGATTCACC<br>CAGTCCAGAGGTGCTGCTAAGAACACGGTGTATCTGCAAAT<br>GAACGCCCTGAAACCTGGGGACACGGCCGTTTATTACTGCG<br>CGGCAGATACGAGGCGGTATACATGCCCGGATATAGCGACT<br>ATGCACAGGAACTTTGATTCCTGGGGCCAGGGGACCCAGGT<br>CACCGTCTCCTCA |
| 96 | ROR1 sdAb32 (DNA) | GATGTCCAGCTGGTGGAGTCTGGGGGAGGCTTGGTGCAGCC<br>TGGGGGGTCTCTGAGACTCACCTGTGCAGCCTCTGGATTCAC<br>TTCGGATTATTATGTCATAGGCTGGTTCCGCCAGGCCCCAGG<br>GAAGGAGCGCGAGGGGGTATCATGTATTAGTAGTAGGTATG<br>CGAACACAAACTATGCAGACTCCGTGAAGGGCCGATTCACC<br>CAGTCCAGAGGTGCTGCTAAGAACACGGTGTATCTGCAAAT<br>GAACGCCCTGAAACCTGGGGACACGGCCGTTTATTACTGCG<br>CGGCAGATACGAGGCGGTATACATGCCCGGATATAGCGACT<br>ATGCACAGGAACTTTGATTCCTGGGGCCAGGGGACCCAGGT<br>CACCGTCTCCTCA |
| 97 | human CD3-ε fragment used in TFPs | DGNEEMGGITQTPYKVSISGTTVILTCPQYPGSEILWQHNDKNI<br>GGDEDDKNIGSDEDHLSLKEFSELEQSGYYVCYPRGSKPEDAN<br>FYLYLRARVCENCMEMDVMSVATIVIVDICITGGLLLLVYYWS<br>KNRKAKAKPVTRGAGAGGRQRGQNKERPPPVPNPDYEPIRKG<br>QRDLYSGLNQRRI |
| 98 | p502_NKG2D_ CD3epsilon ORF, monomer (amino acid sequence) | NSLFNQEVQIPLTESYCGPCPKNWICYKNNCYQFFDESKNWYE<br>SQASCMSQNASLLKVYSKEDQDLLKLVKSYHWMGLVHIPTNG<br>SWQWEDGSILSPNLLTIIEMQKGDCALYASSFKGYIENCSTPNT<br>YICMQRTVGGGSGGGGSGGGGSLEDGNEEMGGITQTPYKVSI<br>SGTTVILTCPQYPGSEILWQHNDKNIGGDEDDKNIGSDEDHLS<br>LKEFSELEQSGYYVCYPRGSKPEDANFYLYLRARVCENCMEMD<br>VMS |
| 99 | p502_CD16 ECD_ CD3epsilon (DNA) | acgcgtGTAGTCTTATGCAATACTCTGTAGTCTTGCAACATGGT<br>AACGATGAGTTAGCAACATGCCTTACAAGGAGAGAAAAAGC<br>ACCGTGCATGCCGATTGGTGGAAGTAAGGTGGTACGATCGT<br>GCCTTATTAGGAAGGCAACAGACGGGTCTGACATGGATTGG<br>ACGAACCACTGAATTGCCGCATTGCAGAGATATTGTATTTAA<br>GTGCCTAGCTCGATACATAAACGGGTCTCTCTGGTTAGACCA<br>GATCTGAGCCTGGGAGCTCTCTGGCTAACTAGGGAACCCACT<br>GCTTAAGCCTCAATAAAGCTTGCCTTGAGTGCTTCAAGTAGT<br>GTGTGCCCGTCTGTTGTGTGACTCTGGTAACTAGAGATCCCT<br>CAGACCCTTTTAGTCAGTGTGGAAAATCTCTAGCAGTGGCGC<br>CCGAACAGGGACTTGAAAGCGAAAGGGAAACCAGAGGAGC<br>TCTCTCGACGCAGGACTCGGCTTGCTGAAGCGCGCACGGCA<br>AGAGGCGAGGGGCGGCGACTGGTGAGTACGCCAAAAATTTT<br>GACTAGCGGAGGCTAGAAGGAGAGAGatgggtgcgagagcgtcagtatta<br>agcgggggagaattAGATCGCGATGGGAAAAAATTCGGTTAAGGCC<br>AGGGGGAAAGAAAAAATATAAATTAAAACATATAGTATGGG<br>CAAGCAGGGAGCTAGAACGATTCGCAGTTAATCCTGGCCTG<br>TTAGAAACATCAGAAGGCTGTAGACAAATACTGGGACAGCT<br>ACAACCATCCCTTCAGACAGGATCAGAAGAACTTAGATCAT<br>TATATAATACAGTAGCAACCCTCTATTGTGTGCATCAAAGGA<br>TAGAGATAAAAGACACCAAGGAAGCTTTAGACAAGATAGAG<br>GAAGAGCAAAACAAAAGTAAGACCACCGCACAGCAAGCGG<br>CCACTGATCTTCAGACCTGGAGGAGGAGATATGAGGGACAA<br>TTGGAGAAGTGAATTATATAAATATAAAGTAGTAAAAATTG<br>AACCATTAGGAGTAGCACCCACCAAGGCAAAGAGAAGAGTG<br>GTGCAGAGAGAAAAAAGAGCAGTGGGAATAGGAGCTTTGTT<br>CCTTGGGTTCTTGGGAGCAGCAGGAAGCACTATGGGCGCAG<br>CGTCAATGACGCTGACGGTACAGGCCAGACAATTATTGTCTG<br>GTATAGTGCAGCAGCAGAACAATTGCTGAGGGCTATTGAG<br>GCGCAACAGCATCTGTTGCAACTCACAGTCTGGGGCATCAA<br>GCAGCTCCAGGCAAGAATCCTGGCTGTGGAAAGATACCTAA<br>AGGATCAACAGCTCCTGGGGATTTGGGGTTGCTCTGGAAAA<br>CTCATTTGCACCACTGCTGTGCCTTGGAATGCTAGTTGGAGT<br>AATAAATCTCTGGAACAGATTTGGAATCACACGACCTGGAT |

APPENDIX A-continued

SEQUENCE SUMMARY

| SEQ ID NO. | Name | Sequence |
|---|---|---|
| | | GGAGTGGGACAGAGAAATTAACAATTACACAAGCTTAATAC |
| | | ACTCCTTAATTGAAGAATCGCAAAACCAGCAAGAAAAGAAT |
| | | GAACAAGAATTATTGGAATTAGATAAATGGGCAAGTTTGTG |
| | | GAATTGGTTTAACATAACAAATTGGCTGTGGTATATAAAATT |
| | | ATTCATAATGATAGTAGGAGGCTTGGTAGGTTTAAGAATAGT |
| | | TTTTGCTGTACTTTCTATAGTGAATAGAGTTAGGCAGGGATA |
| | | TTCACCATTATCGTTTCAGACCCACCTCCCAACCCCGAGGGG |
| | | ACCCGACAGGCCCGAAGGAATAGAAGAAGAAGGTGGAGAG |
| | | AGAGACAGAGACAGATCCATTCGATTAGTGAACGGATCTCG |
| | | ACGGTATCGGTTAACTTTTAAAAGAAAAGGGGGGATTGGGG |
| | | GGTACAGTGCAGGGGAAAGAATAGTAGACATAATAGCAACA |
| | | GACATACAAACTAAAGAATTACAAAAACAAATTACAAAATT |
| | | CAAAATTTTATCGATACTAGTGGATCTGCGATCGCTCCGGTG |
| | | CCCGTCAGTGGGCAGAGCGCACATCGCCCACAGTCCCCGAG |
| | | AAGTTGGGGGGAGGGGTCGGCAATTGAACGGGTGCCTAGAG |
| | | AAGGTGGCGCGGGGTAAACTGGGAAAGTGATGTCGTGTACT |
| | | GGCTCCGCCTTTTTCCCGAGGGTGGGGGAGAACCGTATATAA |
| | | GTGCAGTAGTCGCCGTGAACGTTCTTTTTCGCAACGGGTTTG |
| | | CCGCCAGAACACAGCTGAAGCTTCGAGGGGCTCGCATCTCT |
| | | CCTTCACGCGCCCGCCGCCCTACCTGAGGCCGCCATCCACGC |
| | | CGGTTGAGTCGCGTTCTGCCGCCTCCCGCCTGTGGTGCCTCC |
| | | TGAACTGCGTCCGCCGTCTAGGTAAGTTTAAAGCTCAGGTCG |
| | | AGACCGGGCCTTTGTCCGGCGCTCCCTTGGAGCCTACCTAGA |
| | | CTCAGCCGGCTCTCCACGCTTTGCCTGACCCTGCTTGCTCAA |
| | | CTCTACGTCTTTGTTTCGTTTTCTGTTCTGCGCCGTTACAGAT |
| | | CCAAGCTGTGACCGGCGCCTACTCTAGAgccgccaccATGGCCCT |
| | | GCCTGTGACAGCTCTGCTGCTGCCTCTGGCCCTGCTGCTCCA |
| | | TGCCGCCAGACCCCCCAAGGCTGTAGTATTCCTCGAACCGCA |
| | | GTGGTATCGGGTACTCGAAAAAGACAGTGTAACGCTGAAGT |
| | | GCCAGGGGCCTATAGTCCCGAGGATAACTCAACCCAATGG |
| | | TTCCACAATGAAAGCCTCATCTCTTCACAAGCAAGTTCTTAT |
| | | TTCATAGATGCCGCCACTGTAGATGACTCCGGAGAATATCGG |
| | | TGTCAAACGAATTTGTCTACTCTGAGCGACCCGGTTCAGCTT |
| | | GAGGTACACATAGGGTGGTTGCTTCTCCAAGCCCCCCGGTGG |
| | | GTATTTAAGGAGGAAGATCCAATCCACTTGCGGTGTCACAG |
| | | CTGGAAGAACACAGCCCTTCACAAGGTAACATACTTGCAAA |
| | | ACGGCAAGGGTAGGAAATACTTCCATCACAACAGCGATTTC |
| | | TACATACCAAAAGCAACCCTCAAGGACTCCGGGAGTTATTTC |
| | | TGCCGCGGGCTCTTCGGTTCTAAGAATGTAAGCAGTGAAAC |
| | | GGTCAATATAACCATTACACAGGGTCTCGCGGTTTCTACCAT |
| | | CTCAAGTTTCTTCCCTCCCGGTTATCAAgcggccgcGGGCGGTGG |
| | | TGGTTCTGGGGGCGGGGGGTCTGGAGGAGGGGGAAGTctcgag |
| | | GATGGAAATGAAGAAATGGGAGGGATAACCCAAACTCCATA |
| | | CAAGGTCTCTATCAGCGGTACGACCGTAATTTTGACCTGTCC |
| | | CCAGTATCCTGGTTCCGAAATACTTTGGCAACACAATGATAA |
| | | GAATATCGGTGGAGACGAGGATGATAAGAACATTGGGTCTG |
| | | ATGAAGACCACCTCTCTCTCAAGGAATTTAGCGAGCTTGAAC |
| | | AGTCAGGTTACTACGTGTGTTACCCACGGGGCAGCAAGCCC |
| | | GAGGATGCCAACTTTTACCTGTACCTGCGGGCAAGGGTCTGT |
| | | GAAAACTGTATGGAGATGGATGTGATGAGCGTAGCTACGAT |
| | | TGTAATAGTGGACATCTGCATCACCGGGGTTTGTTGTTGCT |
| | | TGTTTACTACTGGAGTAAAAACAGAAAAGCGAAAGCTAAGC |
| | | CTGTTACCCGGGGAGCCGGGGCTGGCGGAAGGCAGAGGGGT |
| | | CAAAATAAAGAGCGCCCCCCGCCTGTTCCGAATCCAGACTA |
| | | CGAACCCATCCGGAAAGGGCAACGGGATCTCTACTCCGGCT |
| | | TGAATCAGCGAAGAATTTAGTAAGAATTCGAATTTAAATCG |
| | | GATCCGCGGCCGCGTCGACAATCAACCTCTGGATTACAAAA |
| | | TTTGTGAAAGATTGACTGGTATTCTTAACTATGTTGCTCCTTT |
| | | TACGCTATGTGGATACGCTGCTTTAATGCCTTTGTATCATGCT |
| | | ATTGCTTCCCGTATGGCTTTCATTTTCTCCTCCTTGTATAAAT |
| | | CCTGGTTGCTGTCTCTTTATGAGGAGTTGTGGCCCGTTGTCA |
| | | GGCAACGTGGCGTGGTGTGCACTGTGTTTGCTGACGCAACCC |
| | | CCACTGGTTGGGGCATTGCCACCACCTGTCAGCTCCTTTCCG |
| | | GGACTTTCGCTTTCCCCCTCCCTATTGCCACGGCGGAACTCA |
| | | TCGCCGCCTGCCTTGCCCGCTGCTGGACAGGGGCTCGGCTGT |
| | | TGGGCACTGACAATTCCGTGGTGTTGTCGGGGAAATCATCGT |
| | | CCTTTCCTTGGCTGCTCGCCTGTGTTGCCACCTGGATTCTGCG |
| | | CGGGACGTCCTTCTGCTACGTCCCTTCGGCCCTCAATCCAGC |
| | | GGACCTTCCTTCCCGCGGCCTGCTGCCGGCTCTGCGGCCTCT |
| | | TCCGCGTCTTCGCCTTCGCCCTCAGACGAGTCGGATCTCCCT |
| | | TTGGGCCGCCTCCCCGCCTGGTACCTTTAAGACCAATGACTT |
| | | ACAAGGCAGCTGTAGATCTTAGCCACTTTTTAAAAGAAAAG |
| | | GGGGGACTGGAAGGGCTAATTCACTCCCAACGAAGATAAGA |
| | | TCTGCTTTTTGCTTGTACTGGGTCTCTCTGGTTAGACCAGATC |

APPENDIX A-continued

SEQUENCE SUMMARY

| SEQ ID NO. | Name | Sequence |
|---|---|---|
| | | TGAGCCTGGGAGCTCTCTGGCTAACTAGGGAACCCACTGCTT<br>AAGCCTCAATAAAGCTTGCCTTGAGTGCTTCAAGTAGTGTGT<br>GCCCGTCTGTTGTGTGACTCTGGTAACTAGAGATCCCTCAGA<br>CCCTTTTAGTCAGTGTGGAAAATCTCTAGCAGTAGTAGTTCA<br>TGTCATCTTATTATTCAGTATTTATAACTTGCAAAGAAATGA<br>ATATCAGAGAGTGAGAGGAACTTGTTTATTGCAGCTTATAAT<br>GGTTACAAATAAAGCAATAGCATCACAAATTTCACAAATAA<br>AGCATTTTTTTCACTGCATTCTAGTTGTGGTTTGTCCAAACTC<br>ATCAATGTATCTTATCATGTCTGGCTCTAGCTATCCCGCCCCT<br>AACTCCGCCCATCCCGCCCCTAACTCCGCCCAGTTCCGCCCA<br>TTCTCCGCCCCATGGCTGACTAATTTTTTTTATTTATGCAGAG<br>GCCGAGGCCGCCTCGGCCTCTGAGCTATTCCAGAAGTAGTG<br>AGGAGGCTTTTTTGGAGGCCTAGACTTTTGCagagacggcccaaattc<br>gtaatcatggtcatagctgtttcctgtgtgaaattgttatccgctcacaattccacacaacatacgagcc<br>ggaagcataaagtgtaaagcctggggtgcctaatgagtgagctaactcacattaattgcgttgcgctc<br>actgcccgctttccagtcgggaaacctgtcgtgccagctgcattaatgaatcggccaacgcgcggg<br>agaggcggtttgcgtattgggcgctcttccgcttcctcgctcactgactcgctgcgctcggtcgttcgg<br>ctgcggcgagcggtatcagctcactcaaaggcggtaatacggttatccacagaatcaggggataac<br>gcaggaaagaacatgtgagcaaaaggccagcaaaaggccaggaaccgtaaaaaggccgcgttgc<br>tggcgtttttccataggctccgcccccctgacgagcatcacaaaaatcgacgctcaagtcagaggtg<br>gcgaaacccgacaggactataaagataccaggcgtttccccctggaagctccctcgtgcgctctcct<br>gttccgaccctgccgcttaccggatacctgtccgcctttctcccttcgggaagcgtggcgctttctcata<br>gctcacgctgtaggtatctcagttcggtgtaggtcgttcgctccaagctgggctgtgtgcacgaaccc<br>cccgttcagcccgaccgctgcgccttatccggtaactatcgtcttgagtccaacccggtaagacacga<br>cttatcgccactggcagcagccactggtaacaggattagcagagcgaggtatgtaggcggtgctac<br>agagttcttgaagtggtggcctaactacggctacactagaaggacagtatttggtatctgcgctctgct<br>gaagccagttaccttcggaaaaagagttggtagctcttgatccggcaaacaaaccaccgctggtagc<br>ggtggtttttttgtttgcaagcagcagattacgcgcagaaaaaaaggatctcaagaagatcctttgatct<br>tttctacggggtctgacgctcagtggaacgaaaactcacgttaagggattttggtcatgagattatcaa<br>aaaggatcttcacctagatccttttaaattaaaaatgaagttttaaatcaatctaaagtatatatgagtaaa<br>cttggtctgacagttaccaatgcttaatcagtgaggcacctatctcagcgatctgtctatttcgttcatcca<br>tagttgcctgactccccgtcgtgtagataactacgatacgggagggcttaccatctggccccagtgct<br>gcaatgataccgcgagacccacgctcaccggctccagatttatcagcaataaaccagccagccgga<br>agggccgagcgcagaagtggtcctgcaactttatccgcctccatccagtctattaattgttgccggga<br>agctagagtaagtagttcgccagttaatagtttgcgcaacgttgttgccattgctacaggcatcgtggtg<br>tcacgctcgtcgtttggtatggcttcattcagctccggttcccaacgatcaaggcgagttacatgatccc<br>ccatgttgtgcaaaaaagcggttagctccttcggtcctccgatcgttgtcagaagtaagttggccgcag<br>tgttatcactcatggttatggcagcactgcataattctcttactgtcatgccatccgtaagatgcttttctgt<br>gactggtgagtactcaaccaagtcattctgagaatagtgtatgcggcgaccgagttgctcttgcccgg<br>cgtcaatacgggataataccgcgccacatagcagaactttaaaagtgctcatcattggaaaacgttctt<br>cggggcgaaaactctcaaggatcttaccgctgttgagatccagttcgatgtaacccactcgtgcaccc<br>aactgatcttcagcatcttttactttcaccagcgtttctgggtgagcaaaaacaggaaggcaaaatgcc<br>gcaaaaaagggaataagggcgacacggaaatgttgaatactcatactcttcctttttcaatattattgaa<br>gcatttatcagggttattgtctcatgagcggatacatatttgaatgtatttagaaaaataaacaaataggg<br>gttccgcgcacatttccccgaaaagtgccacctgacgtctaagaaaccattattatcatgacattaacct<br>ataaaaataggcgtatcacgaggccattcgtctcgcgcgtttcggtgatgacggtgaaaacctctga<br>cacatgcagctcccggagacggtcacagcttgtctgtaagcggatgccgggagcagacaagcccg<br>tcagggcgcgtcagcgggtgttggcgggtgtcggggctggcttaactatgcggcatcagagcagat<br>tgtactgagagtgcaccatatgcggtgtgaaataccgcacagatgcgtaaggagaaaataccgcatc<br>aggcgccattcgccattcaggctgcgcaactgttgggaagggcgatcggtgcgggcctatcgctat<br>tacgccagctggcgaaaggggggatgtgctgcaaggcgattaagttgggtaacgccagggttttccc<br>agtcacgacgttgtaaaacgacggccagtgccaagctg |
| 100 | p502_anti-CD22_CD3epsilon | acgcgtGTAGTCTTATGCAATACTCTGTAGTCTTGCAACATGGT<br>AACGATGAGTTAGCAACATGCCTTACAAGGAGAGAAAAAGC<br>ACCGTGCATGCCGATTGGTGGAAGTAAGGTGGTACGATCGT<br>GCCTTATTAGGAAGGCAACAGACGGGTCTGACATGGATTGG<br>ACGAACCACTGAATTGCCGCATTGCAGAGATATTGTATTTAA<br>GTGCCTAGCTCGATACATAAACGGGTCTCTCTGGTTAGACCA<br>GATCTGAGCCTGGGAGCTCTCTGGCTAACTAGGGAACCCACT<br>GCTTAAGCCTCAATAAAGCTTGCCTTGAGTGCTTCAAGTAGT<br>GTGTGCCCGTCTGTTGTGTGACTCTGGTAACTAGAGATCCCT<br>CAGACCCTTTTAGTCAGTGTGGAAAATCTCTAGCAGTGGCGC<br>CCGAACAGGGACTTGAAAGCGAAAGGGAAACCAGAGGAGC<br>TCTCTCGACGCAGGACTCGGCTTGCTGAAGCGCGCACGGCA<br>AGAGGCGAGGGGCGGCGACTGGTGAGTACGCCAAAAATTTT<br>GACTAGCGGAGGCTAGAAGGAGAGAGatgggtgcgagagcgtcagtatta<br>agcggggggagaattAGATCGCGATGGGAAAAAATTCGGTTAAGGCC<br>AGGGGGAAAGAAAAAATATAAATTAAAACATATAGTATGGG<br>CAAGCAGGGAGCTAGAACGATTCGCAGTTAATCCTGGCCTG<br>TTAGAAACATCAGAAGGCTGTAGACAAATACTGGGACAGCT<br>ACAACCATCCCTTCAGACAGGATCAGAAGAACTTAGATCAT<br>TATATAATACAGTAGCAACCCTCTATTGTGTGCATCAAAGGA<br>TAGAGATAAAAGACACCAAGGAAGCTTTAGACAAGATAGAG |

APPENDIX A-continued

SEQUENCE SUMMARY

| SEQ ID NO. | Name | Sequence |
|---|---|---|

GAAGAGCAAAACAAAAGTAAGACCACCGCACAGCAAGCGG
CCACTGATCTTCAGACCTGGAGGAGGAGATATGAGGGACAA
TTGGAGAAGTGAATTATATAAATATAAAGTAGTAAAAATTG
AACCATTAGGAGTAGCACCCACCAAGGCAAAGAGAAGAGTG
GTGCAGAGAGAAAAAAGAGCAGTGGGAATAGGAGCTTTGTT
CCTTGGGTTCTTGGGAGCAGCAGGAAGCACTATGGGCGCAG
CGTCAATGACGCTGACGGTACAGGCCAGACAATTATTGTCTG
GTATAGTGCAGCAGCAGAACAATTTGCTGAGGGCTATTGAG
GCGCAACAGCATCTGTTGCAACTCACAGTCTGGGGCATCAA
GCAGCTCCAGGCAAGAATCCTGGCTGTGGAAAGATACCTAA
AGGATCAACAGCTCCTGGGGATTTGGGGTTGCTCTGGAAAA
CTCATTTGCACCACTGCTGTGCCTTGGAATGCTAGTTGGAGT
AATAAATCTCTGGAACAGATTTGGAATCACACGACCTGGAT
GGAGTGGGACAGAGAAATTAACAATTACACAAGCTTAATAC
ACTCCTTAATTGAAGAATCGCAAAACCAGCAAGAAAAGAAT
GAACAAGAATTATTGGAATTAGATAAATGGGCAAGTTTGTG
GAATTGGTTTAACATAACAAATTGGCTGTGGTATATAAAATT
ATTCATAATGATAGTAGGAGGCTTGGTAGGTTTAAGAATAGT
TTTTGCTGTACTTTCTATAGTGAATAGAGTTAGGCAGGGATA
TTCACCATTATCGTTTCAGACCCACCTCCCAACCCCGAGGGG
ACCCGACAGGCCCGAAGGAATAGAAGAAGAAGGTGGAGAG
AGAGACAGAGACAGATCCATTCGATTAGTGAACGGATCTCG
ACGGTATCGGTTAACTTTTAAAAGAAAAGGGGGGATTGGGG
GGTACAGTGCAGGGGAAAGAATAGTAGACATAATAGCAACA
GACATACAAACTAAAGAATTACAAAAACAAATTACAAAATT
CAAAATTTTATCGATACTAGTGGATCTGCGATCGCTCCGGTG
CCCGTCAGTGGGCAGAGCGCACATCGCCCACAGTCCCCGAG
AAGTTGGGGGGAGGGGTCGGCAATTGAACGGGTGCCTAGAG
AAGGTGGCGCGGGGTAAACTGGGAAAGTGATGTCGTGTACT
GGCTCCGCCTTTTTCCCGAGGGTGGGGGAGAACCGTATATAA
GTGCAGTAGTCGCCGTGAACGTTCTTTTTCGCAACGGGTTTG
CCGCCAGAACACAGCTGAAGCTTCGAGGGGCTCGCATCTCT
CCTTCACGCGCCCGCCGCCCTACCTGAGGCCGCCATCCACGC
CGGTTGAGTCGCGTTCTGCCGCCTCCCGCCTGTGGTGCCTCC
TGAACTGCGTCCGCCGTCTAGGTAAGTTTAAAGCTCAGGTCG
AGACCGGGCCTTTGTCCGGCGCTCCCTTGGAGCCTACCTAGA
CTCAGCCGGCTCTCCACGCTTTGCCTGACCCTGCTTGCTCAA
CTCTACGTCTTTGTTTCGTTTTCTGTTCTGCGCCGTTACAGAT
CCAAGCTGTGACCGGCGCCTACTCTAGAgccgccaccatgatctcctggt
gacaagccttctgctctgtgagttaccacacccagcattcctcctgatcccaCAGGTCCAAC
TTCAACAATCAGGACCAGGGCTCGTGAAGCCGTCCCAAACG
CTTAGTCTCACATGCGCCATTAGTGGGGACTCCGTGAGTTCA
AATTCCGCCGCCTGGAATTGGATTAGGCAAAGTCCATCTAGG
GGTCTTGAGTGGCTCGGCCGCACTTACTACAGATCCAAGTGG
TATAACGACTACGCAGTATCCGTAAAATCAAGAATAACAAT
TAATCCAGATACTTCTAAGAACCAATTTAGTCTTCAACTGAA
CAGCGTGACCCCGGAGGATACAGCGGTGTATTATTGTGCGC
GAGAAGTTACCGGGGATCTGGAGGATGCTTTTGATATCTGG
GGCCAAGGAACAATGGTAACCGTTAGTTCAGGCGGTGGTGG
TTCTGGGGGCGGGGGGTCTGGAGGAGGGGGAAGTGATATAC
AAATGACACAGAGCCCTAGTTCCCTTAGTGCCTCAGTTGGGG
ATAGGGTAACAATCACTTGCCGAGCATCACAGACGATATGG
TCCTATCTCAACTGGTATCAACAACGCCCTGGCAAGGCACCC
AACCTGCTGATCTACGCCGCTAGTAGTTTGCAAAGTGGGGTA
CCTAGTAGATTCTCCGGCAGAGGTTCTGGCACTGACTTTACC
TTGACAATCAGCAGCCTCCAAGCAGAAGACTTCGCGACATA
CTACTGTCAGCAAAGTTACTCTATACCTCAGACGTTCGGTCA
GGGGACCAAGCTCGAGATCAAGgcggccgcgGGCGGTGGAGGC
AGTGGTGGTGCGGCTCTGGCGGTGGTGGTAGCCTCGAGGA
CGGGAACGAAGAGATGGGAGGCATAACTCAAACGCCGTATA
AAGTTAGTATAAGTGGAACAACGGTTATATTGACGTGCCCA
CAATATCCAGGATCAGAGATCCTTTGGCAGCATAACGATAA
AAACATCGGCGGCGACGAAGACGACAAAAACATTGGCAGC
GACGAAGACCACCTCAGCCTTAAAGAGTTCTCTGAGTTGGA
ACAAAGCGGGTACTACGTCTGCTATCCACGGGGGTCTAAAC
CCGAGGATGCAAATTTCTACCTGTATCTCAGAGCTAGGGTAT
GCGAAAACTGTATGGAAATGGACGTGATGAGCGTGGCGACT
ATCGTCATAGTAGATATTTGTATTACCGGGGGCTTCTCCTT
CTGGTTTATTATTGGTCTAAGAATCGGAAAGCGAAAGCGAA
ACCCGTAACACGAGGGGCTGGTGCTGGGGGCAGGCAAAGGG
GTCAAAATAAGGAAAGGCCCCCTCCAGTCCCTAATCCTGATT
ACGAGCCGATAAGGAAAGGTCAGCGGGACTTGTACAGCGGT
TTGAACCAGCGGAGGATCTGATAAGAATTCGAATTTAAATC
GGATCCGCGGCCGCGTCGACAATCAACCTCTGGATTACAAA

APPENDIX A-continued

SEQUENCE SUMMARY

| SEQ ID NO. | Name | Sequence |
|---|---|---|
| | | ATTTGTGAAAGATTGACTGGTATTCTTAACTATGTTGCTCCTT<br>TTACGCTATGTGGATACGCTGCTTTAATGCCTTTGTATCATGC<br>TATTGCTTCCCGTATGGCTTTCATTTTCTCCTCCTTGTATAAA<br>TCCTGGTTGCTGTCTCTTTATGAGGAGTTGTGGCCCGTTGTCA<br>GGCAACGTGGCGTGGTGTGCACTGTGTTTGCTGACGCAACCC<br>CCACTGGTTGGGGCATTGCCACCACCTGTCAGCTCCTTTCCG<br>GGACTTTCGCTTTCCCCCTCCCTATTGCCACGGCGGAACTCA<br>TCGCCGCCTGCCTTGCCCGCTGCTGGACAGGGGCTCGGCTGT<br>TGGGCACTGACAATTCCGTGGTGTTGTCGGGGAAATCATCGT<br>CCTTTCCTTGGCTGCTCGCCTGTGTTGCCACCTGGATTCTGCG<br>CGGGACGTCCTTCTGCTACGTCCCTTCGGCCCTCAATCCAGC<br>GGACCTTCCTTCCCGCGGCCTGCTGCCGGCTCTGCGGCCTCT<br>TCCGCGTCTTCGCCTTCGCCCTCAGACGAGTCGGATCTCCCT<br>TTGGGCCGCCTCCCCGCCTGGTACCTTTAAGACCAATGACTT<br>ACAAGGCAGCTGTAGATCTTAGCCACTTTTTAAAAGAAAAG<br>GGGGGACTGGAAGGGCTAATTCACTCCCAACGAAGATAAGA<br>TCTGCTTTTTGCTTGTACTGGGTCTCTCTGGTTAGACCAGATC<br>TGAGCCTGGGAGCTCTCTGGCTAACTAGGGAACCCACTGCTT<br>AAGCCTCAATAAAGCTTGCCTTGAGTGCTTCAAGTAGTGTGT<br>GCCCGTCTGTTGTGTGACTCTGGTAACTAGAGATCCCTCAGA<br>CCCTTTTAGTCAGTGTGGAAAATCTCTAGCAGTAGTAGTTCA<br>TGTCATCTTATTATTCAGTATTTATAACTTGCAAAGAAATGA<br>ATATCAGAGAGTGAGAGGAACTTGTTTATTGCAGCTTATAAT<br>GGTTACAAATAAAGCAATAGCATCACAAATTTCACAAATAA<br>AGCATTTTTTTCACTGCATTCTAGTTGTGGTTTGTCCAAACTC<br>ATCAATGTATCTTATCATGTCTGGCTCTAGCTATCCCGCCCCT<br>AACTCCGCCCATCCCGCCCCTAACTCCGCCCAGTTCCGCCCA<br>TTCTCCGCCCCATGGCTGACTAATTTTTTTTATTTATGCAGAG<br>GCCGAGGCCGCCTCGGCCTCTGAGCTATTCCAGAAGTAGTG<br>AGGAGGCTTTTTTGGAGGCCTAGACTTTTGCagagacggcccaaattc<br>gtaatcatggtcatagctgtttcctgtgtgaaattgttatccgctcacaattccacacaacatacgagcc<br>ggaagcataaagtgtaaagcctggggtgcctaatgagtgagctaactcacattaattgcgttgcgctc<br>actgcccgctttccagtcgggaaacctgtcgtgccagctgcattaatgaatcggccaacgcgcgggg<br>agaggcggtttgcgtattgggcgctcttccgcttcctcgctcactgactcgctgcgctcggtcgttcgg<br>ctgcggcgagcggtatcagctcactcaaaggcggtaatacggttatccacagaatcaggggataac<br>gcaggaaagaacatgtgagcaaaaggccagcaaaaggccaggaaccgtaaaaaggccgcgttgc<br>tggcgtttttccataggctccgcccccctgacgagcatcacaaaaatcgacgctcaagtcagaggtg<br>gcgaaacccgacaggactataaagataccaggcgtttccccctggaagctccctcgtgcgctctcct<br>gttccgaccctgccgcttaccggatacctgtccgcctttctcccttcgggaagcgtggcgctttctcata<br>gctcacgctgtaggtatctcagttcggtgtaggtcgttcgctccaagctgggctgtgtgcacgaaccc<br>cccgttcagcccgaccgctgcgccttatccggtaactatcgtcttgagtccaacccggtaagacacga<br>cttatcgccactggcagcagccactggtaacaggattagcagagcgaggtatgtaggcggtgctac<br>agagttcttgaagtggtggcctaactacggctacactagaaggacagtatttggtatctgcgctctgct<br>gaagccagttaccttcggaaaaagagttggtagctcttgatccggcaaacaaaccaccgctggtagc<br>ggtggtttttttgtttgcaagcagcagattacgcgcagaaaaaaaggatctcaagaagatcctttgatct<br>tttctacggggtctgacgctcagtggaacgaaaactcacgttaagggattttggtcatgagattatcaa<br>aaaggatcttcacctagatccttttaaattaaaaatgaagttttaaatcaatctaaagtatatatgagtaaa<br>cttggtctgacagttaccaatgcttaatcagtgaggcacctatctcagcgatctgtctatttcgttcatcca<br>tagttgcctgactccccgtcgtgtagataactacgatacgggagggcttaccatctggccccagtgct<br>gcaatgataccgcgagacccacgctcaccggctccagatttatcagcaataaaccagccagccgga<br>agggccgagcgcagaagtggtcctgcaactttatccgcctccatccagtctattaattgttgccggga<br>agctagagtaagtagttcgccagttaatagtttgcgcaacgttgttgccattgctacaggcatcgtggtg<br>tcacgctcgtcgtttggtatggcttcattcagctccggttcccaacgatcaaggcgagttacatgatccc<br>ccatgttgtgcaaaaaagcggttagctccttcggtcctccgatcgttgtcagaagtaagttggccgcag<br>tgttatcactcatggttatggcagcactgcataattctactgtcatgccatccgtaagatgatttctgt<br>gactggtgagtactcaaccaagtcattctgagaatagtgtatgcggcgaccgagttgctcttgcccgg<br>cgtcaatacgggataataccgcgccacatagcagaactttaaaagtgctcatcattggaaaacgttctt<br>cggggcgaaaactctcaaggatcttaccgctgttgagatccagttcgatgtaacccactcgtgcaccc<br>aactgatcttcagcatcttttactttcaccagcgtttctgggtgagcaaaaacaggaaggcaaaatgcc<br>gcaaaaaagggaataagggcgacacggaaatgttgaatactcatactcttcctttttcaatattattgaa<br>gcatttatcagggttattgtctcatgagcggatacatatttgaatgtatttagaaaaataaacaaataggg<br>gttccgcgcacatttccccgaaaagtgccacctgacgtctaagaaaccattattatcatgacattaacct<br>ataaaaataggcgtatcacgaggccctttcgtctcgcgcgtttcggtgatgacggtgaaaacctctga<br>cacatgcagctcccggagacggtcacagcttgtctgtaagcggatgccgggagcagacaagcccg<br>tcagggcgcgtcagcgggtgttggcgggtgtcggggctggcttaactatgcggcatcagagcagat<br>tgtactgagagtgcaccatatgcggtgtgaaataccgcacagatgcgtaaggagaaaataccgcatc<br>aggcgccattcgccattcaggctgcgcaactgttgggaagggcgatcggtgcgggcctcttcgctat<br>tacgccagctggcgaaaggggatgtgctgcaaggcgattaagttgggtaacgccagggttttccc<br>agtcacgacgttgtaaaacgacggccagtgccaagctg |
| 101 | Linker 6<br>(amino acid) | GGGGSGGGGS |

APPENDIX A-continued

SEQUENCE SUMMARY

| SEQ ID NO. | Name | Sequence |
|---|---|---|
| 102 | Linker 6 (DNA) | GGTGGCGGAGGTTCTGGAGGTGGAGGTTCC |
| 103 | hBCMA polypeptide canonical sequence UniProt Accession No. Q02223-1 | MLQMAGQCSQNEYFDSLLHACIPCQLRCSSNTPPLTCQRYCNA SVTNSVKGTNAILWTCLGLSLIITSLAVFVLMFLLRKINSEPLKDE FKNTGSGLLGMANIDLEKSRTGDEIILPRGLEYTVEECTCEDCIK SKPKVDSDHCFPLPAMEEGATILVTTKTNDYCKSLPAALSATEI EKSISAR |
| 104 | hCD19 polypeptide canonical sequence UniProt Accession No. P15391 | MPPPRLLFFLLFLTPMEVRPEEPLVVKVEEGDNAVLQCLKGTSD GPTQQLTWSRESPLKPFLKLSLGLPGLGIHMRPLAIWLFIFNVSQ QMGGFYLCQPGPPSEKAWQPGWTVNVEGSGELFRWNVSDLG GLGCGLKNRSSEGPSSPSGKLMSPKLYVWAKDRPEIWEGEPPC LPPRDSLNQSLSQDLTMAPGSTLWLSCGVPPDSVSRGPLSWTH VHPKGPKSLLSLELKDDRPARDMWVMETGLLLPRATAQDAGK YYCHRGNLTMSFHLEITARPVLWHWLLRTGGWKVSAVTLAYL IFCLCSLVGILHLQRALVLRRKRKRMTDPTRRFFKVTPPPGSGP QNQYGNVLSLPTPTSGLGRAQRWAAGLGGTAPSYGNPSSDVQ ADGALGSRSPPGVGPEEEGEGYEEPDSEEDSEFYENDSNLGQD QLSQDGSGYENPEDEPLGPEDEDSFSNAESYENEDEELTQPVAR TMDFLSPHGSAWDPSREATSLGSQSYEDMRGILYAAPQLRSIRG QPGPNHEEDADSYENMDNPDGPDPAWGGGRMGTWSTR |
| 105 | hCD22 beta isoform polypeptide canonical sequence UniProt Accession No. P20273-1 | MHLLGPWLLLLVLEYLAFSDSSKWVFEHPETLYAWEGACVWI PCTYRALDGDLESFILFHNPEYNKNTSKFDGTRLYESTKDGKVP SEQKRVQFLGDKNKNCTLSIHPVHLNDSGQLGLRMESKTEKW MERIHLNVSERPFPPHIQLPPEIQESQEVTLTCLLNFSCYGYPIQL QWLLEGVPMRQAAVTSTSLTIKSVFTRSELKFSPQWSHHGKIVT CQLQDADGKFLSNDTVQLNVKHTPKLEIKVTPSDAIVREGDSV TMTCEVSSSNPEYTTVSWLKDGTSLKKQNTFTLNLREVTKDQS GKYCCQVSNDVGPGRSEEVFLQVQYAPEPSTVQILHSPAVEGS QVEFLCMSLANPLPTNYTWYHNGKEMQGRTEEKVHIPKILPW HAGTYSCVAENILGTGQRGPGAELDVQYPPKKVTTVIQNPMPI REGDTVTLSCNYNSSNPSVTRYEWKPHGAWEEPSLGVLKIQNV GWDNTTIACAACNSWCSWASPVALNVQYAPRDVRVRKIKPLS EIHSGNSVSLQCDFSSSHPKEVQFFWEKNGRLLGKESQLNFDSIS PEDAGSYSCWVNNSIGQTASKAWTLEVLYAPRRLRVSMSPGD QVMEGKSATLTCESDANPPVSHYTWFDWNNQSLPYHSQKLRL EPVKVQHSGAYWCQGTNSVGKGRSPLSTLTVYYSPETIGRRVA VGLGSCLAILILAICGLKLQRRWKRTQSQQGLQENSSGQSFFVR NKKVRRAPLSEGPHSLGCYNPMMEDGISYTTLRFPEMNIPRTG DAESSEMQRPPPDCDDTVTYSALHKRQVGDYENVIPDFPEDEGI HYSELIQFGVGERPQAQENVDYVILKH |
| 106 | CD16 ECD (DNA) | CCCAAGGCTGTAGTATTCCTCGAACCGCAGTGGTATCGGGTA CTCGAAAAAGACAGTGTAACGCTGAAGTGCCAGGGGGCCTA TAGTCCCGAGGATAACTCAACCCAATGGTTCCACAATGAAA GCCTCATCTCTTCACAAGCAAGTTCTTATTTCATAGATGCCG CCACTGTAGATGACTCCGGAGAATATCGGTGTCAAACGAAT TTGTCTACTCTGAGCGACCCGGTTCAGCTTGAGGTACACATA GGGTGGTTGCTTCTCCAAGCCCCCGGTGGGTATTAAGGAG GAAGATCCAATCCACTTGCGGTGTCACAGCTGGAAGAACAC AGCCCTTCACAAGGTAACATACTTGCAAAACGGCAAGGGTA GGAAATACTTCCATCACAACAGCGATTTCTACATACCAAAA GCAACCCTCAAGGACTCCGGGAGTTATTTCTGCCGCGGGCTC TTCGGTTCTAAGAATGTAAGCAGTGAAACGGTCAATATAAC CATTACACAGGGTCTCGCGGTTTCTACCATCTCAAGTTTCTTC CCTCCCGGTTATCAA |
| 107 | human CD3-γ, fragment used in TFPs | FKIPIEELEDRVFVNCNTSITWVEGTVGTLLSDITRLDLGKRILDP RGIYRCNGTDIYKDKESTVQVHYRMCQSCVELDPATVAGIIVT DVIATLLLALGVFCFAGHETGRLSGAADTQALLRNDQVYQPLR DRDDAQYSHLGGNWARNK |
| 108 | human CD3-δ fragment used in TFPs | FKIPIEELEDRVFVNCNTSITWVEGTVGTLLSDITRLDLGKRILDP RGIYRCNGTDIYKDKESTVQVHYRMCQSCVELDPATVAGIIVT DVIATLLLALGVFCFAGHETGRLSGAADTQALLRNDQVYQPLR DRDDAQYSHLGGNWARNK |
| 109 | human CD3-ζ, fragment used in TFPs | RVKFSRSADAPAYQQGQNQLYNELNLGRREEYDVLDKRRGRD PEMGGKPQRRKNPQEGLYNELQKDKMAEAYSEIGMKGERRRG KGHDGLYQGLSTATKDTYDALHMQALPPR |

APPENDIX A-continued

SEQUENCE SUMMARY

| SEQ ID NO. | Name | Sequence |
|---|---|---|
| 110 | human NKG2D type II integral membrane protein, fragment used in TFPs (EDC) | NSLFNQEVQIPLTESYCGPCPKNWICYKNNCYQFFDESKNWYE SQASCMSQNASLLKVYSKEDQDLLKLVKSYHWMGLVHIPTNG SWQWEDGSILSPNLLTIIEMQKGDCALYASSFKGYIENCSTPNT YICMQRTV |

What is claimed is:

1. A recombinant nucleic acid comprising a sequence encoding:
  a T-cell receptor (TCR) fusion protein (TFP) comprising:
    (i) a TCR subunit comprising:
      (A) a TCR extracellular domain,
      (B) a TCR transmembrane domain, and
      (C) a TCR intracellular domain comprising a stimulatory domain, wherein the TCR extracellular domain, the TCR transmembrane domain and the TCR intracellular domain of the TCR subunit are from a single TCR chain, wherein the single TCR chain is a CD3 epsilon chain or a CD3 gamma chain; and
    (ii) a first antigen binding domain that binds to a first antigen, and a second antigen binding domain that binds to a second antigen that is different from the first antigen, and wherein each of the first antigen binding domain and the second antigen binding domain is a single-chain fragment variable (scFv) or a single domain antibody (sdAb) domain; and
  wherein the TFP comprises, from N-terminus to C-terminus, the second antigen binding domain, a $(G4S)_n$ linker, wherein n=1 to 4, the first antigen binding domain and the TCR subunit, and
  wherein the TFP forms a multimeric TCR complex comprising: the TFP, an endogenous TCR alpha chain, an endogenous TCR beta chain, an endogenous CD3 delta chain and an endogenous CD3 zeta chain when expressed on a surface of a T cell.

2. The recombinant nucleic acid of claim 1, wherein the first antigen binding domain is an anti-CD19 binding domain and the second antigen binding domain is an anti-CD22 or an anti-CD20 binding domain.

3. The recombinant nucleic acid of claim 1, wherein the first antigen binding domain is an anti-CD19 binding domain and the second antigen binding domain is an anti-BCMA binding domain.

4. The recombinant nucleic acid of claim 1, wherein the single TCR chain of the TCR subunit is a CD3 epsilon chain.

5. The recombinant nucleic acid of claim 1, wherein the sdAb domain is a $V_H$ domain.

6. The recombinant nucleic acid of claim 1, wherein the single TCR chain of the TCR subunit is a CD3 gamma chain.

7. A pharmaceutical composition comprising
  a human T cell comprising the recombinant nucleic acid of claim 1, and
  a pharmaceutically acceptable excipient.

8. A recombinant nucleic acid comprising a first sequence encoding a first TFP and a second sequence encoding a second TFP, wherein each of the first TFP and the second TFP comprises:
  a TCR subunit comprising:
    (A) at least a portion of a TCR extracellular domain,
    (B) a TCR transmembrane domain, and
    (C) a TCR intracellular domain comprising a stimulatory domain, wherein the TCR extracellular domain, the TCR transmembrane domain and the TCR intracellular domain are from a single TCR chain, wherein the single TCR chain is a CD3 epsilon chain or a CD3 gamma chain;
  wherein
  (i) the first TFP comprises, from N-terminus to C-terminus, a first antigen binding domain, a $(G4S)_n$ linker, wherein n=1 to 4 and the TCR subunit of the first TFP, wherein the first antigen binding domain binds to a first antigen, and (ii) the second TFP comprises, from N-terminus to C-terminus, a second antigen binding domain, a $(G4S)_n$ linker, wherein n=1 to 4 and the TCR subunit of the second TFP, wherein the second antigen binding domain binds to a second antigen that is different from the first antigen, wherein each of the first antigen binding domain and the second antigen binding domain is a single-chain fragment variable (scFv) or a single domain antibody (sdAb) domain;

wherein the first sequence and the second sequence are linked by a sequence encoding a cleavage site, and wherein the first TFP forms a multimeric TCR complex comprising the first TFP, an endogenous TCR alpha chain, an endogenous TCR beta chain, an endogenous CD3 delta chain and an endogenous CD3 zeta chain when expressed on a surface of a T cell, and the second TFP forms a multimeric TCR complex comprising the second TFP, an endogenous TCR alpha chain, an endogenous TCR beta chain, an endogenous CD3 delta chain and an endogenous CD3 zeta chain when expressed on a surface of a T cell.

9. The recombinant nucleic acid of claim 8, wherein the second TFP forms a different multimeric TCR complex comprising the second TFP, an endogenous TCR alpha chain, an endogenous TCR beta chain, an endogenous CD3 delta chain and an endogenous CD3 zeta chain when expressed on a surface of a T cell.

10. The recombinant nucleic acid of claim 8, wherein the single TCR chain of the first TFP and the single TCR chain of the second TFP are the same.

11. The recombinant nucleic acid of claim 8, wherein (i) the first antigen binding domain is an anti-CD19 binding domain and the second antigen binding domain is an anti-BCMA binding domain, or (ii) the first antigen binding domain is an anti-CD19 binding domain and the second antigen binding domain is an anti-CD22 or an anti-CD20 binding domain.

12. The recombinant nucleic acid of claim 10, wherein the single TCR chain of the first TCR subunit is a CD3 epsilon chain; and wherein the single TCR chain of the second TCR subunit is a CD3 epsilon chain.

13. The recombinant nucleic acid of claim 10, wherein the single TCR chain of the first TCR subunit is a CD3 gamma chain; and wherein the single TCR chain of the second TCR subunit is a CD3 gamma chain.

14. The recombinant nucleic acid of claim 8, wherein the sdAb domain is a $V_H$ domain.

15. A pharmaceutical composition comprising a human T cell comprising the recombinant nucleic acid of claim 8, and a pharmaceutically acceptable excipient.

* * * * *